(12) United States Patent  
Miyake et al.

(10) Patent No.: US 8,884,047 B2  
(45) Date of Patent: Nov. 11, 2014

(54) N-SUBSTITUTED CARBAMIC ACID ESTER PRODUCTION METHOD AND ISOCYANATE PRODUCTION METHOD USING THE N-SUBSTITUTED CARBAMIC ACID ESTER

(75) Inventors: Nobuhisa Miyake, Tokyo (JP); Masaaki Shinohata, Tokyo (JP); Atsushi Okubo, Tokyo (JP)

(73) Assignee: Asahi Kasei Chemicals Corporation, Tokyo (JP)

( * ) Notice: Subject to any disclaimer, the term of this patent is extended or adjusted under 35 U.S.C. 154(b) by 509 days.

(21) Appl. No.: 13/001,238

(22) PCT Filed: Sep. 29, 2009

(86) PCT No.: PCT/JP2009/005013  
§ 371 (c)(1),  
(2), (4) Date: Dec. 23, 2010

(87) PCT Pub. No.: WO2011/021258  
PCT Pub. Date: Feb. 24, 2011

(65) Prior Publication Data  
US 2011/0160476 A1  Jun. 30, 2011

(30) Foreign Application Priority Data

Aug. 21, 2009  (JP) ................................. 2009-192250  
Aug. 21, 2009  (JP) ................................. 2009-192268

(51) Int. Cl.
| | | |
|---|---|---|
| C07C 261/00 | (2006.01) | |
| C07C 269/00 | (2006.01) | |
| C07C 271/00 | (2006.01) | |
| C07C 269/04 | (2006.01) | |
| C07C 263/04 | (2006.01) | |

(52) U.S. Cl.  
CPC ............. C07C 263/04 (2013.01); C07C 269/04 (2013.01); C07C 269/00 (2013.01); C07C 2101/14 (2013.01)  
USPC .......................................................... 560/25

(58) Field of Classification Search  
USPC ......... 560/132, 133, 134, 135, 136, 137, 157, 560/25, 28, 32  
See application file for complete search history.

(56) References Cited

U.S. PATENT DOCUMENTS

| | | | |
|---|---|---|---|
| 2,145,242 A | 1/1939 | Arnold | |
| 2,409,701 A | 10/1946 | Loth | |
| 2,409,712 A * | 10/1946 | Schweitzer .................. | 560/345 |
| 2,677,698 A | 5/1954 | Deutschman et al. | |
| 2,692,275 A | 10/1954 | Bortnick | |
| 3,466,346 A | 9/1969 | Graff et al. | |
| 3,734,941 A | 5/1973 | Sydor | |
| 3,873,553 A | 3/1975 | Hearsey | |
| 3,992,430 A | 11/1976 | Bacskai | |
| 4,081,472 A | 3/1978 | Tsumura et al. | |
| 4,097,676 A | 6/1978 | Romano | |
| 4,290,970 A | 9/1981 | Merger et al. | |
| 4,297,501 A | 10/1981 | Becker et al. | |
| 4,381,404 A | 4/1983 | Buysch et al. | |
| 4,388,238 A | 6/1983 | Heitkamper et al. | |
| 4,388,246 A | 6/1983 | Sundermann et al. | |
| 4,388,426 A | 6/1983 | Schure et al. | |
| 4,430,505 A | 2/1984 | Heitkamper et al. | |
| 4,480,110 A | 10/1984 | Heitkamper et al. | |
| 4,482,499 A | 11/1984 | Merger et al. | |
| 4,497,963 A | 2/1985 | Merger et al. | |
| 4,514,339 A | 4/1985 | Romano et al. | |
| 4,611,079 A | 9/1986 | Merger et al. | |
| 4,692,550 A | 9/1987 | Engbert et al. | |
| 4,713,476 A | 12/1987 | Merger et al. | |
| 4,925,971 A * | 5/1990 | Aoki et al. ..................... | 560/137 |
| 5,087,739 A | 2/1992 | Bohmholdt et al. | |
| 5,360,931 A | 11/1994 | Bohmholdt et al. | |
| 5,386,053 A | 1/1995 | Otterbach et al. | |
| 5,744,633 A | 4/1998 | Wilmes et al. | |
| 7,122,697 B2 | 10/2006 | Yoshida et al. | |
| 2008/0227999 A1 | 9/2008 | Molzahn | |
| 2010/0029981 A1 | 2/2010 | Shinohata et al. | |
| 2010/0036154 A1 | 2/2010 | Michalczak et al. | |
| 2010/0069665 A1 | 3/2010 | Shinohata et al. | |
| 2010/0113823 A1 | 5/2010 | Shinohata et al. | |
| 2010/0274046 A1 | 10/2010 | Kloetzer et al. | |
| 2013/0178643 A1 | 7/2013 | Shinohata et al. | |

FOREIGN PATENT DOCUMENTS

| | | |
|---|---|---|
| CA | 2033634 A1 | 7/1991 |
| CA | 2094484 A1 | 10/1993 |
| CN | 101234998 A | 8/2008 |
| CN | 101374802 A | 2/2009 |
| DE | 1 042 891 | 8/1956 |
| DE | 39 28 595 | 8/1989 |
| EP | 0 355 443 | 7/1989 |
| EP | 0 568 782 | 3/1993 |
| EP | 0566925 A2 | 10/1993 |
| EP | 0 657 420 | 11/1994 |
| JP | 52-071433 A | 6/1977 |
| JP | 52-71443 | 6/1977 |

(Continued)

OTHER PUBLICATIONS

Yadav et al., Synlett 2005, No. 20, pp. 3055-3058.*

(Continued)

*Primary Examiner* — Brandon Fetterolf  
*Assistant Examiner* — Blaine G Doletski  
(74) *Attorney, Agent, or Firm* — Morgan, Lewis & Bockius LLP

(57) ABSTRACT

The present invention provides a method for producing N-substituted carbamic acid-O-aryl ester derived from a compound having an ureido group, the method comprising the step of carrying out esterification or esterification and transesterification from the compound having the ureido group and a hydroxy composition containing one type or a plurality of types of hydroxy compounds.

18 Claims, 26 Drawing Sheets

(56) References Cited

FOREIGN PATENT DOCUMENTS

| | | |
|---|---|---|
| JP | 56-103152 A | 8/1981 |
| JP | 56-103153 A | 8/1981 |
| JP | 57-091967 A | 6/1982 |
| JP | 57-112363 A | 7/1982 |
| JP | 59-108754 | 6/1984 |
| JP | H01-203356 A | 8/1989 |
| JP | 02-000759 | 1/1990 |
| JP | 02-000759 A | 1/1990 |
| JP | H02-000262 A | 1/1990 |
| JP | 3-20254 | 1/1991 |
| JP | 4-164060 | 6/1992 |
| JP | H04-221359 A | 8/1992 |
| JP | 5-310677 | 11/1993 |
| JP | 6-41045 | 2/1994 |
| JP | 6-192204 | 7/1994 |
| JP | 6-239826 | 8/1994 |
| JP | 7-157463 | 6/1995 |
| JP | 8-277255 | 10/1996 |
| JP | 08-277255 A | 10/1996 |
| JP | H08-277257 A | 10/1996 |
| JP | H09-255630 A | 9/1997 |
| JP | 2804132 | 7/1998 |
| JP | 2804132 B2 | 7/1998 |
| JP | 2804232 | 7/1998 |
| JP | 2804232 B2 | 7/1998 |
| JP | 3382289 | 12/2002 |
| JP | 2009-502792 A | 1/2009 |
| TW | 200930693 A | 7/2009 |
| WO | 2008/059953 | 5/2008 |
| WO | 2008/084824 | 7/2008 |
| WO | 2008/120645 | 10/2008 |

OTHER PUBLICATIONS

Yadav et al. (Three-Component Coupling Strategy for Expeditious Synthesis of 4-Aminobenzoxazinones on Mineral Support, SYNLETT, No. 20, pp. 3055-3058, 2005 as sited in IDS filed Jan. 13, 2011).*
Office Action issued in corresponding Japanese Patent Application No. 2012-088122 dated Jun. 1, 2012.
Canadian Office Action from corresponding Canadian Patent Application No. 2707336 dated Feb. 27, 2012.
Taiwanese Office Action issued in corresponding Taiwanese Patent Application No. 098134456 dated Apr. 13. 2012.
Miyake, Reactions of Amines with Urea and its Derivatives, III Reactions of Urea with Diamines, Journal of Synthetic Organic Chemistry, 20, 1003-1008, 1962.
Hofmann, Berchte der Deutechen Chemischen Gesellschaft, 3, 653-658, 1870.
Yadav, Three-Component Coupling Strategy for Expeditious Synthesis of 4-Aminobenzoxazinones on Mineral Support, Syn. Lett, 20, 3055-3058, 2005.
Schiff, Berchte der Deutechen Chemischen Gesellschaft, 3, 649-652, 1870.
Harris, Thermal Oligomerization of N,N'-(1,6-hexanediyl)bisurea, Polymer, 35, 3766-3768, 1994.
Stedman, The Methylurethanes of the Isomeric alpha-Hydroxyphenylethyldimethylamines and their Miotic Activity, Journal of the Chemical Society, 609-617, 1929.
Gittos, A New Synthesis of Isocyanates, Journal of the Chemical Society, 141-143, 1976.
Katshalski, The Chemical Structure of Some Diamine Carbamates, Journal of the American Chemical Society, 73, 1829-1831, 1951.
Dyer, Thermal Degradation of Alkyl N-Phenylcarbamates, Journal of the American Chemical Society, 81, 2138-2143, 1959.
Bayer, Das Diisocyanat-Polyadditionsverfahren, 1963.
Yukikagaku Seikagaku Meimeihou, Organic Chemistry and Biochemistry Nomenclature, 1992.
Recommendations 1993.
Recommendations 1979.
Office Action issued in corresponding Chinese Patent Application No. 200980160125.8 dated May 22, 2013. Office action on Chinese Patent Appl. 200980160125.8 was considered to the extent of the pictures.
Office Action issued in corresponding Taiwanese Patent Application No. 101105787 dated Oct. 17, 2013. Office action on Taiwanese Patent Appl. 101105787 was considered to the extent of the US patents 4480110A and 4381404.
Office Action issued in related U.S. Appl. No. 13/821,818 dated Dec. 19, 2013.
Search Report issued in International Application No. PCT/JP2012/054148 dated May 15, 2012.
Japanese Office Action in corresponding Patent Application No. 2010-53996 dated Feb. 23. 2010.
Office Action issued in related Chinese Patent Application No. 200980124092.1 dated Dec. 28, 2012.

* cited by examiner

N-SUBSTITUTED CARBAMIC ACID ESTER PRODUCTION METHOD AND ISOCYANATE PRODUCTION METHOD USING THE N-SUBSTITUTED CARBAMIC ACID ESTER

CROSS-REFERENCE TO RELATED APPLICATIONS

The present application is a U.S. National Phase Application of International Application PCT/JP2009/005013 filed Sep. 29, 2009, which claims the benefit of Japanese Patent Application Nos. 2009-192250, filed Aug. 21, 2009, and 2009-192268, filed Aug. 21, 2009, which are hereby incorporated by reference in their entirety.

TECHNICAL FIELD

The present invention relates to a method for producing N-substituted carbamic acid ester and a method for producing isocyanate that uses the N-substituted carbamic acid ester.

BACKGROUND ART

Isocyanates are widely used as production raw materials of such products as polyurethane foam, paints and adhesives. Although a plurality of reaction mechanisms can be considered for industrial production of isocyanates, the main industrial production method involves reaction of an amine with phosgene (phosgene method) as indicated in the following formula (i), and nearly the entire amount of isocyanates produced throughout the world are produced according to the phosgene method. However, the phosgene method has numerous problems.

Firstly, this method requires the use of a large amount of phosgene as raw material. Phosgene is extremely toxic and requires special handling precautions to prevent exposure of handlers thereof, and also requires special apparatuses to detoxify waste.

Secondly, since highly corrosive hydrogen chloride is produced in large amounts as a by-product of the phosgene method, in addition to requiring a process for detoxifying the hydrogen chloride, in many cases hydrolytic chlorine is contained in the isocyanates produced, which may have a detrimental effect on the weather resistance and heat resistance of polyurethane products in the case of using isocyanates produced using the phosgene method.

On the basis of this background, a method for producing isocyanate compounds is sought that does not use phosgene.

Although examples of such methods may include a method for synthesizing aliphatic isocyanate from an aliphatic nitro compound and carbon monoxide, and a method for converting an aliphatic amide compound to isocyanate by Hoffmann decomposition, both of these methods have poor yield and are inadequate for industrial application.

Methods for obtaining an isocyanate and a hydroxyl compound by thermal decomposition of N-substituted carbamic acid-O-alkyl ester compound have long been known, an example of which is the method of A. W. Hoffmann (see Non-Patent Document 1). This method enables a high yield to be achieved more easily than the methods described above, and the basic reaction employed in this method is indicated in the following formula (ii).

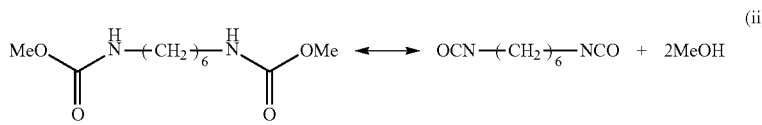

Thermal decomposition represented by the above general formula is reversible, and although the equilibrium thereof is biased towards the N-substituted carbamic acid-O-alkyl ester on the left side at low temperatures, the right side with the isocyanate and a alcohol side are advantageous at high temperatures. Thus, methods for obtaining isocyanate by thermal decomposition of N-substituted carbamic acid-O-alkyl ester are carried out at high temperatures (see, for example, Examples 12 and 13 of Patent Document 1). Here, although dependent on the ester group of the N-substituted carbamic acid-O-alkyl ester, the boiling point of N-substituted carbamic acid-O-methyl ester, for example, is 110° C. (during reduced pressure of about 2 kPa) (line 9 from the top of the right column of Non-Patent Document 2). On the other hand,

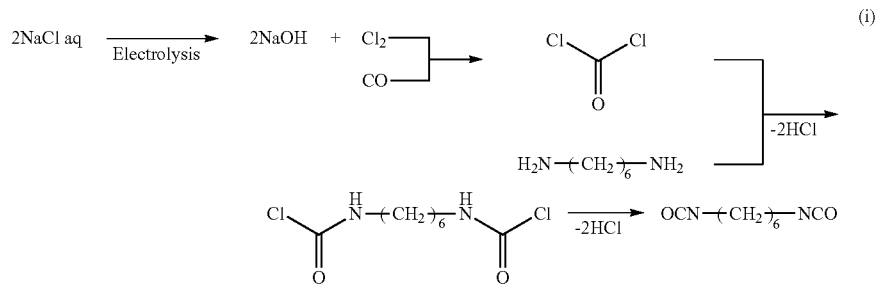

the boiling point of hexamethylene diisocyanate, which is formed in the corresponding thermal decomposition reaction, is 130 to 140° C. (during reduced pressure of about 2 kPa) (Non-Patent Document 3). Namely, this indicates that the N-substituted carbamic acid-O-methyl ester has a lower boiling point than the product in the form of hexamethylene diisocyanate. Although the details of the thermal decomposition temperature of the N-substituted carbamic acid-O-methyl ester are not described, thermal decomposition proceeds at 200° C. or higher. In the case of carrying out the thermal decomposition reaction at the described temperature of 250°

C. under reduced pressure, since these conditions exceed the boiling point of the N-substituted carbamic acid-O-methyl ester, the thermal decomposition reaction occurs in the gaseous phase. Since the raw material in the form of the N-substituted carbamic acid-O-methyl ester along with the product in the form of hexamethylene diisocyanate as well as the by-product in the form of methanol are also present in the gaseous phase, not only is it difficult to control the reaction, but various irreversible side reactions also occur. As indicated in the aforementioned publication by H. Schiff (Non-Patent Document 4) and the research by E. Dyer and G. C. Wright (Non-Patent Document 5), examples of such side reactions result in the formation of substituted ureas, biurets, urethodiones, carbodiimides and isocyanurates. In the case of gaseous phase thermal decomposition of N-substituted carbamic acid-O-alkyl esters, since the concentrations of both the isocyanate and N-substituted carbamic acid-O-alkyl ester are high in the gaseous phase, allophanate compounds form easily as indicated by the following formula (iii). The boiling points of these allophanate compounds are high since they are formed by a crosslinking reaction, and these allophanate compounds liquefy within the reactor simultaneous to their formation. Moreover, even when in this liquefied state, crosslinking among the allophanates proceeds easily due to thermal decomposition of N-substituted carbamic acid-O-alkyl ester groups. Thus, the allophanates gradually solidify resulting in clogging of the reactor.

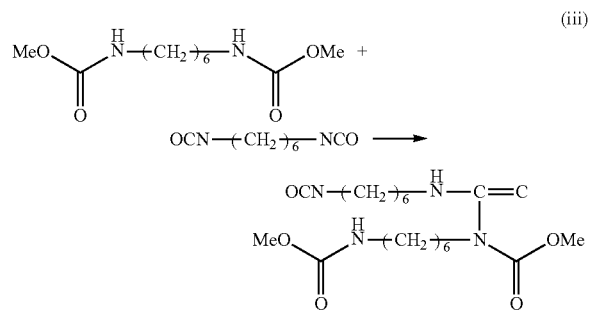

In the case of using an N-substituted carbamic acid-O-alkyl ester as a raw material of a thermal decomposition reaction, these side reactions not only cause decreases in yield and selectivity of the target isocyanate, but also induce the formation of polymers during the production of polyisocyanate in particular, and depending on the case, can cause a situation that makes long-term operation difficult, such as causing the reactor to be clogged by precipitation of polymeric solids.

In addition, research has long been conducted on methods for producing N-substituted carbamic acid-O-alkyl esters as described above. The method described in Patent Document 2 contains the production of aliphatic carbamic acid-O-alkyl ester without using phosgene. In the first stage of this method, an aliphatic carbamic acid-O-alkyl ester is produced from an aliphatic primary amine and urea by reacting N,N'-dialkyl urea and a hydroxy compound, after which the primary amine formed as a by-product is isolated, recovered and returned to the first stage. Since this method not only has a low yield of carbamic acid ester formed, but also requires equipment for recycling the primary amine, the process is extremely complex and is not satisfactory for industrial application.

Methods using urea or carbonic acid derivative (such as carbonic acid ester or carbamic acid ester) have been proposed as alternative methods for producing N-substituted carbamic acid-O-alkyl ester.

The method described in Patent Document 3 contains reacting a primary diamine and alcohol with urea or carbonic acid derivative in the presence of a catalyst followed by conversion to N-substituted carbamic acid-O-alkyl ester. In the method described in Patent Document 4, N-substituted carbamic acid-O-alkyl ester is produced after first producing bis-urea from aliphatic primary amine, urea and alcohol, while the method described in Patent Document 5 involves the partial reaction of urea and alcohol in a first step, followed by supplying diamine to produce N-substituted carbamic acid-O-alkyl ester in a second step. Patent Document 6 describes a method for obtaining N-substituted carbamic acid-O-alkyl ester by reacting a primary amine and non-N-substituted carbamic acid-O-alkyl ester in the presence of alcohol at a ratio of $NH_2$ groups to carbamate to alcohol of 1:0.8 to 10.0:0.25 to 50, at a temperature of from 160 to 300° C. and in the presence or absence of a catalyst, and then removing the ammonia formed as necessary. The method described in Patent Document 7 aromatic diisocyanate and/or polyisocyanate are produced by going through the following two steps. In the first step, an aromatic primary amine and non-N-substituted carbamic acid-O-alkyl ester are reacted in the presence or absence of a catalyst and in the presence or absence of urea and alcohol to obtain N-aryl carbamic acid-O-alkyl ester while removing the ammonia formed as a by-product as necessary, while in the second step, the N-aryl carbamic acid-O-alkyl ester is subjected to thermal decomposition to obtain aromatic isocyanate. The method described in Patent Document 8 contains producing N-alkyl carbamic acid-O-alkyl ester after first producing bis-urea from an aliphatic primary polyamine, urea and alcohol. Patent Document 9 describes a method for producing aliphatic O-alkyl monourethane by reacting an aliphatic primary amine and urea with an aliphatic alcohol.

However, as has been previously described, these thermal decomposition reactions for producing isocyanates from N-substituted carbamic acid-O-alkyl esters require high temperatures, and cause the formation of polymeric compounds attributable to undesirable side reactions as indicated in, for example, the above-mentioned formula (iii).

The majority of undesirable side reactions occur easily at higher temperatures. In addition, isocyanates formed in thermal decomposition reactions tend to increase the longer the duration of contact with the unreacted N-substituted carbamic acid-O-alkyl ester and other reaction components (including those in which a portion of the carbamic acid esters have become isocyanate groups in the case the thermal decomposition reaction raw material is a poly(N-substituted carbamic acid-O-alkyl ester)). Various methods have been proposed for obtaining a favorable isocyanate yield by inhibiting the formation of products of undesirable side reactions during thermal decomposition of N-substituted carbamic acid-O-alkyl esters.

Among N-substituted carbamic acid-O-esters (N-substituted carbamic acid-O-esters refer to carbamic acid esters containing a carbamic acid group and an organic group, and in the explanation of the present invention, indicate N-substituted carbamic acid-O-aryl esters, in which the organic group is derived from an aromatic hydroxy group and/or N-substituted carbamic acid-O-alkyl esters in which the organic group is derived from an alcohol), N-substituted carbamic acid-O-aryl esters, in which the ester group that composes the N-substituted carbamic acid-O-ester is an aromatic group (namely, carbamic acid ester group derived from an aromatic hydroxy group) offer the advantage of allowing the setting of a lower temperature for the thermal decomposition reaction as compared with N-substituted carbamic acid-O-alkyl esters, in which the ester group is an alkyl group (see, for example, Patent Document 10). In other words, the above-mentioned undesirable side reaction products can be inhibited if it were possible to set the thermal decomposition temperature to a low temperature.

On the other hand, the production of such N-substituted carbamic acid-O-aryl esters is more difficult than the production of N-substituted carbamic acid-O-alkyl esters. This is caused by the reactivities of the alcohol and aromatic hydroxy compound used as raw materials of their respective esterification reactions. The first reason for this is that aromatic hydroxy compounds have lower nucleophilicity than alcohols. The second reason is that the esterification reaction proceeds with difficulty due to the weakly acidic nature of aromatic hydroxy compounds.

Patent Document 11 describes a method for producing aliphatic N-substituted carbamic acid-O-aryl ester without using phosgene. In this method, N-substituted carbamic acid-O-aryl ester is produced oxidatively using a precious metal catalyst from a primary amine, carbon monoxide and an aliphatic alcohol or aromatic hydroxy compound. However, this method has the problems of a complex procedure and considerable costs. These problems refer to the use of highly toxic carbon monoxide, and the need to recover the catalyst from the product in the form of N-substituted carbamic acid-O-aryl ester due to the use of an expensive precious metal catalyst. Patent Document 12 describes a method for producing N-substituted carbamic acid-O-aryl ester by reacting an N-alkyl-N,N'-dialkyl urea, an aromatic hydroxy compound and hydrogen chloride gas. However, this method also has a complicated procedure and requires considerable costs. Namely, this method uses corrosive hydrogen chloride gas, consumes an expensive and uncommon urea compound, and results in difficulty in recovering the N-substituted carbamic acid-O-aryl ester from a hydrochloride of N,N'-dialkylamine formed as a by-product. In the method described in Patent Document 13, N-substituted carbamic acid-O-aryl ester is produced by a one-stage reaction between urea, aromatic hydroxy compound and aliphatic primary amine. In the method described in Patent Document 14, urea and an aromatic hydroxy compound are reacted in a first step, and N-substituted carbamic acid-O-aryl ester is produced by reacting with primary amine in a subsequent second step.

Technologies have also been disclosed for improving the low nucleophilicity of aromatic hydroxy compounds and the difficulty in shifting the equilibrium thereof. Patent Document 15 and Patent Document 16 disclose methods for producing aliphatic O-aryl urethane from a single-stage reaction of urea and/or O-aryl carbamate (non-N-substituted carbamic acid-O-aryl ester), aromatic hydroxy compound and aliphatic primary amine. In these methods, considerable improvement is made with respect to the removal of ammonia, such as by using reactive distillation or a method for introducing a large amount of inert gas. Patent Document 17 discloses a method for continuously producing urethane while continuously supplying a primary polyamine, urea and/or non-N-substituted carbamic acid ester and organic hydroxy compound to a reaction column to form the corresponding urethane and continuously extracting ammonia formed within the reaction column from the reaction column. On the other hand, Patent Document 18 describes a method that does not use a lowly nucleophilic aromatic hydroxy compound as described above. This method allows a corresponding N-alkyl carbamic acid-O-aryl ester to be obtained at a yield of 90 to 95% by reacting a primary alkyl amine with a diaryl carbonate in the presence of a solvent such as benzene, dioxane or carbon tetrachloride. This method has the advantage of allowing the obtaining of N-substituted carbamic acid-O-aryl ester at a low temperature as well as high selectivity. However, it is currently difficult to apply this method industrially due to the high cost of the diaryl carbonate.

In the case of methods using safe and inexpensive raw materials in the form of urea and carbonic acid derivatives, it is necessary to use an excess of urea or carbonic acid derivative based on the amino group of the primary amine in order to improve the yield based on the comparatively expensive primary amine. However, this does not mean that these methods have successfully inhibited side reactions or improved selectivity with respect to the primary amine.

The method described in Patent Document 19 contains recovering non-N-substituted carbamic acid-O-aryl ester from a resulting reaction liquid and recycling for use as a raw material of the reaction when producing N-substituted carbamic acid-O-aryl ester by reacting an aliphatic primary polyamine, aromatic hydroxy compound, urea and/or non-N-substituted carbamic acid-O-aryl ester. Namely, this method serves to reduce the amount used of the urea and/or non-N-substituted carbamic acid-O-aryl ester. In this method, after obtaining an aromatic hydroxy compound and isocyanic acid by thermal decomposition of non-N-substituted carbamic acid-O-aryl ester contained in the reaction liquid, and distilling the aromatic hydroxy compound at a low temperature, the isocyanic acid is again reacted with the distilled aromatic hydroxy compound and recovered in the form of non-N-substituted carbamic acid-O-aryl ester. However, in addition to this method having a complex procedure, the recovery rate of the non-N-substituted carbamic acid-O-aryl ester is unsatisfactory.

In this manner, a method for producing N-substituted carbamic acid-O-aryl ester using safe urea or carbonic acid derivative that satisfies the amounts of urea or carbonic acid derivative and primary amine has yet to be disclosed. This is due to the low nucleophilicity of aromatic hydroxy compounds as previously described as well as the low cationicity of the carbonyl carbons of the urea and carbonic acid derivative.

Despite the above-mentioned problems, since it would be extremely industrially useful to obtain isocyanates without using phosgene, various methods have been proposed for improving methods for producing isocyanates using N-substituted carbamic acid-O-esters in addition to those described above. There are methods that are carried out in a gaseous phase at high temperatures as well as methods that are carried out in a liquid phase under comparatively low temperature conditions. As was previously described, however, since there are cases in which side reactions occur during the course of thermal decomposition of N-substituted carbamic acid-O-alkyl esters resulting in the formation of precipitates, polymeric substances and obstructions in the reactor and recovery apparatuses or the formation of substances adhered to the reactor walls, economic efficiency is poor in the case of producing isocyanates over an extended period of time. Thus, although, for example, the use of chemical methods such as the use of a special catalyst (see Patent Document 20 or Patent Document 21), or a catalyst in combination with an inert solvent (see Patent Document 22) have been proposed for improving yield during thermal decomposition of N-substituted carbamic acid-O-alkyl esters, problems encountered during the production of N-substituted carbamic acid-O-aryl esters have yet to be solved. For example, the method described in Patent Document 23 is a method for producing hexamethylene diisocyanate. This method contains thermal decomposition of hexamethylene dicarbamic acid-O-ethyl ester in the presence of a catalyst mixture containing methyl toluene sulfonate and diphenyl tin dichloride while using dibenzyl toluene as a solvent. However, production and isolation of the starting components as well as purification and arbitrary recovery of the solvent and catalyst mixture are not described in detail, and the economic efficiency of this method is extremely low.

In the method described in Patent Document 24, N-substituted carbamic acid-O-alkyl ester is easily decomposed to isocyanate and alcohol in a carbon-containing fluidized bed without using a catalyst. However, the yield of isocyanate obtained in the thermal decomposition reaction is from about 83.8 to 98.7%, and although reaction by-products and the like are not described, since N-substituted carbamic acid-O-alkyl ester is still subjected to thermal decomposition and the resulting compounds contain isocyanate and alcohol that are susceptible to the occurrence of reverse reactions in the same manner as in the prior art, the above-mentioned side reactions cannot be said to be inhibited. In the method described in Patent Document 25, a circulating method to produce an alicyclic diisocyanate by reacting an alicyclic primary diamine, urea and alcohol to obtain an alicyclic dicarbamic acid-O-alkyl ester, followed by subjecting the alicyclic dicarbamic acid-O-alkyl ester to thermal decomposition. This method succeeds at reducing the amounts of materials used by recovering unreacted alcohol, non-N-substituted carbamic acid-O-ester and dialkyl carbonates, and recirculating a portion of the reaction mixture of the thermal decomposition step along with by-products to the initial step. However, this method requires the alicyclic dicarbamic acid-O-alkyl ester to be distilled at a high temperature of about 230° C. to remove residue unable to be used in the production method. Since this high distillation temperature is within the temperature range at which carbamic acid-O-alkyl esters undergo thermal decomposition, isocyanate groups formed during distillation ends up reacting with the alicyclic dicarbamic acid-O-alkyl ester resulting in the possibility of the formation of solid polymers. Although it is described in the examples that yield is maintained over a long operating time, there is no description regarding the presence of accumulation of polymers or clogging of the apparatus due to the occurrence of side reactions.

In addition, the method described in Patent Document 26 involves partially removing worthless by-products prior to thermal decomposition of N-substituted carbamic acid-O-alkyl ester. In this method, however, since N-substituted carbamic acid-O-alkyl ester is also removed together with the partially removed by-products, the yield of isocyanate based on primary amine and carbonic acid derivative is ultimately decreased. In addition, polymeric compounds are formed as a result of by-products remaining in the reactor without being discharged from the reactor being heated, and since these compounds adhered to the reactor, continuous operation over a long period of time is difficult.

In reactions for obtaining N-substituted carbamic acid-O-(alkyl or aryl) esters by reacting urea and carbonic acid derivative (or carbamic acid derivative) with a primary amine and alcohol or aromatic hydroxy compound, urea and carbonic acid derivative (or carbamic acid derivative) are used in excess to improve the selectivity of the expensive primary amine.

A reaction formula of N-substituted carbamic acid-O-alkyl ester in the case of using a primary amine and urea as raw materials is shown in the following formula (iv). Although an adequate amount of urea is present based on the primary amine in the initial phase of the reaction, as the reaction enters the latter phase, the concentrations of both (primary amine and urea) decrease resulting in the N-substituted carbamic acid-O-alkyl ester being present at a high concentration. As was previously described, the cationicity of urea and carbonyl carbons of carbonic acid derivatives is low (due to accepting electron donation by $NH_2$ groups and alkoxy groups) and the difference in reactivity between carbonyl carbons of the product in the form of N-substituted carbamic acid-O-alkyl ester and the primary amine is small. Thus, unless the amount of urea is present in excess based on the primary amine, the reaction proceeds as indicated by formula (v) during the latter phase of the reaction. Namely, the primary amine reacts with the product in the form of N-substituted carbamic acid-O-(alkyl or aryl) ester causing it to be denatured to a compound having undesirable N,N-di-substituted urea bonds. In the case of using polyamine, since each amino group reacts successively, various denatured forms are formed in addition to that shown in the following formula (v). In addition, reactions also occur such as that based on the following formula (vii) involving reaction with isocyanate formed according to the following formula (vi), and it can be easily presumed based on a knowledge of organic chemistry and reaction rates that as the N-substituted carbamic acid-O-(alkyl or aryl) ester accumulates and urea concentration decreases, the formation of these denaturation products increases dramatically. Polymerized high molecular weight substances are naturally additionally formed based on the principles of the formulas (v), (vi) and (vii). Since compounds having N,N-di-substituted urea bonds formed due to this denaturation have low levels of reactivity, re-addition of dissociated alcohol becomes difficult. Although such reactions occur at high temperatures, since the formation of isocyanates by thermal decomposition of N-substituted carbamic acid-O-(alkyl or aryl) ester also begins to occur at high temperatures, this results in the occurrence of a diverse range of side reactions.

(Initial Reaction)

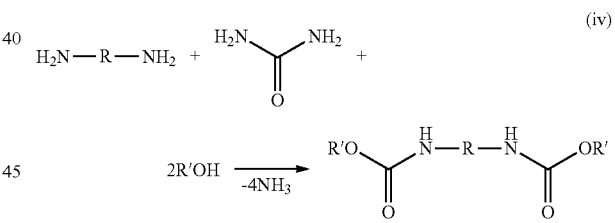

(Latter Reaction: Reaction with N-Substituted carbamic acid-O-(alkyl or aryl) ester)

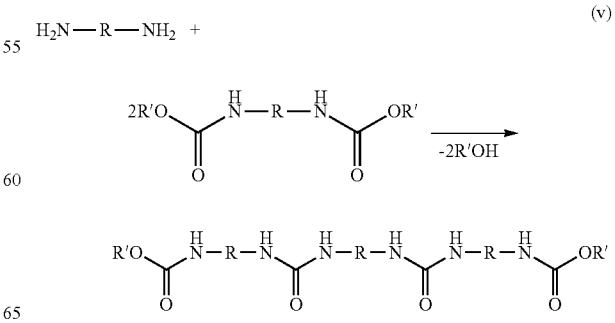

(Latter Reaction: Reaction with Isocyanate)
Isocyanate Formation

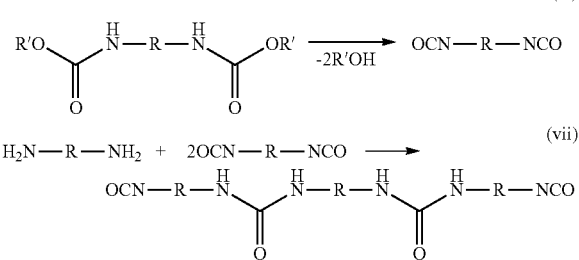

Since polymeric substances formed based on the above-mentioned reactions have extremely low solubility in solvents and the like, they frequently adhere and solidify in the reactor, thereby making such methods industrially unsatisfactory. In response to such problems, although methods have been examined (see Patent Document 4) for producing N-substituted carbamic acid-O-alkyl ester by producing bis-urea from primary amine, urea and alcohol and then reaction the bis-urea with alcohol as previously described, these methods are targeted at reaction with a highly nucleophilic alcohol and are not carried out to solve the problem in thermal decomposition of the N-substituted carbamic acid-O-alkyl ester, thereby preventing such methods from solving the problems that occur during thermal decomposition of N-substituted carbamic acid-O-alkyl ester as described above. In addition, although a method for producing bis-urea has been proposed involving the reaction of molten urea and amine in the absence of a solvent (see, for example, Non-Patent Document 6), due to the high melting temperature of urea (about 135° C.), there are many cases in which the reaction proceeds non-uniformly resulting in the occurrence of urea denaturation reactions and reactions resulting in the formation of compounds having N,N-di-substituted urea bonds, thereby preventing the above-mentioned problems from being solved.

In addition, a method for purifying such polymeric substances by crystallization has also been developed (Patent Document 27). In this method as well, it is difficult to selectively crystallize compounds having similar structures at high yield, while on the other hand, energy is expended for separating solids and liquids as well as recovery of the crystallization solvent.

PRIOR ART DOCUMENTS

Patent Documents

Patent Document 1: U.S. Pat. No. 7,122,697
Patent Document 2: U.S. Pat. No. 2,677,698
Patent Document 3: U.S. Pat. No. 4,713,476
Patent Document 4: EP Application No. 0568782
Patent Document 5: EP Application No. 0657420
Patent Document 6: U.S. Pat. No. 4,497,963
Patent Document 7: U.S. Pat. No. 4,290,970
Patent Document 8: Japanese Patent Application Laid-open No. H6-41045
Patent Document 9: U.S. Pat. No. 2,409,701
Patent Document 10: U.S. Pat. No. 3,992,430
Patent Document 11: U.S. Pat. No. 4,297,501
Patent Document 12: U.S. Pat. No. 3,873,553
Patent Document 13: U.S. Pat. No. 4,925,971
Patent Document 14: Japanese Patent Application Laid-open No. H4-164060
Patent Document 15: Japanese Patent Application Laid-open No. H2-759
Patent Document 16: Japanese Patent Application Laid-open No. H3-20254
Patent Document 17: Japanese Patent Application Laid-open No. H8-277255
Patent Document 18: Japanese Patent Application Laid-open No. S52-71443
Patent Document 19: Japanese Patent Application Laid-open No. H7-157463
Patent Document 20: U.S. Pat. No. 2,692,275
Patent Document 21: U.S. Pat. No. 3,734,941
Patent Document 22: U.S. Pat. No. 4,081,472
Patent Document 23: U.S. Pat. No. 4,388,426
Patent Document 24: U.S. Pat. No. 4,482,499
Patent Document 25: EP Application No. 0355443
Patent Document 26: Japanese Patent No. 3382289
Patent Document 27: Japanese Patent No. 2804132

Non-Patent Documents

Non-Patent Document 1: Berchte der Deutechen Chemischen Gesellschaft, Vol. 3, p. 653, 1870
Non-Patent Document 2: Journal of American Chemical Society, Vol. 73, p. 1831, 1951, line 9 from the top of the right column
Non-Patent Document 3: Journal of American Chemical Society, Perkin Transactions 1: Organic and Bio-Organic Chemistry (1972-1999), pp. 141-143, 1976
Non-Patent Document 4: Berchte der Deutechen Chemischen Gesellschaft, Vol. 3, p. 649, 1870
Non-Patent Document 5: Journal of American Chemical Society, Vol. 81, p. 2138, 1959
Non-Patent Document 6: Polymer, Vol. 35, p. 3766, 1994

DISCLOSURE OF INVENTION

Problems to be Solved by the Invention

As has been described above, even with any of the methods examined thus far, it is still difficult to obtain N-substituted carbamic acid-O-(alkyl or aryl) esters at high yield using urea and non-N-substituted carbamic acid-O-esters as raw materials, and generally the reaction products thereof include compounds having urea bonds (—NHCONH—), compounds having urea terminals (—NHCONH$_2$), compounds having amino group terminals (—NH$_2$) or compounds having allophanate bonds and the like in nearly all cases. In methods using the least expensive and safest raw material in the form of urea, the problem of inhibiting increases in the amounts of urea and primary amine used caused by their side reactions have yet to be solved, and an alternative to the phosgene method has yet to be achieved due to clogging and other problems relating to the process as well as the high production cost of isocyanates.

In this manner, numerous problems involving the production of isocyanate precursors in the form of N-substituted carbamic acid-O-(alkyl or aryl) esters still remain, and there is an urgent need to solve these problems.

As has been previously described, various methods have been proposed as methods for producing N-substituted carbamic acid-O-(alkyl or aryl) ester using urea or carbonic acid derivatives. Corresponding isocyanates are known to be able to be obtained by thermal decomposition of N-substituted carbamic acid-O-(alkyl or aryl) esters.

However, in the case of using an N-substituted carbamic acid-O-aryl ester as a precursor, the formed isocyanate and the raw material in the form of the N-substituted carbamic acid-O-aryl ester react due to the high thermal decomposition temperature resulting in increased susceptibility to the occurrence of denaturation. In addition, in the thermal decomposition reaction, both alcohol and isocyanate are present in the gaseous phase. Since the reaction between alcohol and isocyanate is rapid, a reaction occurs in which the isocyanate returns to N-substituted carbamic acid-O-aryl ester by a reverse reaction in the gaseous phase, thereby resulting in increased susceptibility to the occurrence of clogging of lines such as the line for extracting isocyanate from the reactor.

On the other hand, in the case of using an N-substituted carbamic acid-O-aryl ester as a precursor, there are problems with the production of the N-substituted carbamic acid-O-aryl ester. This is due to the low nucleophilicity of aromatic hydroxy compounds and the difficulty in increasing reaction selectivity for the N-substituted carbamic acid-O-aryl esters from primary amines. The cause of the decrease in selectivity is the slow esterification rate and the reaction rates of other undesirable side reactions being faster than the esterification due to the low nucleophilicity of aromatic hydroxy compounds.

Also, the disclosed methods require the use of an excess of urea or carbonic acid derivative based on the amino groups of the primary amine in order to improve the yield based on the comparative expensive primary amine. However, a method for efficiently recovering and reusing the excess urea or carbonic acid derivative has yet to be described, and increases in basic units of urea or carbonic acid derivative are unable to be avoided.

The inventors of the present invention have previously disclosed a method for inhibiting thermal denaturation reactions of N-substituted carbamic acid-O-alkyl esters by using a specific aromatic hydroxy compound as a reaction solvent (International Patent Publication WO 2008/120645), and have also disclosed a method for improving thermal stability of aromatic hydroxy compounds by having a trace amount of a carbonic acid derivative present during thermal decomposition of N-substituted carbamic acid-O-alkyl ester, which is obtained by reacting carbonic acid ester and primary amine, in the presence of an aromatic hydroxy compound (International Patent Publication WO 2008/084824).

As a result of studies conducted by the inventors of the present invention, it was clearly determined that when a specified amount or more of urea or carbonic acid derivative is present in the reaction liquid of an N-substituted carbamic acid-O-aryl ester obtained by using urea or carbonic acid derivative, the adherence and/or accumulation of insoluble solids presumed to be reactants of the urea and/or carbonic acid derivative and isocyanate is observed during the course of obtaining isocyanate by thermal decomposition of the N-substituted carbamic acid-O-aryl ester, thereby resulting in the potential for causing problems including those relating to long-term operation of production equipment.

An object of the present invention is to provide a method for producing N-substituted carbamic acid-O-aryl ester that is free of the various problems described above, and to provide a method for producing isocyanate by thermal decomposition of the N-substituted carbamic acid-O-aryl ester.

In view of the above, as a result of conducting extensive studies on the above-mentioned problems, the inventors of the present invention found that the problems are solved by obtaining N-substituted carbamic acid-O-aryl ester derived from a compound having ureido groups and an aromatic hydroxy compound from the compound having ureido groups and a specific aromatic hydroxy composition, and producing isocyanate by subjecting the N-substituted carbamic acid-O-aryl ester to thermal decomposition, thereby leading to completion of the present invention.

Namely, in a first aspect thereof, the present invention provides:

[1] A method for producing at least one N-substituted carbamic acid-O-aryl ester (wherein the N-substituted carbamic acid-O-aryl ester refers to an N-substituted carbamic acid ester in which oxygen atoms of the carbamic acid group (—NHCOO—) are bonded to an aromatic ring) derived from a compound having an ureido group represented by the following formula (1) and an aromatic hydroxy composition containing at least one type of aromatic hydroxy compound represented by the following formula (2), the method comprising the step of carrying out esterification or esterification and transesterification from the compound having the ureido group and the aromatic hydroxy composition:

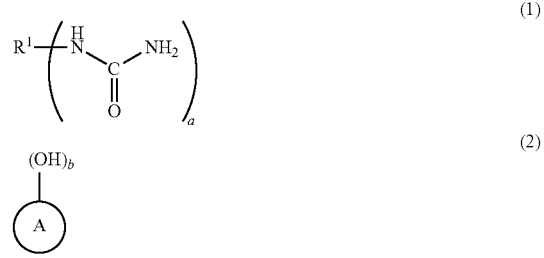

(wherein
$R^1$ represents an organic group containing an integral number of carbon atoms within a range of from 1 to 85, that is substituted by number a of ureido group(s), and the a represents an integer of from 1 to 10, and
ring A represents an organic group, which contains an aromatic group substituted by number b of hydroxy group(s) at arbitrary location(s) that maintain aromatic properties, and which contains an integral number of carbon atoms within a range of from 6 to 50, may be a single or multiple heterocyclic ring, and may be substituted by other substituents, and the b represents an integer of from 1 to 6).

[2] The production method according to item [1] above, wherein the compound having the ureido group is a compound having an ureido group obtained by a process comprising the following step A:

step (A): a step of obtaining at least one type of compound having an ureido group derived from an organic primary amine represented by the following formula (3) and urea by ureidating the organic primary amine and the urea in a liquid phase and eliminating or extracting to a gaseous phase ammonia formed as a by-product in the ureidation reaction:

(wherein
$R^1$ represents an organic group containing an integral number of carbon atoms within a range of from 1 to 85, that is substituted by number c of $NH_2$ group(s), and the c represents an integer of from 1 to 10).

[3] The production method according to item [2] above, wherein the organic primary amine is an organic primary monoamine or an organic primary diamine.

[4] The production method according to item [2] above, wherein the step (A) is carried out in the presence of water and/or alcohol and/or an aromatic hydroxyl composition containing at least one type of aromatic hydroxy compound.

[5] The production method according to item [2], wherein the step (A) is carried out in the presence of an aromatic hydroxy composition containing at least one type of aromatic hydroxy compound represented by the following formula (2):

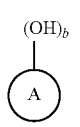

(2)

(wherein
ring A represents an organic group, which contains an aromatic group substituted by number b of hydroxy group(s) at an arbitrary location(s) that maintain aromatic properties, which contains an integral number of carbon atoms within a range of from 6 to 50, may be a single or multiple heterocyclic ring, and may be substituted by other substituents, and the b represents an integer of from 1 to 6).

[6] The production method according to item [2], wherein the step (A) is carried out in the presence of an alcohol represented by the following formula (4):

$R^2OH$ (4)

(wherein
$R^2$ represents an aliphatic group, or an aliphatic group in which an aromatic group is bonded, which contains an integral number of carbon atoms within a range of from 1 to 14, and the OH group of the alcohol represented by formula (4) is an OH group that is not bonded to an aromatic ring).

Further, in a second aspect thereof, the present invention provides:

[7] A composition for transfer and storage of a compound having an ureido group, wherein the number of molecules of at least one type of aromatic hydroxy compound represented by the following formula (2) in an aromatic hydroxy composition that contains the aromatic hydroxy compound, based on the number of the ureido group contained in the compound having the ureido group represented by the following formula (1) in the composition, is an integer of from 1 to 100:

(1)

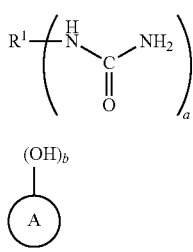

(2)

(wherein
$R^1$ represents an organic group containing an integral number of carbon atoms within a range of from 1 to 85, that is substituted by number a of ureido group(s), and the a represents an integer of from 1 to 10), and ring A represents an organic group, which contains an aromatic group substituted by number b of hydroxy group(s) at arbitrary location(s) that maintain aromatic properties, and which contains an integral number of carbon atoms within a range of from 6 to 50, may be a single or multiple heterocyclic ring, and may be substituted by other substituents, and the b represents an integer of from 1 to 6).

[8] The production method according to item [1] above, further comprising the following steps (A) and (B):

step (A): a step of obtaining at least one type of compound having an ureido group derived from an organic primary amine represented by the following formula (3) and urea by ureidating the organic primary amine and the urea in a liquid phase and eliminating or extracting to a gaseous phase ammonia formed as a by-product in the ureidation reaction, and step (B): a step of obtaining N-substituted carbamic acid-O-aryl ester by reacting the at least one type of compound having the ureido group and the aromatic hydroxy composition containing at least one type of aromatic hydroxy compound represented by the following formula (2) in a liquid phase, and extracting ammonia formed as a by-product to a gaseous phase:

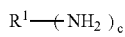

(3)

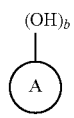

(2)

(wherein
$R^1$ represents an organic group containing an integral number of carbon atoms within a range of from 1 to 85, that is substituted by number c of $NH_2$ group(s), and the c represents an integer of 1 to 10, and ring A represents an organic group, which contains an aromatic group substituted by number b of hydroxy group(s) at arbitrary location(s) that maintain aromatic properties, and which contains an integral number of carbon atoms within a range of from 6 to 50, may be a single or multiple heterocyclic ring, and may be substituted by other substituents, and the b represents an integer of 1 to 6).

[9] The production method according to item [1] above, further comprising the following steps (A), (R) and (P):

step (A): a step of obtaining at least one type of compound having an ureido group derived from an organic primary amine represented by the following formula (3) and urea by ureidating the organic primary amine and the urea in a liquid phase and eliminating or extracting to a gaseous phase ammonia formed as a by-product in the ureidation reaction, step (R): a step of obtaining N-substituted carbamic acid-O—$R^2$ ester by reacting the at least one type of compound having the ureido group and an alcohol represented by the following formula (4) in a liquid phase and extracting ammonia formed as a by-product to a gaseous phase (wherein the N-substituted carbamic acid-O—$R^2$ ester represents an N-substituted carbamic acid ester in which oxygen atoms of the carbamic acid group (—NHCOO—) are bonded to an $R^2$ group derived from an alcohol), and step (P): a step of obtaining N-substituted carbamic acid-O-aryl ester by reacting the N-substituted carbamic acid-O—$R^2$ ester and the aromatic hydroxy composition containing at least one type of aromatic hydroxy compound represented by the following formula (2) in a liquid phase and extracting alcohol formed as a by-product to a gaseous phase:

$$R^1\!-\!(NH_2)_c \quad (3)$$

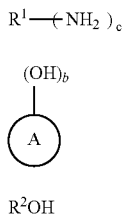
(2)

$$R^2OH \quad (4)$$

(wherein
R$^1$ represents an organic group containing an integral number of carbon atoms within a range of from 1 to 85, that is substituted by number c of NH$_2$ group(s), and the c represents an integer of from 1 to 10, ring A represents an organic group, which contains an aromatic group substituted by number b of hydroxy group(s) at arbitrary location(s) that maintain aromatic properties, and which contains an integral number of carbon atoms within a range of from 6 to 50, may be a single or multiple heterocyclic ring, and may be substituted by other substituents, and the b represents an integer of from 1 to 6, and R$^2$ represents an aliphatic group, or an aliphatic group in which an aromatic group is bonded, which contains an integral number of carbon atoms within a range of from 1 to 14, and the OH group of the alcohol represented by formula (4) is an OH group that is not bonded to an aromatic ring).

[10] The production method according to item [8] or [9] above, wherein the organic primary amine is an aromatic organic primary monoamine represented by the following formula (5), the following step (C) is carried out after the step (B), after the step (R) or after the step (P), and N-substituted carbamic acid-O—(R$^2$ or aryl) ester, in which at least two molecules of the N-substituted carbamic acid-O—(R$^2$ or aryl) ester are crosslinked with a methylene group (—CH$_2$—), is obtained from the N-substituted carbamic acid-O—(R$^2$ or aryl) ester obtained in the step (B), the step (R) or the step (P):

step (C): a step of obtaining N-substituted carbamic acid-O—(R$^2$ or aryl) ester, in which at least two molecules of the N-substituted carbamic acid-O—(R$^2$ or aryl) ester are crosslinked with a methylene group (—CH$_2$—), by reacting the N-substituted carbamic acid-O—(R$^2$ or aryl) ester with formaldehyde or a methylenating crosslinking agent and crosslinking aromatic groups derived from the aromatic organic primary monoamine contained in the N-substituted carbamic acid-O—(R$^2$ or aryl) ester with the methylene group (—CH$_2$—) (wherein the N-substituted carbamic acid-O—(R$^2$ or aryl) ester represents an N-substituted carbamic acid-O—R$^2$ ester or an N-substituted carbamic acid-O-aryl ester):

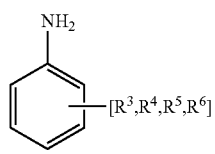
(5)

(wherein
at least one location at the ortho position and/or para position of the NH$_2$ group of an aromatic organic primary monoamine represented by formula (5) is not substituted, groups R$^3$ to R$^6$ respectively represent a group substituted at an arbitrary location that maintains aromatic properties of the ring, groups R$^3$ to R$^6$ may respectively and independently substitute an aromatic ring or groups R$^3$ to R$^6$ may together bond to form a ring with an aromatic ring, groups R$^3$ to R$^6$ are hydrogen atoms or groups selected from the group consisting of groups in which a group selected from the group consisting of an alkyl group, an cycloalkyl group, an aryl group and an aryl group having a hydroxy group is bonded by saturated aliphatic bonds and/or ether bonds, the number of carbon atoms of groups R$^3$ to R$^6$ is an integral number within a range of 0 to 7, and a total number of carbon atoms that compose the aromatic organic primary monoamine represented by formula (5) is an integer of from 6 to 13).

[11] The production method according to item [8] or [9] above, comprising the step of recovering urea by carrying out the following step (D) before the step (B) or the step (P) and/or simultaneous to the step (B) or the step (P):

step (D): a step of removing urea by distillation or sublimation.

[12] The production method according to item [8] or [9] above, comprising the following step (E) of recycling the recovered urea to the step (A):

step (E): a step of recycling urea recovered in step (D) to step (A).

[13] The production method according to item [1] above, comprising the step of obtaining an isocyanate represented by the following formula (6), which is derived from the N-substituted carbamic acid-O-aryl ester, and an aromatic hydroxy composition by carrying out thermal decomposition on the N-substituted carbamic acid-O-aryl ester in the following step (F):

step (F): a step of obtaining an isocyanate and an aromatic hydroxy composition from the N-substituted carbamic acid-O-aryl ester:

$$R^1\!-\!(NCO)_s \quad (6)$$

(wherein
R$^1$ represents an organic group containing an integral number of carbon atoms within a range of from 1 to 85, that is substituted by number s of NCO group(s), and the s represents an integer of from 1 to 10).

[14] The production method according to item [8] or [9] above, comprising the step of separating the aromatic hydroxy composition obtained in the step (F) from the isocyanate, and recycling the aromatic hydroxy composition to the step (A) and/or the step (B), or to the step (A) and/or the step (R) and/or the step (P).

[15] The production method according to any one of items [1], [8] and [9], wherein an aromatic hydroxy compound that composes the aromatic hydroxy composition is at least one type of aromatic hydroxy compound represented by the following formula (7):

(7)

(wherein
ring A represents an aromatic ring selected from a benzene ring, a naphthalene ring and an anthracene ring, the OH groups and groups $R^7$ to $R^{14}$ respectively represent groups substituted at arbitrary location(s) that maintain aromatic properties of ring A, groups $R^7$ to $R^{14}$ may respectively and independently substitute ring A, groups $R^7$ to $R^{14}$ may bond together to form a ring with an aromatic ring by bonding to ring A, groups $R^7$ to $R^{14}$ respectively and independently represent a hydrogen atom, a halogen atom or a group selected from the group consisting of an alkyl group, an cycloalkyl group, an aryl group, an aryl group having a hydroxy group, an aralkyl group and an ether group (substituted and/or unsubstituted alkyl ether and/or substituted and/or unsubstituted aryl ether and/or substituted and/or unsubstituted aralkyl ether group), and/or a group to which one or more types of groups selected from the group are bonded, and/or a group to which one or more types of groups selected from the group are bonded by saturated aliphatic bonds and/or ether bonds, and ring A and groups $R^7$ to $R^{14}$ are composed of an integral total number of carbon atoms within a range of from 6 to 50, b represents an integer of from 1 to 6, d, e, f, g, h, i, j and k represent integers of from 0 to 5, the value of d+e+f+g+h+i+j+k represents an integer equal to 6-b in the case ring A is the benzene ring, represents an integer equal to 8-b in the case ring A is the naphthalene ring, or represents an integer equal to 10-b in the case ring A is the anthracene ring, and a group selected from groups $R^7$ to $R^{14}$ as described above may be cyclically bonded to ring A by carbon-carbon bonds and/or ether bonds).

[16] The composition for transfer and storage of the compound having the ureido group according to item [7] above, wherein the aromatic hydroxy compound that composes the aromatic hydroxy composition is at least one type of aromatic hydroxy compound represented by the following formula (7):

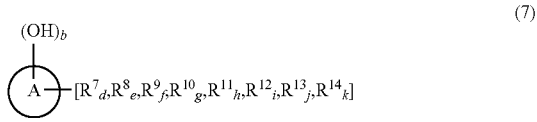

(7)

(wherein ring A represents an aromatic ring selected from a benzene ring, a naphthalene ring and an anthracene ring, the OH groups and groups $R^7$ to $R^{14}$ respectively represent groups substituted at arbitrary location(s) that maintain aromatic properties of ring A, groups $R^7$ to $R^{14}$ may respectively and independently substitute ring A, groups $R^7$ to $R^{14}$ may bond together to form a ring with an aromatic ring by bonding to ring A, groups $R^7$ to $R^{14}$ respectively and independently represent a hydrogen atom, halogen atom or group selected from the group consisting of an alkyl group, a cycloalkyl group, an aryl group, an aryl group having a hydroxy group, an aralkyl group and an ether group (substituted and/or unsubstituted alkyl ether and/or substituted and/or unsubstituted aryl ether and/or substituted and/or unsubstituted aralkyl ether group), and/or a group to which one or more types of groups selected from the group are bonded, and/or a group to which one or more types of groups selected from the group are bonded by saturated aliphatic bonds and/or ether bonds, and ring A and groups $R^7$ to $R^{14}$ are composed of an integral total number of carbon atoms within a range of from 6 to 50, b represents an integer of from 1 to 6, d, e, f, g, h, i, j and k represent integers of from 0 to 5, the value of d+e+f+g+h+i+j+k represents an integer equal to 6-b in the case ring A is the benzene ring, represents an integer equal to 8-b in the case ring A is the naphthalene ring, or represents an integer equal to 10-b in the case ring A is the anthracene ring, and a group selected from groups $R^7$ to $R^{14}$ as described above may be cyclically bonded to ring A by carbon-carbon bonds and/or ether bonds).

[17] The production method according to any one of items [2], [8] and [9], wherein the aromatic hydroxy compound that composes the aromatic hydroxy composition has a standard boiling point that differs by 10° C. or more from the standard boiling point of an isocyanate having a structure in which all amino groups of the organic primary amine (primary amino groups) are converted to isocyanate groups.

[18] The production method according to any one of items [1], [8] and [9], wherein the aromatic hydroxy compound contained in the aromatic hydroxy composition is a monovalent and/or divalent aromatic hydroxy compound (namely, that in which b is 1 and/or 2).

[19] The composition for transfer and storage of the compound having the ureido group according to item [7] above, wherein the aromatic hydroxy compound contained in the aromatic hydroxy composition is a monovalent and/or divalent aromatic hydroxy compound (namely, that in which b is 1 and/or 2).

[20] The production method according to item [18] above, comprising recycling unreacted N-substituted carbamic acid-O-aryl ester that has not been thermally decomposed in the step (F), to the step (A) and/or the step (B) and/or the step (R) and/or the step (P) and/or the step (F).

[21] The production method according to item [8] or [9] above, further comprising the following step (G) of recovering ammonia formed as a by-product in the step (A) and/or the step (B) and/or the step (R); regenerating urea by reacting the ammonia with carbon dioxide; and recycling the urea to the step (A):

step (G): a step of recovering ammonia formed as a by-product, regenerating urea by reacting the ammonia with carbon dioxide, and recycling the urea to step (A)

Advantageous Effects of the Invention

According to the production method of N-substituted carbamic acid-O-aryl ester of the present embodiment, by producing the N-substituted carbamic acid-O-aryl ester from a compound having an ureido group and an aromatic hydroxy composition, inhibiting side reactions and efficiently recovering and reusing urea and the like used in excess in the reaction, N-substituted carbamic acid-O-aryl ester can be produced without any losses in the amounts of urea and organic primary amine used. In addition, since various side reaction products can be inhibited and the various side reaction products can be dissolved by an aromatic hydroxy compound and removed outside the system, operation is possible over a long period of time. Moreover, the composition for transfer and storage of a compound having an ureido group can be preferably used as a raw material for production of the N-substituted carbamic acid-O-aryl ester.

MODE FOR CARRYING OUT THE INVENTION

Figure 1:
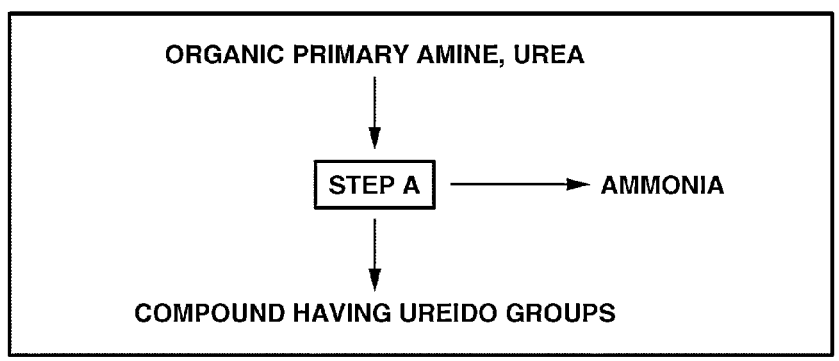
FIG. 1 shows a conceptual drawing depicting a production method of a compound having the ureido group(s) according to a step (A) in the present embodiment.

The following provides a detailed explanation of the best mode for carrying out the present invention (to be referred to as "present embodiment"). Furthermore, the present invention is not limited to the following present embodiment, but rather can be modified in various ways within the scope of the gist thereof.

An explanation is first given of a composition for transfer and storage of a compound having ureido groups in the present embodiment. To begin with, an explanation is given of the composite ratios and so forth of compounds contained in the composition for transfer and storage of a compound having ureido groups, and is followed by a detailed explanation of compounds contained in the composition for transfer and storage of a compound having ureido groups.

The composition for transfer and storage of a compound having ureido groups in the present embodiment refers to a composition for transferring and storing compounds having ureido groups, in which the number of molecules of an aromatic hydroxy compound in an aromatic hydroxy composition (composition containing at least one type of aromatic hydroxy compound represented by the following formula (2)) based on the number of ureido groups contained in a compound having ureido groups represented by the following formula (1) in the composition is an integer of from 1 to 100:

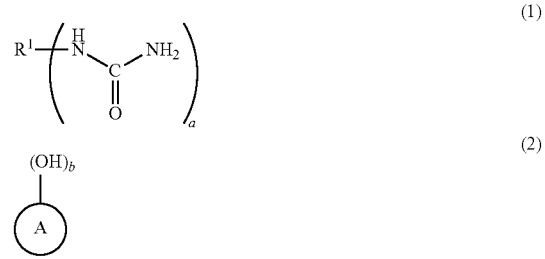

(wherein, $R^1$ represents an organic group which contains an integral number of carbon atoms within a range of from 1 to 85, and which is substituted by a number of ureido groups, and a represents an integer of from 1 to 10, and ring A represents an organic group, which contains an aromatic group substituted by number b of hydroxy groups at arbitrary locations that maintain aromatic properties, and which contains an integral number of carbon atoms within a range of from 6 to 50, may be a single or multiple heterocyclic ring, and may be substituted by other substituents, and b represents an integer of from 1 to 6).

Details of the compound having ureido groups represented by formula (1) and the aromatic hydroxy compound represented by formula (2) will be subsequently explained.

Since the compound having ureido groups used in the present embodiment easily forms hydrogen bonds between molecules thereof due to the ureido groups that compose the compound having ureido groups, there are many cases in which it has a high melting point. In the transfer of such a compound having ureido groups, transfer is carried out by, for example, crushing a solid compound having ureido groups or shaping such as by forming into pellets. Alternatively, methods are also employed in which the compound having ureido groups is heated to a temperature higher than the melting point thereof to transfer the compound having the ureido groups in the form of a liquid. However, in the case of transferring a solid compound having ureido groups that has undergone shaping processing, there are cases in which this causes clogging of the transfer line since there is considerable variation in the shape of the compound having ureido groups. Consequently, there are many cases in which complicated apparatuses are required to stably transfer a fixed amount of compound having the ureido groups or a step is required for aligning the shape of the compound having ureido groups to within a certain range. On the other hand, in the case of heating a compound having the ureido groups and transferring in the form of a liquid, it is necessary to heat the compound having the ureido groups to a temperature higher than the melting point thereof (for example, 150° C.) in consideration of preventing solidification during transfer. In the case of holding the compound having the ureido groups under such high temperatures, there are frequently cases in which isocyanate may be formed at undesirable locations due to the occurrence of a thermal decomposition reaction of the compound having the ureido groups or the occurrence of a thermal denaturation reaction of the compound having the ureido groups. The composition of the present embodiment demonstrates the effect of being able to maintain the stability of the compound having the ureido groups by inhibiting thermal denaturation of the compound having the ureido groups in the composition during transfer or storage of the composition. Although the mechanism by which the effect of inhibiting thermal denaturation of the compound having the ureido groups is demonstrated is not clear, the inventors of the present invention presumed that, as a result of the aromatic hydroxy compound that composes the composition forming a state in which urethane bonds have difficulty in approaching each other due to the formation of hydrogen bonds between ureido bonds (—NHCONH$_2$) of the compound having the ureido groups and the weakly acidic aromatic hydroxy compound, it is difficult for a reaction to occur that forms compounds having ureylene (—NHCONH—) groups.

Furthermore, ureylene groups (—NHCONH—) may be referred to as ureine groups in the explanation of the present embodiment.

The composition for transfer and storage can be preferably used in the production of N-substituted carbamic acid-O-aryl ester in particular (although the term N-substituted carbamic acid-O-aryl ester is used frequently in the following explanations, the term N-substituted carbamic acid-O-aryl ester refers to an N-substituted carbamic acid ester in which oxygen atoms of the carbamic acid group (—NHCOO—) are bonded to an aromatic ring, the aromatic ring referring to an aromatic ring in which a group is bonded to an aromatic group, said group being selected from the group consisting of aromatic groups and/or aliphatic groups, and the aromatic ring being formed by bonding said group of integer numbers of at least 0 with the aromatic group, the details of which will be subsequently described). More specifically, the method contains transferring the composition for transfer and storage to an N-substituted carbamic acid-O-aryl ester synthesis step, applying a compound having ureido groups contained in the composition to an esterification reaction, and recovering the N-substituted carbamic acid-O-aryl ester formed. In general, the N-substituted carbamic acid-O-aryl ester synthesis step is carried out at a high temperature, and if compounds having the ureido groups are supplied in a state of having hydrogen bonds between molecules thereof, denaturation to compounds having thermally stable ureylene groups is thermodynamically advantageous. A compound having ureylene groups is a condensed form of the compound having ureido groups and is a high molecular weight compound. Thus, there are many cases in which problems occur due to the formation of polymers that adhere or solidify in the reactor. In addition, there are many cases in which the compound having the ureido groups contains compounds such as ammonia or urea. These compounds, and particularly urea, frequently undergo thermal decomposition to isocyanic acid and ammonia at the synthesis temperature range of the N-substituted carbamic acid-O-aryl ester synthesis step, and when the isocyanic acid reacts with the compound having ureido groups, they are denatured to compounds having biuret bonds. The compounds having biuret bonds have a high thermal decomposition temperature, and present difficulties in forming N-substituted carbamic acid-O-aryl ester due to reacting with aromatic hydroxy compounds. However, the inventors of the present invention found that denaturation of compounds having ureido groups during transfer and storage of the composition for transfer and storage is inhibited even if the composition for transfer and storage contains specific amounts of this ammonia and urea. This effect is particularly remarkable during long-term storage, and there are many cases in which denaturation is unable to be confirmed even during accelerated evaluation and testing. This finding was heretofore unknown and is surprising. Although the mechanism by which this effect is demonstrated is unclear, the inventors of the present invention have surmised that, during transfer and storage of the composition, the aromatic hydroxy compound inhibits denaturation of compounds of ammonia and urea or the like and the compounds having the ureido groups by trapping water and oxygen present in trace amounts, and when producing N-substituted carbamic acid-O-aryl ester using this composition, the aromatic hydroxy compound also functions as an esterification catalyst of the N-substituted carbamic acid-O-aryl ester.

In the composition for transfer and storage, the ratio of the number of molecules (y) of the aromatic hydroxy compound that composes the aromatic hydroxy composition to the number of ureido groups (x) that compose (or are contained in) the compound having ureido groups is within a range of from 1 to 100. Although y is preferably in excess based on x in the case of assuming the mechanism described above, on the other hand, in consideration of the transfer efficiency of the compound having the ureido groups and the size of the storage tank during storage, the ratio of y to x is preferably within a range of greater than 2 but less than 50, and more preferably within a range of greater than 3 but less than 20.

In the composition for transfer and storage, the compound having the ureido groups contained in the composition is preferably a compound having ureido groups that is obtained by reacting an organic primary amine, urea and/or carbonic acid derivative (to be subsequently explained in detail) and/or isocyanic acid and/or non-N-substituted carbamic acid. In consideration of ease of industrial acquisition, the compound having the ureido groups is more preferably a compound having ureido groups that is obtained by reacting an organic primary amine and urea.

The composition for transfer and storage may also contain components other than the compound having the ureido groups and the aromatic hydroxy compound. Examples of such components may include the above-mentioned ammonia, urea, carbonic acid derivative (the carbonic acid derivative indicated in the present embodiment will be subsequently explained in detail), non-N-substituted carbamic acid, compound having a biuret bond, compound having a ureylene group, water, alcohol, inert gas (such as nitrogen gas, carbon dioxide gas, argon gas or ammonia gas) and N-substituted carbamic acid-O-ester such as N-substituted carbamic acid-O-(alkyl or aryl) ester obtained by reacting the composition for transfer and storage with an aromatic hydroxy composition (to be subsequently explained in detail). Although there are no particular limitations on the amounts at which these components are contained, if unnecessary side reactions appear to occur attributable to the storage temperature and the like, the amounts thereof are preferably adjusted as the occasion demands. Particularly noteworthy components are oxygen, ammonia, water, oxidizing substances and reducing substances. There are many cases in which the composition for transfer and storage contains compounds containing nitrogen atoms, or the aromatic hydroxy composition may be denatured as a result of being oxidized by oxygen resulting in the occurrence of phenomena such as coloring. In addition, since the composition becomes a flammable composition in nearly all cases, oxygen gas is to be managed using known methods in the same manner as ordinary storage of organic chemical substances carried out in this technical field. For example, the concentration of gaseous phase oxygen in a storage tank is controlled by purging with nitrogen so that the oxygen concentration is 10% or less, preferably 1% or less and more preferably 100 ppm or less. In the case of allowing an inert gas such as nitrogen to flow through the gaseous phase, the oxygen concentration of the insert gas is controlled to 10 ppm or less. The dissolved ammonia concentration in the composition is controlled to 1% by weight or less and preferably to 0.1% by weight or less. The control method may be a known method such as purging the liquid phase with an inert gas such as nitrogen gas. Since there are cases in which large amounts of water may cause phenomena that prevent the composition from being uniform, the water concentration in the composition is 10% by weight or less and preferably 1% by weight or less, although dependent upon the components of the composition, and in the case of using the composition as a raw material of an N-substituted carbamic acid-O-aryl ester, the water concentration is more preferably 100 ppm or less since a large amount of water present may cause side reactions attributable to the water. The concentration of water may be controlled by a known method such as the use of a dehydrating agent or desiccant, distilling under a reduced pressure, an increased pressure or a normal pressure, or purging a liquid phase with an inert gas to remove the water together with the inert gas. Since the presence of an oxidizing substance or reducing substance may cause denaturation of the aromatic hydroxy compound, these substances are controlled using a known method for controlling aromatic hydroxy compounds. Oxidizing substances refer to Bronsted acids such as organic acids or inorganic acids and Lewis acids, while reducing substances refer to Bronsted bases such as organic bases or inorganic bases, Lewis bases and hydrogen gas. Reducing substances do not include compounds derived from the composition, such as the above-mentioned ammonia, urea, carbonic acid derivative or compounds that compose the composition (for example, N-substituted carbamic acid-O-esters such as N-substituted carbamic acid-O-aryl ester, N-substituted carbamic acid-O-alkyl ester or N-substituted carbamic acid-O—$R^2$ ester (the N-substituted carbamic acid-O—$R^2$ ester will be subsequently described in detail)). Although there are no particular limitations on the content of N-substituted carbamic acid-O—($R^2$ or aryl) ester (the N-substituted carbamic acid-O—$R^2$ ester will be subsequently described in detail) obtained in a process for producing N-substituted carbamic acid-O-aryl ester from the composition for transfer and storage and an aromatic hydroxy composition (to be subsequently described in detail), since there are cases in which the compound having the ureido groups and the N-substituted carbamic acid-O—($R^2$ or aryl) ester reacts during storage resulting in the formation of a dealcoholized or de-aromatic hydroxylated compound that condenses by forming ureylene bonds, the amount thereof based on the compound having the ureido groups contained in the composition for transfer and storage is controlled to 10 molar equivalents or less and preferably 1 molar equivalent or less. Examples of other components that may be contained may include urea and alcohol. There are no particular limitations on the contents of either of these components. The composition for transfer and storage may be in the form of a slurry or solid. It is preferably in the form of a slurry and more preferably in the form of a liquid. Since urea tends to solidify easily, in consideration of fluidity, it is controlled to 20 molar equivalents or less and preferably 10 molar equivalents or less based on the compound having the ureido groups contained in the composition for transfer and storage. Although there are also no limitations on alcohol, it may be controlled corresponding to the need to distill off alcohol following transfer. For example, the amount of alcohol is controlled to 100 molar equivalents or less and preferably 10 molar equivalents or less based on the compound having the ureido groups contained in the composition for transfer and storage.

Although the term N-substituted carbamic acid-O—($R^2$ or aryl) ester is frequently used in the present specification, this refers to an N-substituted carbamic acid-O—$R^2$ ester or N-substituted carbamic acid-O-aryl ester.

Although there are no particular limitations on the conditions for storage and transfer of the composition, there are conditions at which a thermal decomposition reaction of the compound having the ureido groups occurs extremely easily at high temperatures. Although varying according to the storage period, storage is carried out within a range of from −40 to 280° C., and in cases in which fluidity and stability are impaired, preferably at 0 to 260° C. and more preferably at 40 to 260° C. The storage temperature may be controlled corresponding to the application of the composition, the storage period and the handling ease of the composition. Although transfer is also carried out at a temperature within the temperature range during storage, when using the composition as a raw material of N-substituted carbamic acid-O-aryl ester, and when transferring to the N-substituted carbamic acid-O-aryl ester synthesis step, transfer may be carried out after confirming that transfer can be carried out safely according to the conditions of the reaction step and the equipment used in the reaction step since transfer to the reactor of the synthesis step is typically carried out after preheating to the reaction temperature. Generally, transfer is carried out within a range of from −40 to 280° C., and in cases in which fluidity and stability are impaired, is preferably carried out at 0 to 260° C. and more preferably at 40 to 260° C. Transfer may be controlled depending on the application of the composition, transfer time and handling ease of the composition as previously described. Although there are no particular limitations on pressure during transfer, storage may be carried out under conditions of a reduced pressure to conditions of an increased pressure. When storing under a reduced pressure, since the aromatic hydroxy composition may be distilled off, the ratio of the compound having the ureido groups and the aromatic hydroxy composition in the composition is controlled to be within the previously described range. There are no particular limitations on storage vessels, lines and the like during storage and transfer. A vessel is selected in accordance with applicable handling regulations in consideration of the handling of a flammable organic substance while paying attention to the flash point of the composition being handled. There are also no particular limitations on the material, and a known material can be used. Examples of materials may include glass, stainless steel, carbon steel, Hastelloy, glass-lined base materials and Teflon (registered trademark) coated materials. Known equipment may be incidentally provided as necessary as equipment for storage and transfer of the composition, such as pumps, temperature control equipment or instrumentation.

The composition for transfer and storage of the compound having the ureido groups indicated above may be prepared by mixing the compound having the ureido groups, aromatic hydroxy composition, ammonia, N-substituted carbamic acid-O—($R^2$ or aryl) ester, urea, alcohol, carbonic acid derivative and other components as previously described so as to be formulated as previously described, or may be prepared by adding and/or removing an aromatic hydroxy composition, urea, alcohol, ammonia or carbonic acid derivative and the like so as to be formulated as previously described based on a composition containing a compound having ureido groups obtained in the production of the compound having the ureido groups. The method for producing the compound having the ureido groups can be preferably carried out in the manner subsequently described.

The following provides an explanation of a method for producing N-substituted carbamic acid-O-aryl ester of the present embodiment. The present embodiment refers to a method for producing at least one N-substituted carbamic acid-O-aryl ester (wherein an N-substituted carbamic acid-O-aryl ester refers to an N-substituted carbamic acid ester in which oxygen atoms of the carbamic acid group (—NH-COO—) are bonded to an aromatic ring) derived from a compound having ureido groups and an aromatic hydroxy composition from a compound having ureido groups represented by formula (1) and an aromatic hydroxy composition containing at least one type of aromatic hydroxy compound represented by formula (2), which comprises the step of carrying out an esterification reaction or an esterification reaction and transesterification reaction. (The above-mentioned formulas (1) and (2) will subsequently be explained in detail.)

Namely, the production method of the present embodiment is a method for producing an N-substituted carbamic acid-O-aryl ester derived from a compound having ureido groups and an aromatic hydroxy composition from the compound having ureido groups and the aromatic hydroxy composition (indicating a group of aromatic hydroxy compounds containing at least one type of aromatic hydroxy compound) (and although subsequently described in detail, a method for obtaining N-substituted carbamic acid-O-aryl ester and by-product ammonia by reacting the compound having ureido groups and the aromatic hydroxy composition, as well as a method for obtaining N-substituted carbamic acid-O—$R^2$ ester and by-product alcohol ($R^2OH$) by obtaining an N-substituted carbamic acid-O—$R^2$ ester and by-product ammonia by esterifying the compound having ureido groups and an alcohol (although subsequently explained, the alcohol refers to an alcohol represented by $R^2OH$ in the following formula (4)) followed by transesterifying the N-substituted carbamic acid-O—$R^2$ ester and the aromatic hydroxy composition, are also present embodiments). Namely, the production method of the present embodiment is a method for producing N-substituted carbamic acid-O-aryl ester in a step comprising an esterification reaction from a compound having ureido groups and an aromatic hydroxy composition. More specifically, the production method of the present embodiment is a method for producing N-substituted carbamic acid-O-aryl ester in a step comprising an esterification reaction or an esterification reaction and a transesterification reaction. An esterification reaction refers to a reaction in which ureido groups (—NHCONH$_2$) in a compound having ureido groups are converted to carbamic acid groups and ammonia is formed as a by-product thereof. More specifically, this esterification reaction contains a reaction in which the ureido groups (—NHCONH$_2$) are converted to carbamic acid-O-aryl ester groups (—NHCOOAr) obtained from ureido groups in a compound having ureido groups and an aromatic hydroxy compound, with ammonia being formed as a by-product accompanying the reaction, or a reaction in which the ureido groups (—NHCONH$_2$) are converted to carbamic acid-O—$R^2$ ester groups (—NHCOOR$^2$) obtained from ureido groups in a compound having ureido groups and an alcohol ($R^2OH$), with ammonia being formed as a by-product accompanying the reaction. The Ar indicated for the above-mentioned carbamic acid-O-aryl ester groups refers to a residue in which a single hydrogen atom of a hydroxyl group directly bonded to an aromatic hydrocarbon ring has been removed from an aromatic hydroxy compound. In providing a more detailed explanation of the esterification reaction, the esterification reaction refers to a reaction in which an N-substituted carbamic acid-O-aryl ester represented by formula (43) is obtained from a compound having ureido groups represented by formula (1) to be subsequently indicated and an aromatic hydroxy compound represented by formula (2), with ammonia being formed as a by-product accompanying the reaction, and a reaction in which an N-substituted carbamic acid-O—$R^2$ ester represented by formula (49) is obtained from a compound having ureido groups represented by formula (1) and an alcohol represented by formula (4), with ammonia being formed as a by-product accompanying the reaction. In addition, the above-mentioned transesterification reaction specifically refers to a reaction in which an N-substituted carbamic acid-O—$R^2$ ester represented by formula (49) and an aromatic hydroxy compound are reacted to convert the carbamic acid-O-ester groups (—NHCOOR$^2$) in the N-substituted carbamic acid-O—$R^2$ ester to carbamic acid-O-aryl ester groups (—NHCOOAr), with alcohol ($R^2OH$) being formed as a by-product of the reaction. Ar is the same as previously defined. (These will also be subsequently described in detail.)

Namely, the present embodiment includes the case of obtaining an N-substituted carbamic acid-O-aryl ester by directly carrying out an esterification reaction on a compound having ureido groups and an aromatic hydroxy composition (composition containing at least one type of aromatic hydroxy compound), and the case of obtaining an N-substituted carbamic acid-O-aryl ester by carrying out an esterification reaction on a compound having ureido groups and an alcohol, and then carrying out a transesterification reaction on an aromatic hydroxy composition (composition containing at least one type of aromatic hydroxy compound).

In addition, although the method for producing the compound having ureido groups may be a known method, and can be obtained by, for example, reacting an organic primary amine, urea and/or carbonic acid derivative (to be subsequently described in detail) and/or isocyanic acid and/or non-N-substituted carbamic acid, at least one type of compound having ureido groups derived from an organic primary amine and urea is preferably obtained by a production method that reacts the organic primary amine and urea in a ureidation reaction.

Next, an explanation is given of compounds used in the production method of the present embodiment, and compounds that compose the composition for transfer and storage of compounds having ureido groups.

<Organic Primary Amine>

An organic primary amine used in the present embodiment (wherein an organic primary amine refers to a "primary amine" (mono primary amines and poly primary amines) as defined in rule C-8 of the nomenclature (IUPAC Nomenclature of Organic Chemistry) stipulated by the International Union of Pure and Applied Chemistry (IUPAC) is an organic primary amine represented by the following formula (3). This rule is based on Recommendations on Organic & Biochemical Nomenclature. Hereinafter, in the case of referring to IUPAC rules in the present specification as well as subsequently indicated nomenclature rules defined by IUPAC (with the exception of cases specially citing IUPAC recommendations of other years), such referrals cite "Yukikagaku•Seikagaku Meimeihou" (Organic Chemistry and Biochemistry Nomenclature) (2nd revision published in Japan in 1992 by Nankodo Co., Ltd.), which is based on an edition containing all rules of organic chemistry and biochemistry, along with transliteration rules for Japanese, published as a supplement to "Chemical Fields" in 1980 based on the Recommendations 1979, as well as all subsequent revisions and recommendations. The term "organic" refers generically to a group of compounds considered to be subject to the nomenclature disclosed in the above publications. The subjects may be subjects described in recommendations published in 1993. The subjects may be subjects described in recommendations published in 1993 (in the case it is difficult to acquire the above-mentioned publications published in Japan, 1979 recommendations and 1993 recommendations may be referred to). However, "organic" compounds covered by the nomenclature described above include organometallic compounds and metal complexes. In the present invention, although the following provides explanations of "organic", and/or "organic groups", and/or "substituents" and the like, as well as compounds used in the present embodiment, when not specifically explained, these are composed of atoms that do not include metal atoms and/or semimetals. More preferably, "organic compounds", "organic groups" and "substituents" composed of atoms selected from H (hydrogen atoms), C (carbon atoms), N (nitrogen atoms), O (oxygen atoms), S (sulfur atoms), Cl (chlorine atoms), Br (bromine atoms) and I (iodine atoms) are used in the present embodiment.

In addition, for limitation "aliphatic" and "aromatic" are frequently used in the following explanations. According to the above-mentioned IUPAC rules, organic compounds are described as being classified into aliphatic and aromatic. Aliphatic compounds refer to the definitions of groups in accordance with aliphatic compounds based on the 1995 IUPAC recommendations. Aliphatic compounds are defined in these recommendations as "acyclic or cyclic saturated or unsaturated carbon compounds, excluding aromatic compounds". Aliphatic groups, which are frequently used in the present specification, refer to groups composed of the aliphatic compounds. These groups are such that an R moiety, in which a hydrogen atom has been removed from an aliphatic compound in the form of RH, for example, is defined as a monovalent aliphatic group. In addition, aliphatic and aliphatic groups used in the explanation of the present invention include saturated and unsaturated as well as linear and cyclic aliphatic compounds, and refer to "organic compounds", "organic groups" and "substituents" composed of atoms selected from the above-mentioned H (hydrogen atoms); C (carbon atoms); N (nitrogen atoms); O (oxygen atoms); S (sulfur atoms); Si (silicon atoms); and halogen atoms selected from Cl (chlorine atoms), Br (bromine atoms) and I (iodine atoms). In addition, in the case an aromatic group such as an aralkyl group is bonded to an aliphatic group, such groups are frequently denoted in the manner of "aliphatic group substituted with an aromatic group" or "group composed of an aliphatic group bonded to an aromatic group". This is based on the reactivity in the present embodiment, and because properties relating to reactions of groups in the manner of aralkyl groups closely resemble the reactivity of aliphatic groups and not aromatic groups. In addition, non-aromatic reactive groups including groups such as aralkyl groups and alkyl groups are frequently denoted as "aliphatic groups optionally substituted with an aromatic group", "aliphatic group substituted with an aromatic group" or "aliphatic group bonded to an aromatic group" and the like. Furthermore, although definitions in accordance with nomenclature rules defined by IUPAC as described above are used when explaining general formulas of compounds used in the present specification, terms such as "organic primary amine" or "N-substituted carbamic acid-O-aryl ester" are also used, common names are frequently used for the names of specific groups and names of exemplary compounds.

In addition, although numbers of molecules, numbers of substituents and individual numbers are frequently described in the present specification, these all represent zero or a positive integer (and there are also frequently cases in which zero is treated as a positive integer).

A primary amine refers to a compound having an amino group ($-NH_2$) in which an aliphatic compound and/or aromatic compound and/or aliphatic group and aromatic group are bonded. Namely, an organic primary amine as referred to in the present application indicates a "primary amine" that is classified as being "organic" as previously described.

An organic primary amine preferably used in the present embodiment is an organic primary amine represented by the following formula (3):

$$R^1\text{\textendash}(NH_2)_c \quad (3)$$

(wherein $R^1$ represents an organic group which contains carbon atoms within a range of from 1 to 85, and which is substituted by number c of $NH_2$ groups, and c represents an integer of from 1 to 10).

In formula (3) above, $R^1$ is an organic group classified as "organic" as previously described, and an organic primary amine in the present embodiment refers to an organic primary amine in which number c of $NH_2$ groups are bonded to an organic group containing carbon atoms within a range of from 1 to 85.

$R^1$ represents an aliphatic group, aromatic group or group bonded to an aliphatic group and an aromatic group, and represents a group composed of an acyclic hydrocarbon group or cyclic hydrocarbon group (such as a monocyclic hydrocarbon group, condensed polycyclic hydrocarbon group, crosslinked cyclic hydrocarbon group, spirohydrocarbon group, ring-assembling hydrocarbon group, cyclic hydrocarbon group having a side chain, heterocyclic group, heterocyclic spiro group, hetero-crosslinked ring group or compound ring group), a group bonded from one or more types of groups selected from the above-mentioned acyclic hydrocarbon groups and cyclic hydrocarbon groups, and groups in which the above-mentioned groups are bonded through a covalent bond with a specific non-metal atom (carbon, oxygen, nitrogen, sulfur or silicon). In addition, a covalent bond with a specific non-metal atom (carbon, oxygen, nitrogen, sulfur or silicon) as described above is in a state in which the above-mentioned groups are bonded by a covalent bond with, for example, groups represented by the following formulas (8) to (16).

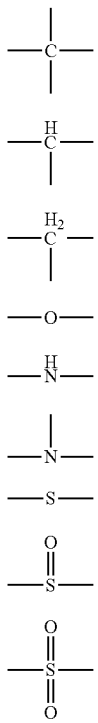

(8)
(9)
(10)
(11)
(12)
(13)
(14)
(15)
(16)

Among these $R^1$ groups, $R^1$ groups that can be preferably used in the present embodiment in consideration of less susceptibility to the occurrence of side reactions contains groups selected from the group consisting of acyclic hydrocarbon groups and cyclic hydrocarbon groups selected from aliphatic groups, aromatic groups and groups bonded to aliphatic groups and aromatic groups (such as a monocyclic hydrocarbon group, condensed polycyclic hydrocarbon group, crosslinked cyclic hydrocarbon group, spirohydrocarbon group, ring-assembling hydrocarbon group or cyclic hydrocarbon group having a side chain), and groups bonded to at least one type of group selected from this group (mutually substituted groups), having carbon atoms within the range of 1 to 85. In consideration of fluidity and the like, the number of carbon atoms of the groups is preferably within a range of from 1 to 70 and more preferably within a range of from 1 to 13.

Preferable examples of organic amines composed by the $R^1$ group may include:

1) optionally aliphatic- and/or aromatic-substituted aromatic organic mono primary amines in which the $R^1$ group has 6 to 85 carbon atoms and contains one or more types of an aromatic ring optionally substituted with an aliphatic group and/or aromatic group, an aromatic group in the $R^1$ group is substituted with an $NH_2$ group, and c is 1, 2) aromatic organic poly primary amines in which the $R^1$ group has 6 to 85 carbon atoms and contains one or more types of an aromatic ring optionally substituted with an aliphatic group and/or aromatic group, an aromatic group in the $R^1$ group is substituted with an $NH_2$ group, and c is 2 or more, and 3) aliphatic organic poly primary amines in which the $R^1$ group is an aliphatic group having 1 to 85 carbon atoms optionally substituted with an aromatic group, and c is 2 or 3. In the above descriptions, atoms bonded to an $NH_2$ group (and preferably carbon atoms) that are contained in an aromatic ring are denoted as aromatic organic amines, while cases of bonding to atoms not in an aromatic ring (mainly carbon) are denoted as aliphatic organic amines. More preferable aliphatic groups are linear hydrocarbon groups, cyclic hydrocarbon groups and at least one type of group selected from the linear hydrocarbon groups and cyclic hydrocarbon groups (referring to, for example, cyclic hydrocarbon groups substituted with a linear hydrocarbon group or linear hydrocarbon groups substituted with a cyclic hydrocarbon group) having 6 to 70 carbon atoms.

The following lists specific examples of preferable organic primary amines.

1) Aromatic Organic Mono Primary Amines

Optionally aliphatic- and/or aromatic-substituted aromatic organic mono primary amines in which the $R^1$ group is a group having 6 to 85 carbon atoms and contains one or more types of an aromatic ring optionally substituted with an aliphatic group and/or aromatic group, an aromatic group in the $R^1$ group is substituted with an $NH_2$ group and c is 1, preferably aromatic organic mono primary amines in which the $R^1$ group is a group having 6 to 70 carbon atoms and c is 1, and more preferably in consideration of fluidity and the like, aromatic organic mono primary amines in which the $R^1$ group has 6 to 13 carbon atoms and c is 1, which are aromatic organic mono primary amines represented by the following formula (5).

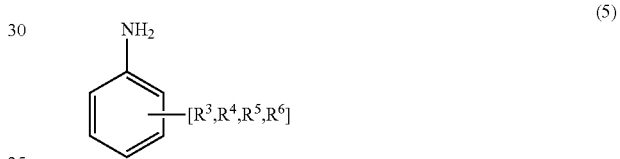

(5)

(wherein
at least one location at the ortho position and/or para position of the $NH_2$ group of an aromatic organic primary monoamine represented by formula (5) is not substituted, groups $R^3$ to $R^6$ respectively represent a group substituted at an arbitrary location that maintains aromatic properties of the ring, groups $R^3$ to $R^6$ may respectively and independently substitute an aromatic ring or groups $R^3$ to $R^6$ may together bond to form a ring with an aromatic ring, groups $R^3$ to $R^6$ are hydrogen atoms or groups composed of groups in which a group selected from the group consisting of an alkyl group, a cycloalkyl group, an aryl group and an aryl group having a hydroxy group is bonded by saturated aliphatic bonds and/or ether bonds, the number of carbon atoms of groups $R^3$ to $R^6$ is an integral number within a range of from 0 to 7, and the total number of carbon atoms that compose the aromatic organic primary monoamine represented by formula (5) is an integer of from 6 to 13).

Preferable examples of aromatic organic mono primary amines represented by formula (5) may include those in which the $R^3$ to $R^6$ groups are hydrogen atoms or groups selected from alkyl groups such as a methyl group or an ethyl group, and examples of such aromatic organic mono primary amines may include aniline, aminotoluene (including isomers), dimethylaniline (including isomers), diethylaniline (including isomers), dipropylaniline (including isomers), aminonaphthalene (including isomers), aminomethylnaphthalene (including isomers), dimethylnaphthylamine (including isomers) and trimethylnaphthylamine (including isomers), with aniline being used more preferably.

2) Aromatic Organic Poly Primary Amines

Aromatic organic poly primary amines in which the $R^1$ group is a group having 6 to 85 carbon atoms and containing one or more aromatic rings optionally substituted with an aliphatic group and/or aromatic group, an aromatic group in the $R^1$ group is substituted with an $NH_2$ group and c is 2 or more, preferably aromatic organic poly primary amines in which the $R^1$ group is a group having 6 to 70 carbon atoms and c is 2 or more, and more preferably in consideration of fluidity and the like, aromatic organic poly primary amines in which the $R^1$ group contains one or more aromatic rings, the aromatic ring are groups of 6 to 13 carbon atoms that may be further substituted with an alkyl group, an aryl group or an aralkyl group, an $NH_2$ group is bonded to the aromatic group contained in the $R^1$ group, and c is 2 or more. Examples of such aromatic organic polyamines may include diaminobenzene (including isomers), diaminotoluene (including isomers), methylenedianiline (including isomers), diaminomesitylene (including isomers), diaminobiphenyl (including isomers), diaminodibenzyl (including isomers), bis(aminophenyl)methane (including isomers), bis(aminophenyl)propane (including isomers), bis(aminophenyl)ether (including isomers), bis(aminophenoxyethane) (including isomers), α α'-diaminoxylene (including isomers), diaminoanisole (including isomers), diaminophenetol (including isomers), diaminonaphthalene (including isomers), diamino-methylbenzene (including isomers), diamino-methylpyridine (including isomers), diamino-methylnaphthalene (including isomers) and polymethylene polyphenyl polyamines represented by the following formula (17).

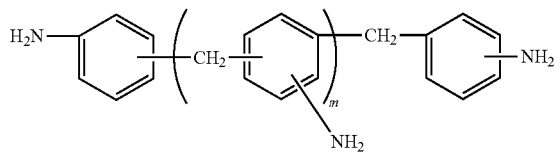

(17)

(wherein, m is an integer of from 0 to 6).

3) Aliphatic Organic Poly Primary Amines

Aliphatic organic poly primary amines in which the $R^1$ group of an organic amine represented by formula (3) is an aliphatic group in which the number of carbon atoms is an integer within a range of from 1 to 85 and which may be substituted with an aromatic group, and c is 2 or 3.

More preferable organic amines are aliphatic organic primary amines in which the aliphatic group is a linear hydrocarbon group, cyclic hydrocarbon group or group to which is bonded at least one type of group selected from the linear hydrocarbon groups and the cyclic hydrocarbon groups (such as cyclic hydrocarbon group substituted with a linear hydrocarbon group or linear hydrocarbon group substituted with a cyclic hydrocarbon group). More preferably, the organic amine is an aliphatic organic poly primary amine in which the $R^1$ group is an aliphatic group that is an acyclic hydrocarbon group, a cyclic hydrocarbon group or a group to which is bonded at least one type of group selected from the acyclic hydrocarbon groups and the cyclic hydrocarbon groups (such as a cyclic hydrocarbon group substituted with an acyclic hydrocarbon group or acyclic hydrocarbon group substituted with a cyclic hydrocarbon group) having 1 to 70 carbon atoms, and c is 2 or 3. In consideration of fluidity and the like during large-volume industrial production, the organic amine is more preferably an aliphatic organic poly primary amine in which the $R^1$ group is an acyclic hydrocarbon group, a cyclic hydrocarbon group or a group to which is bonded at least one type of group selected from the acyclic hydrocarbon groups and the cyclic hydrocarbon groups (such as a cyclic hydrocarbon group substituted with an acyclic hydrocarbon group or an acyclic hydrocarbon group substituted with a cyclic hydrocarbon group) having 6 to 13 carbon atoms and composed of carbon atoms and hydrogen atoms. Namely, this refers to the case in which the $R^1$ group is a linear and/or branched alkyl group, a cycloalkyl group or a group composed of the alkyl groups and cycloalkyl groups. Examples of these organic amines may include aliphatic di-primary amines such as ethylenediamine, diaminopropane (including isomers), diaminobutane (including isomers), diaminopentane (including isomers), diaminohexane (including isomers) or diaminodecane (including isomers); aliphatic triamines such as triaminohexane (including isomers), triaminononane (including isomers) or triaminodecane (including isomers); and, substituted cyclic aliphatic polyamines such as diaminocyclobutane (including isomers), diaminocyclohexane (including isomers), 3-aminomethyl-3,5,5-trimethylcyclohexylamine (cis and/or trans forms) or methylenebis (cyclohexylamine) (including isomers). Examples thereof may include alkyl di-primary amines such as ethylenediamine, diaminopropane (including isomers), diaminobutane (including isomers), diaminopentane (including isomers), diaminohexane (including isomers), diaminoheptane (including isomers), diaminooctane (including isomers), diaminononane (including isomers) or diaminodecane (including isomers); alkyl tri-primary amines such as triaminohexane (including isomers), triaminoheptane (including isomers), triaminooctane (including isomers), triaminononane (including isomers) or triaminodecane (including isomers); cycloalkyl primary amines such as diaminocyclobutane (including isomers), diaminocyclopentane (including isomers) or diaminocyclohexane (including isomers); and, cyclohexyl poly-primary amines substituted with an alkyl group such as 3-aminomethyl-3,5,5-trimethylcyclohexylamine (cis and/or trans form) or methylenebis(cyclohexylamine) (including isomers).

The organic primary amines explained in 1), 2) and 3) above are used preferably, and in particular the organic primary amine is more preferably an organic primary monoamine, organic primary diamine or organic primary triamine (in which c in formula (3) above is an integer of 1, 2 or 3).

<Compound Having Ureido Groups>

A compound having ureido groups used when producing an N-substituted carbamic acid-O-aryl ester from the composition for transfer and storage of the compound having ureido groups of the present embodiment and/or an aromatic hydroxy composition is a compound represented by the following formula (1):

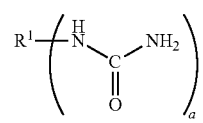

(1)

(wherein $R^1$ represents an organic group which contains an integral number of carbon atoms within a range of from 1 to 85, and which is substituted by a number of ureido groups, and a represents an integer of from 1 to 10).

The compound having the ureido groups represented by formula (1) above is a compound having "ureido groups" as defined in nomenclature rule C-971 stipulated by IUPAC. In formula (1) above, $R^1$ is an organic group classified as "organic" as described above, and the compound having the ureido groups according to the present embodiment is a compound having ureido groups bonded to a number of ureido groups (—NH—CONH$_2$) including carbon atoms within a range of from 1 to 85. $R^1$ represents an aliphatic group, an aromatic group or a group bonded to an aliphatic group and an aromatic group, and represents a group composed of an acyclic hydrocarbon group or a cyclic hydrocarbon group (such as a monocyclic hydrocarbon group, a condensed polycyclic hydrocarbon group, a crosslinked cyclic hydrocarbon group, a spirohydrocarbon group, a ring-assembling hydrocarbon group, a cyclic hydrocarbon group having a side chain, a heterocyclic group, a heterocyclic spiro group, a heterocrosslinked ring group or a heterocyclic group), a group bonded from one or more types of groups selected from the above-mentioned acyclic hydrocarbon groups and cyclic hydrocarbon groups, and groups in which the above-mentioned groups are bonded through a covalent bond with a specific non-metal atom (carbon, oxygen, nitrogen, sulfur or silicon). In addition, a covalent bond with a specific non-metal atom (carbon, oxygen, nitrogen, sulfur or silicon) as described above is in a state in which the above-mentioned groups are bonded by a covalent bond with, for example, groups represented by the following formulas (8) to (16).

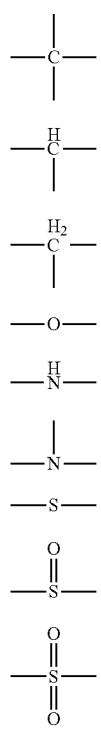

Among these $R^1$ groups, $R^1$ groups that can be preferably used in the present embodiment in consideration of less susceptibility to the occurrence of side reactions contains groups selected from the group consisting of acyclic hydrocarbon groups and cyclic hydrocarbon groups selected from aliphatic groups and aromatic groups (such as a monocyclic hydrocarbon group, a condensed polycyclic hydrocarbon group, a crosslinked cyclic hydrocarbon group, a spirohydrocarbon group, a ring-assembling hydrocarbon group or a cyclic hydrocarbon group having a side chain), and groups bonded to at least one type of group selected from this group (mutually substituted groups), containing 1 to 85 carbon atoms. In consideration of fluidity and the like of the composition for transfer and storage, the number of carbon atoms is preferably 1 to 70 and more preferably 1 to 13.

Preferable examples of compounds having a ureido group composed by the $R^1$ group may include: 1) N-substituted aromatic organic monoureas in which the $R^1$ group has 6 to 85 carbon atoms and contains one or more types of an aromatic ring optionally substituted with an aliphatic group and/or an aromatic group, an aromatic group in the $R^1$ group is substituted with a ureido group, and c is 1, 2) N-substituted aromatic organic polyureas in which the $R^1$ group has 6 to 85 carbon atoms and contains one or more types of an aromatic ring optionally substituted with an aliphatic group and/or an aromatic group, an aromatic group in the $R^1$ group is substituted with a ureido group, and c is 2 or more, and 3) N-substituted aliphatic organic polyureas in which the $R^1$ group is an aliphatic group having 1 to 85 carbon atoms optionally substituted with an aromatic group, and c is 2 or 3. In the above descriptions, compounds in which atoms bonded to a ureido group (mainly carbon atoms) that are contained in an aromatic ring are denoted as N-substituted aromatic organic ureas, while cases of bonding to atoms not in an aromatic ring (mainly carbon atoms) are denoted as N-substituted aliphatic organic ureas. More preferably, an aliphatic group is a linear hydrocarbon group, a cyclic hydrocarbon group and at least one type of group bonded to a group selected from the linear hydrocarbon groups and cyclic hydrocarbon groups (referring to, for example, cyclic hydrocarbon groups substituted with a linear hydrocarbon group or linear hydrocarbon groups substituted with a cyclic hydrocarbon group) having 6 to 70 carbon atoms.

Although the method for producing the compound having the ureido groups may be a known method, and can be obtained by, for example, reacting an organic primary amine, urea and/or carbonic acid derivative (to be subsequently described in detail) and/or isocyanic acid and/or non-N-substituted carbamic acid, at least one type of compound having the ureido groups derived from an organic primary amine and urea is preferably obtained by a production method that reacts the organic primary amine and urea in a ureidation reaction, and in the present embodiment, a compound having ureido groups preferably uses a compound having ureido groups obtained in a process that includes the following step A:

step (A): a step of obtaining at least one type of compound having ureido groups derived from an organic primary amine represented by the following formula (3) and urea by ureidating the organic primary amine and the urea in a liquid phase and eliminating or extracting to a gaseous phase ammonia formed as a by-product in the ureidation reaction:

(wherein $R^1$ represents an organic group which contains an integral number of carbon atoms within a range of 1 to 85, and which is substituted by number c of NH$_2$ groups, and c represents an integer of from 1 to 10).

A compound having ureido groups obtained in step (A) above is a compound having ureido groups that has an organic group derived from the above-mentioned organic primary amine. Namely, this step contains reacting organic primary amino groups (—NH$_2$) of the organic primary amine with urea to form the ureido groups (this reaction is frequently referred to as an ureidation reaction in the present embodiment). (—CONH$_2$) groups within the ureido groups (—NHCONH$_2$) are formed from the urea reacted in the reaction. In addition, a indicated in formula (1) is an integer equal to or less than c indicated in formula (3), and preferably is an integer such that a=c.

Although the term "derived" is frequently used in the present specification, the term "derived" is used in the sense of inheriting a group possessed by a raw material when a functional group of the raw material compound changes in a reaction. For example, in the reaction described above in which the compound having the ureido groups is obtained from an organic primary amine, the compound having the ureido groups has a structure that has inherited the organic primary amino groups (—NH$_2$) of the organic primary amine, while the (—CONH$_2$) groups within the ureido groups refer to (—CONH$_2$) groups contained in the reacted urea (NH$_2$CONH$_2$). Thus, in the above-mentioned formulas (1) and (3), a is an integer equal to or less than c, and a and c are preferably the same integers.

The following indicates specific examples of preferable compounds having ureido groups. A ureido group is the same of a substituent, and in the present specification, is described as the name of a compound in the form of an "N-substituted (substituent name) urea". In order to clearly indicate that the nitrogen atom (N) of the urea is substituted (namely, that the nitrogen atom is not an —NH$_2$ group), "N-substituted" is clearly indicated, the substituent is clearly indicated as being an aromatic group or aliphatic group, and the term "organic" is also intentionally clearly indicated in the sense that the compound is an organic compound. A compound is clearly indicated as being "monourea" in the case of a single ureido group within a molecule thereof, or is clearly indicated as being a "polyurea" in the case of multiple ureido groups within a molecule thereof. Since the compound is an N-substituted urea, even in cases of multiple ureido groups, the ureido groups contained in a compound having ureido groups explained below are indicated by attaching the prefix "poly", "di" or "tri" and the like immediately before the term "urea" as indicated above to facilitate distinction thereof.

Throughout the entire present specification, the descriptions of "substituted" "mono" are not used, but rather descriptions in accordance with IUPAC nomenclature or common names are described when indicating examples of specific compounds.

1) N-Substituted Aromatic Organic Monourea

N-substituted aromatic organic monourea refers to that in which the R$^1$ group has 6 to 85 carbon atoms and contains one or more types of an aromatic ring optionally substituted with an aliphatic group and/or aromatic group, an aromatic group in the R$^1$ group is substituted with a ureido group, and c is 1, preferably refers to an aromatic organic monourea in which the R$^1$ group is a group having 6 to 70 carbon atoms and c is 1, and in consideration of fluidity and the like, more preferably refers to an N-substituted aromatic organic monourea in which the R$^1$ group is a group having 6 to 13 carbon atoms and c is 1, and is an N-substituted aromatic organic monourea represented by the following formula (41):

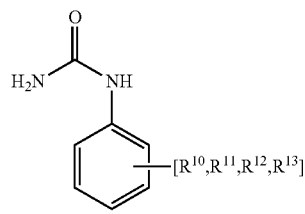

(41)

(wherein
at least one location at the ortho position and/or para position of a ureido group of the N-substituted aromatic organic monourea represented by formula (41) is not substituted, groups R$^{10}$ to R$^{13}$ respectively represent a group substituted at an arbitrary location that maintains aromatic properties of the ring, groups R$^{10}$ to R$^{13}$ may respectively and independently substitute an aromatic ring or groups R$^{10}$ to R$^{13}$ may together bond to form a ring with an aromatic ring, groups R$^{10}$ to R$^{13}$ are hydrogen atoms or groups selected from groups composed of groups in which a group selected from the group consisting of an alkyl group, a cycloalkyl group, an aryl group and an aryl group having a hydroxy group is bonded by saturated aliphatic bonds and/or ether bonds, the number of carbon atoms is an integral number within a range of from 0 to 7, and the total number of carbon atoms that compose the N-substituted aromatic organic monourea represented by formula (41), excluding ureido groups (—NH—CO—NH$_2$), is an integer of 6 to 13).

Preferable examples of such N-substituted aromatic organic monoureas represented by formula (41) may include those in which groups R$^{10}$ to R$^{13}$ are hydrogen atoms or groups selected from alkyl groups such as a methyl group or an ethyl group, and examples of such N-substituted aromatic organic monoureas may include N-phenylurea, N-tolylurea (including isomers), N-dimethylphenylurea (including isomers), N-diethylphenylurea (including isomers), N-dipropylphenylurea (including isomers), N-naphthalen-ylurea (including isomers), N-methylnaphthalen-ylurea (including isomers), N-dimethylnaphthalen-ylurea (including isomers) and N-trimethylnaphthalen-ylurea (including isomers). In particular, N-phenylurea is used more preferably.

2) N-Substituted Aromatic Organic Polyurea

N-substituted aromatic organic polyurea refers to that in which the R$^1$ group is a group having 6 to 85 carbon atoms that contains one or more aromatic rings optionally substituted with an aliphatic group and/or an aromatic group, an aromatic group in the R$^1$ group is substituted with a ureido group and c is 2 or more, preferably an N-substituted aromatic organic polyurea in which the R$^1$ group is a group having 6 to 70 carbon atoms and c is 2 or more, and more preferably in consideration of fluidity and the like, an N-substituted aromatic organic polyurea in which the R$^1$ group contains one or more types of aromatic rings, the aromatic ring has 6 to 13 carbon atoms and may be further substituted with an alkyl group, an aryl group or an aralkyl group, a ureido group is bonded to the aromatic group contained in the R$^1$ group, and c is 2 or more. Examples of such N-substituted aromatic organic polyureas may include N,N'-phenylene diurea (including isomers), N,N'-methylphenylene diurea (including isomers), N,N'-mesitylene diphenylene diurea (including isomers), N,N'-mesitylene diurea (including isomers), N,N'-biphenylene diurea (including isomers), N,N'-dibenzyldiurea (including isomers), N,N'-propan-diylphenylene diurea (including isomers), N,N'-oxydiphenylene diurea (including isomers), N,N'-diphenyl-diyl-dipropan-diyldiurea (including isomers), N,N'-phenylene dimethylene diurea (including isomers), N,N'-methoxyphenylene diurea (including isomers), N,N'-ethoxyphenylene diurea (including isomers), N,N'-naphthalen-diylurea (including isomers), N,N'-pyridine-diyldi methylene diurea (including isomers), N,N'-naphthalen-diyldimethylene diurea (including isomers), and polymethylene polyphenylene polyamines represented by the following formula (42).

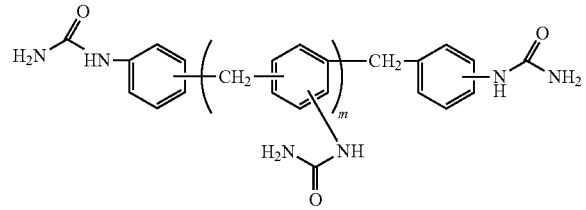

(42)

(wherein
m is an integer of from 0 to 6).

3) N-Substituted Aliphatic Organic Polyurea

N-substituted aliphatic organic polyurea is that in which the $R^1$ group is an aliphatic group having 1 to 85 carbon atoms that is optionally substituted with an aromatic group, and c is 2 or 3. Preferable N-substituted aliphatic organic polyureas are N-substituted aliphatic organic polyureas in which the aliphatic group is a linear hydrocarbon group, a cyclic hydrocarbon group (including aromatic groups) or a group to which is bonded at least one type of group selected from the linear hydrocarbon groups and the cyclic hydrocarbon groups (such as cyclic hydrocarbon group substituted with a linear hydrocarbon group or linear hydrocarbon group substituted with a cyclic hydrocarbon group). More preferably, the N-substituted aliphatic organic polyurea is an N-substituted aliphatic organic polyurea in which the $R^1$ group is an aliphatic group that is an acyclic hydrocarbon group, a cyclic hydrocarbon group or a group to which is bonded at least one type of group selected from the acyclic hydrocarbon groups and the cyclic hydrocarbon groups (such as a cyclic hydrocarbon group substituted with an acyclic hydrocarbon group or acyclic hydrocarbon group substituted with a cyclic hydrocarbon group) having 1 to 70 carbon atoms, and c is 2 or 3. In consideration of fluidity and the like during large-volume industrial production, the N-substituted aliphatic organic polyurea is more preferably an N-substituted aliphatic organic polyurea in which the $R^1$ group is an acyclic hydrocarbon group, a cyclic hydrocarbon group or a group to which is bonded at least one type of group selected from the acyclic hydrocarbon groups and the cyclic hydrocarbon groups (such as a cyclic hydrocarbon group substituted with an acyclic hydrocarbon group or an acyclic hydrocarbon group substituted with a cyclic hydrocarbon group) having 6 to 13 carbon atoms that is composed of carbon atoms and hydrogen atoms. Namely, this refers to the case in which the $R^1$ group is a linear or branched alkyl group, a cycloalkyl group or a group composed of the alkyl groups and cycloalkyl groups. Examples thereof may include N-substituted aliphatic organic polyureas such as methylenediurea, 1,2-dimethylenediurea, 1,3-trimethylenediurea, 1,4-tetramethylenediurea, 1,5-pentamethylenediurea, 1,6-hexamethylenediurea, 1,8-octamethylenediurea, cyclopentane-diurea (including isomers), cyclohexane-diurea (including isomers), cycloheptane-diurea (including isomers), cyclooctane-diurea (including isomers), methylcyclopentane-diurea (including isomers), ethylcyclopentane-diurea (including isomers), methylcyclohexane-diurea (including isomers), ethylcyclohexane-diurea (including isomers), propylcyclohexane-diurea (including isomers), butylcyclohexane-diurea (including isomers), pentylcyclohexane-diurea (including isomers), hexylcyclohexane-diurea (including isomers), dimethylcyclohexane-diurea (including isomers), diethylcyclohexane-diurea (including isomers), dibutylcyclohexane-diurea (including isomers), 1,5,5-trimethylcyclohexane-diurea (including isomers), 1,5,5-triethylcyclohexane diurea (including isomers), 1,5,5-tributylcyclohexane-diurea (including isomers) or 3-ureidomethyl-3,5,5-trimethylcyclohexylurea.

The following provides an explanation of alcohol used in the present embodiment.

<Alcohol>

Although the details of step (A) will be described later, step (A) may be carried out in the presence of water and/or alcohol and/or an aromatic hydroxy composition (composition containing at least one type of aromatic hydroxy compound) in addition to the organic primary amine and urea.

In the case of carrying out step (A) in the presence of an aromatic hydroxy composition, the step (A) is preferably carried out in the presence of the above-mentioned aromatic hydroxy composition (composition containing at least one type of aromatic hydroxy compound represented by the following formula (2)).

In addition, one aspect of the present embodiment is a process for producing N-substituted carbamic acid-O-aryl ester which comprises the step (A), the following step (R) and the following step (P) by carrying out the step (R) (esterification reaction step) to obtain N-substituted carbamic acid-O—$R^2$ ester (the details of which will be subsequently described) and then carrying out the step (P) (transesterification reaction step) to obtain N-substituted carbamic acid-O-aryl ester after having carried out the step (A). An alcohol represented by the following formula (4) is also used for the alcohol used at that time. The aromatic hydroxy composition used in the following step (P) (composition containing at least one type of aromatic hydroxy compound represented by formula (2)) will be subsequently described in detail:

step (R): a step of obtaining N-substituted carbamic acid-O—$R^2$ ester by reacting the at least one type of compound having ureido groups and an alcohol represented by the following formula (4) in a liquid phase and extracting ammonia formed as a by-product to a gaseous phase (where the N-substituted carbamic acid-O—$R^2$ ester represents an N-substituted carbamic acid ester in which oxygen atoms of the carbamic acid group (—NHCOO—) are bonded to an $R^2$ group derived from an alcohol), and step (P): a step of obtaining N-substituted carbamic acid-O-aryl ester by reacting the N-substituted carbamic acid-O—$R^2$ ester and the aromatic hydroxy composition (containing at least one type of aromatic hydroxy compound represented by the following formula (2)) in a liquid phase and extracting alcohol formed as a by-product to a gaseous phase:

An alcohol represented by the following formula (4) is preferably used for the alcohol used in the present embodiment.

$$R^2OH \qquad (4)$$

(wherein
$R^2$ represents a group composed of an aliphatic group or an aliphatic group in which an aromatic group is bonded, which contains an integral number of carbon atoms within a range of from 1 to 14, and the OH group of the alcohol represented by formula (4) is an OH group that is not bonded to an aromatic ring).

A preferable alcohol represented by formula (4) is an alcohol in which the $R^2$ group is a group composed of an aliphatic group or an aliphatic group in which an aromatic group is bonded, and in which the OH group of an alcohol represented by formula (4) is an OH group that is not bonded to an aromatic group. The $R^2$ group represents a group composed of an acyclic hydrocarbon group or a cyclic hydrocarbon group (such as a monocyclic hydrocarbon group, a condensed polycyclic hydrocarbon group, a crosslinked cyclic hydrocarbon group, a spirohydrocarbon group, a ring-assembling hydrocarbon group, a cyclic hydrocarbon group having a side chain, a heterocyclic group, heterocyclic spiro group, a hetero-crosslinked ring group or a heterocyclic group), a group bonded from one or more types of groups selected from the above-mentioned acyclic hydrocarbon groups and cyclic hydrocarbon groups, and a group in which the above-mentioned groups are bonded through a covalent bond with a specific non-metal atom (carbon, oxygen, nitrogen, sulfur or silicon). In addition, a covalent bond with a specific non-metal atom (carbon, oxygen, nitrogen, sulfur or silicon) as described above is in a state in which the above-mentioned groups are bonded by a covalent bond with, for example, groups represented by the following formulas (8) to (16).

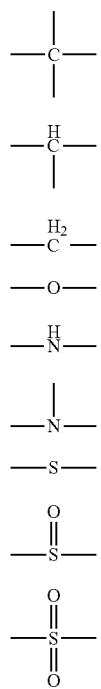

Among these $R^2$ groups, $R^2$ groups that can be preferably used in the present embodiment in consideration of less susceptibility to the occurrence of side reactions contain groups selected from the group consisting of acyclic hydrocarbon groups and cyclic hydrocarbon groups selected from aliphatic groups and/or aliphatic groups in which aromatic groups are bonded (such as a monocyclic hydrocarbon group, a condensed polycyclic hydrocarbon group, a crosslinked cyclic hydrocarbon group, a spirohydrocarbon group, a ring-assembling hydrocarbon group or a cyclic hydrocarbon group having a side chain), groups bonded to at least one type of group selected from this group (mutually substituted groups), and groups in which the above-mentioned groups are substituted with an aromatic group, and which contain a number of carbon atoms within a range of from 1 to 14. In the step (P) of the present embodiment, an N-substituted carbamic acid-O—$R^2$ ester is preferably transesterified with an aromatic hydroxy composition and the by-product alcohol is removed outside the system. Thus, the alcohol used in the step (A) and/or the step (R) preferably has a boiling point that is lower than the aromatic hydroxy compound contained in the aromatic hydroxy composition, and more preferably the $R^2$ group is a group containing a number of carbon atoms within a range of from 1 to 10. The $R^2$ group more preferably contains a number of carbon atoms within a range of from 1 to 8. Even more preferably, $R^2$ is an alkyl group, group in which a cycloalkyl group and an alkyl group are bonded, or an aralkyl group. Preferable examples of such alcohols may include methanol, ethanol, propanol (including isomers), butanol (including isomers), pentanol (including isomers), hexanol (including isomers), heptanol (including isomers), octanol (including isomers), benzyl alcohol, tolyl methanol (including isomers), xylyl methanol (including isomers) and phenylethyl alcohol (including isomers). Even more preferable examples of alcohols may include the alcohols listed above in which $R^2$ is an alkyl group, and among the carbon atoms that compose the alkyl group, the carbon atom at the α position of the hydroxy group (carbon atom that composes the alkyl group to which an OH group is bonded) is a secondary carbon atom (—$CH_2$—).

Next, an explanation is given of the aromatic hydroxy composition (composition containing at least one type of aromatic hydroxy compound represented by formula (2)) used in the present embodiment.

<Aromatic Hydroxy Composition>

There are various methods and steps that use an aromatic hydroxy composition in the present embodiment. An aromatic hydroxy composition is used as a compound that composes the composition for transfer and storage of the compound having the ureido groups as previously described. In addition, the step (A) is preferably carried out in the presence of an aromatic hydroxy composition (composition containing at least one type of aromatic hydroxy compound represented by formula (2)). Further, an aromatic hydroxy composition (composition containing at least one type of aromatic hydroxy compound represented by formula (2)) is used also in the step (P) described in the above explanation of the alcohol. In addition, an example of another aspect of the present embodiment is a method for obtaining N-substituted carbamic acid-O-aryl ester by a process that includes the step (A) (ureidation reaction step) and the following step (B) (esterification reaction step), and an aromatic hydroxy composition (composition containing at least one type of aromatic hydroxy compound represented by formula (2)) is also used in the step (B):

step (B): a step of obtaining N-substituted carbamic acid-O-aryl ester by reacting the at least one type of compound having ureido groups with an aromatic hydroxy composition (composition containing at least one type of aromatic hydroxy compound represented by formula (2)) in a liquid phase and extracting the ammonia formed as a by-product to a gaseous phase.

Although there are cases an aromatic hydroxy composition (composition containing at least one type of aromatic hydroxy compound represented by formula (2)) is used in addition to the steps listed above, the aromatic hydroxy composition used in the present embodiment is an aromatic hydroxy composition that contains at least one type of aromatic hydroxy compound represented by formula (2) as previously described.

An aromatic hydroxy composition in the present embodiment refers to a composition that contains one type of aromatic hydroxy compound or a plurality of types of aromatic hydroxy compounds. The following provides an explanation of aromatic hydroxy compounds preferably used as aromatic hydroxy compounds that compose the aromatic hydroxy composition.

Aromatic hydroxy compounds that compose (or are contained in) the aromatic hydroxy composition are at least one type of aromatic hydroxy compound represented by the following formula (2):

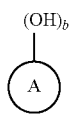

(2)

(wherein ring A represents an organic group which contains 6 to 50 carbon atoms and which contains an aromatic group substituted with number b of hydroxy groups at an arbitrary location that maintains aromatic properties, may be a single ring or multiple rings, may be a heterocyclic ring or may be substituted by other substituents, and b is an integer of from 1 to 6).

Examples of substituents that substitute an aromatic group of an aromatic hydroxy compound represented by formula (2) above may include groups selected from a hydrogen atom, a halogen atom, aliphatic groups and aromatic groups and groups in which the above-mentioned groups are bonded that are composed of acyclic hydrocarbon groups or cyclic hydrocarbon groups (such as a monocyclic hydrocarbon group, a condensed polycyclic hydrocarbon group, a crosslinked cyclic hydrocarbon group, a spirohydrocarbon group, a ring-assembling hydrocarbon group, a cyclic hydrocarbon group having a side chain, a heterocyclic group, a heterocyclic spiro group, a hetero-crosslinked ring group or a heterocyclic group), groups bonded to one or more types of groups selected from the acyclic hydrocarbon groups and the cyclic hydrocarbon groups, and groups in which the above-mentioned groups are bonded through a covalent bond with a specific non-metal atom (carbon, oxygen, nitrogen, sulfur or silicon atom). In addition, covalent bonding with a specific non-metal atom as described above (carbon, oxygen, nitrogen, sulfur or silicon atom) refers to a state in which, for example, a group represented by the following formulas (8) to (11) and formulas (13) to (16) and the above-mentioned groups are bonded with a covalent bond.

Ring A has a structure that contains at least one structure selected from the group consisting of a benzene ring, a naphthalene ring and an anthracene ring, ring A preferably has a structure that contains at least one structure selected from the group consisting of a benzene ring, a naphthalene ring and an anthracene ring, and more preferably ring A has a structure that contains a single benzene ring.

The hydroxy groups bonded to the aromatic group of ring A are hydroxy groups that are bonded to a carbon atom of the aromatic group of ring A, and the number of the hydroxy groups is preferably an integer of from 1 to 6, more preferably an integer of from 1 to 3, even more preferably an integer of from 1 to 2, and still more preferably 1 (namely, b=1).

(8)

(9)

(10)

(11)

(13)

(14)

(15)

(16)

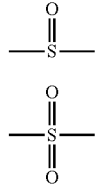

Among such substituents, substituents that can be preferably used in the present embodiment in consideration of less susceptibility to the occurrence of side reactions contain groups selected from the group consisting of acyclic hydrocarbon groups and cyclic hydrocarbon groups (such as a monocyclic hydrocarbon group, a condensed polycyclic hydrocarbon group, a crosslinked cyclic hydrocarbon group, a spirohydrocarbon group, a ring-assembling hydrocarbon group or a cyclic hydrocarbon group having a side chain), and groups bonded to at least one type of group selected from this group (mutually substituted groups).

In addition, in the case of transferring a composition for transfer and storage of a compound having ureido groups at a high temperature or in the case of reacting a compound having ureido groups and/or an N-substituted carbamic acid-O—$R^2$ ester and an aromatic hydroxy composition to obtain an N-substituted carbamic acid-O-aryl ester at a high temperature, ring A of the aromatic hydroxy compound is preferably an aromatic hydroxy compound composed of a group having at least one inactive substituent (including hydrogen atoms) in addition to the aromatic group and hydroxy groups bonded to the aromatic group (here, an inactive substituent refers to, for example, a substituent that does not have an active hydrogen in which the pKa of a compound in which the inactive substituent is bonded to a phenyl group is 30 or less, although it may have an aromatic hydroxyl group).

In providing a more detailed explanation of the substituent, the aromatic hydroxy compound represented by formula (2) is an aromatic hydroxy compound having at least one substituent selected from the groups of substituents indicated below in addition to the aromatic group and hydroxy group bonded to the aromatic group:

(i) a hydrogen atom, (ii) a group composed of carbon atoms and hydrogen atoms (which may also form a ring structure by bonding with ring A), (iii) a group composed of carbon atoms, hydrogen atoms and oxygen atoms (representing, for example, an ether group composed of aliphatic groups, ether group composed of aromatic groups or ether group composed of aliphatic groups and aromatic groups, but excluding groups containing active hydrogen such as a carbonyl group, an ester group, a terminal methine group and an alcoholic OH group, a carboxyl group, a $NH_2$ group, a NH group, a NOH group, a SH group, a $SO_3H$ group or a SOH group), (iv) a halogen atom, and (v) a group composed of atoms selected from carbon atoms, hydrogen atoms, oxygen atoms, nitrogen atoms, sulfur atoms and halogen atoms (but excluding groups containing active hydrogen such as a carbonyl group, an ester group, a terminal methine group and an alcoholic OH group, a carboxyl group, a $NH_2$ group, a NH group, a NOH group, a SH group, a $SO_3H$ group or a SOH group).

Active hydrogen refers to a hydrogen atom bonded to oxygen, sulfur or nitrogen (but excluding aromatic hydroxyl groups). Although aromatic hydroxyl groups (OH groups directly bonded to an aromatic group) are included in the above-mentioned definition of active hydrogen, since the aromatic hydroxyl groups are also contained in the composition of the present embodiment and reaction raw materials and do not have a detrimental effect in particular, aromatic hydroxyl groups are not included in groups containing active hydrogen unless specifically indicated otherwise. Although the "groups containing active hydrogen" are frequently described in other locations of the invention of the present application, the above-mentioned definition applies to such groups.

In addition, ring A is a structure that contains at least one structure selected from the group consisting of a benzene ring, a naphthalene ring and an anthracene ring, and preferably is an aromatic hydroxy compound represented by the following formula (7):

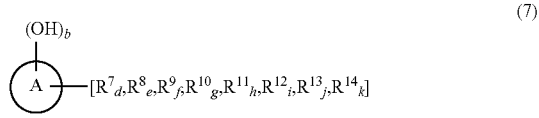

(7)

(wherein ring A represents an aromatic ring selected from a benzene ring, a naphthalene ring and an anthracene ring, the OH groups and groups $R^7$ to $R^{14}$ respectively represent groups substituted at arbitrary locations that maintain aromatic properties of ring A, groups $R^7$ to $R^{14}$ may respectively and independently substitute ring A, groups $R^7$ to $R^{14}$ may bond together to form a ring with ring A, groups $R^7$ to $R^{14}$ respectively and independently represent a hydrogen atom, a halogen atom or a group selected from the group consisting of an alkyl group, a cycloalkyl group, an aryl group, an aryl group having a hydroxy group, an aralkyl group and an ether group (substituted and/or unsubstituted alkyl ether and/or aryl ether and/or aralkyl ether group), and/or a group to which one or more types of groups selected from the group are bonded, and/or a group to which one or more types of groups selected from the group are bonded by saturated aliphatic bonds and/or ether bonds, and ring A and groups $R^7$ to $R^{14}$ are composed of an integral total number of carbon atoms within a range of from 6 to 50, b represents an integer of from 1 to 6, d, e, f, g, h, i, j and k represent integers of from 0 to 5, the value of d+e+f+g+h+i+j+k represents an integer equal to 6-b in the case ring A is a benzene ring, represents an integer equal to 8-b in the case ring A is a naphthalene ring, or represents an integer equal to 10-b in the case ring A is an anthracene ring, and a group selected from groups $R^7$ to $R^{14}$ as described above may be cyclically bonded to ring A by carbon-carbon bonds and/or ether bonds).

In consideration of industrial use, the aromatic hydroxy compound represented by the above-mentioned formula (7) is preferably an aromatic hydroxy compound in which one or two aromatic hydroxyl groups are bonded to ring A (namely, b=1 or 2), and more preferably an aromatic monohydroxy compound in which one aromatic hydroxyl group is bonded to ring A, since they typically have low viscosity.

In addition, since the aromatic hydroxy compound is a compound that has ureido groups by carrying out the step (B) and undergoing esterification, it forms an N-substituted carbamic acid-O-aryl ester derived from the ureido groups and the aromatic hydroxy compound (namely, an N-substituted carbamic acid-O-aryl ester in which the O-aryl group that forms the carbamic acid-O-aryl ester is formed by the aromatic hydroxy compound, while the N-substituted carbamic acid group moiety is formed from the compound having ureido groups), while in the case of carrying out the step (P), an N-substituted carbamic acid-O—$R^2$ ester derived from the N-substituted carbamic acid-O—$R^2$ ester and the aromatic hydroxy compound is formed from the N-substituted carbamic acid-O—$R^2$ ester by carrying out a transesterification reaction (namely, the N-substituted carbamic acid-O-aryl ester is an N-substituted carbamic acid-O—$R^2$ ester in which the O-alkyl ester group of the N-substituted carbamic acid-O—$R^2$ ester has undergone transesterification with the aromatic hydroxy compound). The N-substituted carbamic acid-O-aryl ester is used as an isocyanate precursor. Although the production method of isocyanate derived from the N-substituted carbamic acid-O-aryl ester will be subsequently described in detail, an N-substituted carbamic acid-O-aryl ester obtained by the process of the present embodiment is preferably thermally decomposed in the following step (F) to obtain an isocyanate represented by the following formula (6), which is derived from the N-substituted carbamic acid-O-aryl ester, and an aromatic hydroxy composition:

step (F): a step of obtaining an isocyanate and an aromatic hydroxy composition from the N-substituted carbamic acid-O-aryl ester:

(6)

(wherein $R^1$ represents an organic group which contains an integral number of carbon atoms within a range of from 1 to 85, and which is substituted by number s of NCO groups, and s represents an integer of from 1 to 10).

The production method contains thermally decomposing the N-substituted carbamic acid-O-aryl ester to obtain an aromatic hydroxy compound and isocyanate derived from the N-substituted carbamic acid-O-aryl ester. Herein, isocyanate derived from the N-substituted carbamic acid-O-aryl ester refers to an isocyanate compound in which the carbamic acid O-aryl group (—NHCOOAr, where Ar represents an aryl group derived from the aromatic hydroxy compound) of the N-substituted carbamic acid-O-aryl ester is converted to an isocyanate group (—NCO). In consideration of the reaction formula, the aromatic hydroxy compound formed at that time is an aromatic hydroxy compound contained in the aromatic hydroxy composition reacted with the compound having ureido groups when obtaining the N-substituted carbamic acid-O-aryl ester. Namely, an aromatic hydroxy compound represented by the formula (2), and preferably by the formula (7), is formed as a by-product together with isocyanate during thermal decomposition of the N-substituted carbamic acid-O-aryl ester. In one aspect of the present embodiment, although depending on the particular case, the aromatic hydroxy compound and isocyanate are separated by distillation following the thermal decomposition step, and the separated aromatic hydroxy compound may be recycled in the form of an aromatic hydroxy composition that is reacted with the compound having ureido groups. Namely, this aspect of the present embodiment is a preferable aspect in which the aromatic hydroxy composition obtained in the step (F) is separated from isocyanate, and then used by recycling to the step (A) and/or the step (B), or to the step (A) and/or the step (R) and/or the step (P).

Thus, in consideration of the process through the isocyanate production step in which the step (F) is carried out, it is necessary to take into consideration the separability of the aromatic hydroxy compound serving as a raw material of the N-substituted carbamic acid-O-aryl ester and the isocyanate formed from the N-substituted carbamic acid-O-aryl ester. Although it is difficult to generally define separability, it is defined on the basis of the finding that normally two components to be separated can be adequately separated by distillation industrially if the standard boiling points thereof are 10° C. or more apart. Thus, this definition refers to a value that is limited by currently known separation means, and is not intended to serve as a basis of the present embodiment.

The following Table (1) indicates the standard boiling points of aromatic hydroxy compounds or boiling points at a reduced pressure in the case measurement thereof is difficult at the normal pressure. Although the reactivity of the aromatic hydroxy compound that composes the aromatic hydroxy composition used in the present embodiment with a compound containing a ureido group and/or an N-substituted carbamic acid-O—$R^2$ ester (details regarding this N-substituted carbamic acid-O—$R^2$ ester will be described hereinafter) and/or urea is important, the standard boiling point is also an important selection index with respect to separation of each component. As shown in the following Table (1), the types and numbers of substituents, the locations of substituents and the like have a considerable influence on the boiling point of the aromatic hydroxy compound. Boiling point is a physical property that is also dependent on intermolecular forces, and is commonly known among persons with ordinary skill in the art to be unable to be defined by the structure of a single molecule. Thus, selection of an aromatic hydroxy compound according to an important aspect of the present invention in the form of standard boiling point is carried out by measuring or investigating the structure and properties (standard boiling point) of the desired N-substituted carbamic acid-O—Ar ester (the details of which will be described hereinafter) and/or isocyanate. Measurement of standard boiling point can be carried out with known methods, and can be routinely carried out by a researcher with ordinary skill in the relevant technical field. As has been described above, it is difficult to define separation of aromatic hydroxy compounds used in the present invention with a structure such as a general formula, and the intended method of the present embodiment is not to predict the standard boiling point of an aromatic hydroxy compound. Thus, a person with ordinary skill in the art is able to carry out the present embodiment by referring to or measuring standard boiling point corresponding to the compound used as previously described.

TABLE 1

| Aromatic Hydroxy Compounds | Boiling Point ° C. (values in parentheses indicate pressure during measurement, and the absence of values in parentheses means that measurement was carried out at normal pressure) |
|---|---|
| Phenol | 182 |
| 2-methylphenol | 191 |
| 3-methylphenol | 203 |
| 4-methylphenol | 202 |
| 2,4-dimethylphenol | 211 |
| 2,6-dimethylphenol | 203 |
| 2,5-dimethylphenol | 212 |
| 3,4-dimethylphenol | 227 |
| 3,5-dimethyphenol | 222 |
| 2,4,6-trimethylphenol | 220 |
| 4-propylphenol | 232 |
| 2-propylphenol | 225 |
| 2-(propan-2-yl) phenol | 212 |
| 4-(propan-2-yl) phenol | 212 |
| 3-(propan-2-yl) phenol | 228 |
| 2,6-dimethylphenol | 219 |
| 4-butylphenol | 138-139 (2.40 kPa) |
| 4-pentylphenol | 250 |
| 2-(2-methylbutan-2-yl) phenol | 92 (0.53 kPa) |
| 2,4-bis(propan-2-yl) phenol | 249 |
| 2,6-bis(propan-2-yl) phenol | 256 |
| 2-(phenylmethyl) phenol | 312 |
| 3,5-dimethoxyphenol | 172 (2.27 kPa) |
| 2,6-dimethoxyphenol | 167 (1.33 kPa) |
| 2-ethoxyphenol | 216 |
| 4-heptylphenol | 156 (1.20 kPa) |
| 4-octylphenol | 150 (0.53 kPa) (lit.) |
| 4-butoxyphenol | 278 |
| 4-(2,4,4-trimethylpentan-2-yl) phenol | 175 (4.00 kPa) |
| 2,4-bis(2-methylbutan-2-yl) phenol | 170 (0.267 kPa) |
| Naphthalen-2-ol | 285 |
| Naphthalen-1-ol | 278 |
| Pyrocatechol | 245 |
| Resorcinol | 178 (2.13 kPa) |
| Hydroquinone | 285 |
| Pyrogallol | 309 |
| 2-bromophenol | 195 |
| 3-bromophenol | 236 |
| 4-bromophenol | 235-236 |
| 2-chlorophenol | 175-176 |
| 3-chlorophenol | 214 |
| 4-chlorophenol | 220 |
| 4-chloro-2-methylphenol | 220-225 |
| 2-chloro-4-methylphenol | 195-196 |

In providing an explanation using one of the present embodiments as an example, an organic primary amine represented by the above-mentioned formula (3) and the above-mentioned urea subjected to a ureidation reaction in step (A) to obtain a compound having ureido groups indicated in formula (1), the compound having ureido groups and an aromatic hydroxy composition (composition containing at least one type of aromatic hydroxy compound represented by formula (2) (and preferably by formula (7)) are subjected to an esterification reaction by carrying out the step (B) to obtain a compound having an N-substituted carbamic acid-O-aryl ester group, and the step (F) is carried out using the N-substituted carbamic acid-O-aryl ester to produce an aromatic hydroxy compound and isocyanate derived from the N-substituted carbamic acid-O-aryl ester. Alternatively, an aromatic hydroxy compound and isocyanate derived from the N-substituted carbamic acid-O-aryl ester are produced by a method that comprises the steps (A), (R), (P) and (F). Alternatively, in the case the organic primary amine is an aromatic organic primary monoamine represented by the following formula (5), the following step (C) is carried out after the step (B) or the step (P) (the details of step (C) will be subsequently described), and an N-substituted carbamic acid-O-aryl ester, in which at least two molecules of the N-substituted carbamic acid-O-aryl ester are crosslinked with methylene groups (—CH$_2$—), is obtained from the N-substituted carbamic acid-O-aryl ester obtained in the step (B) or the step (P), followed by carrying out the step (F) to produce an aromatic hydroxy compound and isocyanate derived from the N-substituted carbamic acid-O-aryl ester:

step (C): a step of obtaining N-substituted carbamic acid-O—(R$^2$ or aryl) ester, in which at least two molecules of the N-substituted carbamic acid-O—(R$^2$ or aryl) ester are crosslinked with methylene groups (—CH$_2$—), by reacting the N-substituted carbamic acid-O—(R$^2$ or aryl) ester with formaldehyde or a methylene crosslinking agent, and crosslinking aromatic groups derived from the aromatic organic primary monoamine contained in the N-substituted carbamic acid-O—(R$^2$ or aryl) ester with methylene groups (—CH$_2$—):

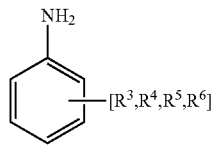

(5)

(wherein at least one location at the ortho position and/or para position of the NH$_2$ group of an aromatic organic primary monoamine represented by formula (5) is not substituted, groups R$^3$ to R$^6$ respectively represent a group substituted at an arbitrary location that maintains aromatic properties of the ring, groups R$^3$ to R$^6$ may respectively and independently substitute an aromatic ring or groups R$^3$ to R$^6$ may together bond to form a ring with an aromatic ring, groups R$^3$ to R$^6$ are hydrogen atoms or groups selected from groups composed of groups in which a group selected from the group consisting of an alkyl group, a cycloalkyl group, an aryl group and an aryl group having a hydroxy group is bonded by saturated aliphatic bonds and/or ether bonds, the number of carbon atoms of groups R$^3$ to R$^6$ is an integral number within a range of from 0 to 7, and the total number of carbon atoms that compose the aromatic organic primary monoamine represented by formula (5) is an integer of from 6 to 13).

Furthermore, although the term "N-substituted carbamic acid-O—(R$^2$ or aryl) ester" is frequently used in the present specification, this refers to "N-substituted carbamic acid-O—R$^2$ ester or N-substituted carbamic acid-O-aryl ester".

Thus, the structures of the aromatic hydroxy compound and isocyanate to be separated following the thermal decomposition reaction are such that the aromatic hydroxy compound is an aromatic hydroxy compound that composes (or is contained in) an aromatic hydroxy composition used when converting a compound having ureido groups to an N-substituted carbamic acid-O-aryl ester, while the other product in the form of the isocyanate is derived from a compound having ureido groups represented by formula (1) or an organic primary amine represented by formula (3) (namely, an isocyanate is obtained having a structure in which a ureido group (—NHCONH$_2$) of the compound having ureido groups is converted to an isocyanate group (—NCO), or a primary amino group (—NH$_2$) of the organic primary amine is converted to an isocyanate group (—NCO)).

Namely, if the standard boiling points of an aromatic hydroxy compound represented by formula (2), or preferably by formula (7), and an isocyanate represented by formula (6) differ by 10° C. or more, the aromatic hydroxy compound and the isocyanate can be separated by currently known techniques. As was previously described, since isocyanate represented by formula (6) obtained by the method of the present embodiment is produced by using as starting materials a compound having ureido groups or an organic primary amine, the standard boiling point of the isocyanate to be produced may be the standard boiling point of an isocyanate in which all ureido groups or all primary amino groups of the compound having ureido groups or the organic primary amine are converted to isocyanate groups. In a preferable aspect, the compound having ureido groups is a compound having ureido groups that is obtained by carrying out the step (A). Namely, an aromatic hydroxy compound is preferable in which the standard boiling point of the aromatic hydroxy compound that composes the aromatic hydroxy composition differs by 10° C. or more from the standard boiling point of an isocyanate having a structure in which all of the amino groups (primary amino groups) of the organic primary amine are converted to isocyanate groups.

Moreover, in consideration of industrial use, an aromatic monohydroxy compound having an easily acquirable benzene ring for the skeleton thereof is preferable. Preferable examples of such an aromatic monohydroxy compound may include aromatic monohydroxy compounds represented by the following formula (31):

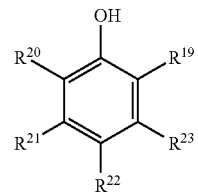

(31)

(wherein

R$^{19}$, R$^{20}$, R$^{21}$, R$^{22}$ and R$^{23}$ are groups independently selected from the above-mentioned groups R$^7$ to R$^{14}$ (excluding aryl groups having a hydroxy group), and the aromatic hydroxy compound represented by formula (31) is an aromatic monohydroxy compound in which the number of carbon atoms is an integer of from 6 to 50, namely the total number of carbon atoms of groups R$^{19}$, R$^{20}$, R$^{21}$, R$^{22}$ and R$^{23}$ is an integer of from 0 to 44).

Among the aromatic monohydroxy compounds represented by the above-mentioned formula (31), groups R$^{19}$, R$^{20}$, R$^{21}$, R$^{22}$ and R$^{23}$ are preferably hydrogen atoms and/or groups respectively and independently selected from the groups indicated in the following (i) to (iii):

(i): a group in which the atom at the α position (atom bonded to the aromatic ring) is a carbon atom, the number of carbon atoms is from 1 to 44, a group bonded to the α position carbon atom is a hydrogen atom, alkyl group having 1 to 43 carbon atoms, cycloalkyl group having 1 to 44 carbon atoms, alkoxy group having 1 to 44 carbon atoms, polyoxyalkylene alkyl ether group having 2 to 44 carbon atoms but not having an OH group on a terminal thereof, aryl group having 6 to 43 carbon atoms, aralkyl group having 7 to 43 carbon atoms or aralkyloxy group having 7 to 19 carbon atoms, and three groups selected from groups in which one or more types of the above groups are bonded are bonded to the carbon atom, (ii) an aryl group in which the number of carbon atoms is from 1 to 44, the aryl group is substituted by substituents, and the substituents are aryl groups that may be substituted with an integral number of from 1 to 5 of the following substituents, the substituents being selected from a hydrogen atom, an alkyl group having 1 to 38 carbon atoms, a cycloalkyl group having 4 to 38 carbon atoms, an alkoxy group having 1 to 38 carbon atoms, a polyoxyalkylene alkyl ether group having 2 to 38 carbon atoms but not having an OH group on a terminal thereof, an aryl group having 6 to 38 carbon atoms, an aralkyl group having 7 to 38 carbon atoms, an aralkyloxy group having 7 to 38 carbon atoms, and a group in which one or more types of the above groups are bonded, (iii) a group in which the atom at the α position (atom bonded to the aromatic ring) is an oxygen atom, the number of carbon atoms is from 1 to 44, and a group bonded to the α position oxygen atom is a group selected from an alkyl group having 1 to 43 carbon atoms, a cycloalkyl group having 4 to 44 carbon atoms, an alkoxy group having 1 to 44 carbon atoms, a polyoxyalkylene alkyl ether group having 2 to 44 carbon atoms but not having an OH group on a terminal thereof, an aryl group having 6 to 43 carbon atoms, an aralkyl group having 7 to 43 carbon atoms, and a group in which one or more types of the above groups are bonded.

Furthermore, although the term "atom at the α position" is used in the above-mentioned formula (31), an "atom at the α position" refers to an atom that composes the groups $R^{19}$, $R^{20}$, $R^{21}$, $R^{22}$ and $R^{23}$ are that is adjacent to a carbon atom on the aromatic hydrocarbon ring to which groups $R^{19}$, $R^{20}$, $R^{21}$, $R^{22}$ and $R^{23}$ are bonded. Examples of these $R^{19}$, $R^{20}$, $R^{21}$, $R^{22}$ and $R^{23}$ may include hydrogen atoms, alkyl groups and/or cycloalkyl groups and/or cycloalkyl groups substituted with an alkyl group and/or alkyl groups substituted with a cycloalkyl group such as a methyl group, an ethyl group, a propyl group (including isomers), a butyl group (including isomers), a pentyl group (including isomers), a hexyl group (including isomers), a heptyl group (including isomers), an octyl group (including isomers), a nonyl group (including isomers), a decyl group (including isomers), a dodecyl group (including isomers), an octadecyl group (including isomers), cyclopentyl group, cyclohexyl group, cycloheptyl group, cyclooctyl group, bis(cyclohexyl) alkane, methylcyclopentyl group (including isomers), ethylcyclopentyl group (including isomers), methylcyclohexyl group (including isomers), ethylcyclohexyl group (including isomers), propylcyclohexyl group (including isomers), butylcyclohexyl group (including isomers), pentylcyclohexyl group (including isomers), hexylcyclohexyl group (including isomers), dimethylcyclohexyl group (including isomers), diethylcyclohexyl group (including isomers) or dibutylcyclohexyl group (including isomers); alkoxy groups and/or cycloalkoxy groups and/or cycloalkoxy groups substituted with an alkoxy group and/or alkoxy groups substituted with a cycloalkoxy group such as a methoxy group, an ethoxy group, propoxy group (including isomers), a butyloxy group (including isomers), a pentyloxy group (including isomers), a hexyloxy group (including isomers), a heptyloxy group (including isomers), an octyloxy group (including isomers), a nonyloxy group (including isomers), a decyloxy group (including isomers), a dodecyloxy group (including isomers), an octadecyloxy group (including isomers), a cyclopentyloxy group (including isomers), a cyclohexyloxy group (including isomers), a cycloheptyloxy group (including isomers), a cyclooctyloxy group (including isomers), a methylcyclopentyloxy group (including isomers), an ethylcyclopentyloxy group (including isomers), a methylcyclohexyloxy group (including isomers), an ethylcyclohexyloxy group (including isomers), a propylcyclohexyloxy group (including isomers), a butylcyclohexyloxy group (including isomers), a pentylcyclohexyloxy group (including isomers), a hexylcyclohexyloxy group (including isomers), a dimethylcyclohexyloxy group (including isomers), a diethylcyclohexyloxy group (including isomers) or a dibutylcyclohexyloxy group (including isomers); substituted or unsubstituted aryl groups such as a phenyl group, a methylphenyl group (including isomers), an ethylphenyl group (including isomers), a propylphenyl group (including isomers), a butylphenyl group (including isomers), a pentylphenyl group (including isomers), a hexylphenyl group (including isomers), a heptylphenyl group (including isomers), an octylphenyl group (including isomers), a nonylphenyl group (including isomers), a decylphenyl group (including isomers), a biphenyl group (including isomers), a dimethylphenyl group (including isomers), a diethylphenyl group (including isomers), a dipropylphenyl group (including isomers), a dibutylphenyl group (including isomers), a dipentylphenyl group (including isomers), a dihexylphenyl group (including isomers), a diheptylphenyl group (including isomers), a terphenyl group (including isomers), a trimethylphenyl group (including isomers), a triethylphenyl group (including isomers), a tripropylphenyl group (including isomers) or a tributylphenyl group (including isomers); substituted or unsubstituted aryloxy groups such as a phenoxy group, a methylphenoxy group (including isomers), an ethylphenoxy group (including isomers), a propylphenoxy group (including isomers), a butylphenoxy group (including isomers), a pentylphenoxy group (including isomers), a hexylphenoxy group (including isomers), a heptylphenoxy group (including isomers), an octylphenoxy group (including isomers), a nonylphenoxy group (including isomers), a decylphenoxy group (including isomers), a phenylphenoxy group (including isomers), a dimethylphenoxy group (including isomers), a diethylphenoxy group (including isomers), a dipropylphenoxy group (including isomers), a dibutylphenoxy group (including isomers), a dipentylphenoxy group (including isomers), a dihexylphenoxy group (including isomers), a diheptylphenoxy group (including isomers), a diphenylphenoxy group (including isomers), a trimethylphenoxy group (including isomers), a triethylphenoxy group (including isomers), a tripropylphenoxy group (including isomers) or a tributylphenoxy group (including isomers); substituted or unsubstituted aralkyl groups such as a phenylmethyl group, a phenylethyl group (including isomers), a phenylpropyl group (including isomers), a phenylbutyl group (including isomers), a phenylpentyl group (including isomers), a phenylhexyl group (including isomers), a phenylheptyl group (including isomers), a phenyloctyl group (including isomers) or a phenylnonyl group (including isomers); aralkyloxy groups such as a phenylmethoxy group, a phenylethoxy group (including isomers), a phenylpropyloxy group (including isomers), a phenylbutyloxy group (including isomers), a phenylpentyloxy group (including isomers), a phenylhexyloxy group (including isomers), a phenylheptyloxy group (including isomers), a phenyloctyloxy group (including isomers) or a phenylnonyloxy group (including isomers), and groups composed of hydroxyaryl groups and alkyl groups such as a hydroxyphenyl group (including isomers), a hydroxyphenoxy group (including isomers), a hydroxyphenylmethyl group (including isomers), a hydroxyphenylethyl group (including isomers) or a hydroxyphenylpropyl group (including isomers).

Preferable examples of aromatic monohydroxy compounds represented by the above-mentioned formula (30) may include the following compounds: phenol, methylphenol (including isomers), ethylphenol (including isomers), propylphenol (including isomers), butylphenol (including isomers), pentylphenol (including isomers), hexylphenol (including isomers), heptylphenol (including isomers), octylphenol (including isomers), nonylphenol (including isomers), decylphenol (including isomers), dodecylphenol (including isomers), octadecylphenol (including isomers), dimethylphenol (including isomers), diethylphenol (including isomers), dipropylphenol (including isomers), dibutylphenol (including isomers), dipentylphenol (including isomers), dihexylphenol (including isomers), diheptylphenol (including isomers), dioctylphenol (including isomers), dinonylphenol (including isomers), didecylphenol (including isomers), didodecylphenol (including isomers), dioctadecylphenol (including isomers), trimethylphenol (including isomers), triethylphenol (including isomers), tripropylphenol (including isomers), tributylphenol (including isomers), tripentylphenol (including isomers), trihexylphenol (including isomers), triheptylphenol (including isomers), trioctylphenol (including isomers), trinonylphenol (including isomers), tridecylphenol (including isomers), tridodecylphenol (including isomers), trioctadecylphenol (including isomers), (methoxymethyl)phenol (including isomers), (ethoxymethyl)phenol (including isomers), (propoxymethyl)phenol (including isomers), (butyloxymethyl)phenol (including isomers), (pentyloxymethyl)phenol (including isomers), (hexyloxymethyl)phenol (including isomers), (heptyloxymethyl)phenol (including isomers), (octyloxymethyl)phenol (including isomers), (nonyloxymethyl)phenol (including isomers), (decyloxymethyl)phenol (including isomers), (dodecyloxymethyl)phenol (including isomers), (octadecyloxymethyl)phenol (including isomers), (cyclopentyloxymethyl)phenol (including isomers), (cyclohexyloxymethyl)phenol (including isomers), (cycloheptyloxymethyl)phenol (including isomers), (cyclooctyloxymethyl)phenol (including isomers), (methylcyclopentyloxymethy) phenol (including isomers), (ethylcyclopentyloxymethyl)phenol (including isomers), (methylcyclohexyloxymethyl)phenol (including isomers), (ethylcyclohexyloxymethyl)phenol (including isomers), (propylcyclohexyloxymethyl)phenol (including isomers), (butylcyclohexyloxymethyl)phenol (including isomers), (pentylcyclohexyloxymethyl)phenol (including isomers), (hexylcyclohexyloxymethyl)phenol (including isomers), (dimethylcyclohexyloxymethyl)phenol (including isomers), (diethylcyclohexyloxymethyl)phenol (including isomers), (dibutylcyclohexyloxymethyl)phenol (including isomers), (phenoxymethyl)phenol, (methylphenoxymethyl)phenol (including isomers), (ethylphenoxymethyl)phenol (including isomers), (propylphenoxymethyl)phenol (including isomers), (butylphenoxymethyl)phenol (including isomers), (pentylphenoxymethyl)phenol (including isomers), (hexylphenoxymethyl)phenol (including isomers), (heptylphenoxymethyl)phenol (including isomers), (octylphenoxymethyl)phenol (including isomers), (nonylphenoxymethyl)phenol (including isomers), (decylphenoxymethyl)phenol (including isomers), (phenylphenoxymethyl)phenol (including isomers), (dimethylphenoxymethyl)phenol (including isomers), (diethylphenoxymethyl)phenol (including isomers), (dipropylphenoxymethyl)phenol (including isomers), (dibutylphenoxymethyl)phenol (including isomers), (dipentylphenoxymethyl)phenol (including isomers), (dihexylphenoxymethyl)phenol (including isomers), (diheptylphenoxymethyl)phenol (including isomers), (diphenylphenoxymethyl)phenol (including isomers), (trimethylphenoxymethyl)phenol (including isomers), (triethylphenoxymethyl)phenol (including isomers), (tripropylphenoxymethyl)phenol (including isomers), (tributylphenoxymethyl)phenol (including isomers), (phenylmethoxymethyl)phenol (including isomers), (phenylethoxymethyl)phenol (including isomers), (phenylpropyloxymethyl)phenol (including isomers), (phenylbutyloxymethyl)phenol (including isomers), (phenylpentyloxymethyl)phenol (including isomers), (phenylhexyloxymethyl)phenol (including isomers), (phenylheptyloxymethyl)phenol (including isomers), (phenyloctyloxymethyl)phenol (including isomers), (phenylnonyloxymethyl)phenol (including isomers), di(methoxymethyl)phenol, di(ethoxymethyl)phenol, di(propoxymethyl)phenol (including isomers), di(butyloxymethyl)phenol (including isomers), di(pentyloxymethyl)phenol (including isomers), di(hexyloxymethyl)phenol (including isomers), di(heptyloxymethyl)phenol (including isomers), di(octyloxymethyl)phenol (including isomers), di(nonyloxymethyl)phenol (including isomers), di(decyloxymethyl)phenol (including isomers), di(dodecyloxymethyl)phenol (including isomers), di(octadecyloxymethyl)phenol (including isomers), di(cyclopentyloxymethyl)phenol (including isomers), di(cyclohexyloxymethyl)phenol (including isomers), di(cycloheptyloxymethyl)phenol (including isomers), di(cyclooctyloxymethyl)phenol (including isomers), di(methylcyclopentyloxymethy) phenol (including isomers), di(ethylcyclopentyloxymethyl)phenol (including isomers), di(methylcyclohexyloxymethyl)phenol (including isomers), di(ethylcyclohexyloxymethyl)phenol (including isomers), di(propylcyclohexyloxymethyl)phenol (including isomers), di(butylcyclohexyloxymethyl)phenol (including isomers), di(pentylcyclohexyloxymethyl)phenol (including isomers), di(hexylcyclohexyloxymethyl)phenol (including isomers), bis(dimethylcyclohexyloxymethyl)phenol (including isomers), bis(diethylcyclohexyloxymethyl)phenol (including isomers), bis(dibutylcyclohexyloxymethyl)phenol (including isomers), di(phenoxymethyl)phenol, di(methylphenoxymethyl)phenol (including isomers), di(ethylphenoxymethyl)phenol (including isomers), di(propylphenoxymethyl)phenol (including isomers), di(butylphenoxymethyl)phenol (including isomers), di(pentylphenoxymethyl)phenol (including isomers), di(hexylphenoxymethyl)phenol (including isomers), di(heptylphenoxymethyl)phenol (including isomers), di(octylphenoxymethyl)phenol (including isomers), di(nonylphenoxymethyl)phenol (including isomers), di(decylphenoxymethyl)phenol (including isomers), di(phenylphenoxymethyl)phenol (including isomers), bis(dimethylphenoxymethyl)phenol (including isomers), bis(diethylphenoxymethyl)phenol (including isomers), bis(dipropylphenoxymethyl)phenol (including isomers), bis(dibutylphenoxymethyl)phenol (including isomers), bis(dipentylphenoxymethyl)phenol (including isomers), bis(dihexylphenoxymethyl)phenol (including isomers), bis(diheptylphenoxymethyl)phenol (including isomers), bis(diphenylphenoxymethyl)phenol (including isomers), di(trimethylphenoxymethyl)phenol (including isomers), di(triethylphenoxymethyl)phenol (including isomers), di(tripropylphenoxymethyl)phenol (including isomers), di(tributylphenoxymethyl)phenol (including isomers), (phenylmethoxymethyl)phenol (including isomers), di(phenylethoxymethyl)phenol (including isomers), di(phenylpropyloxymethyl)phenol (including isomers), di(phenylbutyloxymethyl)phenol (including isomers), di(phenylpentyloxymethyl)phenol (including isomers), di(phenylhexyloxymethyl)phenol (including isomers), di(phenylheptyloxymethyl)phenol (including isomers), di(phenyloctyloxymethyl)phenol (including isomers), di(phenylnonyloxymethyl)phenol (including isomers), tri(methoxymethyl)phenol, tri(ethoxymethyl)phenol, tri(propoxymethyl)phenol (including isomers), tri(butyloxymethyl)phenol (including isomers), tri(pentyloxymethyl)phenol (including isomers), tri(hexyloxymethyl)phenol (including isomers), tri(heptyloxymethyl)phenol (including isomers), tri(octyloxymethyl)phenol (including isomers), tri(nonyloxymethyl)phenol (including isomers), tri(decyloxymethyl) phenol (including isomers), tri(dodecyloxymethyl)phenol (including isomers), tri(octadecyloxymethyl)phenol (including isomers), tri(cyclopentyloxymethyl)phenol (including isomers), tri(cyclohexyloxymethyl)phenol (including isomers), tri(cycloheptyloxymethyl)phenol (including isomers), tri(cyclooctyloxymethyl)phenol (including isomers), tri(methylcyclopentyloxymethy) phenol (including isomers), tri (ethylcyclopentyloxymethyl)phenol (including isomers), tri (methylcyclohexyloxymethyl)phenol (including isomers), tri (ethylcyclohexyloxymethyl)phenol (including isomers), tri (propylcyclohexyloxymethyl)phenol (including isomers), tri (butylcyclohexyloxymethyl)phenol (including isomers), tri (pentylcyclohexyloxymethyl)phenol (including isomers), tri (hexylcyclohexyloxymethyl)phenol (including isomers), bis (dimethylcyclohexyloxymethyl)phenol (including isomers), bis(diethylcyclohexyloxymethyl)phenol (including isomers), bis(dibutylcyclohexyloxymethyl)phenol (including isomers), tri(phenoxymethyl)phenol, tri(methylphenoxymethyl)phenol (including isomers), tri(ethylphenoxymethyl)phenol (including isomers), tri(propylphenoxymethyl)phenol (including isomers), tri(butylphenoxymethyl)phenol (including isomers), tri(pentylphenoxymethyl)phenol (including isomers), tri(hexylphenoxymethyl)phenol (including isomers), tri(heptylphenoxymethyl)phenol (including isomers), tri(octylphenoxymethyl)phenol (including isomers), tri(nonylphenoxymethyl)phenol (including isomers), tri(decylphenoxymethyl)phenol (including isomers), tri(phenylphenoxymethyl)phenol (including isomers), bis(dimethylphenoxymethyl)phenol (including isomers), bis(diethylphenoxymethyl)phenol (including isomers), bis(dipropylphenoxymethyl)phenol (including isomers), bis(dibutylphenoxymethyl)phenol (including isomers), bis(dipentylphenoxymethyl)phenol (including isomers), bis(dihexylphenoxymethyl)phenol (including isomers), bis(diheptylphenoxymethyl)phenol (including isomers), bis(diphenylphenoxymethyl)phenol (including isomers), tri(trimethylphenoxymethyl)phenol (including isomers), tri(triethylphenoxymethyl)phenol (including isomers), tri(tripropylphenoxymethyl)phenol (including isomers), tri(tributylphenoxymethyl)phenol (including isomers), tri(phenylmethoxymethyl)phenol, tri(phenylethoxymethyl) phenol (including isomers), tri(phenylpropyloxymethyl) phenol (including isomers), tri(phenylbutyloxymethyl) phenol (including isomers), tri(phenylpentyloxymethyl) phenol (including isomers), tri(phenylhexyloxymethyl) phenol (including isomers), tri(phenylheptyloxymethyl) phenol (including isomers), tri(phenyloctyloxymethyl) phenol (including isomers), tri(phenylnonyloxymethyl) phenol (including isomers), (phenylmethyl)phenol (including isomers), ((methylphenyl)methyl)phenol (including isomers), ((ethylphenyl)methyl)phenol (including isomers), ((propylphenyl)methyl) phenol (including isomers), ((butylphenyl)methyl)phenol (including isomers), ((pentylphenyl)methyl)phenol (including isomers), ((hexylphenyl)methyl)phenol (including isomers), ((heptylphenyl)methyl)phenol (including isomers), ((octylphenyl)methyl) phenol (including isomers), ((nonylphenyl)methyl)phenol (including isomers), ((decylphenyl)methyl)phenol (including isomers), ((biphenyl)methyl)phenol (including isomers), ((dimethylphenyl)methyl)phenol (including isomers), ((diethylphenyl)methyl)phenol (including isomers), ((dipropylphenyl)methyl)phenol (including isomers), ((dibutylphenyl)methyl)phenol (including isomers), ((dipentylphenyl)methyl)phenol (including isomers), ((dihexylphenyl)methyl)phenol (including isomers), ((diheptylphenyl)methyl)phenol (including isomers), ((terphenyl)methyl)phenol (including isomers), ((trimethylphenyl)methyl)phenol (including isomers), ((triethylphenyl)methyl)phenol (including isomers), ((tripropylphenyl)methyl)phenol (including isomers), ((tributylphenyl)methyl)phenol (including isomers), di(phenylmethyl)phenol (including isomers), di((methylphenyl)methyl)phenol (including isomers), di((ethylphenyl)methyl) phenol (including isomers), di((propylphenyl)methyl)phenol (including isomers), di((butylphenyl)methyl)phenol (including isomers), di((pentylphenyl)methyl)phenol (including isomers), di((hexylphenyl)methyl)phenol (including isomers), di((heptylphenyl)methyl)phenol (including isomers), di((octylphenyl)methyl)phenol (including isomers), di((nonylphenyl)methyl)phenol (including isomers), di((decylphenyl)methyl)phenol (including isomers), di((biphenyl) methyl)phenol (including isomers), di((dimethylphenyl) methyl)phenol (including isomers), di((diethylphenyl) methyl)phenol (including isomers), di((dipropylphenyl) methyl)phenol (including isomers), di((dibutylphenyl) methyl)phenol (including isomers), di((dipentylphenyl) methyl)phenol (including isomers), di((dihexylphenyl) methyl)phenol (including isomers), di((diheptylphenyl) methyl) phenol (including isomers), di((terphenyl)methyl) phenol (including isomers), di((trimethylphenyl)methyl) phenol (including isomers), di((triethylphenyl)methyl) phenol (including isomers), di((tripropylphenyl)methyl)phenol (including isomers), di((tributylphenyl)methyl) phenol (including isomers), tri(phenylmethyl) phenol (including isomers), tri((methylphenyl)methyl) phenol (including isomers), tri((ethylphenyl)methyl) phenol (including isomers), tri((propylphenyl)methyl) phenol (including isomers), tri((butylphenyl)methyl) phenol (including isomers), tri((pentylphenyl)methyl) phenol (including isomers), tri((hexylphenyl)methyl) phenol (including isomers), tri((heptylphenyl) methyl) phenol (including isomers), tri((octylphenyl)methyl) phenol (including isomers), tri((nonylphenyl)methyl) phenol (including isomers), tri((decylphenyl)methyl) phenol (including isomers), tri((biphenyl)methyl) phenol (including isomers), tri((dimethylphenyl)methyl) phenol (including isomers), tri((diethylphenyl)methyl) phenol (including isomers), tri((dipropylphenyl)methyl) phenol (including isomers), tri((dibutylphenyl)methyl) phenol (including isomers), tri((dipentylphenyl)methyl) phenol (including isomers), tri((dihexylphenyl)methyl) phenol (including isomers), tri((diheptylphenyl)methyl) phenol (including isomers), tri((terphenyl)methyl) phenol (including isomers), tri((trimethylphenyl)methyl) phenol (including isomers), tri((triethylphenyl)methyl) phenol (including isomers), tri((tripropylphenyl)methyl) phenol (including isomers), tri((tributylphenyl)methyl) phenol (including isomers), phenylethylphenol (including isomers), phenyl-n-propylphenol (including isomers), phenyl-n-butylphenol (including isomers), phenyl-n-pentylphenol (including isomers), phenyl-n-hexylphenol (including isomers), phenyl-n-heptylphenol (including isomers), phenyl-n-octylphenol (including isomers), phenyl-n-nonylphenol (including isomers), methoxyphenol (including isomers), ethoxyphenol (including isomers), propyloxyphenol (including isomers), butyloxyphenol (including isomers), pentyloxyphenol (including isomers), hexyloxyphenol (including isomers), heptyloxyphenol (including isomers), octyloxyphenol (including isomers), nonyloxyphenol (including isomers), decyloxyphenol (including isomers), dodecyloxyphenol (including isomers), octadecyloxyphenol (including isomers), cyclopentyloxyphenol (including isomers), cyclohexyloxyphenol (including isomers), cycloheptyloxyphenol (including isomers), cyclooctyloxyphenol (including isomers), (methylcyclopentyloxy) phenol (including isomers), (ethylcyclopentyloxy) phenol (including isomers), (methylcyclohexyloxy) phenol (including isomers), (ethylcyclohexyloxy) phenol (including isomers), (propylcyclohexyloxy) phenol (including isomers), (butylcyclohexyloxy) phenol (including isomers), (pentylcyclohexyloxy) phenol (including isomers), (hexylcyclohexyloxy) phenol (including isomers), (dimethylcyclohexyloxy) phenol (including isomers), (diethylcyclohexyloxy) phenol (including isomers), (dibutylcyclohexyloxy) phenol (including isomers), phenoxyphenol, (methylphenyloxy) phenol (including isomers), (ethylphenyloxy) phenol (including isomers), (propylphenyloxy) phenol (including isomers), (butylphenyloxy) phenol (including isomers), (pentylphenyloxy) phenol (including isomers), (hexylphenyloxy) phenol (including isomers), (heptylphenyloxy )phenol (including isomers), (octylphenyloxy) phenol (including isomers), (nonylphenyloxy) phenol (including isomers), (decylphenyloxy) phenol (including isomers), biphenyloxyphenol (including isomers), (dimethylphenyloxy) phenol (including isomers), (diethylphenyloxy) phenol (including isomers), (dipropylphenyloxy) phenol (including isomers), (dibutylphenyloxy) phenol (including isomers), (dipentylphenyloxy) phenol (including isomers), (dihexylphenyloxy) phenol (including isomers), (diheptylphenyloxy) phenol (including isomers), terphenyloxyphenol (including isomers), (trimethylphenyloxy) phenol (including isomers), (triethylphenyloxy) phenol (including isomers), (tripropylphenyloxy) phenol (including isomers), (tributylphenyloxy) phenol (including isomers), (phenylmethyloxy) phenol, (phenylethyloxy) phenol (including isomers), (phenylpropyloxy) phenol (including isomers), (phenylbutyloxy) phenol (including isomers), (phenylpentyloxy) phenol (including isomers), (phenylhexyloxy) phenol (including isomers), (phenylheptyloxy) phenol (including isomers), (phenyloctyloxy) phenol (including isomers), (phenylnonyloxy) phenol (including isomers), dimethoxyphenol (including isomers), diethoxyphenol (including isomers), dipropyloxyphenol (including isomers), dibutyloxyphenol (including isomers), dipentyloxyphenol (including isomers), dihexyloxyphenol (including isomers), diheptyloxyphenol (including isomers), dioctyloxyphenol (including isomers), dinonyloxyphenol (including isomers), didecyloxyphenol (including isomers), didodecyloxyphenol (including isomers), dioctadecyloxyphenol (including isomers), dicyclopentyloxyphenol (including isomers), dicyclohexyloxyphenol (including isomers), dicycloheptyloxyphenol (including isomers), dicyclooctyloxyphenol (including isomers), di(methylcyclopentyloxy) phenol (including isomers), di(ethylcyclopentyloxy) phenol (including isomers), di(methylcyclohexyloxy) phenol (including isomers), di(ethylcyclohexyloxy) phenol (including isomers), di(propylcyclohexyloxy) phenol (including isomers), di(butylcyclohexyloxy) phenol (including isomers), di(pentylcyclohexyloxy) phenol (including isomers), di(hexylcyclohexyloxy) phenol (including isomers), bis(dimethylcyclohexyloxy) phenol (including isomers), bis (diethylcyclohexyloxy) phenol (including isomers), bis (dibutylcyclohexyloxy) phenol (including isomers), phenyloxyphenol, di(methylphenyloxy) phenol (including isomers), di(ethylphenyloxy) phenol (including isomers), di(propylphenyloxy) phenol (including isomers), di(butylphenyloxy) phenol (including isomers), di(pentylphenyloxy) phenol (including isomers), di(hexylphenyloxy) phenol (including isomers), di(heptylphenyloxy) phenol (including isomers), di(octylphenyloxy) phenol (including isomers), di(nonylphenyloxy) phenol (including isomers), di(decylphenyloxy) phenol (including isomers), dibiphenyloxyphenol (including isomers), bis(dimethylphenyloxy) phenol (including isomers), bis(diethylphenyloxy) phenol (including isomers), bis(dipropylphenyloxy) phenol (including isomers), bis(dibutylphenyloxy) phenol (including isomers), bis (dipentylphenyloxy) phenol (including isomers), bis (dihexylphenyloxy) phenol (including isomers), bis (diheptylphenyloxy) phenol (including isomers), diterphenyloxyphenol (including isomers), di(trimethylphenyloxy) phenol (including isomers), di(triethylphenyloxy) phenol (including isomers), di(tripropylphenyloxy) phenol (including isomers), di(tributylphenyloxy) phenol (including isomers), (phenylmethyloxy) phenol, di(phenylethyloxy) phenol (including isomers), di(phenylpropyloxy) phenol (including isomers), di(phenylbutyloxy) phenol (including isomers), di(phenylpentyloxy) phenol (including isomers), di(phenylhexyloxy) phenol (including isomers), di(phenylheptyloxy) phenol (including isomers), di(phenyloctyloxy) phenol (including isomers), di(phenylnonyloxy) phenol (including isomers), trimethoxyphenol (including isomers), triethoxyphenol (including isomers), tripropyloxyphenol (including isomers), tributyloxyphenol (including isomers), tripentyloxyphenol (including isomers), trihexyloxyphenol (including isomers), triheptyloxyphenol (including isomers), trioctyloxyphenol (including isomers), trinonyloxyphenol (including isomers), tridecyloxyphenol (including isomers), tridodecyloxyphenol (including isomers), trioctadecyloxyphenol (including isomers), tricyclopentyloxyphenol (including isomers), tricyclohexyloxyphenol (including isomers), tricycloheptyloxyphenol (including isomers), tricyclooctyloxyphenol (including isomers), tri(methylcyclopentyloxy) phenol (including isomers), tri(ethylcyclopentyloxy) phenol (including isomers), tri(methylcyclohexyloxy) phenol (including isomers), tri(ethylcyclohexyloxy) phenol (including isomers), tri(propylcyclohexyloxy) phenol (including isomers), tri(butylcyclohexyloxy) phenol (including isomers), tri(pentylcyclohexyloxy) phenol (including isomers), tri(hexylcyclohexyloxy) phenol (including isomers), tri(dimethylcyclohexyloxy) phenol (including isomers), tri (diethylcyclohexyloxy) phenol (including isomers), tri(dibutylcyclohexyloxy) phenol (including isomers), phenyloxyphenol, tri(methylphenyloxy) phenol (including isomers), tri(ethylphenyloxy) phenol (including isomers), tri(propylphenyloxy) phenol (including isomers), tri(butylphenyloxy) phenol (including isomers), tri(pentylphenyloxy) phenol (including isomers), tri(hexylphenyloxy) phenol (including isomers), tri(heptylphenyloxy) phenol (including isomers), tri (octylphenyloxy) phenol (including isomers), tri (nonylphenyloxy) phenol (including isomers), tri (decylphenyloxy) phenol (including isomers), tribiphenyloxyphenol (including isomers), tri(dimethylphenyloxy) phenol (including isomers), tri(diethylphenyloxy) phenol (including isomers), tri(dipropylphenyloxy) phenol (including isomers), tri(dibutylphenyloxy) phenol (including isomers), tri(dipentylphenyloxy) phenol (including isomers), tri(dihexylphenyloxy) phenol (including isomers), tri(diheptylphenyloxy) phenol (including isomers), triterphenyloxyphenol (including isomers), tri(trimethylphenyloxy) phenol (including isomers), tri(triethylphenyloxy) phenol (including isomers), tri(tripropylphenyloxy) phenol (including isomers), tri(tributylphenyloxy) phenol (including isomers), (phenylmethyloxy) phenol, tri(phenylethyloxy) phenol (including isomers), tri(phenylpropyloxy) phenol (including isomers), tri(phenylbutyloxy) phenol (including isomers), tri (phenylpentyloxy) phenol (including isomers), tri(phenylhexyloxy) phenol (including isomers), tri(phenylheptyloxy) phenol (including isomers), tri(phenyloctyloxy) phenol(including isomers), tri(phenylnonyloxy) phenol (including isomers), phenylphenol (including isomers), hydroxyphenyl phenol (including isomers), hydroxyphenoxy phenol (including isomers), hydroxyphenylmethyl phenol (including isomers), hydroxyphenylethyl phenol (including isomers), hydroxyphenylpropyl phenol, naphthol (including isomers), phenoxyphenol (including isomers), and diphenoxyphenol (including isomers).

Preferable examples of the above-mentioned aromatic monohydroxy compounds may include those in which at least two of the groups, $R^{19}$, $R^{20}$, $R^{21}$, $R^{22}$ and $R^{23}$ are hydrogen atoms due to ease of transfer, and more preferably the number of carbon atoms that compose the groups $R^{19}$, $R^{20}$, $R^{21}$, $R^{22}$ and $R^{23}$ is from 0 to 13. Even more preferably, the aromatic monohydroxy compound is an aromatic monohydroxy compound in which the groups $R^{20}$, $R^{21}$, $R^{22}$ and $R^{23}$ are groups having 0 to 9 carbon atoms that are selected hydrogen atoms, linear or branched alkyl groups, cycloalkyl groups, substituted or unsubstituted aryl groups, linear or branched alkoxy groups, substituted or unsubstituted aryloxy groups and substituted or unsubstituted aralkyl groups.

The following provides an explanation of an active aromatic monohydroxy compound. An aromatic hydroxy compound represented by the above-mentioned formula (2) and/or formula (7) and/or formula (31) can be preferably used as an aromatic hydroxy compound that composes an aromatic composition used in a composition for transfer and storage of a compound having ureido groups. In addition, it can also be preferably used as the aromatic hydroxy compound that composes an aromatic hydroxy composition used during production of an N-substituted carbamic acid-O-aryl ester by reacting with a compound having ureido groups and/or an N-substituted carbamic acid-O—$R^2$ ester. However, the latter aromatic hydroxy compound that composes an aromatic hydroxy composition used during production of an N-substituted carbamic acid-O-aryl ester is a compound that composes an —O-aryl ester group in an N-substituted carbamic acid-O-aryl ester by reacting with a compound having ureido groups and/or an N-substituted carbamic acid-O—$R^2$ ester. In the case of using the composition for transfer and storage of a compound having ureido groups as a raw material of an N-substituted carbamic acid-O-aryl ester, in the case of producing an N-substituted carbamic acid-O-aryl ester by using a compound having ureido groups as a raw material, or when using as a raw material of an N-substituted carbamic acid-O—$R^2$ ester followed by producing an N-substituted carbamic acid-O-aryl ester, although the aromatic hydroxy compound is included in the above-mentioned formula (2) and/or formula (7) and/or formula (31), an aromatic hydroxy compound represented by the following formula (32) is used particularly preferably (an aromatic hydroxy compound represented by formula (32) is frequently referred to as an "active aromatic hydroxy compound" in the present specification in order to express the ease by which the reaction occurs). The active aromatic hydroxy compound represented by the following formula (32) may be used alone as an aromatic hydroxy composition used in a composition for transfer and storage of a compound having ureido groups, or may be used as one type of aromatic hydroxy compound that composes an aromatic hydroxy composition. In addition, the aromatic hydroxy compound represented by the following formula (32) may be used alone as an aromatic hydroxy composition for obtaining an N-substituted carbamic acid-O-aryl ester by reacting with a compound having ureido groups and/or an N-substituted carbamic acid-O—$R^2$ ester, or may be used as one type of aromatic hydroxy compound that composes an aromatic hydroxy composition. Naturally, a plurality of active aromatic hydroxy compounds represented by the following formula (32) may also be used in each of the cases described above.

The active aromatic monohydroxy compound is represented by the following formula (32):

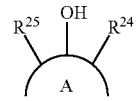

(32)

(wherein ring A represents an organic group, which contains an aromatic group substituted by number b of hydroxy groups at arbitrary locations that maintain aromatic properties, may be a single or multiple heterocyclic ring, and may be substituted by other substituents, and an integral number of from 1 to 6 OH groups represented by formula (32) are substituted on an aromatic ring contained in the ring A (namely, the formula (32) constitutes a portion of the ring A, and an integral number of from 1 to 6 structures to which the above-mentioned $R^{24}$ group, OH group and $R^{25}$ group are adjacent are respectively present on the ring A).

$R^{24}$ and $R^{25}$ are groups bonded to the aromatic ring to which the hydroxy group is bonded, and which are bonded to a carbon atom adjacent to the carbon atom to which the hydroxy group is bonded. An integral number of from 1 to 6 hydroxy groups are bonded to ring A, and thus, an integral number of from 1 to 6 of $R^{24}$ and $R^{25}$ are respectively bonded to ring A. An aromatic hydroxy compound represented by formula (32) is an aromatic hydroxy compound that contains an integral number of carbon atoms within a range of from 6 to 50.

A substituent that substitutes an aromatic group of an aromatic hydroxy compound represented by formula (32) above (while groups $R^{24}$ and $R^{25}$ will be subsequently explained in detail) is selected from the group consisting of a hydrogen atom, a halogen atom, an aliphatic group, an aromatic group and an aliphatic group in which an aromatic group is bonded, is a group composed of an acyclic hydrocarbon group or a cyclic hydrocarbon group (such as a monocyclic hydrocarbon group, a condensed polycyclic hydrocarbon group, a crosslinked cyclic hydrocarbon group, a spirohydrocarbon group, a ring-assembling hydrocarbon group, a cyclic hydrocarbon group having a side chain, a heterocyclic group, a heterocyclic spiro group, a hetero-crosslinked ring group or a heterocyclic group), a group bonded from one or more types of groups selected from the above-mentioned acyclic hydrocarbon groups and cyclic hydrocarbon groups, and groups in which the above-mentioned groups are bonded through a covalent bond with a specific non-metal atom (carbon, oxygen, nitrogen, sulfur or silicon). In addition, a covalent bond with a specific non-metal atom (carbon, oxygen, nitrogen, sulfur or silicon) as described above is in a state in which the above-mentioned groups are bonded by a covalent bond with, for example, groups represented by the above-mentioned formulas (8) to (11) and (13) to (16).

Among such substituents, examples of substituents that can be preferably used in the present embodiment in consideration of less susceptibility to the occurrence of side reactions may include groups selected from the group consisting of acyclic hydrocarbon groups and cyclic hydrocarbon groups (such as a monocyclic hydrocarbon group, a condensed polycyclic hydrocarbon group, a crosslinked cyclic hydrocarbon group, a spirohydrocarbon group, a ring-assembling hydrocarbon group or a cyclic hydrocarbon group having a side chain), and groups bonded to at least one type of group selected from this group (mutually substituted groups).

In addition, in the case of transferring a composition containing a compound having ureido groups at a high temperature, or in the case carrying out a reaction for obtaining an N-substituted carbamic acid-O-aryl ester by reacting a compound having ureido groups and/or an N-substituted carbamic acid O—$R^2$ ester and an aromatic hydroxy composition at a high temperature, the ring A of the aromatic hydroxy compound is preferably composed of a group having at least one inactive substituent (including hydrogen atoms) in addition to the aromatic group and the hydroxy group bonded to the aromatic group (here, an inactive substituent refers to a group in which the inactive substituent does not contain an active hydrogen as previously described, although it may have an aromatic hydroxyl group).

In providing a more detailed explanation of the substituent, an aromatic hydroxy compound represented by formula (32) is an aromatic hydroxy compound having at least one substituent selected from the group of substituents explained in the following (i) to (v) in addition to the aromatic group and the hydroxy group bonded to the aromatic group (while groups $R^{24}$ and $R^{25}$ will be subsequently explained in detail).

(i) a hydrogen atom, (ii) a group composed of carbon atoms and hydrogen atoms (which may also form a condensed ring structure by bonding with ring A), (iii) a group composed of carbon atoms, hydrogen atoms and oxygen atoms (representing, for example, an ether group composed of aliphatic groups, an ether group composed of aromatic groups or an ether group composed of aliphatic groups and aromatic groups, but excluding groups containing active hydrogen such as a carbonyl group, an ester group, a terminal methine group and an alcoholic OH group, a carboxyl group, a $NH_2$ group, a NH group, a NOH group, a SH group, a $SO_3H$ group or a SOH group), (iv) a halogen atom, and (v) a group composed of atoms selected from carbon atoms, hydrogen atoms, oxygen atoms, nitrogen atoms, sulfur atoms and halogen atoms (but excluding groups containing active hydrogen such as a carbonyl group, an ester group, a terminal methine group and an alcoholic OH group, a carboxyl group, a $NH_2$ group, a NH group, a NOH group, a SH group, a $SO_3H$ group or a SOH group).

$R^{24}$ and $R^{25}$ respectively and independently represent any of the groups defined in the following (i) to (v), and $R^{24}$ and $R^{25}$ may further form a condensed ring structure by bonding with ring A. In the case the relationship between ring A and the hydroxyl group in the above-mentioned formula (32), for example, is a structure shown in the following formula (33) or formula (34), although the number of $R^{24}$ and $R^{25}$ bonded to a carbon adjacent to the OH group bonded to the aromatic group that composes ring A may frequently not coincide with the number of the OH groups, in the structure represented by the following formula (33), ring A may be a ring moiety shown on the right side of the following formula (35), while $R^{25}$ may form a ring structure by bonding with ring A. In the case of formula (34), the aromatic hydroxyl group bonded to ring A is the center OH group, while the adjacent OH groups may be groups $R^{24}$ and $R^{25}$, respectively:

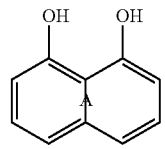

(33)

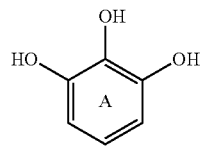

(34)

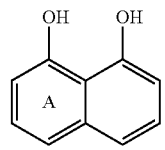

(35)

(i) a hydrogen atom, (ii) a group composed of carbon atoms and hydrogen atoms (which may also form a condensed ring structure by bonding with ring A), in which the atom at the α position (atom that forms the $R^{24}$ and $R^{25}$ that is bonded to the aromatic ring of ring A) is a carbon atom, and the carbon atom is a primary or secondary carbon atom (namely, representing a carbon atom of a methyl group or carbon atom that forms a —$CH_2$— bond), provided that in the case the $R^{24}$ and/or $R^{25}$ form a saturated and/or unsaturated condensed ring structure with ring A and the condensed ring has six members or less, the carbon at the α position may be a tertiary or quaternary carbon atom as in, for example, the case of the following formula (36) or formula (37), and in the case the carbon atom at the α position forms a double bond or triple bond with an atom at the β position (adjacent to an atom that forms the $R^{24}$ and $R^{25}$ that is bonded to the aromatic ring of ring A) as well, the carbon at the α position may be a tertiary or quaternary carbon atom,

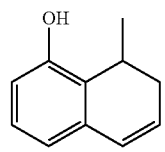

(36)

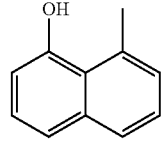

(37)

(iii) a group composed of carbon atoms, hydrogen atoms and oxygen atoms (representing, for example, an ether group composed of aliphatic groups, an ether group composed of aromatic groups or an ether group composed of aliphatic groups and aromatic groups, but not having an alcoholic OH group, a carbonyl group, an ester group, a carboxyl group or a methine group on a terminal thereof), in which the atom at the α position (atom that forms the $R^{24}$ and $R^{25}$ that is bonded to the aromatic ring of ring A) is a carbon atom or oxygen atom, and in the case of a carbon atom, the carbon atom is a primary or secondary carbon atom (namely, a carbon atom of a methyl group or a carbon atom that forms a —CH$_2$— bond), provided that in the case the R$^{24}$ and/or R$^{25}$ form a saturated and/or unsaturated condensed ring structure with ring A and the condensed ring has six members or less, the carbon at the α position may be a tertiary or quaternary carbon atom, and in the case the carbon atom at the α position forms a double bond or triple bond with an atom at the β position (adjacent to an atom that forms the R$^{24}$ and R$^{25}$ that is bonded to the aromatic ring of ring A) as well, the carbon at the α position may be a tertiary or quaternary carbon atom, (iv) a halogen atom, (v) a group composed of atoms selected from carbon atoms, hydrogen atoms, oxygen atoms, nitrogen atoms, sulfur atoms and halogen atoms (but excluding groups containing active hydrogen such as an alcoholic OH group, a carbonyl group, an ester group, a carboxyl group, a terminal methine group, a NH$_2$ group, a NH group, a NOH group, a SH group, a SO$_3$H group or a SOH group), in which the atom at the α position (atom that forms the R$^{24}$ and R$^{25}$ that is bonded to the aromatic ring of ring A) is a carbon atom, oxygen atom or sulfur atom, in the case of a carbon atom, the carbon atom is a primary or secondary carbon atom (namely, a carbon atom of a methyl group or a carbon atom that forms a —CH$_2$— bond), and in the case of a sulfur atom, the sulfur atom is a divalent sulfur atom (namely, a sulfur atom that forms an —S— bond), provided that in the case the R$^{24}$ and/or R$^{25}$ form a saturated and/or unsaturated condensed ring structure with ring A and the condensed ring has six members or less, the carbon at the α position may be a tertiary or quaternary carbon atom, and in the case the carbon atom at the α position forms a double bond or triple bond with an atom at the β position (adjacent to an atom that forms the R$^{24}$ and R$^{25}$ that is bonded to the aromatic ring of ring A) as well, the carbon at the α position may be a tertiary or quaternary carbon atom.

Although the term "active hydrogen" is used here, active hydrogen refers to a hydrogen atom bonded to oxygen, sulfur or nitrogen. However, aromatic hydroxyl groups are excluded. Although aromatic hydroxyl groups (OH groups directly bonded to an aromatic group) also constitute active hydrogen, since the aromatic hydroxyl groups are also contained in the composition of the present embodiment and reaction raw materials and do not have a detrimental effect, aromatic hydroxyl groups are not included in groups containing active hydrogen unless specifically indicated otherwise. Although the "groups containing active hydrogen" are frequently described in other locations of the present embodiment, the above-mentioned definition applies to such groups. Such active hydrogen is highly reactive, and reacts with the organic primary amine, urea compound and the like used in the present embodiment as well as with compounds having ureido groups, N-substituted carbamic acid-O—(R$^2$ or aryl) esters and the like formed in the present embodiment resulting in the formation of reaction by-products, thereby making them undesirable.

In addition, ring A is preferably a structure that contains at least one structure selected from the group consisting of a benzene ring, a naphthalene ring and an anthracene ring. In consideration of the industrial use, the active aromatic hydroxy compound represented by the above-mentioned formula (32) is preferably an aromatic monohydroxy compound in which one or two aromatic hydroxyl groups are bonded to ring A (namely, b=1 or 2), and more preferably an aromatic monohydroxy compound in which one aromatic hydroxyl group is bonded to ring A, since they typically have low viscosity.

As was previously described, an aromatic hydroxy compound represented by formula (2), (7), (31) or (32) is formed as a by-product together with isocyanate during thermal decomposition of the N-substituted carbamic acid-O-aryl ester when carrying out the step (F) (frequently referred to as the thermal decomposition step, thermal decomposition or during thermal decomposition). In one aspect of the present embodiment, although depending on the case, the aromatic hydroxy compound and isocyanate are separated by distillation following the thermal decomposition step, and the separated aromatic hydroxy compound may be recycled in the form of the aromatic hydroxy composition of the present embodiment. Separation is carried out using standard boiling point as an indicator, and the method is selected in accordance with the previously described definition.

Moreover, in consideration of the industrial use, the active aromatic hydroxy compound is preferably an easily acquirable aromatic monohydroxy compound. A preferable example of such an aromatic monohydroxy compound is an aromatic monohydroxy compound represented by the following formula (38):

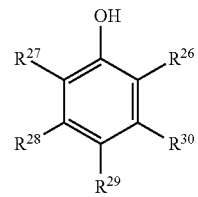

(38)

(wherein

R$^{28}$, R$^{29}$ and R$^{30}$ are groups respectively and independently selected from the above-mentioned groups R$^7$ to R$^{14}$ (excluding aryl groups having a hydroxy group), groups R$^{26}$ and R$^{27}$ are groups respectively and independently selected from the above-mentioned groups R$^{24}$ and R$^{25}$, and the aromatic hydroxy compound represented by formula (38) is an aromatic monohydroxy compound having an integral number of from 6 to 50 carbon atoms, provided that the total number of carbon atoms of groups R$^{26}$, R$^{27}$, R$^{28}$, R$^{29}$ and R$^{30}$ is an integer of from 0 to 44, and R$^{26}$ and R$^{27}$ are respectively and independently any group defined in the following (i) to (iii).

R$^{26}$ and R$^{27}$ are groups respectively and independently selected from the above-mentioned groups R$^{24}$ and R$^{25}$, and are respectively and independently any group defined in the following (i) to (iii):

(i) a hydrogen atom, (ii) a group composed of carbon atoms and hydrogen atoms (which may also form a ring structure by bonding with ring A), in which the atom at the α position (atom that forms the R$^{26}$ and R$^{27}$ that is bonded to the aromatic ring of ring A) is a carbon atom, and the carbon atom is a primary or secondary carbon atom (namely, representing a carbon atom of a methyl group or carbon atom that forms a —CH$_2$— bond), provided that in the case the R$^{26}$ and/or R$^{27}$ form a saturated and/or unsaturated condensed ring structure with an aromatic ring and the condensed ring has six members or less, the carbon at the α position may be a tertiary or quaternary carbon atom as in, for example, the case of the following formula (36) or formula (37), and in the case the carbon atom at the α position forms a double bond or triple bond with an atom at the β position (adjacent to an atom that forms the R$^{26}$ and R$^{27}$ that is bonded to the aromatic ring of ring A) as well, the carbon at the α position may be a tertiary or quaternary carbon atom,

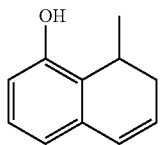
(36)

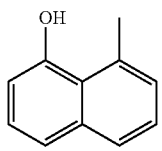
(37)

(iii) a group composed of carbon atoms, hydrogen atoms and oxygen atoms (representing, for example, an ether group composed of aliphatic groups, an ether group composed of aromatic groups or an ether group composed of aliphatic groups and aromatic groups, but not having an alcoholic OH group, a carbonyl group, an ester group, a carboxyl group or a methine group on a terminal thereof), in which the atom at the α position (atom that forms the $R^{26}$ and $R^{27}$ that is bonded to the aromatic ring of ring A) is a carbon atom or an oxygen atom, and in the case of a carbon atom, the carbon atom is a primary or secondary carbon atom (namely, a carbon atom of a methyl group or a carbon atom that forms a —$CH_2$— bond), provided that in the case the $R^{26}$ and/or $R^{27}$ form a saturated and/or unsaturated condensed ring structure and the condensed ring has six members or less, the carbon at the α position may be a tertiary or quaternary carbon atom, and in the case the carbon atom at the α position forms a double bond or triple bond with an atom at the β position (adjacent to an atom that forms the $R^{26}$ and $R^{27}$ that is bonded to the aromatic ring of ring A) as well, the carbon at the α position may be a tertiary or quaternary carbon atom.

Active aromatic monohydroxy compounds in which the $R^{26}$ and the $R^{27}$ are hydrogen atoms are preferable, and examples of such aromatic monohydroxy compounds may include phenol, methylphenol (including isomers), ethylphenol (including isomers), 2-n-propylphenol (including isomers), 2-n-butylphenol (including isomers), 2-n-pentylphenol (including isomers), 2-n-hexylphenol (including isomers), 2-n-heptylphenol (including isomers), 2-n-octylphenol (including isomers), 2-n-nonylphenol (including isomers), 2-n-decylphenol (including isomers), 2-n-dodecylphenol (including isomers), 2-n-octadecylphenol (including isomers), 3-propylphenol (including isomers), 3-butylphenol (including isomers), 3-pentylphenol (including isomers), 3-hexylphenol (including isomers), 3-heptylphenol (including isomers), 3-octylphenol (including isomers), 3-nonylphenol (including isomers), 3-decylphenol (including isomers), 3-dodecylphenol (including isomers), 3-octadecylphenol (including isomers), 4-propylphenol (including isomers), 4-butylphenol (including isomers), 4-pentylphenol (including isomers), 4-hexylphenol (including isomers), 4-heptylphenol (including isomers), 4-octylphenol (including isomers), 4-nonylphenol (including isomers), 4-decylphenol (including isomers), 4-dodecylphenol (including isomers), 4-octadecylphenol (including isomers), dimethylphenol (including isomers), diethylphenol (including isomers), di(n-propyl) phenol (including isomers), di(n-butyl) phenol (including isomers), di(n-pentyl) phenol (including isomers), di(n-hexyl) phenol (including isomers), di(n-heptyl) phenol (including isomers), di(n-octyl) phenol (including isomers), di(n-nonyl) phenol (including isomers), di(n-decyl) phenol (including isomers), di(n-dodecyl) phenol (including isomers), di(n-octadecyl) phenol (including isomers), trimethylphenol (including isomers), triethylphenol (including isomers), tri(n-propyl) phenol (including isomers), tri(n-butyl) phenol (including isomers), tri(n-pentyl) phenol (including isomers), tri(n-hexyl) phenol (including isomers), tri(n-heptyl) phenol (including isomers), tri(n-octyl) phenol (including isomers), tri(n-nonyl) phenol (including isomers), tri(n-decyl) phenol (including isomers), tri(n-dodecyl) phenol (including isomers), tri(n-octadecyl) phenol (including isomers), (methoxymethyl) phenol, (ethoxymethyl) phenol, (propoxymethyl) phenol (including isomers), (butyloxymethyl) phenol (including isomers), (pentyloxymethyl) phenol (including isomers), (hexyloxymethyl) phenol (including isomers), (heptyloxymethyl) phenol (including isomers), (octyloxymethyl) phenol (including isomers), (nonyloxymethyl) phenol (including isomers), (decyloxymethyl) phenol (including isomers), (dodecyloxymethyl) phenol (including isomers), (octadecyloxymethyl) phenol (including isomers), (cyclopentyloxymethyl) phenol, (cyclohexyloxymethyl) phenol, (cycloheptyloxymethyl) phenol, (cyclooctyloxymethyl) phenol, (methylcyclopentyloxymethy) phenol (including isomers), (ethylcyclopentyloxymethyl) phenol (including isomers), (methylcyclohexyloxymethyl) phenol (including isomers), (ethylcyclohexyloxymethyl) phenol (including isomers), (propylcyclohexyloxymethyl) phenol (including isomers), (butylcyclohexyloxymethyl) phenol (including isomers), (pentylcyclohexyloxymethyl) phenol (including isomers), (hexylcyclohexyloxymethyl) phenol (including isomers), (dimethylcyclohexyloxymethyl) phenol (including isomers), (diethylcyclohexyloxymethyl) phenol (including isomers), (dibutylcyclohexyloxymethyl) phenol (including isomers), (phenoxymethyl) phenol, (methylphenoxymethyl) phenol (including isomers), (ethylphenoxymethyl) phenol (including isomers), (propylphenoxymethyl) phenol (including isomers), (butylphenoxymethyl) phenol (including isomers), (pentylphenoxymethyl) phenol (including isomers), (hexylphenoxymethyl) phenol (including isomers), (heptylphenoxymethyl) phenol (including isomers), (octylphenoxymethyl) phenol (including isomers), (nonylphenoxymethyl) phenol (including isomers), (decylphenoxymethyl) phenol (including isomers), (phenylphenoxymethyl) phenol (including isomers), (dimethylphenoxymethyl) phenol (including isomers), (diethylphenoxymethyl) phenol (including isomers), (dipropylphenoxymethyl) phenol (including isomers), (dibutylphenoxymethyl) phenol (including isomers), (dipentylphenoxymethyl) phenol (including isomers), (dihexylphenoxymethyl) phenol (including isomers), (diheptylphenoxymethyl) phenol (including isomers), (diphenylphenoxymethyl) phenol (including isomers), (trimethylphenoxymethyl) phenol (including isomers), (triethylphenoxymethyl) phenol (including isomers), (tripropylphenoxymethyl) phenol (including isomers), (tributylphenoxymethyl) phenol (including isomers), (phenylmethoxymethyl) phenol (including isomers), (phenylethoxymethyl) phenol (including isomers), (phenylpropyloxymethyl) phenol (including isomers), (phenylbutyloxymethyl) phenol (including isomers), (phenylpentyloxymethyl) phenol (including isomers), (phenylhexyloxymethyl) phenol (including isomers), (phenylheptyloxymethyl) phenol (including isomers), (phenyloctyloxymethyl) phenol (including isomers), (phenylnonyloxymethyl) phenol (including isomers), di(methoxymethyl) phenol, di(ethoxymethyl) phenol, di(propoxymethyl) phenol (including isomers), di(butyloxymethyl) phenol (including isomers), di(pentyloxymethyl) phenol (including isomers), di(hexyloxymethyl) phenol (including isomers), di(heptyloxymethyl) phenol (including isomers), di(octyloxymethyl) phenol (including isomers), di(nonyloxymethyl) phenol (including isomers), di(decyloxymethyl) phenol (including isomers), di(dodecyloxymethyl) phenol (including isomers), di(octadecyloxymethyl) phenol (including isomers), di(cyclopentyloxymethyl) phenol (including isomers), di(cyclohexyloxymethyl) phenol (including isomers), di(cycloheptyloxymethyl) phenol (including isomers), di(cyclooctyloxymethyl) phenol (including isomers), di(methylcyclopentyloxymethy) phenol (including isomers), di(ethylcyclopentyloxymethyl) phenol (including isomers), di(methylcyclohexyloxymethyl) phenol (including isomers), di(ethylcyclohexyloxymethyl) phenol (including isomers), di(propylcyclohexyloxymethyl) phenol (including isomers), di(butylcyclohexyloxymethyl) phenol (including isomers), di(pentylcyclohexyloxymethyl) phenol (including isomers), di(hexylcyclohexyloxymethyl) phenol (including isomers), bis(dimethylcyclohexyloxymethyl) phenol (including isomers), bis(diethylcyclohexyloxymethyl) phenol (including isomers), bis(dibutylcyclohexyloxymethyl) phenol (including isomers), di(phenoxymethyl) phenol, di(methylphenoxymethyl) phenol (including isomers), di(ethylphenoxymethyl) phenol (including isomers), di(propylphenoxymethyl) phenol (including isomers), di(butylphenoxymethyl) phenol (including isomers), di(pentylphenoxymethyl) phenol (including isomers), di(hexylphenoxymethyl) phenol (including isomers), di(heptylphenoxymethyl) phenol (including isomers), di(octylphenoxymethyl) phenol (including isomers), di(nonylphenoxymethyl)phenol (including isomers), di(decylphenoxymethyl) phenol (including isomers), di(phenylphenoxymethyl) phenol (including isomers), bis(dimethylphenoxymethyl)phenol (including isomers), bis(diethylphenoxymethyl) phenol (including isomers), bis(dipropylphenoxymethyl) phenol (including isomers), bis(dibutylphenoxymethyl) phenol (including isomers), bis(dipentylphenoxymethyl) phenol (including isomers), bis(dihexylphenoxymethyl) phenol (including isomers), bis(diheptylphenoxymethyl) phenol (including isomers), bis(diphenylphenoxymethyl) phenol (including isomers), di(trimethylphenoxymethyl) phenol (including isomers), di(triethylphenoxymethyl) phenol (including isomers), di(tripropylphenoxymethyl) phenol (including isomers), di(tributylphenoxymethyl) phenol (including isomers), (phenylmethoxymethyl) phenol, di(phenylethoxymethyl) phenol (including isomers), di(phenylpropyloxymethyl) phenol (including isomers), di(phenylbutyloxymethyl) phenol (including isomers), di(phenylpentyloxymethyl) phenol (including isomers), di(phenylhexyloxymethyl) phenol (including isomers), di(phenylheptyloxymethyl) phenol (including isomers), di(phenyloctyloxymethyl) phenol (including isomers), di(phenylnonyloxymethyl) phenol (including isomers), tri(methoxymethyl) phenol, tri(ethoxymethyl) phenol, tri(propoxymethyl) phenol (including isomers), tri(butyloxymethyl) phenol (including isomers), tri(pentyloxymethyl) phenol (including isomers), tri(hexyloxymethyl) phenol (including isomers), tri(heptyloxymethyl) phenol (including isomers), tri(octyloxymethyl) phenol (including isomers), tri(nonyloxymethyl) phenol (including isomers), tri(decyloxymethyl) phenol (including isomers), tri(dodecyloxymethyl) phenol (including isomers), tri(octadecyloxymethyl) phenol (including isomers), tri(cyclopentyloxymethyl) phenol (including isomers), tri(cyclohexyloxymethyl) phenol (including isomers), tri(cycloheptyloxymethyl) phenol (including isomers), tri(cyclooctyloxymethyl) phenol (including isomers), tri(methylcyclopentyloxymethy) phenol (including isomers), tri(ethylcyclopentyloxymethyl )phenol (including isomers), tri(methylcyclohexyloxymethyl) phenol (including isomers), tri(ethylcyclohexyloxymethyl) phenol (including isomers), tri(propylcyclohexyloxymethyl) phenol (including isomers), tri(butylcyclohexyloxymethyl) phenol (including isomers), tri(pentylcyclohexyloxymethyl) phenol (including isomers), tri(hexylcyclohexyloxymethyl) phenol (including isomers), bis(dimethylcyclohexyloxymethyl) phenol (including isomers), bis(diethylcyclohexyloxymethyl) phenol (including isomers), bis(dibutylcyclohexyloxymethyl) phenol (including isomers), tri(phenoxymethyl) phenol, tri(methylphenoxymethyl) phenol (including isomers), tri(ethylphenoxymethyl) phenol (including isomers), tri(propylphenoxymethyl) phenol (including isomers), tri(butylphenoxymethyl) phenol (including isomers), tri(pentylphenoxymethyl) phenol (including isomers), tri(hexylphenoxymethyl) phenol (including isomers), tri(heptylphenoxymethyl) phenol (including isomers), tri(octylphenoxymethyl) phenol (including isomers), tri(nonylphenoxymethyl) phenol (including isomers), tri(decylphenoxymethyl) phenol (including isomers), tri(phenylphenoxymethyl) phenol (including isomers), bis(dimethylphenoxymethyl) phenol (including isomers), bis(diethylphenoxymethyl) phenol (including isomers), bis(dipropylphenoxymethyl) phenol (including isomers), bis(dibutylphenoxymethyl) phenol (including isomers), bis(dipentylphenoxymethyl) phenol (including isomers), bis(dihexylphenoxymethyl) phenol (including isomers), bis(diheptylphenoxymethyl) phenol (including isomers), bis(diphenylphenoxymethyl) phenol (including isomers), tri(trimethylphenoxymethyl) phenol (including isomers), tri(triethylphenoxymethyl) phenol (including isomers), tri(tripropylphenoxymethyl) phenol (including isomers), tri(tributylphenoxymethyl) phenol (including isomers), tri(phenylmethoxymethyl) phenol, tri(phenylethoxymethyl) phenol (including isomers), tri(phenylpropyloxymethyl) phenol (including isomers), tri(phenylbutyloxymethyl) phenol (including isomers), tri(phenylpentyloxymethyl) phenol (including isomers), tri(phenylhexyloxymethyl) phenol (including isomers), tri(phenylheptyloxymethyl) phenol (including isomers), tri(phenyloctyloxymethyl) phenol (including isomers), tri(phenylnonyloxymethyl) phenol (including isomers), (phenylmethyl) phenol (including isomers), ((methylphenyl)methyl) phenol (including isomers), ((ethylphenyl)methyl) phenol (including isomers), ((propylphenyl)methyl) phenol (including isomers), ((butylphenyl)methyl) phenol (including isomers), ((pentylphenyl)methyl) phenol (including isomers), ((hexylphenyl)methyl) phenol (including isomers), ((heptylphenyl)methyl) phenol (including isomers), ((octylphenyl)methyl) phenol (including isomers), ((nonylphenyl)methyl) phenol (including isomers), ((decylphenyl)methyl) phenol (including isomers), ((biphenyl)methyl) phenol (including isomers), ((dimethylphenyl)methyl) phenol (including isomers), ((diethylphenyl)methyl) phenol (including isomers), ((dipropylphenyl)methyl) phenol (including isomers), ((dibutylphenyl)methyl) phenol (including isomers), ((dipentylphenyl)methyl) phenol (including isomers), ((dihexylphenyl)methyl) phenol (including isomers), ((diheptylphenyl)methyl) phenol (including isomers), ((terphenyl)methyl) phenol (including isomers), ((trimethylphenyl)methyl) phenol (including isomers), ((triethylphenyl)methyl) phenol (including isomers), ((tripropylphenyl)methyl) phenol (including isomers), ((tributylphenyl)methyl) phenol (including isomers), di(phenylmethyl) phenol (including isomers), di((methylphenyl)methyl) phenol (including isomers), di((ethylphenyl)methyl) phenol (including isomers), di((propylphenyl)methyl) phenol (including isomers), di((butylphenyl)methyl) phenol (including isomers), di((pentylphenyl)methyl) phenol (including isomers), di((hexylphenyl)methyl) phenol (including isomers), di((heptylphenyl)methyl) phenol (including isomers), di((octylphenyl)methyl) phenol (including isomers), di((nonylphenyl)methyl) phenol (including isomers), di((decylphenyl)methyl) phenol (including isomers), di((biphenyl)methyl) phenol (including isomers), di((dimethylphenyl)methyl) phenol (including isomers), di((diethylphenyl)methyl) phenol (including isomers), di((dipropylphenyl)methyl) phenol (including isomers), di((dibutylphenyl)methyl) phenol (including isomers), di((dipentylphenyl)methyl) phenol (including isomers), di((dihexylphenyl)methyl) phenol (including isomers), di((diheptylphenyl)methyl) phenol(including isomers), di((terphenyl)methyl) phenol (including isomers), di((trimethylphenyl)methyl) phenol (including isomers), di((triethylphenyl)methyl) phenol (including isomers), di((tripropylphenyl)methyl) phenol (including isomers), di((tributylphenyl)methyl) phenol (including isomers), tri (phenylmethyl) phenol (including isomers), tri((methylphenyl)methyl) phenol (including isomers), tri((ethylphenyl)methyl) phenol (including isomers), tri((propylphenyl)methyl) phenol (including isomers), tri((butylphenyl)methyl) phenol (including isomers), tri((pentylphenyl)methyl) phenol (including isomers), tri((hexylphenyl)methyl) phenol (including isomers), tri((heptylphenyl)methyl) phenol (including isomers), tri((octylphenyl)methyl) phenol (including isomers), tri((nonylphenyl)methyl) phenol (including isomers), tri((decylphenyl)methyl) phenol (including isomers), tri((biphenyl)methyl) phenol (including isomers), tri((dimethylphenyl)methyl) phenol (including isomers), tri((diethylphenyl)methyl) phenol (including isomers), tri ((dipropylphenyl)methyl) phenol (including isomers), tri ((dibutylphenyl)methyl) phenol (including isomers), tri ((dipentylphenyl)methyl) phenol (including isomers), tri ((dihexylphenyl)methyl) phenol (including isomers), tri ((diheptylphenyl)methyl) phenol (including isomers), tri ((terphenyl)methyl) phenol (including isomers), tri ((trimethylphenyl)methyl) phenol (including isomers), tri ((triethylphenyl)methyl) phenol (including isomers), tri ((tripropylphenyl)methyl) phenol (including isomers), tri ((tributylphenyl)methyl) phenol (including isomers), phenylethylphenol (including isomers), phenyl-n-propylphenol (including isomers), phenyl-n-butylphenol (including isomers), phenyl-n-pentylphenol (including isomers), phenyl-n-hexylphenol (including isomers), phenyl-n-heptylphenol (including isomers), phenyl-n-octylphenol (including isomers), phenyl-n-nonylphenol (including isomers), methoxyphenol (including isomers), ethoxyphenol (including isomers), propyloxyphenol (including isomers), butyloxyphenol (including isomers), pentyloxyphenol (including isomers), hexyloxyphenol (including isomers), heptyloxyphenol (including isomers), octyloxyphenol (including isomers), nonyloxyphenol (including isomers), decyloxyphenol (including isomers), dodecyloxyphenol (including isomers), octadecyloxyphenol (including isomers), cyclopentyloxyphenol (including isomers), cyclohexyloxyphenol (including isomers), cycloheptyloxyphenol (including isomers), cyclooctyloxyphenol (including isomers), (methylcyclopentyloxy) phenol (including isomers), (ethylcyclopentyloxy) phenol (including isomers), (methylcyclohexyloxy) phenol (including isomers), (ethylcyclohexyloxy) phenol (including isomers), (propylcyclohexyloxy) phenol (including isomers), (butylcyclohexyloxy) phenol (including isomers), (pentylcyclohexyloxy) phenol (including isomers), (hexylcyclohexyloxy) phenol (including isomers), (dimethylcyclohexyloxy) phenol (including isomers), (diethylcyclohexyloxy) phenol (including isomers), (dibutylcyclohexyloxy) phenol (including isomers), phenyloxyphenol, (methylphenyloxy) phenol (including isomers), (ethylphenyloxy) phenol (including isomers), (propylphenyloxy) phenol (including isomers), (butylphenyloxy) phenol (including isomers), (pentylphenyloxy) phenol (including isomers), (hexylphenyloxy) phenol (including isomers), (heptylphenyloxy) phenol (including isomers), (octylphenyloxy) phenol (including isomers), (nonylphenyloxy) phenol (including isomers), (decylphenyloxy) phenol (including isomers), biphenyloxyphenol (including isomers), (dimethylphenyloxy) phenol (including isomers), (diethylphenyloxy) phenol (including isomers), (dipropylphenyloxy) phenol (including isomers), (dibutylphenyloxy) phenol (including isomers), (dipentylphenyloxy) phenol (including isomers), (dihexylphenyloxy) phenol (including isomers), (diheptylphenyloxy) phenol (including isomers), terphenyloxyphenol (including isomers), (trimethylphenyloxy) phenol (including isomers), (triethylphenyloxy) phenol (including isomers), (tripropylphenyloxy) phenol (including isomers), (tributylphenyloxy) phenol (including isomers), (phenylmethyloxy) phenol, (phenylethyloxy) phenol (including isomers), (phenylpropyloxy) phenol (including isomers), (phenylbutyloxy) phenol (including isomers), (phenylpentyloxy) phenol (including isomers), (phenylhexyloxy) phenol (including isomers), (phenylheptyloxy) phenol (including isomers), (phenyloctyloxy) phenol (including isomers), (phenylnonyloxy) phenol (including isomers), dimethoxyphenol (including isomers), diethoxyphenol (including isomers), dipropyloxyphenol (including isomers), dibutyloxyphenol (including isomers), dipentyloxyphenol (including isomers), dihexyloxyphenol (including isomers), diheptyloxyphenol (including isomers), dioctyloxyphenol (including isomers), dinonyloxyphenol (including isomers), didecyloxyphenol (including isomers), didodecyloxyphenol (including isomers), dioctadecyloxyphenol (including isomers), dicyclopentyloxyphenol (including isomers), dicyclohexyloxyphenol (including isomers), dicycloheptyloxyphenol (including isomers), dicyclooctyloxyphenol (including isomers), di(methylcyclopentyloxy) phenol (including isomers), di(ethylcyclopentyloxy) phenol (including isomers), di(methylcyclohexyloxy) phenol (including isomers), di(ethylcyclohexyloxy) phenol (including isomers), di(propylcyclohexyloxy) phenol (including isomers), di(butylcyclohexyloxy) phenol (including isomers), di(pentylcyclohexyloxy) phenol (including isomers), di(hexylcyclohexyloxy) phenol (including isomers), bis(dimethylcyclohexyloxy) phenol (including isomers), bis (diethylcyclohexyloxy) phenol (including isomers), bis (dibutylcyclohexyloxy) phenol (including isomers), phenyloxyphenol, di(methylphenyloxy) phenol (including isomers), di(ethylphenyloxy) phenol (including isomers), di(propylphenyloxy) phenol (including isomers), di(butylphenyloxy) phenol (including isomers), di(pentylphenyloxy) phenol (including isomers), di(hexylphenyloxy) phenol (including isomers), di(heptylphenyloxy) phenol (including isomers), di(octylphenyloxy) phenol (including isomers), di(nonylphenyloxy) phenol (including isomers), di(decylphenyloxy) phenol (including isomers), dibiphenyloxyphenol (including isomers), bis(dimethylphenyloxy) phenol (including isomers), bis(diethylphenyloxy) phenol (including isomers), bis(dipropylphenyloxy) phenol (including isomers), bis(dibutylphenyloxy) phenol (including isomers), bis (dipentylphenyloxy) phenol (including isomers), bis (dihexylphenyloxy) phenol (including isomers), bis (diheptylphenyloxy) phenol (including isomers), diterphenyloxyphenol (including isomers), di(trimethylphenyloxy) phenol (including isomers), di(triethylphenyloxy) phenol (including isomers), di(tripropylphenyloxy) phenol (including isomers), di(tributylphenyloxy) phenol (including isomers), (phenylmethyloxy) phenol, di(phenylethyloxy)

phenol (including isomers), di(phenylpropyloxy) phenol (including isomers), di(phenylbutyloxy) phenol (including isomers), di(phenylpentyloxy) phenol (including isomers), di(phenylhexyloxy) phenol (including isomers), di(phenylheptyloxy) phenol (including isomers), di(phenyloctyloxy) phenol (including isomers), di(phenylnonyloxy) phenol (including isomers), trimethoxyphenol (including isomers), triethoxyphenol (including isomers), tripropyloxyphenol (including isomers), tributyloxyphenol (including isomers), tripentyloxyphenol (including isomers), trihexyloxyphenol (including isomers), triheptyloxyphenol (including isomers), trioctyloxyphenol (including isomers), trinonyloxyphenol (including isomers), tridecyloxyphenol (including isomers), tridodecyloxyphenol (including isomers), trioctadecyloxyphenol (including isomers), tricyclopentyloxyphenol (including isomers), tricyclohexyloxyphenol (including isomers), tricycloheptyloxyphenol (including isomers), tricyclooctyloxyphenol (including isomers), tri(methylcyclopentyloxy) phenol (including isomers), tri(ethylcyclopentyloxy) phenol (including isomers), tri(methylcyclohexyloxy) phenol (including isomers), tri(ethylcyclohexyloxy) phenol (including isomers), tri(propylcyclohexyloxy) phenol (including isomers), tri(butylcyclohexyloxy) phenol (including isomers), tri(pentylcyclohexyloxy) phenol (including isomers), tri(hexylcyclohexyloxy) phenol (including isomers), tri(dimethylcyclohexyloxy) phenol (including isomers), tri(diethylcyclohexyloxy) phenol (including isomers), tri(dibutylcyclohexyloxy) phenol (including isomers), phenoxyphenol, tri(methylphenyloxy) phenol (including isomers), tri(ethylphenyloxy) phenol (including isomers), tri(propylphenyloxy) phenol (including isomers), tri(butylphenyloxy) phenol (including isomers), tri(pentylphenyloxy) phenol (including isomers), tri(hexylphenyloxy) phenol (including isomers), tri(heptylphenyloxy) phenol (including isomers), tri(octylphenyloxy) phenol (including isomers), tri(nonylphenyloxy) phenol (including isomers), tri(decylphenyloxy) phenol (including isomers), tribiphenyloxyphenol (including isomers), tri(dimethylphenyloxy) phenol (including isomers), tri(diethylphenyloxy) phenol (including isomers), tri(dipropylphenyloxy) phenol (including isomers), tri(dibutylphenyloxy) phenol (including isomers), tri(dipentylphenyloxy) phenol (including isomers), tri(dihexylphenyloxy) phenol (including isomers), tri(diheptylphenyloxy) phenol (including isomers), triterphenyloxyphenol (including isomers), tri(trimethylphenyloxy) phenol (including isomers), tri(triethylphenyloxy) phenol (including isomers), tri(tripropylphenyloxy) phenol (including isomers), tri(tributylphenyloxy) phenol (including isomers), (phenylmethyloxy) phenol, tri(phenylethyloxy) phenol (including isomers), tri(phenylpropyloxy) phenol (including isomers), tri(phenylbutyloxy) phenol (including isomers), tri(phenylpentyloxy) phenol (including isomers), tri(phenylhexyloxy) phenol (including isomers), tri(phenylheptyloxy) phenol (including isomers), tri(phenyloctyloxy) phenol (including isomers), tri(phenylnonyloxy) phenol (including isomers), naphthol (including isomers), phenoxyphenol (including isomers), and diphenoxyphenol (including isomers). Particularly preferable examples include aromatic monohydroxy compounds in which the $R^{26}$ and the $R^{27}$ are hydrogen atoms, while other substituents are linear and/or cyclic saturated alkyl groups, naphthol (including isomers), phenoxyphenol (including isomers) and diphenoxyphenol (including isomers).

As has been previously described, an aromatic hydroxy compound having a specific structure is used preferably from the viewpoint of reactivity in the reaction between a compound having ureido groups and/or an N-substituted carbamic acid-O—$R^2$ ester and an aromatic hydroxy composition (namely, an esterification reaction or transesterification reaction).

Conversely, the inventors of the present invention found that, in the case a group bonded to the atom at the α position of a substituent of at least one ortho position of the aromatic hydroxy compound is a bulky substituent, the formation rate of N-substituted carbamic acid-O-aryl ester decreases considerably. More specifically, this refers to an aromatic hydroxy compound in which a substituent in which the atom at the α position is a tertiary or quaternary carbon atom or tertiary nitrogen atom is bonded to at least one ortho position relative to a hydroxy group of the aromatic hydroxy compound. The demonstration of such an effect by this aromatic hydroxy compound is also not found in the prior art. Hereinafter, an aromatic hydroxy compound for which the formation rate of N-substituted carbamic acid-O—Ar ester is low is frequently referred to as a low activity aromatic hydroxy compound.

Moreover, as a result of focusing on the fact that the formation rate of N-substituted carbamic acid-O-aryl ester differs depending on the type of aromatic hydroxy compound as described above, the inventors of the present invention conceived of and completed an N-substituted carbamic acid-O-aryl ester production method that uses an aromatic hydroxy composition containing a plurality of types of aromatic hydroxy compounds.

The aromatic hydroxy compound explained below is a low activity aromatic hydroxy compound that is used in a N-substituted carbamic acid-O-aryl ester production method which uses an aromatic hydroxy composition containing a plurality of types of aromatic hydroxy compounds, and which uses an aromatic hydroxy composition that contains an active aromatic hydroxy compound and a low activity hydroxy compound. Namely, the production method is an N-substituted carbamic acid-O-ester production method that uses an aromatic hydroxy composition containing an aromatic hydroxy compound having a high formation rate of N-substituted carbamic acid-O-aryl ester as indicated above (the above-mentioned active aromatic hydroxy compound) and an aromatic hydroxy compound having a low formation rate of N-substituted carbamic acid-O-ester (frequently referred to as a low activity aromatic hydroxy compound).

The low activity aromatic hydroxy compound described above is represented by the following formula (39):

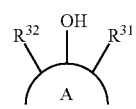

(39)

(wherein ring A represents an organic group, which contains an aromatic group substituted by b number of hydroxy groups at arbitrary locations that maintain aromatic properties, may be a single or multiple heterocyclic ring, and may be substituted by other substituents, and an integral number of from 1 to 6 OH groups represented by formula (39) are substituted on an aromatic ring contained in the ring A (namely, the formula (39) constitutes a portion of the ring A, and an integral number of 1 to 6 structures to which the above-mentioned $R^{31}$ group, OH group and $R^{32}$ group are adjacent are respectively present on the ring A).

$R^{31}$ and $R^{32}$ are groups that substitute the aromatic ring to which the hydroxy group is bonded, and which are bonded to a carbon atom adjacent to the carbon atom to which the hydroxy group is bonded. An integral number of from 1 to 6 hydroxy groups are bonded to ring A, and thus, a maximum integral number of from 1 to 6 of $R^{31}$ and $R^{32}$ are respectively bonded to ring A. An aromatic hydroxy compound represented by formula (39) is an aromatic hydroxy compound that contains an integral number of carbon atoms within a range of from 6 to 50.

Examples of substituents that substitute an aromatic group of the aromatic hydroxy compound represented by formula (39) above (groups $R^{31}$ and $R^{32}$ will be subsequently explained in detail) may include groups selected from a hydrogen atom, a halogen atom, an aliphatic group and an aromatic group that are composed of an acyclic hydrocarbon group or a cyclic hydrocarbon group (such as a monocyclic hydrocarbon group, a condensed polycyclic hydrocarbon group, a crosslinked cyclic hydrocarbon group, a spirohydrocarbon group, a ring-assembling hydrocarbon group, a cyclic hydrocarbon group having a side chain, a heterocyclic group, a heterocyclic spiro group, a hetero-crosslinked ring group or a heterocyclic group), a group bonded from one or more types of groups selected from the above-mentioned acyclic hydrocarbon groups and cyclic hydrocarbon groups, and groups in which the above-mentioned groups are bonded through a covalent bond with a specific non-metal atom (carbon, oxygen, nitrogen, sulfur or silicon). In addition, a covalent bond with a specific non-metal atom (carbon, oxygen, nitrogen, sulfur or silicon) as described above is in a state in which the above-mentioned groups are bonded by a covalent bond with, for example, groups represented by the above-mentioned formulas (8) to (11) and (13) to (16).

Among these substituents, examples of substituents that can be preferably used in the present embodiment in consideration of less susceptibility to the occurrence of side reactions include groups selected from the group consisting of acyclic hydrocarbon groups and cyclic hydrocarbon groups (such as a monocyclic hydrocarbon group, a condensed polycyclic hydrocarbon group, a crosslinked cyclic hydrocarbon group, a spirohydrocarbon group, a ring-assembling hydrocarbon group or a cyclic hydrocarbon group having a side chain), and groups bonded to at least one type of group selected from this group (mutually substituted groups).

In addition, in the case of transferring a composition containing a compound having ureido groups at a high temperature or in the case of reacting a compound having ureido groups and/or an N-substituted carbamic acid-O—$R^2$ ester and an aromatic hydroxy composition to obtain an N-substituted carbamic acid-O-aryl ester at a high temperature, ring A of the aromatic hydroxy compound is preferably an aromatic hydroxy compound composed of a group having at least one inactive substituent (including hydrogen atoms) in addition to the aromatic group and hydroxy groups bonded to the aromatic group (herein an inactive substituent refers to a group in which the inactive substituent does not contain active hydrogen as previously described, although it may have an aromatic hydroxyl group).

In providing a more detailed explanation of the substituent, the aromatic hydroxy compound represented by formula (39) is an aromatic hydroxy compound having at least one substituent selected from the groups of substituents explained in the following (i) to (v) in addition to the aromatic group and hydroxy group bonded to the aromatic group (groups $R^{31}$ and $R^{32}$ will be subsequently explained in detail):

(i) a hydrogen atom,
(ii) a group composed of carbon atoms and hydrogen atoms (which may also form a ring structure by bonding with ring A), (iii) a group composed of carbon atoms, hydrogen atoms and oxygen atoms (representing, for example, an ether group composed of aliphatic groups, ether group composed of aromatic groups or ether group composed of aliphatic groups and aromatic groups, but excluding groups containing active hydrogen such as a carbonyl group, an ester group, a terminal methine group and an alcoholic OH group, a carboxyl group, a $NH_2$ group, a NH group, a NOH group, a SH group, a $SO_3H$ group or a SOH group), (iv) a halogen atom, and (v) a group composed of atoms selected from carbon atoms, hydrogen atoms, oxygen atoms, nitrogen atoms, sulfur atoms and halogen atoms (but excluding groups containing active hydrogen such as a carbonyl group, an ester group, a terminal methine group and an alcoholic OH group, a carboxyl group, a $NH_2$ group, a NH group, a NOH group, a SH group, a $SO_3H$ group or a SOH group).

$R^{31}$ and $R^{32}$ respectively and independently represent any of the groups defined in the following (i) to (viii), at least either one is a group defined in the following (vi) to (viii), and $R^{31}$ and $R^{32}$ may further form a condensed ring structure by bonding with ring A. In the relationship between ring A and the hydroxyl group in the above-mentioned formula (39), for example, although there are frequently cases in which the number of $R^{31}$ and $R^{32}$ groups bonded to a carbon adjacent to an OH group does not coincide with the number of the OH groups (as explained in the above-mentioned formula (32)), such cases are permitted provided that either $R^{31}$ or $R^{32}$ is a group defined in the following (vi) to (viii):

(i) a hydrogen atom, (ii) a group composed of carbon atoms and hydrogen atoms (which may also form a ring structure by bonding with ring A), in which the atom at the α position (atom that forms the $R^{31}$ and $R^{32}$ that is bonded to the aromatic ring of ring A) is a carbon atom, and the carbon atom is a primary or secondary carbon atom (namely, representing a carbon atom of a methyl group or a carbon atom that forms a —$CH_2$— bond), provided that in the case the $R^{31}$ and/or $R^{31}$ form a saturated and/or unsaturated condensed ring structure with ring A and the condensed ring has six members or less, the carbon at the α position may be a tertiary or quaternary carbon atom, and in the case the carbon atom at the α position forms a double bond or triple bond with an atom at the β position (adjacent to an atom that forms the $R^{31}$ and $R^{32}$ that is bonded to the aromatic ring of ring A) as well, the carbon at the α position may be a tertiary or quaternary carbon atom, (iii) a group composed of carbon atoms, hydrogen atoms and oxygen atoms (representing, for example, an ether group composed of aliphatic groups, an ether group composed of aromatic groups or an ether group composed of aliphatic groups and aromatic groups, but not having an alcoholic OH group, a carbonyl group, an ester group, a carboxyl group or a methine group on a terminal thereof), in which the atom at the α position (atom that forms the $R^{31}$ and $R^{32}$ that is bonded to the aromatic ring of ring A) is a carbon atom or oxygen atom, and in the case of a carbon atom, the carbon atom is a primary or secondary carbon atom (namely, a carbon atom of a methyl group or a carbon atom that forms a —$CH_2$— bond), provided that in the case the $R^{31}$ or $R^{32}$ form a saturated and/or unsaturated condensed ring structure with ring A and the condensed ring has six members or less, the carbon at the α position may be a tertiary or quaternary carbon atom, and in the case the carbon atom at the α position forms a double bond or triple bond with an atom at the β position (adjacent to an atom that forms the $R^{31}$ and $R^{32}$ that is bonded to the aromatic ring of ring A) as well, the carbon at the α position may be a tertiary or quaternary carbon atom, (iv) a halogen atom, (v) a group composed of atoms selected from carbon atoms, hydrogen atoms, oxygen atoms, nitrogen atoms, sulfur atoms and halogen atoms (but excluding groups containing active hydrogen such as an alcoholic OH group, a carbonyl group, an ester group, a carboxyl group, a terminal methine group, a $NH_2$ group, a NH group, a NOH group, a SH group, a $SO_3H$ group or a SOH group), in which the atom at the α position (atom that forms the $R^{31}$ and $R^{32}$ that is bonded to the aromatic ring of ring A) is a carbon atom, oxygen atom or sulfur atom, in the case of a carbon atom, the carbon atom is a primary or secondary carbon atom (namely, a carbon atom of a methyl group or a carbon atom that forms a —$CH_2$— bond), and in the case of a sulfur atom, the sulfur atom is a divalent sulfur atom (namely, a sulfur atom that forms an —S— bond), provided that in the case the $R^{31}$ or $R^{32}$ form a saturated and/or unsaturated condensed ring structure with ring A and the condensed ring has six members or less, the carbon at the α position may be a tertiary or quaternary carbon atom, and in the case the carbon atom at the α position forms a double bond or triple bond with an atom at the β position (adjacent to an atom that forms the $R^{31}$ and $R^{32}$ that is bonded to the aromatic ring of ring A) as well, the carbon at the α position may be a tertiary or quaternary carbon atom, (vi) a group composed of carbon atoms and hydrogen atoms (which may also form a ring structure by bonding with ring A), in which the atom at the α position (atom that forms the $R^{31}$ and $R^{32}$ that is bonded to the aromatic ring of ring A) is a carbon atom, and the carbon atom is a tertiary or quaternary carbon atom (namely, a carbon atom that forms a —CH— bond or carbon atom not bonded by hydrogen), provided that in the case the $R^{31}$ and/or $R^{31}$ form a saturated and/or unsaturated condensed ring structure with ring A, the condensed ring may have seven members or more, and in the case the carbon atom at the α position forms a double bond with an atom at the β position (adjacent to an atom that forms the $R^{31}$ and $R^{32}$ that is bonded to the aromatic ring of ring A), the carbon at the α position may be a quaternary carbon atom, but excluding the carbon at the α position forming a triple bond with the atom at the β position, (vii) a group composed of carbon atoms, hydrogen atoms and oxygen atoms (representing, for example, an ether group composed of aliphatic groups, an ether group composed of aromatic groups or an ether group composed of aliphatic groups and aromatic groups, but not having an alcoholic OH group, a carbonyl group, an ester group, a carboxyl group or a methine group on a terminal thereof), in which the atom at the α position (atom that forms the $R^{31}$ and $R^{32}$ that is bonded to the aromatic ring of ring A) is a carbon atom, and the carbon atom is a tertiary or quaternary carbon atom (namely, a carbon atom that forms a —CH— bond or carbon atom not bonded by hydrogen), provided that in the case the $R^{31}$ and/or $R^{32}$ form a saturated and/or unsaturated condensed ring structure with ring A, the condensed ring may have seven members or more, and in the case the carbon atom at the α position forms a double bond with an atom at the β position (adjacent to an atom that forms the $R^{31}$ and $R^{32}$ that is bonded to the aromatic ring of ring A), the carbon at the α position may be a quaternary carbon atom, but excluding the carbon at the α position forming a triple bond with the atom at the β position, and (viii) a group composed of atoms selected from carbon atoms, hydrogen atoms, oxygen atoms, nitrogen atoms, sulfur atoms and halogen atoms (but excluding groups containing active hydrogen such as an alcoholic OH group, a carbonyl group, an ester group, a carboxyl group, a terminal methine group, a $NH_2$ group, a NH group, a NOH group, a SH group, a $SO_3H$ group or a SOH group), in which the atom at the α position (atom that forms the $R^{31}$ and $R^{32}$ that is bonded to the aromatic ring of ring A) is a carbon atom or nitrogen atom, in the case of a carbon atom, the carbon atom is a tertiary or quaternary carbon atom (namely, a carbon atom that forms a —CH— bond or carbon atom not bonded by hydrogen), provided that in the case the $R^{31}$ and/or $R^{32}$ form a saturated and/or unsaturated condensed ring structure with ring A, the condensed ring may have seven members or more, and in the case the carbon atom at the α position forms a double bond with an atom at the β position (adjacent to an atom that forms the $R^{31}$ and $R^{32}$ that is bonded to the aromatic ring of ring A), the carbon at the α position may be a quaternary carbon atom, but excluding the carbon at the α position forming a triple bond with the atom at the β position, while in the case of a nitrogen atom, the nitrogen atom may be a tertiary nitrogen atom that bonds with the atom at the β position with a single bond.

In addition, ring A is preferably a structure that contains at least one structure selected from the group consisting of a benzene ring, a naphthalene ring and an anthracene ring. In consideration of the industrial use, the inactive aromatic hydroxy compound represented by the above-mentioned formula (39) is preferably an aromatic monohydroxy compound in which one or two aromatic hydroxyl groups are bonded to ring A (namely, b=1 or 2), and more preferably an aromatic monohydroxy compound in which one aromatic hydroxyl group is bonded to ring A, since they typically have low viscosity.

Although an explanation of a method for using an inactive aromatic hydroxy compound of the present embodiment will be provided later, in one aspect of the present embodiment, the aromatic hydroxy compound and isocyanate are separated by distillation, and the separated aromatic hydroxy compound may be recycled in the form of an aromatic hydroxy composition that is reacted with the compound having ureido groups. Separation is carried out using standard boiling point as an indicator, and the method is selected in accordance with the previously described definition.

In addition, when the above-mentioned active aromatic hydroxy compound and inactive aromatic hydroxyl compound are used as an aromatic hydroxy composition although it is easy to separate and purify the two components if the aromatic hydroxy compound is selected so that a relationship exists in which the standard boiling point of the active aromatic hydroxy compound is 10° C. or more higher than the standard boiling point of the inactive aromatic hydroxy compound, this is not required. In the case of using a plurality of active aromatic hydroxy compounds and a plurality of inactive aromatic hydroxy compounds, the aromatic hydroxy compounds are selected such that a relationship exists in which the standard boiling point of the active aromatic hydroxy compound having the lowest standard boiling point is 10° C. or more higher than the standard boiling point of the inactive aromatic hydroxy compound having the highest standard boiling point. In consideration of separation and purification, the number of types of active and low-active aromatic hydroxy compounds use is as low as possible, and for example, only one type each is used preferably.

Moreover, in consideration of the industrial use, the inactive aromatic hydroxy compound is preferably an easily acquirable aromatic monohydroxy compound. A preferable example of such an aromatic monohydroxy compound is an aromatic monohydroxy compound represented by the following formula (40):

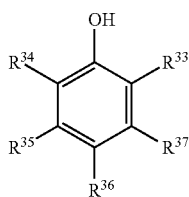

(40)

(wherein
R³⁵, R³⁶ and R³⁷ are groups respectively and independently selected from the above-mentioned groups R⁷ to R¹⁴ (excluding aryl groups having a hydroxy group), groups R³³ and R³⁴ are groups respectively and independently selected from the above-mentioned groups R³¹ and R³², and the aromatic hydroxy compound represented by formula (40) is an aromatic monohydroxy compound having an integral number of from 6 to 50 carbon atoms, provided that the total number of carbon atoms of groups R³³, R³⁴, R³⁵, R³⁶ and R³⁷ is an integer of from 0 to 44, and R³³ and R³⁴ are respectively and independently any group defined in the following (i) to (ii):

(i) a group composed of carbon atoms and hydrogen atoms (which may also form a ring structure by bonding with ring A), in which the atom at the α position (atom that forms the R³³ and R³⁴ that is bonded to the aromatic ring of ring A) is a carbon atom, and the carbon atom is a tertiary or quaternary carbon atom (namely, a carbon atom that forms a —CH— bond or carbon atom not bonded by hydrogen), provided that in the case the R³³ and/or R³⁴ form a saturated and/or unsaturated condensed ring structure with ring A, the condensed ring may have seven members or more, and in the case the carbon atom at the α position forms a double bond with an atom at the β position (adjacent to an atom that forms the R³³ and R³⁴ that is bonded to the aromatic ring of ring A), the carbon at the α position may be a quaternary carbon atom, but excluding the carbon at the α position forming a triple bond with the atom at the β position, and (ii) a group composed of carbon atoms, hydrogen atoms and oxygen atoms (representing, for example, an ether group composed of aliphatic groups, an ether group composed of aromatic groups or an ether group composed of aliphatic groups and aromatic groups, but not having an alcoholic OH group, a carbonyl group, an ester group, a carboxyl group or a methine group on a terminal thereof), in which the atom at the α position (atom that forms the R³³ and R³⁴ that is bonded to the aromatic ring of ring A) is a carbon atom, and the carbon atom is a tertiary or quaternary carbon atom (namely, a carbon atom that forms a —CH— bond or carbon atom not bonded by hydrogen), provided that in the case the R³³ and/or R³⁴ form a saturated and/or unsaturated condensed ring structure with ring A, the condensed ring may have seven members or more, and in the case the carbon atom at the α position forms a double bond with an atom at the β position (adjacent to an atom that forms the R³³ and R³⁴ that is bonded to the aromatic ring of ring A), the carbon at the α position may be a quaternary carbon atom, but excluding the carbon at the α position forming a triple bond with the atom at the β position.

Preferable examples of such aromatic monohydroxy compounds represented by formula (40) may include 2-tert-propylphenol (including isomers), 2-tert-butylphenol (including isomers), 2-tert-pentylphenol (including isomers), 2-tert-hexylphenol (including isomers), 2-tert-heptylphenol (including isomers), 2-tert-octylphenol (including isomers), 2-tert-nonylphenol (including isomers), 2-tert-decylphenol (including isomers), 2-tert-dodecylphenol (including isomers), 2-tert-octadecylphenol (including isomers), 2-sec-propylphenol (including isomers), 2-sec-butylphenol (including isomers), 2-sec-pentylphenol (including isomers), 2-sec-hexylphenol (including isomers), 2-sec-heptylphenol (including isomers), 2-sec-octylphenol (including isomers), 2-sec-nonylphenol (including isomers), 2-sec-decylphenol (including isomers), 2-sec-dodecylphenol (including isomers), 2-sec-octadecylphenol (including isomers), 2,4-di-tert-propylphenol (including isomers), 2,4-di-tert-butylphenol (including isomers), 2,4-di-tert-pentylphenol (including isomers), 2,4-di-tert-hexylphenol (including isomers), 2,4-di-tert-heptylphenol (including isomers), 2,4-di-tert-octylphenol (including isomers), 2,4-di-tert-nonylphenol (including isomers), 2,4-di-tert-decylphenol (including isomers), 2,4-di-tert-dodecylphenol (including isomers), 2,4-di-tert-octadecylphenol (including isomers), 2,4-di-sec-propylphenol (including isomers), 2,4-di-sec-butylphenol (including isomers), 2,4-di-sec-pentylphenol (including isomers), 2,4-di-sec-hexylphenol (including isomers), 2,4-di-sec-heptylphenol (including isomers), 2,4-di-sec-octylphenol (including isomers), 2,4-di-sec-nonylphenol (including isomers), 2,4-di-sec-decylphenol (including isomers), 2,4-di-sec-dodecylphenol (including isomers), 2,4-di-sec-octadecylphenol (including isomers), 2,6-di-tert-propylphenol (including isomers), 2,6-di-tert-butylphenol (including isomers), 2,6-di-tert-pentylphenol (including isomers), 2,6-di-tert-hexylphenol (including isomers), 2,6-di-tert-heptylphenol (including isomers), 2,6-di-tert-octylphenol (including isomers), 2,6-di-tert-nonylphenol (including isomers), 2,6-di-tert-decylphenol (including isomers), 2,6-di-tert-dodecylphenol (including isomers), 2,6-di-tert-octadecylphenol (including isomers), 2,6-di-sec-propylphenol (including isomers), 2,6-di-sec-butylphenol (including isomers), 2,6-di-sec-pentylphenol (including isomers), 2,6-di-sec-hexylphenol (including isomers), 2,6-di-sec-heptylphenol (including isomers), 2,6-di-sec-octylphenol (including isomers), 2,6-di-sec-nonylphenol (including isomers), 2,6-di-sec-decylphenol (including isomers), 2,6-di-sec-dodecylphenol (including isomers), 2,6-di-sec-octadecylphenol (including isomers), 2,4,6-tri-tert-propylphenol (including isomers), 2,4,6-tri-tert-butylphenol (including isomers), 2,4,6-tri-tert-pentylphenol (including isomers), 2,4,6-tri-tert-hexylphenol (including isomers), 2,4,6-tri-tert-heptylphenol (including isomers), 2,4,6-tri-tert-octylphenol (including isomers), 2,4,6-tri-tert-nonylphenol (including isomers), 2,4,6-tri-tert-decylphenol (including isomers), 2,4,6-tri-tert-dodecylphenol (including isomers), 2,4,6-tri-tert-octadecylphenol (including isomers), 2,4,6-tri-sec-propylphenol (including isomers), 2,4,6-tri-sec-butylphenol (including isomers), 2,4,6-tri-sec-pentylphenol (including isomers), 2,4,6-tri-sec-hexylphenol (including isomers), 2,4,6-tri-sec-heptylphenol (including isomers), 2,4,6-tri-sec-octylphenol (including isomers), 2,4,6-tri-sec-nonylphenol (including isomers), 2,4,6-tri-sec-decylphenol (including isomers), 2,4,6-tri-sec-dodecylphenol (including isomers), 2,4,6-tri-sec-octadecylphenol (including isomers), (2-methoxy-2-methylethyl) phenol, (2-ethoxy-2-methylethyl) phenol, (2-propoxy-2-methylethyl) phenol (including isomers), (2-butyloxy-2-methylethyl) phenol (including isomers), (2-pentyloxy-2-methylethyl) phenol (including isomers), (2-hexyloxy-2-methylethyl) phenol (including isomers), (2-heptyloxy-2-methylethyl) phenol (including isomers), (2-octyloxy-2-methylethyl) phenol (including isomers), (2-nonyloxy-2-methylethyl) phenol (including isomers), (2-decyloxy-2-methylethyl) phenol (including isomers), (2-dodecyloxy-2-methylethyl) phenol (including isomers), (2-octadecyloxy-2-methylethyl) phenol (including isomers), (2-cyclopentyloxy-2-methylethyl) phenol (including isomers), (2-cyclohexyloxy-2-methylethyl) phenol (including isomers), (2-cycloheptyloxy-2-methylethyl) phenol (including isomers), (2-cyclooctyloxy-2-methylethyl) phenol (including isomers), (2-(methylcyclopentyloxy)-2-methylethyl) phenol (including isomers), (2-(ethylcyclopentyloxy)-2-methylethyl) phenol (including isomers), (2-(methylcyclohexyloxy)-2-methylethyl) phenol (including isomers), (2-(ethylcyclohexyloxy)-2-methylethyl) phenol (including isomers), (2-(propylcyclohexyloxy)-2-methylethyl) phenol (including isomers), (2-(butylcyclohexyloxy)-2-methylethyl) phenol (including isomers), (2-(pentylcyclohexyloxy)-2-methylethyl) phenol (including isomers), (2-(hexylcyclohexyloxy)-2-methylethyl) phenol (including isomers), (2-(dimethylcyclohexyloxy)-2-methylethyl) phenol (including isomers), (2-(diethylcyclohexyloxy)-2-methylethyl) phenol (including isomers), (2-(dibutylcyclohexyloxy)-2-methylethyl) phenol (including isomers), (2-phenoxy-2-methylethyl) phenol (including isomers), (2-(methylphenoxy)-2-methylethyl) phenol (including isomers), (2-(ethylphenoxy)-2-methylethyl) phenol (including isomers), (2-(propylphenoxy)-2-methylethyl) phenol (including isomers), (2-(butylphenoxy)-2-methylethyl) phenol (including isomers), (2-(pentylphenoxy)-2-methylethyl) phenol (including isomers), (2-(hexylphenoxy)-2-methylethyl) phenol (including isomers), (2-(heptylphenoxy)-2-methylethyl) phenol (including isomers), (2-(octylphenoxy)-2-methylethyl) phenol (including isomers), (2-(nonylphenoxy)-2-methylethyl) phenol (including isomers), (2-(decylphenoxy)-2-methylethyl) phenol (including isomers), (2-(phenylphenoxy)-2-methylethyl) phenol (including isomers), (2-(dimethylphenoxy)-2-methylethyl) phenol (including isomers), (2-(diethylphenoxy)-2-methylethyl) phenol (including isomers), (2-(dipropylphenoxy)-2-methylethyl) phenol (including isomers), (2-(dibutylphenoxy)-2-methylethyl) phenol (including isomers), (2-(dipentylphenoxy)-2-methylethyl) phenol (including isomers), (2-(dihexylphenoxy)-2-methylethyl) phenol (including isomers), (2-(diheptylphenoxy)-2-methylethyl) phenol (including isomers), (2-(diphenylphenoxy)-2-methylethyl) phenol (including isomers), (2-(trimethylphenoxy)-2-methylethyl) phenol (including isomers), (2-(triethylphenoxy)-2-methylethyl) phenol (including isomers), (2-(tripropylphenoxy)-2-methylethyl) phenol (including isomers), (2-(tributylphenoxy)-2-methylethyl) phenol (including isomers), (2-(phenylmethoxy)-2-methylethyl) phenol (including isomers), (2-(phenylethoxy)-2-methylethyl) phenol (including isomers), (2-(phenylpropyloxy)-2-methylethyl) phenol (including isomers), (2-(phenylbutyloxy)-2-methylethyl) phenol (including isomers), (2-(phenylpentyloxy)-2-methylethyl) phenol (including isomers), (2-(phenylhexyloxy)-2-methylethyl) phenol (including isomers), (2-(phenylheptyloxy)-2-methylethyl) phenol (including isomers), (2-(phenyloctyloxy)-2-methylethyl) phenol (including isomers), (2-(phenylnonyloxy)-2-methylethyl) phenol (including isomers), (2-methoxy-2-methylpropyl) phenol, (2-ethoxy-2-methylpropyl) phenol, (2-propoxy-2-methylpropyl) phenol (including isomers), (2-butyloxy-2-methylpropyl) phenol (including isomers), (2-pentyloxy-2-methylpropyl) phenol (including isomers), (2-hexyloxy-2-methylpropyl) phenol (including isomers), (2-heptyloxy-2-methylpropyl) phenol (including isomers), (2-octyloxy-2-methylpropyl) phenol (including isomers), (2-nonyloxy-2-methylpropyl) phenol (including isomers), (2-decyloxy-2-methylpropyl) phenol (including isomers), (2-dodecyloxy-2-methylpropyl) phenol (including isomers), (2-octadecyloxy-2-methylpropyl) phenol (including isomers), (2-cyclopentyloxy-2-methylpropyl) phenol (including isomers), (2-cyclohexyloxy-2-methylpropyl) phenol (including isomers), (2-cycloheptyloxy-2-methylpropyl) phenol (including isomers), (2-cyclooctyloxy-2-methylpropyl) phenol (including isomers), (2-(methylcyclopentyloxy)-2-methylpropyl) phenol (including isomers), (2-(ethylcyclopentyloxy)-2-methylpropyl) phenol (including isomers), (2-(methylcyclohexyloxy)-2-methylpropyl) phenol (including isomers), (2-(ethylcyclohexyloxy)-2-methylpropyl) phenol (including isomers), (2-(propylcyclohexyloxy)-2-methylpropyl) phenol (including isomers), (2-(butylcyclohexyloxy)-2-methylpropyl) phenol (including isomers), (2-(pentylcyclohexyloxy)-2-methylpropyl) phenol (including isomers), (2-(hexylcyclohexyloxy)-2-methylpropyl) phenol (including isomers), (2-(dimethylcyclohexyloxy)-2-methylpropyl) phenol (including isomers), (2-(diethylcyclohexyloxy)-2-methylpropyl) phenol (including isomers), (2-(dibutylcyclohexyloxy)-2-methylpropyl) phenol (including isomers), (2-phenoxy-2-methylpropyl) phenol (including isomers), (2-(methylphenoxy)-2-methylpropyl) phenol (including isomers), (2-(ethylphenoxy)-2-methylpropyl) phenol (including isomers), (2-(propylphenoxy)-2-methylpropyl) phenol (including isomers), (2-(butylphenoxy)-2-methylpropyl) phenol (including isomers), (2-(pentylphenoxy)-2-methylpropyl) phenol (including isomers), (2-(hexylphenoxy)-2-methylpropyl) phenol (including isomers), (2-(heptylphenoxy)-2-methylpropyl) phenol (including isomers), (2-(octylphenoxy)-2-methylpropyl) phenol (including isomers), (2-(nonylphenoxy)-2-methylpropyl) phenol (including isomers), (2-(decylphenoxy)-2-methylpropyl) phenol (including isomers), (2-(phenylphenoxy)-2-methylpropyl) phenol (including isomers), (2-(dimethylphenoxy)-2-methylpropyl) phenol (including isomers), (2-(diethylphenoxy)-2-methylpropyl) phenol (including isomers), (2-(dipropylphenoxy)-2-methylpropyl) phenol (including isomers), (2-(dibutylphenoxy)-2-methylpropyl) phenol (including isomers), (2-(dipentylphenoxy)-2-methylpropyl) phenol (including isomers), (2-(dihexylphenoxy)-2-methylpropyl) phenol (including isomers), (2-(diheptylphenoxy)-2-methylpropyl) phenol (including isomers), (2-(diphenylphenoxy)-2-methylpropyl) phenol (including isomers), (2-(trimethylphenoxy)-2-methylpropyl) phenol (including isomers), (2-(triethylphenoxy)-2-methylpropyl) phenol (including isomers), (2-(tripropylphenoxy)-2-methylpropyl) phenol (including isomers), (2-(tributylphenoxy)-2-methylpropyl) phenol (including isomers), (2-(phenylmethoxy)-2-methylpropyl) phenol (including isomers), (2-(phenylethoxy)-2-methylpropyl) phenol (including isomers), (2-(phenylpropyloxy)-2-methylpropyl) phenol (including isomers), (2-(phenylbutyloxy)-2-methylpropyl) phenol (including isomers), (2-(phenylpentyloxy)-2-methylpropyl) phenol (including isomers), (2-(phenylhexyloxy)-2-methylpropyl) phenol (including isomers), (2-(phenylheptyloxy)-2-methylpropyl) phenol (including isomers), (2-(phenyloctyloxy)-2-methylpropyl) phenol (including isomers), (2-(phenylnonyloxy)-2-methylpropyl) phenol (including isomers), di(2-methoxy-2-methylethyl) phenol (including isomers), di(2-ethoxy-2-methylethyl) phenol (including isomers), di(2-propoxy-2-methylethyl) phenol (including isomers), di(2-butyloxy-2-methylethyl) phenol (including isomers), di(2-pentyloxy-2-methylethyl) phenol (including isomers), di(2-hexyloxy-2-methylethyl) phenol (including isomers), di(2-heptyloxy-2-methylethyl) phenol (including isomers), di(2-octyloxy-2-methylethyl) phenol (including isomers), di(2-nonyloxy-2-methylethyl) phenol (including isomers), di(2-decyloxy-2-methylethyl) phenol (including isomers), di(2-dodecyloxy-2-methylethyl) phenol (including isomers), di(2-octadecyloxy-2-methylethyl) phenol (including isomers), di(2-cyclopentyloxy-2-methylethyl) phenol (including isomers), di(2-cyclohexyloxy-2-methylethyl) phenol (including isomers), di(2-cycloheptyloxy-2-methylethyl) phenol (including isomers), di(2-cyclooctyloxy-2-methylethyl) phenol (including isomers), di(2-(methylcyclopentyloxy)-2-methylethyl) phenol (including isomers), di(2-(ethylcyclopentyloxy)-2-methylethyl) phenol (including isomers), di(2-(methylcyclohexyloxy)-2-methylethyl) phenol (including isomers), di(2-(ethylcyclohexyloxy)-2-methylethyl) phenol (including isomers), di(2-(propylcyclohexyloxy)-2-methylethyl) phenol (including isomers), di(2-(butylcyclohexyloxy)-2-methylethyl) phenol (including isomers), di(2-(pentylcyclohexyloxy)-2-methylethyl) phenol (including isomers), di(2-(hexylcyclohexyloxy)-2-methylethyl) phenol (including isomers), di(2-(dimethylcyclohexyloxy)-2-methylethyl) phenol (including isomers), di(2-(diethylcyclohexyloxy)-2-methylethyl) phenol (including isomers), di(2-(dibutylcyclohexyloxy)-2-methylethyl) phenol (including isomers), di(2-phenoxy-2-methylethyl) phenol (including isomers), di(2-(methylphenoxy)-2-methylethyl) phenol (including isomers), di(2-(ethylphenoxy)-2-methylethyl) phenol (including isomers), di(2-(propylphenoxy)-2-methylethyl) phenol (including isomers), di(2-(butylphenoxy)-2-methylethyl) phenol (including isomers), di(2-(pentylphenoxy)-2-methylethyl) phenol (including isomers), di(2-(hexylphenoxy)-2-methylethyl) phenol (including isomers), di(2-(heptylphenoxy)-2-methylethyl) phenol (including isomers), di(2-(octylphenoxy)-2-methylethyl) phenol (including isomers), di(2-(nonylphenoxy)-2-methylethyl) phenol (including isomers), di(2-(decylphenoxy)-2-methylethyl) phenol (including isomers), di(2-(phenylphenoxy)-2-methylethyl) phenol (including isomers), di(2-(dimethylphenoxy)-2-methylethyl) phenol (including isomers), di(2-(diethylphenoxy)-2-methylethyl) phenol (including isomers), di(2-(dipropylphenoxy)-2-methylethyl) phenol (including isomers), di(2-(dibutylphenoxy)-2-methylethyl) phenol (including isomers), di(2-(dipentylphenoxy)-2-methylethyl) phenol (including isomers), di(2-(dihexylphenoxy)-2-methylethyl) phenol (including isomers), di(2-(diheptylphenoxy)-2-methylethyl) phenol (including isomers), di(2-(diphenylphenoxy)-2-methylethyl) phenol (including isomers), di(2-(trimethylphenoxy)-2-methylethyl) phenol (including isomers), di(2-(triethylphenoxy)-2-methylethyl) phenol (including isomers), di(2-(tripropylphenoxy)-2-methylethyl) phenol (including isomers), di(2-(tributylphenoxy)-2-methylethyl) phenol (including isomers), di(2-(phenylmethoxy)-2-methylethyl) phenol (including isomers), di(2-(phenylethoxy)-2-methylethyl) phenol (including isomers), di(2-(phenylpropyloxy)-2-methylethyl) phenol (including isomers), di(2-(phenylbutyloxy)-2-methylethyl) phenol (including isomers), di(2-(phenylpentyloxy)-2-methylethyl) phenol (including isomers), di(2-(phenylhexyloxy)-2-methylethyl) phenol (including isomers), di(2-(phenylheptyloxy)-2-methylethyl) phenol (including isomers), di(2-(phenyloctyloxy)-2-methylethyl) phenol (including isomers), di(2-(phenylnonyloxy)-2-methylethyl) phenol (including isomers), di(2-methoxy-2-methylpropyl) phenol (including isomers), di(2-ethoxy-2-methylpropyl) phenol (including isomers), di(2-propoxy-2-methylpropyl) phenol (including isomers), di(2-butyloxy-2-methylpropyl) phenol (including isomers), di(2-pentyloxy-2-methylpropyl) phenol (including isomers), di(2-hexyloxy-2-methylpropyl) phenol (including isomers), di(2-heptyloxy-2-methylpropyl) phenol (including isomers), di(2-octyloxy-2-methylpropyl) phenol (including isomers), di(2-nonyloxy-2-methylpropyl) phenol (including isomers), di(2-decyloxy-2-methylpropyl) phenol (including isomers), di(2-dodecyloxy-2-methylpropyl) phenol (including isomers), di(2-octadecyloxy-2-methylpropyl) phenol (including isomers), di(2-cyclopentyloxy-2-methylpropyl) phenol (including isomers), di(2-cyclohexyloxy-2-methylpropyl) phenol (including isomers), di(2-cycloheptyloxy-2-methylpropyl) phenol (including isomers), di(2-cyclooctyloxy-2-methylpropyl) phenol (including isomers), di(2-(methylcyclopentyloxy)-2-methylpropyl) phenol (including isomers), di(2-(ethylcyclopentyloxy)-2-methylpropyl) phenol (including isomers), di(2-(methylcyclohexyloxy)-2-methylpropyl) phenol (including isomers), di(2-(ethylcyclohexyloxy)-2-methylpropyl) phenol (including isomers), di(2-(propylcyclohexyloxy)-2-methylpropyl) phenol (including isomers), di(2-(butylcyclohexyloxy)-2-methylpropyl) phenol (including isomers), di(2-(pentylcyclohexyloxy)-2-methylpropyl) phenol (including isomers), di(2-(hexylcyclohexyloxy)-2-methylpropyl) phenol (including isomers), di(2-(dimethylcyclohexyloxy)-2-methylpropyl) phenol (including isomers), di(2-(diethylcyclohexyloxy)-2-methylpropyl) phenol (including isomers), di(2-(dibutylcyclohexyloxy)-2-methylpropyl) phenol (including isomers), di(2-phenoxy-2-methylpropyl) phenol (including isomers), di(2-(methylphenoxy)-2-methylpropyl) phenol (including isomers), di(2-(ethylphenoxy)-2-methylpropyl) phenol (including isomers), di(2-(propylphenoxy)-2-methylpropyl) phenol (including isomers), di(2-(butylphenoxy)-2-methylpropyl) phenol (including isomers), di(2-(pentylphenoxy)-2-methylpropyl) phenol (including isomers), di(2-(hexylphenoxy)-2-methylpropyl) phenol (including isomers), di(2-(heptylphenoxy)-2-methylpropyl) phenol (including isomers), di(2-(octylphenoxy)-2-methylpropyl) phenol (including isomers), di(2-(nonylphenoxy)-2-methylpropyl) phenol (including isomers), di(2-(decylphenoxy)-2-methylpropyl) phenol (including isomers), di(2-(phenylphenoxy)-2-methylpropyl) phenol (including isomers), di(2-(dimethylphenoxy)-2-methylpropyl) phenol (including isomers), di(2-(diethylphenoxy)-2-methylpropyl) phenol (including isomers), di(2-(dipropylphenoxy)-2-methylpropyl) phenol (including isomers), di(2-(dibutylphenoxy)-2-methylpropyl) phenol (including isomers), di(2-(dipentylphenoxy)-2-methylpropyl) phenol (including isomers), di(2-(dihexylphenoxy)-2-methylpropyl) phenol (including isomers), di(2-(diheptylphenoxy)-2-methylpropyl) phenol (including isomers), di(2-(diphenylphenoxy)-2-methylpropyl) phenol (including isomers), di(2-(trimethylphenoxy)-2-methylpropyl) phenol (including isomers), di(2-(triethylphenoxy)-2-methylpropyl) phenol (including isomers), di(2-(tripropylphenoxy)-2-methylpropyl) phenol (including isomers), di(2-(tributylphenoxy)-2-methylpropyl) phenol (including isomers), di(2-(phenylmethoxy)-2-methylpropyl) phenol (including isomers), di(2-(phenylethoxy)-2-methylpropyl) phenol (including isomers), di(2-(phenylpropyloxy)-2-methylpropyl) phenol (including isomers), di(2-(phenylbutyloxy)-2-methylpropyl) phenol (including isomers), di(2-(phenylpentyloxy)-2-methylpropyl) phenol (including isomers), di(2-(phenylhexyloxy)-2-methylpropyl) phenol (including isomers), di(2-(phenylheptyloxy)-2-methylpropyl) phenol (including isomers), di(2-(phenyloctyloxy)-2-methylpropyl) phenol (including isomers), di(2-(phenylnonyloxy)-2-methylpropyl) phenol (including isomers), tri(2-methoxy-2-methylethyl) phenol (including isomers), tri(2-ethoxy-2-methylethyl) phenol (including isomers), tri(2-propoxy-2-methylethyl) phenol (including isomers), tri(2-butyloxy-2-methylethyl) phenol (including isomers), tri(2-pentyloxy-2-methylethyl) phenol (including isomers), tri(2-hexyloxy-2-methylethyl) phenol (including isomers), tri(2-heptyloxy-2- methylethyl) phenol (including isomers), tri(2-octyloxy-2-methylethyl) phenol (including isomers), tri(2-nonyloxy-2-methylethyl) phenol (including isomers), tri(2-decyloxy-2-methylethyl) phenol (including isomers), tri(2-dodecyloxy-2-methylethyl) phenol (including isomers), tri(2-octadecyloxy-2-methylethyl) phenol (including isomers), tri(2-cyclopentyloxy-2-methylethyl) phenol (including isomers), tri(2-cyclohexyloxy-2-methylethyl) phenol (including isomers), tri(2-cycloheptyloxy-2-methylethyl) phenol (including isomers), tri(2-cyclooctyloxy-2-methylethyl) phenol (including isomers), tri(2-(methylcyclopentyloxy)-2-methylethyl) phenol (including isomers), tri(2-(ethylcyclopentyloxy)-2-methylethyl) phenol (including isomers), tri(2-(methylcyclohexyloxy)-2-methylethyl) phenol (including isomers), tri(2-(ethylcyclohexyloxy)-2-methylethyl) phenol (including isomers), tri(2-(propylcyclohexyloxy)-2-methylethyl) phenol (including isomers), tri(2-(butylcyclohexyloxy)-2-methylethyl) phenol (including isomers), tri(2-(pentylcyclohexyloxy)-2-methylethyl) phenol (including isomers), tri(2-(hexylcyclohexyloxy)-2-methylethyl) phenol (including isomers), tri(2-(trimethylcyclohexyloxy)-2-methylethyl) phenol (including isomers), tri(2-(triethylcyclohexyloxy)-2-methylethyl) phenol (including isomers), tri(2-(tributylcyclohexyloxy)-2-methylethyl) phenol (including isomers), tri(2-phenoxy-2-methylethyl) phenol (including isomers), tri(2-(methylphenoxy)-2-methylethyl) phenol (including isomers), tri(2-(ethylphenoxy)-2-methylethyl) phenol (including isomers), tri(2-(propylphenoxy)-2-methylethyl) phenol (including isomers), tri(2-(butylphenoxy)-2-methylethyl) phenol (including isomers), tri(2-(pentylphenoxy)-2-methylethyl) phenol (including isomers), tri(2-(hexylphenoxy)-2-methylethyl) phenol (including isomers), tri(2-(heptylphenoxy)-2-methylethyl) phenol (including isomers), tri(2-(octylphenoxy)-2-methylethyl) phenol (including isomers), tri(2-(nonylphenoxy)-2-methylethyl) phenol (including isomers), tri(2-(decylphenoxy)-2-methylethyl) phenol (including isomers), tri(2-(phenylphenoxy)-2-methylethyl) phenol (including isomers), tri(2-(trimethylphenoxy)-2-methylethyl) phenol (including isomers), tri(2-(triethylphenoxy)-2-methylethyl) phenol (including isomers), tri(2-(tripropylphenoxy)-2-methylethyl) phenol (including isomers), tri(2-(tributylphenoxy)-2-methylethyl) phenol (including isomers), tri(2-(tripentylphenoxy)-2-methylethyl) phenol (including isomers), tri(2-(trihexylphenoxy)-2-methylethyl) phenol (including isomers), tri(2-(triheptylphenoxy)-2-methylethyl) phenol (including isomers), tri(2-(triphenylphenoxy)-2-methylethyl) phenol (including isomers), tri(2-(trimethylphenoxy)-2-methylethyl) phenol (including isomers), tri(2-(triethylphenoxy)-2-methylethyl) phenol (including isomers), tri(2-(tripropylphenoxy)-2-methylethyl) phenol (including isomers), tri(2-(tributylphenoxy)-2-methylethyl) phenol (including isomers), tri(2-(phenylmethoxy)-2-methylethyl) phenol (including isomers), tri(2-(phenylethoxy)-2-methylethyl) phenol (including isomers), tri(2-(phenylpropyloxy)-2-methylethyl) phenol (including isomers), tri(2-(phenylbutyloxy)-2-methylethyl) phenol (including isomers), tri(2-(phenylpentyloxy)-2-methylethyl) phenol (including isomers), tri(2-(phenylhexyloxy)-2-methylethyl) phenol (including isomers), tri(2-(phenylheptyloxy)-2-methylethyl) phenol (including isomers), tri(2-(phenyloctyloxy)-2-methylethyl) phenol (including isomers), tri(2-(phenylnonyloxy)-2-methylethyl) phenol (including isomers), tri(2-methoxy-2-methylpropyl) phenol (including isomers), tri(2-ethoxy-2-methylpropyl) phenol (including isomers), tri(2-propoxy-2-methylpropyl) phenol (including isomers), tri(2-butyloxy-2-methylpropyl) phenol (including isomers), tri(2-pentyloxy-2-methylpropyl) phenol (including isomers), tri(2-hexyloxy-2-methylpropyl) phenol (including isomers), tri(2-heptyloxy-2-methylpropyl) phenol (including isomers), tri(2-octyloxy-2-methylpropyl) phenol (including isomers), tri(2-nonyloxy-2-methylpropyl) phenol (including isomers), tri(2-decyloxy-2-methylpropyl) phenol (including isomers), tri(2-dodecyloxy-2-methylpropyl) phenol (including isomers), tri(2-octadecyloxy-2-methylpropyl) phenol (including isomers), tri(2-cyclopentyloxy-2-methylpropyl) phenol (including isomers), tri(2-cyclohexyloxy-2-methylpropyl) phenol (including isomers), tri(2-cycloheptyloxy-2-methylpropyl) phenol (including isomers), tri(2-cyclooctyloxy-2-methylpropyl) phenol (including isomers), tri(2-(methylcyclopentyloxy)-2-methylpropyl) phenol (including isomers), tri(2-(ethylcyclopentyloxy)-2-methylpropyl) phenol (including isomers), tri(2-(methylcyclohexyloxy)-2-methylpropyl) phenol (including isomers), tri(2-(ethylcyclohexyloxy)-2-methylpropyl) phenol (including isomers), tri(2-(propylcyclohexyloxy)-2-methylpropyl) phenol (including isomers), tri(2-(butylcyclohexyloxy)-2-methylpropyl) phenol (including isomers), tri(2-(pentylcyclohexyloxy)-2-methylpropyl) phenol (including isomers), tri(2-(hexylcyclohexyloxy)-2-methylpropyl) phenol (including isomers), tri(2-(trimethylcyclohexyloxy)-2-methylpropyl) phenol (including isomers), tri(2-(triethylcyclohexyloxy)-2-methylpropyl) phenol (including isomers), tri(2-(tributylcyclohexyloxy)-2-methylpropyl) phenol (including isomers), tri(2-phenoxy-2-methylpropyl) phenol (including isomers), tri(2-(methylphenoxy)-2-methylpropyl) phenol (including isomers), tri(2-(ethylphenoxy)-2-methylpropyl) phenol (including isomers), tri(2-(propylphenoxy)-2-methylpropyl) phenol (including isomers), tri(2-(butylphenoxy)-2-methylpropyl) phenol (including isomers), tri(2-(pentylphenoxy)-2-methylpropyl) phenol (including isomers), tri(2-(hexylphenoxy)-2-methylpropyl) phenol (including isomers), tri(2-(heptylphenoxy)-2-methylpropyl) phenol (including isomers), tri(2-(octylphenoxy)-2-methylpropyl) phenol (including isomers), tri(2-(nonylphenoxy)-2-methylpropyl) phenol (including isomers), tri(2-(decylphenoxy)-2-methylpropyl) phenol (including isomers), tri(2-(phenylphenoxy)-2-methylpropyl) phenol (including isomers), tri(2-(trimethylphenoxy)-2-methylpropyl) phenol (including isomers), tri(2-(triethylphenoxy)-2-methylpropyl) phenol (including isomers), tri(2-(tripropylphenoxy)-2-methylpropyl) phenol (including isomers), tri(2-(tributylphenoxy)-2-methylpropyl) phenol (including isomers), tri(2-(tripentylphenoxy)-2-methylpropyl) phenol (including isomers), tri(2-(trihexylphenoxy)-2-methylpropyl) phenol (including isomers), tri(2-(triheptylphenoxy)-2-methylpropyl) phenol (including isomers), tri(2-(triphenylphenoxy)-2-methylpropyl) phenol (including isomers), tri(2-(trimethylphenoxy)-2-methylpropyl) phenol (including isomers), tri(2-(triethylphenoxy)-2-methylpropyl) phenol (including isomers), tri(2-(tripropylphenoxy)-2-methylpropyl) phenol (including isomers), tri(2-(tributylphenoxy)-2-methylpropyl) phenol (including isomers), tri(2-(phenylmethoxy)-2-methylpropyl) phenol (including isomers), tri(2-(phenylethoxy)-2-methylpropyl) phenol (including isomers), tri(2-(phenylpropyloxy)-2-methylpropyl) phenol (including isomers), tri(2-(phenylbutyloxy)-2-methylpropyl) phenol (including isomers), tri(2-(phenylpentyloxy)-2-methylpropyl) phenol (including isomers), tri(2-(phenylhexyloxy)-2-methylpropyl) phenol (including isomers), tri(2-(phenylheptyloxy)-2-methylpropyl) phenol (including isomers), tri(2-(phenyloctyloxy)-2-methylpropyl) phenol (including isomers), tri(2-(phenylnonyloxy)-2-methylpropyl) phenol (including isomers), (dimethylamino) phenol, (diethylamino) phenol, (dipropylamino) phenol (including isomers), (dibutylamino) phenol (including isomers), (dipentylamino) phenol (including isomers), (dihexylamino) phenol (including isomers), (diheptylamino) phenol (including isomers), (dioctylamino) phenol (including isomers), (dinonylamino) phenol (including isomers), (didecylamino) phenol (including isomers), (didodecylamino) phenol (including isomers), (dioctadecylamino) phenol (including isomers), (2-phenyl-isopropyl) phenol (including isomers), (2-(methylphenyl)-isopropyl) phenol (including isomers), (2-(ethylphenyl)-isopropyl) phenol (including isomers), (2-(propylphenyl)-isopropyl) phenol (including isomers), (2-(butylphenyl)-isopropyl) phenol (including isomers), (2-(pentylphenyl)-isopropyl) phenol (including isomers), (2-(hexylphenyl)-isopropyl) phenol (including isomers), (2-(heptylphenyl)-isopropyl) phenol (including isomers), (2-(octylphenyl)-isopropyl) phenol (including isomers), (2-(nonylphenyl)-isopropyl) phenol (including isomers), (2-(decylphenyl)-isopropyl) phenol (including isomers), (2-(biphenyl)-isopropyl) phenol (including isomers), (2-(dimethylphenyl)-isopropyl) phenol (including isomers), (2-(diethylphenyl)-isopropyl) phenol (including isomers), (2-(dipropylphenyl)-isopropyl) phenol (including isomers), (2-(dibutylphenyl)-isopropyl) phenol (including isomers), (2-(dipentylphenyl)-isopropyl) phenol (including isomers), (2-(dihexylphenyl)-isopropyl) phenol (including isomers), (2-(diheptylphenyl)-isopropyl) phenol (including isomers), (2-(terphenyl)-isopropyl) phenol, (2-(trimethylphenyl)-isopropyl) phenol (including isomers), (2-(triethylphenyl)-isopropyl) phenol (including isomers), (2-(tripropylphenyl)-isopropyl) phenol (including isomers), (2-(tributylphenyl)-isopropyl) phenol (including isomers), di(2-phenyl-isopropyl) phenol (including isomers), di(2-(methylphenyl)-isopropyl) phenol (including isomers), di(2-(ethylphenyl)-isopropyl) phenol (including isomers), di(2-(propylphenyl)-isopropyl) phenol (including isomers), di(2-(butylphenyl)-isopropyl) phenol (including isomers), di(2-(pentylphenyl)-isopropyl) phenol (including isomers), di(2-(hexylphenyl)-isopropyl) phenol (including isomers), di(2-(heptylphenyl)-isopropyl) phenol (including isomers), di(2-(octylphenyl)-isopropyl) phenol (including isomers), di(2-(nonylphenyl)-isopropyl) phenol (including isomers), di(2-(decylphenyl)-isopropyl) phenol (including isomers), di(2-(biphenyl)-isopropyl) phenol (including isomers), di(2-(dimethylphenyl)-isopropyl) phenol (including isomers), di(2-(diethylphenyl)-isopropyl) phenol (including isomers), di(2-(dipropylphenyl)-isopropyl) phenol (including isomers), di(2-(dibutylphenyl)-isopropyl) phenol (including isomers), di(2-(dipentylphenyl)-isopropyl) phenol (including isomers), di(2-(dihexylphenyl)-isopropyl) phenol (including isomers), di(2-(diheptylphenyl)-isopropyl) phenol (including isomers), di(2-(terphenyl)-isopropyl) phenol, di(2-(trimethylphenyl)-isopropyl) phenol (including isomers), di(2-(triethylphenyl)-isopropyl) phenol (including isomers), di(2-(tripropylphenyl)-isopropyl) phenol (including isomers), di(2-(tributylphenyl)-isopropyl) phenol (including isomers), tri(2-phenyl-isopropyl) phenol (including isomers), tri(2-(methylphenyl)-isopropyl) phenol (including isomers), tri(2-(ethylphenyl)-isopropyl) phenol (including isomers), tri(2-(propylphenyl)-isopropyl) phenol (including isomers), tri(2-(butylphenyl)-isopropyl) phenol (including isomers), tri(2-(pentylphenyl)-isopropyl) phenol (including isomers), tri(2-(hexylphenyl)-isopropyl) phenol (including isomers), tri(2-(heptylphenyl)-isopropyl) phenol (including isomers), tri(2-(octylphenyl)-isopropyl) phenol (including isomers), tri(2-(nonylphenyl)-isopropyl) phenol (including isomers), tri(2-(decylphenyl)-isopropyl) phenol (including isomers), tri(2-(biphenyl)-isopropyl) phenol (including isomers), tri(2-(dimethylphenyl)-isopropyl) phenol (including isomers), tri(2-(diethylphenyl)-isopropyl) phenol (including isomers), tri(2-(dipropylphenyl)-isopropyl) phenol (including isomers), tri(2-(dibutylphenyl)-isopropyl) phenol (including isomers), tri(2-(dipentylphenyl)-isopropyl) phenol (including isomers), tri(2-(dihexylphenyl)-isopropyl) phenol (including isomers), tri(2-(diheptylphenyl)-isopropyl) phenol (including isomers), tri(2-(terphenyl)-isopropyl) phenol, tri(2-(trimethylphenyl)-isopropyl) phenol (including isomers), tri(2-(triethylphenyl)-isopropyl) phenol (including isomers), tri(2-(tripropylphenyl)-isopropyl) phenol (including isomers), tri(2-(tributylphenyl)-isopropyl) phenol (including isomers), (2-phenyl-sec-butyl) phenol (including isomers), (2-(methylphenyl)-sec-butyl) phenol (including isomers), (2-(ethylphenyl)-sec-butyl) phenol (including isomers), (2-(propylphenyl)-sec-butyl) phenol (including isomers), (2-(butylphenyl)-sec-butyl) phenol (including isomers), (2-(pentylphenyl)-sec-butyl) phenol (including isomers), (2-(hexylphenyl)-sec-butyl) phenol (including isomers), (2-(heptylphenyl)-sec-butyl) phenol (including isomers), (2-(octylphenyl)-sec-butyl) phenol (including isomers), (2-(nonylphenyl)-sec-butyl) phenol (including isomers), (2-(decylphenyl)-sec-butyl) phenol (including isomers), (2-(biphenyl)-sec-butyl) phenol (including isomers), (2-(dimethylphenyl)-sec-butyl) phenol (including isomers), (2-(diethylphenyl)-sec-butyl) phenol (including isomers), (2-(dipropylphenyl)-sec-butyl) phenol (including isomers), (2-(dibutylphenyl)-sec-butyl) phenol (including isomers), (2-(dipentylphenyl)-sec-butyl) phenol (including isomers), (2-(dihexylphenyl)-sec-butyl) phenol (including isomers), (2-(diheptylphenyl)-sec-butyl) phenol (including isomers), (2-(terphenyl)-sec-butyl) phenol, (2-(trimethylphenyl)-sec-butyl) phenol (including isomers), (2-(triethylphenyl)-sec-butyl) phenol (including isomers), (2-(tripropylphenyl)-sec-butyl) phenol (including isomers), (2-(tributylphenyl)-sec-butyl) phenol (including isomers), di(2-phenyl-sec-butyl) phenol (including isomers), di(2-(methylphenyl)-sec-butyl) phenol (including isomers), di(2-(ethylphenyl)-sec-butyl) phenol (including isomers), di(2-(propylphenyl)-sec-butyl) phenol (including isomers), di(2-(butylphenyl)-sec-butyl) phenol (including isomers), di(2-(pentylphenyl)-sec-butyl) phenol (including isomers), di(2-(hexylphenyl)-sec-butyl) phenol (including isomers), di(2-(heptylphenyl)-sec-butyl) phenol (including isomers), di(2-(octylphenyl)-sec-butyl) phenol (including isomers), di(2-(nonylphenyl)-sec-butyl) phenol (including isomers), di(2-(decylphenyl)-sec-butyl) phenol (including isomers), di(2-(biphenyl)-sec-butyl) phenol (including isomers), di(2-(dimethylphenyl)-sec-butyl) phenol (including isomers), di(2-(diethylphenyl)-sec-butyl) phenol (including isomers), di(2-(dipropylphenyl)-sec-butyl) phenol (including isomers), di(2-(dibutylphenyl)-isopropyl) phenol (including isomers), di(2-(dipentylphenyl)-sec-butyl) phenol (including isomers), di(2-(dihexylphenyl)-sec-butyl) phenol (including isomers), di(2-(diheptylphenyl)-sec-butyl) phenol (including isomers), di(2-(terphenyl)-sec-butyl) phenol, di(2-(trimethylphenyl)-sec-butyl) phenol (including isomers), di(2-(triethylphenyl)-sec-butyl) phenol (including isomers), di(2-(tripropylphenyl)-sec-butyl) phenol (including isomers), di(2-(tributylphenyl)-sec-butyl) phenol (including isomers), tri(2-phenyl-sec-butyl) phenol (including isomers), tri(2-(methylphenyl)-sec-butyl) phenol (including isomers), tri(2-(ethylphenyl)-sec-butyl) phenol (including isomers), tri(2-(propylphenyl)-sec-butyl) phenol (including isomers), tri(2-(butylphenyl)-sec-butyl) phenol (including isomers), tri(2-(pentylphenyl)-sec-butyl) phenol (including isomers), tri(2-(hexylphenyl)-sec-butyl) phenol (including isomers), tri(2-(heptylphenyl)-sec-butyl) phenol (including isomers), tri(2-(octylphenyl)-sec-butyl) phenol (including isomers), tri (2-(nonylphenyl)-sec-butyl) phenol (including isomers), tri (2-(decylphenyl)-sec-butyl) phenol (including isomers), tri (2-(biphenyl)-isopropyl) phenol (including isomers), tri(2-(dimethylphenyl)-isopropyl) phenol (including isomers), tri (2-(diethylphenyl)-sec-butyl) phenol (including isomers), tri (2-(dipropylphenyl)-sec-butyl) phenol (including isomers), tri(2-(dibutylphenyl)-sec-butyl) phenol (including isomers), tri(2-(dipentylphenyl)-sec-butyl) phenol (including isomers), tri(2-(dihexylphenyl)-sec-butyl) phenol (including isomers), tri(2-(diheptylphenyl)-sec-butyl) phenol (including isomers), tri(2-(terphenyl)-sec-butyl) phenol, tri(2-(trimethylphenyl)-sec-butyl) phenol (including isomers), tri(2-(triethylphenyl)-sec-butyl) phenol (including isomers), tri(2-(tripropylphenyl)-sec-butyl) phenol (including isomers), and tri(2-(tributylphenyl)-sec-butyl) phenol (including isomers).

More preferable examples thereof may include aromatic monohydroxy compounds in which groups $R^{33}$, $R^{34}$, $R^{35}$, $R^{36}$ and $R^{37}$ are linear and/or cyclic saturated alkyl groups, and in which at least one of $R^{33}$ and $R^{34}$ has a tertiary or quaternary carbon atom for the carbon atom at the α position.

<Carbonic Acid Derivative>

The carbonic acid derivative in the present embodiment refers to a compound represented by the following formula (19). In the case of using the composition for transfer and storage of the compound having the ureido groups in an N-substituted carbamic acid-O—$R^2$ ester production step or N-substituted carbamic acid-O-aryl ester production step, namely in the above-mentioned step (R), step (P) or step (B), or in the case of using a component recycled from these production steps when producing a compound having ureido groups, the carbonic acid derivative is a component that may be contained in the composition for transfer and storage of the compound having the ureido groups. In addition, the carbonic acid derivative is a component that also serves as a raw material of a compound having ureido groups.

(19)

(wherein

X and Y represent organic groups or amino groups (—$NH_2$) having 1 to 50 carbon atoms, provided that X and Y are not simultaneously amino groups, and the value of the number of carbon atoms is an integral value).

Examples of compounds represented by the above-mentioned formula (19) that are used in the present embodiment may include non-N-substituted carbamic acid-O-aryl esters, non-N-substituted carbamic acid-O—$R^2$ esters and carbonic acid esters. Although the expressions "non-N-substituted carbamic acids", "non-N-substituted carbamic acid-O-aryl esters" and "non-N-substituted carbamic acid-O—$R^2$ esters" are used in the explanation of the present embodiment and as general formula names of compounds, here the term "non-N-substituted carbamic acid" is used in the sense of the $NH_2$ group of the carbamoyl group ($NH_2$—CO—) not being substituted by a substituent. Namely, the $NH_2$ group of the carbamoyl group ($NH_2$—CO—) of a non-N-substituted carbamic acid is an $NH_2$ group.

A non-N-substituted carbamic acid-O—$R^2$ ester represented by the following formula (21) is preferably used for the non-N-substituted carbamic acid-O—$R^2$ ester:

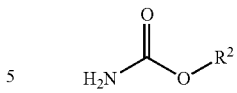
(21)

(wherein the $R^2$ group is the same as the $R^2$ group of an alcohol represented by formula (4) and represents a group composed of an aliphatic group to which is bonded an aliphatic group or aromatic group containing an integral number of carbon atoms within a range of from 1 to 14, and the —O—$R^2$ group of the non-N-substituted carbamic acid-O—$R^2$ ester represented by formula (21) is an $R^{20}$ group of $R^2$OH of an alcohol represented by formula (4)).

The non-N-substituted carbamic acid-O—$R^2$ ester may be formed as a by-product during production of N-substituted carbamic acid-O-aryl ester in a process comprising the step (A) and/or the step (R) that use an alcohol (namely, a process in which alcohol is used), or may be a non-N-substituted carbamic acid-O—$R^2$ ester produced by the known method. The known method is preferably a method for obtaining non-N-substituted carbamic acid-O—$R^2$ ester from urea and alcohol as shown in the following reaction formula (23) by reacting isocyanic acid (HNCO) and alcohol as shown in the following reaction formula (22), and a non-N-substituted carbamic acid-O—$R^2$ ester represented by formula (21) above can be obtained by using an alcohol represented by formula (4) for the alcohol used at that time.

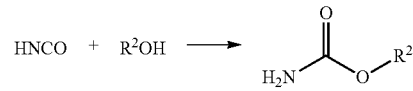
(22)

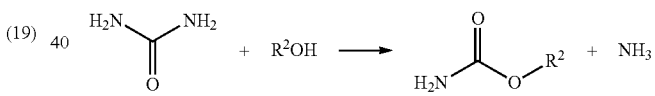
(23)

$R^2$ groups listed as examples in the explanation of an alcohol represented by formula (4) can be preferably used for the $R^2$ group.

Examples of such non-N-substituted carbamic acid-O—$R^2$ esters represented by formula (21) may include methyl carbamate, ethyl carbamate, propyl carbamate (including isomers), butyl carbamate (including isomers), pentyl carbamate (including isomers), hexyl carbamate (including isomers), heptyl carbamate (including isomers), octyl carbamate (including isomers), nonyl carbamate (including isomers), decyl carbamate (including isomers), undecyl carbamate (including isomers), dodecyl carbamate (including isomers), tridecyl carbamate (including isomers), tetradecyl carbamate (including isomers), pentadecyl carbamate (including isomers), hexadecyl carbamate (including isomers), heptadecyl carbamate (including isomers), octadecyl carbamate (including isomers), nonadecyl carbamate (including isomers), benzyl carbamate, (methylbenzyl) carbamate (including isomers), (dimethylbenzyl) carbamate (including isomers), (phenylethyl) carbamate (including isomers), (phenylpropyl) carbamate (including isomers), (phenylbutyl) carbamate (including isomers), (phenylpentyl) carbamate (including isomers), (phenylhexyl) carbamate (including isomers), (phenylheptyl) carbamate (including isomers), (phenyloctyl)

carbamate (including isomers) and (phenylnonyl) carbamate (including isomers). More preferable examples include non-N-substituted carbamic acid alkyl esters and non-N-substituted carbamic acid aralkyl esters.

Compounds having ureido groups can be obtained from the above-mentioned non-N-substituted carbamic acid-O—$R^2$ esters by reacting with organic primary amine using the known method. The reaction formula is shown in the following formula (24). In formula (24), although a monoamine structure is shown for the structure of the organic primary amine, the structure may also be that of an organic primary polyamine.

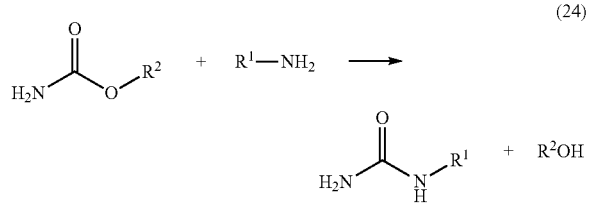

(24)

In the present embodiment, although a compound having ureido groups is preferably obtained by carrying out the step (A) in which an organic primary amine and urea are reacted, the reaction of reaction formula (24) above may also be carried out simultaneously thereto. In addition, this method is preferable since it enables reaction side-products to be used effectively.

A non-N-substituted carbamic acid-O-aryl ester represented by the following formula (25) is preferably used for the non-N-substituted carbamic acid-O-aryl ester:

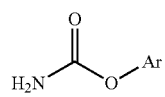

(25)

(wherein

Ar represents a group derived from an aromatic hydroxy compound that composes an aromatic hydroxy composition, and the Ar—O— group represents a residue in which a hydrogen atom of a hydroxyl group bonded directly to an aromatic hydrocarbon ring has been removed from the aromatic hydroxy compound).

The compound represented by formula (25) may be a non-N-substituted carbamic acid-O-aryl ester either formed as a by-product during production of N-substituted carbamic acid-O-aryl ester by a process comprising any of the step (A), step (P) or step (B) using an aromatic hydroxy composition, or produced using the known method. The known method is preferably a method in non-N-substituted carbamic acid-O-aryl ester is obtained from urea and aromatic hydroxy compound as shown in the following reaction formula (27) in a reaction between isocyanic acid (HNCO) and aromatic hydroxy compound as shown in the following reaction formula (26), and by using an aromatic hydroxy compound represented by formula (2) for the aromatic hydroxy compound used at that time, a non-N-substituted carbamic acid-O-aryl ester represented by formula (25) above can be obtained:

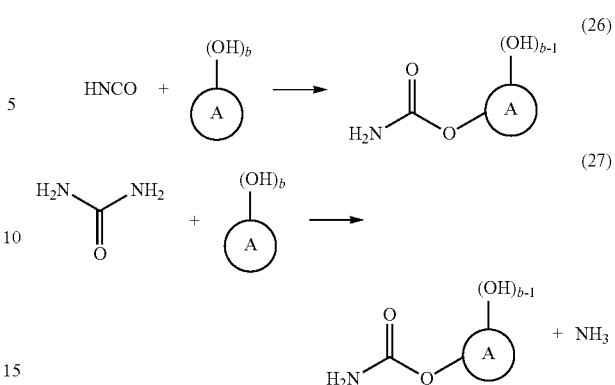

(wherein
ring A and b are the same as defined for the aromatic hydroxy compound represented by formula (2), and the oxygen-ring A bond bonded to the carbamoyl group ($NH_2$—CO—) contained in the structure of the non-N-substituted carbamic acid-O-aryl ester represented in formulas (26) and (27) represents a residue in which a hydrogen atom has been removed from a hydroxy group bonded to the aromatic ring of the aromatic hydroxy compound).

In the above description, although a structure is shown in which only a single hydroxy group of the aromatic hydroxy compound reacted, a polyvalent non-N-substituted carbamic acid-O-aryl ester may be formed having a structure other than that indicated above.

Since an aromatic hydroxy compound is generally used in excess in the present embodiment, the structure is such that the ratio between carbamic acid groups in the non-N-substituted carbamic acid-O-aryl ester and groups derived from an aromatic hydroxy residue derived from formula (2) is generally 1:1.

A compound having ureido groups can be obtained from the above-mentioned non-N-substituted carbamic acid-O-aryl ester by reacting with organic primary amine using the known method. The reaction formula is shown in the following formula (28):

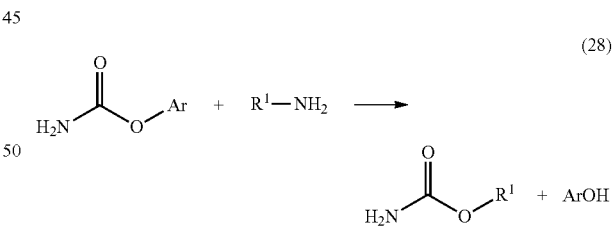

(28)

(wherein
Ar is the same as that defined for the Ar explained in the above-mentioned formula (25)).

In the present embodiment, although the compound having the ureido groups is preferably obtained by carrying out the step (A) containing reacting organic primary amine and urea, the reaction shown in formula (28) above may also be carried out simultaneous thereto. In formula (28), although both the non-N-substituted carbamic acid-O-aryl ester and the organic primary amine are represented as being monovalent (having one reaction site), these may also be a polyvalent non-N-substituted carbamic acid-O-aryl ester and organic primary polyamine, respectively.

In addition, this method is preferable since it enables reaction side-products to be used effectively. In addition, in the step (A) the reaction of formula (24) derived from the above-mentioned non-N-substituted carbamic acid-O—$R^2$ ester and the reaction of formula (28) derived from a non-N-substituted carbamic acid-O-aryl ester may also be carried out simultaneously.

A structure in which one or more hydroxy groups bonded to an aromatic contained in an aromatic hydroxy compound listed as an example in the explanation of an aromatic hydroxy compound represented by formula (2) has been removed can be preferably used for the Ar group. Namely, a residue in which a hydrogen atom of a hydroxyl group directly bonded to an aromatic hydrocarbon ring has been removed from an aromatic hydroxy compound represented by formula (2) can be preferably used for the —O—Ar group of the non-N-substituted carbamic acid-O-aryl ester of the above-mentioned formula (25). In addition, among aromatic hydroxy compounds represented by formula (2), an aromatic monohydroxy compound represented by formula (31) or formula (32) is preferable, while an active aromatic monohydroxy compound represented by formula (38) is more preferable. Naturally, one type or two or more types may be used.

Examples of such non-N-substituted carbamic acid-O-aryl ester represented by formula (21) may include phenyl carbamate, (methylphenyl) carbamate (including isomers), (ethylphenyl) carbamate (including isomers), (propylphenyl) carbamate (including isomers), (butylphenyl) carbamate (including isomers), (pentylphenyl) carbamate (including isomers), (hexylphenyl) carbamate (including isomers), (heptylphenyl) carbamate (including isomers), (octylphenyl) carbamate (including isomers), (nonylphenyl) carbamate (including isomers), (decylphenyl) carbamate (including isomers), (biphenyl)carbamate (including isomers), (dimethylphenyl) carbamate (including isomers), (diethylphenyl) carbamate (including isomers), (dipropylphenyl) carbamate (including isomers), (dibutylphenyl) carbamate (including isomers), (dipentylphenyl) carbamate (including isomers), (dihexylphenyl) carbamate (including isomers), (diheptylphenyl) carbamate (including isomers), (terphenyl) carbamate (including isomers), (trimethylphenyl) carbamate (including isomers), (triethylphenyl) carbamate (including isomers), (tripropylphenyl) carbamate (including isomers) and (tributylphenyl) carbamate (including isomers). Preferable examples thereof may include non-N-substituted carbamic acid-O-aryl esters in which the aryl group of the —O-aryl ester is a phenyl group substituted with an alkyl group or a phenyl group.

As has been described above, a non-N-substituted carbamic acid-O—($R^2$ or aryl) ester represented by formula (21) or formula (25) can be effectively used as a synthesis raw material of a compound having ureido groups. Although there are cases in which a complexly substituted monomer or polymer of a urea compound, biuret or nurate and the like may also be contained at that time as a carbonic acid derivative in addition to the previously described urea, alcohol, ammonia, N-substituted carbamic acid ester and subsequently explained carbonic acid ester and the like, there are no problems with such compound being contained. Furthermore, although there are cases in which the term "non-N-substituted carbamic acid-O—($R^2$ or aryl) ester" is used in the explanation of the present specification, this refers to "an N-substituted carbamic acid-O—$R^2$ ester or N-substituted carbamic acid-O-aryl ester".

<N-Substituted Carbamic Acid-O-Aryl Ester>

The N-substituted carbamic acid-O-aryl ester produced with the method of the present embodiment is a compound represented by the following formula (43). Although subsequently explained in detail, the present embodiment refers to a method for esterifying a compound having ureido groups and an aromatic hydroxy composition, or a method for obtaining an N-substituted carbamic acid-O—$R^2$ ester by esterifying a compound having ureido groups and an alcohol followed by transesterifying the N-substituted carbamic acid-O—$R^2$ ester and an aromatic hydroxy composition to obtain N-substituted carbamic acid-O-aryl ester (and the N-substituted carbamic acid-O-aryl ester refers to an N-substituted carbamic acid ester in which an oxygen atom of the carbamic acid group (—NHCOO—) is bonded to an aromatic ring). In providing a more detailed explanation, the O-aryl group in the carbamic acid-O-aryl ester group of the N-substituted carbamic acid-O-aryl ester is a residue in which a hydrogen atom has been removed from a single hydroxy group (OH group) bonded to an aromatic ring carbon atom of an aromatic hydroxy compound. Namely, the former method described above is a method for esterifying a ureido group (—NHCONH$_2$) and an aromatic hydroxy compound to obtain a carbamic acid-O-aryl group (—NHCOOAr), while the latter method described above is a method for esterifying a ureido group (—NHCONH$_2$) and an alcohol to obtain a carbamic acid-O—$R^2$ group (—NHCOOR$^2$) followed by transesterifying with an aromatic hydroxy compound to obtain a carbamic acid-O-aryl group (—NHCOOAr):

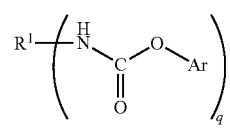

(43)

(wherein $R^1$ represents a group derived from an organic primary amine or compound having ureido groups as previously defined, Ar represents a group derived from an aromatic hydroxy compound represented by formula (2) that composes an aromatic hydroxy composition, and the Ar—O— group represents a residue in which a single hydrogen atom of a hydroxyl group bonded directly to an aromatic hydrocarbon ring has been removed from the aromatic hydroxy compound, and q represents an integer of from 1 to a or an integer of from 1 to c, and a and c are as previously defined).

The specific structure of the N-substituted carbamic acid-O-aryl ester represented by formula (43) above is determined by the organic primary amine and/or compound having ureido groups and aromatic hydroxy composition used. For example, in the case of using a compound having ureido groups represented by formula (1) and/or an organic primary amine represented by formula (3) and using an aromatic hydroxy compound represented by formula (2) for the aromatic hydroxy composition, an N-substituted carbamic acid-O-aryl ester represented by the following formula (44) is obtained, in the case of using an organic primary amine represented by formula (5) and an aromatic hydroxy compound represented by formula (2) for the aromatic hydroxy composition (and in the case b=1), an N-substituted carbamic acid-O-aryl ester represented by the following formula (45) is obtained, in the case of using a compound having ureido groups represented by formula (1) and/or an organic primary amine represented by formula (3) and using an aromatic hydroxy compound represented by formula (7) for the aromatic hydroxy composition, an N-substituted carbamic acid- O-aryl ester represented by the following formula (46) is obtained, and in the case of using an organic primary amine represented by formula (5) and an aromatic hydroxy compound represented by formula (2) for the aromatic hydroxy composition (and in the case b=1) and producing by a method that includes the step (C), an N-substituted poly(carbamic acid-O-aryl ester) represented by the following formula (47) is obtained (the above-mentioned N-substituted poly(carbamic acid-O-aryl ester) refers to an N-substituted carbamic acid-O-alkyl ester having a plurality of carbamic acid-O-aryl ester groups in a molecule thereof). In this manner, a diverse range of N-substituted carbamic acid-O-aryl esters can be obtained with the production method of the present embodiment, and can be typically represented by the above-mentioned formula (43). (Although the term "aryl", according to nomenclature rules defined by IUPAC, refers to a monovalent aromatic ring, and the term "aryl" is used in the present embodiment since a suitable term that generically refers to compounds in the present embodiment was unable to be found, the group referred to by the N-substituted carbamic acid-O-aryl ester of the present embodiment contains the N-substituted carbamic acid-O-aryl esters indicated above. Alternatively, an N-substituted carbamic acid-O-aryl ester in the present embodiment may also be referred to as an N-substituted carbamic acid-O—Ar ester, or in other words, Ar has the same meaning as previously described.):

aromatic group separately reacting with a compound having ureido groups in the case of using a polyvalent aromatic hydroxy compound, since an excess of aromatic hydroxy compound is used in the present embodiment, generally an N-substituted carbamic acid-O-aryl ester represented by formula (43) above is obtained.

Although all possible examples of specific compounds cannot be listed since the production method of the present embodiment can be applied to a diverse range of compounds having ureido groups, organic primary amines, alcohols and aromatic hydroxy compounds as previously described, examples of such specific compounds may include N,N'-hexanediyl-di(carbamic acid phenyl ester), N,N'-hexanediyl-di(carbamic acid (methylphenyl)ester) (including isomers), N,N'-hexanediyl-di(carbamic acid (ethylphenyl)ester) (including isomers), N,N'-hexanediyl-di(carbamic acid (propylphenyl)ester) (including isomers), N,N'-hexanediyl-di(carbamic acid (butylphenyl)ester) (including isomers), N,N'-hexanediyl-di(carbamic acid (pentylphenyl)ester) (including isomers), methylene-di(cyclohexylcarbamic acid phenyl ester) (including isomers), methylene-di(cyclohexylcarbamic acid (methylphenyl)ester) (including isomers), methylene-di(cyclohexylcarbamic acid (ethylphenyl)ester) (including isomers), methylene-di(cyclohexylcarbamic acid (propylphenyl)ester) (including isomers), methylene-di(cyclohexylcarbamic acid (butylphenyl)ester) (including iso-

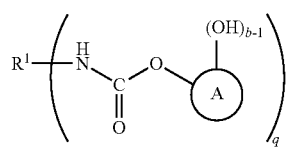
(44)

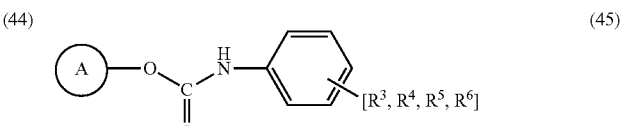
(45)

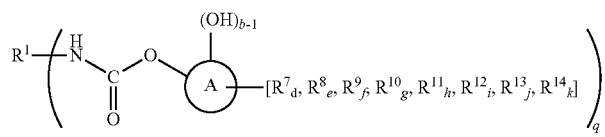
(46)

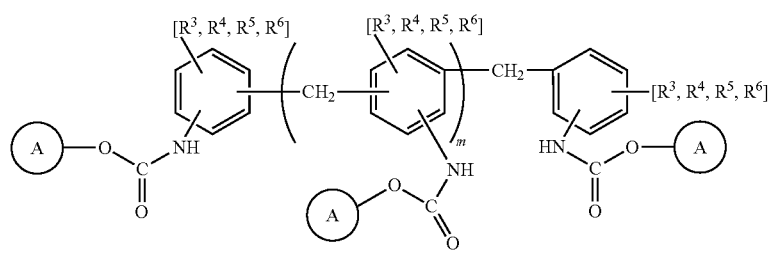
(47)

(wherein
R$^1$ represents a group derived from an organic primary amine as previously defined,
ring A represents a group derived from an aromatic hydroxy compound that composes an aromatic hydroxy composition as previously defined, which is a residue in which a single hydrogen atom of a hydroxyl group directly bonded to an aromatic hydrocarbon ring has been removed from the aromatic hydroxy compound,
R$^3$ to R$^{14}$ represent groups as previously defined,
b, d, e, f, g, h, i, j, k, m and q are integers as previously defined, and
q represents an integer of from 1 to a or an integer of from 1 to c, and a and c are as previously defined).

Although a polymer having a complex structure may be obtained as a result of a plurality of hydroxy groups on the mers), methylene-di(cyclohexylcarbamic acid (pentylphenyl)ester) (including isomers), methylene-di(cyclohexylcarbamic acid (hexylphenyl)ester) (including isomers), methylene-di(cyclohexylcarbamic acid (heptylphenyl)ester) (including isomers), methylene-di(cyclohexylcarbamic acid (octylphenyl)ester) (including isomers), 3-(phenoxycarbonylamino-methyl)-3,5,5-trimethylcyclohexyl carbamic acid phenyl ester, 3-(methylphenoxycarbonylamino-methyl)-3,5,5-trimethylcyclohexyl carbamic acid (methylphenyl)ester (including isomers), 3-(ethylphenoxycarbonylamino-methyl)-3,5,5-trimethylcyclohexyl carbamic acid (ethylphenyl)ester (including isomers), 3-(propylphenoxycarbonylamino-methyl)-3,5,5-trimethylcyclohexyl carbamic acid (propylphenyl)ester (including isomers), 3-(butylphenoxycarbonylamino-methyl)-3,5,5- trimethylcyclohexyl carbamic acid (butylphenyl)ester (including isomers), 3-(pentylphenoxycarbonylamino-methyl)-3,5,5-trimethylcyclohexyl carbamic acid (pentylphenyl)ester (including isomers), 3-(hexylphenoxycarbonylamino-methyl)-3,5,5-trimethylcyclohexyl carbamic acid (hexylphenyl)ester (including isomers), 3-(heptylphenoxycarbonylamino-methyl)-3,5,5-trimethylcyclohexyl carbamic acid (heptylphenyl)ester (including isomers), 3-(octylphenoxycarbonylamino-methyl)-3,5,5-trimethylcyclohexyl carbamic acid (octylphenyl)ester (including isomers), toluene-di(carbamic acid phenyl ester) (including isomers), toluene-di(carbamic acid (methylphenyl)ester) (including isomers), toluene-di(carbamic acid (ethylphenyl)ester) (including isomers), toluene-di(carbamic acid (propylphenyl)ester) (including isomers), toluene-di(carbamic acid (butylphenyl)ester) (including isomers), toluene-di(carbamic acid (pentylphenyl)ester) (including isomers), toluene-di(carbamic acid (hexylphenyl) ester) (including isomers), toluene-di(carbamic acid (heptylphenyl)ester) (including isomers), toluene-di(carbamic acid (octylphenyl)ester) (including isomers), N,N'-(methanediyl-diphenyl)-di(carbamic acid phenyl ester) (including isomers), N,N'-(methanediyl-diphenyl)-di(carbamic acid (methylphenyl)ester) (including isomers), N,N'-(methanediyl-diphenyl)-di(carbamic acid (ethylphenyl)ester) (including isomers), N,N'-(methanediyl-diphenyl)-di (carbamic acid (propylphenyl)ester) (including isomers), N,N'-(methanediyl-diphenyl)-di(carbamic acid (butylphenyl) ester) (including isomers), N,N'-(methanediyl-diphenyl)-di(carbamic acid (pentylphenyl) ester) (including isomers), N,N'-(methanediyl-diphenyl)-di(carbamic acid (hexylphenyl)ester) (including isomers), N,N'-(methanediyl-diphenyl)-di(carbamic acid (heptylphenyl)ester) (including isomers) and N,N'-(methanediyl-diphenyl)-di(carbamic acid (octylphenyl)ester) (including isomers). Preferable N-substituted carbamic acid-O-aryl esters contain N-substituted carbamic acid-O-aryl esters obtained by using preferable compounds previously explained for the above-mentioned organic primary amines, aromatic hydroxy compounds and compounds having ureido groups, examples of which may include N-substituted carbamic acid-O-aryl esters obtained by reacting an active aromatic monohydroxy compound with an N-substituted aromatic organic monourea, N-substituted aromatic organic polyurea or N-substituted aliphatic organic polyurea, and N-substituted carbamic acid-O-aryl esters obtained by condensing an N-substituted carbamic acid-O-aryl ester obtained from an active aromatic monohydroxy compound and an N-substituted aromatic organic monourea with a condensing agent. In addition, N-substituted carbamic acid-O-aryl esters are also preferable in which all ureido groups or primary amino groups contained in a compound having ureido groups or organic primary amine are substituted with carbamic acid-O-aryl ester groups (namely, a=q or c=q).

<N-Substituted Carbamic Acid-O—$R^2$ Ester>

An N-substituted carbamic acid O—$R^2$ ester produced with the production method of the present embodiment is a compound represented by the following formula (49). Although subsequently explained in detail, the present invention as referred to here indicates a compound obtained when producing an N-substituted carbamic acid-O-aryl ester by a process that includes the above-mentioned step (R). This is a compound in which a compound having ureido groups is esterified with an alcohol represented by formula (4) to convert the ureido groups (—NHCONH$_2$) to carbamic acid-O—$R^2$ ester groups (—NHCOOR$^2$). Namely, this is an N-substituted carbamic acid-O—$R^2$ ester, which is obtained by reacting at least one type of compound having ureido groups with an alcohol represented by formula (4) in a liquid phase followed by extracting the ammonia formed as a by-product to a gaseous phase, and the N-substituted carbamic acid-O—$R^2$ ester refers to an N-substituted carbamic acid ester in which oxygen atoms of the carbamic acid group (—NHCOO—) are bonded to the $R^2$ group derived from the alcohol. In providing a more detailed explanation, the OR$^2$ group in the carbamic acid-O—$R^2$ ester group (—NHCOOR$^2$) of the N-substituted carbamic acid-O—$R^2$ ester is a residue in which a hydrogen atom has been removed from a single hydroxy group (OH group) bonded to a carbon atom of the alcohol:

(49)

(wherein $R^1$ represents a group derived from an organic primary amine as previously defined, $R^2$ represents a group derived from an alcohol as previously defined, r is an integer of from 1 to a or from 1 to c, and a and c are as previously defined).

Although all possible examples of specific compounds cannot be listed since the production method of the present embodiment can be applied to a diverse range of compounds having ureido groups, organic primary amines and alcohols as previously described, examples of such specific compounds may include N,N'-hexanediyl-di(carbamic acid methyl ester), N,N'-hexanediyl-di(carbamic acid ethyl ester), N,N'-hexanediyl-di(carbamic acid propyl ester) (including isomers), N,N'-hexanediyl-di(carbamic acid butyl ester) (including isomers), N,N'-hexanediyl-di(carbamic acid pentyl ester) (including isomers), N,N'-hexanediyl-di(carbamic acid hexyl ester) (including isomers), methylene-di(cyclohexylcarbamic acid methyl ester), methylene-di(cyclohexylcarbamic acid ethyl ester), methylene-di(cyclohexylcarbamic acid propyl ester) (including isomers), methylene-di(cyclohexylcarbamic acid butyl ester) (including isomers), methylene-di(cyclohexylcarbamic acid pentyl ester) (including isomers), methylene-di(cyclohexylcarbamic acid hexyl ester) (including isomers), methylene-di(cyclohexylcarbamic acid heptyl ester) (including isomers), methylene-di(cyclohexylcarbamic acid octyl ester) (including isomers), 3-(methoxycarbonylamino-methyl)-3,5,5-trimethylcyclohexyl carbamic acid methyl ester, 3-(ethoxycarbonylamino-methyl)-3,5,5-trimethylcyclohexyl carbamic acid ethyl ester (including isomers), 3-(propyloxycarbonylamino-methyl)-3,5,5-trimethylcyclohexyl carbamic acid propyl ester (including isomers), 3-(butyloxycarbonylamino-methyl)-3,5,5-trimethylcyclohexyl carbamic acid butyl ester (including isomers), 3-(pentyloxycarbonylamino-methyl)-3,5,5-trimethylcyclohexyl carbamic acid pentyl ester (including isomers), 3-(hexyloxycarbonylamino-methyl)-3,5,5-trimethylcyclohexyl carbamic acid hexyl ester (including isomers), 3-(heptyloxycarbonylamino-methyl)-3,5,5-trimethylcyclohexyl carbamic acid heptyl ester (including isomers), 3-(octyloxycarbonylamino-methyl)-3,5,5-trimethylcyclohexyl carbamic acid octyl ester (including isomers), toluene-di(carbamic acid methyl ester) (including isomers), toluene-di(carbamic acid ethyl ester) (including isomers), toluene-di(carbamic acid propyl ester) (including isomers), toluene-di(carbamic acid butyl ester)

(including isomers), toluene-di(carbamic acid pentyl ester) (including isomers), toluene-di(carbamic acid hexyl ester) (including isomers), toluene-di(carbamic acid heptyl ester) (including isomers), toluene-di(carbamic acid octyl ester) (including isomers), N,N'-(methanediyl-diphenyl)-di(carbamic acid methyl ester) (including isomers), N,N'-(methanediyl-diphenyl)-di(carbamic acid ethyl ester) (including isomers), N,N'-(methanediyl-diphenyl)-di(carbamic acid propyl ester) (including isomers), N,N'-(methanediyl-diphenyl)-di(carbamic acid butyl ester) (including isomers), N,N'-(methanediyl-diphenyl)-di(carbamic acid pentyl ester) (including isomers), N,N'-(methanediyl-diphenyl)-di(carbamic acid hexyl ester) (including isomers), N,N'-(methanediyl-diphenyl)-di(carbamic acid heptyl ester) (including isomers) and N,N'-(methanediyl-diphenyl)-di(carbamic acid octyl ester) (including isomers). Preferable N-substituted carbamic acid-O—$R^2$ esters contain N-substituted carbamic acid-O—$R^2$ esters obtained by using preferable compounds previously explained for the above-mentioned organic primary amines, alcohols and compounds having ureido groups, examples of which may include N-substituted carbamic acid-O—$R^2$ esters obtained by reacting an alcohol with an N-substituted aromatic organic monourea, N-substituted aromatic organic polyurea or N-substituted aliphatic organic polyurea, and N-substituted carbamic acid-O—$R^2$ esters obtained by condensing an N-substituted carbamic acid-O—$R^2$ ester obtained from an alcohol and an N-substituted aromatic organic monourea with a condensing agent. In addition, N-substituted carbamic acid-O—$R^2$ esters are also preferable in which all ureido groups or primary amino groups contained in a compound having ureido groups or organic primary amine are substituted with carbamic acid-O-alkyl ester groups (namely, a=r).

<Carbonic Acid Ester>

The carbonic acid ester is a component that is preferably contained at a specific amount in the composition for transfer and storage of the present embodiment.

A carbonic acid ester refers to a compound in which one or both of the two hydrogen atoms of carbonic acid ($CO(OH)_2$) are substituted with an aliphatic group or aromatic group. A compound represented by the following formula (20) is preferably used in the present embodiment:

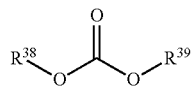

(20)

(wherein $R^{38}$ and $R^{39}$ are groups that are respectively and independently selected from the above-mentioned $R^2$ and Ar groups).

The above-mentioned carbonic acid ester is formed by a reaction between urea and an alcohol and/or aromatic hydroxy compound, a reaction between an N-substituted carbamic acid-O—($R^2$ or aryl) ester and an alcohol and/or aromatic hydroxy compound, or a disproportionation reaction of the formed carbonic acid ester.

Examples of the $R^2$ and Ar groups may include the $R^2$ and Ar groups explained for the N-substituted carbamic acid-O—($R^2$ or aryl) ester.

Examples of carbonic acid ester represented by the formula (20) may include dimethyl carbonate, diethyl carbonate, dipropyl carbonate (including isomers), dibutyl carbonate (including isomers), dipentyl carbonate (including isomers), dihexyl carbonate (including isomers), diheptyl carbonate (including isomers), dioctyl carbonate (including isomers), dinonyl carbonate (including isomers), didecyl carbonate (including isomers), diundecyl carbonate (including isomers), didodecyl carbonate (including isomers), ditridecyl carbonate (including isomers), ditetradecyl carbonate (including isomers), dipentadecyl carbonate (including isomers), dihexadecyl carbonate (including isomers), diheptadecyl carbonate (including isomers), dioctadecyl carbonate (including isomers), dinonadecyl carbonate (including isomers), diphenyl carbonate (including isomers), di(methylphenyl) carbonate (including isomers), di(ethylphenyl) carbonate (including isomers), di(propylphenyl) carbonate (including isomers), di(butylphenyl) carbonate (including isomers), di(pentylphenyl) carbonate (including isomers), di(hexylphenyl) carbonate (including isomers), di(heptylphenyl) carbonate (including isomers), di(octylphenyl) carbonate (including isomers), di(nonylphenyl) carbonate (including isomers), di(decylphenyl) carbonate (including isomers), di(biphenyl) carbonate (including isomers), di(dimethylphenyl) carbonate (including isomers), di(diethylphenyl) carbonate (including isomers), di(dipropylphenyl) carbonate (including isomers), di(dibutylphenyl) carbonate (including isomers), di(dipentylphenyl) carbonate (including isomers), di(dihexylphenyl) carbonate (including isomers), di(diheptylphenyl) carbonate (including isomers), di(phenylphenyl) carbonate (including isomers), di(trimethylphenyl) carbonate (including isomers), di(triethylphenyl) carbonate (including isomers), di(tripropylphenyl) carbonate (including isomers), di(tributylphenyl) carbonate (including isomers), di(phenylmethyl) carbonate (including isomers), di(phenylethyl) carbonate (including isomers), di(phenylpropyl) carbonate (including isomers), di(phenylbutyl) carbonate (including isomers), di(phenylpentyl) carbonate (including isomers), di(phenylhexyl) carbonate (including isomers), di(phenylheptyl) carbonate (including isomers), di(phenyloctyl) carbonate (including isomers) di(phenylnonyl) carbonate (including isomers), (methyl)(ethyl) carbonate, (methyl)(propyl) carbonate (including isomers), (methyl)(butyl) carbonate (including isomers), (methyl)(pentyl) carbonate (including isomers), (methyl)(hexyl) carbonate (including isomers), (methyl)(heptyl) carbonate (including isomers), (methyl)(octyl) carbonate (including isomers), (methyl)(nonyl) carbonate (including isomers), (methyl)(decyl) carbonate (including isomers), (methyl)(undecyl) carbonate (including isomers), (methyl) (dodecyl) carbonate (including isomers), (methyl)(tridecyl) carbonate (including isomers), (methyl)(tetradecyl) carbonate (including isomers), (methyl)(pentadecyl) carbonate (including isomers), (methyl)(hexadecyl) carbonate (including isomers), (methyl)(heptadecyl) carbonate (including isomers), (methyl)(octadecyl) carbonate (including isomers), (methyl)(nonadecyl) carbonate (including isomers), (methyl) (phenyl) carbonate (including isomers), (methyl)(methylphenyl) carbonate (including isomers), (methyl)(ethylphenyl) carbonate (including isomers), (methyl)(propylphenyl) carbonate (including isomers), (methyl)(butylphenyl) carbonate (including isomers), (methyl)(pentylphenyl) carbonate (including isomers), (methyl)(hexylphenyl) carbonate (including isomers), (methyl)(heptylphenyl) carbonate (including isomers), (methyl)(octylphenyl) carbonate (including isomers), (methyl)(nonylphenyl) carbonate (including isomers), (methyl)(decylphenyl) carbonate (including isomers), (methyl)(biphenyl) carbonate (including isomers), (methyl)(dimethylphenyl) carbonate (including isomers), (methyl)(diethylphenyl) carbonate (including isomers), (methyl) (dipropylphenyl) carbonate (including isomers), (methyl) (dibutylphenyl) carbonate (including isomers), (methyl) (dipentylphenyl) carbonate (including isomers), (methyl)

(dihexylphenyl) carbonate (including isomers), (methyl)(diheptylphenyl) carbonate (including isomers), (methyl)(phenylphenyl) carbonate (including isomers), (methyl)(trimethylphenyl) carbonate (including isomers), (methyl)(triethylphenyl) carbonate (including isomers), (methyl)(tripropylphenyl) carbonate (including isomers), (methyl)(tributylphenyl) carbonate (including isomers), (methyl)(phenylmethyl) carbonate (including isomers), (methyl)(phenylethyl) carbonate (including isomers), (methyl)(phenylpropyl) carbonate (including isomers), (methyl)(phenylbutyl) carbonate (including isomers), (methyl)(phenylpentyl) carbonate (including isomers), (methyl)(phenylhexyl) carbonate (including isomers), (methyl)(phenylheptyl) carbonate (including isomers), (methyl)(phenyloctyl) carbonate (including isomers), (methyl)(phenylnonyl) carbonate (including isomers), (ethyl)(propyl) carbonate (including isomers), (ethyl)(butyl) carbonate (including isomers), (ethyl)(pentyl) carbonate (including isomers), (ethyl)(hexyl) carbonate (including isomers), (ethyl)(heptyl) carbonate (including isomers), (ethyl)(octyl) carbonate (including isomers), (ethyl)(nonyl) carbonate (including isomers), (ethyl)(decyl) carbonate (including isomers), (ethyl)(undecyl) carbonate (including isomers), (ethyl)(dodecyl) carbonate (including isomers), (ethyl)(tridecyl) carbonate (including isomers), (ethyl)(tetradecyl) carbonate (including isomers), (ethyl)(pentadecyl) carbonate (including isomers), (ethyl)(hexadecyl) carbonate (including isomers), (ethyl)(heptadecyl) carbonate (including isomers), (ethyl)(octadecyl) carbonate (including isomers), (ethyl)(nonadecyl) carbonate (including isomers), (ethyl)(phenyl) carbonate (including isomers), (ethyl)(methylphenyl) carbonate (including isomers), (ethyl)(ethylphenyl) carbonate (including isomers), (ethyl)(propylphenyl) carbonate (including isomers), (ethyl)(butylphenyl) carbonate (including isomers), (ethyl)(pentylphenyl) carbonate (including isomers), (ethyl)(hexylphenyl) carbonate (including isomers), (ethyl)(heptylphenyl) carbonate (including isomers), (ethyl)(octylphenyl) carbonate (including isomers), (ethyl)(nonylphenyl) carbonate (including isomers), (ethyl)(decylphenyl) carbonate (including isomers), (ethyl)(biphenyl) carbonate (including isomers), (ethyl)(dimethylphenyl) carbonate (including isomers), (ethyl)(diethylphenyl) carbonate (including isomers), (ethyl)(dipropylphenyl) carbonate (including isomers), (ethyl)(dibutylphenyl) carbonate (including isomers), (ethyl)(dipentylphenyl) carbonate (including isomers), (ethyl)(dihexylphenyl) carbonate (including isomers), (ethyl)(diheptylphenyl) carbonate (including isomers), (ethyl)(phenylphenyl) carbonate (including isomers), (ethyl)(trimethylphenyl) carbonate (including isomers), (ethyl)(triethylphenyl) carbonate (including isomers), (ethyl)(tripropylphenyl) carbonate (including isomers), (ethyl)(tributylphenyl) carbonate (including isomers), (ethyl)(phenylmethyl) carbonate (including isomers), (ethyl)(phenylethyl) carbonate (including isomers), (ethyl)(phenylpropyl) carbonate (including isomers), (ethyl)(phenylbutyl) carbonate (including isomers), (ethyl)(phenylpentyl) carbonate (including isomers), (ethyl)(phenylhexyl) carbonate (including isomers), (ethyl)(phenylheptyl) carbonate (including isomers), (ethyl)(phenyloctyl) carbonate (including isomers), (ethyl)(phenylnonyl) carbonate (including isomers), (propyl)(butyl) carbonate (including isomers), (propyl)(pentyl) carbonate (including isomers), (propyl)(hexyl) carbonate (including isomers), (propyl)(heptyl) carbonate (including isomers), (propyl)(octyl) carbonate (including isomers), (propyl)(nonyl) carbonate (including isomers), (propyl)(decyl) carbonate (including isomers), (propyl)(undecyl) carbonate (including isomers), (propyl)(dodecyl) carbonate (including isomers), (propyl)(tridecyl) carbonate (including isomers), (propyl)(tetradecyl) carbonate (including isomers), (propyl)(pentadecyl) carbonate (including isomers), (propyl)(hexadecyl) carbonate (including isomers), (propyl)(heptadecyl) carbonate (including isomers), (propyl)(octadecyl) carbonate (including isomers), (propyl)(nonadecyl) carbonate (including isomers), (propyl)(phenyl) carbonate (including isomers), (propyl)(methylphenyl) carbonate (including isomers), (propyl)(ethylphenyl) carbonate (including isomers), (propyl)(propylphenyl) carbonate (including isomers), (propyl)(butylphenyl) carbonate (including isomers), (propyl)(pentylphenyl) carbonate (including isomers), (propyl)(hexylphenyl) carbonate (including isomers), (propyl)(heptylphenyl) carbonate (including isomers), (propyl)(octylphenyl) carbonate (including isomers), (propyl)(nonylphenyl) carbonate (including isomers), (propyl)(decylphenyl) carbonate (including isomers), (propyl)(biphenyl) carbonate (including isomers), (propyl)(dimethylphenyl) carbonate (including isomers), (propyl)(diethylphenyl) carbonate (including isomers), (propyl)(dipropylphenyl) carbonate (including isomers), (propyl)(dibutylphenyl) carbonate (including isomers), (propyl)(dipentylphenyl) carbonate (including isomers), (propyl)(dihexylphenyl) carbonate (including isomers), (propyl)(diheptylphenyl) carbonate (including isomers), (propyl)(phenylphenyl) carbonate (including isomers), (propyl)(trimethylphenyl) carbonate (including isomers), (propyl)(triethylphenyl) carbonate (including isomers), (propyl)(tripropylphenyl) carbonate (including isomers), (propyl)(tributylphenyl) carbonate (including isomers), (propyl)(phenylmethyl) carbonate (including isomers), (propyl)(phenylethyl) carbonate (including isomers), (propyl)(phenylpropyl) carbonate (including isomers), (propyl)(phenylbutyl) carbonate (including isomers), (propyl)(phenylpentyl) carbonate (including isomers), (propyl)(phenylhexyl) carbonate (including isomers), (propyl)(phenylheptyl) carbonate (including isomers), (propyl)(phenyloctyl) carbonate (including isomers), (propyl)(phenylnonyl) carbonate (including isomers), (butyl)(pentyl) carbonate (including isomers), (butyl)(hexyl) carbonate (including isomers), (butyl)(heptyl) carbonate (including isomers), (butyl)(octyl) carbonate (including isomers), (butyl)(nonyl) carbonate (including isomers), (butyl)(decyl) carbonate (including isomers), (butyl)(undecyl) carbonate (including isomers), (butyl)(dodecyl) carbonate (including isomers), (butyl)(tridecyl) carbonate (including isomers), (butyl)(tetradecyl) carbonate (including isomers), (butyl)(pentadecyl) carbonate (including isomers), (butyl)(hexadecyl) carbonate (including isomers), (butyl)(heptadecyl) carbonate (including isomers), (butyl)(octadecyl) carbonate (including isomers), (butyl)(nonadecyl) carbonate (including isomers), (butyl)(phenyl) carbonate (including isomers), (butyl)(methylphenyl) carbonate (including isomers), (butyl)(ethylphenyl) carbonate (including isomers), (butyl)(propylphenyl) carbonate (including isomers), (butyl)(butylphenyl) carbonate (including isomers), (butyl)(pentylphenyl) carbonate (including isomers), (butyl)(hexylphenyl) carbonate (including isomers), (butyl)(heptylphenyl) carbonate (including isomers), (butyl)(octylphenyl) carbonate (including isomers), (butyl)(nonylphenyl) carbonate (including isomers), (butyl)(decylphenyl) carbonate (including isomers), (butyl)(biphenyl) carbonate (including isomers), (butyl)(dimethylphenyl) carbonate (including isomers), (butyl)(diethylphenyl) carbonate (including isomers), (butyl)(dipropylphenyl) carbonate (including isomers), (butyl)(dibutylphenyl) carbonate (including isomers), (butyl)(dipentylphenyl) carbonate (including isomers), (butyl)(dihexylphenyl) carbonate (including isomers), (butyl)(diheptylphenyl) carbonate (including isomers), (butyl)(phenylphenyl) carbonate (including isomers), (butyl)(trimethylphenyl) carbonate (including isomers), (butyl)(triethylphenyl) carbonate (including isomers), (butyl)(tripropylphenyl) carbonate (including isomers), (butyl)(tributylphenyl) carbonate (including isomers), (butyl)(phenylmethyl) carbonate (including isomers), (butyl)(phenylethyl) carbonate (including isomers), (butyl)(phenylpropyl) carbonate (including isomers), (butyl)(phenylbutyl) carbonate (including isomers), (butyl)(phenylpentyl) carbonate (including isomers), (butyl)(phenylhexyl) carbonate (including isomers), (butyl)(phenylheptyl) carbonate (including isomers), (butyl)(phenyloctyl) carbonate (including isomers), (butyl)(phenylnonyl) carbonate (including isomers), (pentyl)(hexyl) carbonate (including isomers), (pentyl)(heptyl) carbonate (including isomers), (pentyl)(octyl) carbonate (including isomers), (pentyl)(nonyl) carbonate (including isomers), (pentyl)(decyl) carbonate (including isomers), (pentyl)(undecyl) carbonate (including isomers), (pentyl)(dodecyl) carbonate (including isomers), (pentyl)(tridecyl) carbonate (including isomers), (pentyl)(tetradecyl) carbonate (including isomers), (pentyl)(pentadecyl) carbonate (including isomers), (pentyl)(hexadecyl) carbonate (including isomers), (pentyl)(heptadecyl) carbonate (including isomers), (pentyl)(octadecyl) carbonate (including isomers), (pentyl)(nonadecyl) carbonate (including isomers), (pentyl)(phenyl) carbonate (including isomers), (pentyl)(methylphenyl) carbonate (including isomers), (pentyl)(ethylphenyl) carbonate (including isomers), (pentyl)(propylphenyl) carbonate (including isomers), (pentyl)(butylphenyl) carbonate (including isomers), (pentyl)(pentylphenyl) carbonate (including isomers), (pentyl)(hexylphenyl) carbonate (including isomers), (pentyl)(heptylphenyl) carbonate (including isomers), (pentyl)(octylphenyl) carbonate (including isomers), (pentyl)(nonylphenyl) carbonate (including isomers), (pentyl)(decylphenyl) carbonate (including isomers), (pentyl)(biphenyl) carbonate (including isomers), (pentyl)(dimethylphenyl) carbonate (including isomers), (pentyl)(diethylphenyl) carbonate (including isomers), (pentyl)(dipropylphenyl) carbonate (including isomers), (pentyl)(dibutylphenyl) carbonate (including isomers), (pentyl)(dipentylphenyl) carbonate (including isomers), (pentyl)(dihexylphenyl) carbonate (including isomers), (pentyl)(diheptylphenyl) carbonate (including isomers), (pentyl)(phenylphenyl) carbonate (including isomers), (pentyl)(trimethylphenyl) carbonate (including isomers), (pentyl)(triethylphenyl) carbonate (including isomers), (pentyl)(tripropylphenyl) carbonate (including isomers), (pentyl)(tributylphenyl) carbonate (including isomers), (pentyl)(phenylmethyl) carbonate (including isomers), (pentyl)(phenylethyl) carbonate (including isomers), (pentyl)(phenylpropyl) carbonate (including isomers), (pentyl)(phenylbutyl) carbonate (including isomers), (pentyl)(phenylpentyl) carbonate (including isomers), (pentyl)(phenylhexyl) carbonate (including isomers), (pentyl)(phenylheptyl) carbonate (including isomers), (pentyl)(phenyloctyl) carbonate (including isomers), (pentyl)(phenylnonyl) carbonate (including isomers), (hexyl)(heptyl) carbonate (including isomers), (hexyl)(octyl) carbonate (including isomers), (hexyl)(nonyl) carbonate (including isomers), (hexyl)(decyl) carbonate (including isomers), (hexyl)(undecyl) carbonate (including isomers), (hexyl)(dodecyl) carbonate (including isomers), (hexyl)(tridecyl) carbonate (including isomers), (hexyl)(tetradecyl) carbonate (including isomers), (hexyl)(pentadecyl) carbonate (including isomers), (hexyl)(hexadecyl) carbonate (including isomers), (hexyl)(heptadecyl) carbonate (including isomers), (hexyl)(octadecyl) carbonate (including isomers), (hexyl)(nonadecyl) carbonate (including isomers), (hexyl)(phenyl) carbonate (including isomers), (hexyl)(methylphenyl) carbonate (including isomers), (hexyl)(ethylphenyl) carbonate (including isomers), (hexyl)(propylphenyl) carbonate (including isomers), (hexyl)(butylphenyl) carbonate (including isomers), (hexyl)(pentylphenyl) carbonate (including isomers), (hexyl)(hexylphenyl) carbonate (including isomers), (hexyl)(heptylphenyl) carbonate (including isomers), (hexyl)(octylphenyl) carbonate (including isomers), (hexyl)(nonylphenyl) carbonate (including isomers), (hexyl)(decylphenyl) carbonate (including isomers), (hexyl)(biphenyl) carbonate (including isomers), (hexyl)(dimethylphenyl) carbonate (including isomers), (hexyl)(diethylphenyl) carbonate (including isomers), (hexyl)(dipropylphenyl) carbonate (including isomers), (hexyl)(dibutylphenyl) carbonate (including isomers), (hexyl)(dipentylphenyl) carbonate (including isomers), (hexyl)(dihexylphenyl) carbonate (including isomers), (hexyl)(diheptylphenyl) carbonate (including isomers), (hexyl)(phenylphenyl) carbonate (including isomers), (hexyl)(trimethylphenyl) carbonate (including isomers), (hexyl)(triethylphenyl) carbonate (including isomers), (hexyl)(tripropylphenyl) carbonate (including isomers), (hexyl)(tributylphenyl) carbonate (including isomers), (hexyl)(phenylmethyl) carbonate (including isomers), (hexyl)(phenylethyl) carbonate (including isomers), (hexyl)(phenylpropyl) carbonate (including isomers), (hexyl)(phenylbutyl) carbonate (including isomers), (hexyl)(phenylpentyl) carbonate (including isomers), (hexyl)(phenylhexyl) carbonate (including isomers), (hexyl)(phenylheptyl) carbonate (including isomers), (hexyl)(phenyloctyl) carbonate (including isomers), (hexyl)(phenylnonyl) carbonate (including isomers), (heptyl)(octyl) carbonate (including isomers), (heptyl)(nonyl) carbonate (including isomers), (heptyl)(decyl) carbonate (including isomers), (heptyl)(undecyl) carbonate (including isomers), (heptyl)(dodecyl) carbonate (including isomers), (heptyl)(tridecyl) carbonate (including isomers), (heptyl)(tetradecyl) carbonate (including isomers), (heptyl)(pentadecyl) carbonate (including isomers), (heptyl)(hexadecyl) carbonate (including isomers), (heptyl)(heptadecyl) carbonate (including isomers), (heptyl)(octadecyl) carbonate (including isomers), (heptyl)(nonadecyl) carbonate (including isomers), (heptyl)(phenyl) carbonate (including isomers), (heptyl)(methylphenyl) carbonate (including isomers), (heptyl)(ethylphenyl) carbonate (including isomers), (heptyl)(propylphenyl) carbonate (including isomers), (heptyl)(butylphenyl) carbonate (including isomers), (heptyl)(pentylphenyl) carbonate (including isomers), (heptyl)(hexylphenyl) carbonate (including isomers), (heptyl)(heptylphenyl) carbonate (including isomers), (heptyl)(octylphenyl) carbonate (including isomers), (heptyl)(nonylphenyl) carbonate (including isomers), (heptyl)(decylphenyl) carbonate (including isomers), (heptyl)(biphenyl) carbonate (including isomers), (heptyl)(dimethylphenyl) carbonate (including isomers), (heptyl)(diethylphenyl) carbonate (including isomers), (heptyl)(dipropylphenyl) carbonate (including isomers), (heptyl)(dibutylphenyl) carbonate (including isomers), (heptyl)(dipentylphenyl) carbonate (including isomers), (heptyl)(dihexylphenyl) carbonate (including isomers), (heptyl)(diheptylphenyl) carbonate (including isomers), (heptyl)(phenylphenyl) carbonate (including isomers), (heptyl)(trimethylphenyl) carbonate (including isomers), (heptyl)(triethylphenyl) carbonate (including isomers), (heptyl)(tripropylphenyl) carbonate (including isomers), (heptyl)(tributylphenyl) carbonate (including isomers), (heptyl)(phenylmethyl) carbonate (including isomers), (heptyl)

(phenylethyl) carbonate (including isomers), (heptyl) (phenylpropyl) carbonate (including isomers), (heptyl) (phenylbutyl) carbonate (including isomers), (heptyl) (phenylpentyl) carbonate (including isomers), (heptyl) (phenylhexyl) carbonate (including isomers), (heptyl) (phenylheptyl) carbonate (including isomers), (heptyl) (phenyloctyl) carbonate (including isomers), (heptyl) (phenylnonyl) carbonate (including isomers), (octyl)(nonyl) carbonate (including isomers), (octyl)(decyl) carbonate (including isomers), (octyl)(undecyl) carbonate (including isomers), (octyl)(dodecyl) carbonate (including isomers), (octyl)(tridecyl) carbonate (including isomers), (octyl) (tetradecyl) carbonate (including isomers), (octyl) (pentadecyl) carbonate (including isomers), (octyl) (hexadecyl) carbonate (including isomers), (octyl) (heptadecyl) carbonate (including isomers), (octyl) (octadecyl) carbonate (including isomers), (octyl) (nonadecyl) carbonate (including isomers), (octyl)(phenyl) carbonate (including isomers), (octyl)(methylphenyl) carbonate (including isomers), (octyl)(ethylphenyl) carbonate (including isomers), (octyl)(propylphenyl) carbonate (including isomers), (octyl)(butylphenyl) carbonate (including isomers), (octyl)(pentylphenyl) carbonate (including isomers), (octyl)(hexylphenyl) carbonate (including isomers), (octyl)(heptylphenyl) carbonate (including isomers), (octyl) (octylphenyl) carbonate (including isomers), (octyl)(nonylphenyl) carbonate (including isomers), (octyl)(decylphenyl) carbonate (including isomers), (octyl)(biphenyl) carbonate (including isomers), (octyl)(dimethylphenyl) carbonate (including isomers), (octyl)(diethylphenyl) carbonate (including isomers), (octyl)(dipropylphenyl) carbonate (including isomers), (octyl)(dibutylphenyl) carbonate (including isomers), (octyl)(dipentylphenyl) carbonate (including isomers), (octyl)(dihexylphenyl) carbonate (including isomers), (octyl)(diheptylphenyl) carbonate (including isomers), (octyl)(phenylphenyl) carbonate (including isomers), (octyl)(trimethylphenyl) carbonate (including isomers), (octyl)(triethylphenyl) carbonate (including isomers), (octyl) (tripropylphenyl) carbonate (including isomers), (octyl) (tributylphenyl) carbonate (including isomers), (octyl) (phenylmethyl) carbonate (including isomers), (octyl) (phenylethyl) carbonate (including isomers), (octyl) (phenylpropyl) carbonate (including isomers), (octyl) (phenylbutyl) carbonate (including isomers), (octyl) (phenylpentyl) carbonate (including isomers), (octyl) (phenylhexyl) carbonate (including isomers), (octyl) (phenylheptyl) carbonate (including isomers), (octyl) (phenyloctyl) carbonate (including isomers), (octyl) (phenylnonyl) carbonate (including isomers), (methylphenyl)(ethylphenyl) carbonate (including isomers), (methylphenyl)(propylphenyl) carbonate (including isomers), (methylphenyl)(butylphenyl) carbonate (including isomers), (methylphenyl)(pentylphenyl) carbonate (including isomers), (methylphenyl)(hexylphenyl) carbonate (including isomers), (methylphenyl)(heptylphenyl) carbonate (including isomers), (methylphenyl)(octylphenyl) carbonate (including isomers), (methylphenyl)(nonylphenyl) carbonate (including isomers), (methylphenyl)(decylphenyl) carbonate (including isomers), (methylphenyl)(biphenyl) carbonate (including isomers), (methylphenyl)(dimethylphenyl) carbonate (including isomers), (methylphenyl)(diethylphenyl) carbonate (including isomers), (methylphenyl)(dipropylphenyl) carbonate (including isomers), (methylphenyl)(dibutylphenyl) carbonate (including isomers), (methylphenyl)(dipentylphenyl) carbonate (including isomers), (methylphenyl) (dihexylphenyl) carbonate (including isomers), (methylphenyl)(diheptylphenyl) carbonate (including isomers), (methylphenyl)(phenylphenyl) carbonate (including isomers), (methylphenyl)(trimethylphenyl) carbonate (including isomers), (methylphenyl)(triethylphenyl) carbonate (including isomers), (methylphenyl)(tripropylphenyl) carbonate (including isomers), (methylphenyl)(tributylphenyl) carbonate (including isomers), (methylphenyl)(phenylmethyl) carbonate (including isomers), (methylphenyl)(phenylethyl) carbonate (including isomers), (methylphenyl) (phenylpropyl) carbonate (including isomers), (methylphenyl)(phenybutyl) carbonate (including isomers), (methylphenyl)(phenylpentyl) carbonate (including isomers), (methylphenyl)(phenyhexyl) carbonate (including isomers), (methylphenyl)(phenylheptyl) carbonate (including isomers), (methylphenyl)(phenyloctyl) carbonate (including isomers), (methylphenyl)(phenylnonyl) carbonate (including isomers), (ethylphenyl)(propylphenyl) carbonate (including isomers), (ethylphenyl)(butylphenyl) carbonate (including isomers), (ethylphenyl)(pentylphenyl) carbonate (including isomers), (ethylphenyl)(hexylphenyl) carbonate (including isomers), (ethylphenyl)(heptylphenyl) carbonate (including isomers), (ethylphenyl)(octylphenyl) carbonate (including isomers), (ethylphenyl)(nonylphenyl) carbonate (including isomers), (ethylphenyl)(decylphenyl) carbonate (including isomers), (ethylphenyl)(biphenyl) carbonate (including isomers), (ethylphenyl)(dimethylphenyl) carbonate (including isomers), (ethylphenyl)(diethylphenyl) carbonate (including isomers), (ethylphenyl)(dipropylphenyl) carbonate (including isomers), (ethylphenyl)(dibutylphenyl) carbonate (including isomers), (ethylphenyl)(dipentylphenyl) carbonate (including isomers), (ethylphenyl)(dihexylphenyl) carbonate (including isomers), (ethylphenyl)(diheptylphenyl) carbonate (including isomers), (ethylphenyl)(phenylphenyl) carbonate (including isomers), (ethylphenyl)(trimethylphenyl) carbonate (including isomers), (ethylphenyl) (triethylphenyl) carbonate (including isomers), (ethylphenyl) (tripropylphenyl) carbonate (including isomers), (ethylphenyl)(tributylphenyl) carbonate (including isomers), (ethylphenyl)(phenylmethyl) carbonate, (ethylphenyl)(phenylethyl) carbonate (including isomers), (ethylphenyl)(phenylpropyl) carbonate (including isomers), (ethylphenyl) (phenybutyl) carbonate (including isomers), (ethylphenyl) (phenylpentyl) carbonate (including isomers), (ethylphenyl) (phenyhexyl) carbonate (including isomers), (ethylphenyl) (phenylheptyl) carbonate (including isomers), (ethylphenyl) (phenyloctyl) carbonate (including isomers), (ethylphenyl) (phenylnonyl) carbonate (including isomers), (propylphenyl) (propylphenyl) carbonate (including isomers), (propylphenyl)(butylphenyl) carbonate (including isomers), (propylphenyl)(pentylphenyl) carbonate (including isomers), (propylphenyl)(hexylphenyl) carbonate (including isomers), (propylphenyl)(heptylphenyl) carbonate (including isomers), (propylphenyl)(octylphenyl) carbonate (including isomers), (propylphenyl)(nonylphenyl) carbonate (including isomers), (propylphenyl)(decylphenyl) carbonate (including isomers), (propylphenyl)(biphenyl) carbonate (including isomers), (propylphenyl)(dimethylphenyl) carbonate (including isomers), (propylphenyl)(diethylphenyl) carbonate (including isomers), (propylphenyl)(dipropylphenyl) carbonate (including isomers), (propylphenyl)(dibutylphenyl) carbonate (including isomers), (propylphenyl)(dipentylphenyl) carbonate (including isomers), (propylphenyl)(dihexylphenyl) carbonate (including isomers), (propylphenyl)(diheptylphenyl) carbonate (including isomers), (propylphenyl)(phenylphenyl) carbonate (including isomers), (propylphenyl)(trimethylphenyl) carbonate (including isomers), (propylphenyl)(triethylphenyl) carbonate (including isomers), (propylphenyl) (tripropylphenyl) carbonate (including isomers), (propylphenyl)(tributylphenyl) carbonate (including isomers), (propylphenyl)(phenylmethyl) carbonate (including isomers), (propylphenyl)(phenylethyl) carbonate (including isomers), (propylphenyl)(phenylpropyl) carbonate (including isomers), (propylphenyl)(phenybutyl) carbonate (including isomers), (propylphenyl)(phenylpentyl) carbonate (including isomers), (propylphenyl)(phenyhexyl) carbonate (including isomers), (propylphenyl)(phenylheptyl) carbonate (including isomers), (propylphenyl)(phenyloctyl) carbonate (including isomers), (propylphenyl)(phenylnonyl) carbonate (including isomers), (butylphenyl)(pentylphenyl) carbonate (including isomers), (butylphenyl)(hexylphenyl) carbonate (including isomers), (butylphenyl)(heptylphenyl) carbonate (including isomers), (butylphenyl)(octylphenyl) carbonate (including isomers), (butylphenyl)(nonylphenyl) carbonate (including isomers), (butylphenyl)(decylphenyl) carbonate (including isomers), (butylphenyl)(biphenyl) carbonate (including isomers), (butylphenyl)(dimethylphenyl) carbonate (including isomers), (butylphenyl)(diethylphenyl) carbonate (including isomers), (butylphenyl)(dipropylphenyl) carbonate (including isomers), (butylphenyl)(dibutylphenyl) carbonate (including isomers), (butylphenyl)(dipentylphenyl) carbonate (including isomers), (butylphenyl)(dihexylphenyl) carbonate (including isomers), (butylphenyl)(diheptylphenyl) carbonate (including isomers), (butylphenyl)(phenylphenyl) carbonate (including isomers), (butylphenyl)(trimethylphenyl) carbonate (including isomers), (butylphenyl)(triethylphenyl) carbonate (including isomers), (butylphenyl)(tripropylphenyl) carbonate (including isomers), (butylphenyl)(tributylphenyl) carbonate (including isomers), (butylphenyl)(phenylmethyl) carbonate (including isomers), (butylphenyl)(phenylethyl) carbonate (including isomers), (butylphenyl)(phenylpropyl) carbonate (including isomers), (butylphenyl)(phenybutyl) carbonate (including isomers), (butylphenyl)(phenylpentyl) carbonate (including isomers), (butylphenyl)(phenyhexyl) carbonate (including isomers), (butylphenyl)(phenylheptyl) carbonate (including isomers), (butylphenyl)(phenyloctyl) carbonate (including isomers), (butylphenyl)(phenylnonyl) carbonate (including isomers), (pentylphenyl)(hexylphenyl) carbonate (including isomers), (pentylphenyl)(heptylphenyl) carbonate (including isomers), (pentylphenyl)(octylphenyl) carbonate (including isomers), (pentylphenyl)(nonylphenyl) carbonate (including isomers), (pentylphenyl)(decylphenyl) carbonate (including isomers), (pentylphenyl)(biphenyl) carbonate (including isomers), (pentylphenyl)(dimethylphenyl) carbonate (including isomers), (pentylphenyl)(diethylphenyl) carbonate (including isomers), (pentylphenyl)(dipropylphenyl) carbonate (including isomers), (pentylphenyl)(dibutylphenyl) carbonate (including isomers), (pentylphenyl)(dipentylphenyl) carbonate (including isomers), (pentylphenyl)(dihexylphenyl) carbonate (including isomers), (pentylphenyl)(diheptylphenyl) carbonate (including isomers), (pentylphenyl)(phenylphenyl) carbonate (including isomers), (pentylphenyl)(trimethylphenyl) carbonate (including isomers), (pentylphenyl)(triethylphenyl) carbonate (including isomers), (pentylphenyl)(tripropylphenyl) carbonate (including isomers), (pentylphenyl)(tributylphenyl) carbonate (including isomers), (pentylphenyl)(phenylmethyl) carbonate (including isomers), (pentylphenyl)(phenylethyl) carbonate (including isomers), (pentylphenyl)(phenylpropyl) carbonate (including isomers), (pentylphenyl)(phenybutyl) carbonate (including isomers), (pentylphenyl)(phenylpentyl) carbonate (including isomers), (pentylphenyl)(phenyhexyl) carbonate (including isomers), (pentylphenyl)(phenylheptyl) carbonate (including isomers), (pentylphenyl)(phenyloctyl) carbonate (including isomers), (pentylphenyl)(phenylnonyl) carbonate (including isomers), (hexylphenyl)(heptylphenyl) carbonate (including isomers), (hexylphenyl)(octylphenyl) carbonate (including isomers), (hexylphenyl)(nonylphenyl) carbonate (including isomers), (hexylphenyl)(decylphenyl) carbonate (including isomers), (hexylphenyl)(biphenyl) carbonate (including isomers), (hexylphenyl)(dimethylphenyl) carbonate (including isomers), (hexylphenyl)(diethylphenyl) carbonate (including isomers), (hexylphenyl)(dipropylphenyl) carbonate (including isomers), (hexylphenyl)(dibutylphenyl) carbonate (including isomers), (hexylphenyl)(dipentylphenyl) carbonate (including isomers), (hexylphenyl)(dihexylphenyl) carbonate (including isomers), (hexylphenyl)(diheptylphenyl) carbonate (including isomers), (hexylphenyl)(phenylphenyl) carbonate (including isomers), (hexylphenyl)(trimethylphenyl) carbonate (including isomers), (hexylphenyl)(triethylphenyl) carbonate (including isomers), (hexylphenyl)(tripropylphenyl) carbonate (including isomers), (hexylphenyl)(tributylphenyl) carbonate (including isomers), (hexylphenyl)(phenylmethyl) carbonate (including isomers), (hexylphenyl)(phenylethyl) carbonate (including isomers), (hexylphenyl)(phenylpropyl) carbonate (including isomers), (hexylphenyl)(phenybutyl) carbonate (including isomers), (hexylphenyl)(phenylpentyl) carbonate (including isomers), (hexylphenyl)(phenyhexyl) carbonate (including isomers), (hexylphenyl)(phenylheptyl) carbonate (including isomers), (hexylphenyl)(phenyloctyl) carbonate (including isomers), (hexylphenyl)(phenylnonyl) carbonate (including isomers), (dimethylphenyl)(diethylphenyl) carbonate (including isomers), (dimethylphenyl)(dipropylphenyl) carbonate (including isomers), (dimethylphenyl)(dibutylphenyl) carbonate (including isomers), (dimethylphenyl)(dipentylphenyl) carbonate (including isomers), (dimethylphenyl)(dihexylphenyl) carbonate (including isomers), (dimethylphenyl)(diheptylphenyl) carbonate (including isomers), (dimethylphenyl)(phenylphenyl) carbonate (including isomers), (dimethylphenyl)(trimethylphenyl) carbonate (including isomers), (dimethylphenyl)(triethylphenyl) carbonate (including isomers), (dimethylphenyl)(tripropylphenyl) carbonate (including isomers), (dimethylphenyl)(tributylphenyl) carbonate (including isomers), (dimethylphenyl)(phenylmethyl) carbonate (including isomers), (dimethylphenyl)(phenylethyl) carbonate (including isomers), (dimethylphenyl)(phenylpropyl) carbonate (including isomers), (dimethylphenyl)(phenybutyl) carbonate (including isomers), (dimethylphenyl)(phenylpentyl) carbonate (including isomers), (dimethylphenyl)(phenyhexyl) carbonate (including isomers), (dimethylphenyl)(phenylheptyl) carbonate (including isomers), (dimethylphenyl)(phenyloctyl) carbonate (including isomers), (dimethylphenyl)(phenylnonyl) carbonate (including isomers), (diethylphenyl)(dipropylphenyl) carbonate (including isomers), (diethylphenyl)(dibutylphenyl) carbonate (including isomers), (diethylphenyl)(dipentylphenyl) carbonate (including isomers), (diethylphenyl)(dihexylphenyl) carbonate (including isomers), (diethylphenyl)(diheptylphenyl) carbonate (including isomers), (diethylphenyl)(phenylphenyl) carbonate (including isomers), (diethylphenyl)(trimethylphenyl) carbonate (including isomers), (diethylphenyl)(triethylphenyl) carbonate (including isomers), (diethylphenyl)(tripropylphenyl) carbonate (including isomers), (diethylphenyl)(tributylphenyl) carbonate (including isomers), (diethylphenyl)(phenylmethyl) carbonate (including isomers), (diethylphenyl)(phenylethyl) carbonate (including isomers), (diethylphenyl)(phenylpropyl) carbonate (including isomers), (diethylphenyl)(phenybutyl) carbonate (including isomers), (diethylphenyl)(phenylpentyl) carbonate (including isomers), (diethylphenyl)(phenyhexyl) carbonate (including isomers), (diethylphenyl)(phenylheptyl) carbonate (including isomers), (diethylphenyl)(phenyloctyl) carbonate (including isomers), (diethylphenyl)(phenylnonyl) carbonate (including isomers), (dipropylphenyl)(dibutylphenyl) carbonate (including isomers), (dipropylphenyl)(dipentylphenyl) carbonate (including isomers), (dipropylphenyl)(dihexylphenyl) carbonate (including isomers), (dipropylphenyl)(diheptylphenyl) carbonate (including isomers), (dipropylphenyl)(phenylphenyl) carbonate (including isomers), (dipropylphenyl)(trimethylphenyl) carbonate (including isomers), (dipropylphenyl)(triethylphenyl) carbonate (including isomers), (dipropylphenyl)(tripropylphenyl) carbonate (including isomers), (dipropylphenyl)(tributylphenyl) carbonate (including isomers), (dipropylphenyl)(phenylmethyl) carbonate (including isomers), (dipropylphenyl)(phenylethyl) carbonate (including isomers), (dipropylphenyl)(phenylpropyl) carbonate (including isomers), (dipropylphenyl)(phenylbutyl) carbonate (including isomers), (dipropylphenyl)(phenylpentyl) carbonate (including isomers), (dipropylphenyl)(phenylhexyl) carbonate (including isomers), (dipropylphenyl)(phenylheptyl) carbonate (including isomers), (dipropylphenyl)(phenyloctyl) carbonate (including isomers), (dipropylphenyl)(phenylnonyl) carbonate (including isomers), (dibutylphenyl)(dipentylphenyl) carbonate (including isomers), (dibutylphenyl)(dihexylphenyl) carbonate (including isomers), (dibutylphenyl)(diheptylphenyl) carbonate (including isomers), (dibutylphenyl)(phenylphenyl) carbonate (including isomers), (dibutylphenyl)(trimethylphenyl) carbonate (including isomers), (dibutylphenyl)(triethylphenyl) carbonate (including isomers), (dibutylphenyl)(tripropylphenyl) carbonate (including isomers), (dibutylphenyl)(tributylphenyl) carbonate (including isomers), (dibutylphenyl)(phenylmethyl) carbonate (including isomers), (dibutylphenyl)(phenylethyl) carbonate (including isomers), (dibutylphenyl)(phenylpropyl) carbonate (including isomers), (dibutylphenyl)(phenybutyl) carbonate (including isomers), (dibutylphenyl)(phenylpentyl) carbonate (including isomers), (dibutylphenyl)(phenyhexyl) carbonate (including isomers), (dibutylphenyl)(phenylheptyl) carbonate (including isomers), (dibutylphenyl)(phenyloctyl) carbonate (including isomers), (dibutylphenyl)(phenylnonyl) carbonate (including isomers), (dipentylphenyl)(dihexylphenyl) carbonate (including isomers), (dipentylphenyl)(diheptylphenyl) carbonate (including isomers), (dipentylphenyl)(phenylphenyl) carbonate (including isomers), (dipentylphenyl)(trimethylphenyl) carbonate (including isomers), (dipentylphenyl)(triethylphenyl) carbonate (including isomers), (dipentylphenyl)(tripropylphenyl) carbonate (including isomers), (dipentylphenyl)(tributylphenyl) carbonate (including isomers), (dipentylphenyl)(phenylmethyl) carbonate (including isomers), (dipentylphenyl)(phenylethyl) carbonate (including isomers), (dipentylphenyl)(phenylpropyl) carbonate (including isomers), (dipentylphenyl)(phenylbutyl) carbonate (including isomers), (dipentylphenyl)(phenylpentyl) carbonate (including isomers), (dipentylphenyl)(phenyhexyl) carbonate (including isomers), (dipentylphenyl)(phenylheptyl) carbonate (including isomers), (dipentylphenyl)(phenyloctyl) carbonate (including isomers), (dipentylphenyl)(phenylnonyl) carbonate (including isomers), (trimethylphenyl)(triethylphenyl) carbonate (including isomers), (trimethylphenyl)(tripropylphenyl) carbonate (including isomers), (trimethylphenyl)(tributylphenyl) carbonate (including isomers), (trimethylphenyl)(phenylmethyl) carbonate (including isomers), (trimethylphenyl)(phenylethyl)carbonate (including isomers), (trimethylphenyl)(phenylpropyl)carbonate (including isomers), (trimethylphenyl)(phenybutyl)carbonate (including isomers), (trimethylphenyl)(phenylpentyl)carbonate (including isomers), (trimethylphenyl)(phenyhexyl) carbonate (including isomers), (trimethylphenyl)(phenylheptyl)carbonate (including isomers), (trimethylphenyl)(phenyloctyl)carbonate (including isomers) and (trimethylphenyl)(phenylnonyl)carbonate (including isomers).

A trace amount of carbonic acid ester is formed as a by-product during production of N-substituted carbamic acid-O-aryl ester from the composition for transfer and storage of a compound having ureido groups of the present embodiment and an aromatic hydroxy compound and/or during production of N-substituted carbamic acid-O—$R^2$ ester from a compound having ureido groups and an alcohol as previously described. A preferable aspect involves producing the N-substituted carbamic acid-O-aryl ester followed by recycling the compounds used in each step when producing isocyanate by thermally decomposing the N-substituted carbamic acid-O-aryl ester. The carbonic acid ester may be contained at that time when the composition for transfer and storage of a compound having ureido groups is produced by recovering the carbonic acid ester along with the aromatic hydroxy compound. The carbonic acid ester formed as a by-product is a carbonic acid ester derived from the aromatic hydroxy compound and/or alcohol used when producing the N-substituted carbamic acid-O-aryl ester, namely a carbonic acid ester in which $R^{38}OH$ and $R^{39}OH$, in which hydroxyl groups have been added to $R^{38}$ and $R^{39}$ of the above-mentioned formula (20), correspond to the above-mentioned aromatic hydroxy compound and/or alcohol. When producing N-substituted carbamic acid-O-aryl ester using the compound for transfer and storage of a compound having ureido groups that contains the carbonic acid ester, there is also a mechanism by which N-substituted carbamic acid-O—($R^2$ or aryl) ester is regenerated by addition to an undesirable compound having ureylene groups that is formed due to condensation of the N-substituted carbamic acid-O—($R^2$ or aryl) ester, thereby making this aspect preferable. In addition, although there may be cases in which complexly substituted monomers or polymers of urea compounds, biurets or nurates and the like are contained in addition to the urea compound, carbamic acid ester and carbonic acid ester, there are no problems with such compounds being contained.

A brief explanation has been provided of several steps in the explanation of compounds used in the present embodiment as described above. Next, a detailed explanation is given of a method for producing N-substituted carbamic acid-O-aryl ester from a compound having ureido groups and an aromatic hydroxy composition, as well as a detailed explanation of each step contained in the method for producing isocyanate from N-substituted carbamic acid-O-aryl ester. The production method of N-substituted carbamic acid-O-aryl ester of the present embodiment is a method for producing at least one N-substituted carbamic acid-O-aryl ester derived from a compound having ureido groups and an aromatic hydroxy composition comprising a step of carrying out an esterification reaction or steps for carrying out an esterification reaction and a transesterification reaction from the compound having ureido groups represented by formula (1) and the aromatic hydroxy composition containing at least one type of aromatic hydroxy compound represented by formula (2) (herein the N-substituted carbamic acid-O-aryl ester refers to an N-substituted carbamic acid ester in which an oxygen atom of the carbamic acid group (—NHCOO—) is bonded to an aromatic ring, or in other words, an N-substituted carbamic acid-O-ester derived from the compound having ureido groups and the aromatic hydroxy compound).

More specifically, the production method is a method for producing N-substituted carbamic acid-O-aryl ester comprising a step of esterifying a compound having ureido groups and at least one type of aromatic hydroxy composition represented by formula (2), or a method for producing the N-substituted carbamic acid-O-aryl ester comprising a step of esterifying a compound having ureido groups and an alcohol represented by formula (4) to obtain N-substituted carbamic acid-O—R² ester, and a step of transesterifying the N-substituted carbamic acid-O—R² ester and the aromatic hydroxy composition. More specifically, the production method is a method for producing N-substituted carbamic acid-O-aryl ester from the compound having ureido groups and the aromatic hydroxy composition that comprises a step (B), or a method for producing the N-substituted carbamic acid-O-aryl ester from the compound having ureido groups, the aromatic hydroxy composition and an alcohol represented by formula (4) that comprises a step (R) and a step (P). Preferably, the compound having ureido groups is a compound having ureido groups obtained in step (A), and the above-mentioned production methods respectively contains a production method that comprises the step (A) and the step (B) and a production method that comprises the step (A), the step (R) and the step (P). The above-mentioned N-substituted carbamic acid-O—R² ester refers to an N-substituted carbamic acid-O-ester derived from a compound having ureido groups and an R² group of an alcohol represented by formula (4).

First, a brief explanation is provided of the previously mentioned steps (A), (B), (C), (R), (P) and (F) along with the following steps (D), (E) and (G) that are also included in the production method of the present embodiment.

<Step (D)>

The following step (D) is carried out to recover urea before step (B), step (R) or step (P), or simultaneous to step (B), step (R) or step (P):

step (D): a step of removing urea by distillation or sublimation.

<Step (E)>

Step (E): a step of recycling the urea recovered in step (D) to step (A).

<Step (G)>

The following step (G) is carried out to recover ammonia formed as a by-product in step (A) and/or step (B) and/or step (R), react with carbon dioxide to regenerate urea, and recycle the urea to step (A):

step (G): a step of recovering ammonia formed as a by-product, reacting with carbon dioxide to regenerate urea, and recycling the urea to step (A).

The above-mentioned steps (D), (E) and (G) will be subsequently described in detail.

The production method of N-substituted carbamic acid-O-aryl ester of the present embodiment enables the production of diverse N-substituted carbamic acid-O-aryl esters by selecting the compounds used, such as organic primary amine, aromatic hydroxy composition and additionally alcohol and the like, together with selecting and combining the above-mentioned steps (A) to (G), and further enables the obtaining of isocyanate from the N-substituted carbamic acid-O-aryl ester.

<Production Method of Compound Having Ureido Groups>

As was previously described, the compound having the ureido groups used in the present embodiment may be a compound having ureido groups that is obtained by the known method. Preferably, it is a compound having ureido groups that is obtained using the following step (A):

step (A): a step of obtaining at least one type of compound having ureido groups derived from an organic primary amine represented by the following formula (3) and urea by ureidating the organic primary amine and the urea in a liquid phase and eliminating or extracting to a gaseous phase ammonia formed as a by-product in the ureidation reaction.

The term "eliminated" does not refer to an ammonia radical, but rather to dissolving and/or dispersing in a liquid phase.

FIG. 1 shows a conceptual drawing of the step (A) in the present embodiment. In addition, the above-mentioned ureidation reaction indicates a reaction between an amino group of an organic primary amine and an ureido group, namely a reaction in which the organic primary amine is converted to a compound having ureido groups.

As a result of extensive studies conducted by the inventors of the present invention, the inventors of the present invention surmised the reaction mechanism by which a compound having ureido groups is formed from an organic primary amine and urea to be as indicated below, although the entirety of which is not yet clear. Furthermore, in order to simplify the following explanation, an organic primary amine having two amino groups is shown for the organic primary amine. Naturally, cases of using an organic primary amine other than that shown here can be considered in the same manner.

The reaction for forming a compound having ureido groups from an organic primary amine and urea appears to be as shown in the following formula (111), and proceeds while forming ammonia as a by-product although not shown in the formula:

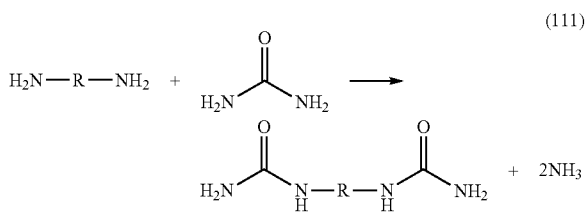

(111)

(wherein

R represents an organic group substituted with two substituents).

In the reaction for forming a compound having ureido groups of formula (111) above, a reaction, for example, in which a compound having ureylene groups is formed from a compound having ureido groups and organic primary amine as represented by the following formula (113), or for example, a reaction in which a compound having biuret groups is formed by condensing a compound having ureido groups as represented by the following formula (114), may occur concomitantly as side reactions (the reaction formulas used to explain the present embodiment are for indicating the concepts of the reactions (whether compounds are reactants or products), and frequently do not indicate numbers indicating stoichiometric ratios):

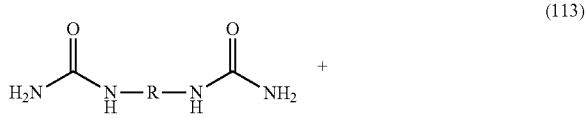

(113)

-continued

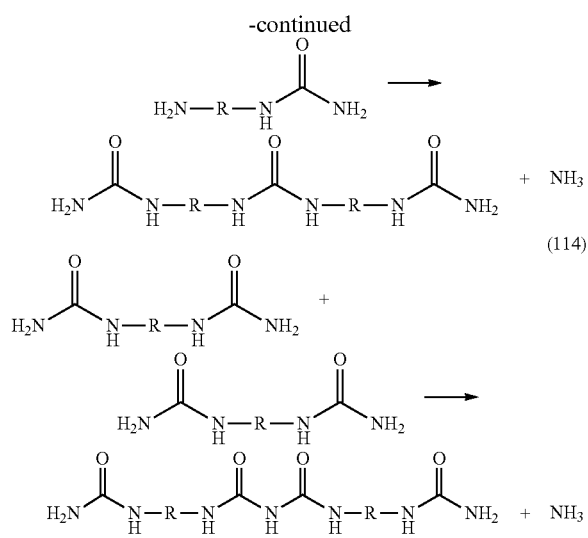

(wherein

R represents a divalent organic group).

The following provides an explanation of the amounts of organic primary amine and urea used as raw materials in step (A). The amount of urea is within a range of a stoichiometric ratio of from 1 to 100 times based on amino groups of the organic primary amine. Although previously explained for non-N-substituted carbamic acid ester, a compound having ureido groups can be obtained by reacting with organic primary amine in the same manner as urea also in the case of non-N-substituted carbamic acid-O—$R^2$ ester and/or N-substituted carbamic acid-O-aryl ester. Namely, the amounts of urea indicated previously and indicated to follow are stoichiometric values of the total of urea, non-N-substituted carbamic acid-O—$R^2$ ester and non-N-substituted carbamic acid O-aryl ester. In the case the amount used of urea (and non-N-substituted carbamic acid ester) is low, since complexly substituted carbonyl compounds and the like attributable to formula (113) above are formed easily, it is preferable to use an excess of urea and non-N-substituted carbamic acid ester.

In addition, urea and non-N-substituted carbamic acid ester present in excess in the reaction system of step (A) are presumed to have the effect of stabilizing the compound having ureido groups formed (non-N-substituted carbamic acid-O—$R^2$ ester and/or non-N-substituted carbamic acid-O-aryl ester are frequently collectively referred to as non-N-substituted carbamic acid ester). According to studies conducted by the inventors of the present invention, there are cases in which compounds having a biuret bond (such as the compound on the right side of the following formula (125)) or compounds having a biuret terminal (compound on the right side of the following formula (126)) are formed during the course of producing the compound having ureido groups depending on the reaction conditions. In order to selectively form a target compound having ureido groups, it is important to inhibit the formation of such compounds. As a result of extensive studies conducted by the inventors of the present invention, it was surprisingly found that there is an intimate relationship between the amount of urea (and the amount of non-N-substituted carbamic acid ester) in the reaction system and the amounts of such compounds formed, and that the amounts of such compounds are reduced the larger the amount of amount of urea (and non-N-substituted carbamic acid ester) present. Although the mechanism by which urea present in the reaction system demonstrates this effect is unclear, the inventors of the present invention made the presumptions indicated below regarding this mechanism.

First, the mechanism by which compounds having a biuret bond and compounds having a biuret terminal are formed is considered. The compound having ureido groups forms a compound having an isocyanate terminal (—NCO group) and ammonia due to thermal decomposition of the ureido groups depending on the reaction conditions (according to the following formula (124), for example):

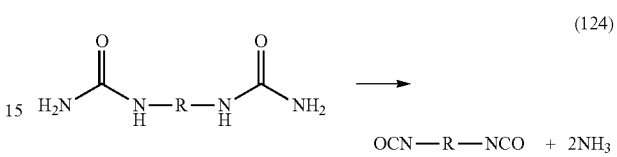

(wherein

R represents a divalent organic group).

There is presumed to be cases in which the compound having an isocyanate terminal reacts with urea (and non-N-substituted carbamic acid ester) (as in, for example, the following formulas (125) and (126) explained using urea) to form a compound having a biuret bond or compound having a biuret terminal:

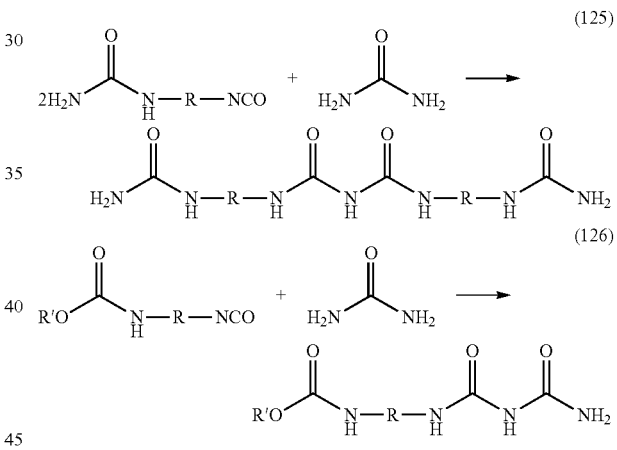

(wherein

R represents a divalent organic group).

The urea (and non-N-substituted carbamic acid ester) is presumed to stabilize the ureido groups by coordinating with the ureido groups by hydrogen bonding in the reaction liquid, and has the effect of inhibiting the first reaction in particular (namely the reaction represented by formula (124) above) among this series of reactions.

In this manner, the use of an excess amount of urea (and non-N-substituted carbamic acid ester) is important for selectively forming the compound having ureido groups. However, the use of an overly excessive amount of urea (and non-N-substituted carbamic acid ester) increases the size of the reactor making industrial application difficult, or as will be described later, may hinder separation and recovery of the urea (and non-N-substituted carbamic acid ester). Thus, the amount of urea used in terms of the stoichiometric ratio based on amino groups of the organic primary amine is preferably within a range of from 1 to 100 times, more preferably within a range of from 1.1 to 10 times and most preferably within a range of from 1.5 to 5 times.

In addition, it is also necessary to pay attention to the procedure when carrying out the reaction in consideration of the role of the urea (and non-N-substituted carbamic acid ester) as described above. Namely, a method is preferably carried out in which, for example, the entire amount of urea (and non-N-substituted carbamic acid ester) used is dissolved in advance in a reaction solvent (the details of which will be subsequently described) followed by addition of the organic primary amine to this mixed solution so as to continuously maintain the number of molecules of urea (and non-N-substituted carbamic acid ester) in the reaction system in a state of excess (and in a state of large excess if possible) based on the number of amino groups of the organic primary amine.

Next, an explanation is given of the ammonia concentration in the system. Furthermore, the preferable range of the ammonia concentration described here refers to the ammonia concentration in the reaction liquid after the compound having ureido groups has formed to a certain degree (such as at a yield of not less than 5% based on the organic amine), and does not refer to that at the start of the reaction.

The reaction in which N-substituted carbamic acid-O—($R^2$ and/or aryl) ester is formed (such as the reaction of the following formula (118)) is an equilibrium reaction, and the equilibrium is considerably biased towards the reactants side. However, as a result of studies conducted by the inventors of the present invention, the reaction in which the compound having ureido groups is formed (reaction of the above-mentioned formula (117)) was determined to be a reaction in which the equilibrium thereof is considerably biased towards the products side or be an irreversible reaction, and be virtually independent of the ammonia concentration in the system. Such a finding was heretofore unknown and is surprising. Thus, it was found that the compound having ureido groups can be formed selectively by maintaining the ammonia concentration in the reaction liquid of step (A) at a certain level or higher and inhibiting the formation of N-substituted carbamic acid ester by a reaction between the compound having ureido groups formed and an aromatic hydroxy compound (reaction of the above-mentioned formula (118)), and it was further found that the compound having ureido groups can be obtained with good selectivity by inhibiting side reactions by maintaining the ammonia concentration at a certain level or higher. In previously disclosed methods for producing compounds having ureido groups, side reaction products easily formed when obtaining a compound having ureido groups according to the above-mentioned reaction, and were contained within a range at which N-substituted carbamic acid-O-alkyl ester formed in accordance with the following formula (118) is simultaneously formed in large amounts, thus resulting in the serious problem of the concomitant occurrence of side reactions attributable to the N-substituted carbamic acid-O-alkyl ester. In order to solve this problem, the amount of the urea (and non-N-substituted carbamic acid ester) used and/or the ammonia concentration is important. The ammonia concentration preferable for demonstrating such an effect is higher than 10 ppm, more preferably higher than 100 ppm, even more preferably higher than 300 ppm, and most preferably higher than 1000 ppm.

Furthermore, although the term "N-substituted carbamic acid-O—($R^2$ and/or aryl) ester" is used in the explanation of the present specification, this refers to "N-substituted carbamic acid-O—$R^2$ ester and/or N-substituted carbamic acid-O-aryl ester":

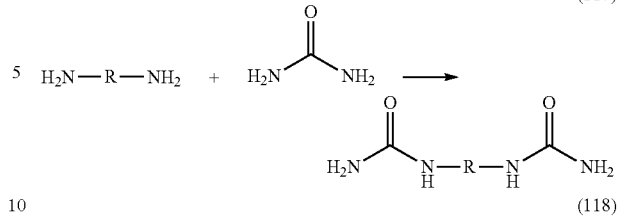

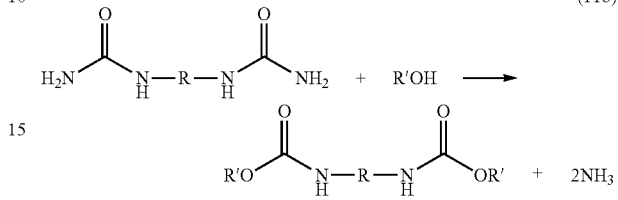

(wherein
R represents an organic group substituted with two substituents, and
R'OH represents a monovalent hydroxy compound (alcohol or aromatic hydroxy compound)).

Step (A) can be carried out at a reaction temperature within a range of from 30 to 250° C. Although a high temperature is preferable to increase the reaction rate, on the other hand, since undesirable reactions occur at high temperatures (such as decomposition of the carbonic acid derivative) resulting in the formation of complexly substituted urea compounds and carbonyl compounds, the reaction temperature is preferably within a range of from 50 to 200° C. and more preferably within a range of from 70 to 180° C. The known cooling apparatus or heating apparatus may be installed in the reactor for carrying out step (A) to maintain a constant reaction temperature.

Although varying according to the types of compounds used, composition of the reaction system, reaction temperature, reaction apparatus and the like, generally the reaction is preferably carried out at a reaction pressure within a range of from 0.01 kPa to 10 MPa (absolute pressure), and in consideration of ease of the industrial application, is preferably carried out at reaction pressure within a range of from 0.1 kPa to 5 MPa (absolute pressure).

There are no particular limitations on the reaction time (residence time in the case of a continuous method) in the step (A), and the reaction time is generally from 0.001 to 100 hours, preferably from 0.01 to 80 hours and more preferably from 0.1 to 50 hours. In addition, the reaction may be terminated after confirming that a desired amount of the compound having ureido groups has been formed by sampling the reaction liquid and determining the amount of the compound having ureido groups by liquid chromatography, for example. Although step (A) is a step of producing a compound having ureido groups, in step (A), if a large amount of amino groups derived from unreacted organic amine are present, compounds having ureylene groups and the like are formed during storage when using in the form of a composition for transfer and storage of a compound having ureido groups, or in step (B) or step (R) using the reaction liquid after step (A), which frequently not only causes a decrease in the amount of N-substituted carbamic acid-O-ester formed, but also causes adhesion and solidification in the reactor. Thus, in step (A), it is preferable to reduce the amount of amino groups derived from the organic primary amine by forming the compound having ureido groups at as high a yield as possible. More specifically, the reaction is preferably continued until the ratio of the number of amino groups derived from the organic primary amine to the number of ureido groups composing the compound having ureido groups becomes preferably 0.25 or less, more preferably 0.1 or less, and even more preferably 0.05 or less.

In the present embodiment, a catalyst can be used as necessary, and examples of catalysts that can be used may include organic metal compounds and inorganic metal compounds of tin, lead, copper or titanium, and basic catalysts such as alcoholate of alkaline metals or alkaline earth metals in the form of methylates, ethylates and butyrates (including isomers) of lithium, sodium, potassium, calcium or barium. If a catalyst is added, since there are many cases in which it is necessary to remove the catalyst, the reaction is preferably carried out without adding a catalyst. In the case of using a catalyst, the catalyst may be removed after the reaction. Since there are cases in which a catalyst may have a detrimental effect on compounds in the steps of the present embodiment, the catalyst is preferably separated or removed during the course of obtaining isocyanate by thermally decomposing N-substituted carbamic acid-O-aryl ester and purifying the isocyanate. If isocyanate is stored with the catalyst present, discoloration and other undesirable phenomena may occur. The known method can be used to remove the catalyst, and methods such as membrane separation, distillative separation or crystallization can be used. The catalyst is preferably removed for the reasons described above without being limited to step (A). More preferably, the catalyst is removed at completion of each step in which it is used. Known methods as previously described can be preferably used to remove the catalyst.

The reaction of step (A) is preferably carried out in a liquid phase in the presence of a solvent from the viewpoint of lowering the viscosity of the reaction liquid and/or making the reaction system homogeneous. Examples of solvents that can be preferably used as reaction solvents may include alkanes such as pentane (including isomers), hexane (including isomers), heptane (including isomers), octane (including isomers), nonane (including isomers) or decane (including isomers); aromatic hydrocarbons and alkyl-substituted aromatic hydrocarbons such as benzene, toluene, xylene (including isomers), ethyl benzene, diisopropyl benzene (including isomers), dibutyl benzene (including isomers) or naphthalene; nitrile compounds such as acetonitrile or benzonitrile; aromatic compounds substituted with a halogen or nitro group such as chlorobenzene, dichlorobenzene (including isomers), bromobenzene, dibromobenzene (including isomers), chloronaphthalene, bromonaphthalene, nitrobenzene or nitronaphthalene; polycyclic hydrocarbon compounds such as diphenyl, substituted diphenyl, diphenyl methane, terphenyl, anthracene or dibenzyl toluene (including isomers); aliphatic hydrocarbons such as cyclohexane, cyclopentane, cyclooctane or ethylcyclohexane; ketones such as methyl ethyl ketone or acetophenone; esters such as dibutyl phthalate, dihexyl phthalate, dioctyl phthalate or benzylbutyl phthalate; ethers and thioethers such as tetrahydrofuran, 1,4-dioxane, 1,2-dimethoxyethane, diphenyl ether or diphenyl sulfide; ketone compounds such as acetone or methyl ethyl ketone; ester compounds such as ethyl acetate or ethyl benzoate; sulfoxides such as dimethylsulfoxide or diphenylsulfoxide, and hydroxy compounds such as water, alcohols or aromatic hydroxy compounds. However, from the viewpoint of solubility of the product in the form of the compound having ureido groups, the reaction solvent is preferably water or a hydroxy composition (composition containing alcohol and/or aromatic hydroxy compound), and more preferably a hydroxy composition (the hydroxy composition being a hydroxy composition composed of one type or a plurality of types of hydroxy compounds (alcohol represented by formula (4) and/or aromatic hydroxy compound represented by formula (2)), and a hydroxy composition preferably used as a reaction solvent in step (A) is hereinafter referred to as "hydroxy composition a"). Furthermore, these solvents can be used alone or as a mixture of two or more types thereof.

Although hydroxy compounds that compose the hydroxy composition a may be completely identical, partially identical or different from the hydroxy composition used in step (B), step (R) or step (P) (composition composed of the aromatic hydroxy compound and/or alcohol that composes the aromatic hydroxy composition), in order to facilitate the procedure, the hydroxy composition a is preferably either the same as the hydroxy composition used in step (B) or step (P) or is a composition composed of that hydroxy composition. Although an explanation thereof is provided to follow, the reaction of step (A) is more preferably either carried out in the presence of an aromatic hydroxy composition (composition containing at least one type of aromatic hydroxy compound represented by the following formula (2)), or the reaction of step (A) is carried out in the presence of an alcohol or aromatic hydroxy composition followed by the addition of an aromatic hydroxy composition (composition containing at least one type of aromatic hydroxy compound represented by the following formula (2)). The step (A) is more preferably carried out in the presence of an aromatic hydroxy composition (composition containing at least one type of aromatic hydroxy compound represented by the following formula (2)). Although only alcohol may be used in the case of carrying out step (R) after step (A), in this case, an aromatic hydroxy composition (composition containing at least one type of aromatic hydroxy compound represented by the following formula (2)) is added after carrying out the reaction of step (A).

Although the reaction solvents indicated here can be used in an arbitrary amount, in the case of using an alcohol for the reaction solvent, it can be used at a stoichiometric ratio within a range of greater than 1 time to less than 100 times based on the amino groups of the organic primary amine. Although it is preferable to use an excess of alcohol based on the amino groups of the organic primary amine in order to improve the fluidity of the reaction liquid and allow the reaction to proceed efficiently, since problems may result such as an increase in the size of the reactor if an overly excessive amount of alcohol is used, the alcohol can be used at a stoichiometric ratio more preferably within a range of greater than 5 times to less than 50 times and even more preferably within a range of greater than 8 times to less than 20 times the amino groups of the organic primary amine.

In addition, in the case of using an aromatic hydroxy composition for the reaction solvent of step (A), it can be used at a stoichiometric ratio within a range of greater than 1 time to less than 100 times the amino groups of the organic primary amine. Although it is preferable to use an excess of alcohol based on the amino groups of the organic primary amine in order to improve the fluidity of the reaction liquid and allow the reaction to proceed efficiently, since problems may result such as an increase in the size of the reactor if an overly excessive amount of alcohol is used, alcohol can be used at a stoichiometric ratio more preferably within a range of greater than 2 times to less than 50 times and even more preferably within a range of greater than 3 times to less than 20 times the amino groups of the organic primary amine.

Among hydroxy compounds represented by compounds selected from alcohols represented by the above-mentioned formula (4) and aromatic hydroxy compounds represented by formula (2), an aromatic hydroxy compound is used preferably in consideration of solubility of the compound having ureido groups formed. For example, although Japanese Examined Patent Publication No. H2-48539 describes to the effect that a compound having ureido groups is poorly soluble in n-butanol, with respect to this point, aromatic hydroxy compounds frequently have superior solubility for compounds having ureido groups. Moreover, aromatic hydroxy compounds also demonstrate the effect of promoting reactions between organic primary amine and urea (and non-N-substituted carbamic acid ester). Although the mechanism by which this effect is demonstrated is unclear, it has been surmised by the inventors of the present invention that, although urea (and non-N-substituted carbamic acid ester) generally tend to adopt an associated state due to hydrogen bonding, aromatic hydroxy compounds have acidic hydroxy groups, and the hydroxy groups inhibit association between the urea (and non-N-substituted carbamic acid ester), thereby making it easier for amines to approach the reaction sites of the urea (and non-N-substituted carbamic acid ester) (which are presumed to be carbons that compose the carbonyl groups of the urea (and non-N-substituted carbamic acid ester)).

In the case of using an aromatic hydroxy composition for the reaction solvent, although an aromatic hydroxy compound may be used alone or mixed with other solvents, the amount of the aromatic hydroxy compound used is within the range of the previously described values. In the case of adding an aromatic hydroxy composition (composition containing at least one type of aromatic hydroxy compound represented by the following formula (2)) after having carried out step (A) in the presence of alcohol as well, the aromatic hydroxy composition is used within the previously described ranges. At that time, the amount of alcohol used during the reaction of step (A) is also used at the stoichiometric ratio indicated for the aromatic hydroxy compound based on the organic primary amine as previously described. In the case of using water in step (A), the water is preferably used together with an aromatic hydroxy composition and/or alcohol. Although water alone may be used as a solvent, it may be necessary to remove the water following completion of step (A). When an aromatic hydroxy compound in the amount described above is added to obtain a composition for transfer and storage of a compound having ureido groups by using a compound having ureido groups obtained in step (A), there are cases in which the reaction liquid separates into an aqueous phase and organic phase or the aromatic hydroxy compound and compound having ureido groups solidify. In addition, when step (R) or step (B) is carried out after adding the aromatic hydroxy compound in the amount described above following completion of step (A), a homogeneous liquid may be unable to be transferred or transfer pumps and lines may become clogged for the reasons described above. Thus, in the case of using only water for the solvent in step (A), the water is removed before or after adding the aromatic hydroxy compound. Although varying according to the compounds used and composition, water is removed until the amount of water is within a range of from 10 ppm to 10% by weight, preferably from 10 ppm to 5% by weight and more preferably from 10 ppm to 2% by weight in the reaction liquid (or mixed liquid) following removal thereof. The known method for removing water can be used for the water removal method, and examples of methods that can be used may preferably include removal by distillation at a reduced pressure or a normal pressure, the use of an adsorbent such as zeolite, the addition of a hydrolyzable compound such as an acetal followed by removal of water by a hydrolysis reaction, and removal of water with a compound that reacts with water in the manner of N,N-dicyclohexylcarbodiimide. Water is more preferably removed by distillation. In the case of using water together with an aromatic hydroxy composition and/or alcohol as a solvent in step (A), the amount of water in the reaction is within a range of from 10 ppm to 10% by weight, preferably from 10 ppm to 5% by weight, and more preferably from 10 ppm to 2% by weight. The inventors of the present invention surprisingly found that the reaction of step (A) demonstrates an improvement in reaction rate due to the presence of water. Thus, having water present during the reaction is a preferable method. Although the details of this effect have not been determined, it is presumed that the water demonstrates the effect of enhancing nucleophilicity of the organic primary amine.

There are no particular limitations on the reaction apparatus used when carrying out the reaction, and the known reactor can be used. For example, conventionally known reactors can be suitably combined, such as a stirring tank, a pressurized stirring tank, a depressurized stirring tank, a column type reactor, a distillation column, a packed column or a thin film distiller. A tank-type reactor provided with a stirrer is used preferably. There are no particular limitations on the material of the reactors, and known materials can be used. Examples thereof may include glass, stainless steel, carbon steel, Hastelloy, glass-lined base materials and Teflon (registered trademark) coated materials. Materials such as SUS304, SUS316 or SUS316L are inexpensive and can be used preferably. Known process apparatuses such as a flow meter, a thermometer and other measuring instruments or a reboiler, a pump or a condenser and the like may be added as necessary, a known method such as steam or a heater may be used for heating, and a known method such as air cooling, cooling water or brine can be used for cooling. Steps may also be added as necessary. For example, steps and apparatuses able to be conceived by a person or engineer with ordinary skill in the art may be added, such as a step of removing the ammonia formed, a step of purifying the organic primary amine, a step of dissolving the urea in the aromatic hydroxy compound, a step of dissolving the aromatic hydroxy compound, a step of separating the alcohol, a step of separating and/or purifying the aromatic hydroxy compound, a step of purifying the compound having ureido groups from the formed reaction liquid or a step of incinerating or discarding by-products and the like.

In the case of using a reaction solvent in step (A), the reaction solvent may be removed from the reaction liquid of step (A) hen preparing the composition for transfer and storage of a compound having ureido groups to a desired composition or prior to carrying out step (B) or step (R), or the composition may be prepared or the step may be carried out without removing the reaction solvent. In particular, the hydroxy compound used as a reaction solvent is step (A) is preferably used as is as a portion of the hydroxy composition of step (B) or step (R).

Ammonia formed as a by-product in the step (A) may be recovered in the form of ammonia gas by introducing into a condenser provided in the reactor at a reduced pressure or a normal pressure, and condensing all or a portion of the hydroxy composition used in step (A) with a compound having carbonyl groups derived from urea.

In the present embodiment, by carrying out a process that includes a step of esterifying, or esterifying and transesterifying a compound having ureido groups (and preferably a compound having N-substituted ureido groups) and an aromatic hydroxy composition containing at least one type of aromatic hydroxy compound represented by formula (2) (namely, a process that includes step (B) or step (R) and step (P)), examples of aspects of a method for producing at least one N-substituted carbamic acid-O-aryl ester derived from the compound having ureido groups and the aromatic hydroxy composition (where the N-substituted carbamic acid-O-aryl ester refers to an N-substituted carbamic acid ester in which an oxygen atom of the carbamic acid group (—NHCOO—) is bonded to an aromatic ring) include the five aspects indicated below if the method additionally includes a method for carrying out step (C). Other aspects are also possible based on the present embodiment, and the present embodiment is not limited to the five aspects indicated below.

Examples of aspects of the present embodiment may include the following five routes that are carried out after obtaining a compound having ureido groups or after obtaining at least one type of compound having ureido groups (or reaction liquid containing a compound having ureido groups) by carrying out step (A):

route 1) method for carrying out step (B);
route 2) method for carrying out step (B) and then step (C);
route 3) method for carrying out step (R) and then step (P)
route 4) method for carrying out step (R), step (P) and then step (C); and,
route 5) method for carrying out step (R), step (C) and then step (P).

A method that includes step (B) is a method for obtaining N-substituted carbamic acid-O-aryl ester from a compound having ureido groups (or reaction liquid containing a compound having ureido groups) and an aromatic hydroxy composition by an esterification reaction, while a method that includes step (R) is a method for obtaining N-substituted carbamic acid-O-aryl ester by esterifying a compound having ureido groups and an alcohol to obtain an N-substituted carbamic acid-O—$R^2$ ester, and then transesterifying the N-substituted carbamic acid-O—$R^2$ ester and aromatic hydroxy composition in a step that includes step (P).

In either of the above-mentioned methods, N-substituted carbamic acid-O-aryl ester is obtained from the compound having the ureido groups (or after obtaining the same) and the aromatic hydroxy composition.

An explanation is first given of route 1).
<Route 1)>
Route 1) comprises a method for carrying out step (B).
Route 1) is a method for producing an N-substituted carbamic acid-O-aryl ester by reacting a compound having ureido groups and an aromatic hydroxy composition or from a composition for transfer and storage of a compound having ureido groups.
<Step (B)>
Step (B): A step of obtaining N-substituted carbamic acid-O-aryl ester by reacting the at least one type of compound having ureido groups and an aromatic hydroxy composition (composition containing at least one type or aromatic hydroxy compound represented by formula (2)) in a liquid phase and then extracting ammonia formed as a by-product to a gaseous phase (the reaction is an esterification reaction).

At least one type of compound having the ureido groups may be a compound having ureido groups produced using the known method provided it is the compound having ureido groups represented by formula (1). It is preferably at least one type of compound having ureido groups produced in step (A) or a reaction liquid containing at least one type of compound having ureido groups produced in step (A). The reaction liquid refers to the liquid resulting from completion of the reaction of step (A) and/or a reaction liquid to which has been added an aromatic hydroxy composition (composition containing at least one type of aromatic hydroxy compound represented by formula (2)) after having carried out the reaction of step (A) in the presence of an alcohol or aromatic hydroxy composition, and represents a reaction liquid containing at least one type of compound having ureido groups and a hydroxy composition. Alternatively, a composition for transfer and storage of a compound having ureido groups as previously explained may be used in place of the reaction liquid containing at least one type of compound having ureido groups produced in the above-mentioned step (A), and this method is also one aspect of the present embodiment.

Figure 2:
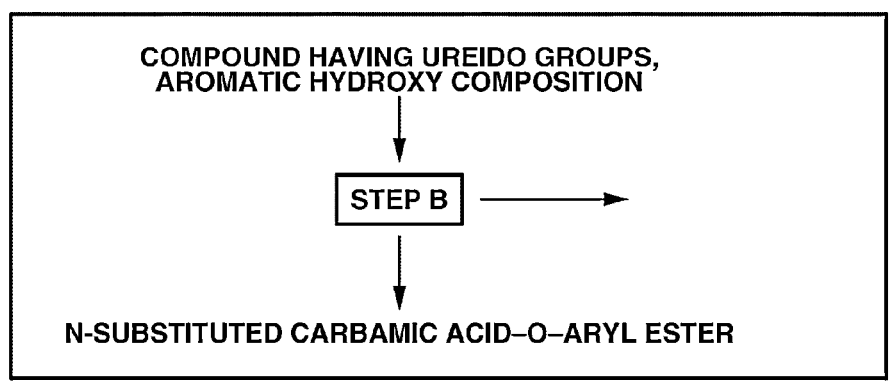
FIG. 2 shows a conceptual drawing depicting a step (B) in the present embodiment.

Step (B) may be a step of producing N-substituted carbamic acid-O-aryl ester by esterifying a compound having ureido groups and an aromatic hydroxy composition, and is a preferable aspect. FIG. 2 shows a conceptual drawing depicting the step (B).

The organic primary amine used in this route is an organic primary amine represented by formula (3), the compound having the ureido groups obtained in step (A) of this route is a compound having ureido groups represented by formula (1) derived from the organic primary amine, and the N-substituted carbamic acid-O-aryl ester obtained in step (B) of this route is an N-substituted carbamic acid-O-aryl ester represented by formula (43) derived from the compound having ureido groups. Indications of specific examples of each of these compounds are respectively contained in previous explanations thereof.

As was previously described, in the case the hydroxy composition a used as a reaction solvent in step (A) is the same as the hydroxy composition of step (B) (namely, composition containing an alcohol represented by formula (4) and/or an aromatic hydroxy compound represented by formula (2) that contains the aromatic hydroxy composition used in step (B)), step (B) can be carried out as is by using the reaction liquid obtained in step (A). In addition, in the case the hydroxy composition a used as a reaction solvent in step (A) differs from the hydroxy composition of step (B), step (B) may be carried out after newly adding a hydroxy compound to the reaction liquid obtained in step (A), one or a plurality of types of hydroxy compounds may be newly added to the reaction liquid obtained in step (A) followed by carrying out step (B) after separating all or a portion of the hydroxy composition used as a reaction solvent of step (A), or step (B) may be carried out after removing all or a portion of the hydroxy composition used as a reaction solvent in step (A) followed by newly adding one or a plurality of types of hydroxy compounds. Herein, the newly added hydroxy compound is an aromatic hydroxy composition containing at least one type of aromatic hydroxy compound represented by the above-mentioned formula (2).

Among these, the aromatic hydroxy composition used in step (B) is preferably an aromatic hydroxy composition containing an aromatic hydroxy compound represented by formula (7) or formula (31), and more preferably an aromatic hydroxy composition containing an active aromatic hydroxy compound, and even more preferably an aromatic hydroxy composition represented by formula (32) and even more preferably by formula (38) in order to conduct step (B). As was previously described, a method for producing N-substituted carbamic acid-O-alkyl ester by using a compound having ureido groups and reacting with alcohol is disclosed in Japanese Patent Application Laid-open No. H6-41045. As was previously explained, this N-substituted carbamic acid-O-alkyl ester is susceptible to thermal denaturation and easily forms a compound having ureylene groups. In addition, if the N-substituted carbamic acid-O-alkyl ester is subjected to thermal decomposition in an attempt to produce isocyanate, the thermal decomposition temperature becomes high and a reverse reaction of the thermal decomposition reaction occurs easily. As a result of studies conducted by the inventors of the present invention, in the case of obtaining N-substituted carbamic acid-O-aryl ester by reacting a compound having ureido groups and an aromatic hydroxy compound, it was found that N-substituted carbamic acid-O-aryl ester can be obtained at high yield without undergoing thermal denaturation.

There are no particular limitations on the method for separating the reaction solvent used in step (A), and although a known method such as distillative separation, membrane separation or extraction separation can be used, distillative separation is preferable. In the case of carrying out step (B) after having carried out step (A), there are cases in which step (A) is preferably carried out in the presence of an aromatic hydroxy composition, and there are also cases in which step (A) is preferably carried out in the absence of alcohol and in the presence of an aromatic hydroxy composition. As was previously described, in the case of using a compound having ureido groups for the starting raw material as well, there are many cases in which N-substituted carbamic acid-O-alkyl ester is susceptible to thermal denaturation. As a result of studies conducted by the inventors of the present invention, even if an alcohol is used in step (A) and a trace amount of N-substituted carbamic acid-O—$R^2$ ester is formed in step (B), denaturation was found to be significantly inhibited even in the presence of an aromatic hydroxy composition.

In the case of carrying out step (B) in the presence of alcohol, since there are cases in which a trace amount of N-substituted carbamic acid-O—$R^2$ ester is formed together with N-substituted carbamic acid-O-aryl ester, the alcohol is preferably removed before carrying out step (B) or simultaneous to carrying out step (B). Since N-substituted carbamic acid-O—$R^2$ ester is a compound that has a higher thermal decomposition temperature when carrying out step (F) as compared with N-substituted carbamic acid-O-aryl ester, in the case of route 1) or route 2) that includes step (B), alcohol is preferably not used in step (A) whenever possible (namely, alcohol is not used throughout the entire step) to inhibit the amount of N-substituted carbamic acid-O—$R^2$ ester formed.

Although varying according to the compounds reacted, the reaction conditions for producing N-substituted carbamic acid-O-aryl ester by reacting a compound having ureido groups and an aromatic hydroxy composition of step (B) are such that the amount of aromatic hydroxy compound in the aromatic hydroxy composition used has a stoichiometric ratio within a range of from 1 to 500 times based on the ureido groups of the compound having ureido groups used. Although it is preferable to use an excess of aromatic hydroxy compound since complexly substituted carbonyl compounds and high molecular weight compounds having carbonyl bonds in molecules thereof form easily if the stoichiometric ratio is less than 1 time, in consideration of the size of the reactor, the stoichiometric ratio is preferably within a range of from 1 to 100 times, more preferably within a range of from 2 to 50 times and even more preferably within a range of from 3 to 20 times.

Although varying according to the compounds used, the reaction temperature is preferably within a range of from 100 to 350° C. If the temperature is lower than 100° C., the reaction slows or the reaction hardly proceeds at all, or complexly substituted carbonyl compounds increase, thereby making this undesirable. On the other hand, at temperatures higher than 350° C., the N-substituted carbamic acid-O-aryl ester either remains in step (A), the urea (and non-N-substituted carbamic acid ester) formed in the system of step (B) decompose, the hydroxy composition is subjected to dehydrogenative denaturation, or decomposition and denaturation reactions of the product in the form of N-substituted carbamic acid-O-aryl ester occur easily, thereby making this undesirable. From such viewpoints, the reaction temperature is more preferably within a range of from 120 to 320° C. and even more preferably within a range of from 140 to 300° C.

As has been previously described, the reaction by which N-substituted carbamic acid-O-aryl ester is formed is an equilibrium reaction, and since the reaction is biased towards the reactants side, the reaction is preferably carried out while removing ammonia formed as a by-product outside the system as much as possible. Ammonia is preferably removed so that the ammonia concentration in the reaction liquid is preferably 1000 ppm or less, more preferably 300 ppm or less, even more preferably 100 ppm or less and most preferably 30 ppm or less (being contained in the reaction liquid refers to being contained in a liquid phase when carrying out the step (B)). Ammonia can be removed using methods such as reactive distillation, use of an inert gas, membrane separation and adsorptive separation. For example, the reactive distillation refers to a method for separating continuously formed ammonia during the reaction by distillation in the form of a gas. This can be carried out while boiling an aromatic hydroxy compound, solvent or hydroxy composition in order to increase the distillation efficiency of the ammonia. In addition, a method using an inert gas refers to a method for separating continuously formed ammonia during the reaction from the reaction system in the form of a gas along with the inert gas. Examples of inert gases used may include nitrogen, helium, argon, carbon dioxide, methane, ethane and propane, these may be used alone or as a mixture, and a method in which the inert gas is introduced into the reaction system is preferable. Examples of adsorbents used in methods using adsorptive separation may include adsorbents able to be used under the temperature conditions at which the reaction is carried out, such as silica, alumina, various types of zeolite or diatomaceous earth. These methods for removing ammonia outside the system may be carried out alone or a plurality of types may be carried out in combination.

A catalyst can be used in the reaction for the purpose of increasing the reaction rate, for example. Examples of catalysts that are used preferably may include basic catalysts such as methylates, ethylates or butyrates (including isomers) of lithium, sodium, potassium, calcium or barium, rare earth elements, antimony or bismuth alone or oxides, sulfides and salts thereof, boron alone or boron compounds, metals of the copper family, zinc family, aluminum family, carbon family and titanium family in the periodic table as well as metal oxides and sulfides thereof, and carbides and nitrides of elements of the carbon family excluding carbon, titanium family, vanadium family and chromium family in the periodic table. Although there are no particular limitations on the amount of catalyst used in the case of using a catalyst, a catalyst can be used within a range of a stoichiometric ratio of from 0.0001 to 100 times the ureido groups of the compound having ureido groups. Since there are many cases in which it is necessary to remove the catalyst if a catalyst is added, the reaction is preferably carried out without adding a catalyst.

Although varying according to the composition of the reaction system, reaction temperature, method used to remove ammonia, reaction apparatus and the like, the reaction pressure is generally within a range of from 0.01 Pa to 10 MPa (absolute pressure), and in consideration of ease of industrial application, the reaction pressure is more preferably within a range of from 0.1 Pa to 5 MPa (absolute pressure), and in consideration of removing gaseous ammonia outside the system, even more preferably from 0.1 Pa to 1.5 MPa (absolute pressure).

Although varying according to the composition of the reaction system, reaction temperature, method used to remove ammonia, reaction apparatus, reaction pressure and the like, the reaction time (residence time in the case of a continuous reaction) is generally from 0.01 to 100 hours. The reaction time can also be determined according to the formed amount of the target compound in the form of N-substituted carbamic acid-O-aryl ester (and depending on the case, the total amount resulting from adding the amount of N-substituted carbamic acid-O—$R^2$ ester). For example, the reaction may be stopped after having sampled the reaction liquid, determined the content of N-substituted carbamic acid-O-aryl ester (and depending on the case, the total amount resulting from adding the amount of N-substituted carbamic acid-O—$R^2$ ester) in the reaction liquid and confirming that the N-substituted carbamic acid-O-aryl ester has been formed at a yield of 10% or more based on the compound having ureido groups, or the reaction may be stopped after having confirmed that the yield is 90% or more. Isocyanate is obtained by applying the reaction liquid containing the N-substituted carbamic acid-O-aryl ester in step (B) to the thermal decomposition reaction in step (F). At this time, if the content of N-substituted carbamic acid-O-aryl ester is low (namely, yield is low) in step (B), a decrease in the yield of isocyanate may result. Thus, the yield is preferably 50% or more, more preferably 80% or more and even more preferably 90% or more.

Although the use of a reaction solvent is not necessarily required in the reaction, a suitable solvent is preferably used as a reaction solvent for the purpose of facilitating the reaction procedure, examples of which include alkanes such as pentane (including isomers), hexane (including isomers), heptane (including isomers), octane (including isomers), nonane (including isomers) or decane (including isomers); aromatic hydrocarbons and alkyl-substituted aromatic hydrocarbons such as benzene, toluene, xylene (including isomers), ethyl benzene, diisopropyl benzene (including isomers), dibutyl benzene (including isomers) or naphthalene; nitrile compounds such as acetonitrile or benzonitrile; aromatic compounds substituted with a halogen or nitro group such as chlorobenzene, dichlorobenzene (including isomers), bromobenzene, dibromobenzene (including isomers), chloronaphthalene, bromonaphthalene, nitrobenzene or nitronaphthalene; polycyclic hydrocarbon compounds such as diphenyl, substituted diphenyl, diphenyl methane, terphenyl, anthracene or dibenzyl toluene (including isomers); aliphatic hydrocarbons such as cyclohexane, cyclopentane, cyclooctane or ethylcyclohexane; ketones such as methyl ethyl ketone or acetophenone; esters such as dibutyl phthalate, dihexyl phthalate, dioctyl phthalate or benzylbutyl phthalate; ethers and thioethers such as tetrahydrofuran, 1,4-dioxane, 1,2-dimethoxyethane, diphenyl ether or diphenyl sulfide; ketone compounds such as acetone or methyl ethyl ketone; ester compounds such as ethyl acetate or ethyl benzoate; and sulfoxides such as dimethylsulfoxide or diphenylsulfoxide. Naturally, a hydroxy composition used in excess in the reaction is also preferably used as a reaction solvent.

The reaction is carried out in a system having a gaseous phase containing a hydroxy composition, a compound having carbonyl groups derived from urea (a compound that inherits a carbonyl group possessed by urea, such as a non-N-substituted carbamic acid ester or biuret, which refers to a compound excluding N-substituted carbamic acid-O-esters) and ammonia produced as a by-product in the reaction, and a liquid phase in which the reaction is carried out. Although the majority of the reaction is carried out in the liquid phase, it may also be carried out in the gaseous phase depending on the reaction conditions. At that time, the volumetric content of the liquid phase in the reaction in which the reaction is carried out is preferably 50% or less. In the case of carrying out the reaction continuously over a long period of time, although polymeric by-products may form due to fluctuations in operating conditions (such as temperature or pressure) and the like, if the volumetric content of the liquid phase in the reactor is high, adhesion and accumulation of such polymeric by-products in the reactor can be avoided. However, since the efficiency of removal of by-product ammonia may become poor and the yield of the N-substituted carbamic acid-O-aryl ester may decrease if the volumetric content of the liquid phase is excessively high, the volumetric content of the liquid phase based on the gaseous phase is preferably 50% or less, more preferably 30% or less and even more preferably 20% or less (the volumetric content of the liquid phase refers to volumetric ratio of the liquid phase based on the volume of the reaction tank in the case of a tank-type reactor, the volume of the stage lower than the feed stage (not including the tank bottom and reboiler) in the case of a column-type reactor, or the volume of the thin film distiller in the case of a thin film distiller).

Although there are no particular limitations on the reaction apparatus used when carrying out the reaction and a known reactor can be used, a tank-type and/or column-type reactor is used preferably. The reactor used is preferably equipped with a condenser.

As was previously described, the reaction is preferably carried out in a system containing a gaseous phase containing a hydroxy composition, a compound having carbonyl groups derived from urea and ammonia produced as a by-product in the reaction, and a liquid phase in which the reaction is carried out under conditions such that the volumetric content of the liquid phase in the reactor in which the reaction is carried out is 50% or less, and a reactor that satisfies these conditions is selected for the reactor in which the reaction is carried out.

More specifically, conventionally known reactors can be suitably combined and used, examples of which may include a stirring tank, a pressurized stirring tank, a depressurized stirring tank, a column-type reactor, a distillation column, a packed column or a thin film distiller.

There are no particular limitations on the type of condenser provided in the reactor and the known condenser can be used. For example, conventionally known condensers such as a multitubular cylindrical condenser, a double tube condenser, a single tube condenser or an air-cooled condenser can be suitably combined and used. The condenser may be provided inside the reactor or outside the reactor, or may be connected with the reactor by a line, and various types can be employed in consideration of the forms of the reactor and condenser, the manner in which condensed liquid is handled and the like.

There are no particular limitations on the materials of the reactor and condenser and known materials can be used. Examples of materials that can be used may include glass, stainless steel, carbon steel, Hastelloy, glass-lined base materials and Teflon (registered trademark) coated materials. Materials such as SUS304, SUS316 or SUS316L are inexpensive and can be used preferably. Known process apparatuses such as a flow meter, a thermometer and other measuring instruments or a reboiler, a pump or a condenser and the like may be added as necessary, a known method such as steam or a heater may be used for heating, and a known method such as air cooling, cooling water or brine can be used for cooling. Steps may also be added as necessary. For example, steps and apparatuses able to be conceived by a person or engineer with ordinary skill in the art may be added, such as a step of dissolving the compound having ureido groups in the aromatic hydroxy composition, a step of dissolving the aromatic hydroxy compound, a step of separating alcohol, a step of separating and/or purifying the aromatic hydroxy compound, a step of purifying N-substituted carbamic acid-O-aryl ester from the formed reaction liquid, or a step of incinerating or discarding by-products and the like.

Step (B) is a step of producing N-substituted carbamic acid-O-aryl ester by reacting a compound having ureido groups and an aromatic hydroxy composition in a liquid phase using a reactor (equipped with a condenser). The gaseous component formed in the step (B) containing a compound having carbonyl groups derived from urea and ammonia formed as a by-product in the reaction is introduced into the condenser provided in the reactor and all or a portion of the aromatic hydroxy composition and compound having carbonyl groups derived from urea are condensed followed by recovery of ammonia in the form of a gas. At that time, the compound having carbonyl groups derived from urea that is contained in ammonia recovered as a gas from the condenser is present at a specific amount or less. Namely, the ratio of the number of carbonyl groups (—C(=O)—) contained in the compound having carbonyl groups derived from urea contained in the ammonia to the number of ammonia molecules is 1 or less, preferably 0.5 or less, more preferably 0.1 or less and even more preferably 0.01 or less. The reason for making the amount of the compound having carbonyl groups derived from urea contained in the ammonia to be within a specific range is to avoid adhesion and accumulation of solid components in the line for transferring ammonia from the condenser.

Although all solid components that adhere and accumulate in the line for transferring ammonia cannot be identified, as a result of studies conducted by the inventors of the present invention, the majority were determined to be compounds having carbonyl groups. Although one possible method for avoiding adhesion and accumulation of such solid components contains heating the line for transferring ammonia to decompose compounds having carbonyl groups, according to studies conducted by the inventors of the present invention, there are many cases in which heating alone causes polymerization of decomposition products (such as isocyanic acid) or reaction with other compounds having carbonyl groups, thereby making it difficult to completely avoid adhesion and accumulation of solid components. In addition, in the case of simply heating the line, it was determined that compounds having carbonyl groups contained in the ammonia and their decomposition products solidify as a result of being rapidly cooled at the outlet of the line for transferring ammonia (such as the portion in contact with the atmosphere), thereby frequently resulting in prominent adhesion and accumulation of solid components. As a result of conducting extensive studies regarding this problem, the inventors of the present invention surprisingly found that the problem of adhesion and accumulation of solid components can be solved by making the amount of the compound having carbonyl groups derived from carbonic acid derivative contained in the ammonia to be equal to or less than the specific amount described above. Although the mechanism by which this effect is demonstrated is unclear, the inventors of the present invention surmised that adhesion and accumulation in the line is caused by the compound having carbonyl groups derived from the carbonic acid derivative itself as well as decomposition and/or polymerization products of the compound having carbonyl groups derived from the carbonic acid derivative, and that by making the amount of carbonyl groups contained in the compound having carbonyl groups derived from the carbonic acid derivative equal to or less than a specific concentration, adhesion of the compound having carbonyl groups derived from the carbonic acid derivative itself as well as the reaction rates of decomposition and/or polymerization of that compound are lowered considerably.

On the other hand, the condensed aromatic hydroxy composition and compound having carbonyl groups derived from urea are made to be such that the stoichiometric ratio of the condensed aromatic hydroxy composition to the condensed compound having carbonyl groups derived from urea is 1 or more, preferably 2 or more and more preferably 3 or more. The reason for defining such ranges is to enable a mixture of the aromatic hydroxy composition and compound having carbonyl groups derived from urea condensed in the condenser to be in the form of a homogeneous liquid mixture. As a result, not only is handling of the mixture easier, but occurrence of problems such as adhesion and accumulation of solid components in the condenser can be avoided.

Moreover, in step (B) the mixture of the aromatic hydroxy composition and the compound having carbonyl groups derived from urea condensed by the condenser may be circulated within the reactor and reused in the reaction of step (A). At that time, the concentration of ammonia contained in the mixture is preferably 5000 ppm or less, more preferably 3000 ppm or less and even more preferably 2000 ppm or less.

As has been described above, although various compounds are recovered in the form of compounds having carbonyl groups derived from urea, there are no particular limitations on the reuse of these compounds.

<Route 2)>

Route 2) is a method for carrying out step (B) followed by carrying out step (C). Route 2) is one aspect of the method indicated in route 1).

The method of route 2) is a method for obtaining N-substituted carbamic acid-O-aryl ester from the N-substituted carbamic acid-O-aryl ester of step (B) in which the organic primary amine is an aromatic organic primary monoamine represented by the following formula (5), the following step (C) is carried out after step (B), and at least two molecules of the N-substituted carbamic acid-O-aryl ester are crosslinked with methylene groups (—CH$_2$—). Preferably, the aromatic hydroxy compound constituting the aromatic hydroxy composition used in step (A) and/or step (B) is an aromatic monohydroxy compound.

Step (C): a step of obtaining N-substituted carbamic acid-O—(R$^2$ or aryl) ester, in which at least two molecules of the N-substituted carbamic acid-O—(R$^2$ or aryl) ester are crosslinked with methylene groups (—CH$_2$—), by reacting the N-substituted carbamic acid-O—(R$^2$ or aryl) ester with formaldehyde or a methylenating crosslinking agent and crosslinking aromatic groups derived from the aromatic organic primary monoamine contained in the N-substituted carbamic acid-O—(R$^2$ or aryl) ester with the methylene groups (—CH$_2$—)

The N-substituted carbamic acid-O—R$^2$ ester in the route 2) represents an N-substituted carbamic acid-O—R$^2$ ester formed as a by-product in the case of using an alcohol in step (A) and/or step (B).

In this route, step (A) is carried out using an organic primary amine represented by the following formula is used for the organic primary amine to obtain a compound having ureido groups derived from the organic primary amine, after which step (B) is carried out to obtain N-substituted carbamic acid-O-aryl ester derived from the compound having ureido groups, followed by carrying out step (C). Namely, the organic primary amine used in this route is an organic primary amine represented by formula (5), the compound having ureido groups obtained in step (A) of this route is a compound having ureido groups represented by formula (41) derived from the organic primary amine, and more specifically a compound having ureido groups represented by formula (148), and the N-substituted carbamic acid-O-aryl ester obtained in step (B) of this route is an N-substituted carbamic acid-O-aryl ester represented by formula (43) derived from the compound having ureido groups, and more specifically an N-substituted carbamic acid-O-aryl ester represented by the following formula (149). Indications of specific examples of each of these compounds are respectively contained in previous explanations thereof.

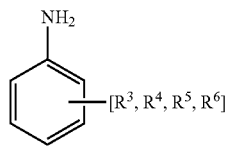

(5)

(wherein
at least one location at the ortho position and/or para position of the $NH_2$ group of an aromatic organic primary monoamine represented by formula (5) is not substituted, groups $R^3$ to $R^6$ respectively represent a group substituted at an arbitrary location that maintains aromatic properties of the ring, groups $R^3$ to $R^6$ may respectively and independently substitute an aromatic ring or groups $R^3$ to $R^6$ may together bond to form a ring with an aromatic ring, groups $R^3$ to $R^6$ are hydrogen atoms or groups selected from groups composed of groups in which a group selected from the group consisting of an alkyl group, a cycloalkyl group, an aryl group and an aryl group having a hydroxy group is bonded by saturated aliphatic bonds and/or ether bonds, the number of carbon atoms of groups $R^3$ to $R^6$ is an integral number within a range of from 0 to 7, and the total number of carbon atoms that compose the aromatic organic primary monoamine represented by formula (5) is an integer of from 6 to 13).

In this case, the compound having ureido groups obtained in step (A) is at least one type of compound having ureido groups represented by the following formula (148). In addition, the groups $R^3$, $R^4$, $R^5$ and $R^6$ in the following formula (148) are selected from the groups $R^3$, $R^4$, $R^5$ and $R^6$ of an organic primary amine represented by the above-mentioned formula (5), and the compound having ureido groups is a compound in which amino groups (—$NH_2$ groups) of the organic primary amine represented by formula (5) are in the form of ureido groups (—NH—CO—$NH_2$):

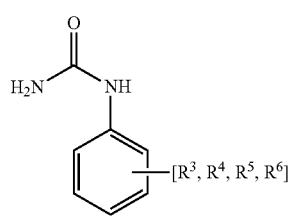

(148)

(wherein
at least one location at the ortho position and/or para position of the ureido group of an N-substituted aromatic organic monourea represented by formula (148) is not substituted, groups $R^3$ to $R^6$ respectively represent a group substituted at an arbitrary location that maintains aromatic properties of the ring, groups $R^3$ to $R^6$ may respectively and independently substitute an aromatic ring or groups $R^3$ to $R^6$ may together bond to form a ring with an aromatic ring, groups $R^3$ to $R^6$ are hydrogen atoms or groups selected from groups composed of groups in which a group selected from the group consisting of an alkyl group, a cycloalkyl group, an aryl group and an aryl group having a hydroxy group is bonded by saturated aliphatic bonds and/or ether bonds, the number of carbon atoms of groups $R^3$ to $R^6$ is an integral number within a range of from 0 to 7, and the total number of carbon atoms that compose the N-substituted aromatic organic monourea represented by formula (148), excluding ureido groups (—NH—CO—$NH_2$), is an integer of from 6 to 13).

In this case, the N-substituted carbamic acid-O-aryl ester obtained in step (B) is at least one type of N-substituted carbamic acid-O-aryl ester represented by the following formula (149). In addition, the groups $R^3$, $R^4$, $R^5$ and $R^6$ in the following formula (149) are selected from the groups $R^3$, $R^4$, $R^5$ and $R^6$ of an organic primary amine represented by the above-mentioned formula (5), and the compound is a compound in which ureido groups (—NH—CO—$NH_2$) of a compound having ureido groups represented by formula (148) are in the form of carbamic acid-O-aryl ester groups:

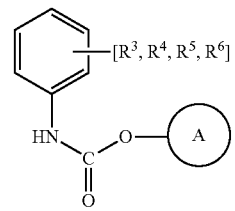

(149)

(wherein
groups $R^3$ to $R^6$ are the groups indicated above).

In steps (A) and (B) of this route, the organic primary amine used is an organic primary amine represented by formula (5), and steps (A) and (B) of this route are carried out under the conditions of steps (A) and (B) of route 1).

Step (C) is a step of obtaining N-substituted carbamic acid-O—($R^2$ or aryl) ester, in which at least two molecules of the N-substituted carbamic acid-O—($R^2$ or aryl) ester are crosslinked with methylene groups (—$CH_2$—), by crosslinking at least one type of N-substituted carbamic acid-O-aryl ester (or reaction liquid containing the same) obtained in step (B) with methylene groups (—$CH_2$—). As a result of carrying out step (C), N-substituted carbamic acid-O-aryl ester is obtained in which at least two molecules of at least one type of N-substituted carbamic acid-O-aryl ester represented by the following formula (150) are crosslinked with the methylene groups (—$CH_2$—). Herein, when carrying out route 2), an aromatic hydroxy composition containing an aromatic monohydroxy compound is preferably used for the aromatic hydroxy compound used in step (A) and/or step (B) as previously described (namely, an aromatic hydroxy compound in which b=1 in the aromatic hydroxy compound represented by formula (2)). Although a polyvalent aromatic hydroxy compound may be used, crosslinking may occur at locations other than the desired locations at that time. In the following formula (150), in the case of using the above-mentioned aromatic monohydroxy compound (namely in the case b=1), ring A of the following formula does not have other aromatic hydroxy groups or alcoholic hydroxy groups. An aromatic hydroxy compound represented by the above-mentioned formula (31) is preferable for the aromatic monohydroxy compound, the case of using an active aromatic hydroxy compound, of the active aromatic hydroxy compounds, represented by formula (38) is more preferable, and the case of using an aromatic hydroxy compound represented by formula (38), in which groups $R^{26}$ and $R^{27}$ are hydrogen atoms while other substituents are linear and/or cyclic saturated alkyl groups, or the case of being naphthol (including isomers), phenoxyphenol (including isomers) or diphenoxyphenol (including isomers), in which the ortho position or para position of the hydroxy group is not substituted, is even more preferable.

Although compounds in which m is an integer from 0 to 6 are represented by the formula (150), this value can be adjusted according to the amount used and reaction rate of the methylenating crosslinking agent that is reacted (to be subsequently explained and frequently referred to as a methylenating agent):

products such as polyaromatic hydroxy compounds, or the amount of methylenating crosslinking agent used may increase, aromatic hydroxy compounds are preferably separated. The known method can be used for the separation method, and although varying according to the compounds used, examples of separation methods that can be used may include a distillation method, an extraction separation method that uses the difference in solubility between the N-substituted carbamic acid-O-aryl ester and aromatic hydroxy compound, and a filtration method carried out by solidifying either the N-substituted carbamic acid-O-aryl ester or aromatic hydroxy compound. Although these methods cannot be indicated specifically since they depend on the respective

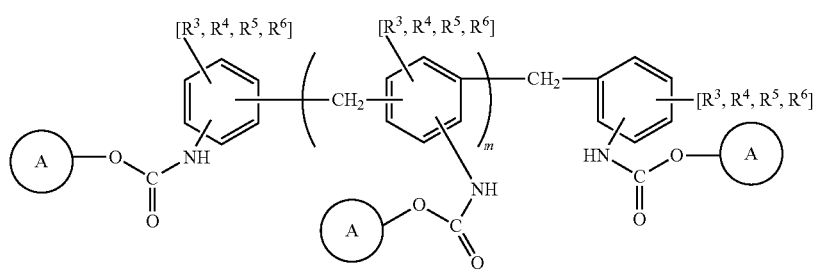

(150)

(wherein $R^1$ represents a group derived from an organic primary amine as previously defined, ring A represents a group derived from an aromatic hydroxy compound that composes an aromatic hydroxy composition as previously defined, and which represents a residue in which one hydrogen atom of hydroxyl groups directly bonded to an aromatic hydrocarbon ring has been removed from the aromatic hydroxy compound, groups $R^3$ to $R^6$ represent groups as previously defined, and m represents an integer of from 0 to 6).

Although a monoisocyanate can be produced by applying the N-substituted carbamic acid-O-mono(aryl ester) represented by the above-mentioned formula (149) to a thermal decomposition reaction as is, when considering that isocyanates are typically used in applications such as paint and polyurethane, the isocyanate is preferably a polyfunctional isocyanate. Thus, a method can be carried out in which, after having preliminarily polymerized the N-substituted carbamic acid mono (aryl ester) by the above-mentioned step (C), the polymer is applied to a thermal decomposition reaction to obtain a polyfunctional isocyanate. The above-mentioned N-substituted carbamic acid-O-mono(aryl ester) refers to an N-substituted carbamic acid-O-aryl ester having one carbamic acid-O-aryl ester group in a molecule thereof.

The following provides an explanation of the step (C). In the following explanation, the N-substituted carbamic acid-O-aryl ester obtained in step (B) of route 2) is frequently indicated as N-substituted carbamic acid-O-mono(aryl ester) or N-substituted carbamic acid monoaryl ester.

The known method (see, for example, Federal Republic of Germany Patent No. 1042891) can be used for the step (C).

Prior to carrying out step (C), the aromatic hydroxy composition obtained in step (B) is separated from the reaction liquid containing the resulting N-substituted carbamic acid-O-aryl ester. Although step (C) may be carried out in the presence of an aromatic hydroxy compound, since the aromatic hydroxy compound may be crosslinked by the methylenating crosslinking agent resulting in the formation of byphysical properties of the compounds used, the method and conditions thereof can be adequately selected within the scope of knowledge of a person with ordinary skill in the art.

When carrying out step (C), the aromatic hydroxy compound is removed until the amount of aromatic hydroxy compound present following the above-mentioned separation procedure is a stoichiometric ratio of 1 time or less, preferably 0.5 times and more preferably 0.1 times based on the N-substituted carbamic acid-O-aryl ester. At this time, the aromatic hydroxy compound may be removed in the presence of solvent used in step (C) to be subsequently explained.

Examples of methylenating crosslinking agents preferably used in the step (C) may include formaldehyde, paraformaldehyde, trioxane, dialkoxymethanes having a lower alkyl group having 1 to 6 carbon atoms (such as dimethoxymethane, diethoxymethane, dipropoxymethane, dipentanoxymethane or dihexyloxymethane), and diacyloxymethanes having a lower carboxyl group such as diacetoxymethane or dipropioxymethane. These may be used alone or two or more types may be used as a mixture. Among these methylenating crosslinking agents, aqueous solutions of formaldehyde are particularly preferable in consideration of cases of industrial application, ease of handling of the methylenating crosslinking agent and the like.

In carrying out the reaction of the step (C), although there are no particular limitations on the ratio of N-substituted carbamic acid-O-mono(aryl ester) to methylenating crosslinking agent, the N-substituted carbamic acid-O-monoaryl ester is preferably used at a stoichiometric ratio of from 2 to 20 times the methylenating crosslinking agent. Although the formation of polynuclear forms (referring to N-substituted carbamic acid-O-aryl esters in which three or more aromatic rings (aromatic rings derived from organic primary amine) are bonded by a methylene crosslinked structure, or in other words, compounds in which m is an integer of from 1 or more in the above-mentioned formula (150)) is inhibited the greater the amount of N-substituted carbamic acid-monoaryl ester used, if an overly excessive amount of N-substituted carbamic acid-O-monoaryl ester is used, there are many cases in which the remaining amount of raw material N-substituted carbamic acid-O-mono(aryl ester) increases. Thus, the amount of N-substituted carbamic acid-O-monoaryl ester used in terms of the stoichiometric ratio with the methylenating crosslinking agent is more preferably within a range of from 3 to 15 times and even more preferably within a range of from 5 to 10 times.

An acid catalyst is preferably used as a catalyst in the condensation reaction. Examples of acid catalysts may include inorganic acids such as hydrochloric acid, sulfuric acid, phosphoric acid or boric acid, and organic acids such as formic acid, acetic acid, oxalic acid or toluenesulfonic acid. In addition, acids referred to as super strong acids such as hydrobromic acid, perchloric acid, chlorosulfonic acid or trifluoromethanesulfonic acid are also effective. In addition, ion exchange resins having acidic groups such as carboxyl groups or sulfonate groups as well as acids referred to as Lewis acids, such as trifluoroboric acid, iron chloride, aluminum chloride, zinc chloride or titanium chloride, are also effective.

In the case of a protonic acid such as the above-mentioned inorganic acids, organic acids or super strong acids, the amount of these acids used is within a range of a stoichiometric ratio of from 0.001 to 10, and preferably within a range of from 0.01 to 5, based on the raw material N-substituted carbamic acid ester. In addition, in the case these acids are used in the form of aqueous solutions, they can be used at a concentration within a range of from 10 to 95% by weight and preferably within a range of from 20 to 80% by weight based on the amount of water in the reaction system. If the concentration is less than 10% by weight, the reaction rate of the condensation reaction becomes extremely slow, while if the concentration exceeds 95% by weight, hydrolysis of the raw material and other undesirable side reactions may occur.

The condensation reaction can be carried out in the presence or absence of solvent. Examples of solvents that are used preferably may include linear, branched or cyclic hydrocarbons such as pentane, hexane, heptane, octane, nonane, decane, hexadecane, cyclopentane or cyclohexane; aromatic hydrocarbons such as benzene, toluene or xylene and their alkyl-, halogen- and nitro-substituted forms; halogenated hydrocarbons such as chloroform, methylene chloride, carbon tetrachloride, dichloroethane, trichloroethane or tetrachloroethane; aliphatic alkyl esters such as methyl acetate or ethyl acetate; and ethers such as diethyl ether, diisopropyl ether, dioxane or tetrahydrofuran. In addition, thioacetals, acetals or acylals are used preferably since they do not form free formaldehyde under the reaction conditions and do not substantially form water by reacting with water formed as a by-product in the reaction. Acetals and acylals are used particularly preferably. In addition, the above-mentioned acids themselves are also preferably used as solvents. These solvents may be used alone or two or more types may be used as a mixture.

These solvents can be used at a weight ratio within a range of from 0.1 to 100 times and preferably within a range of from 0.2 to 50 times based on the raw material N-substituted carbamic acid-O-monoaryl ester.

The reaction temperature is preferably from 10 to 160° C., more preferably from 20 to 140° C. and even more preferably from 50 to 120° C. Although the reaction is advantageously carried out at a high temperature in order to increase the reaction rate and complete the reaction quickly, an excessively high temperature may cause undesirable side reactions such as hydrolysis.

Although varying according to the reaction method, compounds used and reaction conditions, the reaction time can be within a range of from 1 minute to 20 hours. In addition, the reaction may be terminated when the reduction in the amount of raw material N-substituted carbamic acid-O-monoaryl ester has reached a certain level by sampling the reaction liquid and using the known analytical method such as liquid chromatography, or the reaction may be terminated when the average molecular weight of the product in the form of N-substituted carbamic acid-O-aryl ester has reached a certain level by using the known analytical method such as gel permeation chromatography.

The N-substituted carbamic acid-O-aryl ester obtained by the method described above is an N-substituted carbamic acid-O-aryl ester represented by the above-mentioned formula (150). Although those N-substituted carbamic acid-O-aryl esters in which m is 0 are preferable in consideration ease of handling and particularly solution viscosity and the like, there are no problems with containing trinuclear or larger polynuclear forms (namely, compounds represented by formula (150) in which m is 1 or more) provided they do not contradict the purport of the present embodiment.

The N-substituted carbamic acid-O-aryl ester obtained in step (C) is preferably used in step (F).

Compounds remaining in the reaction liquid of step (C) may be removed from the reaction liquid (such as the methylenating agent, reaction solvent or catalyst used in step (C)). The known method can be used for the removal method, and although examples of such methods may include membrane separation, distillative separation and crystallization, distillative separation is preferable. In the case of removing a compound remaining in the reaction liquid of step (C) by distillative separation, by adding the aromatic hydroxy composition used in the subsequent step (F) to the reaction liquid of step (C) to obtain a mixed liquid, followed by removing the compounds remaining in the reaction liquid of step (C) (such as the methylenating agent, reaction solvent or catalyst used in step (C)) from the mixed liquid, distillative separation can be carried out without causing precipitation of the N-substituted carbamic acid ester, thereby making this method preferable.

Although caution is required with respect to the materials of the reactor and the condenser since an acid is used in step (C), there are no particular limitations on the materials provided they do not cause problems such as corrosion attributable to the compounds used in step (C), and known materials can be used. Examples of materials that can be used may include glass, stainless steel, carbon steel, Hastelloy, glass-lined base materials and Teflon (registered trademark) coated materials. Known process apparatuses such as a flow meter, a thermometer and other measuring instruments or a reboiler, a pump or a condenser and the like may be added as necessary, the known method such as steam or a heater may be used for heating, and the known method such as air cooling, cooling water or brine can be used for cooling. Steps may also be added as necessary, and for example, steps and apparatuses able to be conceived by a person or engineer with ordinary skill in the art may be added.

<Route 3)>

Route 3) is a route that includes a method for carrying out step (R) followed by carrying out step (P).

First, N-substituted carbamic acid-O—$R^2$ ester is obtained in step (R) using a compound having ureido groups, after which the N-substituted carbamic acid-O—$R^2$ ester and an aromatic hydroxy composition are reacted in step (P) to obtain N-substituted carbamic acid-O-aryl ester. Alternatively, a compound having ureido groups (or reaction liquid containing the same) is obtained in step (A) and step (R) is carried out using the compound having ureido groups (or reaction liquid containing the same) followed by carrying out step (P) to obtain N-substituted carbamic acid-O-aryl ester.

<Step (R)> N-Substituted Carbamic Acid-O—$R^2$ Ester Production Step

Step (R) is a step of producing N-substituted carbamic acid-O—$R^2$ ester by reacting a compound having ureido groups with alcohol. Alternatively, N-substituted carbamic acid-O—$R^2$ ester is produced by reacting (esterifying) a compound having ureido groups (or reaction liquid containing the same) obtained in step (A) with an alcohol.

Figure 3:
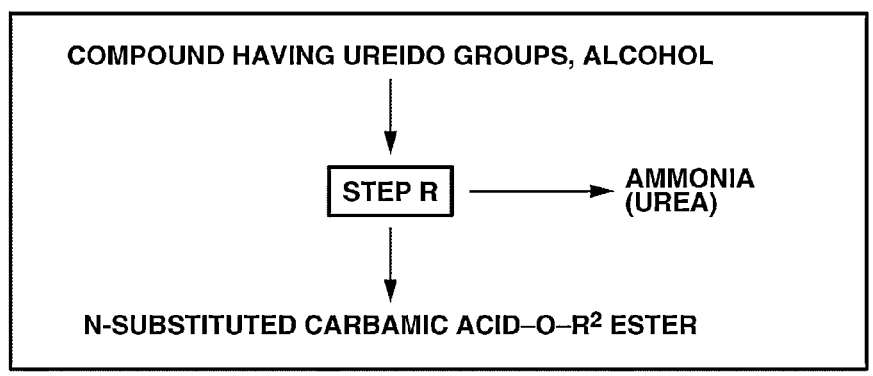
FIG. 3 shows a conceptual drawing depicting a step (R) in the present embodiment.

FIG. 3 is a conceptual drawing depicting the step (R).

The compound having ureido groups obtained in step (A) of this route is a compound having ureido groups represented by formula (1) that is derived from the organic primary amine, the N-substituted carbamic acid-O—$R^2$ ester obtained in step (R) of this route is an N-substituted carbamic acid-O—$R^2$ ester represented by formula (49) that is derived from the compound having ureido groups and an alcohol, and the N-substituted carbamic acid-O-aryl ester obtained in step (P) of this route is an N-substituted carbamic acid-O-aryl ester represented by formula (43) that is derived from the N-substituted carbamic acid-O—$R^2$ ester and an aromatic hydroxy composition.

As was previously stated, in the case the hydroxy composition a used as a reaction solvent in step (A) is the same as the hydroxy composition of step (R) (namely, a composition containing an alcohol represented by formula (4), including the alcohol represented by formula (4) used in step (R), and/or an aromatic hydroxy compound represented by formula (2)), step (R) can be carried out directly by using the reaction liquid obtained in step (A). In addition, in the case the hydroxy composition a used as a reaction solvent in step (A) differs from the hydroxy composition of step (R), step (R) may be carried out after newly adding a hydroxy compound (alcohol represented by formula (4) and/or aromatic hydroxy compound represented by formula (2)) to the reaction liquid obtained in step (A), one or a plurality of types of hydroxy compounds may be newly added to the reaction liquid obtained in step (A) followed by carrying out step (R) after separating all or a portion of the hydroxy composition used as a reaction solvent of step (A), or step (R) may be carried out after removing all or a portion of the hydroxy composition used as a reaction solvent in step (A) followed by newly adding one or a plurality of types of hydroxy compounds. Herein, the newly added hydroxy compound is an alcohol represented by formula (4) and/or an aromatic hydroxy composition. There are no particular limitations on the method for separating the reaction solvent used in step (A), and although the known method such as distillative separation, membrane separation or extraction separation can be used, distillative separation is preferable. In the case of carrying out step (R) after having carried out step (A), there are cases in which step (A) is preferably carried out in the presence of an alcohol, and there are also cases in which step (A) is preferably carried out in the absence of an aromatic hydroxy composition and in the presence of alcohol. In the case of carrying out step (R) in the presence of an aromatic hydroxy compound, although there are cases in which a trace amount of N-substituted carbamic acid-O-aryl ester is formed together with N-substituted carbamic acid-O—$R^2$ ester, in the method for producing N-substituted carbamic acid-O-aryl ester of the present embodiment, after carrying out step (R) this does not present any problem whatsoever since the N-substituted carbamic acid-O—$R^2$ ester is converted to N-substituted carbamic acid-O-aryl ester by carrying out a step (P) to be subsequently explained.

As was previously described, with respect to a method for producing N-substituted carbamic acid-O-alkyl ester by using a compound having ureido groups and reacting with alcohol, a method that coincides with the objective of obtaining a corresponding isocyanate and alcohol by thermal decomposition of the N-substituted carbamic acid-O-alkyl ester is disclosed in Japanese Patent Application Laid-open No. H6-41045. As was previously explained, this method is susceptible to the formation of by-products when obtaining a compound having ureido groups, contains a range over which in which a large amount of N-substituted carbamic acid-O-alkyl ester is simultaneously formed, and the N-substituted carbamic acid-O-alkyl ester is susceptible to thermal denaturation causing compounds having ureylene groups to be easily formed. In addition, if isocyanate is attempted to be produced by thermally decomposing the N-substituted carbamic acid-O-alkyl ester, the thermal decomposition temperature becomes higher resulting in increased susceptibility to a reverse reaction of the thermal decomposition reaction and increased susceptibility to the occurrence of clogging of the thermal decomposition reactor. As a result of studies conducted by the inventors of the present invention, in the case of obtaining N-substituted carbamic acid-O-aryl ester by reacting a compound having ureido groups and an aromatic hydroxy compound, it was found that N-substituted carbamic acid-O-aryl ester can be obtained at high yield with little thermal denaturation.

On the other hand, although there are many cases in which compounds having ureylene groups and the like are formed as by-products even in cases of obtaining N-substituted carbamic acid-O—$R^2$ ester from a compound having ureido groups and alcohol, when obtaining N-substituted carbamic acid-O—$R^2$ ester from a compound having ureido groups and alcohol, it was found that the formation of by-products can be inhibited considerably if an aromatic hydroxy compound is present. Although this is thought to be due to association of the compound having ureido groups inhibiting the aromatic hydroxy compound thereby inhibiting side reactions, such a finding is not present in the prior art and is an effect that was first discovered by the inventors of the present invention. Thus, although depending on the particular case, step (R) is preferably carried out in the presence of an aromatic hydroxy composition or aromatic hydroxy compound when carrying out step (R) as well. In this case, the aromatic hydroxy composition or aromatic hydroxy compound is selected from aromatic hydroxy compounds represented by formula (2), and is preferably an aromatic hydroxy compound represented by formula (7), and more preferably an aromatic hydroxy compound represented by formula (31). Although a preferable method for using a plurality of types of aromatic hydroxy compounds will be subsequently explained, the aromatic hydroxy compound or aromatic hydroxy composition is preferably selected in accordance with the criteria explained therein.

Although varying according to the compounds reacted, the reaction conditions for producing N-substituted carbamic acid-O—$R^2$ ester by reacting a compound having ureido groups and an alcohol of step (R) are such that the amount of alcohol used has a stoichiometric ratio within a range of from 1 to 500 times based on the ureido groups of the compound having ureido groups used. Although it is preferable to use an excess of alcohol since complexly substituted carbonyl compounds and high molecular weight compounds having carbonyl bonds in molecules thereof form easily if the stoichiometric ratio is less than 1 time, in consideration of the size of the reactor, the stoichiometric ratio is preferably within a range of from 1 to 100 times, more preferably within a range of from 5 to 50 times and even more preferably within a range of from 8 to 20 times.

Although varying according to the compounds used, the reaction temperature is preferably within a range of from 100 to 350° C. If the temperature is lower than 100° C., the reaction slows or the reaction hardly proceeds at all, or complexly substituted carbonyl compounds increase, thereby making this undesirable. On the other hand, at temperatures higher than 350° C., the N-substituted carbamic acid-O—$R^2$ ester either remains in step (A), the urea (and non-N-substituted carbamic acid ester) formed in the system of step (R) decompose, the hydroxy composition is subjected to dehydrogenative denaturation, or decomposition and denaturation reactions of the product in the form of N-substituted carbamic acid-O—$R^2$ ester occur easily, thereby making this undesirable. From such viewpoints, the reaction temperature is more preferably within a range of from 120 to 320° C. and even more preferably within a range of from 140 to 300° C.

As has been previously described, the reaction by which N-substituted carbamic acid-O—$R^2$ ester is formed is an equilibrium reaction, and since the reaction is biased towards the reactants side, the reaction is preferably carried out while removing ammonia formed as a by-product outside the system as much as possible. Ammonia is preferably removed so that the ammonia concentration in the reaction liquid is preferably 1000 ppm or less, more preferably 300 ppm or less, even more preferably 100 ppm or less and most preferably 30 ppm or less (being contained in the reaction liquid refers to being contained in a liquid phase when carrying out the step (R)). Ammonia can be removed using methods such as reactive distillation, use of an inert gas, membrane separation and adsorptive separation. For example, the reactive distillation refers to a method for separating continuously formed ammonia during the reaction by distillation in the form of a gas. This can be carried out while boiling alcohol, a solvent or hydroxy composition in order to increase the distillation efficiency of the ammonia. In addition, a method using an inert gas refers to a method for separating continuously formed ammonia during the reaction from the reaction system in the form of a gas along with the inert gas. Examples of inert gases used may include nitrogen, helium, argon, carbon dioxide, methane, ethane and propane, these may be used alone or as a mixture, and a method in which the inert gas is introduced into the reaction system is preferable. Examples of adsorbents used in methods using adsorptive separation may include adsorbents able to be used under the temperature conditions at which the reaction is carried out, such as silica, alumina, various types of zeolite or diatomaceous earth. These methods for removing ammonia outside the system may be carried out alone or a plurality of types may be carried out in combination.

A catalyst can be used in the reaction for the purpose of increasing the reaction rate, for example. Examples of catalysts that are used preferably may include basic catalysts such as methylates, ethylates or butyrates (including isomers) of lithium, sodium, potassium, calcium or barium, rare earth elements, antimony or bismuth alone or oxides, sulfides and salts thereof, boron alone or boron compounds, metals of the copper family, zinc family, aluminum family, carbon family and titanium family in the periodic table as well as metal oxides and sulfides thereof, and carbides and nitrides of elements of the carbon family excluding carbon, titanium family, vanadium family and chromium family in the periodic table. Although there are no particular limitations on the amount of catalyst used in the case of using a catalyst, a catalyst can be used within the range of a stoichiometric ratio of from 0.0001 to 100 times the ureido groups of the compound having ureido groups. Since there are many cases in which it is necessary to remove the catalyst if a catalyst is added, the reaction is preferably carried out without adding a catalyst.

Although varying according to the composition of the reaction system, reaction temperature, method used to remove ammonia, reaction apparatus and the like, the reaction pressure is normally within a range of from 0.01 Pa to 10 MPa (absolute pressure), and in consideration of ease of industrial application, the reaction pressure is more preferably within a range of from 0.1 Pa to 5 MPa (absolute pressure), and in consideration of removing gaseous ammonia outside the system, even more preferably from a to 1.5 MPa (absolute pressure).

Although varying according to the composition of the reaction system, reaction temperature, method used to remove ammonia, reaction apparatus, reaction pressure and the like, the reaction time (residence time in the case of a continuous reaction) is generally from 0.01 to 100 hours. The reaction time can also be determined according to the formation amount of the target compound in the form of N-substituted carbamic acid-O—$R^2$ ester (and depending on the case, the total amount resulting from adding the amount of N-substituted carbamic acid-O-aryl ester). For example, the reaction may be stopped after having sampled the reaction liquid, determined the content of N-substituted carbamic acid ester in the reaction liquid (and depending on the case, the total amount resulting from adding the amount of N-substituted carbamic acid-O-aryl ester) and confirming that the N-substituted carbamic acid-O—$R^2$ ester has been formed at a yield of 10% or more based on the compound having ureido groups, or the reaction may be stopped after having confirmed that the yield is 90% or more. The reaction liquid containing the N-substituted carbamic acid-O—$R^2$ ester obtained in step (R) is converted to N-substituted carbamic acid-O-aryl ester in a process that contains step (P) to be subsequently described, followed by obtaining an isocyanate in step (F). At that time, if the content of N-substituted carbamic acid-O—$R^2$ ester in step (R) is low (the yield thereof is low), there are cases in which this can cause a decrease in the yield of isocyanate. Thus, the yield of the N-substituted carbamic acid-O—$R^2$ ester is preferably 50% or more, more preferably 80% or more and even more preferably 90% or more.

Although the use of a reaction solvent is not necessarily required in the reaction, a suitable solvent is preferably used as a reaction solvent for the purpose of facilitating the reaction procedure, examples of which include alkanes such as pentane (including isomers), hexane (including isomers), heptane (including isomers), octane (including isomers), nonane (including isomers) or decane (including isomers); aromatic hydrocarbons and alkyl-substituted aromatic hydrocarbons such as benzene, toluene, xylene (including isomers), ethyl benzene, diisopropyl benzene (including isomers), dibutyl benzene (including isomers) or naphthalene; nitrile compounds such as acetonitrile or benzonitrile; aromatic compounds substituted with a halogen or nitro group such as chlorobenzene, dichlorobenzene (including isomers), bromobenzene, dibromobenzene (including isomers), chloronaphthalene, bromonaphthalene, nitrobenzene or nitronaphthalene; polycyclic hydrocarbon compounds such as diphenyl, substituted diphenyl, diphenyl methane, terphenyl, anthracene or dibenzyl toluene (including isomers); aliphatic hydrocarbons such as cyclohexane, cyclopentane, cyclooctane or ethylcyclohexane; ketones such as methyl ethyl ketone or acetophenone; esters such as dibutyl phthalate, dihexyl phthalate, dioctyl phthalate or benzylbutyl phthalate; ethers and thioethers such as tetrahydrofuran, 1,4-dioxane, 1,2-dimethoxyethane, diphenyl ether or diphenyl sulfide; ketone compounds such as acetone or methyl ethyl ketone; ester compounds such as ethyl acetate or ethyl benzoate; and sulfoxides such as dimethylsulfoxide or diphenylsulfoxide. Naturally, a hydroxy composition used in excess in the reaction is also preferably used as a reaction solvent.

The reaction is carried out in a system having a gaseous phase containing a hydroxy composition, a compound having carbonyl groups derived from urea (a compound that inherits a carbonyl group possessed by urea, such as a non-N-substituted carbamic acid ester or biuret, which refers to a compound excluding N-substituted carbamic acid-O-esters) and ammonia produced as a by-product in the reaction, and a liquid phase in which the reaction is carried out. Although the majority of the reaction is carried out in the liquid phase, it may also be carried out in the gaseous phase depending on the reaction conditions. At that time, the volumetric content of the liquid phase in the reaction in which the reaction is carried out is preferably 50% or less. In the case of carrying out the reaction continuously over a long period of time, although polymeric by-products may form due to fluctuations in operating conditions (such as temperature or pressure) and the like, if the volumetric content of the liquid phase in the reactor is high, adhesion and accumulation of such polymeric by-products in the reactor can be avoided. However, since the efficiency of removal of by-product ammonia may become poor and the yield of the N-substituted carbamic acid-O—$R^2$ ester (and depending on the case, the total amount resulting from adding the amount of N-substituted carbamic acid-O-aryl ester) may decrease if the volumetric content of the liquid phase is excessively high, the volumetric content of the liquid phase based on the gaseous phase is preferably 50% or less, more preferably 30% or less and even more preferably 20% or less (the volumetric content of the liquid phase refers to volumetric ratio of the liquid phase based on the volume of the reaction tank in the case of a tank-type reactor, the volume of the stage lower than the feed stage (not including the tank bottom and reboiler) in the case of a column-type reactor, or the volume of the thin film distiller in the case of a thin film distiller).

Although there are no particular limitations on the reaction apparatus used when carrying out the reaction and the known reactor can be used, a tank-type and/or a column-type reactor is used preferably. The reactor used is preferably equipped with a condenser.

As was previously described, the reaction is preferably carried out in a system having a gaseous phase containing a hydroxy composition, a compound having carbonyl groups derived from urea and ammonia produced as a by-product in the reaction, and a liquid phase in which the reaction is carried out under conditions such that the volumetric content of the liquid phase in the reactor is 50% or less, and a reactor that satisfies these conditions is selected for the reactor in which the reaction is carried out.

More specifically, conventionally known reactors can be suitably combined and used, examples of which may include a stirring tank, a pressurized stirring tank, a reduced pressure stirring tank, a column-type reactor, a distillation column, a packed column or a thin film distiller.

There are no particular limitations on the type of condenser provided in the reactor and the known condenser can be used. For example, conventionally known condensers such as a multitubular cylindrical condenser, a double tube condenser, a single tube condenser or an air-cooled condenser can be suitably combined and used. The condenser may be provided inside the reactor or provided outside the reactor or may be connected with the reactor by a line, and various types can be employed in consideration of the forms of the reactor and condenser, the manner in which condensed liquid is handled and the like. There are no particular limitations on the materials of the reactor and condenser and known materials can be used. Examples of materials that can be used may include glass, stainless steel, carbon steel, Hastelloy, glass-lined base materials and Teflon (registered trademark) coated materials. Materials such as SUS304, SUS316 or SUS316L are inexpensive and can be used preferably. Known process apparatuses such as a flow meter, a thermometer and other measuring instruments or a reboiler, a pump or a condenser and the like may be added as necessary, the known method such as steam or a heater may be used for heating, and the known method such as air cooling, cooling water or brine can be used for cooling. Steps may also be added as necessary. For example, steps and apparatuses able to be conceived by a person or engineer with ordinary skill in the art may be added, such as a step of dissolving the urea in the aromatic hydroxy compound, a step of dissolving the aromatic hydroxy compound, a step of separating the alcohol, a step of separating and/or purifying the aromatic hydroxy compound, a step of purifying the N-substituted carbamic acid-O—$R^2$ ester from the formed reaction liquid or a step of incinerating or discarding by-products and the like.

Step (R) is a step of producing N-substituted carbamic acid-O—$R^2$ ester by reacting a compound having ureido groups and an alcohol in a liquid phase using a reactor (equipped with a condenser). The gaseous component formed in the step (R) containing a compound having carbonyl groups derived from urea and ammonia formed as a by-product in the reaction is introduced into the condenser provided in the reactor and all or a portion of the alcohol and compound having carbonyl groups derived from urea are condensed followed by recovery of ammonia in the form of a gas.

At that time, the compound having carbonyl groups derived from urea that is contained in ammonia recovered as a gas from the condenser is present at a specific amount or less. Namely, the ratio of the number of carbonyl groups (—C(═O)—) contained in the compound having carbonyl groups derived from urea contained in the ammonia to the number of ammonia molecules is 1 or less, preferably 0.5 or less, more preferably 0.1 or less and even more preferably 0.01 or less. The reason for making the amount of the compound having carbonyl groups derived from urea contained in the ammonia to be within a specific range is to avoid adhesion and accumulation of solid components in the line for transferring ammonia from the condenser.

Although all solid components that adhere and accumulate in the line for transferring ammonia cannot be identified, as a result of studies conducted by the inventors of the present invention, the majority were determined to be compounds having carbonyl groups. Although one possible method for avoiding adhesion and accumulation of such solid components contains heating the line for transferring ammonia to decompose compounds having carbonyl groups, according to studies conducted by the inventors of the present invention, there are many cases in which heating alone causes polymerization of decomposition products (such as isocyanic acid) or reaction of the decomposition products with other compounds having carbonyl groups, thereby making it difficult to completely avoid adhesion and accumulation of solid components. In addition, in the case of simply heating the line, it was determined that compounds having carbonyl groups contained in the ammonia and their decomposition products solidify as a result of being rapidly cooled at the outlet of the line for transferring ammonia (such as the portion in contact with the atmosphere), thereby frequently resulting in prominent adhesion and accumulation of solid components. As a result of conducting extensive studies regarding this problem, the inventors of the present invention surprisingly found that the problem of adhesion and accumulation of solid components can be solved by making the amount of the compound having carbonyl groups derived from carbonic acid derivative contained in the ammonia to be equal to or less than the specific amount described above. Although the mechanism by which this effect is demonstrated is unclear, the inventors of the present invention surmised that adhesion and accumulation in the line is caused by the compound having carbonyl groups derived from the carbonic acid derivative itself as well as decomposition and/or polymerization products of the compound having carbonyl groups derived from the carbonic acid derivative, and that by making the amount of carbonyl groups contained in the compound having carbonyl groups derived from the carbonic acid derivative equal to or less than a specific concentration, adhesion of the compound having carbonyl groups derived from the carbonic acid derivative itself as well as the reaction rates of decomposition and/or polymerization of that compound are lowered considerably.

On the other hand, the condensed hydroxy composition and compound having carbonyl groups derived from urea are made to be such that the stoichiometric ratio of the condensed hydroxy composition to the condensed compound having carbonyl groups derived from urea is 1 or more, preferably 2 or more and more preferably 3 or more. The reason for defining such ranges is to enable a mixture of the hydroxy composition and compound having carbonyl groups derived from urea condensed in the condenser to be in the form of a homogeneous liquid mixture. As a result, not only is handling of the mixture easier, but occurrence of problems such as adhesion and accumulation of solid components in the condenser can be avoided.

Moreover, the mixture of the hydroxy composition and the compound having carbonyl groups derived from urea condensed by the condenser in step (R) may be circulated within the reactor and reused in the reaction of step (A). At that time, the amount of ammonia contained in the mixture is preferably 5000 ppm or less, more preferably 3000 ppm or less and even more preferably 2000 ppm or less.

As has been described above, although various compounds are recovered in the form of compounds having carbonyl groups derived from urea, there are no particular limitations on the reuse of these compounds.

<Step (P)> Transesterification Step

Although the N-substituted carbamic acid-O—$R^2$ ester produced according to step (R) also allows the obtaining of isocyanate by thermal decomposition of the N-substituted carbamic acid-O—$R^2$ ester, a more preferably used N-substituted carbamic acid ester is an N-substituted carbamic acid-O-aryl ester.

In general, N-substituted carbamic acid-O-aryl esters are more susceptible to thermal decomposition than N-substituted carbamic acid-O—$R^2$ esters, and are known to easily decompose to the corresponding isocyanate and aromatic hydroxy compound.

After converting an easily thermally decomposable N-substituted carbamic acid-O-aryl ester by a transesterification reaction according to step (P), the resulting N-substituted carbamic acid-O-aryl ester can be used in an isocyanate reaction. Furthermore, since this step is a step of converting the ester group of the N-substituted carbamic acid-O—$R^2$ ester, it is also generally referred to as a "transesterification step" in the present embodiment.

Step (P): a step of obtaining N-substituted carbamic acid-O-aryl ester by reacting N-substituted carbamic acid-O—$R^2$ ester and an aromatic hydroxy composition (composition containing at least one type of aromatic hydroxy compound represented by the following formula (2)) in a liquid phase and extracting alcohol formed as a by-product to a gaseous phase.

Figure 4:
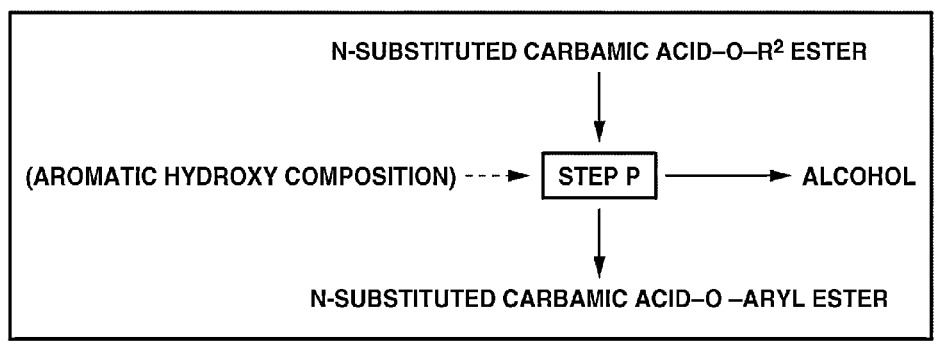
FIG. 4 shows a conceptual drawing depicting a step (P) in the present embodiment.

FIG. 4 shows a conceptual drawing depicting the step (P).

Furthermore, an alcohol derived from N-substituted carbamic acid-O—$R^2$ ester is formed in the step (P). The following provides an explanation of step (P).

Here, the target N-substituted carbamic acid-O—$R^2$ ester refers to an N-substituted carbamic acid-O—$R^2$ ester represented by the above-mentioned formula (49).

The aromatic hydroxy compound in the reacted aromatic hydroxy composition may be any of an aromatic hydroxy compound represented by the above-mentioned formula (2), formula (7), formula (31), formula (32), formula (38), formula (39) or formula (40). The case in which an aromatic hydroxy compound represented by formula (7) or formula (31) is contained is preferable, the case in which an aromatic hydroxy composition is used that contains an active aromatic hydroxy compound represented by formula (32) is more preferable, and the case in which an aromatic hydroxy composition is used that contains an active aromatic hydroxy compound represented by formula (38) is even more preferable.

Various methods can be carried out for the step (P) according to the compounds used and the like with reference to known methods (see, for example, WO 2008/059953).

Although varying according to the compounds reacted, the reaction conditions of step (P) are such that the amount of aromatic hydroxy compound in the aromatic hydroxy composition used has a stoichiometric ratio within a range of from 2 to 1000 times based on the ester groups that compose the raw material N-substituted carbamic acid-O—$R^2$ ester. Although it is preferable to use an excess of the aromatic hydroxy compound based on ester groups that compose the raw material N-substituted carbamic acid-O—$R^2$ ester in order to complete the reaction quickly, in consideration of the size of the reactor, the stoichiometric ratio is preferably within a range of from 2 to 100 times and more preferably within a range of from 5 to 50 times.

The reaction temperature is generally within a range of from 100 to 300° C., and a high temperature is preferable for increasing the reaction rate, but since side reactions may occur easily at high temperatures, the reaction temperature is preferably within a range of from 150 to 250° C. A known cooling apparatus or heating apparatus may be installed in the reactor for maintaining a constant reaction temperature. In addition, although varying according to the types of compounds used and the reaction temperature, the reaction may be carried out at reduced pressure, normal pressure or increased pressure and generally at a reaction pressure within a range of from 20 to $1 \times 10^6$ Pa. There are no particular limitations on the reaction time (residence time in the case of a continuous method), and is generally from 0.001 to 100 hours, preferably from 0.01 to 50 hours and more preferably from 0.1 to 30 hours. In addition, the reaction can be terminated after confirming that a desired amount of the target N-substituted carbamic acid-O-aryl ester has been formed by sampling the reaction liquid and determining the amount formed by liquid chromatography, for example.

Although a catalyst is not necessarily required in step (P), a catalyst may be used without problem to lower the reaction temperature or complete the reaction more quickly. The catalyst is used at 0.01 to 30% by weight and preferably at 0.5 to 20% by weight based on the weight of the N-substituted carbamic acid-O—$R^2$ ester. Examples of catalysts may include Lewis acids as well as transition metal compounds that form a Lewis acid, organic tin compounds, copper group metals, zinc or iron group metal compounds, and more specifically, Lewis acids and transition metal compounds that form a Lewis acid represented by $AlX_3$, $TiX_3$, $TiX_4$, $VOX_3$, $VX_5$, $ZnX_2$, $FeX_3$ or $SnX_4$ (wherein X represents a halogen, an acetoxy group, an alkoxy group or an aryloxy group); organic tin compounds represented by $(CH_3)_3SnOCHCH_3$, $(C_2H_5)SnOCOC_6H_5$, $Bu_3SnOCOCH_3$, $Ph_3SnOCOCH_3$, $Bu_2Sn(OCOCH_3)_2$, $Bu_2Sn(OCOC_{11}H_{23})_2$, $Ph_3SnOCH_3$, $(C_2H_5)_3SnOPh$, $Bu_2Sn(OCH_3)_2$, $Bu_2Sn(OC_2H_5)_2$, $Bu_2Sn(OPh)_2$, $Ph_2Sn(CH_3)_2$, $(C_2H_5)_3SnOH$, $PhSnOH$, $Bu_2SnO$, $(C_8H_{17})_2SnO$, $Bu_2SnCl_2$ or $BuSnO(OH)$; copper family metal compounds represented by $CuCl$, $CuCl_2$, $CuBr$, $CuBr_2$, $CuI$, $CuI_2$, $Cu(OAc)_2$, $Cu(acac)_2$, copper olefinate, $Bu_2Cu$, $(CH_3O)_2Cu$, $AgNO_3$, $AgBr$, silver picrate or $AgC_6H_6ClO_4$; zinc compounds represented by $Zn(acac)_2$; and, iron family metal compounds represented by $Fe(C_{10}H_5)(CO)_5$, $Fe(CO)_5$, $Fe(C_4H_6)(CO)_3$, $Co(mesytilene)_2(PEt_2Ph_2)$, $CoC_5F_5(CO)_7$ or ferrocene. (In the above listing of examples, Bu refers to a butyl group, Ph refers to a phenyl group, and acac refers to an acetyl acetone chelate ligand.) Amines such as 1,4-diazabicyclo[2,2,2]octane, triethylenediamine or triethylamine are suitable for use as catalysts, while organic metal catalysts such as dibutyl tin dilaurate, lead octoate or stannous octoate are particularly preferable. These compounds may be used alone or two or more types may be used as a mixture.

Although the use of a reaction solvent is not necessarily required in the present embodiment, a suitable inert solvent can be preferably used as a reaction solvent for the purpose of facilitating the reaction procedure and the like, examples of which may include alkanes such as hexane (including isomers), heptane (including isomers), octane (including isomers), nonane (including isomers) or decane (including isomers); aromatic hydrocarbons and alkyl-substituted aromatic hydrocarbons such as benzene, toluene, xylene (including isomers), ethyl benzene, diisopropyl benzene (including isomers), dibutyl benzene (including isomers) or naphthalene; aromatic compounds substituted with a halogen or nitro group such as chlorobenzene, dichlorobenzene (including isomers), bromobenzene, dibromobenzene (including isomers), chloronaphthalene, bromonaphthalene, nitrobenzene or nitronaphthalene; polycyclic hydrocarbon compounds such as diphenyl, substituted diphenyl, diphenyl methane, terphenyl, anthracene or dibenzyl toluene (including isomers); aliphatic hydrocarbons such as cyclohexane, cyclopentane, cyclooctane or ethylcyclohexane; ketones such as methyl ethyl ketone or acetophenone; esters such as dibutyl phthalate, dihexyl phthalate, dioctyl phthalate or benzylbutyl phthalate; ethers and thioethers such as diphenyl ether or diphenyl sulfide; sulfoxides such as dimethylsulfoxide or diphenylsulfoxide; and silicone oil. These solvents can be used alone or two or more types can be used as a mixture.

The transesterification reaction in the present embodiment is an equilibrium reaction. Thus, it is preferable to allow the reaction to proceed while removing the product in the form of alcohol (alcohol derived from the raw material N-substituted carbamic acid-O—$R^2$ ester) from the reaction system in order to carry out transesterification efficiently. Thus, if the aromatic hydroxy compound is selected such that the standard boiling point of the aromatic hydroxy compound used in transesterification is higher than the standard boiling point of the alcohol derived from the raw material N-substituted carbamic acid-O—$R^2$ ester, the compound having the lowest standard boiling point in the reaction system becomes the alcohol derived from the raw material N-substituted carbamic acid-O—$R^2$ ester, thereby facilitating removal of products from the reaction system. Based on the finding that normally industrially adequate distillative separation is possible if the standard boiling points of two components to be separated are 10° C. or more apart, an aromatic hydroxy compound is preferably used such that the standard boiling point of the compound having the lowest standard boiling point in the aromatic hydroxy composition (based on a comparison of standard boiling points) is 10° C. or more higher than the standard boiling point of the alcohol.

In addition, transesterification is preferably carried out by the continuous method to allow transesterification to proceed efficiently. Namely, the raw material N-substituted carbamic acid-O—$R^2$ ester and the aromatic hydroxy composition are continuously supplied to a reactor, transesterification is carried out, alcohol derived from the raw material N-substituted carbamic acid-O—$R^2$ ester that is formed is extracted from the reactor in the form of a gaseous component, and a reaction liquid containing the N-substituted carbamic acid-O-aryl ester formed and the aromatic hydroxy composition is continuously extracted from the bottom of the reactor.

Although the material of the reactor and lines used to carry out transesterification may be known materials provided they do not have a detrimental effect on the starting substances and reactants, materials such as SUS304, SUS316 or SUS316L are inexpensive and can be used preferably. Known process apparatuses such as a flow meter, a thermometer and other measuring instruments or a reboiler, a pump or a condenser and the like may be added as necessary, the known method such as steam or a heater may be used for heating, and the known method such as air cooling, cooling water or brine can be used for cooling. Steps may also be added as necessary. For example, steps and apparatuses able to be conceived by a person or engineer with ordinary skill in the art may be added, such as a step of dissolving the aromatic hydroxy compound, a step of separating the alcohol, a step of separating and/or purifying the aromatic hydroxy compound, a step of purifying the N-substituted carbamic acid-O-aryl ester from the formed reaction liquid or a step of incinerating or discarding by-products and the like.

There are no particular limitations on the type of reactor, and a known tank-type or a column-type reactor can be used. Various known methods are used for such a reactor, examples of which may include types using reactors containing a stirring tank, a multistage stirring tank, a distillation column, a multistage distillation column, a multitubular reactor, a continuous multistage distillation column, a packed column, a thin film evaporator, a reactor provided with a support inside, a forced circulation reactor, a falling film evaporator, a falling drop evaporator, a trickle flow reactor or a bubble column, and types using combinations thereof. Methods using a thin film evaporator or a column-type reactor are preferable from the viewpoint of efficiently shifting the equilibrium to the products side, while a structure having a large gas-liquid contact area is preferable for being able to rapidly transfer the alcohol derived from the raw material N-substituted carbamic acid-O—$R^2$ ester formed to the gaseous phase.

A multistage distillation column refers to a distillation column having multiple stages in which the number of theoretical plates of distillation is 2 or more, and any multistage distillation column may be used provided it allows continuous distillation. Any multistage distillation column can be used for the multistage distillation column provided it is ordinarily used as a multistage distillation column, examples of which may include tray column types using a tray such as a bubble tray, a porous plate tray, a valve tray or a counter-current tray, and packed column types packed with various types of packing materials such as a raschig ring, a lessing ring, a pole ring, Berl saddle, Interlock saddle, Dixon packing, McMahon packing, Helipack, Sulzer packing or Mellapak. Any packed column can be used provided the column is packed with a known packing material as described above. Moreover, a combination tray-packed column type is also used preferably that combines a tray portion with a portion packed with a packing material.

A line for supplying inert gas and/or liquid inert solvent from the lower portion of the reactor may be separately attached, and in the case the mixture of the target N-substituted carbamic acid-O-aryl ester and aromatic hydroxy compound contains raw material N-substituted carbamic acid-O—$R^2$ ester, a line may be attached for re-circulating all or a portion of the mixture to the reactor. Furthermore, in the case of using the above-mentioned inert solvent, the inert solvent may be in the form of a gas and/or a liquid.

The gaseous component extracted from the reactor containing alcohol derived from the raw material N-substituted carbamic acid-O—$R^2$ ester is preferably purified using a known method such as that which uses a distillation column, and can be reused as an alcohol of step (A) and/or step (R).

<Route 4)>

Route 4) is a method for carrying out step (R) followed by carrying out step (P) and step (C). Route 4) is one aspect of the method indicated in route 2).

The method of route 4) is a method for obtaining N-substituted carbamic acid-O-aryl ester, in which at least two molecules of the N-substituted carbamic acid-O-aryl ester are crosslinked with methylene (—$CH_2$—) groups, from the N-substituted carbamic acid-O-aryl ester obtained in step (P) by carrying out the following step (C) after step (P), in which the organic primary amine used in step (A) is an aromatic organic primary monoamine represented by the following formula (5). An aromatic monohydroxy compound is preferably used for the aromatic hydroxy compound that composes the aromatic hydroxy composition used in step (A) and/or step (R) and/or step (P).

Step (C): a step of obtaining N-substituted carbamic acid-O—($R^2$ or aryl) ester, in which at least two molecules of the N-substituted carbamic acid-O—($R^2$ or aryl) ester are crosslinked with methylene groups (—$CH_2$—), by reacting the N-substituted carbamic acid-O—($R^2$ or aryl) ester with formaldehyde or a methylenating crosslinking agent and crosslinking aromatic groups derived from the aromatic organic primary monoamine contained in the N-substituted carbamic acid-O—($R^2$ or aryl) ester with the methylene groups (—$CH_2$—).

The N-substituted carbamic acid-O—$R^2$ ester of this route 4) refers to unreacted N-substituted carbamic acid-O—$R^2$ ester in step (P).

In this route, step (A) is carried out using an organic primary amine represented by the following formula for the organic primary amine to obtain a compound having ureido groups represented by formula (1) derived from the organic primary amine, followed by carrying out step (R) to obtain an N-substituted carbamic acid-O—$R^2$ ester derived from the compound having ureido groups, carrying out step (P) to obtain an N-substituted carbamic acid-O-aryl ester derived from the compound having ureido groups, and finally carrying out step (C). Namely, the organic primary amine used in this route is an organic primary amine represented by formula (5), the compound having ureido groups obtained in step (A) of this route is a compound having ureido groups represented by formula (41) derived from the organic primary amine, the N-substituted carbamic acid-O—$R^2$ ester obtained in step (R) of this route is an N-substituted carbamic acid-O—$R^2$ ester in which r=1 that is represented by formula (49) and derived from the ureido groups and an alcohol, and more specifically an N-substituted carbamic acid-O—$R^2$ ester represented by the following formula (146), and the N-substituted carbamic acid-O-aryl ester obtained in step (P) of this route is an N-substituted carbamic acid-O-aryl ester in which q=1 that is represented by formula (43) and derived from the N-substituted carbamic acid-O—$R^2$ ester and an aromatic hydroxy composition, and more specifically an N-substituted carbamic acid-O-aryl ester represented by the following formula (149). Indications of specific examples of each of these compounds are respectively contained in previous explanations thereof.

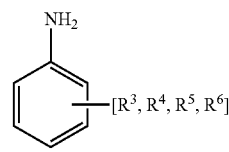

(5)

(wherein,
at least one location at the ortho position and/or para position of the $NH_2$ group of an aromatic organic primary monoamine represented by formula (5) is not substituted, groups $R^3$ to $R^6$ respectively represent a group substituted at an arbitrary location that maintains aromatic properties of the ring, groups $R^3$ to $R^6$ may respectively and independently substitute an aromatic ring or groups $R^3$ to $R^6$ may together bond to form a ring with an aromatic ring, groups $R^3$ to $R^6$ are hydrogen atoms or groups selected from groups composed of groups in which a group selected from the group consisting of an alkyl group, a cycloalkyl group, an aryl group and an aryl group having a hydroxy group is bonded by saturated aliphatic bonds and/or ether bonds, the number of carbon atoms of groups $R^3$ to $R^6$ is an integral number within a range of from 0 to 7, and the total number of carbon atoms that compose the aromatic organic primary monoamine represented by formula (5) is an integer of from 6 to 13).

In this case, the compound having ureido groups obtained in step (A) is at least one type of compound having ureido groups represented by the following formula (148). In addition, the groups $R^3$, $R^4$, $R^5$ and $R^6$ in the following formula (148) are selected from the groups $R^3$, $R^4$, $R^5$ and $R^6$ of an organic primary amine represented by the above-mentioned formula (5), and is a compound in which amino groups (—$NH_2$ groups) of the organic primary amine represented by formula (5) are in the form of ureido groups (—NH—CO—$NH_2$):

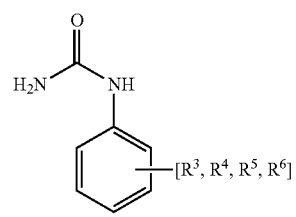

(148)

(wherein
at least one location at the ortho position and/or para position of the ureido group of an N-substituted aromatic organic monourea represented by formula (148) is not substituted, groups $R^3$ to $R^6$ respectively represent a group substituted at an arbitrary location that maintains aromatic properties of the ring, groups $R^3$ to $R^6$ may respectively and independently substitute an aromatic ring or groups $R^3$ to $R^6$ may together bond to form a ring with an aromatic ring, groups $R^3$ to $R^6$ are hydrogen atoms or groups selected from groups composed of groups in which a group selected from the group consisting of an alkyl group, a cycloalkyl group, an aryl group and an aryl group having a hydroxy group is bonded by saturated aliphatic bonds and/or ether bonds, the number of carbon atoms of groups $R^3$ to $R^6$ is an integral number within a range of from 0 to 7, and the total number of carbon atoms that compose the N-substituted aromatic organic monourea represented by formula (148), excluding ureido groups (—NH—CO—NH$_2$), is an integer of from 6 to 13).

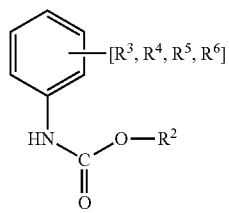

(146)

(wherein
groups $R^2$ to $R^6$ are the groups indicated above).

In this case, the N-substituted carbamic acid-O-aryl ester obtained in step (P) by carrying out step (R) is at least one type of N-substituted carbamic acid-O-aryl ester represented by the following formula (149). In addition, the groups $R^3$, $R^4$, $R^5$ and $R^6$ in the following formula (149) are selected from the groups $R^3$, $R^4$, $R^5$ and $R^6$ of an organic primary amine represented by the above-mentioned formula (5), and is a compound in which ureido groups (—NH—CO—NH$_2$) of a compound having ureido groups represented by formula (148) are in the form of carbamic acid-O-aryl ester groups:

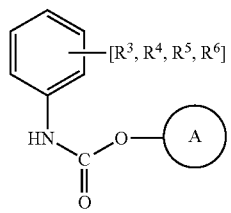

(149)

(wherein
groups $R^3$ to $R^6$ are the groups indicated above).

In steps (A), (R) and (P) of this route, the organic primary amine used is an organic primary amine represented by formula (5), and steps (A), (R) and (P) of this route are carried out under the conditions of steps (A), (R) and (P) of route 3).

Although varying according to the compounds reacted, the reaction conditions for producing N-substituted carbamic acid-O—R$^2$ ester by reacting a compound having ureido groups and an alcohol of step (R) are such that the amount of alcohol used has a stoichiometric ratio within a range of from 1 to 500 times based on the ureido groups of the compound having ureido groups used. Although it is preferable to use an excess of alcohol since complexly substituted carbonyl compounds and high molecular weight compounds having carbonyl bonds in molecules thereof form easily if the stoichiometric ratio is less than 1 time, in consideration of the size of the reactor, the stoichiometric ratio is preferably within a range of from 1 to 200 times, more preferably within a range of from 1.5 to 100 times and even more preferably within a range of from 2 to 50 times.

Although varying according to the compounds used, the reaction temperature is preferably within a range of from 100 to 350° C. If the temperature is lower than 100° C., the reaction slows or the reaction hardly proceeds at all, or complexly substituted carbonyl compounds increase, thereby making this undesirable. On the other hand, at temperatures higher than 350° C., the N-substituted carbamic acid-O—R$^2$ ester either remains in step (A), the urea (and non-N-substituted carbamic acid ester) formed in the system of step (R) decompose, the hydroxy composition is subjected to dehydrogenative denaturation, or decomposition and denaturation reactions of the product in the form of N-substituted carbamic acid-O—R$^2$ ester occur easily, thereby making this undesirable. From such viewpoints, the reaction temperature is more preferably within a range of from 120 to 320° C. and even more preferably within a range of from 140 to 300° C.

As has been previously described, the reaction by which N-substituted carbamic acid-O—R$^2$ ester is formed is an equilibrium reaction, and since the reaction is biased towards the reactants side, the reaction is preferably carried out while removing ammonia formed as a by-product outside the system as much as possible. Ammonia is preferably removed so that the ammonia concentration in the reaction liquid is preferably 1000 ppm or less, more preferably 300 ppm or less, even more preferably 100 ppm or less and most preferably 30 ppm or less (being contained in the reaction liquid refers to being contained in a liquid phase when carrying out the step (R)). Ammonia can be removed using methods such as reactive distillation, use of an inert gas, membrane separation and adsorptive separation. For example, the reactive distillation refers to a method for separating continuously formed ammonia during the reaction by distillation in the form of a gas. This can be carried out while boiling alcohole, an aromatic hydroxy compound, solvent or hydroxy composition in order to increase the distillation efficiency of the ammonia. In addition, a method using an inert gas refers to a method for separating continuously formed ammonia during the reaction from the reaction system in the form of a gas along with the inert gas. Examples of inert gases used may include nitrogen, helium, argon, carbon dioxide, methane, ethane and propane, these may be used alone or as a mixture, and a method in which the inert gas is introduced into the reaction system is preferable. Examples of adsorbents used in methods using adsorptive separation may include adsorbents able to be used under the temperature conditions at which the reaction is carried out, such as silica, alumina, various types of zeolite or diatomaceous earth. These methods for removing ammonia outside the system may be carried out alone or a plurality of types may be carried out in combination.

A catalyst can be used in the reaction for the purpose of increasing the reaction rate, for example. Examples of catalysts that are used preferably may include basic catalysts such as methylates, ethylates or butyrates (including isomers) of lithium, sodium, potassium, calcium or barium, rare earth elements, antimony or bismuth alone or oxides, sulfides and salts thereof, boron alone or boron compounds, metals of the copper family, zinc family, aluminum family, carbon family and titanium family in the periodic table as well as metal oxides and sulfides thereof, and carbides and nitrides of elements of the carbon family excluding carbon, titanium family, vanadium family and chromium family in the periodic table. Although there are no particular limitations on the amount of catalyst used in the case of using a catalyst, a catalyst can be used within the range of a stoichiometric ratio of from 0.0001 to 100 times the ureido groups of the compound having ureido groups.

Although varying according to the composition of the reaction system, reaction temperature, method used to remove ammonia, reaction apparatus and the like, the reaction pressure is generally within a range of preferably from 0.01 Pa to 10 MPa (absolute pressure), and in consideration of ease of industrial application, the reaction pressure is more preferably within a range of from 0.1 Pa to 5 MPa (absolute pressure), and in consideration of removing gaseous ammonia outside the system, even more preferably from 0.1 Pa to 1.5 MPa (absolute pressure).

Although varying according to the composition of the reaction system, reaction temperature, method used to remove ammonia, reaction apparatus, reaction pressure and the like, the reaction time (residence time in the case of a continuous reaction) is generally from 0.01 to 100 hours. The reaction time can also be determined according to the formation amount of the target compound in the form of N-substituted carbamic acid-O—$R^2$ ester (and depending on the case, the total amount resulting from adding the amount of N-substituted carbamic acid-O-aryl ester). For example, the reaction may be stopped after having sampled the reaction liquid, determined the content of N-substituted carbamic acid ester in the reaction liquid (and depending on the case, the total amount resulting from adding the amount of N-substituted carbamic acid-O-aryl ester) and confirming that the N-substituted carbamic acid-O—$R^2$ ester has been formed at a yield of 10% or more based on the compound having ureido groups, or the reaction may be stopped after having confirmed that the yield is 90% or more. The reaction liquid containing the N-substituted carbamic acid-O—$R^2$ ester obtained in step (R) is converted to N-substituted carbamic acid-O-aryl ester in a process that contains step (P) to be subsequently described, followed by obtaining an isocyanate in step (F). At that time, if the content of N-substituted carbamic acid-O—$R^2$ ester in step (R) is low (the yield thereof is low), there are cases in which this can cause a decrease in the yield of isocyanate. Thus, the yield of the N-substituted carbamic acid-O—$R^2$ ester is preferably 50% or more, more preferably 80% or more and even more preferably 90% or more.

Although the use of a reaction solvent is not necessarily required in the reaction, a suitable solvent is preferably used as a reaction solvent for the purpose of facilitating the reaction procedure, examples of which may include alkanes such as pentane (including isomers), hexane (including isomers), heptane (including isomers), octane (including isomers), nonane (including isomers) or decane (including isomers); aromatic hydrocarbons and alkyl-substituted aromatic hydrocarbons such as benzene, toluene, xylene (including isomers), ethyl benzene, diisopropyl benzene (including isomers), dibutyl benzene (including isomers) or naphthalene; nitrile compounds such as acetonitrile or benzonitrile; aromatic compounds substituted with a halogen or nitro group such as chlorobenzene, dichlorobenzene (including isomers), bromobenzene, dibromobenzene (including isomers), chloronaphthalene, bromonaphthalene, nitrobenzene or nitronaphthalene; polycyclic hydrocarbon compounds such as diphenyl, substituted diphenyl, diphenyl methane, terphenyl, anthracene or dibenzyl toluene (including isomers); aliphatic hydrocarbons such as cyclohexane, cyclopentane, cyclooctane or ethylcyclohexane; ketones such as methyl ethyl ketone or acetophenone; esters such as dibutyl phthalate, dihexyl phthalate, dioctyl phthalate or benzylbutyl phthalate; ethers and thioethers such as tetrahydrofuran, 1,4-dioxane, 1,2-dimethoxyethane, diphenyl ether or diphenyl sulfide; ketone compounds such as acetone or methyl ethyl ketone; ester compounds such as ethyl acetate or ethyl benzoate; and sulfoxides such as dimethylsulfoxide or diphenylsulfoxide. Naturally, a hydroxy composition used in excess in the reaction is also preferably used as a reaction solvent.

The reaction is carried out in a system having a gaseous phase containing a hydroxy composition, a compound having carbonyl groups derived from urea (a compound that inherits a carbonyl group possessed by urea, such as a non-N-substituted carbamic acid ester or biuret, which refers to a compound excluding N-substituted carbamic acid-O-esters) and ammonia produced as a by-product in the reaction, and a liquid phase in which the reaction is carried out. Although the majority of the reaction is carried out in the liquid phase, it may also be carried out in the gaseous phase depending on the reaction conditions. At that time, the volumetric content of the liquid phase in the reaction in which the reaction is carried out is preferably 50% or less. In the case of carrying out the reaction continuously over a long period of time, although polymeric by-products may form due to fluctuations in operating conditions (such as temperature or pressure) and the like, if the volumetric content of the liquid phase in the reactor is high, adhesion and accumulation of such polymeric by-products in the reactor can be avoided. However, since the efficiency of removal of by-product ammonia may become poor and the yield of the N-substituted carbamic acid-O—$R^2$ ester (and depending on the case, the total amount resulting from adding the amount of N-substituted carbamic acid-O-aryl ester) may decrease if the volumetric content of the liquid phase is excessively high, the volumetric content of the liquid phase based on the gaseous phase is preferably 50% or less, more preferably 30% or less and even more preferably 20% or less (the volumetric content of the liquid phase refers to volumetric ratio of the liquid phase based on the volume of the reaction tank in the case of a tank-type reactor, the volume of the stage lower than the feed stage (not including the tank bottom and reboiler) in the case of a column-type reactor, or the volume of the thin film distiller in the case of a thin film distiller).

Although there are no particular limitations on the reaction apparatus used when carrying out the reaction and a known reactor can be used, a tank-type and/or a column-type reactor is used preferably. The reactor used is preferably equipped with a condenser.

As was previously described, the reaction is preferably carried out in a system containing a gaseous phase containing a hydroxy composition, a compound having carbonyl groups derived from urea and ammonia produced as a by-product in the reaction, and a liquid phase in which the reaction is carried out, and under conditions such that the volumetric content of the liquid phase in the reactor in which the reaction is carried out is 50% or less, and a reactor that satisfies these conditions is selected for the reactor in which the reaction is carried out.

More specifically, conventionally known reactors can be suitably combined and used, examples of which may include a stirring tank, a pressurized stirring tank, a depressurized stirring tank, a column-type reactor, a distillation column, a packed column or a thin film distiller.

There are no particular limitations on the type of condenser provided in the reactor and the known condenser can be used. For example, conventionally known condensers such as a multitubular cylindrical condenser, a double tube condenser, a single tube condenser or an air-cooled condenser can be suitably combined and used. The condenser may be provided inside the reactor or outside the reactor, or may be connected with the reactor by a line, and various types can be employed in consideration of the forms of the reactor and condenser, the manner in which condensed liquid is handled and the like.

There are no particular limitations on the materials of the reactor and condenser and known materials can be used. Examples of materials that can be used may include glass, stainless steel, carbon steel, Hastelloy, glass-lined base materials and Teflon (registered trademark) coated materials. Materials such as SUS304, SUS316 or SUS316L are inexpensive and can be used preferably. Known process apparatuses such as a flow meter, a thermometer and other measuring instruments or a reboiler, a pump or a condenser and the like may be added as necessary, the known method such as steam or a heater may be used for heating, and the known method such as air cooling, cooling water or brine can be used for cooling. Steps may also be added as necessary. For example, steps and apparatuses able to be conceived by a person or engineer with ordinary skill in the art may be added, such as a step of dissolving the compound having ureido groups in the aromatic hydroxy composition, a step of dissolving the aromatic hydroxy compound, a step of separating alcohol, a step of separating and/or purifying the aromatic hydroxy compound, a step of purifying N-substituted carbamic acid-O—$R^2$ ester from the formed reaction liquid, or a step of incinerating or discarding by-products and the like.

Step (R) is a step of producing N-substituted carbamic acid-O—$R^2$ ester by reacting (esterifying) a compound having ureido groups and an alcohol in a liquid phase using a reactor (equipped with a condenser). The gaseous component formed in the step (R) containing a compound having carbonyl groups derived from urea and ammonia formed as a by-product in the reaction is introduced into the condenser provided in the reactor and all or a portion of the alcohol and compound having carbonyl groups derived from urea are condensed followed by recovery of ammonia in the form of a gas.

At that time, the compound having carbonyl groups derived from urea that is contained in ammonia recovered as a gas from the condenser is present at a specific amount or less. Namely, the ratio of the number of carbonyl groups (—C(=O)—) contained in the compound having carbonyl groups derived from urea contained in the ammonia to the number of ammonia molecules is 1 or less, preferably 0.5 or less, more preferably 0.1 or less and even more preferably 0.01 or less. The reason for making the amount of the compound having carbonyl groups derived from urea contained in the ammonia to be within a specific range is to avoid adhesion and accumulation of solid components in the line for transferring ammonia from the condenser.

Although all solid components that adhere and accumulate in the line for transferring ammonia cannot be identified, as a result of studies conducted by the inventors of the present invention, the majority were determined to be compounds having carbonyl groups. Although one possible method for avoiding adhesion and accumulation of such solid components contains heating the line for transferring ammonia to decompose compounds having carbonyl groups, according to studies conducted by the inventors of the present invention, there are many cases in which heating alone causes polymerization of decomposition products (such as isocyanic acid) or reaction with other compounds having carbonyl groups, thereby making it difficult to completely avoid adhesion and accumulation of solid components. In addition, in the case of simply heating the line, it was determined that compounds having carbonyl groups contained in the ammonia and their decomposition products solidify as a result of being rapidly cooled at the outlet of the line for transferring ammonia (such as the portion in contact with the atmosphere), thereby frequently resulting in prominent adhesion and accumulation of solid components. As a result of conducting extensive studies regarding this problem, the inventors of the present invention found that the problem of adhesion and accumulation of solid components can be solved by making the amount of the compound having carbonyl groups derived from the carbonic acid derivative contained in the ammonia to be equal to or less than the specific amount described above. Although the mechanism by which this effect is demonstrated is unclear, the inventors of the present invention surmised that adhesion and accumulation in the line is caused by the compound having carbonyl groups derived from the carbonic acid derivative itself as well as decomposition and/or polymerization products of the compound having carbonyl groups derived from the carbonic acid derivative, and that by making the amount of carbonyl groups contained in the compound having carbonyl groups derived from the carbonic acid derivative equal to or less than a specific concentration, adhesion of the compound having carbonyl groups derived from the carbonic acid derivative itself as well as the reaction rates of decomposition and/or polymerization of that compound are lowered considerably.

On the other hand, the condensed hydroxy composition and compound having carbonyl groups derived from urea are made to be such that the stoichiometric ratio of the condensed hydroxy composition to the condensed compound having carbonyl groups derived from urea is 1 or more, preferably 2 or more and more preferably 3 or more. The reason for defining such ranges is to enable a mixture of the hydroxy composition and compound having carbonyl groups derived from urea condensed in the condenser to be in the form of a homogeneous liquid mixture. As a result, not only is handling of the mixture easier, but occurrence of problems such as adhesion and accumulation of solid components in the condenser can be avoided.

Moreover, the mixture of the hydroxy composition and the compound having carbonyl groups derived from urea condensed by the condenser in step (R) may be circulated within the reactor and reused in the reaction of step (A). At that time, the amount of ammonia contained in the mixture is preferably 5000 ppm or less, more preferably 3000 ppm or less and even more preferably 2000 ppm or less.

As has been described above, although various compounds are recovered in the form of compounds having carbonyl groups derived from urea, there are no particular limitations on the reuse of these compounds.

<Step (P)> Esterification Step

Since this step is a step of converting the ester group of an N-substituted carbamic acid-O—$R^2$ ester, it is also generally referred to as an "esterification step" in the present embodiment.

Figure 5:
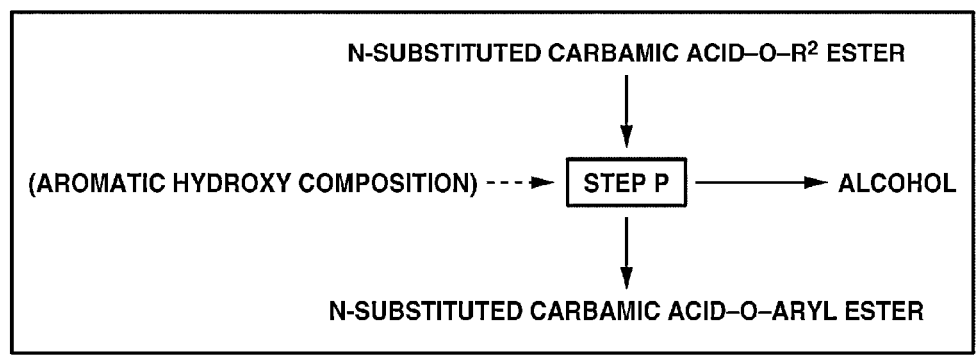
FIG. 5 shows a conceptual drawing depicting a step (P) in the present embodiment.

FIG. 5 shows a conceptual drawing depicting the step (P).

Furthermore, an alcohol derived from N-substituted carbamic acid-O—$R^2$ ester is formed in this step (P). The following provides an explanation of the step (P).

The aromatic hydroxy compound in the reacted aromatic hydroxy composition may be any of an aromatic hydroxy compound represented by the above-mentioned formula (2), formula (7), formula (31), formula (32), formula (38), formula (39) or formula (40). The case in which an aromatic hydroxy compound represented by formula (7) or formula (31) is contained is preferable, the case in which an aromatic hydroxy composition is used that contains an active aromatic hydroxy compound represented by formula (32) is more preferable, and the case in which an aromatic hydroxy composition is used that contains an active aromatic hydroxy compound represented by formula (38) is even more preferable.

Various methods can be carried out for the step (P) according to the compounds used and the like with reference to known methods (see, for example, WO 2008/059953).

Although varying according to the compounds reacted, the reaction conditions of step (P) are such that the amount of aromatic hydroxy compound in the aromatic hydroxy composition used has a stoichiometric ratio within a range of from 2 to 1000 times based on the ester groups that compose the raw material N-substituted carbamic acid-O—$R^2$ ester. Although it is preferable to use an excess of the aromatic hydroxy compound based on ester groups that compose the raw material N-substituted carbamic acid-O—$R^2$ ester in order to complete the reaction quickly, in consideration of the size of the reactor, the stoichiometric ratio is preferably within a range of from 2 to 100 times and more preferably within a range of from 5 to 50 times.

The reaction temperature is generally within a range of from 100 to 300° C., and a high temperature is preferable for increasing the reaction rate, but since side reactions may occur easily at high temperatures, the reaction temperature is preferably within a range of from 150 to 250° C. A known cooling apparatus or heating apparatus may be installed in the reactor for maintaining a constant reaction temperature. In addition, although varying according to the types of compounds used and the reaction temperature, the reaction may be carried out at reduced pressure, normal pressure or increased pressure and normally at a reaction pressure within a range of from 20 to $1 \times 10^6$ Pa. There are no particular limitations on the reaction time (residence time in the case of a continuous method), and is generally from 0.001 to 100 hours, preferably from 0.01 to 50 hours and more preferably from 0.1 to 30 hours. In addition, the reaction can be terminated after confirming that a desired amount of the target N-substituted carbamic acid-O-aryl ester has been formed by sampling the reaction liquid and determining the amount formed by liquid chromatography, for example.

Although a catalyst is not necessarily required in step (P), a catalyst may be used without problem to lower the reaction temperature or complete the reaction more quickly. The catalyst is used at 0.01 to 30% by weight and preferably at 0.5 to 20% by weight based on the weight of the N-substituted carbamic acid-O—$R^2$ ester. Examples of catalysts may include Lewis acids as well as transition metal compounds that form a Lewis acid, organic tin compounds, copper group metals, zinc or iron group metal compounds, and more specifically, Lewis acids and transition metal compounds that form a Lewis acid represented by $AlX_3$, $TiX_3$, $TiX_4$, $VOX_3$, $VX_5$, $ZnX_2$, $FeX_3$ or $SnX_4$ (wherein X represents a halogen, an acetoxy group, an alkoxy group or an aryloxy group); organic tin compounds represented by $(CH_3)_3SnOCHCH_3$, $(C_2H_5)SnOCOC_6H_6$, $Bu_3SnOCOCH_3$, $Ph_3SnOCOCH_3$, $Bu_2Sn(OCOCH_3)_2$, $Bu_2Sn(OCOC_{11}H_{23})_2$, $Ph_3SnOCH_3$, $(C_2H_5)_3SnOPh$, $Bu_2Sn(OCH_3)_2$, $Bu_2Sn(OC_2H_5)_2$, $Bu_2Sn(OPh)_2$, $Ph_2Sn(CH_3)_2$, $(C_2H_5)_3SnOH$, $PhSnOH$, $Bu_2SnO$, $(C_8H_{17})_2SnO$, $Bu_2SnCl_2$ or $BuSnO(OH)$; copper family metal compounds represented by $CuCl$, $CuCl_2$, $CuBr$, $CuBr_2$, $CuI$, $CuI_2$, $Cu(OAc)_2$, $Cu(acac)_2$, copper olefinate, $Bu_2Cu$, $(CH_3O)_2Cu$, $AgNO_3$, $AgBr$, silver picrate or $AgC_6H_6ClO_4$; zinc compounds represented by $Zn(acac)_2$; and, iron family metal compounds represented by $Fe(C_{10}H_8)(CO)_5$, $Fe(CO)_5$, $Fe(C_4H_6)(CO)_3$, $Co(mesytilene)_2(PEt_2Ph_2)$, $CoC_5F_5(CO)_7$ or ferrocene. (In the above listing of examples, Bu refers to a butyl group, Ph refers to a phenyl group, and acac refers to an acetyl acetone chelate ligand.) Amines such as 4-diazabicyclo [2,2,2]octane, triethylenediamine or triethylamine are suitable for use as catalysts, while organic metal catalysts such as dibutyl tin dilaurate, lead octoate or stannous octoate are particularly preferable. These compounds may be used alone or two or more types may be used as a mixture.

Although the use of a reaction solvent is not necessarily required in the present embodiment, a suitable inert solvent can be preferably used as a reaction solvent for the purpose of facilitating the reaction procedure and the like, examples of which may include alkanes such as hexane (including isomers), heptane (including isomers), octane (including isomers), nonane (including isomers) or decane (including isomers); aromatic hydrocarbons and alkyl-substituted aromatic hydrocarbons such as benzene, toluene, xylene (including isomers), ethyl benzene, diisopropyl benzene (including isomers), dibutyl benzene (including isomers) or naphthalene; aromatic compounds substituted with a halogen or nitro group such as chlorobenzene, dichlorobenzene (including isomers), bromobenzene, dibromobenzene (including isomers), chloronaphthalene, bromonaphthalene, nitrobenzene or nitronaphthalene; polycyclic hydrocarbon compounds such as diphenyl, substituted diphenyl, diphenyl methane, terphenyl, anthracene or dibenzyl toluene (including isomers); aliphatic hydrocarbons such as cyclohexane, cyclopentane, cyclooctane or ethylcyclohexane; ketones such as methyl ethyl ketone or acetophenone; esters such as dibutyl phthalate, dihexyl phthalate, dioctyl phthalate or benzylbutyl phthalate; ethers and thioethers such as diphenyl ether or diphenyl sulfide; sulfoxides such as dimethylsulfoxide or diphenylsulfoxide; and silicone oil. These solvents can be used alone or two or more types can be used as a mixture.

The transesterification reaction in the present embodiment is an equilibrium reaction. Thus, it is preferable to allow the reaction to proceed while removing the product in the form of alcohol (alcohol derived from the raw material N-substituted carbamic acid-O—$R^2$ ester) from the reaction system in order to carry out transesterification efficiently. Thus, if the aromatic hydroxy compound is selected such that the standard boiling point of the aromatic hydroxy compound used in transesterification is higher than the standard boiling point of the alcohol derived from the raw material N-substituted carbamic acid-O—$R^2$ ester, the compound having the lowest standard boiling point in the reaction system becomes the alcohol derived from the raw material N-substituted carbamic acid-O—$R^2$ ester, thereby facilitating removal of products from the reaction system. Based on the finding that normally industrially adequate distillative separation is possible if the standard boiling points of two components to be separated are 10° C. or more apart, an aromatic hydroxy compound is preferably used such that the standard boiling point of the compound having the lowest standard boiling point in the aromatic hydroxy composition (based on a comparison of standard boiling points) is 10° C. or more higher than the standard boiling point of the alcohol.

In addition, transesterification is preferably carried out by a continuous method to allow transesterification to proceed efficiently. Namely, the raw material N-substituted carbamic acid-O—$R^2$ ester and the aromatic hydroxy composition are continuously supplied to a reactor, transesterification is carried out, alcohol derived from the raw material N-substituted carbamic acid-O—$R^2$ ester that is formed is extracted from the reactor in the form of a gaseous component, and a reaction liquid containing the N-substituted carbamic acid-O-aryl ester formed and the aromatic hydroxy composition is continuously extracted from the bottom of the reactor.

Although the material of the reactor and lines used to carry out transesterification may be known materials provided they do not have a detrimental effect on the starting substances and reactants, materials such as SUS304, SUS316 or SUS316L are inexpensive and can be used preferably. Known process apparatuses such as a flow meter, a thermometer and other measuring instruments or a reboiler, a pump or a condenser and the like may be added as necessary, the known method such as steam or a heater may be used for heating, and the known method such as air cooling, cooling water or brine can be used for cooling. Steps may also be added as necessary. For example, steps and apparatuses able to be conceived by a person or engineer with ordinary skill in the art may be added, such as a step of dissolving the aromatic hydroxy compound, a step of separating the alcohol, a step of separating and/or purifying the aromatic hydroxy compound, a step of purifying the N-substituted carbamic acid-O-aryl ester from the formed reaction liquid or a step of incinerating or discarding by-products and the like. There are no particular limitations on the type of reactor, and a known tank-type or a column-type reactor can be used. Various known methods are used for such a reactor, examples of which may include types using reactors containing a stirring tank, a multistage stirring tank, a distillation column, a multistage distillation column, a multitubular reactor, a continuous multistage distillation column, a packed column, a thin film evaporator, a reactor provided with a support inside, a forced circulation reactor, a falling film evaporator, a falling drop evaporator, a trickle flow reactor or a bubble column, and types using combinations thereof. Methods using a thin film evaporator or a column-type reactor are preferable from the viewpoint of efficiently shifting the equilibrium to the products side, while a structure having a large gas-liquid contact area is preferable for being able to rapidly transfer the alcohol derived from the raw material N-substituted carbamic acid-O—R² ester formed to the gaseous phase.

A multistage distillation column refers to a distillation column having multiple stages in which the number of theoretical plates of distillation is 2 or more, and any multistage distillation column may be used provided it allows continuous distillation. Any multistage distillation column can be used for the multistage distillation column provided it is ordinarily used as a multistage distillation column, examples of which may include tray column types using a tray such as a bubble tray, a porous plate tray, a valve tray or a counter-current tray, and packed column types packed with various types of packing materials such as a raschig ring, a lessing ring, a pole ring, Berl saddle, Interlock saddle, a Dixon packing, a McMahon packing, Helipack, a Sulzer packing or Mellapak. Any packed column can be used provided the column is packed with the known packing material as described above. Moreover, a combination tray-packed column type is also used preferably that combines a tray portion with a portion packed with a packing material.

A line for supplying inert gas and/or liquid inert solvent from the lower portion of the reactor may be separately attached, and in the case the mixture of the target N-substituted carbamic acid-O-aryl ester and aromatic hydroxy compound contains raw material N-substituted carbamic acid-O—R² ester, a line may be attached for re-circulating all or a portion of the mixture to the reactor. Furthermore, in the case of using the above-mentioned inert solvent, the inert solvent may be in the form of a gas and/or a liquid.

The gaseous component extracted from the reactor containing alcohol derived from the raw material N-substituted carbamic acid-O—R² ester is preferably purified using the known method such as that which uses a distillation column, and can be reused as an alcohol of step (A) and/or step (R).

Step (C) is a step of obtaining N-substituted carbamic acid-O—(R² or aryl) ester, in which at least two molecules of the N-substituted carbamic acid-O—(R² or aryl) ester are crosslinked with methylene groups (—CH₂—), by crosslinking at least one type of N-substituted carbamic acid-O-aryl ester (or reaction liquid containing the same) obtained in step (P) with methylene groups (—CH₂—). As a result of carrying out step (C), N-substituted carbamic acid-O-aryl ester is obtained in which at least two molecules of at least one type of N-substituted carbamic acid-O-aryl ester represented by the following formula (150) are crosslinked with the methylene groups (—CH₂—). Here, when carrying out route 2), an aromatic hydroxy composition containing an aromatic hydroxy compound is preferably used for the aromatic hydroxy compound used in step (A) and/or step (R) and/or step (P) as previously described (namely, an aromatic hydroxy compound in which b=1 in the aromatic hydroxy compound represented by formula (2)). Although a polyvalent aromatic hydroxy compound may be used, crosslinking may occur at locations other than the desired locations at that time. In the following formula (150), in the case of using the above-mentioned aromatic hydroxy compound (namely in the case b=1), ring A of the following formula does not have other aromatic hydroxy groups or alcoholic hydroxy groups. An aromatic hydroxy compound represented by the above-mentioned formula (31) is preferable for the aromatic hydroxy compound, the case of using an active aromatic hydroxy compound represented by formula (38) is more preferable, and the case of using an aromatic hydroxy compound represented by formula (38), in which groups R²⁶ and R²⁷ are hydrogen atoms while other substituents are linear and/or cyclic saturated alkyl groups, or the case of being naphthol (including isomers), phenoxyphenol (including isomers) or diphenoxyphenol (including isomers), in which the ortho position or para position of the hydroxy group is not substituted, is even more preferable.

Although compounds in which m is an integer from 0 to 6 are represented by the formula (150), this value can be adjusted according to the amount used and reaction rate of the methylenating crosslinking agent that is reacted (to be subsequently explained and frequently referred to as a methylenating agent):

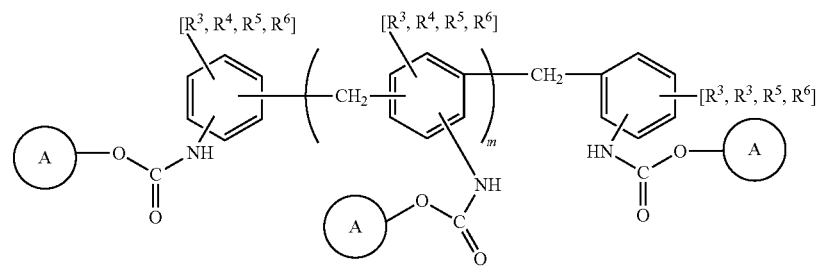

(150)

(wherein

R¹ represents a group derived from an organic primary amine as previously defined, ring A represents a group derived from an aromatic hydroxy compound that composes an aromatic hydroxy composition as previously defined, and which represents a residue in which at least one hydrogen atom of hydroxyl groups directly bonded to an aromatic hydrocarbon ring has been removed from the aromatic hydroxy compound, groups $R^3$ to $R^6$ represent previously defined groups, and m represents an integer of from 0 to 6).

Although a monoisocyanate can be produced by applying the N-substituted carbamic acid-O-mono(aryl ester) represented by the above-mentioned formula (149) to a thermal decomposition reaction as is, when considering that isocyanates are typically used in applications such as paint and polyurethane, the isocyanate is preferably a polyfunctional isocyanate. Thus, a method can be carried out in which, after having preliminarily polymerized the N-substituted carbamic acid-O-mono(aryl ester) by the above-mentioned step (C), the polymer is applied to a thermal decomposition reaction to obtain a polyfunctional isocyanate.

The following provides an explanation of the step (C). In the following explanation, the N-substituted carbamic acid-O-aryl ester obtained in step (P) of route 4) is frequently indicated as N-substituted carbamic acid-O-mono(aryl ester) or N-substituted carbamic acid monoaryl ester.

The known method (see, for example, Federal Republic of Germany Patent No. 1042891) can be used for the step (C).

Prior to carrying out step (C), the aromatic hydroxy composition obtained in step (P) is separated from the reaction liquid containing the resulting N-substituted carbamic acid-O-aryl ester. Although step (C) may be carried out in the presence of an aromatic hydroxy compound, since the aromatic hydroxy compound may be crosslinked by the methylenating crosslinking agent resulting in the formation of by-products such as polyaromatic hydroxy compounds, or the amount of methylenating crosslinking agent used may increase, aromatic hydroxy compounds are preferably separated. The known method can be used for the separation method, and although varying according to the compounds used, examples of separation methods that can be used may include a distillation method, an extraction separation method that uses the difference in solubility between the N-substituted carbamic acid-O-aryl ester and aromatic hydroxy compound, and a filtration method carried out by solidifying either the N-substituted carbamic acid-O-aryl ester or aromatic hydroxy compound. Although these methods cannot be indicated specifically since they depend on the respective physical properties of the compounds used, the method and conditions thereof can be adequately selected within the scope of knowledge of a person with ordinary skill in the art.

When carrying out step (C), the aromatic hydroxy compound is removed until the amount of aromatic hydroxy compound present following the above-mentioned separation procedure is a stoichiometric ratio of 1 time or less, preferably 0.5 times and more preferably 0.1 times based on the N-substituted carbamic acid-O-aryl ester. At this time, the aromatic hydroxy compound may be removed in the presence of solvent used in step (C) to be subsequently explained.

Examples of methylenating crosslinking agents preferably used in the step (C) may include formaldehyde, paraformaldehyde, trioxane, dialkoxymethanes having a lower alkyl group having 1 to 6 carbon atoms (such as dimethoxymethane, diethoxymethane, dipropoxymethane, dipentanoxymethane or dihexyloxymethane), and diacyloxymethanes having a lower carboxyl group such as diacetoxymethane or dipropioxymethane. These may be used alone or two or more types may be used as a mixture. Among these methylenating agents, aqueous solutions of formaldehyde are particularly preferable in consideration of cases of industrial application, ease of handling of the methylenating crosslinking agent and the like.

In carrying out the reaction of the step (C), although there are no particular limitations on the ratio of N-substituted carbamic acid-O-mono(aryl ester) to methylenating crosslinking agent, the N-substituted carbamic acid-O-monoaryl ester is preferably used at a stoichiometric ratio of from 2 to 20 times the methylenating crosslinking agent. Although the formation of polynuclear forms (referring to N-substituted carbamic acid-O-aryl esters in which three or more aromatic rings (aromatic rings derived from organic primary amine) are bonded by a methylene crosslinked structure, or in other words, compounds in which m is an integer of 1 or more in the above-mentioned formula (150)) is inhibited the greater the amount of N-substituted carbamic acid-monoaryl ester used, if an overly excessive amount of N-substituted carbamic acid-O-monoaryl ester is used, there are many cases in which the remaining amount of raw material N-substituted carbamic acid-O-mono(aryl ester) increases. Thus, the amount of N-substituted carbamic acid-O-monoaryl ester used in terms of the stoichiometric ratio with the methylenating crosslinking agent is more preferably within a range of from 3 to 15 times and even more preferably within a range of from 5 to 10 times.

An acid catalyst is preferably used as a catalyst in the condensation reaction. Examples of acid catalysts may include inorganic acids such as hydrochloric acid, sulfuric acid, phosphoric acid or boric acid, and organic acids such as formic acid, acetic acid, oxalic acid or toluenesulfonic acid. In addition, acids referred to as super strong acids such as hydrobromic acid, perchloric acid, chlorosulfonic acid or trifluoromethanesulfonic acid are also effective. In addition, ion exchange resins having acidic groups such as carboxyl groups or sulfonate groups as well as acids referred to as Lewis acids, such as trifluoroboric acid, iron chloride, aluminum chloride, zinc chloride or titanium chloride, are also effective.

In the case of a protonic acid such as the above-mentioned inorganic acids, organic acids or super strong acids, the amount of these acids used is within a range of a stoichiometric ratio of from 0.001 to 10, and preferably within a range of from 0.01 to 5, based on the raw material N-substituted carbamic acid ester. In addition, in the case these acids are used in the form of aqueous solutions, they can be used at a concentration within a range of from 10 to 95% by weight and preferably within a range of from 20 to 80% by weight based on the amount of water in the reaction system. If the concentration is less than 10% by weight, the reaction rate of the condensation reaction becomes extremely slow, while if the concentration exceeds 95% by weight, hydrolysis of the raw material and other undesirable side reactions may occur.

The condensation reaction can be carried out in the presence or absence of solvent. Examples of solvents that are used preferably may include linear, branched or cyclic hydrocarbons such as pentane, hexane, heptane, octane, nonane, decane, hexadecane, cyclopentane or cyclohexane; aromatic hydrocarbons such as benzene, toluene or xylene and their alkyl-, halogen- and nitro-substituted forms; halogenated hydrocarbons such as chloroform, methylene chloride, carbon tetrachloride, dichloroethane, trichloroethane or tetrachloroethane; aliphatic alkyl esters such as methyl acetate or ethyl acetate; and ethers such as diethyl ether, diisopropyl ether, dioxane or tetrahydrofuran. In addition, thioacetals, acetals or acylals are used preferably since they do not form free formaldehyde under the reaction conditions and do not substantially form water by reacting with water formed as a by-product in the reaction. Acetals and acylals are used particularly preferably. In addition, the above-mentioned acids themselves are also preferably used as solvents. These solvents may be used alone or two or more types may be used as a mixture.

These solvents can be used at a weight ratio within a range of from 0.1 to 100 times and preferably within a range of from 0.2 to 50 times based on the raw material N-substituted carbamic acid-O-monoaryl ester.

The reaction temperature is preferably from 10 to 160° C., more preferably from 20 to 140° C. and even more preferably from 50 to 120° C. Although the reaction is advantageously carried out at a high temperature in order to increase the reaction rate and complete the reaction quickly, an excessively high temperature may cause undesirable side reactions such as hydrolysis.

Although varying according to the reaction method, compounds used and reaction conditions, the reaction time can be within a range of from 1 minute to 20 hours. In addition, the reaction may be terminated when the reduction in the amount of raw material N-substituted carbamic acid-O-monoaryl ester has reached a certain level by sampling the reaction liquid and using the known analytical method such as liquid chromatography, or the reaction may be terminated when the average molecular weight of the product in the form of N-substituted carbamic acid-O-aryl ester has reached a certain level by using the known analytical method such as gel permeation chromatography.

The N-substituted carbamic acid-O-aryl ester obtained by the method described above is an N-substituted carbamic acid-O-aryl ester represented by the above-mentioned formula (150). Although those N-substituted carbamic acid-O-aryl esters in which m is 0 are preferable in consideration ease of handling and particularly solution viscosity and the like, there are no problems with containing trinuclear or larger polynuclear forms (namely, compounds represented by formula (150) in which m is 1 or more) provided they do not contradict the purport of the present embodiment.

The N-substituted carbamic acid-O-aryl ester obtained in step (C) is preferably used in step (F).

Compounds remaining in the reaction liquid of step (C) may be removed from the reaction liquid (such as the methylenating agent, reaction solvent or catalyst used in step (C)). The known method can be used for the removal method, and although examples of such methods may include membrane separation, distillative separation and crystallization, distillative separation is preferable. In the case of removing a compound remaining in the reaction liquid of step (C) by distillative separation, by adding the aromatic hydroxy composition used in the subsequent step (F) to the reaction liquid of step (C) to obtain a mixed liquid, followed by separating by distillation the compounds remaining in the reaction liquid of step (C) (such as the methylenating agent, reaction solvent or catalyst used in step (C)) from the mixed liquid, distillative separation can be carried out without causing precipitation of the N-substituted carbamic acid ester, thereby making this method preferable.

Although caution is required with respect to the materials of the reactor and the condenser since an acid is used in step (C), there are no particular limitations on the materials provided they do not cause problems such as corrosion attributable to the compounds used in step (C), and the known materials can be used. Examples of materials that can be used may include glass, stainless steel, carbon steel, Hastelloy, glass-lined base materials and Teflon (registered trademark) coated materials. Known process apparatuses such as a flow meter, a thermometer and other measuring instruments or a reboiler, a pump or a condenser and the like may be added as necessary, the known method such as steam or a heater may be used for heating, and the known method such as air cooling, cooling water or brine can be used for cooling. Steps may also be added as necessary, and for example, steps and apparatuses able to be conceived by a person or engineer with ordinary skill in the art may be added.

<Route 5)>

Route 5) is a method for carrying out step (R), carrying out step (C) and carrying out step (P). Route 5) is one aspect of the method indicated in route 3).

The method of route 5) is a method for obtaining N-substituted carbamic acid-O—$R^2$ ester, in which at least two molecules of the N-substituted carbamic acid-O—$R^2$ ester are crosslinked with methylene (—$CH_2$—) groups, from the N-substituted carbamic acid-O—$R^2$ ester obtained in step (R) by carrying out the following step (C) after step (R), in which the organic primary amine used in step (A) is an aromatic organic primary monoamine represented by the following formula (5), and then carrying out step (P) to obtain N-substituted carbamic acid-O-aryl ester derived from the N-substituted carbamic acid-O—$R^2$ ester and aromatic hydroxy composition, in which at least two molecules of the N-substituted carbamic acid-O—$R^2$ ester are crosslinked with the methylene groups (—$CH_2$—), by reacting the N-substituted carbamic acid-O—$R^2$ ester, in which at least two molecules of the N-substituted carbamic acid-O—$R^2$ ester are crosslinked with the methylene groups (—$CH_2$—), and the aromatic hydroxy composition.

Step (C): a step of obtaining N-substituted carbamic acid-O—($R^2$ or aryl) ester, in which at least two molecules of the N-substituted carbamic acid-O—($R^2$ or aryl) ester are crosslinked with methylene groups (—$CH_2$—), by reacting the N-substituted carbamic acid-O—($R^2$ or aryl) ester with formaldehyde or a methylenating crosslinking agent and crosslinking aromatic groups derived from the aromatic organic primary monoamine contained in the N-substituted carbamic acid-O—($R^2$ or aryl) ester with the methylene groups (—$CH_2$—).

The N-substituted carbamic acid-O-aryl ester of this route 5) refers to N-substituted carbamic acid-O-aryl ester formed in trace amounts when using an aromatic hydroxy composition in step (A) and/or step (R).

In this route, step (A) is carried out using an organic primary amine represented by the following formula (5) for the organic primary amine to obtain a compound having ureido groups represented by formula (1) derived from the organic primary amine, followed by carrying out step (R) to obtain an N-substituted carbamic acid-O—$R^2$ ester derived from the compound having ureido groups, carrying out step (C) to obtain N-substituted carbamic acid-O—$R^2$ ester, in which at least two molecules of the N-substituted carbamic acid-O—$R^2$ ester are crosslinked with methylene groups (—$CH_2$—), and finally carrying out step (P) to obtain an N-substituted carbamic acid-O-aryl ester derived from the N-substituted carbamic acid-O—$R^2$ ester and aromatic hydroxy composition, in which the N-substituted carbamic acid-O—$R^2$ ester are crosslinked with methylene groups (—$CH_2$—).

Namely, the organic primary amine used in this route is an organic primary amine represented by formula (5), the compound having ureido groups obtained in step (A) of this route is a compound having ureido groups represented by formula (41) derived from the organic primary amine, and more specifically a compound having ureido groups represented by formula (148), the N-substituted carbamic acid-O—R² ester obtained in step (R) of this route is an N-substituted carbamic acid-O—R² ester in which r=1 that is represented by formula (49) and derived from the ureido groups and an alcohol, and more specifically an N-substituted carbamic acid-O—R² ester represented by the following formula (146), the N-substituted carbamic acid-O—R² ester obtained in step (C) of this route is an N-substituted carbamic acid-O—R² ester represented by the following formula (151) derived from the N-substituted carbamic acid-O—R² ester, and the N-substituted carbamic acid-O-aryl ester obtained in step (P) of this route is an N-substituted carbamic acid-O-aryl ester represented by formula (150) derived from the N-substituted carbamic acid-O—R² ester and an aromatic hydroxy composition. Indications of specific examples of each of these compounds are respectively contained in previous explanations thereof.

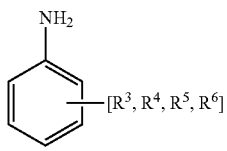

(5)

(wherein
at least one location at the ortho position and/or para position of the NH₂ group of an aromatic organic primary monoamine represented by formula (5) is not substituted, groups $R^3$ to $R^6$ respectively represent a group substituted at an arbitrary location that maintains aromatic properties of the ring, groups $R^3$ to $R^6$ may respectively and independently substitute an aromatic ring or groups $R^3$ to $R^6$ may together bond to form a ring with an aromatic ring, groups $R^3$ to $R^6$ are hydrogen atoms or groups selected from groups composed of groups in which a group selected from the group consisting of an alkyl group, a cycloalkyl group, an aryl group and an aryl group having a hydroxy group is bonded by saturated aliphatic bonds and/or ether bonds, the number of carbon atoms of groups $R^3$ to $R^6$ is an integral number within a range of from 0 to 7, and the total number of carbon atoms that compose the aromatic organic primary monoamine represented by formula (5) is an integer of from 6 to 13).

In this case, the compound having ureido groups obtained in step (A) is at least one type of compound having ureido groups represented by the following formula (148). In addition, the groups $R^3$, $R^4$, $R^5$ and $R^6$ in the following formula (148) are selected from the groups $R^3$, $R^4$, $R^5$ and $R^6$ of an organic primary amine represented by the above-mentioned formula (5), and is a compound in which amino groups (—NH₂ groups) of the organic primary amine represented by formula (5) are in the form of ureido groups (—NH—CO—NH₂):

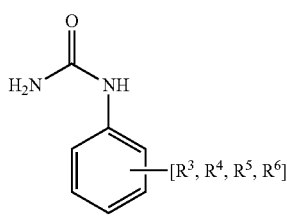

(148)

(wherein
at least one location at the ortho position and/or para position of the ureido group of an N-substituted aromatic organic monourea represented by formula (148) is not substituted, groups $R^3$ to $R^6$ respectively represent a group substituted at an arbitrary location that maintains aromatic properties of the ring, groups $R^3$ to $R^6$ may respectively and independently substitute an aromatic ring or groups $R^3$ to $R^6$ may together bond to form a ring with an aromatic ring, groups $R^3$ to $R^6$ are hydrogen atoms or groups selected from groups composed of groups in which a group selected from the group consisting of an alkyl group, a cycloalkyl group, an aryl group and an aryl group having a hydroxy group is bonded by saturated aliphatic bonds and/or ether bonds, the number of carbon atoms of groups $R^3$ to $R^6$ is an integral number within a range of from 0 to 7, and the total number of carbon atoms that compose the N-substituted aromatic aromatic organic monourea represented by formula (148), excluding ureido groups (—NH—CO—NH₂), is an integer of from 6 to 13).

In this case, the N-substituted carbamic acid-O—R² ester obtained in step (R) by carrying out step (A) is at least one type of N-substituted carbamic acid-O—R² ester represented by the following formula (146). In addition, the groups $R^3$, $R^4$, $R^5$ and $R^6$ in the following formula (146) are selected from the groups $R^3$, $R^4$, $R^5$ and $R^6$ of a compound having ureido groups represented by the above-mentioned formula (148), and is a compound in which ureido groups (—NH—CO—NH₂) of a compound having ureido groups represented by formula (148) are in the form of carbamic acid-O—R² ester groups of the group $R^2$ deriving from alcohole:

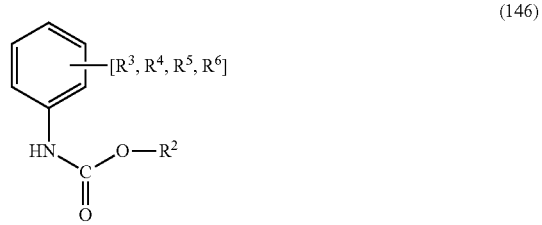

(146)

(wherein
groups $R^2$ to $R^6$ are the groups indicated above).

In this case, the N-substituted carbamic acid-O—R² ester obtained in step (C) by carrying out step (R) is at least one type of N-substituted carbamic acid-O—R² ester represented by the following formula (151). In addition, the groups $R^3$, $R^4$, $R^5$ and $R^6$ in the following formula (151) are selected from the groups $R^3$, $R^4$, $R^5$ and $R^6$ of an organic primary amine represented by the above-mentioned formula (5):

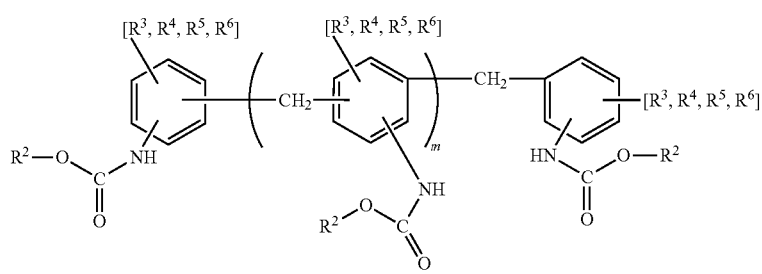

(151)

(wherein groups $R^2$ to $R^6$ are the groups indicated above, and m is an integer from 0 to 6).

In steps (A) and (R) of this route, the organic primary amine used is an organic primary amine represented by formula (5), and steps (A), (R) and (P) of this route are carried out under the conditions of steps (A) and (R) of route 4. In addition, step (C) of this route is carried out under the conditions of step (C) of route 4 with the exception that the reacted raw material is N-substituted carbamic acid-O—$R^2$ ester. In addition, in contrast to the raw material used in route 4) being N-substituted carbamic acid-O-mono($R^2$ or aryl) ester, step (P) of this route is carried out under the conditions of step (P) described in route 4) with the exception of the raw material used being an N-substituted carbamic acid-O—$R^2$ ester in which the N-substituted carbamic acid-O—$R^2$ ester is crosslinked with methylene groups (—CH2—).

Although varying according to the compounds reacted, the reaction conditions for producing N-substituted carbamic acid-O—$R^2$ ester by reacting a compound having ureido groups and an alcohol of step (R) are such that the amount of alcohol used has a stoichiometric ratio within a range of from 1 to 500 times based on the ureido groups of the compound having ureido groups used. Although it is preferable to use an excess of alcohol since complexly substituted carbonyl compounds and high molecular weight compounds having carbonyl bonds in molecules thereof form easily if the stoichiometric ratio is less than 1 time, in consideration of the size of the reactor, the stoichiometric ratio is preferably within a range of from 1 to 200 times, more preferably within a range of from 1.5 to 100 times and even more preferably within a range of from 2 to 50 times.

Although varying according to the compounds used, the reaction temperature is preferably within a range of from 100 to 350° C. If the temperature is lower than 100° C., the reaction slows or the reaction hardly proceeds at all, or complexly substituted carbonyl compounds increase, thereby making this undesirable. On the other hand, at temperatures higher than 350° C., the N-substituted carbamic acid-O—$R^2$ ester either remains in step (A), the urea (and non-N-substituted carbamic acid ester) formed in the system of step (R) decompose, the hydroxy composition is subjected to dehydrogenative denaturation, or decomposition and denaturation reactions of the product in the form of N-substituted carbamic acid-O—$R^2$ ester occur easily, thereby making this undesirable. From such viewpoints, the reaction temperature is more preferably within a range of from 120 to 320° C. and even more preferably within a range of from 140 to 300° C.

As has been previously described, the reaction by which N-substituted carbamic acid-O—$R^2$ ester is formed is an equilibrium reaction, and since the reaction is biased towards the reactants side, the reaction is preferably carried out while removing ammonia formed as a by-product outside the system as much as possible. Ammonia is preferably removed so that the ammonia concentration in the reaction liquid is preferably 1000 ppm or less, more preferably 300 ppm or less, even more preferably 100 ppm or less and most preferably 30 ppm or less (being contained in the reaction liquid refers to being contained in a liquid phase when carrying out the step (R)). Ammonia can be removed using methods such as reactive distillation, use of an inert gas, membrane separation and adsorptive separation. For example, the reactive distillation refers to a method for separating continuously formed ammonia during the reaction by distillation in the form of a gas. This can be carried out while boiling alcohole, a solvent or hydroxy composition in order to increase the distillation efficiency of the ammonia. In addition, a method using an inert gas refers to a method for separating continuously formed ammonia during the reaction from the reaction system in the form of a gas along with the inert gas. Examples of inert gases used may include nitrogen, helium, argon, carbon dioxide, methane, ethane and propane, these may be used alone or as a mixture, and a method in which the inert gas is introduced into the reaction system is preferable. Examples of adsorbents used in methods using adsorptive separation may include adsorbents able to be used under the temperature conditions at which the reaction is carried out, such as silica, alumina, various types of zeolite or diatomaceous earth. These methods for removing ammonia outside the system may be carried out alone or a plurality of types may be carried out in combination.

A catalyst can be used in the reaction for the purpose of increasing the reaction rate, for example. Examples of catalysts that are used preferably may include basic catalysts such as methylates, ethylates or butyrates (including isomers) of lithium, sodium, potassium, calcium or barium, rare earth elements, antimony or bismuth alone or oxides, sulfides and salts thereof, boron alone or boron compounds, metals of the copper family, zinc family, aluminum family, carbon family and titanium family in the periodic table as well as metal oxides and sulfides thereof, and carbides and nitrides of elements of the carbon family excluding carbon, titanium family, vanadium family and chromium family in the periodic table. Although there are no particular limitations on the amount of catalyst used in the case of using a catalyst, a catalyst can be used within the range of a stoichiometric ratio of from 0.0001 to 100 times the ureido groups of the compound having ureido groups.

Although varying according to the composition of the reaction system, reaction temperature, method used to remove ammonia, reaction apparatus and the like, the reaction pressure is generally within a range of preferably from 0.01 Pa to 10 MPa (absolute pressure), and in consideration of ease of the industrial application, the reaction pressure is more preferably within a range of from 0.1 Pa to 5 MPa (absolute pressure), and in consideration of removing gaseous ammonia outside the system, even more preferably from 0.1 Pa to 1.5 MPa (absolute pressure).

Although varying according to the composition of the reaction system, reaction temperature, method used to remove ammonia, reaction apparatus, reaction pressure and the like, the reaction time (residence time in the case of a continuous reaction) is generally from 0.01 to 100 hours. The reaction time can also be determined according to the formation amount of the target compound in the form of N-substituted carbamic acid-O—$R^2$ ester (and depending on the case, the total amount resulting from adding the amount of N-substituted carbamic acid-O-aryl ester). For example, the reaction may be stopped after having sampled the reaction liquid, determined the content of N-substituted carbamic acid ester in the reaction liquid (and depending on the case, the total amount resulting from adding the amount of N-substituted carbamic acid-O-aryl ester) and confirming that the N-substituted carbamic acid-O—$R^2$ ester has been formed at a yield of 10% or more based on the compound having ureido groups, or the reaction may be stopped after having confirmed that the yield is 90% or more. The reaction liquid containing the N-substituted carbamic acid-O—$R^2$ ester obtained in step (R) is converted to N-substituted carbamic acid-O-aryl ester in a process that contains step (P) to be subsequently described, followed by obtaining an isocyanate in step (F). At that time, if the content of N-substituted carbamic acid-O—$R^2$ ester in step (R) is low (the yield thereof is low), there are cases in which this can cause a decrease in the yield of isocyanate. Thus, the yield of the N-substituted carbamic acid-O—$R^2$ ester is preferably 50% or more, more preferably 80% or more and even more preferably 90% or more.

Although the use of a reaction solvent is not necessarily required in the reaction, a suitable solvent is preferably used as a reaction solvent for the purpose of facilitating the reaction procedure, examples of which may include alkanes such as pentane (including isomers), hexane (including isomers), heptane (including isomers), octane (including isomers), nonane (including isomers) or decane (including isomers); aromatic hydrocarbons and alkyl-substituted aromatic hydrocarbons such as benzene, toluene, xylene (including isomers), ethyl benzene, diisopropyl benzene (including isomers), dibutyl benzene (including isomers) or naphthalene; nitrile compounds such as acetonitrile or benzonitrile; aromatic compounds substituted with a halogen or nitro group such as chlorobenzene, dichlorobenzene (including isomers), bromobenzene, dibromobenzene (including isomers), chloronaphthalene, bromonaphthalene, nitrobenzene or nitronaphthalene; polycyclic hydrocarbon compounds such as diphenyl, substituted diphenyl, diphenyl methane, terphenyl, anthracene or dibenzyl toluene (including isomers); aliphatic hydrocarbons such as cyclohexane, cyclopentane, cyclooctane or ethylcyclohexane; ketones such as methyl ethyl ketone or acetophenone; esters such as dibutyl phthalate, dihexyl phthalate, dioctyl phthalate or benzylbutyl phthalate; ethers and thioethers such as tetrahydrofuran, 1,4-dioxane, 1,2-dimethoxyethane, diphenyl ether or diphenyl sulfide; ketone compounds such as acetone or methyl ethyl ketone; ester compounds such as ethyl acetate or ethyl benzoate; and sulfoxides such as dimethylsulfoxide or diphenylsulfoxide. Naturally, a hydroxy composition used in excess in the reaction is also preferably used as a reaction solvent.

The reaction is carried out in a system having a gaseous phase containing a hydroxy composition, a compound having carbonyl groups derived from urea (a compound that inherits a carbonyl group possessed by urea, such as a non-N-substituted carbamic acid ester or biuret, which refers to a compound excluding N-substituted carbamic acid-O-esters) and ammonia produced as a by-product in the reaction, and a liquid phase in which the reaction is carried out. Although the majority of the reaction is carried out in the liquid phase, it may also be carried out in the gaseous phase depending on the reaction conditions. At that time, the volumetric content of the liquid phase in the reaction in which the reaction is carried out is preferably 50% or less. In the case of carrying out the reaction continuously over a long period of time, although polymeric by-products may form due to fluctuations in operating conditions (such as temperature or pressure) and the like, if the volumetric content of the liquid phase in the reactor is high, adhesion and accumulation of such polymeric by-products in the reactor can be avoided. However, since the efficiency of removal of by-product ammonia may become poor and the yield of the N-substituted carbamic acid-O—$R^2$ ester (and depending on the case, the total amount resulting from adding the amount of N-substituted carbamic acid-O-aryl ester) may decrease if the volumetric content of the liquid phase is excessively high, the volumetric content of the liquid phase based on the gaseous phase is preferably 50% or less, more preferably 30% or less and even more preferably 20% or less (the volumetric content of the liquid phase refers to volumetric ratio of the liquid phase based on the volume of the reaction tank in the case of a tank-type reactor, the volume of the stage lower than the feed stage (not including the tank bottom and reboiler) in the case of a column-type reactor, or the volume of the thin film distiller in the case of a thin film distiller).

Although there are no particular limitations on the reaction apparatus used when carrying out the reaction and a known reactor can be used, a tank-type and/or a column-type reactor is used preferably. The reactor used is preferably equipped with a condenser.

As was previously described, the reaction is preferably carried out in a system containing a gaseous phase containing a hydroxy composition, a compound having carbonyl groups derived from urea and ammonia produced as a by-product in the reaction, and a liquid phase in which the reaction is carried out, and under conditions such that the volumetric content of the liquid phase in the reactor in which the reaction is carried out is 50% or less, and a reactor that satisfies these conditions is selected for the reactor in which the reaction is carried out.

More specifically, conventionally known reactors can be suitably combined and used, examples of which may include a stirring tank, a pressurized stirring tank, a depressurized stirring tank, a column-type reactor, a distillation column, a packed column or a thin film distiller.

There are no particular limitations on the type of condenser provided in the reactor and the known condenser can be used. For example, conventionally known condensers such as a multitubular cylindrical condenser, a double tube condenser, a single tube condenser or an air-cooled condenser can be suitably combined and used. The condenser may be provided inside the reactor or outside the reactor, or may be connected with the reactor by a line, and various types can be employed in consideration of the forms of the reactor and condenser, the manner in which condensed liquid is handled and the like.

There are no particular limitations on the materials of the reactor and condenser and known materials can be used. Examples of materials that can be used may include glass, stainless steel, carbon steel, Hastelloy, glass-lined base materials and Teflon (registered trademark) coated materials. Materials such as SUS304, SUS316 or SUS316L are inexpensive and can be used preferably. Known process apparatuses such as a flow meter, a thermometer and other measuring instruments or a reboiler, a pump or a condenser and the like may be added as necessary, the known method such as steam or a heater may be used for heating, and the known method such as air cooling, cooling water or brine can be used for cooling. Steps may also be added as necessary. For example, steps and apparatuses able to be conceived by a person or engineer with ordinary skill in the art may be added, such as a step of dissolving the compound having ureido groups in the aromatic hydroxy composition, a step of dissolving the aromatic hydroxy compound, a step of separating alcohol, a step of separating and/or purifying the aromatic hydroxy compound, a step of purifying N-substituted carbamic acid-O—$R^2$ ester from the formed reaction liquid, or a step of incinerating or discarding by-products and the like.

Step (R) is a step of producing N-substituted carbamic acid-O—$R^2$ ester by reacting a compound having ureido groups and an alcohol in a liquid phase using a reactor (equipped with a condenser). The gaseous component formed in the step (R) containing a compound having carbonyl groups derived from urea and ammonia formed as a by-product in the reaction is introduced into the condenser provided in the reactor and all or a portion of the alcohol and compound having carbonyl groups derived from urea are condensed followed by recovery of ammonia in the form of a gas.

At that time, the compound having carbonyl groups derived from urea that is contained in ammonia recovered as a gas from the condenser is present at a specific amount or less. Namely, the ratio of the number of carbonyl groups (—C(=O)—) contained in the compound having carbonyl groups derived from urea contained in the ammonia to the number of ammonia molecules is 1 or less, preferably 0.5 or less, more preferably 0.1 or less and even more preferably 0.01 or less. The reason for making the amount of the compound having carbonyl groups derived from urea contained in the ammonia to be within a specific range is to avoid adhesion and accumulation of solid components in the line for transferring ammonia from the condenser.

Although all solid components that adhere and accumulate in the line for transferring ammonia cannot be identified, as a result of studies conducted by the inventors of the present invention, the majority were determined to be compounds having carbonyl groups. Although one possible method for avoiding adhesion and accumulation of such solid components contains heating the line for transferring ammonia to decompose compounds having carbonyl groups, according to studies conducted by the inventors of the present invention, there are many cases in which heating alone causes polymerization of decomposition products (such as isocyanic acid) or reaction of the decomposition products with other compounds having carbonyl groups, thereby making it difficult to completely avoid adhesion and accumulation of solid components. In addition, in the case of simply heating the line, it was determined that compounds having carbonyl groups contained in the ammonia and their decomposition products solidify as a result of being rapidly cooled at the outlet of the line for transferring ammonia (such as the portion in contact with the atmosphere), thereby frequently resulting in prominent adhesion and accumulation of solid components. As a result of conducting extensive studies regarding this problem, the inventors of the present invention surprisingly found that the problem of adhesion and accumulation of solid components can be solved by making the amount of the compound having carbonyl groups derived from carbonic acid derivative contained in the ammonia to be equal to or less than the specific amount described above. Although the mechanism by which this effect is demonstrated is unclear, the inventors of the present invention surmised that adhesion and accumulation in the line is caused by the compound having carbonyl groups derived from the carbonic acid derivative itself as well as decomposition and/or polymerization products of the compound having carbonyl groups derived from the carbonic acid derivative, and that by making the amount of carbonyl groups contained in the compound having carbonyl groups derived from the carbonic acid derivative equal to or less than a specific concentration, adhesion of the compound having carbonyl groups derived from the carbonic acid derivative itself as well as the reaction rates of decomposition and/or polymerization of that compound are lowered considerably.

On the other hand, the condensed hydroxy composition and compound having carbonyl groups derived from urea are made to be such that the stoichiometric ratio of the condensed hydroxy composition to the condensed compound having carbonyl groups derived from urea is 1 or more, preferably 2 or more and more preferably 3 or more. The reason for defining such ranges is to enable a mixture of the hydroxy composition and compound having carbonyl groups derived from urea condensed in the condenser to be in the form of a homogeneous liquid mixture. As a result, not only is handling of the mixture easier, but occurrence of problems such as adhesion and accumulation of solid components in the condenser can be avoided.

Moreover, the mixture of the hydroxy composition and the compound having carbonyl groups derived from urea condensed by the condenser in step (R) may be circulated within the reactor and reused in the reaction of step (A). At that time, the amount of ammonia contained in the mixture is preferably 5000 ppm or less, more preferably 3000 ppm or less and even more preferably 2000 ppm or less.

As has been described above, although various compounds are recovered in the form of compounds having carbonyl groups derived from urea, there are no particular limitations on the reuse of these compounds.

Step (C) of this route is a step of obtaining N-substituted carbamic acid-O—$R^2$ ester, in which at least two molecules of the N-substituted carbamic acid-O—$R^2$ ester are crosslinked with methylene groups (—$CH_2$—), by crosslinking at least one type of N-substituted carbamic acid-O—$R^2$ ester (or reaction liquid containing the same) obtained in step (R) with methylene groups (—$CH_2$—). As a result of carrying out step (C), N-substituted carbamic acid-O-aryl ester is obtained in which at least two molecules of at least one type of N-substituted carbamic acid-O-aryl ester represented by the above-mentioned formula (151) are crosslinked with the methylene groups (—$CH_2$—).

Here, when carrying out route 5), preferably an aromatic hydroxy compound represented by formula (2), and more preferably an aromatic hydroxy compound represented by formula (7), is used for the aromatic hydroxy compound that composes the aromatic hydroxy composition used in step (A) and/or step (R) as previously described. More preferably, the aromatic hydroxy compound is that represented by formula (31), naphthol (including isomers), phenoxyphenol (including isomers) or diphenoxyphenol (including isomers), in which the ortho position or para position of the hydroxy group is not substituted, or an aromatic monohydroxy compound in which groups $R^{19}$ and $R^{23}$ of an aromatic hydroxy compound represented by formula (31) are linear and/or cyclic saturated alkyl groups. The aromatic hydroxy compound that composes the aromatic hydroxy composition used in step (P) of route 5) is preferably an active aromatic hydroxy compound, an aromatic hydroxy compound selected from aromatic hydroxy compounds represented by formula (32), and more preferably an aromatic hydroxy compound represented by formula (38).

Although compounds in which m is an integer from 0 to 6 are represented by the formulas (151) and (150), this value can be adjusted according to the amount used and reaction rate of the methylenating crosslinking agent that is reacted (to be subsequently explained and frequently referred to as a methylenating agent):

When carrying out step (C), the aromatic hydroxy compound is removed until the amount of aromatic hydroxy compound present following the above-mentioned separation procedure is a stoichiometric ratio of 1 time or less, preferably 0.5 times and more preferably 0.1 times based on the N-substituted carbamic acid-O—$R^2$ ester. At this time, the aromatic hydroxy compound may be removed in the presence of solvent used in step (C) to be subsequently explained.

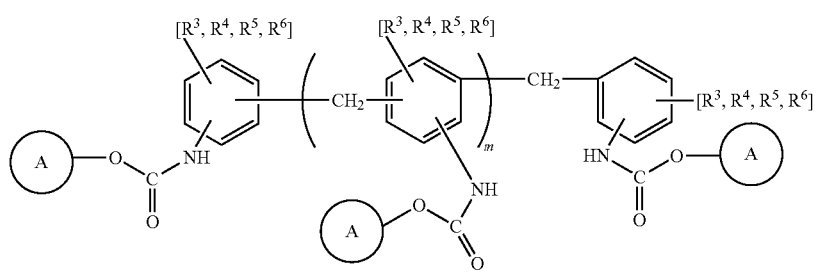

(150)

(wherein $R^1$ represents a group derived from an organic primary amine as previously defined, ring A represents a group derived from an aromatic hydroxy compound that composes an aromatic hydroxy composition as previously defined, and which represents a residue in which a single hydrogen atom of hydroxyl groups directly bonded to an aromatic hydrocarbon ring has been removed from the aromatic hydroxy compound, and $R^3$ to $R^6$ represent previously defined groups, and m represents an integer of from 0 to 6).

The following provides an explanation of the step (C). In the following explanation, the N-substituted carbamic acid-O—$R^2$ ester obtained in step (R) of route 5) is frequently indicated as N-substituted carbamic acid-O-mono($R^2$ ester) or N-substituted carbamic acid mono-$R^2$ ester.

The known method (see, for example, Federal Republic of Germany Patent No. 1042891) can be used for the step (C).

Prior to carrying out step (C), in the case of having used an aromatic hydroxy composition in step (R), the aromatic hydroxy composition obtained in step (R) is separated from the reaction liquid containing the resulting N-substituted carbamic acid-O—$R^2$ ester. Although step (C) may be carried out in the presence of an aromatic hydroxy compound, since the aromatic hydroxy compound may be crosslinked by the methylenating crosslinking agent resulting in the formation of by-products such as polyaromatic hydroxy compounds, or the amount of methylenating crosslinking agent used may increase, aromatic hydroxy compounds are preferably separated. The known method can be used for the separation method, and although varying according to the compounds used, examples of separation methods that can be used may include a distillation method, an extraction separation method that uses the difference in solubility between the N-substituted carbamic acid-O—$R^2$ ester and aromatic hydroxy compound, and a filtration method carried out by solidifying either the N-substituted carbamic acid-O—$R^2$ ester or aromatic hydroxy compound. Although these methods cannot be indicated specifically since they depend on the respective physical properties of the compounds used, the method and conditions thereof can be adequately selected within the scope of knowledge of a person with ordinary skill in the art.

Examples of methylenating crosslinking agents preferably used in the step (C) may include formaldehyde, paraformaldehyde, trioxane, dialkoxymethanes having a lower alkyl group having 1 to 6 carbon atoms (such as dimethoxymethane, diethoxymethane, dipropoxymethane, dipentanoxymethane or dihexyloxymethane), and diacyloxymethanes having a lower carboxyl group such as diacetoxymethane or dipropioxymethane. These may be used alone or two or more types may be used as a mixture. Among these methylenating crosslinking agents, aqueous solutions of formaldehyde are particularly preferable in consideration of cases of the industrial application, ease of handling of the methylenating crosslinking agent and the like.

In carrying out the reaction of the step (C), although there are no particular limitations on the ratio of N-substituted carbamic acid-O-mono($R^2$ ester) to methylenating crosslinking agent, the N-substituted carbamic acid-O-mono($R^2$ ester) is preferably used at a stoichiometric ratio of from 2 to 20 times the methylenating crosslinking agent. Although the formation of polynuclear forms (referring to N-substituted carbamic acid-O—$R^2$ esters in which three or more aromatic rings (aromatic rings derived from organic primary amine) are bonded by a methylene crosslinked structure, or in other words, compounds in which m is an integer of 1 or more in the above-mentioned formula (151)) is inhibited the greater the amount of N-substituted carbamic acid-mono ($R^2$ ester) used, if an overly excessive amount of N-substituted carbamic acid-O-mono($R^2$ ester) is used, there are many cases in which the remaining amount of raw material N-substituted carbamic acid-O-mono($R^2$ ester) increases. Thus, the amount of N-substituted carbamic acid-O-mono($R^2$ ester) used in terms of the stoichiometric ratio with the methylenating crosslinking agent is more preferably within a range of from 3 to 15 times and even more preferably within a range of from 5 to 10 times.

An acid catalyst is preferably used as a catalyst in the condensation reaction. Examples of acid catalysts may include inorganic acids such as hydrochloric acid, sulfuric acid, phosphoric acid or boric acid, and organic acids such as formic acid, acetic acid, oxalic acid or toluenesulfonic acid. In addition, acids referred to as super strong acids such as hydrobromic acid, perchloric acid, chlorosulfonic acid or trifluoromethanesulfonic acid are also effective. In addition, ion exchange resins having acidic groups such as carboxyl groups or sulfonate groups as well as acids referred to as Lewis acids, such as trifluoroboric acid, iron chloride, aluminum chloride, zinc chloride or titanium chloride, are also effective.

In the case of a protonic acid such as the above-mentioned inorganic acids, organic acids or super strong acids, the amount of these acids used is within a range of a stoichiometric ratio of from 0.001 to 10, and preferably within a range of from 0.01 to 5, based on the raw material N-substituted carbamic acid ester. In addition, in the case these acids are used in the form of aqueous solutions, they can be used at a concentration within a range of from 10 to 95% by weight and preferably within a range of 20 to 80% by weight based on the amount of water in the reaction system. If the concentration is less than 10% by weight, the reaction rate of the condensation reaction becomes extremely slow, while if the concentration exceeds 95% by weight, hydrolysis of the raw material and other undesirable side reactions may occur.

The condensation reaction can be carried out in the presence or absence of solvent. Examples of solvents that are used preferably may include linear, branched or cyclic hydrocarbons such as pentane, hexane, heptane, octane, nonane, decane, hexadecane, cyclopentane or cyclohexane; aromatic hydrocarbons such as benzene, toluene or xylene and their alkyl-, halogen- and nitro-substituted forms; halogenated hydrocarbons such as chloroform, methylene chloride, carbon tetrachloride, dichloroethane, trichloroethane or tetrachloroethane; aliphatic alkyl esters such as methyl acetate or ethyl acetate; and ethers such as diethyl ether, diisopropyl ether, dioxane or tetrahydrofuran. In addition, thioacetals, acetals or acylals are used preferably since they do not form free formaldehyde under the reaction conditions and do not substantially form water by reacting with water formed as a by-product in the reaction. Acetals and acylals are used particularly preferably. In addition, the above-mentioned acids themselves are also preferably used as solvents. These solvents may be used alone or two or more types may be used as a mixture.

These solvents can be used at a weight ratio within a range of from 0.1 to 100 times and preferably within a range of from 0.2 to 50 times based on the raw material N-substituted carbamic acid-O-mono($R^2$ ester).

The reaction temperature is preferably from 10 to 160° C., more preferably from 20 to 140° C. and even more preferably from 50 to 120° C. Although the reaction is advantageously carried out at a high temperature in order to increase the reaction rate and complete the reaction quickly, an excessively high temperature may cause undesirable side reactions such as hydrolysis.

Although varying according to the reaction method, compounds used and reaction conditions, the reaction time can be within a range of from 1 minute to 20 hours. In addition, the reaction may be terminated when the reduction in the amount of raw material N-substituted carbamic acid-O-mono($R^2$ ester) has reached a certain level by sampling the reaction liquid and using the known analytical method such as liquid chromatography, or the reaction may be terminated when the average molecular weight of the product in the form of N-substituted carbamic acid-O-aryl ester has reached a certain level by using the known analytical method such as gel permeation chromatography.

The N-substituted carbamic acid-O—$R^2$ ester obtained by the method described above is an N-substituted carbamic acid-O—$R^2$ ester represented by the above-mentioned formula (151). Although those N-substituted carbamic acid-O—$R^2$ esters in which m is 0 are preferable in consideration ease of handling and particularly solution viscosity and the like, there are no problems with containing trinuclear or larger polynuclear forms (namely, compounds represented by formula (151) in which m is 1 or more) provided they do not contradict the purport of the present embodiment.

The N-substituted carbamic acid-O—$R^2$ ester obtained in step (C) is preferably used in step (P).

Compounds remaining in the reaction liquid of step (C) may be removed from the reaction liquid (such as the methylenating agent, reaction solvent or catalyst used in step (C)). The known method can be used for the removal method, and although examples of such methods may include membrane separation, distillative separation and crystallization, distillative separation is preferable. In the case of removing a compound remaining in the reaction liquid of step (C) by distillative separation, by adding the aromatic hydroxy composition used in the subsequent step (P) to the reaction liquid of step (C) to obtain a mixed liquid, followed by distilling and separating the compounds remaining in the reaction liquid of step (C) (such as the methylenating agent, reaction solvent or catalyst used in step (C)) from the mixed liquid, distillative separation can be carried out without causing precipitation of the N-substituted carbamic acid ester, thereby making this method preferable.

Although caution is required with respect to the materials of the reactor and the condenser since an acid is used in step (C), there are no particular limitations on the materials provided they do not cause problems such as corrosion attributable to the compounds used in step (C), and known materials can be used. Examples of materials that can be used may include glass, stainless steel, carbon steel, Hastelloy, glass-lined base materials and Teflon (registered trademark) coated materials. Known process apparatuses such as a flow meter, a thermometer and other measuring instruments or a reboiler, a pump or a condenser and the like may be added as necessary, the known method such as steam or a heater may be used for heating, and the known method such as air cooling, cooling water or brine can be used for cooling. Steps can also be added as necessary, and for example, steps and apparatuses able to be conceived by a person or engineer with ordinary skill in the art may be added.

<Step (P)> Transesterification Step

Since this step is a step of converting the ester group of the N-substituted carbamic acid-O—$R^2$ ester, it is also generally referred to as a "transesterification step" in the present embodiment.

Step (P): a step of obtaining N-substituted carbamic acid-O-aryl ester by reacting N-substituted carbamic acid-O—$R^2$ ester and an aromatic hydroxy composition (composition containing at least one type of aromatic hydroxy compound represented by the following formula (2)) in a liquid phase and extracting alcohol formed as a by-product to a gaseous phase.

Figure 6:
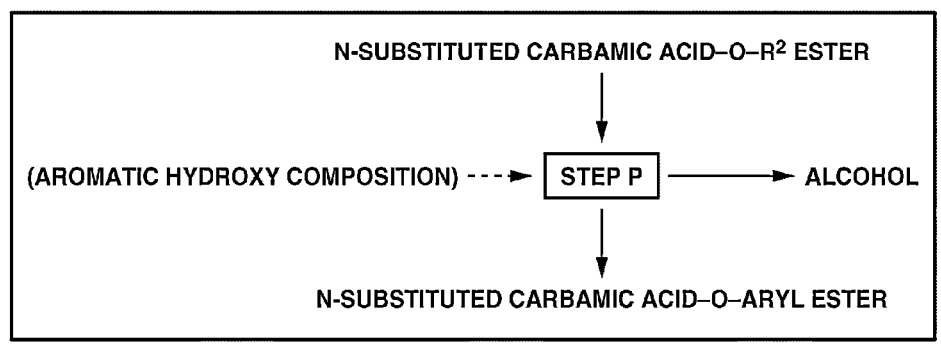
FIG. 6 shows a conceptual drawing depicting a step (P) in the present embodiment.

FIG. 6 shows a conceptual drawing depicting the step (P).

Furthermore, an alcohol derived from N-substituted carbamic acid-O—$R^2$ ester is formed in the step (P). The following provides an explanation of step (P).

The aromatic hydroxy compound in the reacted aromatic hydroxy composition may be any of an aromatic hydroxy compound represented by the above-mentioned formula (2), formula (7), formula (31), formula (32), formula (38), formula (39) or formula (40). The case in which an aromatic hydroxy compound represented by formula (7) or formula (31) is contained is preferable, the case in which an aromatic hydroxy composition is used that contains an active aromatic hydroxy compound represented by formula (32) is more preferable, and the case in which an aromatic hydroxy composition is used that contains an active aromatic hydroxy compound represented by formula (38) is even more preferable.

Various methods can be carried out for the step (P) according to the compounds used and the like with reference to the known methods (see, for example, WO 2008/059953).

Although varying according to the compounds reacted, the reaction conditions of step (P) are such that the amount of aromatic hydroxy compound in the aromatic hydroxy composition used has a stoichiometric ratio within a range of from 2 to 1000 times based on the ester groups that compose the raw material N-substituted carbamic acid-O—$R^2$ ester. Although it is preferable to use an excess of the aromatic hydroxy compound based on ester groups that compose the raw material N-substituted carbamic acid-O—$R^2$ ester in order to complete the reaction quickly, in consideration of the size of the reactor, the stoichiometric ratio is preferably within a range of from 2 to 100 times and more preferably within a range of from 5 to 50 times.

The reaction temperature is generally within a range of from 100 to 300° C., and a high temperature is preferable for increasing the reaction rate, but since side reactions may occur easily at high temperatures, the reaction temperature is preferably within a range of from 150 to 250° C. The known cooling apparatus or heating apparatus may be installed in the reactor for maintaining a constant reaction temperature. In addition, although varying according to the types of compounds used and the reaction temperature, the reaction may be carried out at reduced pressure, normal pressure or increased pressure and generally at a reaction pressure within a range of from 20 to $1 \times 10^6$ Pa. There are no particular limitations on the reaction time (residence time in the case of a continuous method), and is generally from 0.001 to 100 hours, preferably from 0.01 to 50 hours and more preferably from 0.1 to 30 hours. In addition, the reaction can be terminated after confirming that a desired amount of the target N-substituted carbamic acid-O-aryl ester has been formed by sampling the reaction liquid and determining the amount formed by liquid chromatography, for example.

Although a catalyst is not necessarily required in step (P), a catalyst may be used without problem to lower the reaction temperature or complete the reaction more quickly. The catalyst is used at 0.01 to 30% by weight and preferably at 0.5 to 20% by weight based on the weight of the N-substituted carbamic acid-O—$R^2$ ester. Examples of catalysts may include Lewis acids as well as transition metal compounds that form a Lewis acid, organic tin compounds, copper group metals, zinc or iron group metal compounds, and more specifically, Lewis acids and transition metal compounds that form a Lewis acid represented by $AlX_3$, $TiX_3$, $TiX_4$, $VOX_3$, $VX_5$, $ZnX_2$, $FeX_3$ or $SnX_4$ (wherein, X represents a halogen, an acetoxy group, an alkoxy group or an aryloxy group); organic tin compounds represented by $(CH_3)_3SnOCHCH_3$, $(C_2H_5)SnOCOC_6H_6$, $Bu_3SnOCOCH_3$, $Ph_3SnOCOCH_3$, $Bu_2Sn(OCOCH_3)_2$, $Bu_2Sn(OCOC_{11}H_{23})_2$, $Ph_3SnOCH_3$, $(C_2H_5)_3SnOPh$, $Bu_2Sn(OCH_3)_2$, $Bu_2Sn(OC_2H_5)_2$, $Bu_2Sn(OPh)_2$, $Ph_2Sn(CH_3)_2$, $(C_2H_5)_3SnOH$, $PhSnOH$, $Bu_2SnO$, $(C_8H_{17})_2SnO$, $Bu_2SnCl_2$ or $BuSnO(OH)$; copper family metal compounds represented by $CuCl$, $CuCl_2$, $CuBr$, $CuBr_2$, $CuI$, $CuI_2$, $Cu(OAc)_2$, $Cu(acac)_2$, copper olefinate, $Bu_2Cu$, $(CH_3O)_2Cu$, $AgNO_3$, $AgBr$, silver picrate or $AgC_6H_6ClO_4$; zinc compounds represented by $Zn(acac)_2$; and, iron family metal compounds represented by $Fe(C_{10}H_8)(CO)_5$, $Fe(CO)_5$, $Fe(C_4H_6)(CO)_3$, $Co(mesitylene)_2(PEt_2Ph_2)$, $CoC_5F_5(CO)_7$ or ferrocene. (In the above listing of examples, Bu refers to a butyl group, Ph refers to a phenyl group, and acac refers to an acetyl acetone chelate ligand.) Amines such as 1,4-diazabicyclo[2,2,2]octane, triethylenediamine or triethylamine are suitable for use as catalysts, while organic metal catalysts such as dibutyl tin dilaurate, lead octoate or stannous octoate are particularly preferable. These compounds may be used alone or two or more types may be used as a mixture.

Although the use of a reaction solvent is not necessarily required in the present embodiment, a suitable inert solvent can be preferably used as a reaction solvent for the purpose of facilitating the reaction procedure and the like, examples of which may include alkanes such as hexane (including isomers), heptane (including isomers), octane (including isomers), nonane (including isomers) or decane (including isomers); aromatic hydrocarbons and alkyl-substituted aromatic hydrocarbons such as benzene, toluene, xylene (including isomers), ethyl benzene, diisopropyl benzene (including isomers), dibutyl benzene (including isomers) or naphthalene; aromatic compounds substituted with a halogen or nitro group such as chlorobenzene, dichlorobenzene (including isomers), bromobenzene, dibromobenzene (including isomers), chloronaphthalene, bromonaphthalene, nitrobenzene or nitronaphthalene; polycyclic hydrocarbon compounds such as diphenyl, substituted diphenyl, diphenyl methane, terphenyl, anthracene or dibenzyl toluene (including isomers); aliphatic hydrocarbons such as cyclohexane, cyclopentane, cyclooctane or ethylcyclohexane; ketones such as methyl ethyl ketone or acetophenone; esters such as dibutyl phthalate, dihexyl phthalate, dioctyl phthalate or benzylbutyl phthalate; ethers and thioethers such as diphenyl ether or diphenyl sulfide; sulfoxides such as dimethylsulfoxide or diphenylsulfoxide; and silicone oil. These solvents can be used alone or two or more types can be used as a mixture.

The transesterification reaction in the present embodiment is an equilibrium reaction. Thus, it is preferable to allow the reaction to proceed while removing the product in the form of alcohol (alcohol derived from the raw material N-substituted carbamic acid-O—$R^2$ ester) from the reaction system in order to carry out transesterification efficiently. Thus, if the aromatic hydroxy compound is selected such that the standard boiling point of the aromatic hydroxy compound used in transesterification is higher than the standard boiling point of the alcohol derived from the raw material N-substituted carbamic acid-O—$R^2$ ester, the compound having the lowest standard boiling point in the reaction system becomes the alcohol derived from the raw material N-substituted carbamic acid-O—$R^2$ ester, thereby facilitating removal of products from the reaction system. Based on the finding that generally industrially adequate distillative separation is possible if the standard boiling points of two components to be separated are 10° C. or more apart, an aromatic hydroxy compound is preferably used such that the standard boiling point of the compound having the lowest standard boiling point in the aromatic hydroxy composition (based on a comparison of standard boiling points) is 10° C. or more higher than the standard boiling point of the alcohol.

In addition, transesterification is preferably carried out by a continuous method to allow transesterification to proceed efficiently. Namely, the raw material N-substituted carbamic acid-O—$R^2$ ester and the aromatic hydroxy composition are continuously supplied to a reactor, transesterification is carried out, alcohol derived from the raw material N-substituted carbamic acid-O—$R^2$ ester that is formed is extracted from the reactor in the form of a gaseous component, and a reaction liquid containing the N-substituted carbamic acid-O-aryl ester formed and the aromatic hydroxy composition is continuously extracted from the bottom of the reactor.

Although the material of the reactor and lines used to carry out transesterification may be known materials provided they do not have a detrimental effect on the starting substances and reactants, materials such as SUS304, SUS316 or SUS316L are inexpensive and can be used preferably. Known process apparatuses such as a flow meter, a thermometer and other measuring instruments or a reboiler, a pump or a condenser and the like may be added as necessary, the known method such as steam or a heater may be used for heating, and the known method such as air cooling, cooling water or brine can be used for cooling. Steps may also be added as necessary. For example, steps and apparatuses able to be conceived by a person or engineer with ordinary skill in the art may be added, such as a step of dissolving the aromatic hydroxy compound, a step of separating the alcohol, a step of separating and/or purifying the aromatic hydroxy compound, a step of purifying the N-substituted carbamic acid-O-aryl ester from the formed reaction liquid or a step of incinerating or discarding by-products and the like. There are no particular limitations on the type of reactor, and a known tank-type or a column-type reactor can be used. Various known methods are used for such a reactor, examples of which may include types using reactors containing a stirring tank, a multistage stirring tank, a distillation column, a multistage distillation column, a multitubular reactor, a continuous multistage distillation column, a packed column, a thin film evaporator, a reactor provided with a support inside, a forced circulation reactor, a falling film evaporator, a falling drop evaporator, a trickle flow reactor or a bubble column, and types using combinations thereof. Methods using a thin film evaporator or a column-type reactor are preferable from the viewpoint of efficiently shifting the equilibrium to the products side, while a structure having a large gas-liquid contact area is preferable for being able to rapidly transfer the alcohol derived from the raw material N-substituted carbamic acid-O—$R^2$ ester formed to the gaseous phase.

The multistage distillation column refers to a distillation column having multiple stages in which the number of theoretical plates of distillation is 2 or more, and any multistage distillation column may be used provided it allows continuous distillation. Any multistage distillation column can be used for the multistage distillation column provided it is ordinarily used as a multistage distillation column, examples of which may include tray column types using a tray such as a bubble tray, a porous plate tray, a valve tray or a countercurrent tray, and packed column types packed with various types of packing materials such as a raschig ring, a lessing ring, a pole ring, a Berl saddle, a Interlock saddle, a Dixon packing, a McMahon packing, a Helipack, Sulzer packing or Mellapak. Any packed column can be used provided the column is packed with the known packing material as described above. Moreover, a combination tray-packed column type is also used preferably that combines a tray portion with a portion packed with a packing material.

A line for supplying inert gas and/or liquid inert solvent from the lower portion of the reactor may be separately attached, and in the case the mixture of the target N-substituted carbamic acid-O-aryl ester and aromatic hydroxy compound contains raw material N-substituted carbamic acid-O—$R^2$ ester, a line may be attached for re-circulating all or a portion of the mixture to the reactor. Furthermore, in the case of using the above-mentioned inert solvent, the inert solvent may be in the form of a gas and/or a liquid.

The gaseous component extracted from the reactor containing alcohol derived from the raw material N-substituted carbamic acid-O—$R^2$ ester is preferably purified using the known method such as that which uses a distillation column, and can be reused as an alcohol of step (A) and/or step (R).

The following provides an explanation of step (F) for obtaining isocyanate by thermally decomposing an N-substituted carbamic acid-O-aryl ester obtained in the above-mentioned routes 1) to 5).

<Step (F): Step of Obtaining Isocyanate by Thermal Decomposition Reaction of N-Substituted Carbamic Acid-O-Aryl Ester>

Step (F) is a method for obtaining isocyanate represented by the following formula (6), derived from an N-substituted carbamic acid-O-aryl ester, and an aromatic hydroxy composition by thermally decomposing the N-substituted carbamic acid-O-aryl ester in the following step (F).

Step (F): a step of obtaining an isocyanate and aromatic hydroxy composition from N-substituted carbamic acid-O-aryl ester:

(wherein $R^1$ represents an organic group which has an integral number of carbon atoms within a range of from 1 to 85, and which is substituted with number s of NCO groups, and s represents an integer of from 1 to 10).

The N-substituted carbamic acid-O-aryl ester produced according to the method described above is preferably used to produce isocyanate. The following provides an explanation of a step of producing isocyanate by applying the N-substituted carbamic acid-O-aryl ester to a thermal decomposition reaction (to be referred to as step (F)).

Although a solvent may or may not be used in the step (F), it is preferably carried out in the presence of an aromatic hydroxy composition. Since an aromatic hydroxy composition is used in routes 1), 3) and 5) when carrying out step (B) or step (P), step (F) may be carried out using the reaction liquid obtained in those steps, or step (F) may be carried out by adjusting the amount of aromatic hydroxy composition if necessary. Alternatively, since an aromatic hydroxy composition is used in step (C) of routes 2) and 4), step (F) may be carried out by reusing the separated aromatic hydroxy composition, the amount of aromatic hydroxy composition used may be adjusted, or an aromatic hydroxy composition may be newly prepared and used. The solvent used in step (C) may be separated from the N-substituted carbamic acid-O-aryl ester or may be used with the aromatic hydroxy composition.

Although adjustment of the amount of aromatic hydroxy composition or the preparation of a new aromatic hydroxy composition has been described above, the amount thereof is such that the ratio of the number of aromatic hydroxy compounds in the aromatic hydroxy composition to the total number of ester groups of the —O-aryl ester contained in the N-substituted carbamic acid-O-aryl ester is from 0.2 to 50, preferably from 0.3 to 30 and more preferably from 1 to 20 in consideration of transfer efficiency of the N-substituted carbamic acid-O-aryl ester and size of the storage tank during storage. Examples of other solvents that may be added may include suitable inert solvents for the purpose of facilitating the reaction procedure and the like, including alkanes such as hexane (including isomers), heptane (including isomers), octane (including isomers), nonane (including isomers) or decane (including isomers); aromatic hydrocarbons and alkyl-substituted aromatic hydrocarbons such as benzene, toluene, xylene (including isomers), ethyl benzene, diisopropyl benzene (including isomers), dibutyl benzene (including isomers) or naphthalene; aromatic compounds substituted with a halogen or nitro group such as chlorobenzene, dichlorobenzene (including isomers), bromobenzene, dibromobenzene (including isomers), chloronaphthalene, bromonaphthalene, nitrobenzene or nitronaphthalene; polycyclic hydrocarbon compounds such as diphenyl, substituted diphenyl, diphenyl methane, terphenyl, anthracene or dibenzyl toluene (including isomers); aliphatic hydrocarbons such as cyclohexane, cyclopentane, cyclooctane or ethylcyclohexane; ketones such as methyl ethyl ketone or acetophenone; and dibutyl phthalate, dihexyl phthalate or dioctyl phthalate.

The reaction temperature of the thermal decomposition reaction carried out in step (F) is generally within a range of from 100 to 300° C., and although a high temperature is preferable for increasing the reaction rate, since side reactions as previously described may be induced by the N-substituted carbamic acid-O-aryl ester and/or product in the form of isocyanate at high temperatures, the reaction temperature is preferably within a range of from 150 to 250° C. The known cooling apparatus or heating apparatus may be installed in the reactor to maintain a constant reaction temperature. In addition, although varying according to the types of compounds used and the reaction temperature, the reaction may be carried out at reduced pressure, normal pressure or increased pressure and normally at a reaction pressure within a range of from 20 to $1 \times 10^6$ Pa. There are no particular limitations on the reaction time (residence time in the case of a continuous method), and is generally from 0.001 to 100 hours, preferably from 0.005 to 50 hours and more preferably from 0.01 to 10 hours.

Although a catalyst is preferably not used in the present embodiment, in the case of using a catalyst in any of the steps when producing the N-substituted carbamic acid-O-aryl ester, the catalyst residue may be supplied to the thermal decomposition step, although the presence of such catalyst residue does not present a problem.

In the case of having stored an N-substituted carbamic acid-O-aryl ester at a high temperature for a long period of time, there are cases in which side reactions occur such as a reaction by which urea bond-containing compounds are formed by an ester decarboxylation reaction of two molecules of N-substituted carbamic acid-O-aryl ester, or a reaction by which allophanate groups are formed by a reaction with isocyanate formed by thermal decomposition of N-substituted carbamic acid-O-aryl ester. Thus, the amount of time during which the N-substituted carbamic acid-O-aryl ester and the isocyanate are held at a high temperature is preferably as short as possible. Thus, the thermal decomposition reaction is preferably carried out in the form of the continuous method. The continuous method refers to a method in which a mixture containing the N-substituted carbamic acid-O-aryl ester is continuously supplied to a reactor where it is subjected to a thermal decomposition reaction, and the isocyanate and aromatic hydroxy compound formed are continuously extracted from the thermal decomposition reactor. In this continuous method, low boiling point components formed by thermal decomposition of urethane are preferably recovered from the upper portion of the thermal decomposition reactor in the form of gaseous phase components, while the remainder is recovered from the bottom of the thermal decomposition reactor in the form of liquid phase components. Although all compounds present in the thermal decomposition reactor can be recovered as gaseous phase components, the presence of liquid phase components in the thermal decomposition reactor has the effect of dissolving polymeric substances formed by side reactions caused by the N-substituted carbamic acid-O-aryl ester and/or isocyanate, thereby preventing adhesion and solidification of the polymeric substances in the thermal decomposition reactor. Although isocyanate and aromatic hydroxy compound are formed by thermal decomposition of N-substituted carbamic acid-O-aryl ester, at least one of these compounds is recovered in the form of a gaseous phase component. Which compound is recovered as a gaseous phase component is dependent upon such factors as the conditions of the thermal decomposition reaction.

Here, although the term "low boiling point component formed by thermal decomposition of N-substituted carbamic acid-O-aryl ester" used in the present embodiment is equivalent to the aromatic hydroxy compound and/or isocyanate formed by thermal decomposition of the N-substituted carbamic acid-O-aryl ester, it particularly refers to a compound that is able to be present as a gas under the conditions in which the thermal decomposition reaction is carried out.

For example, a method can be employed in which the isocyanate and aromatic hydroxy compound formed by the thermal decomposition reaction can be recovered in the form of gaseous phase components, while a liquid phase component is recovered that contains N-substituted carbamic acid-O-aryl ester. In this method, the isocyanate and aromatic hydroxy compound may be recovered separately in the thermal decomposition reactor. The recovered gaseous phase component that contains isocyanate is preferably supplied to a distillation apparatus for separating and purifying the isocyanate in the gaseous phase. Although the recovered gaseous phase component that contains isocyanate can be supplied to a distillation apparatus after converting to a liquid phase with a condenser and the like, there are many cases in which the apparatus becomes complex and the amount of energy used becomes large, thereby making this undesirable. In the case the liquid phase component contains N-substituted carbamic acid-O-aryl ester, all or a portion of the liquid phase component is preferably supplied to the upper portion of the thermal decomposition reactor where the N-substituted carbamic acid-O-aryl ester is again subjected to a thermal decomposition reaction. The upper portion of the thermal decomposition reactor as referred to here indicates the portion two or more stages above the bottom of the column in terms of the number of theoretical plates in the case of the thermal decomposition reactor being a distillation column, while in the case the thermal decomposition reactor is a thin film distiller, indicates the portion above the heated transfer surface portion. When supplying all or a portion of the liquid phase component to the upper portion of the thermal decomposition reactor, the liquid phase component is transferred while holding at a temperature of preferably from 50 to 180° C., more preferably from 70 to 170° C. and even more preferably from 100 to 150° C.

In addition, a method can also be employed in which, for example, the isocyanate and aromatic hydroxy compound formed by the thermal decomposition reaction are recovered in the form of gaseous phase components, while a liquid phase component containing N-substituted carbamic acid-O-aryl ester is recovered from the bottom of the thermal decomposition reactor. In this method as well, the recovered gaseous component that contains isocyanate is preferably supplied to a distillation apparatus for separating and purifying the isocyanate in the gaseous phase. On the other hand, all or a portion of the liquid phase component that contains N-substituted carbamic acid-O-aryl ester is supplied to the upper portion of the thermal decomposition reactor where the N-substituted carbamic acid-O-aryl ester is again subjected to a thermal decomposition reaction. When supplying all or a portion of the liquid phase component to the upper portion of the thermal decomposition reactor, the liquid phase component is transferred while holding at a temperature of preferably from 50 to 180° C., more preferably from 70 to 170° C. and even more preferably from 100 to 150° C.

Moreover, a method can also be employed in which, for example, the aromatic hydroxy compound among the isocyanate and aromatic hydroxy compound formed by the thermal decomposition reaction is recovered in the form of a gaseous phase component, while a mixture containing the isocyanate is recovered in the form of a liquid phase component from the bottom of the thermal decomposition reactor. In this case, the liquid phase component is supplied to a distillation apparatus to recover the isocyanate. In the case N-substituted carbamic acid-O-aryl ester is contained in the liquid phase component, all or a portion of the mixture containing N-substituted carbamic acid-O-aryl ester is preferably supplied to the upper portion of the thermal decomposition reactor and the N-substituted carbamic acid-O-aryl ester is again subjected to a thermal decomposition reaction. When supplying all or a portion of the liquid phase component to the thermal decomposition reactor, the liquid phase component is transferred while holding at a temperature of preferably from 50 to 180° C., more preferably from 70 to 170° C. and even more preferably from 100 to 150° C.

Although previously described, in the thermal decomposition reaction, the liquid phase component is preferably recovered from the bottom of the thermal decomposition reactor. This is because the presence of a liquid phase component in the thermal decomposition reactor has the effect of dissolving polymeric substances formed by side reactions caused by the N-substituted carbamic acid-O-aryl ester and/or isocyanate as previously described, thereby enabling the polymeric substances to be discharged from the thermal decomposition reactor and preventing adhesion and solidification of the polymeric substances in the thermal decomposition reactor.

In the case the liquid phase component contains N-substituted carbamic acid-O-aryl ester, although all or a portion of the liquid phase component is supplied to the upper portion of the thermal decomposition reactor where the N-substituted carbamic acid-O-aryl ester is again subjected to a thermal decomposition reaction, polymeric by-products may accumulate in the liquid phase component if this step is repeated. In this case, all or a portion of the liquid phase component can be removed from the reaction system or held to a fixed concentration to reduce accumulation of polymeric by-products.

Although there are no particular limitations on the type of the thermal decomposition reactor, the known distillation apparatus is used preferably in order to efficiently recover gaseous phase components. Various known methods are used for such a reaction vessel, examples of which may include types using reaction vessels containing a distillation column, a multistage distillation column, a multitubular reactor, a continuous multistage distillation column, a packed column, a thin film evaporator, a reactor provided with a support inside, a forced circulation reactor, a falling film evaporator or a falling drop evaporator, and types using combinations thereof. From the viewpoint of rapidly removing low boiling point components from the reaction system, a method using a tubular reactor is preferable, while a method using a reactor such as a tubular thin film evaporator or a tubular falling film evaporator is more preferable, and a structure having a large gas-liquid contact area is preferable for being able to rapidly transfer the low boiling point components formed to the gaseous phase.

Although the known material may be used for the material of the thermal decomposition reactor and lines provided it does not have a detrimental effect on the urethane or products in the form of the aromatic hydroxy compound and isocyanate, SUS304, SUS316 or SUS316L are inexpensive and can be used preferably.

The aromatic hydroxy compounds contained in the gaseous phase components and/or liquid phase component obtained in the thermal decomposition reaction as described above can each be separated, recovered and reused. More specifically, aromatic hydroxy compounds can be reused as aromatic hydroxy compounds used in step (A) and/or step (A) and/or step (B) and/or step (R) and/or step (P). In other words, it is preferable that the aromatic hydroxy composition obtained in the step (F) is separated from isocyanate, and then used by recycling to the step (A) and/or the step (B) described in route 1), or to the step (A) and/or the step (R) and/or the step (P) described in route 3).

In addition, in a preferable aspect of the present embodiment, unreacted N-substituted carbamic acid-O-aryl ester that did not undergo thermal decomposition in step (F) is preferably used by recycling to the above-mentioned step (A) and/or step (B) and/or step (R) and/or step (P) and/or step (F).

<Cleaning the Reactor>

There are cases in which polymeric side-reaction products may be formed, albeit in minute amounts, in the production N-substituted carbamic acid-O-aryl ester and the production of isocyanate using the N-substituted carbamic acid-O-aryl ester of the present embodiment. Since these polymeric side-reaction products have a high solubility with respect to aromatic hydroxy composition used in the present embodiment, they are removed from the reactor in the form of a solution of the aromatic hydroxy composition. However, in cases of fluctuations in reaction apparatus operating conditions or cases of long-term operation, the polymeric side-reaction products may adhere to the reactor.

In such cases, the inside (and particularly the inner walls) of the reactor can be cleaned with an acid that is a good solvent of the polymeric side-reaction products to keep the inside of the reactor clean.

There are no particular limitations on the cleaning acid provided it dissolves the polymeric side-reaction products, and although both organic acids and inorganic acids may be used, organic acids are used preferably. Although examples of organic acids that can be used may include carboxylic acid, sulfonic acid, sulfinic acid, phenols, enols, thiophenols, imides, oximes and aromatic sulfonamides, carboxylic acid and phenols are used preferably. Examples of such compounds may include saturated or unsaturated aliphatic monocarboxylic acid compounds such as formic acid, acetic acid, propionic acid, n-butyric acid, isobutyric acid, valeric acid, isovaleric acid, 2-methylbutanoic acid, pivalic acid, hexanoic acid, isocaproic acid, 2-ethylbutanoic acid, 2,2-dimethylbutanoic acid, heptanoic acid (including isomers), octanoic acid (including isomers), nonanoic acid (including isomers), decanoic acid (including isomers), undecanoic acid (including isomers), dodecanoic acid (including isomers), tetradecanoic acid (including isomers), hexadecanoic acid (including isomers), acrylic acid, crotic acid, isocrotic acid, vinylacetic acid, methacrylic acid, angelic acid, tiglic acid, arylacetate or undecenoic acid (including isomers); saturated or unsaturated aliphatic dicarboxylic acids such as oxalic acid, malonic acid, succinic acid, glutaric acid, adipic acid, heptanedioic acid (including isomers), octanedioic acid (including isomers), nonanedioic acid (including isomers), decanedioic acid (including isomers), maleic acid, fumaric acid, methylmaleic acid, methylfumaric acid, pentenedioic acid (including isomers), itaconic acid or allylmalonic acid; saturated or unsaturated aliphatic tricarboxylic acid compounds such as 1,2,3-propanetricarboxylic acid, 1,2,3-propenetricarboxylic acid or 2,3-dimethylbutane-1,2,3-tricarboxylic acid; aromatic carboxylic acid compounds such as benzoic acid, methylbenzoic acid (including isomers), ethylbenzoic acid (including isomers), propylbenzoic acid (including isomers), dimethylbenzoic acid (including isomers) or trimethylbenzoic acid (including isomers); aromatic dicarboxylic acid compounds such as phthalic acid, isophthalic acid, terephthalic acid or methylisophthalic acid; aromatic tricarboxylic acid compounds such as hemimellitic acid, trimellitic acid or trimesic acid; phenol; mono-substituted phenols such as methyl phenol (including isomers), ethyl phenol (including isomers), propyl phenol (including isomers), butyl phenol (including isomers), pentyl phenol (including isomers), hexyl phenol (including isomers), heptyl phenol (including isomers), octyl phenol (including isomers), nonyl phenol (including isomers), decyl phenol (including isomers), dodecyl phenol (including isomers), phenyl phenol (including isomers), phenoxyphenol (including isomers) or cumyl phenol (including isomers); and dimethyl phenol (including isomers), diethyl phenol (including isomers), dipropyl phenol (including isomers), dibutyl phenol (including isomers), dipentyl phenol (including isomers), dihexyl phenol (including isomers), diheptyl phenol (including isomers), dioctyl phenol (including isomers), dinonyl phenol (including isomers), didecyl phenol (including isomers), didodecyl phenol (including isomers), diphenyl phenol (including isomers), diphenoxyphenol (including isomers) or dicumyl phenol (including isomers). In consideration of effects in the case of the cleaning solvent remaining after cleaning the thermal decomposition reactor, more preferable examples of these organic acids may include aromatic hydroxy compounds, while even more preferable examples may include compounds of the same types as aromatic hydroxy compounds formed in the production method of N-substituted carbamic acid-O-aryl ester and/or thermal decomposition reaction of N-substituted carbamic acid-O-aryl ester of the present embodiment.

Furthermore, in the case of using an aromatic hydroxy compound for the cleaning acid, the standard boiling point of the aromatic hydroxy compound preferably has a difference in boiling point of 10° C. or more from the standard boiling point of isocyanate formed by the thermal decomposition reaction of N-substituted carbamic acid-O-aryl ester described above from the viewpoint of cleaning effects.

Various methods can be used to clean the reactor using the above-mentioned cleaning solvent, examples of which may include a method in which the reactor is cleaned by introducing the cleaning solvent from the upper portion of the reactor, and a method in which the inside of the reactor is cleaned by introducing the cleaning agent into the bottom of the reactor and then boiling the cleaning reagent up through the reactor.

It is not necessary to carry out the cleaning procedure each time the reaction is carried out, but rather can be determined arbitrarily based on the compounds used, operating rate and the like, and the cleaning procedure is preferably carried out once every 1 to 20000 hours of operating time, more preferably once every one day to one year of operating time, and even more preferably once every one month to one year of operating time. The reactor may be equipped with a line for introducing the cleaning agent.

The steps (D), (E) and (G) explained below are carried out in addition to the above-mentioned method.

<Step (D)>

Urea is recovered by carrying out the following step (D) before step (B), step (R) or step (P) and/or simultaneous to step (B), step (R) or step (P):

step (D): a step of removing urea by distillation or sublimation.

When producing the compound having the ureido groups as described in step (A), urea is preferably used in excess based on the organic primary amine. At this time, since compounds having ureylene groups may be formed as by-products in the case an excess amount of unreacted urea is present in step (B), step (R) or step (P) while still containing an excess of urea, the urea is separated by distillation or sublimation. The known method can be used for the separation method, and although varying according to the compounds used, a method such as filtration, distillation or sublimation can be used. A method that is carried out simultaneous to step (B), step (R) or step (P) is preferable.

Namely, in the reaction carried out in step (B), step (R) or step (P), a gas containing a hydroxy composition (the hydroxy composition refers to a composition containing at least one type of aromatic hydroxy composition and/or aromatic hydroxy compound and/or alcohol), compound having carbonyl groups derived from urea and ammonia formed as a by-product in the reaction is introduced into a condenser provided in the reactor, and all or a portion of the hydroxy composition and the compound having carbonyl groups derived from urea are condensed.

At that time, the condensed hydroxy composition is preferably present at a stoichiometric ratio of 1 or more based on the condensed urea and compound having carbonyl groups derived from urea.

In the present embodiment, a "compound having carbonyl groups derived from urea" that is condensed in the condenser includes compounds having carbonyl groups derived from urea used in the reaction with organic amine, urea and hydroxy composition, the urea itself used as a raw material (including unreacted urea and/or the excess portion in the case of having been used in excess based on organic amine), compounds obtained by a reaction between the urea and the hydroxy composition, and compounds obtained by a reaction between same or different types of carbonic acid derivatives. Although it is difficult to identify all compounds having carbonyl groups derived from urea, specific examples may include isocyanic acid, urea, urea compounds such as biurets or nurates, non-N-substituted carbamic acid-O-esters in which the ester groups are groups derived from the hydroxy composition, and carbonic acid esters in which the ester groups are groups derived from the hydroxy composition. Compounds having carbonyl groups derived from a carbonic acid derivative can be quantified by the method that detects carbonyl groups contained in the compound such as infrared spectroscopy, near infrared spectroscopy, Raman spectroscopy or ultraviolet spectroscopy, or by a method that specifically analyzes compounds formed such as gas chromatography, liquid chromatography or NMR. Many of these compounds having carbonyl groups derived from urea have a high melting point and tend to precipitate easily. Among the above-mentioned compounds having carbonyl groups derived from urea, urea in particular requires the greatest caution since it is formed in large amounts (detected amounts) and has a melting point of 135° C.

As a result of making the stoichiometric ratio of the condensed hydroxy composition to be 1 or more based on the condensed compound having carbonyl groups derived from the urea in the condensation procedure, a mixture thereof can be obtained in the form of a homogeneous liquid mixture in the condenser. Thus, not only does this facilitate handling of the mixture, but it is also possible to avoid the occurrence of problems such as adhesion and accumulation of solid components in the condenser. In addition, as will be described later, this is also effective for reducing the amount of compounds having carbonyl groups derived from the urea contained in ammonia recovered from the condenser to equal to or less than a specific amount. The amount of the condensed hydroxy composition based on the condensed compound having carbonyl groups derived from the urea in terms of the stoichiometric ratio is more preferably 2 or more and even more preferably 3 or more. In order to ensure that the amount of the condensed hydroxy composition based on the condensed compound having carbonyl groups derived from the urea is within the above ranges, the condenser is preferably maintained at a temperature at least 90° C. lower than the standard boiling point of the hydroxy composition.

<Production Method of N-Substituted Carbamic Acid-O-Aryl Ester Using an Aromatic Hydroxy Composition Containing a Plurality of Types of Aromatic Hydroxy Compounds>

An N-substituted carbamic acid-O-aryl ester can be produced in the above-mentioned steps 1) to 5) using an aromatic hydroxy composition containing a plurality of types of aromatic hydroxy compounds.

In addition, in the case of carrying out step (D) in route 1) or route 2), a gas containing the aromatic hydroxy composition, urea and compound having carbonyl groups derived from urea is condensed in a condenser in order to recover the urea and compound having carbonyl groups derived from urea in the form of a homogeneous solution. Consequently, the aromatic hydroxy composition preferably contains an aromatic hydroxy compound that is easily vaporized to a certain degree under the reaction conditions. On the other hand, since the compound having ureido groups and the aromatic hydroxy composition mainly react in the liquid phase to form N-substituted carbamic acid-O— aryl ester, the aromatic hydroxy composition preferably contains an aromatic hydroxy compound that is present as a liquid under the reaction conditions. Thus, an aromatic hydroxy composition that contains a plurality of types of aromatic hydroxy compounds having different standard boiling points can be preferably used for the aromatic hydroxy composition.

In this case, there are many cases in which, when all of the plurality of types of aromatic hydroxy compounds having different standard boiling points form N-substituted carbamic acid ester by reacting with the compound having ureido groups, a plurality of types of aromatic hydroxy compounds are formed together with isocyanate during production of isocyanate by thermal decomposition of the N-substituted carbamic acid ester, thereby making separation of the aromatic hydroxy compounds complex. Therefore, a method for producing N-substituted carbamic acid-O-aryl ester having ester groups derived from an active aromatic hydroxy compound with high selectivity is preferably carried out by using a combination of an active aromatic hydroxy compound and an inactive aromatic hydroxy compound. Moreover, if aromatic hydroxy compounds are selected such that the standard boiling point of the active aromatic hydroxy compound is the highest in the aromatic hydroxy composition, the concentration of the active aromatic hydroxy compound increases in the liquid phase in which the formation reaction of the N-substituted carbamic acid-O-aryl ester mainly takes place, thereby making it possible to form an N-substituted carbamic acid-O-ester derived from the active aromatic hydroxy compound with higher selectivity. An inactive aromatic hydroxy compound having a standard boiling point lower than the standard boiling point of the active aromatic hydroxy compound is preferably introduced into the condenser in the form of a gaseous phase component and condensed in the condenser together with the compound having carbonyl groups derived from the carbonic acid derivative.

Figure 7:
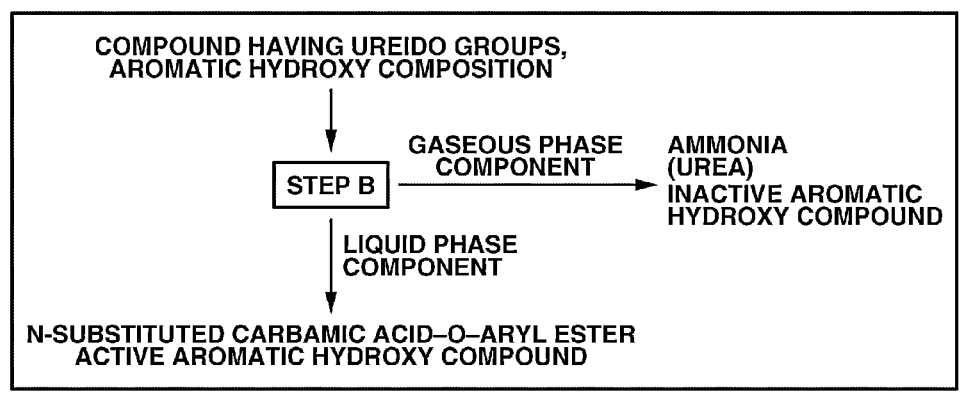
FIG. 7 shows a conceptual drawing depicting an N-substituted carbamic acid ester production method that uses an aromatic hydroxy composition containing an active aromatic hydroxy compound and an inactive aromatic hydroxy compound in the present embodiment.

FIG. 7 shows a conceptual drawing of a production method of N-substituted carbamic acid ester that uses an aromatic hydroxy composition composed of a plurality of types of aromatic hydroxy compounds as described above (here, for the sake of simplicity of the explanation, an aromatic hydroxy composition is described that contains two types of aromatic hydroxy compounds containing an active aromatic hydroxy compound and an inactive aromatic hydroxy compound).

An example of this type of active aromatic hydroxy compound is an aromatic hydroxy compound represented by formula (32), and preferably an aromatic hydroxy compound represented by formula (38). In addition, an example of an inactive aromatic hydroxy compound is an aromatic hydroxy compound represented by formula (39), and more preferably an aromatic hydroxy compound represented by formula (40). Although it is difficult to generally define separability, based on the finding that generally two components to be separated can be adequately separated by distillation industrially if the standard boiling points thereof are 10° C. or more apart, the difference between the standard boiling points of the active aromatic hydroxy compound and the inactive aromatic hydroxy compound is preferably such that the compound having the highest standard boiling point is an active aromatic hydroxy compound, while the compound having the lowest standard boiling point is an inactive aromatic hydroxy compound, and is preferably selected such that the standard boiling point is 10° C. or more higher, and more preferably 20° C. or more higher, based on the compound having the highest boiling point, and is also selected in consideration of the difference with the standard boiling point of the isocyanate formed as previously described. In this case, an active aromatic hydroxy compound is selected having a standard boiling point that is 10° C. or more apart from that of the isocyanate formed. In the case of using an aromatic hydroxy compound having a standard boiling point higher than that of isocyanate, an active aromatic hydroxy compound is selected that has a standard boiling point 10° C. or more higher than that of the isocyanate, and in the case of using an aromatic hydroxy compound having a standard boiling point lower than that of isocyanate, an active aromatic hydroxy compound is selected that has a standard boiling point 10° C. or more lower than that of the isocyanate.

<Step (E)>

Step (E): a step of recycling urea recovered in step (D) to step (A).

Step (E) is a step of recycling urea recovered in step (D) as described above to step (A). The use of recycling is preferable since it allows the amount of urea used to be reduced. In step (E), the mixture recovered in step (D) may be recycled directly to step (A) or only the urea may be recycled. Components to be recycled may be separated as necessary or components may be added before recycling to step (A). Separation and addition can be carried out using known methods, and the urea, compound having carbonyl groups derived from urea and hydroxy composition and the like are analyzed and then suitably recycled.

<Step (G)>

The following step (G) is carried out to recover ammonia formed as a by-product in step (A) and/or step (B) and/or step (R) and react the ammonia with carbon dioxide to regenerate urea followed by recycling the urea to step (A):

Step (G): a step of recovering ammonia formed as a by-product, regenerating urea by reacting the ammonia with carbon dioxide, and recycling the urea to step (A).

In the present embodiment, ammonia discharged from the condenser in the above-mentioned step (A), step (B) and/or step (R) absorbs water resulting in the formation of aqueous ammonia, and although this can be used in refrigerants of ammonia-absorption refrigerators, textile oil cleaners, raw rubber coagulants, production of various types of ammonia salts, treatment of nitrogen oxides generated by thermoelectric power plants and the like or production of photographic emulsions and so forth, or can be used in the form of liquid ammonia by employing a method such as deep cooling separation in such applications as raw materials of nitrogen fertilizers, raw materials of synthetic fibers (such as caprolactam or acrylonitrile), treatment of nitrogen oxides generation by thermoelectric power plants and the like or refrigerants, it is preferably used to synthesize urea. The following provides an explanation of this urea synthesis step (to be referred to as step (G)).

The conventionally known method can be employed to produce urea by reacting ammonia and carbon dioxide, an example of which may include reacting ammonia and carbon dioxide at a pressure within a range of from 20 to 40 MPa and temperature within a range of from 190 to 200° C. such that the ratio of ammonia to carbon dioxide is within a range of a stoichiometric ratio of from 3 to 5.

The urea produced by such a method may be used in the reaction of step (A).

Although the following indicates an example of a preferable aspect that combines the above-mentioned method, there are no particular limitations on other aspects provided they are based on the above-mentioned method. Additional steps (such as steps (D), (E), (F) or (G)) may not be carried out or additional steps may be suitably selected and carried out. Step (F) is carried out when producing isocyanate from N-substituted carbamic acid-O-aryl ester. In the following aspect, a hydroxy composition refers to a composition containing at least one type of component selected from an aromatic hydroxy composition and/or aromatic hydroxy compound and/or alcohol. In the case accumulation of a by-product is observed in each step, the by-product is preferably suitably removed outside the system from the recycled composition or together with the recycled composition, and may be removed using the known method. The removal method can be suitably determined by a person with ordinary skill in the art. Examples of methods that can be used may include a method for partially removing a liquid phase component and/or gaseous phase component outside the system, and a method for removing a solid component by filtration and the like.

Figure 8:
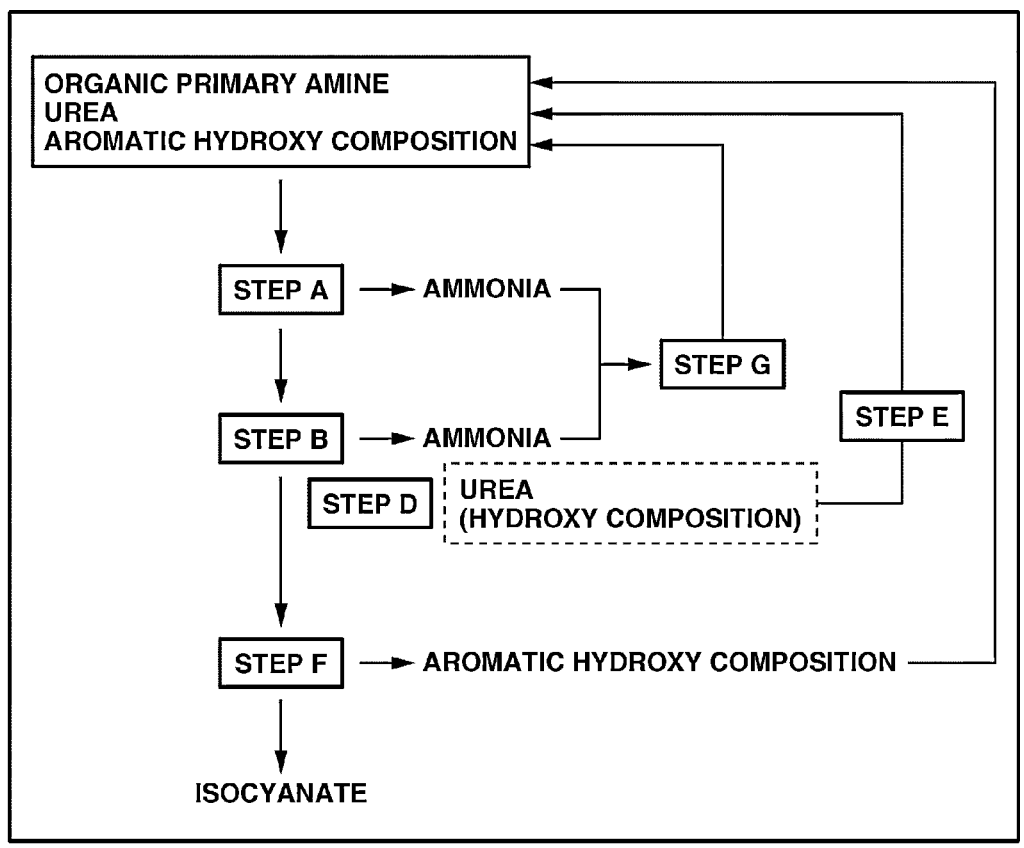
FIG. 8 shows a conceptual drawing depicting one aspect of the present embodiment that combines a route 1) with steps (D), (E), (F) and (G)

FIG. 8 shows a conceptual drawing depicting one aspect of the present embodiment that combines route 1) with steps (D), (E), (F) and (G).

First, the compound having the ureido groups is produced in step (A) by reacting the organic primary amine and urea. In this step (A), the aromatic hydroxy composition acts mainly as a reaction solvent. In the reaction of step (A), ammonia formed as a by-product can be extracted from the reaction liquid until the ammonia concentration in the reaction liquid is within the preferable ranges previously described. The reaction liquid obtained in step (A) contains a compound having ureido groups and an aromatic hydroxy composition, and the reaction liquid may be a composition for transfer and storage of a compound having ureido groups of the present embodiment depending on the raw materials used, composite ratio of the raw materials, reaction conditions of step (A) and the like. In the subsequent step (B), N-substituted carbamic acid-O-aryl ester is produced by reacting the compound having ureido groups and an aromatic hydroxy compound. Ammonia formed as a by-product in the reaction of this step (B) is extracted from the reaction liquid until the ammonia concentration is within the preferable ranges previously described, and is used in step (G) along with the ammonia extracted in step (A). The urea produced in step (G) is reused as a raw material of step (A). In addition, step (D) is carried out simultaneous to the step (B). Namely, unreacted or excess urea is removed by distillation or sublimation. At this time, the urea is distilled off together with a portion of the aromatic hydroxy composition, and is preferably removed and recovered in the form of a mixture with the aromatic hydroxy composition. The urea recovered in step (D) is reused as a raw material of step (A) by carrying out step (E).

The N-substituted carbamic acid-O-aryl ester obtained in step (B) is subjected to thermal decomposition in the subsequent step (F), resulting in the formation of the corresponding isocyanate and aromatic hydroxy composition. The aromatic hydroxy composition separated from the isocyanate in step (F) is reused as a raw material of step (A).

Figure 9:
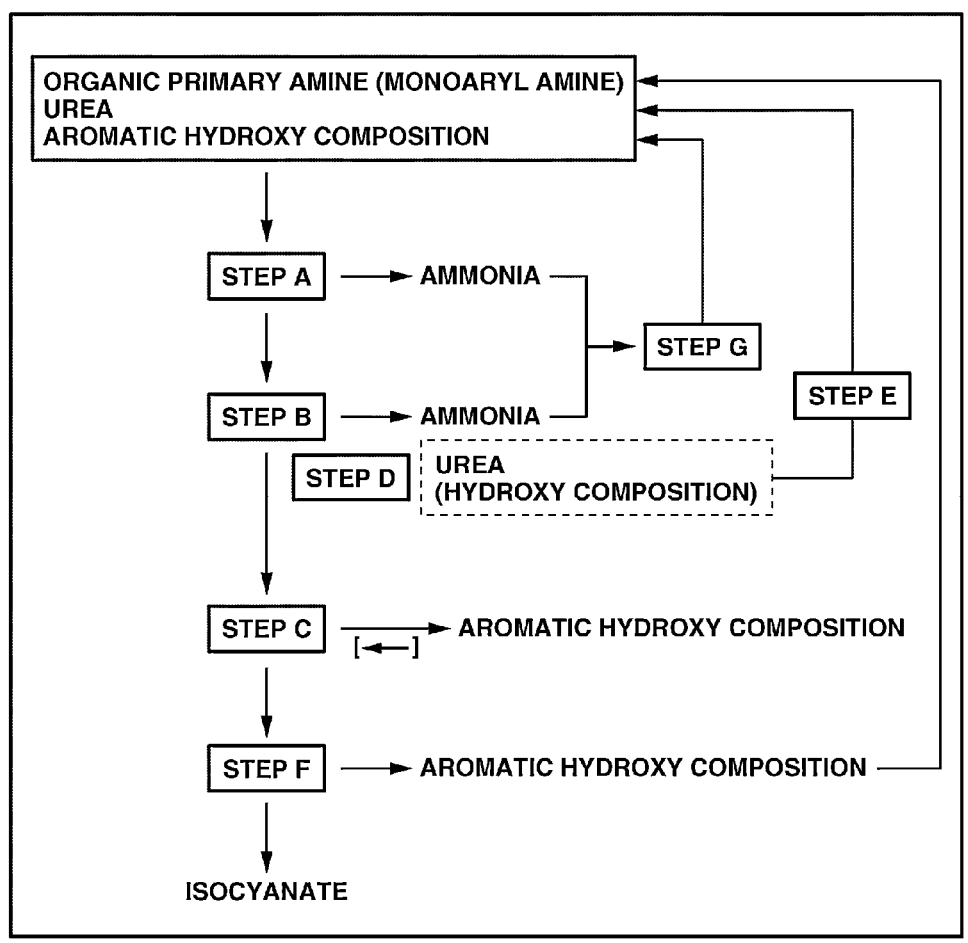
FIG. 9 shows a conceptual drawing depicting one aspect of the present embodiment that combines a route 2) with steps (D), (E), (F) and (G)

FIG. 9 shows a conceptual drawing depicting one aspect of the present embodiment that combines route 2) with steps (D), (E), (F) and (G).

This route 2) is an example of a preferable aspect in the case of using a monoaryl amine for the organic primary amine.

First, organic primary amine (monoaryl amine) and urea are reacted in step (A) to produce the compound having the ureido groups. In this step (A), the aromatic hydroxy composition acts mainly as a reaction solvent. In the reaction of step (A), ammonia formed as a by-product can be extracted from the reaction liquid until the ammonia concentration in the reaction liquid is within the preferable ranges previously described. The reaction liquid obtained in step (A) contains the compound having the ureido groups and the aromatic hydroxy composition, and the reaction liquid may be a composition for transfer and storage of the compound having theureido groups of the present embodiment depending on the raw materials used, composite ratio of the raw materials, reaction conditions of step (A) and the like. In the subsequent step (B), N-substituted carbamic acid-O-mono(aryl ester) is produced by reacting the compound having the ureido groups and the aromatic hydroxy compound. Ammonia formed as a by-product in the reaction of this step (B) is extracted from the reaction liquid until the ammonia concentration is within the preferable ranges previously described, and is used in step (G) along with the ammonia extracted in step (A). The urea produced in step (G) is reused as a raw material of step (A). In addition, step (D) is carried out simultaneous to the step (B). Namely, unreacted or excess urea is removed by distillation or sublimation. At this time, the urea is distilled off together with a portion of the aromatic hydroxy composition, and is preferably removed and recovered in the form of a mixture with the aromatic hydroxy composition. The urea recovered in step (D) is reused as a raw material of step (A) by carrying out step (E).

The N-substituted carbamic acid-O-mono(aryl ester) obtained in step (B) is used to produce N-substituted carbamic acid-O-aryl ester, in which at least two molecules of the N-substituted carbamic acid-O-mono(aryl ester) are crosslinked with methylene ($-CH_2-$) groups by crosslinking with the methylene groups in the subsequent step (C). When carrying out the step (C), the aromatic hydroxy composition used in step (B) is separated from the reaction liquid containing N-substituted carbamic acid-O-mono(aryl ester). After carrying out step (C), aromatic hydroxy composition is preferably added to the resulting N-substituted carbamic acid-O-aryl ester to subject the N-substituted carbamic acid-O-aryl ester to a thermal decomposition reaction in step (F). In step (F), the N-substituted carbamic acid-O-aryl ester obtained in step (C) is subjected to thermal decomposition to form the corresponding isocyanate and an aromatic hydroxy composition. The aromatic hydroxy composition separated from the isocyanate in step (F) is reused as a raw material of step (A).

Figure 10:
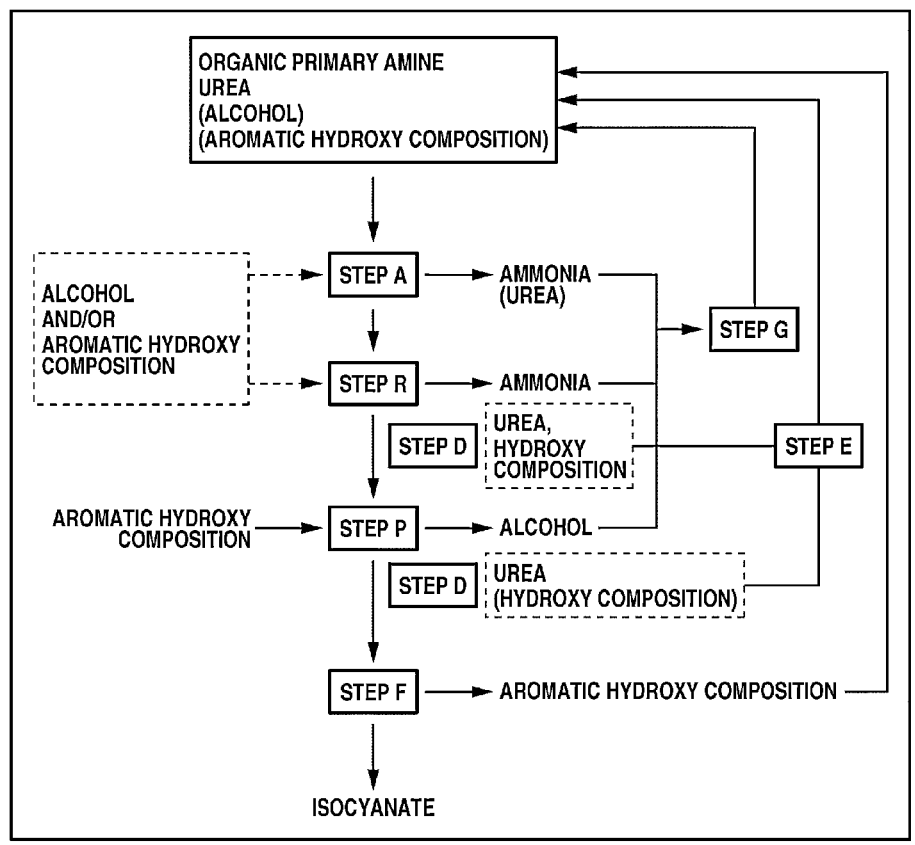
FIG. 10 shows a conceptual drawing depicting one aspect of the present embodiment that combines a route 3) with steps (D), (E), (F) and (G)

FIG. 10 shows a conceptual drawing depicting one aspect of the present embodiment that combines route 3) with steps (D), (E), (F) and (G).

First, organic primary amine and urea are reacted in step (A) to produce a compound having ureido groups. An alcohol and/or aromatic hydroxy composition are preferably used for the reaction solvent in this step (A). In the reaction of step (A), ammonia formed as a by-product can be extracted from the reaction liquid until the ammonia concentration in the reaction liquid is within the preferable ranges previously described. A portion of unreacted or excess urea may be extracted as a gaseous phase component at that time. The reaction liquid obtained in step (A) may be a composition for transfer and storage of the compound having the ureido groups of the present embodiment depending on the raw materials used, composite ratio of the raw materials, reaction conditions of step (A) and the like. In the subsequent step (R), N-substituted carbamic acid-O—$R^2$ ester is produced by reacting the compound having the ureido groups and alcohol. Ammonia formed as a by-product in the reaction of this step (R) is extracted from the reaction liquid until the ammonia concentration is within the preferable ranges previously described, and is used in step (G) along with the ammonia extracted in step (A). The urea produced in step (G) is reused as a raw material of step (A). In addition, step (D) is carried out simultaneous to the step (R). Namely, unreacted or excess urea is removed by distillation or sublimation. At this time, the urea is distilled off together with a portion of the aromatic hydroxy composition (alcohol and/or aromatic hydroxy composition), and is preferably removed and recovered in the form of a mixture with the aromatic hydroxy composition. The urea recovered in step (D) is reused as a raw material of step (A) by carrying out step (E).

Next, the N-substituted carbamic acid-O—$R^2$ ester obtained in step (R) is converted to N-substituted carbamic acid-O-aryl ester by reacting with an aromatic hydroxy composition in step (P). Alcohol derived from the N-substituted carbamic acid-O—$R^2$ ester that is produced as a by-product by this reaction is reused in step (A). In addition, in the case removal of urea is inadequate in step (D) that is carried out simultaneous to step (R), step (D) can also be carried out simultaneous to step (P) to remove urea in the reaction liquid. The urea recovered in the step (D) is also reused as a raw material of step (A) by similarly carrying out step (E).

The N-substituted carbamic acid-O-aryl ester obtained in step (P) is subjected to a thermal decomposition reaction in the subsequent step (F) to form the corresponding isocyanate and an aromatic hydroxy composition. The aromatic hydroxy composition separated from the isocyanate in step (F) is reused as a raw material of step (A).

Figure 11:
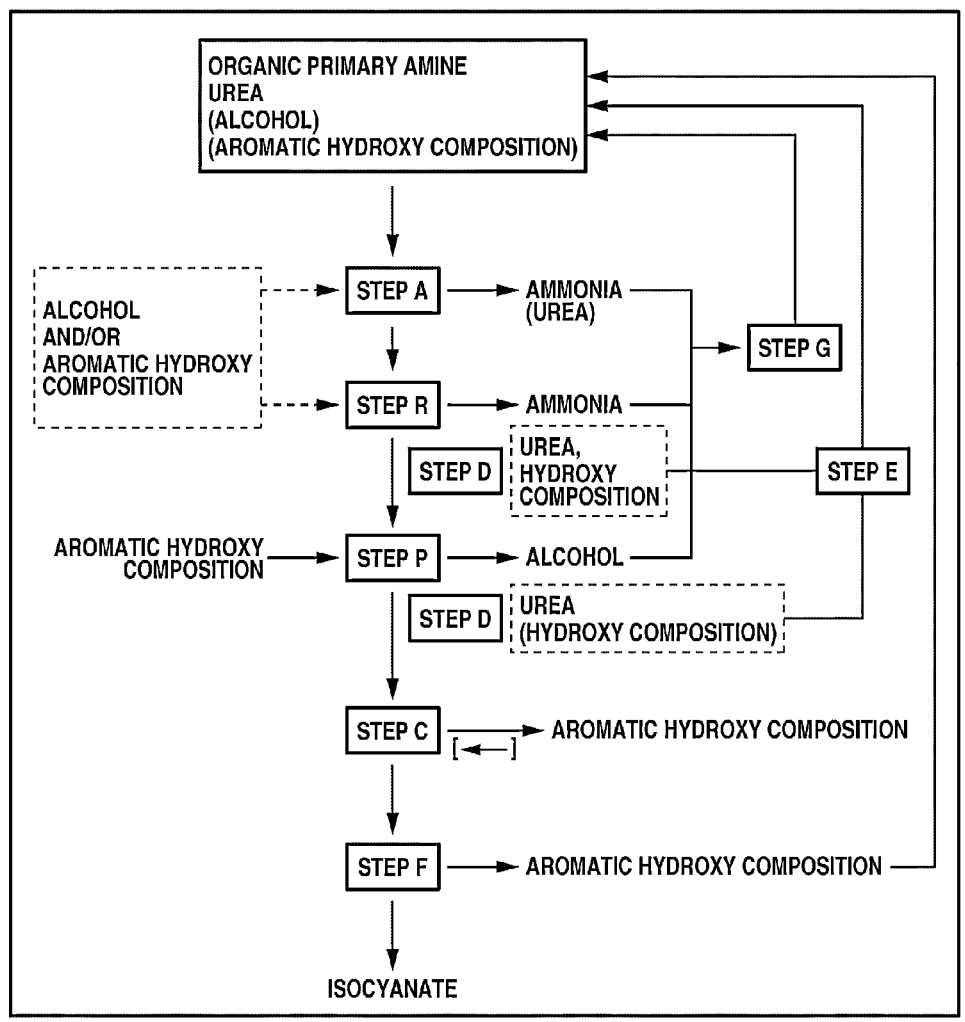
FIG. 11 shows a conceptual drawing depicting one aspect of the present embodiment that combines a route 4) with steps (D), (E), (F) and (G)

FIG. 11 shows a conceptual drawing depicting one aspect of the present embodiment that combines route 4) with steps (D), (E), (F) and (G).

This route 4) is an example of a preferable aspect in the case of using a monoaryl amine for the organic primary amine.

First, organic primary amine (monoaryl amine) and urea are reacted in step (A) to produce the compound having the ureido groups. In this step (A), an alcohol and/or aromatic hydroxy composition are preferably used for the reaction solvent. In the reaction of step (A), ammonia formed as a by-product can be extracted from the reaction liquid until the ammonia concentration in the reaction liquid is within the preferable ranges previously described. At that time, a portion of the unreacted or excess urea may also be extracted as a gaseous phase component. The reaction liquid obtained in step (A) may be a composition for transfer and storage of a compound having ureido groups of the present embodiment depending on the raw materials used, composite ratio of the raw materials, reaction conditions of step (A) and the like. In the subsequent step (R), N-substituted carbamic acid-O-mono($R^2$ ester) is produced by reacting the compound having ureido groups and alcohol. Ammonia formed as a by-product in the reaction of this step (R) is extracted from the reaction liquid until the ammonia concentration is within the preferable ranges previously described, and is used in step (G) along with the ammonia extracted in step (A). The urea produced in step (G) is reused as a raw material of step (A). In addition, step (D) is carried out simultaneous to the step (R). Namely, unreacted or excess urea is removed by distillation or sublimation. At this time, the urea is distilled off together with a portion of a hydroxy composition (alcohol and/or aromatic hydroxy composition), and is preferably removed and recovered in the form of a mixture with the hydroxy composition. The urea recovered in step (D) is reused as a raw material of step (A) by carrying out step (E).

Next, the N-substituted carbamic acid-O-mono($R^2$ ester) obtained in step (R) is converted to N-substituted carbamic acid-O-mono(aryl ester) by reacting with an aromatic hydroxy composition in step (P). Alcohol derived from the N-substituted carbamic acid-O-mono($R^2$ ester) that is produced as a by-product by this reaction is reused in step (A). In addition, in the case removal of urea is inadequate in step (D) that is carried out simultaneous to step (R), step (D) can also be carried out simultaneous to step (P) to remove urea in the reaction liquid. The urea recovered in the step (D) is also reused as a raw material of step (A) by similarly carrying out step (E).

The N-substituted carbamic acid-O-mono(aryl ester) obtained in step (P) is used to produce N-substituted carbamic acid-O-aryl ester, in which at least two molecules of the N-substituted carbamic acid-O-mono(aryl ester) are crosslinked with methylene (—$CH_2$—) groups by crosslinking with the methylene groups in the subsequent step (C). When carrying out the step (C), aromatic hydroxy composition remaining in the reaction liquid of step (P) is separated from the reaction liquid containing N-substituted carbamic acid-O-mono(aryl ester). After carrying out step (C), aromatic hydroxy composition is preferably added to the resulting N-substituted carbamic acid-O-aryl ester to subject the N-substituted carbamic acid-O-aryl ester to a thermal decomposition reaction in step (F).

In step (F), the N-substituted carbamic acid-O-aryl ester obtained in step (C) is subjected to thermal decomposition to form the corresponding isocyanate and an aromatic hydroxy composition. The aromatic hydroxy composition separated from the isocyanate in step (F) is reused as a raw material of step (A).

Figure 12:
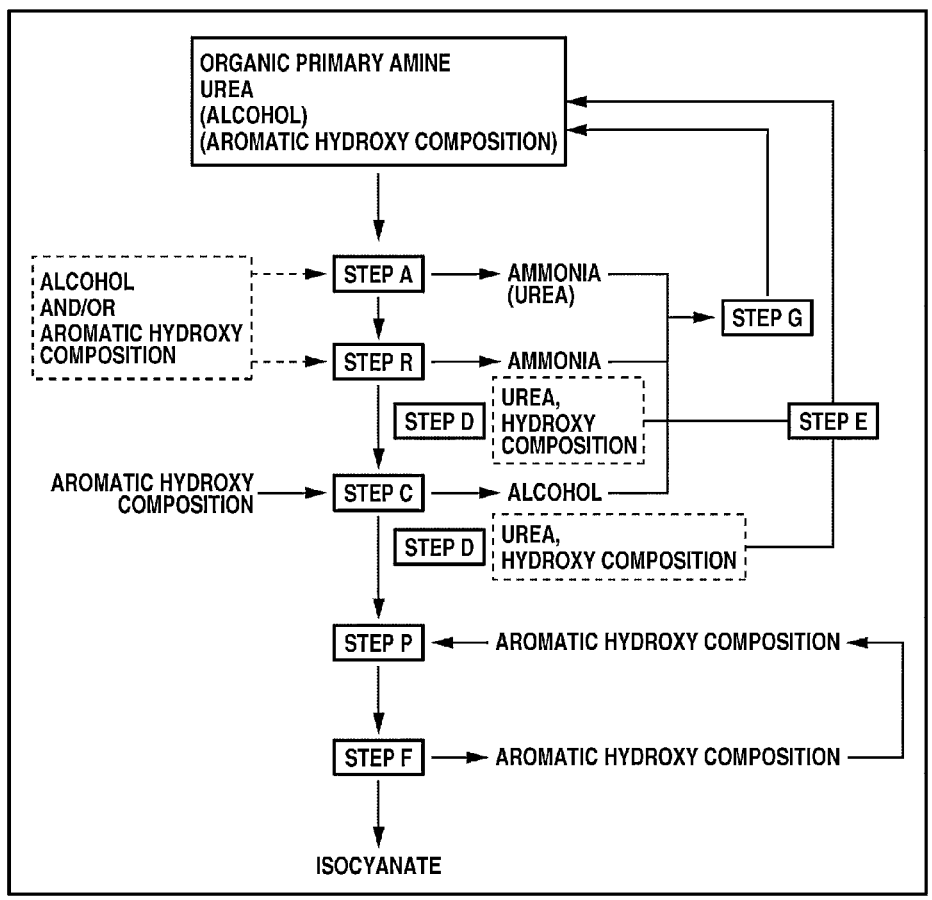
FIG. 12 shows a conceptual drawing depicting one aspect of the present embodiment that combines a route 5) with steps (D), (E), (F) and (G)

FIG. 12 shows a conceptual drawing depicting one aspect of the present embodiment that combines route 5) with steps (D), (E), (F) and (G).

This route 5) is an example of a preferable aspect in the case of using a monoaryl amine for the organic primary amine.

First, organic primary amine (monoaryl amine) and urea are reacted in step (A) to produce the compound having the ureido groups. In this step (A), an alcohol and/or aromatic hydroxy composition are preferably used for the reaction solvent. In the reaction of step (A), ammonia formed as a by-product can be extracted from the reaction liquid until the ammonia concentration in the reaction liquid is within the preferable ranges previously described. At that time, a portion of the unreacted or excess urea may also be extracted as a gaseous phase component. The reaction liquid obtained in step (A) may be a composition for transfer and storage of a compound having ureido groups of the present embodiment depending on the raw materials used, composite ratio of the raw materials, reaction conditions of step (A) and the like. In the subsequent step (R), N-substituted carbamic acid-O- mono($R^2$ ester) is produced by reacting the compound having the ureido groups and alcohol. Ammonia formed as a by-product in the reaction of this step (R) is extracted from the reaction liquid until the ammonia concentration is within the preferable ranges previously described, and is used in step (G) along with the ammonia extracted in step (A). The urea produced in step (G) is reused as a raw material of step (A). In addition, step (D) is carried out simultaneous to the step (R). Namely, unreacted or excess urea is removed by distillation or sublimation. At this time, the urea is distilled off together with a portion of a hydroxy composition (alcohol and/or aromatic hydroxy composition), and is preferably removed and recovered in the form of a mixture with the hydroxy composition. The urea recovered in step (D) is reused as a raw material of step (A) by carrying out step (E).

Next, the N-substituted carbamic acid-O-mono($R^2$ ester) obtained in step (R) is used to produce N-substituted carbamic acid-O—$R^2$ ester, in which at least two molecules of the N-substituted carbamic acid-O-mono($R^2$ ester) are crosslinked with methylene (—$CH_2$—) groups by crosslinking with the methylene groups in step (C). When carrying out the step (C), aromatic hydroxy composition remaining in the reaction liquid of step (R) is separated from the reaction liquid containing N-substituted carbamic acid-O-mono($R^2$ ester). In addition, in the case removal of urea is inadequate in step (D) that is carried out simultaneously to step (R), step (D) may also be carried out simultaneously when separating hydroxy composition remaining n the reaction liquid of step (R) from the reaction liquid followed by recovery of urea and hydroxy composition. The recovered urea and hydroxy composition are reused as raw materials of step (A) by carrying out step (E).

After carrying out step (C), the resulting N-substituted carbamic acid-O—$R^2$ ester is subjected to a transesterification reaction of step (P). Alcohol derived from the N-substituted carbamic acid-O—$R^2$ ester that is formed as a by-product by this reaction is reused in step (A).

The N-substituted carbamic acid-O-aryl ester obtained in step (P) is subjected to a thermal decomposition reaction in step (F) to form the corresponding isocyanate and an aromatic hydroxy composition. The aromatic hydroxy composition separated from the isocyanate in step (F) is reused as the aromatic hydroxy composition of step (P).

EXAMPLES

Although the following provides a detailed explanation of the present invention based on examples thereof, the scope of the present invention is not limited by these examples.

<Analytical Methods>
1) NMR Analysis
Apparatus: JNM-A400 FT-N MR system, JEOL Ltd., Japan
(1) Preparation of $^1$H- and $^{13}$C-NMR Analysis Samples
About 0.3 g of sample solution were weighed followed by the addition of about 0.7 g of heavy chloroform (99.8%, Aldrich Corp., USA) and 0.05 g of internal standard in the form of tetramethyl tin (guaranteed reagent, Wako Pure Chemical Industries, Ltd., Japan) and mixing to uniformity to obtain solutions used as NMR analysis samples.
(2) Quantitative Analysis
Analyses were performed for each standard and quantitative analyses were performed on the analysis sample solutions based on the resulting calibration curve.

2) Liquid Chromatography
Apparatus: LC-10AT system, Shimadzu Corp., Japan
Column: lnertsil-ODS column, GL Sciences Inc., Japan, two columns connected in series
Developing solvent: Mixed liquid of 5 mmol/L aqueous ammonium acetate solution (solution A) and acetonitrile (solution B)
Developing solvent flow rate: 2 mL/min
Column temperature: 35° C.
Detector: R.I. detector (refractometer) and PDA detector (photodiode array detector, measuring wavelength range: 200 to 300 nm)
(1) Liquid Chromatography Analysis Samples
About 0.1 g of sample were weighed followed by the addition of about 1 g of tetrahydrofuran (dehydrated, Wako Pure Chemical Industries, Ltd., Japan) and about 0.02 g of internal standard in the form of 1,1-diethyl urea (Tokyo Chemical Industry Co., Ltd., Japan) and mixing to uniformity to obtain solutions used as liquid chromatography analysis samples.
(2) Quantitative Analysis
Analyses were performed for each standard and quantitative analyses were performed on the analysis sample solutions based on the resulting calibration curve.
3) Water Analysis
Apparatus: Micro Water Content Analyzer Model CA-21, Mitsubishi Chemical Analytech Co., Ltd., Japan
(1) Quantitative Analysis
About 1 g of sample was weighed out and injected into the micro water content analyzer to determine the water content of the sample.
4) Analysis of Ammonia Concentrations in Liquids and Solids
Apparatus: IC2001 Ion Chromatograph (Tosoh Corp., Japan)
Column: SuperIC-CR
Developing solution: Solution obtained by mixing 1 L of water and about 0.25 g of 18-Crown-6 (Wako Pure Chemical Industries, Ltd., Japan) and about 2.1 mL of 2 mol/L methanesulfonic acid (Wako Pure Chemical Industries, Ltd., Japan).
(1) Ion Chromatography Analysis Samples
About 0.15 g of sample were weighed followed by the addition of about 1 g of toluene and about 15 g of 2 mmol/L aqueous nitric acid solution, mixing well and allowing to stand undisturbed for about 2 hours. The aqueous layer was then removed and used as the ion chromatography analysis sample.
(2) Quantitative Analysis
A calibration curve was prepared using Cation Mixed Standard II (Kanto Chemical Co., Inc., Japan), and the amounts of ammonia in the analysis sample solutions were quantified based on the calibration curve.

Furthermore, the names of compounds used in the following examples are explained using nomenclature rules defined by IUPAC as well as common names.

Example 1

Production of N-Substituted Carbamic Acid-O-Aryl Ester by Route 1

Step (A): Production of Compound Having Ureido Groups
The apparatus used in FIG. 13 was used.
41.84 kg of p-heptyl phenol (Schenectady Chemicals, USA) and 3.10 kg of urea were mixed in a storage tank 101 heated to 120° C. with a line 13 closed to obtain a mixture for use as an aromatic hydroxy composition. The water concentration in the mixture was about 15 ppm. The mixture was transferred to a stirring tank 103 (with baffles) heated to 120° C. 1.50 kg of organic amine in the form of hexamethylenediamine were then supplied at the rate of about 20 g/min (supply rate of organic amine) from a storage tank 102 to the stirring tank 103 via a line 12 while stirring the stirring tank 103. Formation of ammonia from a line 19 was confirmed. Following completion of supplying hexamethylenediamine, stirring was continued for about 2 hours and the reaction liquid was sampled. As a result of analyzing the reaction liquid by liquid chromatography, the reaction liquid was found to contain 6.3% by weight of a compound having ureido groups in the form of 6-hexamethylene diurea. In addition, the ammonia concentration in the solution was 6300 ppm. Unreacted amino group terminals were not detected. The ratio of the number of molecules of p-heptyl phenol to the number of ureido groups in the reaction liquid was 7.5.

Line 13 was opened and the reaction liquid was transferred to a storage tank 104 via the line 13.

Steps (B) and (D): Production of N-Substituted Carbamic Acid-O-Aryl Ester and Recovery of Urea The apparatus shown in FIG. 13 was continued to be used.

A packed column 105 packed with a packing material (Helipack No. 3) was heated to 240° C. and the pressure inside the column was set to 26 kPa. The reaction liquid obtained in step (A) was fed from a line 14 provided in the packed column 105 at the rate of about 1.5 g/min. Since the reaction is initially in an unsteady state, the sample at that time was discarded. The amount of reaction liquid fed after the reaction had reached a steady state was about 35.1 kg. The reaction liquid was recovered in a storage tank 110 through a line 16 provided in the bottom of the packed column 105. A gaseous phase component was condensed from a line 15 provided in the top of the packed column 105 with a condenser 106, and the resulting liquid phase component was recovered in a storage tank 109 via a gas-liquid separator 108. When reaction liquid recovered in the storage tank 109 was analyzed by $^1$H-NMR, the condensed component was found to contain urea and p-heptyl phenol. The amount of reaction liquid recovered in the storage tank 110 was 23.0 kg. When the reaction liquid was analyzed by liquid chromatography and $^1$H-NMR, the reaction liquid was found to contain N,N'-hexanediyl-di(carbamic acid(p-heptylphenyl)ester), and the yield of N,N'-hexanediyl-di(carbamic acid(p-heptylphenyl)ester) based on hexamethylenediamine was about 97%. The urea content of the reaction liquid was below the detection limit. In addition, N,N'-bis(6-(p-heptylphenoxycarbaminohexyl)urea was not detected. The ammonia concentration of the reaction liquid was 9.0 ppm.

On the other hand, the amount of mixture recovered in the storage tank 109 was 13.5 kg. This mixture contained an aromatic hydroxy compound (p-heptyl phenol) and urea, and the content of the aromatic hydroxy compound (p-heptyl phenol) in the mixture was 85.4% by weight, while the urea content was 10.2% by weight.

Step (F): Production of Isocyanate by Thermal Decomposition of N-Substituted Carbamic Acid-O-Aryl Ester The apparatus shown in FIG. 17 was used.

A thin film distillation apparatus 602 (Kobelco Eco-Solutions Co., Ltd., Japan) having a heat-conducting surface area of 0.2 m$^2$ was heated to 220° C. and the pressure within the thin film distillation apparatus was set to about 1.3 kPa. The reaction liquid recovered in the storage tank 110 in step (B) was placed in a storage tank 601 and supplied to the thin film distillation apparatus at the rate of about 1800 g/hr via a line 60. A liquid component was extracted from a line 62 provided in the bottom of thin film distillation apparatus 602 and recovered in a storage tank 603.

The liquid component recovered in the storage tank 603 was again supplied to the thin film distillation apparatus 602 through a line 63. A gaseous component containing hexamethylene diisocyanate and p-heptyl phenol was extracted from a line 61 provided in the upper portion of the thin film distillation apparatus 602. The gaseous component was introduced into a distillation column 604, and the low boiling point component was separated by distillation. A liquid phase component was supplied to a distillation column 609 from a line 68 provided at a portion of the distillation column 604 lower than the feed line and further subjected to distillative separation. The gaseous phase component was condensed in a condenser 610 via a line 69 and recovered in a storage tank 612 through a gas-liquid separator 611.

When the condensate was analyzed by $^1$H-NMR and gas chromatography, the condensate was found to contain about 99% by weight of hexamethylene diisocyanate. The yield based on the organic amine of step (A) (hexamethylene diamine) was about 90%. A mixture containing p-heptyl phenol was obtained in a storage tank 614.

Step (E): Production of N-Substituted Carbamic Acid Ester by Reusing Mixture Obtained in Condenser The ammonia concentration of the mixture recovered in the storage tank 109 in step (B) of Example 1 was 820 ppm. 12.8 kg of p-heptyl phenol and 0.578 kg of urea were added to the mixture followed by transferring to the stirring tank 103 and carrying out the same method as step (A) using 0.92 kg of hexamethylenediamine. A solution containing 6.3% by weight of 1,6-hexanediurea was obtained. The same method as step (B) was carried out using this solution instead of the solution of step (A). The reaction liquid recovered in a storage tank 610 contained N,N'-hexanediyl-di(carbamic acid(p-heptylphenyl)ester), and the yield of N,N'-hexanediyl-di(carbamic acid(p-heptylphenyl)ester) based on hexamethylenediamine was about 97%.

Example 2

Production of N-Substituted Carbamic Acid-O-Aryl Ester by Route 1

Step (A): Production of Compound Having Ureido Groups

Figure 14:
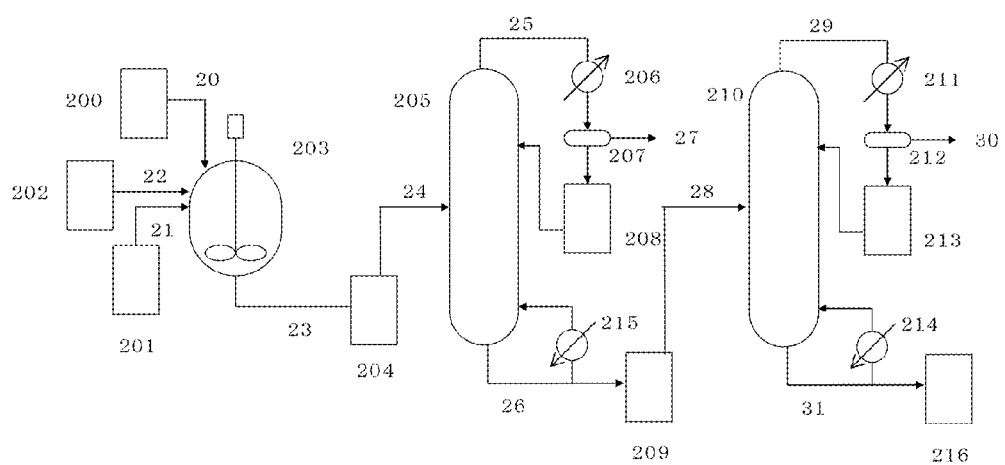
FIG. 14 shows a conceptual drawing depicting an N-substituted carbamic acid ester production apparatus in an example of the present embodiment.

The apparatus shown in FIG. 14 was used.

A mixture of 1.92 kg of urea and 11.9 kg of solvent (1-butanol) was transferred from a storage tank 200 to a stirring tank 203 heated to 120° C. with a line 23 closed. 0.930 kg of organic amine in the form of hexamethylenediamine were then supplied at the rate of about 5 g/min (supply rate of organic amine) from a storage tank 201 to the stirring tank 103 via a line 21 while stirring the stirring tank 203. Following completion of supplying hexamethylenediamine, stirring was continued for about 1 hour. When the reaction liquid was analyzed by liquid chromatography, it was found to contain 11.2% by weight of 1,1'-(hexane-1,6-diyl)diurea. In addition, the ammonia concentration in the solution was 7500 ppm. The ratio of unreacted amino groups to ureido groups was 0.001. 23.1 kg of aromatic hydroxy compound in the form of p-heptyl phenol were transferred from a storage tank 202 to the stirring tank 203 followed by transferring to a storage tank 204 after obtaining a homogeneous solution.

Step (D): Separation and Recovery of Urea

The apparatus shown in FIG. 14 was continued to be used. A packed column 205 packed with a packing (Helipack No. 3) was heated to about 120° C. and the pressure inside the column was set to 10 kPa. The reaction liquid obtained in step (A) was fed to the packed column 205 at the rate of about 8.2 g/min from a line 24 provided in the packed column 205. A gaseous component was recovered from a line 25 and after condensing in a condenser 206, was recovered in a storage tank 208. The recovered liquid obtained in the storage tank 208 was a mixed liquid containing 1-butanol and urea. A residual liquid recovered in a storage tank 209 from the bottom of the packed column 205 via a line 26 was a mixed liquid containing 1,1'-(hexane-1,6-diyl)diurea and p-heptyl phenol. The recovered amount of the residual liquid was about 13.5 kg. The concentration of 1,1'-(hexane-1,6-diyl)diurea in the residual liquid was about 12.0% by weight, and the ratio of the number of p-heptyl phenol molecules to the number of ureido groups was about 2.9.

On the other hand, about 9.8 kg of the mixture of 1-butanol and urea were recovered in the storage tank 208. The amount of 1-butanol contained in the mixture was 92.5% by weight while the amount of urea was 7.1% by weight.

Step (B): Production of N-Substituted Carbamic Acid-O-Aryl Ester

The apparatus shown in FIG. 14 was continued to be used. A packed column 210 packed with a packing material (Helipack No. 3) was heated to 250° C. and the pressure inside the column was set to 26 kPa. The residual liquid recovered in the storage tank 209 in step (D) was fed from a line 28 provided in the packed column 210 at the rate of about 3.8 g/min. Since the reaction is initially in an unsteady state, the sample at that time was discarded. The amount of reaction liquid fed after the reaction had reached a steady state was about 8.95 kg. The reaction liquid was recovered in a storage tank 216 through a line 31 provided in the bottom of the packed column 210. A gaseous phase component was extracted from a line 29 provided in the top of the packed column 210 and condensed with a condenser 211, and the resulting liquid phase component was recovered in a storage tank 213 via a gas-liquid separator 212 and circulated to the packed column 210. On the other hand, ammonia was discharged in the form of a gaseous component from a line 31. The ammonia was absorbed in water and recovered in the form of aqueous ammonia. When the reaction liquid recovered in a storage tank 216 was analyzed by liquid chromatography and $^1$H-NMR, the reaction liquid was found to contain N,N'-hexanediyl-di(carbamic acid(p-heptylphenyl)ester), and the yield of N,N'-hexanediyl-di(carbamic acid(p-heptylphenyl)ester) based on hexamethylenediamine was about 95%. In addition, the ammonia concentration in the reaction liquid was 8.0 ppm.

Step (F): Production of Isocyanate by Thermal Decomposition of N-Substituted Carbamic Acid-O-Aryl Ester The apparatus shown in FIG. 17 was used.

The thin film distillation apparatus 602 having a heat-conducting surface area of 0.2 m$^2$ was heated to 220° C. and the pressure within the thin film distillation apparatus was set to about 1.3 kPa. The reaction liquid recovered in the storage tank 110 in step (B) was placed in the storage tank 601 and supplied to the thin film distillation apparatus at the rate of about 1500 g/hr via the line 60. A liquid component was extracted from the line 62 provided in the bottom of thin film distillation apparatus 602 and recovered in the storage tank 603. The liquid component recovered in the storage tank 603 was again supplied to the thin film distillation apparatus 602 through the line 63. A gaseous component containing hexamethylene diisocyanate and p-heptyl phenol was extracted from the line 61 provided in the upper portion of the thin film distillation apparatus 602. The gaseous component was introduced into the distillation column 604, and the low boiling point component was separated by distillation. A liquid phase component was supplied to the distillation column 609 from the line 68 provided at a portion of the distillation column 604 lower than the feed line and further subjected to distillative separation. The gaseous phase component was condensed in the condenser 610 via the line 69 and recovered in the storage tank 612 through the gas-liquid separator 611.

When the condensate was analyzed by $^1$H-NMR and gas chromatography, the condensate was found to contain about 99% by weight of hexamethylene diisocyanate. The yield based on organic amine (hexamethylene diamine) was about 90%.

Step (E): Production of N-Substituted Carbamic Acid Ester by Reusing Mixture Obtained in Condenser The ammonia concentration of the mixture recovered in the storage tank 109 in step (D) of Example 2 was 550 ppm. 0.962 kg of urea were added to the mixture (without adding solvent) followed by transferring to the stirring tank 103 and carrying out the same method as step (A) using 0.930 kg of hexamethylenediamine. A solution containing 14.1% by weight of 1,6-hexane bis-urea was obtained. The same method as step (B) was carried out using this solution instead of the solution of step (A). The reaction liquid recovered in the storage tank 610 contained N,N'-hexanediyl-di(carbamic acid(p-heptylphenyl)ester), and the yield of N,N'-hexanediyl-di(carbamic acid(p-heptylphenyl)ester) based on hexamethylenediamine was about 95%.

Example 3

Step (A): Production of Compound Having Ureido Groups

Figure 13:
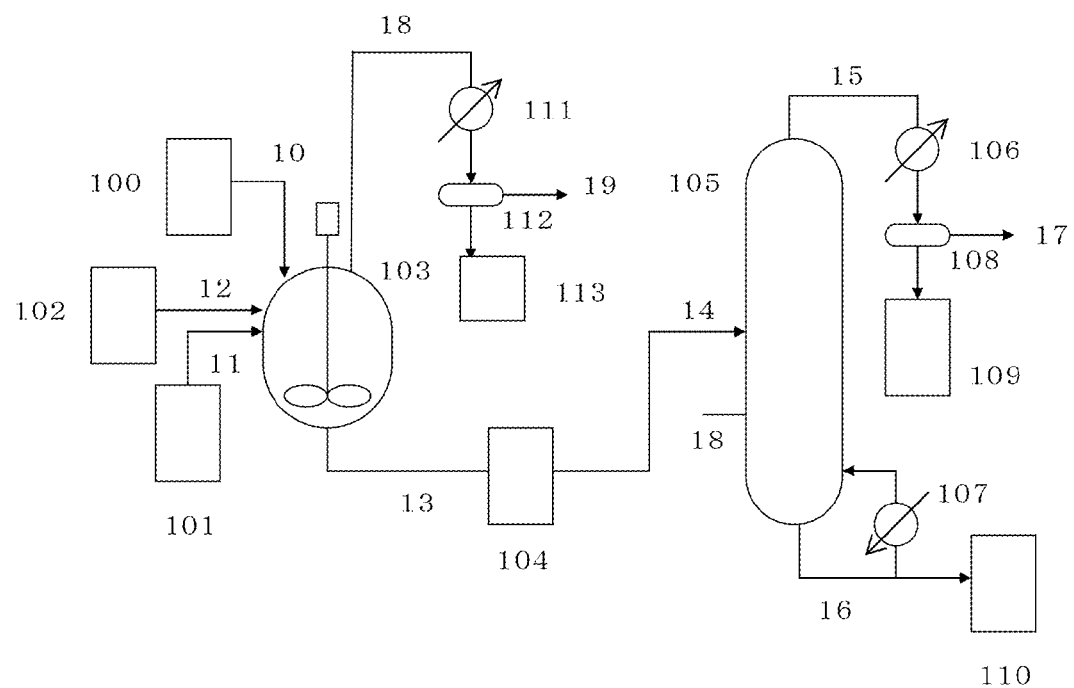
FIG. 13 shows a conceptual drawing depicting an N-substituted carbamic acid ester production apparatus in an example of the present embodiment.

The apparatus used in FIG. 13 was used.

13.6 kg of 1-butanol as the hydroxy compound and 2.49 kg of urea were mixed in the storage tank 101 heated to 120° C. with the line 13 closed to obtain a mixture. The mixture was transferred to the stirring tank 103 (with baffles) heated to 120° C. 1.07 kg of organic amine in the form of hexamethylenediamine were then supplied at the rate of about 20 g/min (supply rate of organic amine) from the storage tank 102 to the stirring tank 103 via the line 12 while stirring the stirring tank 103. Following completion of supplying hexamethylenediamine, stirring was continued for about 2 hours and the reaction liquid was sampled. As a result of analyzing the reaction liquid by liquid chromatography, the reaction liquid was found to contain 10.9% by weight of a compound having ureido groups in the form of 1,1'-(hexane-1,6-diyl) diurea. In addition, the ammonia concentration in the solution was 4300 ppm. Unreacted amino group terminals were not detected. 26.6 kg of a hydroxy compound in the form of p-heptyl phenol were added to the reaction liquid to obtain a homogeneous solution. The ratio of the number of molecules of p-heptyl phenol to the number of ureido groups in the reaction liquid was 7.6. Line 13 was opened and the reaction liquid was transferred to the storage tank 104 via the line 13.

Steps (B) and (D): Production of N-Substituted Carbamic Acid-O-Aryl Ester and Recovery of Urea The apparatus shown in FIG. 13 was continued to be used.

The packed column 105 packed with a packing material (Helipack No. 3) was heated to 240° C. and the pressure inside the column was set to 50 kPa. The reaction liquid obtained in step (A) was fed from the line 14 provided in the packed column 105 at the rate of about 3.8 g/min. Since the reaction is initially in an unsteady state, the sample at that time was discarded. The amount of reaction liquid fed after the reaction had reached a steady state was about 37.8 kg. The reaction liquid was recovered in the storage tank 110 through the line 16 provided in the bottom of the packed column 105. A gaseous phase component was condensed from the line 15 provided in the top of the packed column 105 with the condenser 106, and the resulting liquid phase component was recovered in the storage tank 109 via the gas-liquid separator 108. The amount of the condensed component recovered in the storage tank 109 was 13.3 kg, and when the condensed component was analyzed by $^1$H-NMR, the condensed component was found to contain urea and 1-butanol. The urea content was 9.09% by weight and the 1-butanol content was 89.1% by weight. When the reaction liquid recovered in the storage tank 110 was analyzed by liquid chromatography and $^1$H-NMR, the reaction liquid was found to contain N,N'-hexanediyl-di(carbamic acid(p-heptylphenyl)ester), and the yield of N,N'-hexanediyl-di(carbamic acid(p-heptylphenyl) ester) based on hexamethylenediamine was about 94%. Urea was not detected in the reaction liquid. The amount of ammonia contained in the reaction liquid was 8.1 ppm.

Step (F): Production of Isocyanate by Thermal Decomposition of N-Substituted Carbamic Acid-O-Aryl Ester The apparatus shown in FIG. 17 was used.

The thin film distillation apparatus 602 having a heat-conducting surface area of 0.2 m$^2$ was heated to 220° C. and the pressure within the thin film distillation apparatus was set to about 1.3 kPa. The reaction liquid recovered in the storage tank 110 in step (B) was placed in the storage tank 601 and supplied to the thin film distillation apparatus at the rate of about 1800 g/hr via the line 60. A liquid component was extracted from the line 62 provided in the bottom of thin film distillation apparatus 602 and recovered in the storage tank 603. The liquid component recovered in the storage tank 603 was again supplied to the thin film distillation apparatus 602 through the line 63. A gaseous component containing hexamethylene diisocyanate and p-heptyl phenol was extracted from the line 61 provided in the upper portion of the thin film distillation apparatus 602. The gaseous component was introduced into the distillation column 604, and the low boiling point component was separated by distillation. A liquid phase component was supplied to the distillation column 609 from the line 68 provided at a portion of the distillation column 604 lower than the feed line and further subjected to distillative separation. The gaseous phase component was condensed in the condenser 610 via the line 69 and recovered in the storage tank 612 through the gas-liquid separator 611.

When the condensate was analyzed by $^1$H-NMR and gas chromatography, the condensate was found to contain about 99% by weight of hexamethylene diisocyanate. The yield based on the organic amine (hexamethylene diamine) was about 90%.

Example 4

Production of N-Substituted Carbamic Acid-O-Aryl Ester by Route 2

Route (A): Production of Compound Having Ureido Groups

The apparatus used in FIG. 13 was used.

43.5 kg of an aromatic hydroxy compound in the form of 4-tert-amyl phenol and 3.61 kg of urea were mixed in the storage tank 101 heated to 80° C. with the line 13 closed, and the mixture was transferred to the stirring tank 103 heated to 80° C. 1.12 kg of aniline were then supplied at the rate of about 10 g/min (supply rate of aniline) from the storage tank 102 to the stirring tank 603 via the line 12 while stirring the stirring tank 103. Following completion of supplying hexamethylenediamine, stirring was continued for about 28 hours and the reaction liquid was sampled. As a result of analyzing the reaction liquid by liquid chromatography, the reaction liquid was found to contain 4.5% by weight of N-phenylurea. The ratio of the number of molecules of 4-tert-amyl phenol to the number of ureido groups in the reaction liquid was 11. The amount of ammonia contained in the reaction liquid was 3800 ppm.

Line 63 was opened and the reaction liquid was transferred to the storage tank 604 via the line 63.

Steps (B) and (D): Production of N-Substituted Carbamic Acid Mono(O-Aryl Ester)

The apparatus shown in FIG. 13 was continued to be used.

The packed column 105 packed with a packing material (Helipack No. 3) was heated to 200° C. and the pressure inside the column was set to 8 kPa. The reaction liquid obtained in step (A) was fed from the line 14 provided in the packed column 105 at the rate of about 1.6 g/min. Since the reaction is initially in an unsteady state, the sample at that time was discarded. The amount of reaction liquid fed after the reaction had reached a steady state was about 8.95 kg. The reaction liquid was recovered in the storage tank 110 through the line 16 provided in the bottom of the packed column 105. A gaseous phase component was introduced into the condenser 106 from the line 15 provided in the top of the packed column 105, and the resulting liquid phase component was recovered in the storage tank 109 via the gas-liquid separator 108. When the condensed component recovered in the storage tank 109 was analyzed by $^1$H-NMR, the condensed component was found to contain urea and 4-tert-amyl phenol. The amount of reaction liquid recovered in the storage tank 110 was 8.72 kg. When the reaction liquid was analyzed by liquid chromatography and $^1$H-NMR, the reaction liquid was found to contain N-phenylcarbamic acid (4-tert-amylphenyl)ester, and the yield of N-phenylcarbamic acid (4-tert-amylphenyl) ester based on aniline was about 93%. The amount of ammonia contained in the reaction liquid was 5.6 ppm.

Step (C): Condensation of N-substituted Carbamic Acid Mono(-O-Aryl Ester)

Figure 15:
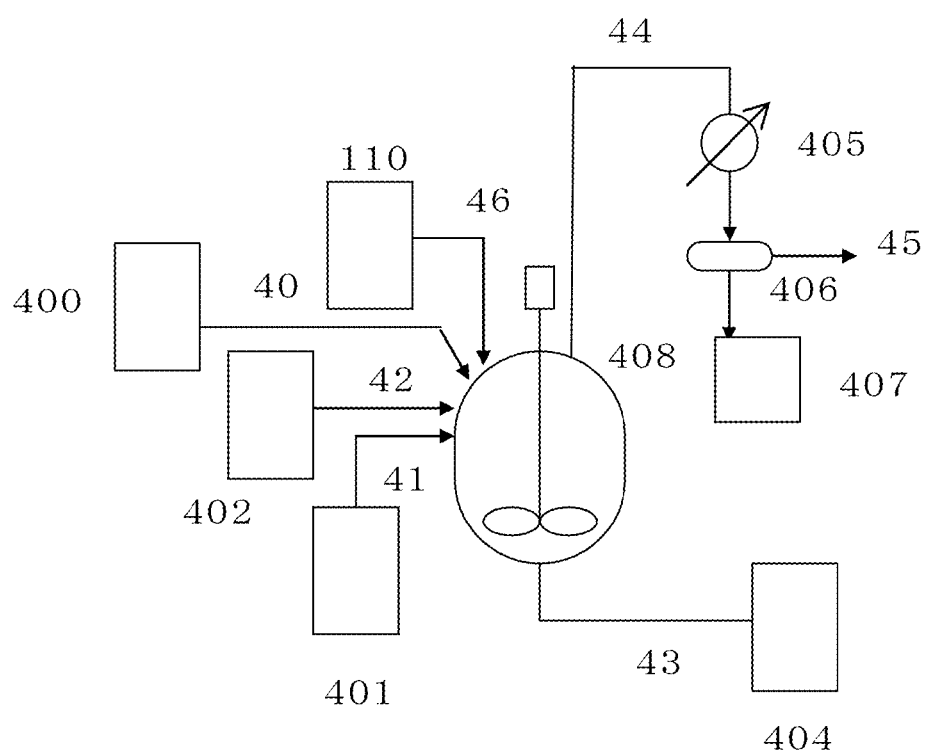
FIG. 15 shows a conceptual drawing depicting an N-substituted carbamic acid ester production apparatus in an example of the present embodiment.

The apparatus shown in FIG. 15 was used.

The reaction liquid recovered in the storage tank 110 in step (B) was placed in a stirring tank 408. The stirring tank 408 was heated to 160° C. and the pressure inside was set to 2 kPa followed by distilling off the aromatic hydroxy compound. The aromatic hydroxy compound in the form of 4-tert-amyl phenol was condensed in a condenser 405 via a line 44 and recovered in a storage tank 407. Next, 1.14 kg of methylal (formaldehyde dimethyl acetal) from a storage tank 400, 4.70 kg of nitrobenzole from a storage tank 401, and 5.6 kg of sulfuric acid from a storage tank 402 were added to the stirring tank 408 followed by heating for 10 hours at 100° C. while stirring the stirring tank 408. Solvent and unreacted substances were then distilled off by maintaining the temperature inside the stirring tank 408 at 100° C. and reducing the pressure inside to 1 kPa. When the resulting compound was analyzed by liquid chromatography, it was found to be a mixture containing about 55% by weight of N,N'-(methanediyl-diphenyl)-di(carbamic acid(4-tert-amylphenyl)ester). About 5.1 kg of an aromatic hydroxy compound (4-tert-amyl phenol) were added to the mixture to obtain a homogeneous solution followed by transferring the solution to a storage tank 404.

Step (F): Production of Isocyanate by Thermal Decomposition of N-Substituted Carbamic Acid-O-Aryl Ester The apparatus shown in FIG. 18 was used.

A thin film distillation apparatus 1002 (Kobelco Eco-Solutions Co., Ltd., Japan) having a heat-conducting surface area of 0.2 m$^2$ was heated to 260° C. and the pressure within the thin film distillation apparatus was set to about 1.5 kPa. The reaction liquid recovered in the storage tank 404 in step (C) was placed in a storage tank 1001 and supplied to the thin film distillation apparatus at the rate of about 1200 g/hr via a line A1. A liquid component was extracted from a line A4 provided in the bottom of thin film distillation apparatus 1002 and recovered in a storage tank 1003. The liquid component recovered in the storage tank 1003 was again supplied to the thin film distillation apparatus 1002 through a line A3. A gaseous component was extracted from a line A4 provided in the upper portion of the thin film distillation apparatus 1002. The gaseous component was introduced into a distillation column 1004, and the low boiling point component was separated by distillation. A liquid phase component was supplied to a distillation column 1009 from a line A8 provided at a portion of the distillation column 1004 lower than the feed line and further subjected to distillative separation. A liquid phase component was supplied to a distillation column 1014 from a line A12 provided at a portion of the distillation column 1009 lower than the feed line and further subjected to distillative separation.

A gaseous phase component was extracted from a line A13 provided in the top of the distillation column 1014 and condensed in a condenser 1015, and the condensate was recovered in a storage tank 1019. When the condensate was analyzed by $^1$H-NMR, it was found to be a solution containing about 99% by weight of 4,4'-diphenylmethane diisocyanate (MDI). The yield based on aniline was about 50%.

Step (E): Production of N-Substituted Carbamic Acid Ester by Reusing Mixture Obtained in Condenser When the ammonia content of the mixture recovered in the storage tank 109 in step (B) of Example 3 was analyzed, it was found to be 1800 ppm. 19.0 kg of 4-tert-amyl phenol and 0.690 kg of urea were added to 14.7 kg of the mixture followed by transferring to the stirring tank 603 and carrying out the same method as step (A) using 0.820 kg of aniline. A solution containing 4.5% by weight of phenylurea was obtained. The same method as step (B) was carried out using this solution instead of the solution of step (A). The yield of N-phenylcarbamic acid (4-tert-amylphenyl) ester in the reaction liquid recovered in the storage tank 110 based on aniline was about 93%.

Example 5

Production of N-Substituted Carbamic Acid-O-Aryl Ester by Route 3

Route (A): Production of Compound Having Ureido Groups

The apparatus used in FIG. 13 was used.

14.6 kg of a solvent (1-octanol, Wako Pure Chemical Industries, Ltd., Japan) and 1.47 kg of urea were mixed in the storage tank 101 heated to 120° C. with the line 13 closed, and the mixture was transferred to the stirring tank 103 (internal volume: 80 L, provided with baffles) heated to 120° C. 0.87 kg of an organic amine in the form of 3-aminomethyl-3,5,5-trimethylcyclohexylamine were then supplied at the rate of about 10 g/min from the storage tank 102 to the stirring tank 103 via the line 12 while stirring the stirring tank 103. Following completion of supplying the 3-aminomethyl-3,5,5-trimethylcyclohexylamine, stirring was continued for about 2 hours and the reaction liquid was sampled. As a result of analyzing the reaction liquid by liquid chromatography, the reaction liquid was found to contain about 7.87% by weight of 3-(ureidomethyl)-3,5,5-trimethylcyclohexylurea. In addition, the concentration of ammonia in the reaction liquid was 7300 ppm. 13.4 kg of an aromatic hydroxy compound in the form of p-dodecyl phenol were added from the storage tank 101 to obtain a homogeneous solution. Line 13 was opened and the solution was transferred to the storage tank 104 via the line 13.

Steps (R) and (D): Production of N-Substituted Carbamic Acid-O-Alkyl Ester and Recovery of Urea The apparatus shown in FIG. 13 was continued to be used.

A packed column 105 packed with a packing material (Helipack No. 3) was heated to 190° C. The reaction liquid obtained in step (A) was fed from a line 14 provided in the packed column 105 at the rate of about 1.1 g/min. Since the reaction is initially in an unsteady state, the sample at that time was discarded. The amount of reaction liquid fed after the reaction had reached a steady state was about 15.1 kg. The reaction liquid was recovered in a storage tank 110 through a line 16 provided in the bottom of the packed column 105. A gaseous phase component was condensed from a line 15 provided in the top of the packed column 105 with a condenser 106, and the resulting liquid phase component was recovered in a storage tank 109 via a gas-liquid separator 108. When a condensed component recovered in the storage tank 109 was analyzed by $^1$H-NMR, the condensed component was found to contain 1-octanol and urea. The amount of reaction liquid recovered in the storage tank 110 was 8.80 kg. When the reaction liquid was analyzed by liquid chromatography and $^1$H-NMR, the reaction liquid was found to contain 3-((1-octyloxy)carbonylamidomethyl)-3,5,5-trimethylcyclohexyl carbamic acid (1-octyl)ester, and the yield based on 3-aminomethyl-3,5,5-trimethylcyclohexylamine was about 95%. The ammonia concentration of the reaction liquid was 5.8 ppm.

Step (P): Transesterification Reaction

Figure 16:
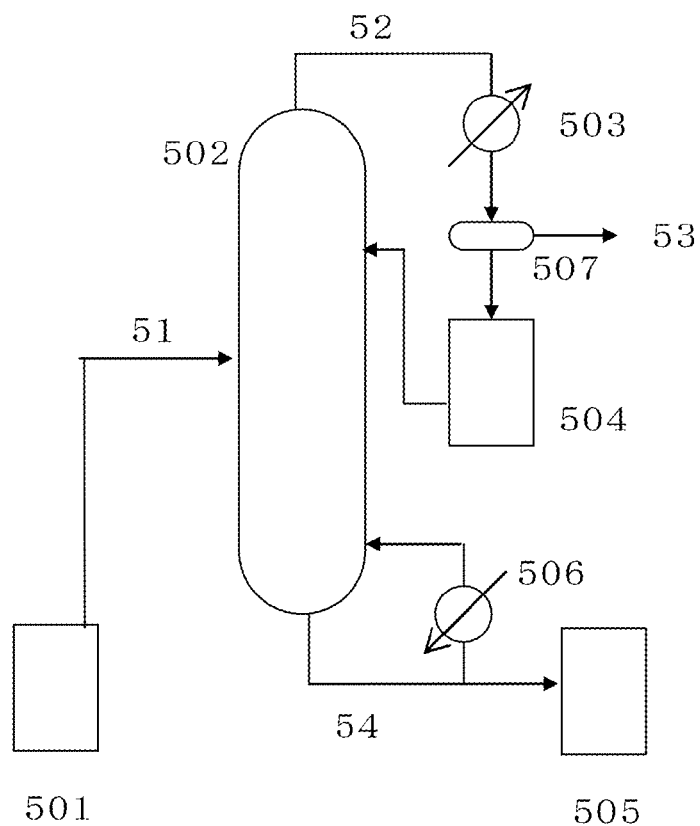
FIG. 16 shows a conceptual drawing depicting a transesterification reaction apparatus in an example of the present embodiment.

The apparatus shown in FIG. 16 was used.

0.5% by weight of a catalyst in the form of dibutyl tin dilaurate was added to the reaction liquid obtained in the step described above, and the resulting solution was placed in a storage tank 501. A packed column 502 packed with a packing material (Helipack No. 3) was heated to 260° C. and the pressure inside the column was set to 26 kPa. The mixture in the storage tank 501 was fed from a line 51 provided in the packed column 502 at the rate of about 1.9 g/min. A reaction liquid was recovered in a storage tank 505 via a line 54 provided in the bottom of the packed column 502. A gaseous phase component was introduced into a condenser 503 from a line 52 provided in the top of the packed column 502, and the resulting liquid phase component was recovered in a storage tank 504 through a gas-liquid separator 507. The amount of reaction liquid recovered in the storage tank 505 was 18.2 kg. When the reaction liquid was analyzed by liquid chromatography and $^1$H-NMR, the reaction liquid was found to be a solution containing 3-((p-dodecylphenyloxy)carbonylamidomethyl)-3,5,5-trimethylcyclohexyl carbamic acid (p-dodecylphenyl)ester, and the yield based on 3-aminomethyl-3,5,5-trimethylcyclohexylamine was about 89%.

Step (F): Production of Isocyanate by Thermal Decomposition of N-Substituted Carbamic Acid-O-Aryl Ester The apparatus shown in FIG. 17 was used.

A thin film distillation apparatus 602 (Kobelco Eco-Solutions Co., Ltd., Japan) having a heat-conducting surface area of 0.2 m$^2$ was heated to 220° C. and the pressure within the thin film distillation apparatus was set to about 1.3 kPa. The reaction liquid recovered in the storage tank 110 in step (B) was placed in a storage tank 601 and supplied to the thin film distillation apparatus at the rate of about 1080 g/hr via a line 60. A liquid component was extracted from a line 62 provided in the bottom of thin film distillation apparatus 602 and recovered in a storage tank 603. The liquid component recovered in the storage tank 603 was again supplied to the thin film distillation apparatus 602 through a line 63. A gaseous component containing isophorone diisocyanate and p-dodecyl phenol was extracted from a line 61 provided in the upper portion of the thin film distillation apparatus 602. The gaseous component was introduced into a distillation column 604, and the low boiling point component was separated by distillation. A liquid phase component was supplied to a distillation column 609 from a line 68 provided at a portion of the distillation column 604 lower than the feed line and further subjected to distillative separation. The gaseous phase component was condensed in a condenser 610 via a line 69 and recovered in a storage tank 612 through a gas-liquid separator 611.

When the condensate was analyzed by $^1$H-NMR and gas chromatography, the condensate was found to contain about 99% by weight of isophorone diisocyanate. The yield based on the organic amine (3-aminomethyl-3,5,5-trimethylcyclohexylamine) was about 83%.

Step (E): Production of N-Substituted Carbamic Acid Ester by Reusing Mixture Obtained in Condenser When the ammonia concentration of the mixture recovered in the storage tank 109 in step (B) of Example 4 was analyzed, it was found to be 1300 ppm. 7.57 kg of 1-octanol and 0.70 kg of urea were added to 9.4 kg of the mixture followed by transferring to the stirring tank 103 and carrying out the same method as step (A) using 0.87 kg of 3-aminomethyl-3,5,5-trimethylcyclohexylamine. A solution containing 6.3% by weight of 3-(ureidomethyl)-3,5,5-trimethylcyclohexylurea was obtained. The same method as step (B) was carried out using this solution instead of the solution of step (A). The reaction liquid recovered in a storage tank 110 contained 3-((3-methylbutyloxy)carbonylamidomethyl)-3,5,5-trimethylcyclohexyl carbamic acid (3-methylbutyl)ester, and the yield of 3-((3-methylbutyloxy)carbonylamidomethyl)-3,5,5-trimethylcyclohexyl carbamic acid (3-methylbutyl)ester based on 3-aminomethyl-3,5,5-trimethylcyclohexylamine was about 95%.

Example 6

Production of N-Substituted Carbamic Acid-O-Aryl Ester by Route 4

Route (A): Production of Compound Having Ureido Groups

The apparatus used in FIG. 13 was used.

33.5 kg of a solvent (1-nonanol) and 3.34 kg of urea were mixed in the storage tank 101 heated to 90° C. with the line 13 closed, and the mixture was transferred to the stirring tank 103 heated to 90° C. 1.08 kg of aniline were then supplied at the rate of about 12 g/min from the storage tank 102 to the stirring tank 603 via the line 12 while stirring the stirring tank 103. Following completion of supplying the aniline, stirring was continued for about 28 hours and the reaction liquid was sampled. As a result of analyzing the reaction liquid by liquid chromatography, the reaction liquid was found to contain about 5.6% by weight of phenylurea. The concentration of ammonia in the reaction liquid was 7900 ppm. Unreacted amino groups were not detected. Following the reaction, 25.9 kg of an aromatic hydroxy compound in the form of 2-phenyl phenol were added to obtain a mixture. The ratio of the number of alcohol molecules to the number of ureido groups in the mixture was 10.1. Line 63 was opened and the mixture was transferred to the storage tank 604 via the line 63.

Steps (R) and (D): Production of N-Substituted Carbamic Acid Mono(-O—$R^2$ Ester)

The packed column 105 packed with a packing material (Helipack No. 3) was heated to 210° C. and the pressure inside the column was set to 50 kPa. The reaction liquid obtained in step (A) was fed from the line 14 provided in the packed column 105 at the rate of about 1.2 g/min. Since the reaction is initially in an unsteady state, the sample at that time was discarded. The amount of reaction liquid fed after the reaction had reached a steady state was about 35.8 kg. The reaction liquid was recovered in the storage tank 110 through the line 16 provided in the bottom of the packed column 105. A gaseous phase component was introduced into the condenser 106 from the line 15 provided in the top of the packed column 105, and the resulting liquid phase component was recovered in the storage tank 109 via the gas-liquid separator 108. When the condensed component recovered in the storage tank 109 was analyzed by $^1$H-NMR, the condensed component was found to contain urea and 1-nonanol. The amount of the reaction liquid recovered in the storage tank 110 was 18.9 kg. When the reaction liquid was analyzed by liquid chromatography and $^1$H-NMR, the reaction liquid was found to contain N-phenyl carbamic acid-(nonylester), and the yield of N-phenyl carbamic acid-(nonylester) based on aniline was about 91%.

Step (P): Production of N-Substituted Carbamic Acid Mono(-O-Aryl Ester) by Transesterification Reaction The apparatus shown in FIG. 16 was used.

0.5% by weight of a catalyst in the form of dibutyl tin dilaurate was added to the mixture obtained in step (B) and placed in the storage tank 501. A packed column 502 packed with a packing material (Helipack No. 3) and having an inner diameter of 20 mm was heated to 260° C. and the pressure inside the column was set to 26 kPa. The reaction liquid obtained in step (A) was fed from the line 51 provided in the packed column 105 at the rate of about 1.9 g/min. A reaction liquid was recovered in the storage tank 505 via the line 54 provided in the bottom of the packed column 502. A gaseous phase component was introduced into the condenser 503 from the line 52 provided in the top of the packed column 502, and the resulting liquid phase component was recovered in the storage tank 504 through the gas-liquid separator 507. The amount of reaction liquid recovered in the storage tank 505 was 26.4 kg. When the reaction liquid was analyzed by liquid chromatography and $^1$H-NMR, the reaction liquid was found to be a solution containing N-phenyl carbamic acid (2-phenylphenyl)ester, and the yield of N-phenyl carbamic acid (2-phenylphenyl) ester based on aniline was about 89%.

Step (C): Condensation of N-Substituted Carbamic Acid Mono(-O-Aryl Ester)

The apparatus shown in FIG. 15 was used.

The reaction liquid recovered in the storage tank 505 in step (B) was placed in the stirring tank 408. The stirring tank 408 was heated to 160° C. and the pressure inside was set to 1 kPa followed by distilling off 2-phenyl phenol. The 2-phenyl phenol was condensed in the condenser 405 via the line 44 and recovered in the storage tank 407. Next, 2.04 kg of methylal from the storage tank 400, 1.94 kg of nitrobenzole from the storage tank 401, and 1.02 kg of sulfuric acid from the storage tank 402 were added to the stirring tank 408 followed by heating for 24 hours at 90° C. while stirring the stirring tank 408. Solvent and unreacted substances were then distilled off by maintaining the temperature of the stirring tank 408 at 90° C. and reducing the pressure inside to about 1 kPa. When the resulting compound was analyzed by liquid chromatography, it was found to be a mixture containing about 53% by weight of N,N'-(methanediyl-diphenyl)-bis(carbamic acid(2-phenylphenyl)ester).

Step (F): Production of Isocyanate by Thermal Decomposition of N-Substituted

Carbamic Acid-O-Aryl Ester

Figure 18:
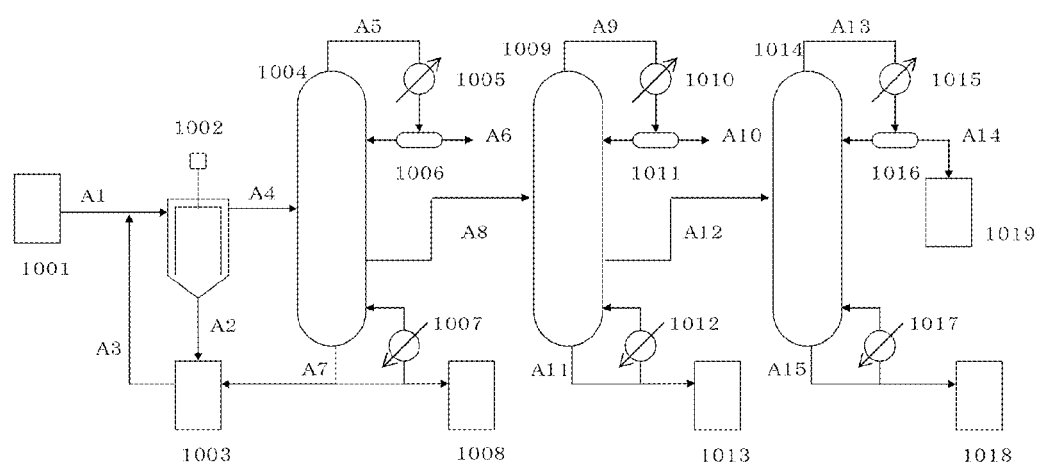
FIG. 18 shows a conceptual drawing depicting an isocyanate production apparatus in an example of the present embodiment.

The apparatus shown in FIG. 18 was used.

A thin film distillation apparatus 1002 (Kobelco Eco-Solutions Co., Ltd., Japan) having a heat-conducting surface area of 0.2 m² was heated to 260° C. and the pressure within the thin film distillation apparatus was set to about 1.5 kPa. The reaction liquid recovered in the storage tank 404 in step (C) was placed in a storage tank 1001 and supplied to the thin film distillation apparatus at the rate of about 1200 g/hr via a line A1. A liquid component was extracted from a line A4 provided in the bottom of thin film distillation apparatus 1002 and recovered in a storage tank 1003. The liquid component recovered in the storage tank 1003 was again supplied to the thin film distillation apparatus 1002 through a line A3. A gaseous component was extracted from a line A4 provided in the upper portion of the thin film distillation apparatus 1002. The gaseous component was introduced into a distillation column 1004, and the low boiling point component was separated by distillation. A liquid phase component was supplied to a distillation column 1009 from a line A8 provided at a portion of the distillation column 1004 lower than the feed line and further subjected to distillative separation. A liquid phase component was supplied to the distillation column 1014 from the line A12 provided at a portion of the distillation column 1009 lower than the feed line and further subjected to distillative separation.

A gaseous phase component was extracted from the line A13 provided in the top of the distillation column 1014 and condensed in the condenser 1015, and the condensate was recovered in the storage tank 1019. When the condensate was analyzed by ¹H-NMR, it was found to be a solution containing about 99% by weight of 4,4'-diphenylmethane diisocyanate (MDI). The yield based on aniline was about 54%.

Step (E): Production of N-Substituted Carbamic Acid Ester by Reusing Mixture Obtained in Condenser When the ammonia content of the mixture recovered in the storage tank 109 in step (R) of Example 5 was analyzed, it was found to be 1500 ppm. 11.4 kg of 1-nonanol and 1.47 kg of urea were added to 14.7 kg of the mixture followed by transferring to the stirring tank 603 and carrying out the same method as step (A) using 1.08 kg of aniline. A solution containing about 6.8% by weight of phenylurea was obtained. The same method as step (B) was carried out using this solution instead of the solution of step (A). The yield of N-phenylcarbamic acid-(nonylester) in the reaction liquid recovered in the storage tank 110 based on aniline was about 91%.

Example 7

Production of N-Substituted Carbamic Acid-O-Aryl Ester by Route 5

Step (A): Production of Compound Having Ureido Groups

The apparatus used in FIG. 13 was used.

25.4 kg of a solvent (1-heptanol) and 3.50 kg of urea were mixed in the storage tank 101 heated to 90° C. with the line 13 closed, and the mixture was transferred to the stirring tank 103 heated to 90° C. 1.13 kg of aniline were then supplied at the rate of about 18 g/min from the storage tank 102 to the stirring tank 103 via the line 12 while stirring the stirring tank 603. Following completion of supplying the aniline, stirring was continued for about 28 hours and the reaction liquid was sampled. As a result of analyzing the reaction liquid by liquid chromatography, the reaction liquid was found to contain about 7.4% by weight of phenylurea. The concentration of ammonia in the reaction liquid was 8300 ppm. Unreacted amino groups were not detected. 24.2 kg of a hydroxy compound in the form of 2,4-di-tert-amyl phenol (Tokyo Chemical Industry Co., Ltd., Japan) were added to the reaction liquid to obtain a mixture. The ratio of the number of alcohol molecules to the number of ureido groups in the mixture was 9.0.

Line 63 was opened and the mixture was transferred to the storage tank 604 via the line 63.

Steps (R) and (D): Production of N-Substituted Carbamic Acid Mono(-O-Alkyl Ester)

The packed column 105 packed with a packing material (Helipack No. 3) and having a diameter of 40 mm was heated to 190° C. and the pressure inside the column was set to 50 kPa. The reaction liquid obtained in step (A) was fed from the line 14 provided in the packed column 105 at the rate of about 1.0 g/min. Since the reaction is initially in an unsteady state, the sample at that time was discarded. The amount of reaction liquid fed after the reaction had reached a steady state was about 28.0 kg. The reaction liquid was recovered in the storage tank 110 through the line 16 provided in the bottom of the packed column 105. A gaseous phase component was condensed in the condenser 106 from the line 15 provided in the top of the packed column 105, and the resulting liquid phase component was recovered in the storage tank 109 via the gas-liquid separator 108. When the condensed component recovered in the storage tank 109 was analyzed by ¹H-NMR, the condensed component was found to contain urea and 1-heptanol. The amount of the reaction liquid recovered in the storage tank 110 was 13.8 kg. When the reaction liquid was analyzed by liquid chromatography and ¹H-NMR, the reaction liquid was found to contain N-phenyl carbamic acid (1-heptyl)ester, and the yield based on aniline was about 90%.

Step (C): Condensation of N-Substituted Carbamic Acid Mono(-O-Alkyl Ester)

The apparatus shown in FIG. 15 was used.

The reaction liquid recovered in the storage tank 110 in step (R) was placed in the stirring tank 408. The stirring tank 408 was heated to 160° C. and the pressure inside was set to 1 kPa followed by distilling off 1-heptanol. The 1-heptanol was condensed in the condenser 405 via the line 44 and recovered in the storage tank 407. Next, 1.30 kg of methylal from the storage tank 400, 7.34 kg of nitrobenzole from the storage tank 401, and 1.33 kg of sulfuric acid from the storage tank 402 were added to the stirring tank 408 followed by heating for 10 hours at 100° C. while stirring the stirring tank 408. Solvent and unreacted substances were then distilled off by maintaining the temperature of the stirring tank 408 at 100° C. and reducing the pressure inside to about 1 kPa. When the resulting compound was analyzed by liquid chromatography, it was found to be a mixture containing about 63% by weight of N,N'-(methanediyl-diphenyl)-bis(carbamic acid octyl ester). 24.2 kg of an aromatic hydroxy compound in the form of 2,4-di-tert-amyl phenol were then added to the mixture to obtain a mixture.

Step (P): Production of N-Substituted Carbamic Acid-O-Aryl Ester by Transesterification Reaction The apparatus shown in FIG. 16 was used.

0.5% by weight of a catalyst in the form of dibutyl tin dilaurate was added to the mixture obtained in step (C) and placed in the storage tank 501. The packed column 502 packed with a packing material (Helipack No. 3) and having an inner diameter of 20 mm was heated to 250° C. and the pressure inside the column was set to 20 kPa. The reaction liquid obtained in step (A) was fed from the line 51 provided in the packed column 502 at the rate of about 1.3 g/min. A reaction liquid was recovered in the storage tank 505 via the line 54 provided in the bottom of the packed column 502. A gaseous phase component was introduced into the condenser 503 from the line 52 provided in the top of the packed column 502, and the resulting liquid phase component was recovered in the storage tank 504 through the gas-liquid separator 507. The amount of reaction liquid recovered in the storage tank 505 was 25.0 kg. When the reaction liquid was analyzed by liquid chromatography and $^1$H-NMR, the reaction liquid was found to be a solution containing N,N'-(methanediyl-diphenyl)-bis(carbamic acid(2,4-di-tert-amylphenyl)ester).

Step (F): Production of Isocyanate by Thermal Decomposition of N-Substituted Carbamic Acid-O-Aryl Ester The apparatus shown in FIG. 18 was used.

A thin film distillation apparatus 1002 (Kobelco Eco-Solutions Co., Ltd., Japan) having a heat-conducting surface area of 0.2 m$^2$ was heated to 260° C. and the pressure within the thin film distillation apparatus was set to about 1.5 kPa. The reaction liquid recovered in the storage tank 404 in step (C) was placed in a storage tank 1001 and supplied to the thin film distillation apparatus at the rate of about 1200 g/hr via a line A1. A liquid component was extracted from a line A4 provided in the bottom of thin film distillation apparatus 1002 and recovered in a storage tank 1003. The liquid component recovered in the storage tank 1003 was again supplied to the thin film distillation apparatus 1002 through a line A3. A gaseous component was extracted from a line A4 provided in the upper portion of the thin film distillation apparatus 1002. The gaseous component was introduced into a distillation column 1004, and the low boiling point component was separated by distillation. A liquid phase component was supplied to a distillation column 1009 from a line A8 provided at a portion of the distillation column 1004 lower than the feed line and further subjected to distillative separation. A liquid phase component was supplied to the distillation column 1014 from the line A12 provided at a portion of the distillation column 1009 lower than the feed line and further subjected to distillative separation.

A gaseous phase component was extracted from the line A13 provided in the top of the distillation column 1014 and condensed in the condenser 1015, and the condensate was recovered in the storage tank 1019. When the condensate was analyzed by $^1$H-NMR, it was found to be a solution containing about 99% by weight of 4,4'-diphenylmethane diisocyanate (MDI). The yield based on aniline was about 47%.

Step (E): Production of N-Substituted Carbamic Acid Ester by Reusing Mixture Obtained in Condenser When the ammonia content of the mixture recovered in the storage tank 109 in step (B) of Example 6 was analyzed, it was found to be 900 ppm. 9.48 kg of 1-heptanol and 1.54 kg of urea were added to the mixture followed by transferring to the stirring tank 603 and carrying out the same method as step (A) using 1.12 kg of aniline. A solution containing about 7.4% by weight of phenylurea was obtained. The same method as step (B) was carried out using this solution instead of the solution of step (A). The yield of N-phenylcarbamic acid-(heptylester) in the reaction liquid recovered in the storage tank 110 based on aniline was about 90%.

Examples 8 to 30

Figure 17:
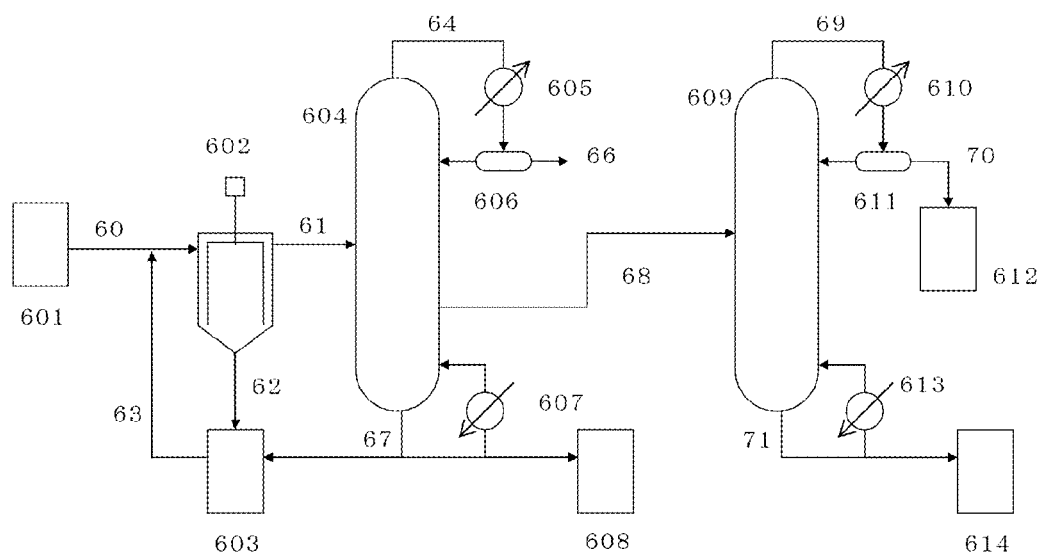
FIG. 17 shows a conceptual drawing depicting an isocyanate production apparatus in an example of the present embodiment.

The same method as Example 1 was carried out while changing the compounds and reaction conditions used. The compounds and reaction conditions used in step (A) of Examples 8 to 30 along with the results are shown in Tables 2 and 3. In addition, the compounds and reaction conditions used in steps (B) and (D) of Examples 8 to 30 along with the results are shown in Tables 4 and 5. In addition, the compounds and reaction conditions used in step (F) of Examples 8 to 30 along with the results are shown in Tables 6 and 7. Although "FIG. 17" and "FIG. 18" are indicated in the "apparatus drawing" column for step (F), "FIG. 17" indicates that the same method as step (F) of Example 1 was carried out using an apparatus as shown in FIG. 17. On the other hand, "FIG. 18" indicates that the same method as step (F) of Example 4 was carried out using an apparatus as shown in FIG. 18. In addition, the compounds and reaction conditions used in step (E) of Examples 8 to 30 along with the results are shown in Tables 8 and 9. Furthermore, the reaction conditions and results for Example 1 are also shown in Tables 2 to 9 to clarify correspondence with the description of Example 1.

In addition, the following abbreviations are used in the tables of the examples.

HDA: Hexamethylenediamine
IPDA: 3-aminomethyl-3,5,5-trimethylcyclohexylamine
TDA: 2,4-toluenediamine
MDA: 4,4'-methylenedianiline
H-MDA: 4,4'-methylenedi(cyclohexylamine)

TABLE 2

| | Step (A) | | | | | | |
|---|---|---|---|---|---|---|---|
| | Temperature | | | Amount | Aromatic hydroxy compound | | |
| Example | of stirring tank 103 (° C.) | Organic amine (amount used) | | of urea used | Name | Amount used | Water content |
| Example 1 | 120 | HDA | (1.50 kg) | 3.10 kg | p-heptyl phenol | (41.8 kg) | 15 ppm |
| Example 8 | 190 | HDA | (1.42 kg) | 3.31 kg | 2-naphthol | (29.9 kg) | 13 ppm |
| Example 9 | 150 | HDA | (1.29 kg) | 2.68 kg | 4-phenyl phenol | (18.9 kg) | 16 ppm |
| Example 10 | 100 | HDA | (1.14 kg) | 2.42 kg | 2-ethoxyphenol | (18.9 kg) | 20 ppm |
| Example 11 | 130 | IPDA | (1.82 kg) | 2.25 kg | 4-cumyl phenol | (14.5 kg) | 16 ppm |
| Example 12 | 100 | IPDA | (1.22 kg) | 1.64 kg | 4-(1,1,3,3-tetramethylbutyl)phenol | (8.26 kg) | 630 ppm |
| Example 13 | 100 | IPDA | (1.19 kg) | 1.61 kg | p-nonyl phenol | (61.6 kg) | 20 ppm |
| Example 14 | 110 | IPDA | (1.01 kg) | 1.35 kg | p-dodecyl phenol | (62.3 kg) | 58 ppm |
| Example 15 | 100 | TDA | (2.11 kg) | 3.38 kg | p-dodecyl phenol | (19 kg) | 720 ppm |

TABLE 2-continued

| Example | | | | | | | |
|---|---|---|---|---|---|---|---|
| Example 16 | 90 | TDA | (3.51 kg) | 1.99 kg | 4-tert-butyl phenol | (16.4 kg) | 14 ppm |
| Example 17 | 70 | TDA | (1.19 kg) | 2.46 kg | p-nonyl phenol | (38.6 kg) | 530 ppm |
| Example 18 | 80 | TDA | (1.21 kg) | 2.49 kg | 2-naphthol | (28.6 kg) | 210 ppm |

| | Step (A) | | | |
|---|---|---|---|---|
| | Solution after reaction | | | |
| Example | Organic amine supply rate | Compound having ureido groups formed | Concentration of compound having ureido groups | Ammonia concentration (ppm) | Ratio of number of molecules of aromatic hydroxy compound to number of ureido groups |
| Example 1 | 20 g/min | 1,1'-(hexane-1,6-diyl) diurea | 6.3 wt % | 6300 ppm | 7.5 |
| Example 8 | 83 g/min | 1,1'-(hexane-1,6-diyl) diurea | 7.2 wt % | 6200 ppm | 8.6 |
| Example 9 | 20 g/min | 1,1'-(hexane-1,6-diyl) diurea | 10 wt % | 5100 ppm | 5.1 |
| Example 10 | 15 g/min | 1,1'-(hexane-1,6-diyl) diurea | 11.3 wt % | 4500 ppm | 9.2 |
| Example 11 | 42 g/min | 3-(ureidomethyl)-3,5,5-trimethylcyclohexylurea | 14.9 wt % | 3500 ppm | 3.2 |
| Example 12 | 20 g/min | 3-(ureidomethyl)-3,5,5-trimethylcyclohexylurea | 14.6 wt % | 7800 ppm | 3.3 |
| Example 13 | 20 g/min | 3-(ureidomethyl)-3,5,5-trimethylcyclohexylurea | 2.7 wt % | 6200 ppm | 20.4 |
| Example 14 | 20 g/min | 3-(ureidomethyl)-3,5,5-trimethylcyclohexylurea | 2.3 wt % | 3800 ppm | 20.6 |
| Example 15 | 20 g/min | 2,4-toluenediurea | 12.2 wt % | 8820 ppm | 2.5 |
| Example 16 | 13 g/min | 2,4-toluenediurea | 18.6 wt % | 3600 ppm | 2.5 |
| Example 17 | 17 g/min | 2,4-toluenediurea | 4.8 wt % | 8210 ppm | 9.1 |
| Example 18 | 20 g/min | 2,4-toluenediurea | 6.4 wt % | 4200 ppm | 10.1 |

TABLE 3

| | Step (A) | | | | | |
|---|---|---|---|---|---|---|
| | Temperature of stirring tank 103 (° C.) | Organic amine (amount used) | Amount of urea used | Aromatic hydroxy compound | | Water content |
| Example | | | | Name | Amount used | |
| Example 19 | 80 | TDA | (1.53 kg) | 3.08 kg | 3,5-dimethoxy phenol | (32.8 kg) | 150 ppm |
| Example 20 | 100 | MDA | (0.53 kg) | 0.64 kg | 4-(1,1,3,3-tetramethylbutyl) phenol | (44.1 kg) | 35 ppm |
| Example 21 | 80 | MDA | (0.53 kg) | 0.75 kg | 3,5-dimethoxy phenol | (51.0 kg) | 40 ppm |
| Example 22 | 100 | H-MDA | (0.41 kg) | 2.03 kg | 4-ethyl phenol | (31.9 kg) | 80 ppm |
| Example 23 | 100 | H-MDA | (1.38 kg) | 2.05 kg | 2-tert-amyl phenol | (37.7 kg) | 120 ppm |
| Example 24 | 200 | HDA | (0.93 kg) | 8.65 kg | Hydroquinone | (52.9 kg) | 330 ppm |
| Example 25 | 180 | IPDA | (0.83 kg) | 4.39 kg | Bisphenol A | (53.4 kg) | 20 ppm |
| Example 26 | 120 | HDA | (0.93 kg) | 2.02 kg | 2,4-di-tert-amyl phenol | (56.3 kg) | 32 ppm |
| Example 27 | 120 | HDA | (0.53 kg) | 1.15 kg | 2,4-dicumyl phenol | (55.8 kg) | 50 ppm |
| Example 28 | 130 | HDA | (1.09 kg) | 2.31 kg | 2-phenyl phenol | (55.9 kg) | 14 ppm |

TABLE 3-continued

| Example | | | | | | | |
|---|---|---|---|---|---|---|---|
| Example 29 | 130 | IPDA | (1.15 kg) | 1.66 kg | 2,6-diisopropyl phenol | (32.5 kg) | 90 ppm |
| Example 30 | 100 | IPDA | (1.15 kg) | 2.03 kg | 4-chlorophenol | (52.1 kg) | 310 ppm |

| | Step (A) | | | |
|---|---|---|---|---|
| | Solution after reaction | | | |
| Example | Organic amine supply rate | Compound having ureido groups formed | Concentration of compound having ureido groups | Ammonia concentration (ppm) | Ratio of number of molecules of aromatic hydroxy compound to number of ureido groups |
| Example 19 | 20 g/min | 2,4-toluenediurea | 6.9 wt % | 3200 ppm | 8.6 |
| Example 20 | 90 g/min | 4,4'-methanediyl diphenyldiurea | 1.6 wt % | 2250 ppm | 41.2 |
| Example 21 | 20 g/min | 4,4'-methanediyl diphenyldiurea | 1.1 wt % | 1080 ppm | 120.7 |
| Example 22 | 25 g/min | 4,4'-methanediyl dicyclohexyldiurea | 5.7 wt % | 5210 ppm | 19.4 |
| Example 23 | 24 g/min | 4,4'-methanediyl dicyclohexyldiurea | 4.7 wt % | 3620 ppm | 17.9 |
| Example 24 | 170 g/min | 1,1'-(hexane-1,6-diyl) diurea | 2.3 wt % | 2400 ppm | 33.3 |
| Example 25 | 180 g/min | 3-(ureidomethyl)-3,5,5-trimethylcyclohexylurea | 2.1 wt % | 2200 ppm | 24.7 |
| Example 26 | 42 g/min | 1,1'-(hexane-1,6-diyl) diurea | 2.8 wt % | 2300 ppm | 15.3 |
| Example 27 | 45 g/min | 1,1'-(hexane-1,6-diyl) diurea | 1.6 wt % | 1100 ppm | 18.9 |
| Example 28 | 38 g/min | 1,1-(hexane-1,6-diyl) diurea | 3.2 wt % | 1020 ppm | 17.9 |
| Example 29 | 29 g/min | 3-(ureidomethyl)-3,5,5-trimethylcyclohexylurea | 4.5 wt % | 1900 ppm | 13.8 |
| Example 30 | 40 g/min | 3-(ureidomethyl)-3,5,5-trimethylcyclohexylurea | 3.1 wt % | 1200 ppm | 30.6 |

TABLE 4

| | Step (B) | | | | | Step (D) | | |
|---|---|---|---|---|---|---|---|---|
| Example | Temperature of packed column 105 (° C.) | Pressure of packed column 105 (kPa) | Fed amount (kg) | N-substituted carbamic acid-O-aryl ester formed (yield based on organic amine) | | Ammonia concentration in reaction liquid | Recovered amt. in storage tank 109 (kg) | Aromatic hydroxy compound content (%) | Urea content (%) |
| Example 1 | 240 | 26 | 35.1 | N,N'-hexanediyl-di(carbamic acid (p-heptylphenyl) ester | (97%) | 9.0 ppm | 13.5 | 85.4 | 10.2 |
| Example 8 | 240 | 15 | 32.5 | N,N'-hexanediyl-di(carbamic acid (2-napthyl) ester) | (92%) | 11.8 ppm | 11.1 | 80.7 | 14.3 |
| Example 9 | 280 | 30 | 21.1 | N,N'-hexanediyl-di(carbamic acid (4-phenylphenyl) ester) | (97%) | 9.5 ppm | 7.5 | 73.5 | 15.2 |
| Example 10 | 210 | 40 | 20.0 | N,N'-hexanediyl-di(carbamic acid (2-ethoxyphenyl) ester) | (75%) | 330 ppm | 6.8 | 79.8 | 15.7 |
| Example 11 | 280 | 30 | 17.3 | 3-(4-(α,α-dimethylbenzyl)phenoxy)carbonyl-amino-methyl)-3,5,5-trimethylcyclohexyl carbamic acid (4-(α,α-dimethylbenzyl)phenyl) ester | (95%) | 7.5 ppm | 5.5 | 80.1 | 16.0 |
| Example 12 | 230 | 20 | 9.3 | 3-((-4-(1,1,3,3-tetramethylbutyl)phenoxy)carbonyl-amino-methyl-3,5,5-trimethylcyclohexyl carbamic acid (4-(1,1,3,3-tetramethylbutyl)phenyl) ester | (84%) | 8.1 ppm | 5.9 | 70.9 | 24.0 |
| Example 13 | 210 | 20 | 60.7 | 3-((p-nonylphenoxy)carbonylamino-methyl)-3,5,5-trimethylcyclohexyl carbamic acid (p-nonylphenyl) ester | (85%) | 290 ppm | 19.9 | 95.7 | 3.5 |

TABLE 4-continued

| | Step (B) | | | | | Step (D) | | |
|---|---|---|---|---|---|---|---|---|
| Example | Temperature of packed column 105 (° C.) | Pressure of packed column 105 (kPa) | Fed amount (kg) | N-substituted carbamic acid-O-aryl ester formed (yield based on organic amine) | | Ammonia concentration in reaction liquid | Recovered amt. in storage tank 109 (kg) | Aromatic hydroxy compound content (%) | Urea content (%) |
| Example 14 | 230 | 40 | 61.5 | 3-((p-dodecylphenoxy)carbonylamino-methyl)-3,5,5-trimethylcyclohexyl carbamic acid (p-dodecylphenyl) ester | (78%) | 305 ppm | 7.8 | 90.1 | 7.9 |
| Example 15 | 220 | 15 | 23.8 | Toluene-2,4-di(carbamic acid (4-(1,1,3,3-tetramethylbutyl)phenyl) ester) | (73%) | 5.9 ppm | 8.8 | 61.3 | 30.7 |
| Example 16 | 210 | 26 | 22.5 | Toluene-2,4-di(carbamic acid (4-tert-butylphenyl) ester) | (65%) | 6.9 ppm | 8.2 | 55.9 | 37.9 |
| Example 17 | 250 | 20 | 40.5 | Toluene-2,4-di(carbamic acid (p-nonylphenyl) ester) | (91%) | 8.2 ppm | 13.5 | 89.0 | 8.9 |
| Example 18 | 240 | 20 | 29.5 | Toluene-2,4-di(carbamic acid (2-naphthyl) ester) | (70%) | 980 ppm | 9.9 | 86.1 | 11.9 |

TABLE 5

| | Step (B) | | | | | Step (D) | | |
|---|---|---|---|---|---|---|---|---|
| Example | Temperature of packed column 105 (° C.) | Pressure of packed column 105 (kPa) | Fed amount (kg) | N-substituted carbamic acid-O-aryl ester formed (yield based on organic amine) | | Ammonia concentration in reaction liquid | Recovered amt. in storage tank 109 (kg) | Aromatic hydroxy compound content (%) | Urea content (%) |
| Example 19 | 250 | 30 | 34.6 | Toluene-2,4-di(carbamic acid (3,5-dimethoxyphenyl) ester) | (62%) | 1050 ppm | 11.6 | 85.4 | 12.5 |
| Example 20 | 250 | 45 | 43.8 | N,N'-(4,4'-methanediyl-diphenyl)-di(carbamic acid (4-(1,1,3,3-tetramethylbutyl)phenyl) ester) | (87%) | 11 ppm | 14.4 | 97.7 | 2.0 |
| Example 21 | 220 | 30 | 43.8 | N,N'-(4,4'-methanediyl-diphenyl)-di(carbamic acid(3,5-dimethoxyphenyl) ester) | (88%) | 15 ppm | 14.6 | 97.1 | 2.3 |
| Example 22 | 200 | 70 | 33.6 | N,N'-(4,4'-methanediyl-dicyclohexyl)-di(carbamic acid (4-ethylphenyl) ester) | (92%) | 29 ppm | 11.3 | 89.5 | 10.4 |
| Example 23 | 230 | 35 | 43.9 | N,N'-(4,4'-methanediyl-dicyclohexyl)-di(carbamic acid (2-tert-amylphenyl) ester) | (93%) | 11 ppm | 18.1 | 65.5 | 33.4 |
| Example 24 | 250 | 40 | 55.8 | N,N'-hexanediyl-di(carbamic acid (4-hydroxyphenyl) ester) | (68%) | 9.5 ppm | 22.7 | 69.1 | 30.0 |
| Example 25 | 280 | 15 | 56.3 | N,N'-hexanediyl-di(carbamic acid (4-(2-(4-hydroxyphenyl)-2-methyl-ethyl)phenyl) ester) | (69%) | 6.5 ppm | 20.8 | 81.5 | 17.0 |
| Example 26 | 240 | 30 | 53.9 | N,N'-hexanediyl-di(carbamic acid (2,4-di-tert-amylphenyl) ester) | (75%) | 8.3 ppm | 17.9 | 92.4 | 5.0 |
| Example 27 | 280 | 10 | 55.0 | N,N'-hexanediyl-di(carbamic acid (2,4-di-cumylphenyl) ester) | (70%) | 5.4 ppm | 18.2 | 95.1 | 2.9 |
| Example 28 | 270 | 20 | 53.9 | N,N'-hexanediyl-di(carbamic acid (2-phenylphenyl) ester) | (81%) | 4.4 ppm | 17.9 | 92.2 | 5.6 |
| Example 29 | 220 | 20 | 33.5 | 3-((2,6-diisopropylphenoxy)carbonyl-amino-methyl)-3,5,5-trimethylcyclohexyl carbamic acid (2,6-diisopropylphenyl) ester | (54%) | 8.1 ppm | 11.0 | 90.4 | 6.8 |
| Example 30 | 210 | 60 | 50.5 | 3-((4-chlorophenoxy)carbonylamino-methyl)-3,5,5-trimethylcyclohexyl carbamic acid (4-chlorophenyl) ester | (90%) | 5.9 ppm | 16.8 | 92.0 | 6.1 |

TABLE 6

| | | Step (F) | | | |
|---|---|---|---|---|---|
| Example | Apparatus drawing | Temperature of thin film distillation apparatus (° C.) | Pressure of thin film distillation apparatus (kPa) | Recovered isocyanate (yield based on organic amine) | |
| Example 1 | FIG. 17 | 220 | 1.3 | Hexamethylene diisocyanate | (90%) |
| Example 8 | FIG. 17 | 200 | 1.0 | Hexamethylene diisocyanate | (93%) |

TABLE 6-continued

| Example | Apparatus drawing | Step (F) Temperature of thin film distillation apparatus (° C.) | Pressure of thin film distillation apparatus (kPa) | Recovered isocyanate (yield based on organic amine) | |
|---|---|---|---|---|---|
| Example 9 | FIG. 17 | 210 | 2.0 | Hexamethylene diisocyanate | (92%) |
| Example 10 | FIG. 18 | 190 | 1.0 | Hexamethylene diisocyanate | (71%) |
| Example 11 | FIG. 17 | 220 | 1.5 | Isophorone diisocyanate | (92%) |
| Example 12 | FIG. 17 | 210 | 1.0 | Isophorone diisocyanate | (81%) |
| Example 13 | FIG. 17 | 220 | 1.0 | Isophorone diisocyanate | (83%) |
| Example 14 | FIG. 17 | 230 | 0.5 | Isophorone diisocyanate | (75%) |
| Example 15 | FIG. 17 | 190 | 0.8 | 2,4-tolylene diisocyanate | (65%) |
| Example 16 | FIG. 18 | 190 | 0.8 | 2,4-tolylene diisocyanate | (58%) |
| Example 17 | FIG. 17 | 200 | 1.2 | 2,4-tolylene diisocyanate | (86%) |
| Example 18 | FIG. 17 | 210 | 1.0 | 2,4-tolylene diisocyanate | (65%) |

TABLE 7

| Example | Apparatus drawing | Step (F) Temperature of thin film distillation apparatus (° C.) | Pressure of thin film distillation apparatus (kPa) | Recovered isocyanate (yield based on organic amine) | |
|---|---|---|---|---|---|
| Example 19 | FIG. 17 | 220 | 2.5 | 2,4-tolylene diisocyanate | (59%) |
| Example 20 | FIG. 18 | 240 | 0.8 | 4,4'-diphenylmethane diisocyanate | (72%) |
| Example 21 | FIG. 18 | 250 | 1.0 | 4,4'-diphenylmethane diisocyanate | (66%) |
| Example 22 | FIG. 18 | 260 | 1.3 | 4,4'-dicyclohexylmethane diisocyanate | (89%) |
| Example 23 | FIG. 18 | 260 | 1.3 | 4,4'-dicyclohexylmethane diisocyanate | (89%) |
| Example 24 | FIG. 17 | 250 | 1.0 | Hexamethylene diisocyanate | (63%) |
| Example 25 | FIG. 17 | 250 | 1.0 | Isophorone diisocyanate | (56%) |
| Example 26 | FIG. 17 | 250 | 1.0 | Hexamethylene diisocyanate | (66%) |
| Example 27 | FIG. 17 | 250 | 1.0 | Hexamethylene diisocyanate | (62%) |
| Example 28 | FIG. 17 | 250 | 1.0 | Hexamethylene diisocyanate | (75%) |
| Example 29 | FIG. 18 | 250 | 1.0 | Isophorone diisocyanate | (50%) |
| Example 30 | FIG. 18 | 250 | 1.0 | Isophorone diisocyanate | (56%) |

TABLE 8

| Example | Step (E) Ammonia content of mixture recovered in storage tank 109 | Organic amine (amount used) | | Amount of urea added | Aromatic hydroxy compound added (amount used) | | Yield of N-substituted carbamic acid-O-aryl ester based on organic amine |
|---|---|---|---|---|---|---|---|
| Example 1 | 820 | HDA | (0.92 kg) | 3.10 kg | p-heptyl phenol | (41.8 kg) | 97% |
| Example 8 | 1200 | HDA | (1.18 kg) | 1.03 kg | 2-napthol | (15.2 kg) | 97% |
| Example 9 | 5300 | HDA | (1.19 kg) | 0.55 kg | 4-phenyl phenol | (8.29 kg) | 88% |
| Example 10 | 530 | HDA | (1.14 kg) | 0.63 kg | 2-ethoxy phenol | (9.53 kg) | 75% |
| Example 11 | 940 | IPDA | (1.80 kg) | 1.33 kg | 4-cumyl phenol | (9.97 kg) | 95% |
| Example 12 | 2200 | IPDA | (1.29 kg) | 0.98 kg | 4-(1,1,3,3-tetramethylbutyl) phenol | (6.52 kg) | 80% |
| Example 13 | 1500 | IPDA | (1.19 kg) | 0.89 kg | p-nonyl phenol | (42.5 kg) | 85% |
| Example 14 | 1200 | IPDA | (1.01 kg) | 0.74 kg | p-dodecyl phenol | (55.3 kg) | 78% |

TABLE 9

| Example | Step (E) Ammonia content of mixture recovered in storage tank 109 | Organic amine (amount used) | | Amount of urea added | Aromatic hydroxy compound added (amount used) | | Yield of N-substituted carbamic acid-O-aryl ester based on organic amine |
|---|---|---|---|---|---|---|---|
| Example 15 | 1350 | TDA | (2.11 kg) | 1.98 kg | p-dodecyl phenol | (13.7 kg) | 73% |
| Example 16 | 450 | TDA | (3.51 kg) | 3.61 kg | 4-tert-butyl phenol | (11.8 kg) | 65% |
| Example 17 | 190 | TDA | (1.20 kg) | 1.04 kg | p-nonyl phenol | (24.6 kg) | 91% |
| Example 18 | 320 | TDA | (1.23 kg) | 1.35 kg | 2-naphthol | (20.5 kg) | 70% |
| Example 19 | 1500 | TDA | (1.42 kg) | 2.86 kg | 3,5-dimethoxy phenol | (30.5 kg) | 62% |
| Example 20 | 560 | MDA | (0.53 kg) | 0.31 kg | 4-(1,1,3,3-tetramethylbutyl) phenol | (29.9 kg) | 87% |
| Example 21 | 270 | MDA | (0.41 kg) | 0.32 kg | 3,5-dimethoxy phenol | (36.9 kg) | 88% |
| Example 22 | 3200 | H-MDA | (1.45 kg) | 0.35 kg | 4-ethyl phenol | (17.7 kg) | 85% |
| Example 23 | 350 | H-MDA | (1.29 kg) | 0.10 kg | 2-tert-amyl phenol | (22.4 kg) | 93% |

Examples 31 to 42

The same method as Example 2 was carried out while changing the compounds and reaction conditions used. The compounds and reaction conditions used in step (A) of Examples 31 to 42 along with the results are shown in Table 10. In addition, the compounds and reaction conditions used in step (D) of Examples 21 to 32 along with the results are shown in Table 11. The compounds and reaction conditions used in steps (B) and (F) of Examples 26 to 37 along with the results are shown in Table 12. Although "FIG. 17" and "FIG. 18" are indicated in the "apparatus drawing" column for step (F) in Table 12, "FIG. 17" indicates that the same method as step (F) of Example 1 was carried out using an apparatus as shown in FIG. 17. On the other hand, "FIG. 18" indicates that the same method as step (F) of Example 4 was carried out using an apparatus as shown in FIG. 18. In addition, the compounds and reaction conditions used in step (E) of Examples 31 to 42 along with the results are shown in Table 13.

TABLE 10

| | Step (A) | | | | | | | | | | |
|---|---|---|---|---|---|---|---|---|---|---|---|
| Example | Temp. of storage tank 203 (° C.) | Organic amine | (amount used) | Amount of urea used | Solvent | (amount used) | Organic amine supply rate | Compound having ureido groups | Conc. of compound having ureido groups | Residual NH₃ | Aromatic hydroxy compound added after reaction | (amount used) |
| Example 2 | 120 | HDA | (0.93 kg) | 1.92 kg | 1-butanol | (11.9 kg) | 20 g/min | 1,1'-(hexane-1,6-diyl)diurea | 11.2 wt % | 7500 ppm | p-heptyl phenol | (23.1 kg) |
| Example 31 | 120 | HDA | (1.02 kg) | 2.27 kg | 2,6-dimethyl phenol | (10.7 kg) | 30 g/min | 1,1'-(hexane-1,6-diyl)diurea | 13.0 wt % | 4300 ppm | p-nonyl phenol | (19.3 kg) |
| Example 32 | 100 | HDA | (1.02 kg) | 2.37 kg | 2-isopropyl phenol | (6.21 kg) | 32 g/min | 1,1'-(hexane-1,6-diyl)diurea | 16.4 wt % | 6200 ppm | 4-phenyl phenol | (22.4 kg) |
| Example 33 | 90 | HDA | (1.53 kg) | 3.16 kg | Phenol | (9.90 kg) | 20 g/min | 1,1'-(hexane-1,6-diyl)diurea | 18.5 wt % | 8200 ppm | 2-naphthol | (18.9 kg) |
| Example 34 | 150 | IPDA | (1.42 kg) | 2.15 kg | 1-butanol | (5.55 kg) | 40 g/min | 3-(ureido-methyl)-3,5,5-trimethyl-cyclohexyl-urea | 17.1 wt % | 3400 ppm | 4-tert-amyl phenol | (17.8 kg) |
| Example 35 | 100 | IPDA | (1.39 kg) | 2.50 kg | 2-methyl phenol | (9.71 kg) | 50 g/min | 3-(ureido-methyl)-3,5,5-trimethyl-cyclohexyl-urea | 13.3 wt % | 5600 ppm | p-dodecyl phenol | (25.7 kg) |
| Example 36 | 110 | TDA | (2.53 kg) | 5.22 kg | 2,4,6-trimethyl phenol | (7.05 kg) | 20 g/min | 2,4-toluene-diurea | 16.0 wt % | 3500 ppm | 4-cumyl phenol | (19.5 kg) |
| Example 37 | 90 | TDA | (1.05 kg) | 2.32 kg | 2-bromo-phenol | (14.9 kg) | 20 g/min | 2,4-toluene-diurea | 9.8 wt % | 9100 ppm | 3,5-dimethoxy phenol | (14.6 kg) |
| Example 38 | 80 | TDA | (1.14 kg) | 2.24 kg | 3-methyl-1-butanol | (2.14 kg) | 20 g/min | 2,4-toluene-diurea | 27.3 wt % | 9300 ppm | 4-(1,1,3,3-tetramethyl-butyl) phenol | (23.1 kg) |
| Example 39 | 100 | MDA | (1.64 kg) | 1.99 kg | 2-isopropyl phenol | (12.4 kg) | 40 g/min | 4,4'-methane-diyl-diphenyl-diurea | 14.7 wt % | 2800 ppm | 1-naphthol | (11.9 kg) |
| Example 40 | 80 | MDA | (1.86 kg) | 2.31 kg | 1-butanol | (10.4 kg) | 30 g/min | 4,4'-methane-diyl diphenyl-diurea | 16.0 wt % | 3200 ppm | p-heptyl phenol | (14.4 kg) |
| Example 41 | 160 | H-MDA | (1.75 kg) | 2.90 kg | 2-methyl phenol | (13.5 kg) | 50 g/min | 4,4'-methane diyl dicyclohexyl-diurea | 13.6 wt % | 2800 ppm | 2,4,6-trimethyl phenol | (11.3 kg) |

TABLE 10-continued

| | Step (A) | | | | | | | | |
|---|---|---|---|---|---|---|---|---|---|
| Example | Temp. of storage tank 203 (° C.) | Organic amine (amount used) | Amount of urea used | Solvent (amount used) | Organic amine supply rate | Compound having ureido groups | Conc. of compound having ureido groups | Residual NH$_3$ | Aromatic hydroxy compound added after reaction (amount used) |
| Example 42 | 130 | H-MDA (1.63 kg) | 2.83 kg | 1-heptanol (7.02 kg) | 40 g/min | 4,4'-methane-diyl dicyclo-hexyl-diurea | 13.8 wt % | 3200 ppm | 4-ethoxy phenol (10.7 kg) |

TABLE 11

| | Step (D) | | | | | | | |
|---|---|---|---|---|---|---|---|---|
| | | | Storage tank 209 | | | Storage tank 208 | | |
| Example | Temp. of distillation column 205 (° C.) | Pressure in distillation column 205 (kPa) | Amt. recovered in storage tank 209 (kg) | Conc. of compound having ureido groups in residual liquid (wt %) | Ratio of no. of molecules of aromatic hydroxy compound to no. of ureido groups | Amt. recovered in storage tank 208 (kg) | Hydroxy compound content (%) | Urea content (%) |
| Example 2 | 120 | 10 | 13.5 | 12 | 3.9 | 12.8 | 92.5 | 7.1 |
| Example 31 | 125 | 5 | 21.5 | 8.3 | 5.0 | 11.6 | 91.7 | 7.2 |
| Example 32 | 130 | 8 | 28.9 | 6.3 | 8.8 | 7.5 | 81.7 | 17.5 |
| Example 33 | 130 | 15 | 22.3 | 11.7 | 5.0 | 10.8 | 91.1 | 8.5 |
| Example 34 | 150 | 15 | 20.0 | 6.9 | 9.9 | 6.7 | 82.9 | 15.6 |
| Example 35 | 120 | 10 | 28.4 | 6.3 | 7.0 | 10.5 | 90.9 | 8.8 |
| Example 36 | 140 | 10 | 26.2 | 9.1 | 4.1 | 7.9 | 87.8 | 11.0 |
| Example 37 | 140 | 8 | 16.7 | 10.5 | 5.6 | 15.8 | 93.9 | 5.9 |
| Example 38 | 110 | 50 | 25.2 | 4.9 | 9.4 | 3.3 | 65.0 | 32.1 |
| Example 39 | 120 | 15 | 14.4 | 16.0 | 5.1 | 13.2 | 92.7 | 7.2 |
| Example 40 | 110 | 10 | 17.1 | 13.4 | 4.7 | 11.6 | 89.6 | 9.8 |
| Example 41 | 130 | 5 | 15.2 | 15.8 | 5.1 | 13.9 | 93.1 | 6.5 |
| Example 42 | 130 | 3 | 13.1 | 11.2 | 7.8 | 9.0 | 78.7 | 20.0 |

TABLE 12

| | Step (B) | | | | Step (F) | | | |
|---|---|---|---|---|---|---|---|---|
| Example | Temp. of distillation column 210 (° C.) | Pressure of distillation column 210 (kPa) | N-substituted carbamic acid-O-aryl ester (yield based on organic amine) | Ammonia concentration in reaction liquid | Apparatus drawing | Thin film distillation apparatus temp. (° C.) | Thin film distillation apparatus pressure (kPa) | Recovered isocyanate (yield based on organic amine) |
| Example 2 | 250 | 26 | N,N'-hexanediyl-di(carbamic acid (p-heptylphenyl) ester) (95%) | 8.0 ppm | FIG. 17 | 220 | 1.3 | Hexamethylene diisocyanate (90%) |
| Example 31 | 240 | 30 | N,N'-hexanediyl-di(carbamic acid (p-nonylphenyl) ester) (96%) | 8.3 ppm | FIG. 17 | 200 | 2.0 | Hexamethylene diisocyanate (92%) |
| Example 32 | 260 | 30 | N,N'-hexanediyl-di(carbamic acid (4-phenylphenyl) ester) (81%) | 9.7 ppm | FIG. 17 | 220 | 2.0 | Hexamethylene diisocyanate (73%) |
| Example 33 | 230 | 25 | N,N'-hexanediyl-di(carbamic acid (2-naphthyl) ester) (93%) | 6.5 ppm | FIG. 17 | 200 | 1.0 | Hexamethylene diisocyanate (89%) |
| Example 34 | 230 | 40 | 3-((4-tert-amino-phenoxy)carbonylamino-methyl)-3,5,5-trimethyl-cyclohexyl carbamic acid (4-tert-aminophenyl) ester (62%) | 3.8 ppm | FIG. 18 | 210 | 1.3 | Isophorone diisocyanate (57%) |

TABLE 12-continued

| | Step (B) | | | | | Step (F) | | | |
|---|---|---|---|---|---|---|---|---|---|
| Example | Temp. of distillation column 210 (° C.) | Pressure of distillation column 210 (kPa) | N-substituted carbamic acid-O-aryl ester (yield based on organic amine) | | Ammonia concentration in reaction liquid | Apparatus drawing | Thin film distillation apparatus temp. (° C.) | Thin film distillation apparatus pressure (kPa) | Recovered isocyanate (yield based on organic amine) |
| Example 35 | 245 | 20 | 3-((p-dodecyl-phenoxy)carbonylamino-methyl)-3,5,5-trimethylcyclohexyl carbamic acid (p-dodecylphenyl) ester | (81%) | 9.1 ppm | FIG. 17 | 230 | 2.0 | Isophorone diisocyanate (73%) |
| Example 36 | 220 | 15 | Toluene-2,4-di(carbamic acid (4-cumylphenyl) ester) | (52%) | 8.5 ppm | FIG. 17 | 200 | 40.0 | 2,4-tolylene diisocyanate (45%) |
| Example 37 | 240 | 30 | Toluene-2,4-di(carbamic acid (3,5-dimethoxyphenyl) ester) | (88%) | 5.4 ppm | FIG. 17 | 190 | 0.4 | 2,4-tolylene diisocyanate (82%) |
| Example 38 | 230 | 25 | Toluene-2,4-di(carbamic acid (4-(1,1,3,3-tetramethylbutyl)phenyl) ester) | (61%) | 9.2 ppm | FIG. 17 | 210 | 0.8 | 2,4-tolylene diisocyanate (54%) |
| Example 39 | 250 | 40 | N,N'-(4,4'-methanediyl-diphenyl)-di(carbamic acid (1-napthyl) ester) | (88%) | 7.7 ppm | FIG. 18 | 250 | 0.7 | 4,4'-diphenylmethane diisocyanate (85%) |
| Example 40 | 230 | 20 | N,N'-(4,4'-methanediyl-diphenyl-di(carbamic acid (p-heptylphenyl) ester) | (82%) | 6.9 ppm | FIG. 18 | 260 | 1.0 | 4,4'-diphenylmethane diisocyanate (71%) |
| Example 41 | 220 | 60 | N,N'-(4,4'-methanediyl-dicyclohexyl)-di(carbamic acid (2,4,6-trimethylphenyl) ester) | (90%) | 8.1 ppm | FIG. 18 | 240 | 0.8 | 4,4-dicyclohexyl-methane diisocyanate (87%) |
| Example 42 | 200 | 80 | N,N'-(4,4'-methanediyl-dicyclohexyl)-di(carbamic acid (4-ethoxyphenyl) ester) | (60%) | 3.9 ppm | FIG. 18 | 250 | 0.8 | 4,4'-dicyclohexyl-methane diisocyanate (51%) |

TABLE 13

| | Step (E) | | | | | |
|---|---|---|---|---|---|---|
| Example | Ammonia content of mixture recovered in storage tank 208 | Organic amine (amount used) | | Amount of urea added | Solvent added (amount used) | | Yield of N-substituted carbamic acid-O-aryl ester based on organic amine |
| Example 2 | 550 | HDA | (0.93 kg) | 0.96 kg | (Not used) | | 95% |
| Example 31 | 640 | HDA | (1.3 kg) | 1.93 kg | 2,6-dimethyl phenol | (3.04 kg) | 96% |
| Example 32 | 950 | HDA | (1.02 kg) | 1.00 kg | (Not used) | | 81% |
| Example 33 | 2930 | HDA | (1.91 kg) | 3.00 kg | Phenol | (2.49 kg) | 89% |
| Example 34 | 630 | IPDA | (1.72 kg) | 1.65 kg | 1-hexanol | (1.94 kg) | 95% |
| Example 35 | 590 | IPDA | (1.42 kg) | 1.59 kg | (Not used) | | 73% |
| Example 36 | 460 | TDA | (2.53 kg) | 4.26 kg | (Not used) | | 53% |
| Example 37 | 1150 | TDA | (1.70 kg) | 2.82 kg | 2-bromophenol | (9.35 kg) | 88% |
| Example 38 | 1900 | TDA | (1.14 kg) | 1.28 kg | (Not used) | | 61% |
| Example 39 | 910 | MDA | (1.63 kg) | 1.04 kg | (Not used) | | 88% |
| Example 41 | 4890 | H-MDA | (1.75 kg) | 1.94 kg | 2-methyl phenol | (0.52 kg) | 84% |
| Example 42 | 1020 | H-MDA | (1.82 kg) | 1.24 kg | 1-heptanol | (0.96 kg) | 61% |

Examples 43 to 49

The same method as Example 3 was carried out while changing the compounds and reaction conditions used. The compounds and reaction conditions used in step (A) of Examples 43 to 49 along with the results are shown in Table 14. In addition, the compounds and reaction conditions used in steps (B) and (D) of Examples 43 to 49 along with the results are shown in Table 15. Although "FIG. 17" and "FIG. 18" are indicated in the "apparatus drawing" column for step (F) in Table 15, "FIG. 17" indicates that the same method as step (F) of Example 1 was carried out using an apparatus as shown in FIG. 17. On the other hand, "FIG. 18" indicates that the same method as step (F) of Example 4 was carried out using an apparatus as shown in FIG. 18. In addition, the compounds and reaction conditions used in step (E) of Examples 43 to 49 along with the results are shown in Table 16.

TABLE 14

| | Step (A) | | | | | |
|---|---|---|---|---|---|---|
| Example | Temp. of distillation column 103 (° C.) | Organic amine (amount used) | | Amount of urea used | Solvent (amount used) | | Organic amine supply rate |
| Example 3 | 100 | HDA | (1.07 kg) | 2.49 kg | 1-butanol | (13.6 kg) | 20 g/min |
| Example 43 | 120 | HDA | (1.06 kg) | 1.97 kg | 1-butanol | (13.5 kg) | 20 g/min |
| Example 44 | 120 | HDA | (1.05 kg) | 1.19 kg | 1-butanol | (13.4 kg) | 20 g/min |
| Example 45 | 110 | HDA | (1.1 kg) | 2.44 kg | 2,6-dimethyl phenol | (11.5 kg) | 32 g/min |
| Example 46 | 120 | HDA | (1.02 kg) | 2.37 kg | 2-phenyl ethanol | (10.7 kg) | 29 g/min |
| Example 47 | 90 | HDA | (1.45 kg) | 2.99 kg | Phenol | (9.4 kg) | 30 g/min |
| Example 48 | 120 | IPDA | (1.39 kg) | 2.11 kg | Ethylene glycol monobutyl ether | (19.3 kg) | 43 g/min |
| Example 49 | 120 | IPDA | (1.42 kg) | 2.15 kg | 2-methyl phenol | (9.01 kg) | 33 g/min |

| | Step (A) | | | | |
|---|---|---|---|---|---|
| Example | Compound having ureido groups | Conc. of compound having ureido groups | Residual amount of NH₃ | Aromatic hydroxy compound added after reaction (amount added) | | Ratio of aromatic hydroxy compound to ureido groups |
| Example 3 | 1,1'-(hexane-1,6-diyl)diurea | 10.9 wt % | 4300 ppm | p-heptyl phenol | (26.6 kg) | 7.7 |
| Example 43 | 1,1'-(hexane-1,6-diyl)diurea | 11.2 wt % | 4400 ppm | p-heptyl phenol | (26.3 kg) | 7.7 |
| Example 44 | 1,1'-(hexane-1,6-diyl)diurea | 11.7 wt % | 4200 ppm | p-heptyl phenol | (26.1 kg) | 7.7 |
| Example 45 | 1,1'-(hexane-1,6-diyl)diurea | 13.0 wt % | 4200 ppm | 4-phenyl phenol | (16.1 kg) | 10.1 |
| Example 46 | 1,1'-(hexane-1,6-diyl)diurea | 12.7 wt % | 6500 ppm | p-nonyl phenol | (29.0 kg) | 7.6 |
| Example 47 | 1,1'-(hexane-1,6-diyl)diurea | 18.5 wt % | 7300 ppm | 2-naphthol | (18.0 kg) | 9.2 |
| Example 48 | 3-(ureidomethyl)-3,5,5-trimethylcyclohexylurea | 9.1 wt % | 4800 ppm | 4-tert-amyl phenol | (17.4 kg) | 6.6 |
| Example 49 | 3-(ureidomethyl)-3,5,5-trimethylcyclohexylurea | 17.1 wt % | 4200 ppm | 4-cumyl phenol | (23.1 kg) | 11.7 |

TABLE 15

| | Step (B) | | | | | Step (D) | | |
|---|---|---|---|---|---|---|---|---|
| Example | Temp. of distillation column 105 (° C.) | Pressure of distillation column 105 (kPa) | Fed amount (kg) | N-substituted carbamic acid-O-aryl ester (yield based on aromatic amine) | | Ammonia concentration in reaction liquid | Amount recovered in storage tank 109 (kg) | Aromatic hydroxy compound content (%) | Urea content (%) |
| Example 3 | 240 | 50 | 37.8 | N,N'-hexanediyl-di(carbamic acid (p-hetpylphenyl) ester) | (94%) | 8.1 ppm | 13.3 | 89.1 | 9.1 |
| Example 43 | 240 | 30 | 36.5 | N,N'-hexanediyl-di(carbamic acid (p-heptylphenyl) ester) | (93%) | 5.8 ppm | 12.6 | 92.4 | 5.8 |
| Example 44 | 240 | 30 | 35.8 | N,N'-hexanediyl-di(carbamic acid (p-heptylphenyl) ester) | (93%) | 6.9 ppm | 11.9 | 97.2 | 0.9 |
| Example 45 | 240 | 30 | 30.6 | N,N'-hexanediyl-di(carbamic acid (p-nonylphenyl) ester) | (96%) | 4.7 ppm | 7.5 | 95.1 | 4.3 |
| Example 46 | 260 | 30 | 16.9 | N,N'-hexanediyl-di(carbamic acid (4-phenylphenyl) ester) | (93%) | 8.8 ppm | 3.7 | 91.2 | 8.3 |
| Example 47 | 230 | 25 | 18.9 | N,N'-hexanediyl-di(carbamic acid (2-naphthyl) ester) | (93%) | 6.9 ppm | 5.3 | 90.4 | 9.1 |
| Example 48 | 230 | 40 | 18.6 | 3-(4-tert-amylphenoxy)carbonylamino-methyl)-3,5,5-trimethylcyclohexyl carbamic acid (4-tert-amylphenyl) ester | (95%) | 5.8 ppm | 20.4 | 94.4 | 3.5 |

TABLE 15-continued

| | Step (B) | | | | | Step (D) | | |
|---|---|---|---|---|---|---|---|---|
| Example | Temp. of distillation column 105 (° C.) | Pressure of distillation column 105 (kPa) | Fed amount (kg) | N-substituted carbamic acid-O-aryl ester (yield based on aromatic amine) | Ammonia concentration in reaction liquid | Amount recovered in storage tank 109 (kg) | Aromatic hydroxy compound content (%) | Urea content (%) |
| Example 49 | 240 | 20 | 23.4 | 3-((p-dodecylphenoxy)carbonylamino-methyl-3,5,5-trimethylcyclohexyl carbamic acid (p-dodecylphenyl) ester (94%) | 8.9 ppm | 3.4 | 94.2 | 5.1 |

TABLE 16

| | | Step (F) | | |
|---|---|---|---|---|
| Example | Apparatus drawing | Thin film distillation apparatus temp. (° C.) | Thin film distillation apparatus pressure (kPa) | Recovered isocyanate (yield based on organic amine) |
| Example 3 | FIG. 17 | 220 | 1.3 | Hexamethylene diisocyanate (90%) |
| Example 43 | FIG. 17 | 200 | 2.0 | Hexamethylene diisocyanate (84%) |
| Example 44 | FIG. 17 | 200 | 2.0 | Hexamethylene diisocyanate (74%) |
| Example 45 | FIG. 17 | 200 | 2.0 | Hexamethylene diisocyanate (92%) |
| Example 46 | FIG. 17 | 220 | 2.0 | Hexamethylene diisocyanate (90%) |
| Example 47 | FIG. 17 | 200 | 1.0 | Hexamethylene diisocyanate (89%) |
| Example 48 | FIG. 18 | 210 | 1.3 | Isophorone diisocyanate (90%) |
| Example 49 | FIG. 17 | 230 | 2.0 | Isophorone diisocyanate (89%) |

Examples 50 to 52

The same method as Example 4 was carried out while changing the compounds and reaction conditions used. The compounds and reaction conditions used in step (A) of Examples 50 to 52 along with the results are shown in Table 17. In addition, the compounds and reaction conditions used in steps (B) and (D) of Examples 50 to 52 along with the results are shown in Table 18. The compounds and reaction conditions used in step (C) of Examples 50 to 52 along with the results are shown in Table 19. The reaction conditions of step (F) of Examples 50 to 52 are shown in Table 20. Furthermore, the description of "FIG. 18" in the "apparatus drawing" column in Table 20 indicates that an apparatus as shown in FIG. 18 was used for step (F).

TABLE 17

| | Step (A) | | | | | | | |
|---|---|---|---|---|---|---|---|---|
| Example | Temp. of stirring tank 103 (° C.) | Amount of aniline used | Amount of urea used | Aromatic hydroxy compound (amount used) | | Aniline supply rate | Ratio of aromatic hydroxy compound to no. of molecules of N-phenylurea | Concentration of N-phenylurea | Residual amount of NH$_3$ |
| Example 4 | 80 | 1.12 kg | 3.61 kg | 4-tert-amyl phenol | (43.5 kg) | 50 g/min | 11 | 4.5 wt % | 3800 ppm |
| Example 50 | 150 | 1.14 kg | 3.89 kg | 2-naphthol | (17.6 kg) | 60 g/min | 5.1 | 9.7 wt % | 5300 ppm |
| Example 51 | 130 | 1.08 kg | 2.79 kg | 4-(1,1,3,3-tetramethylbutyl) phenol | (23.9 kg) | 45 g/min | 5.1 | 7.6 wt % | 6700 ppm |
| Example 52 | 90 | 1.21 kg | 2.73 kg | p-heptyl phenol | (19.9 kg) | 40 g/min | 4.1 | 9.7 wt % | 9200 ppm |

TABLE 18

| | Step (B) | | | | | Step (D) | | |
|---|---|---|---|---|---|---|---|---|
| Example | Temp. of packed column 105 (° C.) | Pressure of packed column 105 (kPa) | Fed amount (kg) | N-substituted carbamic acid mono (O-aryl ester) (yield based on organic amine) | Ammonia concentration in reaction liquid | Amount recovered in storage tank 109 (kg) | Aromatic hydroxy compound content (%) | Urea content (%) |
| Example 4 | 200 | 8 | 8.95 | N-phenyl carbamic acid (4-tert-amylphenyl) ester (93%) | 5.6 ppm | 14.7 | 86.7 | 13.0 |
| Example 50 | 210 | 15 | 21.1 | N-phenyl carbamic acid (2-naphthyl) ester (88%) | 8.6 ppm | 7.9 | 70.1 | 28.8 |

TABLE 18-continued

| | Step (B) | | | | | Step (D) | | |
|---|---|---|---|---|---|---|---|---|
| Example | Temp. of packed column 105 (° C.) | Pressure of packed column 105 (kPa) | Fed amount (kg) | N-substituted carbamic acid mono (O-aryl ester) (yield based on organic amine) | | Ammonia concentration in reaction liquid | Amount recovered in storage tank 109 (kg) | Aromatic hydroxy compound content (%) | Urea content (%) |
| Example 51 | 230 | 20 | 25.3 | N-phenyl carbamic acid (4-(1,1,3,3-tetramethylbutyl)phenyl) ester | (84%) | 6.9 ppm | 8.6 | 84.5 | 15.2 |
| Example 52 | 220 | 25 | 21.2 | N-phenyl carbamic acid (p-heptylphenyl) ester | (86%) | 7.7 ppm | 7.0 | 84.3 | 15.1 |

TABLE 19

| | Distillation of aromatic hydroxy compound | | Step (C) | | | | | Distillation of solvent, unreacted substances, etc. | | Addition of aromatic hydroxy compound | |
|---|---|---|---|---|---|---|---|---|---|---|---|
| Example | Temp. of stirring tank 408 (° C.) | Pressure in stirring tank 408 (kPa) | Methylal (kg) | Nitrobenzole (kg) | Sulfuric acid (kg) | Reaction temp. (° C.) | Reaction time (hr) | Temp. or stirring tank 408 (° C.) | Pressure in stirring tank 408 (kPa) | Added aromatic hydroxy compound | (amount added) |
| Example 4 | 160 | 2 | 1.14 | 4.7 | 5.6 | 100 | 10 | 100 | 1 | 4-tert-amyl phenol | (5.1 kg) |
| Example 50 | 150 | 1 | 3.12 | 7.36 | 2.23 | 100 | 10 | 100 | 1 | 1-naphthol | (3.8 kg) |
| Example 51 | 150 | 1 | 4.05 | 10.8 | 2.46 | 110 | 8 | 100 | 1 | 4-(1,1,3,3-tetramethylbutyl)phenol | (4.2 kg) |
| Example 52 | 150 | 1 | 2.63 | 8.98 | 2.39 | 100 | 15 | 100 | 1 | p-heptyl phenol | (3.8 kg) |

TABLE 20

| | | Step (F) | | |
|---|---|---|---|---|
| Example | Apparatus drawing | Temp. of thin film distillation apparatus 1002 (° C.) | Pressure of thin film distillation apparatus 1002 (kPa) | Yield of MDI based on aniline |
| Example 4 | FIG. 18 | 260 | 1.5 | 55% |
| Example 50 | FIG. 18 | 250 | 1.0 | 45% |
| Example 51 | FIG. 18 | 240 | 0.8 | 51% |
| Example 52 | FIG. 18 | 230 | 0.1 | 44% |

Examples 53 to 67

The same method as Example 5 was carried out while changing the compounds and reaction conditions used. The compounds and reaction conditions used in step (A) of Examples 53 to 67 along with the results are shown in Tables 21 and 22. In addition, the compounds and reaction conditions used in steps (R) and (D) of Examples 53 to 67 along with the results are shown in Tables 23 and 24. The compounds and reaction conditions used in steps (P) and (F) of Examples 53 to 67 along with the results are shown in Tables 25 and 26. Although "FIG. 17" and "FIG. 18" are indicated in the "apparatus drawing" column for step (F) in Tables 25 and 26, "FIG. 17" indicates that the same method as step (F) of Example 1 was carried out using an apparatus as shown in FIG. 17. On the other hand, "FIG. 18" indicates that the same method as step (F) of Example 4 was carried out using an apparatus as shown in FIG. 18. In addition, the compounds and reaction conditions used in step (E) of Examples 53 to 67 along with the results are shown in Table 27.

TABLE 21

| | Step (A) | | | | | | | |
|---|---|---|---|---|---|---|---|---|
| Example | Reaction temp. (° C.) | Organic amine (amount used) | | Amount of urea used | Alcohol (amount used) | | Organic amine supply rate | Compound having ureido groups |
| Example 5 | 120 | IPDA | (0.87 kg) | 1.47 kg | 1-octanol | (14.6 kg) | 10 g/min | 3-(ureidomethyl)-3,3,5-trimethylcyclohexylurea |
| Example 53 | 100 | HDA | (1.11 kg) | 2.29 kg | 2-phenyl ethanol | (23.3 kg) | 20 g/min | 1,6-hexamethylene diurea |
| Example 54 | 120 | HDA | (1.32 kg) | 2.73 kg | Diethylene glycol monobutyl ether | (55.3 kg) | 38 g/min | 1,6-hexamethylene diurea |
| Example 55 | 120 | HDA | (1.28 kg) | 2.65 kg | Isodecyl alcohol | (29.6 kg) | 20 g/min | 1,6-hexamethylene diurea |

TABLE 21-continued

| Example | Reaction temp. (°C.) | Organic amine (amount used) | | Amount of urea used | Alcohol (amount used) | | Organic amine supply rate | Compound having ureido groups |
|---|---|---|---|---|---|---|---|---|
| Example 56 | 120 | HDA | (0.53 kg) | 1.15 kg | 4-phenyl-1-butanol | (54.8 kg) | 35 g/min | 1,6-hexamethylene diurea |
| Example 57 | 110 | IPDA | (1.13 kg) | 1.87 kg | 1-hexanol | (16.9 kg) | 30 g/min | 3-(ureidomethyl)-3,5,5-trimethylcyclohexylurea |
| Example 58 | 130 | IPDA | (1.29 kg) | 1.73 kg | Isodecyl alcohol | (41.9 kg) | 44 g/min | 3-(ureidomethyl)-3,5,5-trimethylcyclohexylurea |
| Example 59 | 120 | IPDA | (1.68 kg) | 2.67 kg | 1-nonanol | (25.6 kg) | 30 g/min | 3-(ureidomethyl)-3,5,5-trimethylcyclohexylurea |

| | Step (A) | | | | |
|---|---|---|---|---|---|
| Example | Conc. of compound having ureido groups | Residual amount of $NH_3$ | Aromatic hydroxy compound added after reaction (amount added) | | Ratio of alcohol to no. of ureido groups |
| Example 5 | 7.8 wt % | 7300 ppm | p-dodecyl phenol | (13.4 kg) | 11.3 |
| Example 53 | 7.1 wt % | 8800 ppm | 4-(1,1,3,3-tetramethylbutyl) phenol | (19.7 kg) | 10.3 |
| Example 54 | 3.8 wt % | 3600 ppm | 2,4-di-tert-amyl phenol | (18.7 kg) | 15.5 |
| Example 55 | 6.5 wt % | 3500 ppm | 2-naphthol | (15.9 kg) | 8.8 |
| Example 56 | 1.1 wt % | 4200 ppm | p-dodecyl phenol | (29.6 kg) | 58 |
| Example 57 | 8.5 wt % | 3900 ppm | 2-phenyl phenol | (11.3 kg) | 12.8 |
| Example 58 | 4.2 wt % | 3000 ppm | 2-naphthol | (7.6 kg) | 18 |
| Example 59 | 8.3 wt % | 2800 ppm | 4-nonyl phenol | (26.1 kg) | 9.3 |

TABLE 22

| Example | Reaction temp. (°C.) | Organic amine (amount used) | | Amount of urea used | Alcohol (amount used) | | Organic amine supply rate | Compound having ureido groups |
|---|---|---|---|---|---|---|---|---|
| Example 60 | 120 | IPDA | (1.71 kg) | 2.53 kg | Ethylene glycol monobutyl ether | (38.3 kg) | 38 g/min | 3-(ureidomethyl)-3,5,5-trimethylcyclohexylurea |
| Example 61 | 70 | TDA | (1.33 kg) | 3.29 kg | 2-ethyl-1-hexanol | (28.4 kg) | 65 g/min | 2,4-toluenediurea |
| Example 62 | 90 | TDA | (1.29 kg) | 6.34 kg | Cyclohexanol | (21.1 kg) | 79 g/min | 2,4-toluenediurea |
| Example 63 | 120 | TDA | (1.22 kg) | 4.79 kg | 3-methoxy-3-methyl-1-butanol | (23.6 kg) | 60 g/min | 2,4-toluenediurea |
| Example 64 | 120 | TDA | (1.28 kg) | 3.78 kg | 2-phenyl ethanol | (25.6 kg) | 65 g/min | 2,4-toluenediurea |
| Example 65 | 80 | MDA | (1.08 kg) | 3.23 kg | 4-phenyl-1-butanol | (24.5 kg) | 86 g/min | 4,4'-methanediyl diphenyl diurea |
| Example 66 | 70 | MDA | (1.11 kg) | 2.69 kg | Ethylene glycol mono-2-ethyl hexyl ether | (29.1 kg) | 65 g/min | 4,4'-methanediyl diphenyl diurea |
| Example 67 | 120 | H-MDA | (1.42 kg) | 1.99 kg | Ethylene glycol monobutyl ether | (15.9 kg) | 44 g/min | 4,4'-methanediyl dicyclohexyl diurea |

| | Step (A) | | | | |
|---|---|---|---|---|---|
| Example | Conc. of compound having ureido groups | Residual amount of $NH_3$ | Aromatic hydroxy compound added after reaction (amount added) | | Ratio of alcohol to no. of ureido groups |
| Example 60 | 5.9 wt % | 1900 ppm | p-dodecyl phenol | (34.3 kg) | 11.3 |
| Example 61 | 6.5 wt % | 3400 ppm | p-heptyl phenol | (16.7 kg) | 10.7 |
| Example 62 | 7 wt % | 7300 ppm | 2-phenyl phenol | (14.4 kg) | 11.0 |
| Example 63 | 4.5 wt % | 3500 ppm | p-heptyl phenol | (19.2 kg) | 11.0 |

TABLE 22-continued

|  |  |  |  |  |  |  |
|---|---|---|---|---|---|---|
| Example 64 | 6.6 wt % | 4200 ppm | p-dodecyl phenol | (33 kg) | 11.0 |
| Example 65 | 5.1 wt % | 8400 ppm | 4-phenyl phenol | (9.3 kg) | 15.6 |
| Example 66 | 4.4 wt % | 6300 ppm | 2,4-dicumyl phenol | (14.8 kg) | 16.7 |
| Example 67 | 9.9 wt % | 4400 ppm | 2,6-dimethoxy phenol | (10.4 kg) | 10.6 |

TABLE 23

| | Step (R) | | | | |
|---|---|---|---|---|---|
| Example | Temp. of distillation column 105 (° C.) | Distillation column 105 pressure (kPa) | Fed amount (kg) | N-substituted carbamic acid-O-aryl ester (yield based on organic amine) | |
| Example 5 | 260 | 26 | 15.1 | 3-((1-octyloxy)carbonylamino-methyl)-3,5,5-trimethylcyclohexyl carbamic acid (1-octyl) ester | (95%) |
| Example 53 | 240 | 13 | 45.2 | N,N'-hexanediyl-di(carbamic acid (2-phenylethyl) ester) | (92%) |
| Example 54 | 240 | 15 | 75.2 | N,N'-hexanediyl-di(carbamic acid (2-(2-(butyloxy)ethyloxy)ethyl) ester) | (93%) |
| Example 55 | 240 | 15 | 47.2 | N,N'-hexanediyl-di(carbamic acid isodecyloxy ester) | (83%) |
| Example 56 | 240 | 13 | 66.8 | N,N'-hexanediyl-di(carbamic acid (4-phenylbutyloxy) ester) | (81%) |
| Example 57 | 220 | 7 | 28.5 | 3-((4-phenylbutyloxy)carbonylamino-methyl)-3,5,5-trimethylcyclohexyl carbamic acid (4-phenylbutyl) ester | (92%) |
| Example 58 | 210 | 8 | 51.1 | 3-(isodecyloxycarbonylamino-methyl)-3,5,5-trimethylcyclohexyl carbamic acid isodecyl ester | (89%) |
| Example 59 | 210 | 10 | 53.2 | 3-(nonyloxycarbonylamino-methyl)-3,5,5-trimethylcyclohexyl carbamic acid nonyl ester | (80%) |

| | Step (R) Ammonia concentration in reaction liquid | Step (D) | | |
|---|---|---|---|---|
| Example | | Amt. recovered in storage tank 109 (kg) | Alcohol content (%) | Urea content (%) |
| Example 5 | 5.8 ppm | 4.4 | 89.9 | 9.8 |
| Example 53 | 9.5 ppm | 13.8 | 90.3 | 8.4 |
| Example 54 | 8.5 ppm | 29.1 | 94.4 | 4.6 |
| Example 55 | 11.8 ppm | 14.7 | 89.4 | 8.9 |
| Example 56 | 4.2 ppm | 15.1 | 94.1 | 4.0 |
| Example 57 | 7.7 ppm | 9.1 | 91.4 | 7.6 |
| Example 58 | 7.4 ppm | 21.5 | 95.4 | 3.4 |
| Example 59 | 92 ppm | 12.0 | 85.8 | 12.1 |

TABLE 24

| | Step (R) | | | | |
|---|---|---|---|---|---|
| Example | Temp. of distillation column 105 (° C.) | Distillation column 105 pressure (kPa) | Fed amount (kg) | N-substituted carbamic acid-O-aryl ester (yield based on organic amine) | |
| Example 60 | 220 | 13 | 75.6 | 3-((2-butyloxy-ethyloxy)carbonylamino-methyl)-3,5,5-trimethylcyclohexyl carbamic acid (2-butyloxy-ethyl) ester | (72%) |
| Example 61 | 210 | 13 | 45.4 | Toluene-2,4-di(carbamic acid (2-ethylhexyl) ester) | (84%) |
| Example 62 | 220 | 13 | 41.2 | Toluene-2,4-di(carbamic acid cyclohexyl ester) | (82%) |
| Example 63 | 210 | 26 | 46.8 | Toluene-2,4-di(carbamic acid (3-methoxy-3-methylbutyl) ester) | (69%) |
| Example 64 | 220 | 26 | 61.5 | Toluene-2,4-di(carbamic acid (p-dodecylphenyl) ester) | (62%) |

TABLE 24-continued

| | | | | | |
|---|---|---|---|---|---|
| Example 65 | 220 | 13 | 33.9 | N,N'-(4,4'-methanediyl-diphenyl)-di(carbamic acid hexyl ester) | (83%) |
| Example 66 | 210 | 13 | 45.4 | N,N'-(4,4'-methanediyl-diphenyl)-di(carbamic acid 2-(2-ethylhexyloxy)ethyl) ester) | (81%) |
| Example 67 | 210 | 8 | 27.2 | N,N'-(4,4'-methanediyl-dicyclohexyl)-di(carbamic acid (2-butyloxy)ethyl ester | (88%) |

| | Step (R) Ammonia concentration in reaction liquid | Step (D) | | |
|---|---|---|---|---|
| Example | | Amt. recovered in storage tank 109 (kg) | Alcohol content (%) | Urea content (%) |
| Example 60 | 108 ppm | 16.8 | 90.5 | 7.9 |
| Example 61 | 5.3 ppm | 16.2 | 86.5 | 11.7 |
| Example 62 | 6.1 ppm | 16.6 | 65.8 | 30.2 |
| Example 63 | 920 ppm | 11.7 | 64.9 | 28.5 |
| Example 64 | 1010 ppm | 19.1 | 76.5 | 20.4 |
| Example 65 | 3.9 ppm | 14.4 | 76.4 | 20.1 |
| Example 66 | 4.5 ppm | 16.5 | 85.5 | 12.1 |
| Example 67 | 7.2 ppm | 9.2 | 86.0 | 12.2 |

TABLE 25

| | Step (P) | | | | |
|---|---|---|---|---|---|
| Example | Catalyst (conc. based on raw material liquid) | | Distillation column 502 temp. (° C.) | Distillation column 502 press. (kPa) | N-substituted carbamic acid-O-aryl ester (yield based on organic amine) |
| Example 5 | Dibutyl tin dilaurate | 0.5 wt % | 260 | 26 | 3-((p-dodecylphenoxy)carbonylamino-methyl)-3,5,5-trimethylcyclohexyl carbamic acid (p-dodecylphenyl) ester (89%) |
| Example 53 | Dibutyl tin dilaurate | 0.5 wt % | 220 | 20 | N,N'-hexanediyl-di(carbamic acid (4-(1,1,3,3-tetramethylbutyl)phenyl) ester) (88%) |
| Example 54 | Lead octoate | 0.1 wt % | 240 | 15 | N,N'-hexanediyl-di(carbamic acid (2,4-di-tert-amylphenyl) ester) (89%) |
| Example 55 | Dibutyl tin dilaurate | 0.8 wt % | 250 | 25 | N,N'-hexanediyl-di(carbamic acid (2-naphthyl) ester) (81%) |
| Example 56 | Dibutyl tin dilaurate | 0.8 wt % | 240 | 25 | N,N'-hexanediyl-di(carbamic acid (p-dodecylphenyl) ester) (79%) |
| Example 57 | Zinc acetate | 1.0 wt % | 250 | 40 | 3-((2-phenylphenoxy)carbonylamino-methyl)-3,5,5-trimethylcyclohexyl carbamic acid (2-phenylphenyl) ester (88%) |
| Example 58 | Dibutyl tin dilaurate | 1.4 wt % | 230 | 20 | 3-((p-dodecylphenoxy)carbonylamino-methyl)-3,5,5-trimethylcyclohexyl carbamic acid (2-naphthyl) ester (86%) |
| Example 59 | Dibutyl tin dilaurate | 0.8 wt % | 230 | 20 | 3-((4-nonylphenoxy)carbonylamino-methyl)-3,5,5-trimethylcyclohexyl carbamic acid (4-nonylphenyl) ester (78%) |

| | | Step (F) | | |
|---|---|---|---|---|
| Example | Apparatus drawing | Thin film distillation apparatus temp. (° C.) | Thin film distillation apparatus press. (kPa) | Recovered isocyanate (yield based on organic amine) |
| Example 5 | FIG. 17 | 220 | 1.3 | Hexamethylene diisocyanate (83%) |
| Example 53 | FIG. 17 | 220 | 1.3 | Hexamethylene diisocyanate (83%) |
| Example 54 | FIG. 17 | 230 | 2.0 | Hexamethylene diisocyanate (83%) |
| Example 55 | FIG. 17 | 230 | 1.5 | Hexamethylene diisocyanate (75%) |
| Example 56 | FIG. 17 | 230 | 1.3 | Hexamethylene diisocyanate (74%) |
| Example 57 | FIG. 17 | 230 | 1.0 | Isophorone diisocyanate (82%) |

TABLE 25-continued

| | Example 58 | FIG. 18 | 240 | 1.0 | Isophorone diisocyanate | (81%) |
|---|---|---|---|---|---|---|
| | Example 59 | FIG. 17 | 240 | 1.2 | Isophorone diisocyanate | (73%) |

TABLE 26

Step (P)

| Example | Catalyst (conc. based on raw material liquid) | | Distillation column 502 temp. (° C.) | Distillation column 502 press. (kPa) | N-substituted carbamic acid-O-aryl ester (yield based on organic amine) | |
|---|---|---|---|---|---|---|
| Example 60 | Dibutyl tin dilaurate | 1.0 wt % | 230 | 20 | 3-((2-naphthyl)carbonylamino-methyl)-3,5,5-trimethylcyclohexyl carbamic acid (2-naphthyl) ester | (69%) |
| Example 61 | Dibutyl tin dilaurate | 1.3 wt % | 220 | 15 | Toluene-2,4-di(carbamic acid (p-heptylphenyl) ester) | (79%) |
| Example 62 | Lead octoate | 1.0 wt % | 220 | 25 | Toluene-2,4-di(carbamic acid (2-phenylphenyl) ester) | (77%) |
| Example 63 | Dibutyl tin dilaurate | 1.0 wt % | 210 | 10 | Toluene-2,4-di(carbamic acid (p-heptylphenyl) ester) | (66%) |
| Example 64 | Dibutyl tin dilaurate | 1.2 wt % | 210 | 10 | Toluene-2,4-di(carbamic acid (p-dodecylphenyl) ester) | (59%) |
| Example 65 | Zinc acetate | 0.9 wt % | 240 | 10 | N,N'-(4,4'-methanediyl-diphenyl)-di(carbamic acid (4-phenylphenyl) ester) | (78%) |
| Example 66 | Dibutyl tin dilaurate | 0.9 wt % | 240 | 6 | N,N'-(4,4'-methanediyl-diphenyl)-di(carbamic acid (2,4-dicumylphenyl) ester) | (75%) |
| Example 67 | Zinc acetate | 1.0 wt % | 200 | 20 | N,N'-(4,4'-methanediyl-dicyclohexyl)-di(carbamic acid (2,6-dimethoxyphenyl) ester) | (80%) |

Step (F)

| Example | Apparatus drawing | Thin film distillation apparatus temp. (° C.) | Thin film distillation apparatus press. (kPa) | Recovered isocyanate (yield based on organic amine) | |
|---|---|---|---|---|---|
| Example 60 | FIG. 17 | 240 | 1.0 | Isophorone diisocyanate | (65%) |
| Example 61 | FIG. 17 | 210 | 0.8 | 2,4-tolylene diisocyanate | (75%) |
| Example 62 | FIG. 17 | 200 | 0.5 | 2,4-tolylene diisocyanate | (73%) |
| Example 63 | FIG. 17 | 200 | 0.8 | 2,4-tolylene diisocyanate | (62%) |
| Example 64 | FIG. 17 | 200 | 0.8 | 2,4-tolylene diisocyanate | (54%) |
| Example 65 | FIG. 18 | 270 | 1.0 | 4,4'-diphenylmethane diisocyanate | (71%) |
| Example 66 | FIG. 17 | 280 | 1.5 | 4,4'-diphenylmethane diisocyanate | (69%) |
| Example 67 | FIG. 18 | 250 | 0.5 | 4,4'-dicyclohexylmethane diisocyanate | (74%) |

TABLE 27

Step (E)

| Example | Ammonia content of mixture recovered in storage tank 109 | Organic amine (amount used) | | Amount of urea added | Solvent added (amount added) | | Yield of N-substituted carbamic acid-O-aryl ester based on organic amine |
|---|---|---|---|---|---|---|---|
| Example 5 | 1300 | IPDA | (0.87 kg) | 0.70 kg | 1-octanol | (7.57 kg) | 95% |
| Example 53 | 1320 | HDA | (1.21 kg) | 1.40 kg | 2-phenyl ethanol | (13.0 kg) | 83% |
| Example 54 | 1400 | HDA | (1.32 kg) | 1.46 kg | Diethylene glycol monobutyl ether | (27.8 kg) | 83% |

TABLE 27-continued

| | | Step (E) | | | | | |
|---|---|---|---|---|---|---|---|
| Example | Ammonia content of mixture recovered in storage tank 109 | Organic amine (amount used) | | Amount of urea added | Solvent added (amount added) | | Yield of N-substituted carbamic acid-O-aryl ester based on organic amine |
| Example 57 | 1200 | IPDA | (1.22 kg) | 0.98 kg | 1-hexanol | (10.0 kg) | 82% |
| Example 58 | 1100 | IPDA | (1.29 kg) | 0.94 kg | Isodecyl alcohol | (21.3 kg) | 81% |
| Example 61 | 520 | TDA | (1.18 kg) | 1.13 kg | 2-ethyl-1-hexanol | (11.1 kg) | 75% |
| Example 62 | 1320 | TDA | (1.52 kg) | 2.72 kg | Cyclohexanol | (14.1 kg) | 73% |
| Example 65 | 950 | MDA | (1.28 kg) | 1.90 kg | 4-phenyl-1-butanol | (18.1 kg) | 71% |
| Example 66 | 710 | MDA | (1.10 kg) | 0.79 kg | Ethylene glycol mono-2-ethyl hexyl ether | (15.0 kg) | 69% |
| Example 67 | 550 | H-MDA | (1.42 kg) | 0.91 kg | Ethylene glycol monobutyl ether | (8.01 kg) | 74% |

Examples 68 to 70

The same method as Example 6 was carried out while changing the compounds and reaction conditions used. The compounds and reaction conditions used in step (A) of Examples 68 to 70 along with the results are shown in Table 28. In addition, the compounds and reaction conditions used in steps (R) and (D) of Examples 68 to 70 along with the results are shown in Table 29. The compounds and reaction conditions used in step (P) of Examples 68 to 70 along with the results are shown in Table 30. The compounds and reaction conditions used in step (C) of Examples 68 to 70 along with the results are shown in Table 31. The compounds and reaction conditions used in step (F) of Examples 68 to 70 along with the results are shown in Table 32. Although "FIG. 17" and "FIG. 18" are indicated in the "apparatus drawing" column for step (F) in Table 32, "FIG. 17" indicates that the same method as step (F) of Example 1 was carried out using an apparatus as shown in FIG. 17. On the other hand, "FIG. 18" indicates that the same method as step (F) of Example 4 was carried out using an apparatus as shown in FIG. 18.

TABLE 28

| | Step (A) | | | | | | |
|---|---|---|---|---|---|---|---|
| Example | Stirring tank 103 temp. (° C.) | Amount of aniline used | Amount of urea used | Solvent (amount used) | | Organic amine supply rate |
| Example 6 | 90 | (1.08 kg) | 3.34 kg | 1-nonanol | (33.5 kg) | 12 g/min |
| Example 68 | 150 | (1.22 kg) | 6.53 kg | 2-phenyl ethanol | (28.8 kg) | 30 g/min |
| Example 69 | 130 | (1.32 kg) | 8.51 kg | Ethylene glycol monobutyl ether | (41.9 kg) | 35 g/min |
| Example 70 | 90 | (0.98 kg) | 5.69 kg | 3-methoxy-3-methyl-1-butanol | (31.1 kg) | 25 g/min |

| | Step (A) | | | | |
|---|---|---|---|---|---|
| Example | Concentration of compound having ureido groups | Residual amount of NH$_3$ | Aromatic hydroxy compound added after reaction (amount added) | | Ratio of alcohol to no. of ureido groups |
| Example 6 | 5.6 wt % | 7900 ppm | 2-phenyl phenol | (25.9 kg) | 10.1 |
| Example 68 | 4.7 wt % | 5300 ppm | 4-(1,1,3,3-tetramethylbutyl) phenol | (27.0 kg) | 9.6 |
| Example 69 | 3.6 wt % | 6700 ppm | p-heptyl phenol | (16.4 kg) | 13.3 |
| Example 70 | 3.6 wt % | 9200 ppm | 4-ethoxy phenol | (14.5 kg) | 13.4 |

TABLE 29

| | Steps (R) and (D) | | | |
|---|---|---|---|---|
| Example | Packed column 105 temp. (° C.) | Packed column 105 pressure (kPa) | N-substituted carbamic acid mono(-O-alkyl ester) (yield based on organic amine) | |
| Example 6 | 210 | 50 | N-phenyl-carbamic acid nonyl ester | (91%) |
| Example 68 | 220 | 50 | N-phenyl-carbamic acid (2-phenylethylester) | (88%) |
| Example 69 | 172 | 100 | N-phenyl-carbamic acid (2-(1-butyloxy)ethyl ester | (88%) |
| Example 70 | 175 | 100 | N-phenyl-carbamic acid ((3-methoxy-3-methylbutyl) ester) | (85%) |

TABLE 30

| Example | Catalyst (concentration based on raw material liquid) | | Reaction temp. (° C.) | Pressure (kPa) | N-substituted carbamic acid mono(-O-aryl ester) (yield based on organic amine) | |
|---|---|---|---|---|---|---|
| Example 6 | Dibutyl tin dilaurate | 0.5 wt % | 260 | 26 | N-phenyl-carbamic acid (2-phenylphenylester) | (89%) |
| Example 68 | Dibutyl tin dilaurate | 0.2 wt % | 250 | 20 | N-phenyl-carbamic acid (4-(1,1,3,3-tetramethylbutyl)phenylester) | (83%) |
| Example 69 | Lead octoate | 0.2 wt % | 240 | 10 | N-phenyl-carbamic acid (p-heptylphenylester) | (81%) |
| Example 70 | Zinc acetate | 0.2 wt % | 220 | 60 | N-phenyl-carbamic acid (4-ethoxyphenylester) | (82%) |

TABLE 31

| Example | Distillation of aromatic hydroxy compound | | Step (C) | | | | | Distillation of solvent, unreacted substances, etc. | | Addition of aromatic hydroxy compound | |
|---|---|---|---|---|---|---|---|---|---|---|---|
| | Stirring tank 408 temp. (° C.) | Stirring tank 408 press. (kPa) | Methylal (kg) | Nitrobenzole (kg) | Sulfuric acid (kg) | Reaction temp. (° C.) | Reaction time (hr) | Stirring tank 408 temp. (° C.) | Stirring tank 408 press. (kPa) | Aromatic hydroxy compound added | (amount added) |
| Example 6 | 160 | 1 | 2.04 | 1.94 | 1.02 | 90 | 24 | 90 | 1 | 2-phenyl phenol | (25.9 kg) |
| Example 68 | 150 | 1 | 0.76 | 2.11 | 0.39 | 100 | 10 | 100 | 1 | 4-(1,1,3,3-tetramethylbutyl) phenol | (3.5 kg) |
| Example 69 | 150 | 1 | 0.64 | 2.14 | 0.62 | 110 | 8 | 100 | 1 | p-heptyl phenol | (5.4 kg) |
| Example 70 | 150 | 1 | 2.63 | 8.98 | 2.39 | 100 | 15 | 100 | 1 | 4-ethoxy phenol | (5.8 kg) |

TABLE 32

| Example | Apparatus drawing | Step (F) | | Yield of MDI based on aniline |
|---|---|---|---|---|
| | | Thin film distillation apparatus 1002 temp. (° C.) | Thin film distillation apparatus 1002 pressure (kPa) | |
| Example 6 | FIG. 18 | 260 | 1.5 | 91% |
| Example 68 | FIG. 18 | 250 | 1.0 | 43% |
| Example 69 | FIG. 18 | 240 | 0.8 | 50% |
| Example 70 | FIG. 18 | 230 | 0.1 | 47% |

Examples 71 to 73

The same method as Example 7 was carried out while changing the compounds and reaction conditions used. The compounds and reaction conditions used in step (A) of Examples 71 to 73 along with the results are shown in Table 33. In addition, the compounds and reaction conditions used in steps (R) and (D) of Examples 71 to 73 along with the results are shown in Table 34. The compounds and reaction conditions used in step (C) of Examples 71 to 73 along with the results are shown in Table 35. The reaction conditions used in steps (P) and (F) of Examples 71 to 73 along with the results are shown in Table 36. Although "FIG. 18" is indicated in the "apparatus drawing" column for step (F) in Table 36, "FIG. 18" indicates that the same method as step (F) of Example 4 was carried out using an apparatus as shown in FIG. 18.

TABLE 33

| Example | Step (A) | | | | | | | | | |
|---|---|---|---|---|---|---|---|---|---|---|
| | Distillation column 105 temp. (° C.) | Amount of aniline used (kg) | Amount of urea used (kg) | Solvent (amount added) | | Organic amine supply rate | Conc. of compound having ureido groups | Residual amount of NH$_3$ | Hydroxy compound added after reaction (amount added) | | Ratio of alcohol to no. of ureido groups |
| Example 7 | 90 | (1.13 kg) | 3.50 kg | 1-heptanol | (25.4 kg) | 18 g/min | 7.4 wt % | 8300 ppm | 2,4-di-tert-amyl phenol | (24.4 kg) | 9.0 |
| Example 71 | 100 | (1.53 kg) | 9.87 kg | 1-heptanol | (47.7 kg) | 30 g/min | 3.6 wt % | 4200 ppm | Phenol | (4.6 kg) | 13.4 |
| Example 72 | 120 | (1.39 kg) | 8.96 kg | Phenol | (16.9 kg) | 40 g/min | 7.3 wt % | 3800 ppm | 4-phenyl-1-butanol | (22.4 kg) | 5.4 |

TABLE 33-continued

Step (A)

| Example | Distillation column 105 temp. (° C.) | Amount of aniline used (kg) | Amount of urea used (kg) | Solvent (amount added) | | Organic amine supply rate | Conc. of compound having ureido groups | Residual amount of NH₃ | Hydroxy compound added after reaction (amount added) | | Ratio of alcohol to no. of ureido groups |
|---|---|---|---|---|---|---|---|---|---|---|---|
| Example 73 | 90 | (1.29 kg) | 8.32 kg | Cyclohexanol | (34.7 kg) | 30 g/min | 4.1 wt % | 5500 ppm | 2-isopropyl phenol | (7.6 kg) | 13.4 |

TABLE 34

Steps (R) and (D)

| Example | Distillation column 105 temp. (° C.) | N-substituted carbamic acid mono(-O-alkyl) ester (yield based on organic amine) | |
|---|---|---|---|
| Example 7 | 190 | N-phenyl carbamic acid (1-heptyl) ester | (90%) |
| Example 71 | 240 | N-phenyl carbamic acid (1-heptyl) ester | (85%) |
| Example 72 | 240 | N-phenyl carbamic acid (4-phenylbutyl) ester | (76%) |
| Example 73 | 220 | N-phenyl carbamic acid cyclohexyl ester | (84%) |

TABLE 35

| | Hydroxy compound distillation | | Step (C) | | | | | Hydroxy compound distillation | | Addition of aromatic hydroxy compound | |
|---|---|---|---|---|---|---|---|---|---|---|---|
| Example | Stirring tank 408 temp (° C.) | Stirring tank 408 pressure (kPa) | Methylal (kg) | Nitrobenzole (kg) | Sulfuric acid (kg) | Reaction temp. (° C.) | Reaction time (hr) | Stirring tank 408 temp. (° C.) | Stirring tank 408 pressure (kPa) | Added aromatic hydroxy compound | (amount added) |
| Example 7 | 160 | 1 | 1.30 | 7.34 | 1.33 | 100 | 10 | 100 | 1 | 2,4-di-tert-amyl phenol | (24.2 kg) |
| Example 71 | 150 | 1 | 0.72 | 2.4 | 0.96 | 100 | 10 | 100 | 1 | 4-tert-amyl phenol | (16.8 kg) |
| Example 72 | 150 | 1 | 1.13 | 3.76 | 1.5 | 110 | 8 | 100 | 1 | 2,4-di-tert-amyl phenol | (26.2 kg) |
| Example 73 | 150 | 1 | 0.75 | 2.5 | 0.86 | 110 | 9 | 100 | 1 | 2,6-dimethoxy phenol | (15.9 kg) |

TABLE 36

| | Step (P) | | | | Step (F) | | | |
|---|---|---|---|---|---|---|---|---|
| | | | | | | Thin film distillation | Thin film distillation | |
| Example | Catalyst (concentration based on raw material liquid) | | Reaction temp. (° C.) | Pressure (kPa) | Apparatus drawing | apparatus 1002 temp. (° C.) | apparatus 1002 pressure (kPa) | Yield of MDI based on aniline |
| Example 7 | Dibutyl tin dilaurate | 0.5 wt % | 250 | 30 | FIG. 18 | 250 | 1.0 | 47% |
| Example 71 | Dibutyl tin dilaurate | 1.2 wt % | 250 | 50 | FIG. 18 | 250 | 1.0 | 46% |
| Example 72 | Lead octoate | 1.2 wt % | 220 | 20 | FIG. 18 | 230 | 0.8 | 40% |
| Example 73 | Zinc acetate | 1.0 wt % | 230 | 15 | FIG. 18 | 220 | 0.1 | 49% |

Example 74

Step (74-1): Production of Compound Having Ureido Groups

Figure 19:
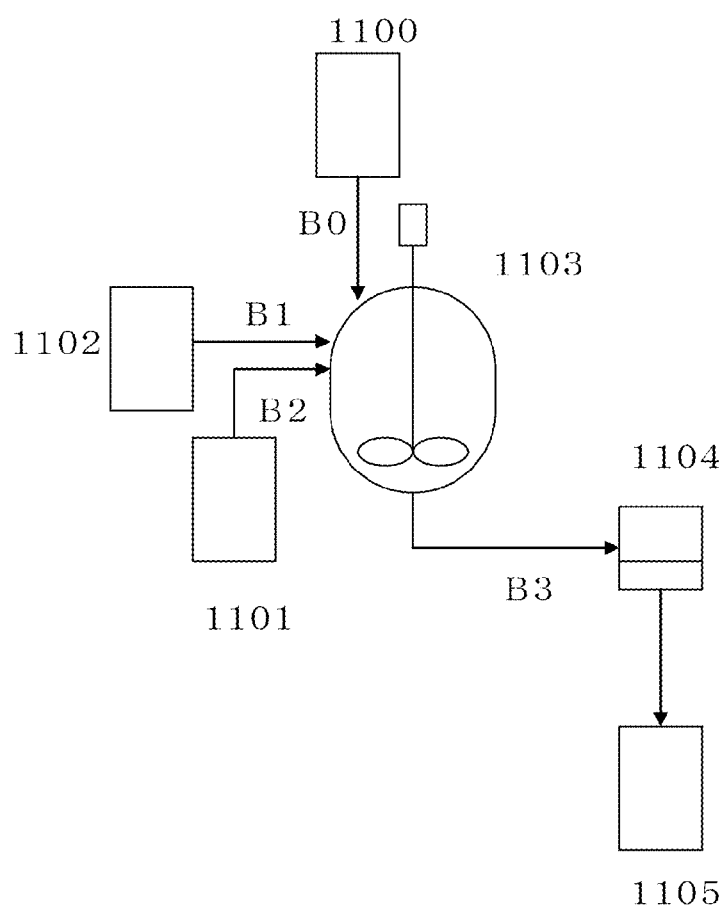
FIG. 19 shows a conceptual drawing depicting an apparatus for producing a compound having ureido groups in an example of the present embodiment.

The apparatus shown in FIG. 19 was used.

2.54 kg of urea were transferred from a storage tank 1100 to a stirring tank 1103 with a line B3 closed. After melting the urea by heating the stirring tank 1103 to 150° C., 0.820 kg of hexamethylenediamine were supplied at the rate of about 10 g/min from a storage tank 1101 to the stirring tank 1103 via a line A1 while stirring the stirring tank 1103. Following completion of supplying hexamethylenediamine, stirring was continued for about 1 hour and about 8.5 kg of water were placed in the stirring tank 1103 from a storage tank 1102 to form a slurry-like solution. The slurry-like solution was fed to a pressurized filtration apparatus 1104 and the solid component was separated by filtration. When the recovered solid component was analyzed by ¹H-NMR, it was found to contain a compound having ureylene groups. About 50 kg of water at about 80° C. was added to the solid component followed by stirring to obtain a dispersion, and the dispersion was filtered to obtain a filtrate. A solid component that precipitated following cooling of the filtrate was separated and recovered. The recovered solid component was heated to about 100° C. and dried with a dryer containing a nitrogen atmosphere to obtain 125 g of a solid. When the solid was analyzed by $^1$H-NMR, it was found to be 1,1'-(hexane-1,6-diyl)diurea. The above-mentioned procedure was then repeated 10 times to obtain about 1270 g of 1,1'-(hexane-1,6-diyl)diurea.

Step (B): Production of N-Substituted Carbamic Acid-O-Aryl Ester

Figure 20:
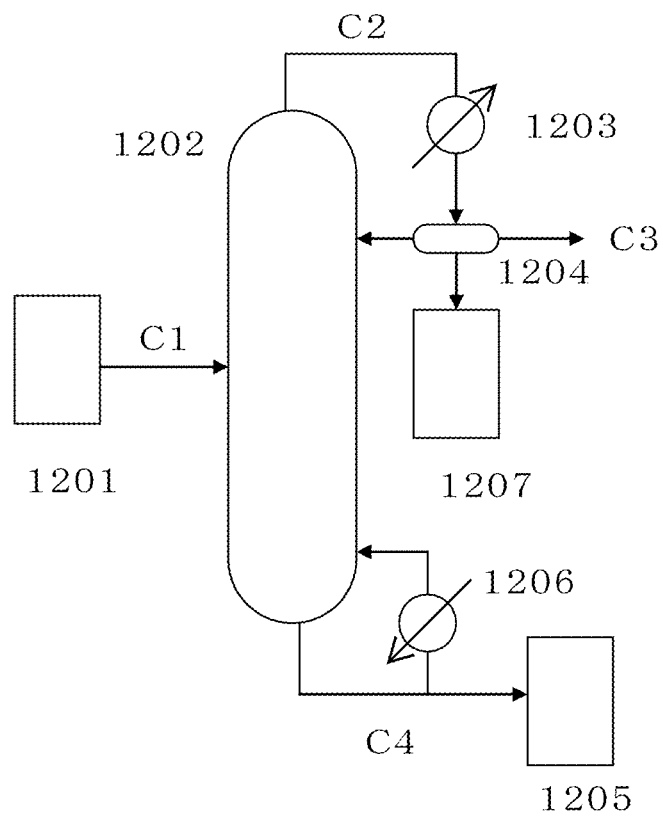
FIG. 20 shows a conceptual drawing depicting an N-substituted carbamic acid ester production apparatus in a comparative example of the present embodiment.

The apparatus shown in FIG. 20 was used.

The 1,1'-(hexane-1,6-diyl)diurea obtained in step (74-1) and 25.9 kg of 4-(1,1,3,3-tetramethylbutyl)phenol were mixed to obtain a raw material solution that was placed in a storage tank 1201.

A packed column 1202 packed with a packing material (Helipack No. 3) was heated to 240° C. and the pressure inside the column was set to 26 kPa. The above-mentioned raw material solution was fed at the rate of about 3.5 g/min from a line C1 provided in the packed column 1202. Since the reaction is initially in an unsteady state, the sample at that time was discarded. The amount of reaction liquid fed after the reaction had reached a steady state was about 23.2 kg. The reaction liquid was recovered in a storage tank 1205 through a line C4 provided in the bottom of the packed column 1202. A gaseous phase component was extracted from a line C2 provided in the top of the packed column 1202 and condensed with a condenser 1203, and the resulting liquid phase component was circulated to the packed column 1202 via a gas-liquid separator 1204. On the other hand, ammonia was recovered in the form of a gaseous component from the gas-liquid separator 1204. When the reaction liquid recovered in the storage tank 1205 was analyzed by liquid chromatography and $^1$H-NMR, the reaction liquid was found to contain N,N'-hexanediyl-di(carbamic acid (4-(1,1,3,3-tetramethylbutyl)phenyl)ester), and the yield of N,N'-hexanediyl-di(carbamic acid (4-(1,1,3,3-tetramethylbutyl)phenyl)ester) based on hexamethylenediamine was about 86%.

Step (F): Production of Isocyanate by Thermal Decomposition of N-Substituted Carbamic Acid-O-Aryl Ester The apparatus shown in FIG. 17 was used.

A thin film distillation apparatus 602 having a heat-conducting surface area of 0.2 m$^2$ was heated to 220° C. and the pressure within the thin film distillation apparatus was set to about 1.3 kPa. The reaction liquid recovered in the storage tank 110 in step (B) was placed in a storage tank 601 and supplied to the thin film distillation apparatus at the rate of about 1800 g/hr via a line 60. A liquid component was extracted from a line 62 provided in the bottom of thin film distillation apparatus 602 and recovered in a storage tank 603. The liquid component recovered in the storage tank 603 was again supplied to the thin film distillation apparatus 602 through a line 63. A gaseous component containing hexamethylene diisocyanate and p-heptyl phenol was extracted from a line 61 provided in the upper portion of the thin film distillation apparatus 602. The gaseous component was introduced into a distillation column 604, and the low boiling point component was separated by distillation. A liquid phase component was supplied to a distillation column 609 from a line 68 provided at a portion of the distillation column 604 lower than the feed line and further subjected to distillative separation. The gaseous component was condensed in the condenser 610 via a line 69 and recovered in a storage tank 612 through a gas-liquid separator 611.

When the condensed liquid was analyzed by $^1$H-NMR and gas chromatography, the condensate was found to contain about 99% by weight of hexamethylene diisocyanate. The yield based on hexamethylene diamine was about 80%.

Example 75

Step (75-1): Production of Compound Having Ureido Groups

The same method as step (74-1) of Example 74 was carried out with the exception of using 3.41 kg of urea and 1.11 kg of hexamethylenediamine. The same procedure was then repeated 10 times and the resulting 1,1'-(hexane-1,6-diyl)diurea was mixed with about 25.6 kg of 4-ethoxy phenol and obtain a homogeneous solution. When the solution was analyzed by $^1$H-NMR, it was found to be a solution containing 6.3% by weight of 1,1'-(hexane-1,6-diyl)diurea and 7.7% by weight of urea.

Step (B): Production of N-Substituted Carbamic Acid-O-Aryl Ester

The apparatus shown in FIG. 20 was used.

The solution obtained in step (75-1) was transferred to the storage tank 401.

The packed column 1202 was heated to 240° C. and the pressure inside the column was set to 26 kPa. The solution obtained in step (75-1) was fed at the rate of about 3.7 g/min from the line 41 provided in the packed column 1202. Since the reaction is initially in an unsteady state, the sample at that time was discarded. The amount of reaction liquid fed after the reaction had reached a steady state was about 24.3 kg. The reaction liquid was recovered in the storage tank 1205 through the line 44 provided in the bottom of the packed column 1202. A gaseous phase component was extracted from the line C2 provided in the top of the packed column 1202 and condensed with the condenser 1203 maintained at about 85° C., and the resulting liquid phase component was recovered in a storage tank 1207 via the gas-liquid separator 1204. On the other hand, ammonia was recovered in the form of a gaseous component from the gas-liquid separator 1204. When the reaction liquid recovered in the storage tank 1205 was analyzed by liquid chromatography and $^1$H-NMR, the reaction liquid was found to contain N,N'-hexanediyl-di(carbamic acid (4-ethoxyphenyl)ester), and the yield of N,N'-hexanediyl-di(carbamic acid (4-ethoxyphenyl)ester) based on hexamethylenediamine was about 93%. The amount of solution recovered in the storage tank 1207 was 16.1 kg, and when the solution was analyzed by $^1$H-NMR, it was found to contain 11.6% by weight of urea.

Example 76

Step (76-1): Production of Compound Having Ureido Groups

The same method as step (74-1) of Example 74 was carried out with the exception of using 3.33 kg of urea and using 1.18 kg of 3-aminomethyl-3,5,5-trimethylcyclohexylamine instead of hexamethylenediamine. The same procedure was then repeated 10 times to obtain 1.53 kg of a solid. When the solid was analyzed by $^1$H-NMR, it was found to be 3-(ureidomethyl)-3,5,5-trimethylcyclohexyl urea.

Step (B): Production of N-Substituted Carbamic Acid-O-Aryl Ester

The solid obtained in step (76-1) was mixed with 21.3 kg of p-heptyl phenol to obtain a raw material solution was placed in the storage tank 401.

The same procedure as Example (56-2) was carried out with the exception of feeding the raw material solution at the rate of about 2.8 g/min. The amount of reaction liquid fed after the reaction had reached a steady state was about 19.7 kg. When the reaction liquid recovered in the storage tank 405 was analyzed by liquid chromatography and $^1$H-NMR, the reaction liquid was found to contain 3-((p-heptylphenoxy)carbonylamino-methyl)-3,5,5-trimethylcyclohexyl carbamic acid (p-heptylphenyl)ester, and the yield of 3-((p-heptylphenoxy)carbonylamino-methyl)-3,5,5-trimethylcyclohexyl carbamic acid (p-heptylphenyl)ester based on 3-aminomethyl-3,5,5-trimethylcyclohexylamine was about 83%.

Example 77

Step (77-1): Production of Compound Having Ureido Groups

The apparatus shown in FIG. 19 was used.

3.01 kg of urea from the storage tank 1100 and 5.21 kg of water from the storage tank 1102 were transferred to the stirring tank 1103 with the line B3 closed. The stirring tank 1103 was heated to 90° C. to obtain a homogeneous solution, and 0.970 kg of hexamethylenediamine were supplied at the rate of about 8 g/min from the storage tank 1101 to the stirring tank 1103 via the line B1 while stirring the stirring tank 1103. Following completion of supplying hexamethylenediamine, stirring was continued for about 1 hour. A slurry-like solution was obtained. The slurry-like solution was fed to the pressurized filtration apparatus 1104 and the solid component was separated by filtration. The recovered filtrate was cooled to about 20° C. and a solid component that precipitated was separated by filtration and recovered. The solid component was heated to about 100° C. and dried with a dryer containing a nitrogen atmosphere to obtain 0.32 kg of a solid. When the solid was analyzed by $^1$H-NMR, it was found to be 1,1'-(hexane-1,6-diyl)diurea. The above-mentioned procedure was then repeated 5 times to obtain about 1.48 kg of 1,1'-(hexane-1,6-diyl) diurea.

Step (B): Production of N-Substituted Carbamic Acid-O-Aryl Ester

The apparatus shown in FIG. 20 was used.

The 1,1'-(hexane-1,6-diyl)diurea obtained in step (77-1) and 15.6 kg of 4-cumyl phenol were mixed to obtain a raw material solution that was placed in the storage tank 1201.

The packed column 1202 was heated to 240° C. and the pressure inside the column was set to 26 kPa. The above-mentioned raw material solution was fed at the rate of about 3.5 g/min from the line C1 provided in the packed column 1202. Since the reaction is initially in an unsteady state, the sample at that time was discarded. The amount of reaction liquid fed after the reaction had reached a steady state was about 15.6 kg. The reaction liquid was recovered in the storage tank 406 through the line C4 provided in the bottom of the packed column 1202. A gaseous phase component was extracted from the line C2 provided in the top of the packed column 402 and condensed with a condenser 1203, and the resulting liquid phase component was circulated to the packed column 1202 via a gas-liquid separator 1204. On the other hand, ammonia was recovered in the form of a gaseous component from the gas-liquid separator 1204. When the reaction liquid recovered in the storage tank 1205 was analyzed by liquid chromatography and $^1$H-NMR, the reaction liquid was found to contain N,N'-hexanediyl-di(carbamic acid (4-cumylphenyl)ester), and the yield of N,N'-hexanediyl-di(carbamic acid (4-cumylphenyl)ester) based on hexamethylenediamine was about 83%.

Step (F): Production of Isocyanate by Thermal Decomposition of N-Substituted Carbamic Acid-O-Aryl Ester The apparatus shown in FIG. 17 was used.

A thin film distillation apparatus 602 having a heat-conducting surface area of 0.2 m$^2$ was heated to 220° C. and the pressure within the thin film distillation apparatus was set to about 1.3 kPa. The reaction liquid recovered in the storage tank 110 in step (B) was placed in a storage tank 601 and supplied to the thin film distillation apparatus at the rate of about 1800 g/hr via a line 60. A liquid component was extracted from a line 62 provided in the bottom of thin film distillation apparatus 602 and recovered in a storage tank 603. The liquid component recovered in the storage tank 603 was again supplied to the thin film distillation apparatus 602 through a line 63. A gaseous component containing hexamethylene diisocyanate and 4-cumylphenol was extracted from a line 61 provided in the upper portion of the thin film distillation apparatus 602. The gaseous component was introduced into a distillation column 604, and the low boiling point component was separated by distillation. A liquid phase component was supplied to a distillation column 609 from a line 68 provided at a portion of the distillation column 604 lower than the feed line and further subjected to distillative separation.

When the condensed liquid was analyzed by $^1$H-NMR and gas chromatography, the condensate was found to contain about 99% by weight of hexamethylene diisocyanate. The yield based on hexamethylene diamine was about 80%.

Example 78

Step (A): Production of Compound Having Ureido Groups

The same method as step (A) of Example 1 was carried out with the exception of using 34.3 kg of p-heptyl phenol, 2.92 kg of urea and 1.38 kg of hexamethylenediamine. Following completion of the reaction, the reaction liquid was sampled, and as a result of analyzing the reaction liquid by liquid chromatography, it was found to contain 6.1% by weight of a compound having ureido groups in the form of 1,1'-(hexane-1,6-diyl)diurea. In addition, the ammonia concentration in the solution was 5500 ppm. Unreacted amino group terminals were not detected. The ratio of the number of molecules of p-heptyl phenol to the number of ureido groups was 7.7.

The line 13 was then opened and the reaction liquid was transferred to the storage tank 104 via the line 13.

Step (B): Production of N-Substituted Carbamic Acid-O-Aryl Ester

The apparatus shown in FIG. 13 was used.

The packed column 105 packed with a packing material (Helipack No. 3) was heated to 240° C. and the pressure inside the column was set to 26 kPa. The reaction liquid obtained in step (A) was fed at the rate of about 1.5 g/min from the line 14 provided in the packed column 105. Since the reaction is initially in an unsteady state, the sample at that time was discarded. The amount of reaction liquid fed after the reaction had reached a steady state was about 36.3 kg. The reaction liquid was recovered in the storage tank 110 through the line 16 provided in the bottom of the packed column 105. A gaseous phase component was condensed in the condenser 106 maintained at about 85° C. from the line 15 provided in the top of the packed column 105, and the resulting liquid phase component was circulated to the packed column 105 via the gas-liquid separator 108. The amount of reaction liquid recovered in the storage tank 110 was 35.9 kg. When the reaction liquid was analyzed by liquid chromatography and $^1$H-NMR, the reaction liquid was found to contain N,N'-hexanediyl-di(carbamic acid (p-heptylphenyl)ester) and urea. The yield of N,N'-hexanediyl-di(carbamic acid (p-heptylphenyl)ester) based on hexamethylenediamine was about 89%.

Step (F): Production of Isocyanate by Thermal Decomposition of N-Substituted Carbamic Acid-O-Aryl Ester The apparatus shown in FIG. 17 was used.

A thin film distillation apparatus 602 having a heat-conducting surface area of 0.2 m² was heated to 220° C. and the pressure within the thin film distillation apparatus was set to about 1.3 kPa. The reaction liquid recovered in the storage tank 110 in step (B) was placed in a storage tank 601 and supplied to the thin film distillation apparatus at the rate of about 1800 g/hr via a line 60. A liquid component was extracted from a line 62 provided in the bottom of thin film distillation apparatus 602 and recovered in a storage tank 603. The liquid component recovered in the storage tank 603 was again supplied to the thin film distillation apparatus 602 through a line 63. A gaseous component containing hexamethylene diisocyanate and p-heptyl phenol was extracted from a line 61 provided in the upper portion of the thin film distillation apparatus 602. The gaseous component was introduced into a distillation column 604, and the low boiling point component was separated by distillation. A liquid phase component was supplied to a distillation column 609 from a line 68 provided at a portion of the distillation column 604 lower than the feed line and further subjected to distillative separation. The gaseous phase component was condensed in a condenser 610 via a line 69 and recovered in a storage tank 612 through a gas-liquid separator 611.

When the condensate was analyzed by $^1$H-NMR and gas chromatography, the condensate was found to contain about 99% by weight of hexamethylene diisocyanate. The yield based on the organic amine (hexamethylene diamine) was about 79%.

Example 79

Steps (A) and (B): Production of N-Substituted Carbamic Acid-O-Aryl Ester

Figure 21:
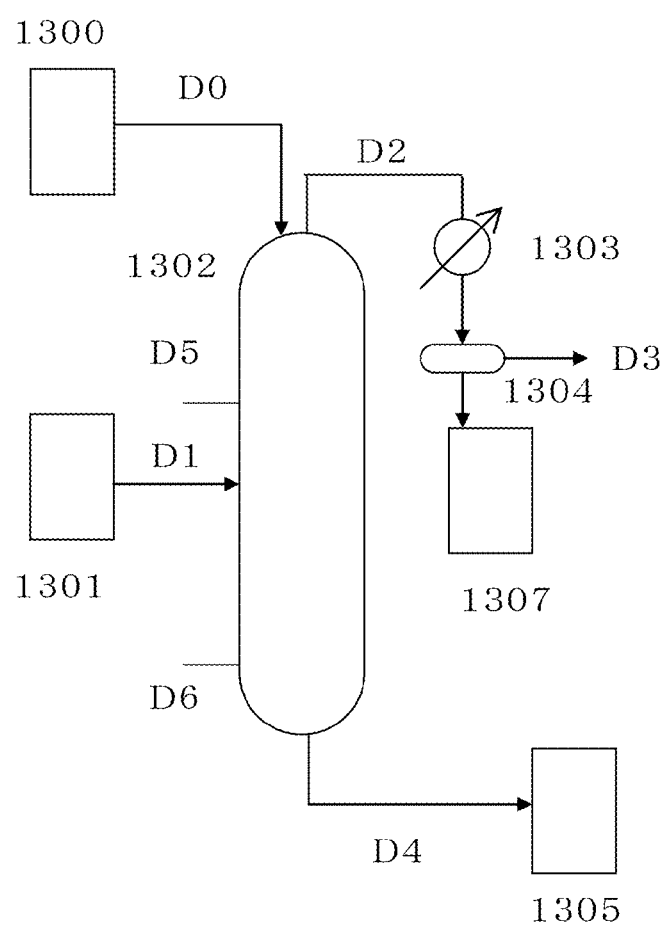
FIG. 21 shows a conceptual drawing depicting an N-substituted carbamic acid ester production apparatus in an example of the present embodiment.

The apparatus shown in FIG. 21 was used.

1.31 kg of hexamethylenediamine and 3.39 kg of urea were mixed into 3.5 kg of water to obtain a homogeneous aqueous solution. The aqueous solution was placed in a storage tank 1300. A portion of a distillation column 1302 packed with a packing material (Helipack No. 3) above a line D1 was heated to 200° C., while a portion of the distillation column 1302 below the line D1 was heated to 240° C., and the aqueous solution in the storage tank 1300 was fed at the rate of about 1.6 g/min from a line D0 while feeding nitrogen gas at the rate of 0.1 N L/min from a line D6. In addition, 4-(1,1,3,3-tetramethylbutyl)phenol was fed from a line 1301 at the rate of about 16.1 g/min. When reaction liquid was sampled from a sampling line D5 provided above the line D1 and analyzed by $^1$H-NMR and liquid chromatography, the reaction liquid was found to contain 1,1'-(hexane-1,6-diyl)diurea. In addition, in an analysis of the reaction liquid, compounds having amino groups (such as hexamethylenediamine or 6-ureido-hexamethyleneamine) were not detected.

Reaction liquid was recovered in a storage tank 1305 from a line D4 provided in the bottom of the distillation column 1302. When the reaction liquid recovered in the storage tank 1305 was analyzed by $^1$H-NMR and liquid chromatography, the reaction liquid was found to be a solution containing N,N'-hexanediyl-di(carbamic acid (4-(1,1,3,3-tetramethylbutyl)phenyl)ester). The yield of N,N'-hexanediyl-di(carbamic acid (4-(1,1,3,3-tetramethylbutyl)phenyl)ester) based on hexamethylenediamine was 78%.

Example 80

Steps (A) and (R): Production of N-Substituted Carbamic Acid-O-Alkyl Ester

The apparatus shown in FIG. 21 was used.

1.25 kg of hexamethylenediamine and 3.23 kg of urea were mixed into 3.3 kg of water to obtain a homogeneous aqueous solution. The aqueous solution was placed in the storage tank 1300. A portion of the distillation column 1302 packed with a packing material (Helipack No. 3) above the line D1 was heated to 200° C., while a portion of the distillation column 1302 below the line D1 was heated to 240° C., and the aqueous solution in the storage tank 1300 was fed at the rate of about 1.55 g/min from the line D0 while feeding nitrogen gas at the rate of 0.1 N L/min from the line D6. In addition, 2-phenyl ethanol was fed from the line 1301 at the rate of about 9.13 g/min. When reaction liquid was sampled from the sampling line D5 provided above the line D1 and analyzed by $^1$H-NMR and liquid chromatography, the reaction liquid was found to contain 1,1'-(hexane-1,6-diyl)diurea. In addition, in an analysis of the reaction liquid, compounds having amino groups (such as hexamethylenediamine or 6-ureido-hexamethyleneamine) were not detected.

Reaction liquid was recovered in the storage tank 1305 from the line D4 provided in the bottom of the distillation column 1302. When the reaction liquid recovered in the storage tank 1305 was analyzed by $^1$H-NMR and liquid chromatography, the reaction liquid was found to be a solution containing N,N'-hexanediyl-di(carbamic acid (2-phenylethyl) ester). The yield of N,N'-hexanediyl-di(carbamic acid (2-phenylethyl)ester) based on hexamethylenediamine was 75%.

Step (P): Production of N-Substituted Carbamic Acid-O-Aryl Ester by Transesterification Reaction The apparatus shown in FIG. 16 was used.

20.7 kg of p-heptyl phenol were added to the reaction liquid obtained in the above step to obtain a homogeneous solution that was placed in the storage tank 501.

The packed column 502 packed with a packing material (Helipack No. 3) was heated to 260° C. and the pressure inside the column was set to 26 kPa. The mixture in the storage tank 501 was fed at the rate of about 2.3 g/min from the line 51 provided in the packed column 502. A reaction liquid was recovered in the storage tank 505 via the line 54 provided in the bottom of the packed column 502. A gaseous phase component was introduced into the condenser 503 from the line 52 provided in the top of the packed column 502, and the resulting liquid phase component was recovered in the storage tank 504 through the gas-liquid separator 507. When the reaction liquid recovered in the storage tank 505 was analyzed by liquid chromatography and $^1$H-NMR, the reaction liquid was found to be a solution containing N,N'-hexanediyl-di(carbamic acid(p-heptylphenyl)ester), and the yield of N,N'-hexanediyl-di(carbamic acid(p-heptylphenyl)ester) based on hexamethylenediamine was 71%.

Example 81

Step (G): Urea Regeneration Step

Example 1 was repeated and ammonia obtained from lines 19 and 17 in steps (A) and (B) was recovered in the form of liquid ammonia using a liquefaction apparatus.

Ammonia pressurized to 17.6 MPa, heated to 150° C. and supplied at the rate of 3.44 kg/hr, carbon dioxide pressurized to 17.6 MPa and supplied at the rate of 2.20 kg/hr and a condensate to be described later were supplied to a urea synthesis tube 1401 and reacted at 190° C.

The urea synthesis liquid that appeared from the urea synthesis tube was supplied to a high-pressure separator 1402, while carbon dioxide simultaneously supplied from a line 21 was contacted with the urea synthesis liquid at the rate of 2.20 kg/hr to decompose non-converted products at 195° C. followed by separating a gaseous mixture containing ammonia at 4.26 kg/hr, carbon dioxide at 2.43 kg/hr and water at 0.50 kg/hr from a urea aqueous solution containing urea at 6.0 kg/hr, ammonia at 2.88 kg/hr, carbon dioxide at 2.34 kg/hr and water at 3.01 kg/hr. The urea aqueous solution was depressurized to 1.76 MPa and then 0.20 MPa to separate residual non-converted products, and then subjected to final treatment to obtain urea at the rate of 6.0 kg/hr. The separated non-converted products were absorbed with water to obtain an ammonia carbamate aqueous solution at 1.76 MPa containing ammonia at 2.84 kg/hr, carbon dioxide at 2.34 kg/hr and water at 1.21 kg/hr.

The gaseous mixture was then supplied to a condenser 1403 to aspirate and pressurize the ammonia carbamate aqueous solution pressurized to 17.6 MPa. The resulting condensate was recirculated to the urea synthesis tube 1401.

Step (A): Production of Compound Having Ureido Groups Using Urea Produced in Step (G)

The same method as step (A) of Example 1 was carried out with the exception of using 40.0 kg of p-heptyl phenol, 3.33 kg of the urea produced in step (G) above and 1.61 kg of hexamethylenediamine. The reaction liquid contained 6.3% by weight of 1,1'-(hexane-1,6-diyl)diurea. In addition, the concentration of ammonia in the solution was 6300 ppm. Unreacted amino group terminals were not detected.

Steps (B) and (D): Production of N-Substituted Carbamic Acid-O-Aryl Ester and Recovery of Urea The same method as step (B) of Example 1 was carried out with the exception of using the solution obtained in step (A) above followed by recovery of the reaction liquid in the storage tank 110. When the reaction liquid was analyzed by liquid chromatography and $^1$H-NMR, the reaction liquid was found to contain N,N'-hexanediyl-di(carbamic acid(p-heptylphenyl)ester), and the yield of N,N'-hexanediyl-di(carbamic acid(p-heptylphenyl)ester) based on hexamethylenediamine was about 97%.

Example 82

Step (G): Urea Regeneration Step

Figure 22:
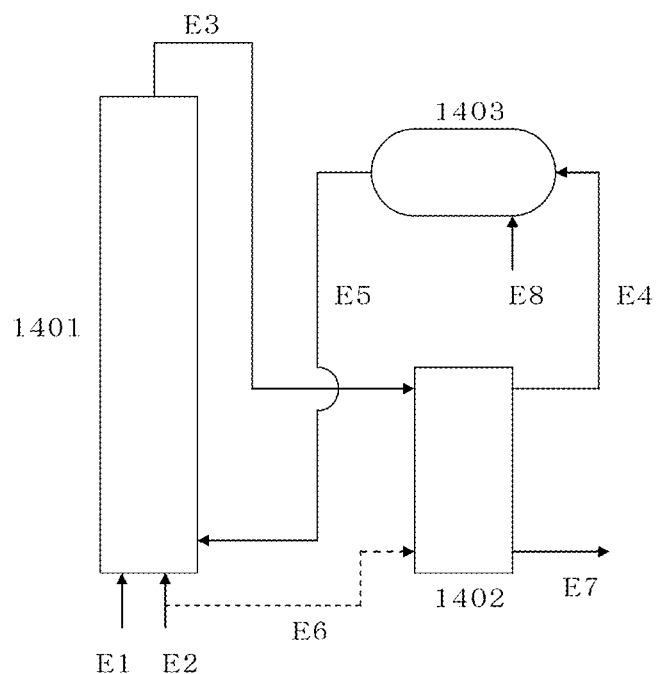
FIG. 22 shows a conceptual drawing depicting a urea production apparatus in an example of the present embodiment.
Figure 23:
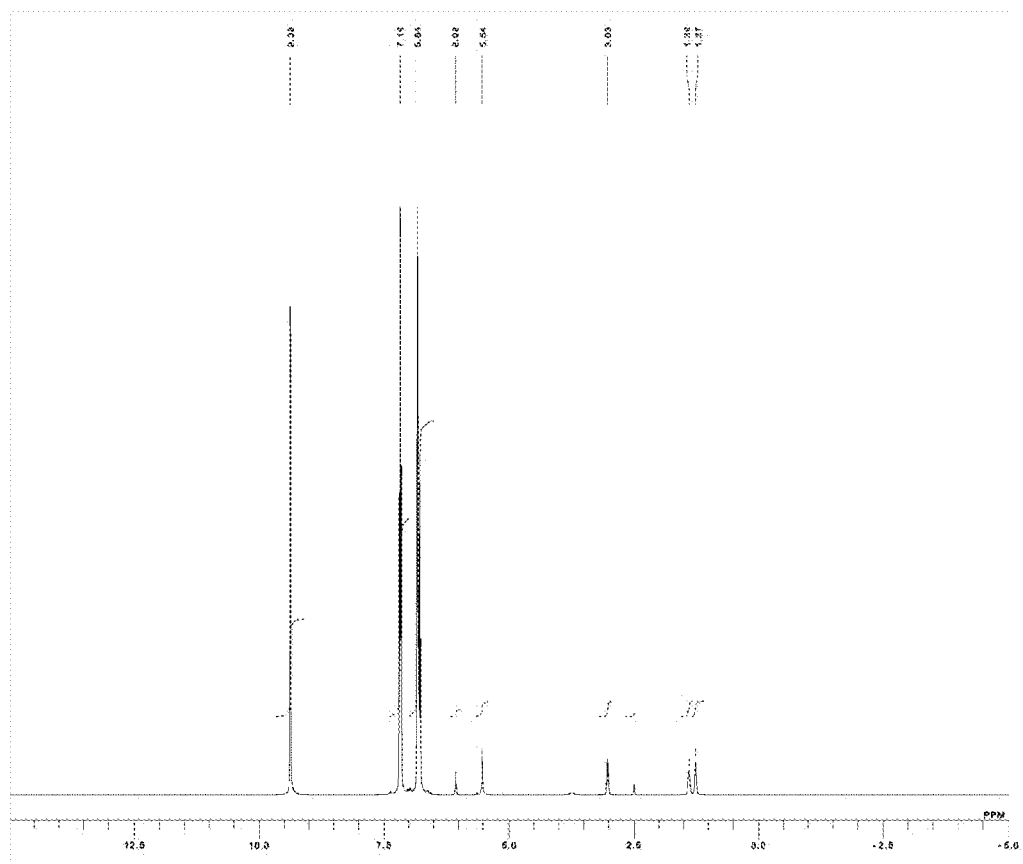
FIG. 23 shows the $^1$H-NMR spectrum of a composition for transfer and storage of a compound having the ureido groups of Example 97 of the present embodiment.
Figure 24:
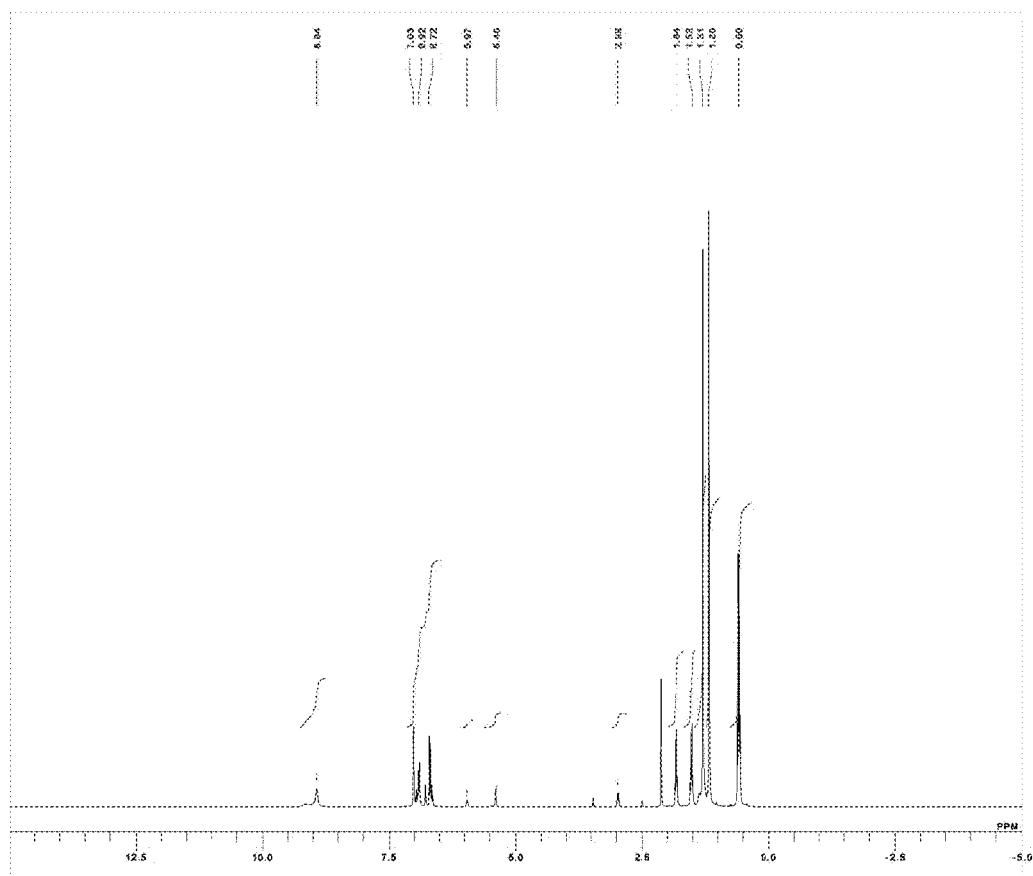
FIG. 24 shows the $^1$H-NMR spectrum of a composition for transfer and storage of a compound having the ureido groups of Example 106 of the present embodiment.
Figure 25:
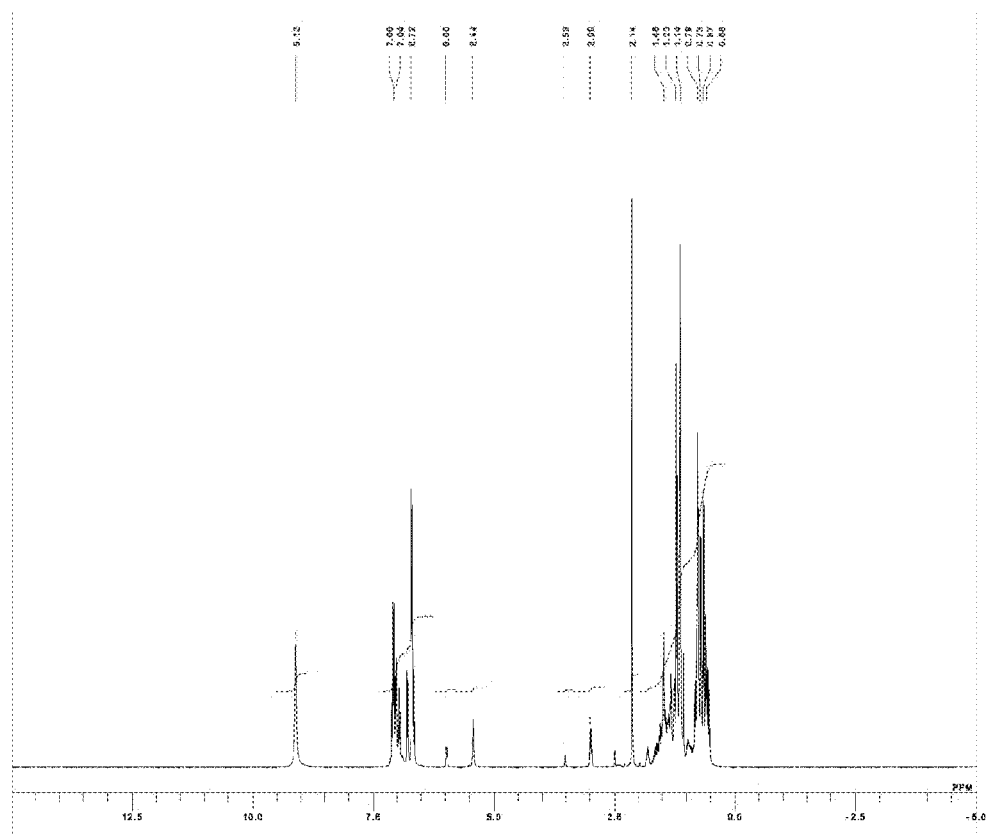
FIG. 25 shows the $^1$H-NMR spectrum of a composition for transfer and storage of a compound having the ureido groups of Example 122 of the present embodiment.
Figure 26:
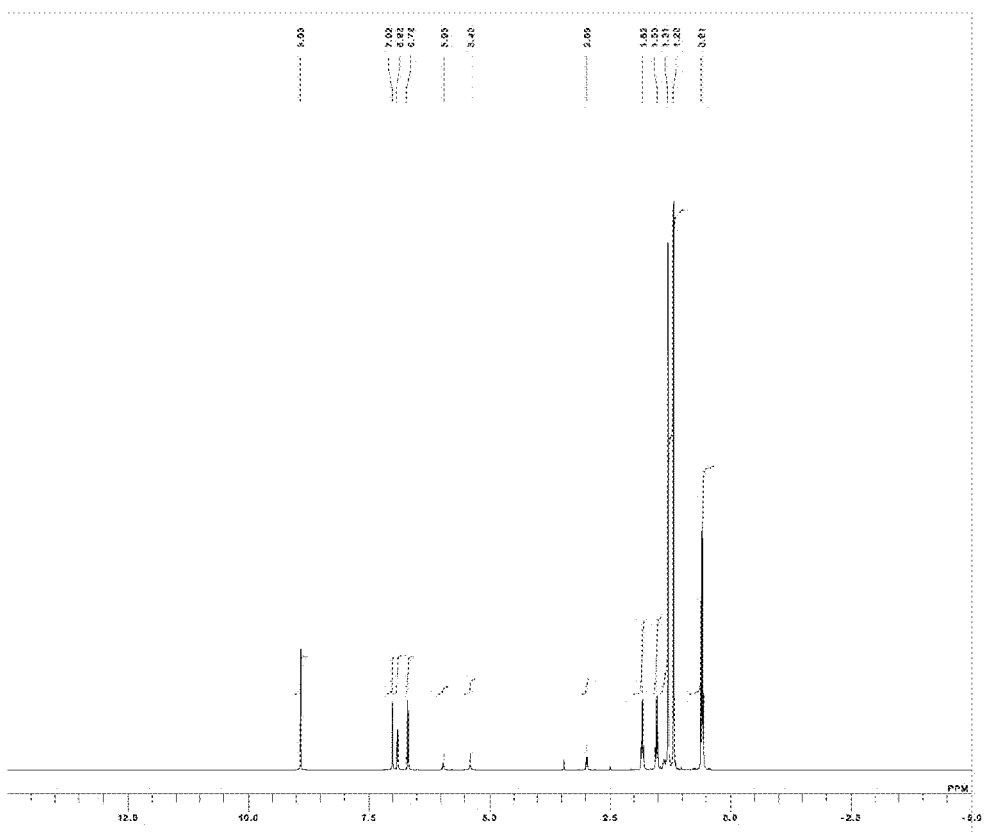
FIG. 26 shows the $^1$H-NMR spectrum of a composition for transfer and storage of a compound having the ureido groups of Example 142 of the present embodiment.

The apparatus shown in FIG. 22 was used.

Example 5 was repeated and ammonia obtained from lines 19 and 17 in steps (A) and (R) was recovered in the form of liquid ammonia using a liquefaction apparatus.

Ammonia pressurized to 17.6 MPa, heated to 150° C. and supplied at the rate of 3.44 kg/hr, carbon dioxide pressurized to 17.6 MPa and supplied at the rate of 2.20 kg/hr and a condensate to be described later were supplied to the urea synthesis tube 1401 and reacted at 190° C.

The urea synthesis liquid that appeared from the urea synthesis tube was supplied to the high-pressure separator 1402, while carbon dioxide simultaneously supplied from a line 21 was contacted with the urea synthesis liquid at the rate of 2.20 kg/hr to decompose non-converted products at 195° C. followed by separating a gaseous mixture containing ammonia at 4.26 kg/hr, carbon dioxide at 2.43 kg/hr and water at 0.50 kg/hr from a urea aqueous solution containing urea at 6.0 kg/hr, ammonia at 2.88 kg/hr, carbon dioxide at 2.34 kg/hr and water at 3.01 kg/hr. The urea aqueous solution was depressurized to 1.76 MPa and then 0.20 MPa to separate residual non-converted products, and then subjected to final treatment to obtain urea at the rate of 6.0 kg/hr. The separated non-converted products were absorbed with water to obtain an ammonia carbamate aqueous solution at 1.76 MPa containing ammonia at 2.84 kg/hr, carbon dioxide at 2.34 kg/hr and water at 1.21 kg/hr.

The gaseous mixture was then supplied to the condenser 1403 to aspirate and pressurize the ammonia carbamate aqueous solution pressurized to 17.6 MPa. The resulting condensate was recirculated to the urea synthesis tube 1401.

Step (A): Production of N-Substituted Carbamic Acid Ester Using Urea Regenerated in Step (G)

Production of Compound Having Ureido Groups

The same method as step (A) of Example 5 was carried out with the exception of using 14.6 kg of 1-octanol, 1.47 kg of the urea produced in step (G) above and 0.87 kg of 3-aminomethyl-3,5,5-trimethylcyclohexylamine. As a result of analyzing the resulting reaction liquid by liquid chromatography, it was found to contain about 7.8% by weight of 3-(ureidomethyl)-3,5,5-trimethylcyclohexylurea. In addition, the ammonia concentration in the solution was 7300 ppm. 13.4 kg of an aromatic hydroxy compound in the form of p-dodecyl phenol were added from the storage tank 101 to obtain a homogeneous solution. Line 13 was then opened and the solution was transferred to the storage tank 104 via the line 13.

Steps (R) and (D): Production of N-Substituted Carbamic Acid-O-Alkyl Ester and Recovery of Urea The same method as steps (R) and (D) of Example 4 was carried out with the exception of using the reaction liquid obtained in step (A) that used the regenerated urea described above. The amount of reaction liquid recovered in the storage tank 110 was 8.80 kg. When the reaction liquid was analyzed by liquid chromatography and $^1$H-NMR, the reaction liquid was found to contain 3-((1-octyloxy)carbonylamidomethyl)-3,5,5-trimethylcyclohexyl carbamic acid (1-octyl) ester, and the yield based on 3-aminomethyl-3,5,5-trimethylcyclohexylamine was about 95%.

Step (P): Transesterification Reaction

The same method as step (P) of Example 4 was carried out with the exception of using the reaction liquid obtained in steps (R) and (D) above. When the reaction liquid recovered in the storage tank 505 was analyzed by liquid chromatography and $^1$H-NMR, the reaction liquid was found to be a solution containing 3-((p-(dodecylphenyoxy)carbonylaminomethyl)-3,5,5-trimethylcyclohexyl carbamic acid (p-dodecylphenyl)ester), and the yield based on 3-aminomethyl-3,5,5-trimethylcyclohexylamine was 89%.

Example 83

Step (A): Production of Compound Having Ureido Groups

The same method as step (A) of Example 1 was carried out with the exception of using 1.33 kg of hexamethylenediamine, 3.09 kg of urea, 28.1 kg of 2-naphthol instead of p-heptyl phenol and heating the storage tank 103 to 120° C.

A reaction liquid was obtained that contained 7.2% by weight of 1,1'-(hexane-1,6-diyl)diurea and 6100 ppm of ammonia.

Steps (B) and (D): Production of N-Substituted Carbamic Acid-O-Aryl Ester

The same method as steps (B) and (D) of Example 1 was carried out with the exception of heating the packed column 105 to 240° C., setting the internal pressure to 15 kPa and using the reaction liquid obtained in step (A) above.

A reaction liquid was obtained that contained N,N'-hexanediyl-di(carbamic acid (2-naphthyl)ester), and the yield of N,N'-hexanediyl-di(carbamic acid (2-naphthyl) ester) based on hexamethylenediamine was about 97%. The concentration of ammonia in the reaction liquid was about 8 ppm.

Step (F): Production of Isocyanate by Thermal Decomposition of N-Substituted Carbamic Acid-O-Alkyl Ester The apparatus shown in FIG. 17 was used.

The thin film distillation apparatus 602 was heated to 220° C. and the pressure within the thin film distillation apparatus was set to about 1.0 kPa. The reaction liquid obtained in step (B) above was placed in the storage tank 601 and supplied to the thin film distillation apparatus at the rate of about 1800 g/hr via the line 60. A liquid component was extracted from the line 62 provided in the bottom of thin film distillation apparatus 602 and recovered in the storage tank 603 (the liquid component recovered in the storage tank 603 was not supplied to the thin film distillation apparatus 602). About 15.2 kg of a solution were obtained in the storage tank 603. A gaseous component containing hexamethylene diisocyanate and 2-naphthol was extracted from the line 61 provided in the upper portion of the thin film distillation apparatus 602. The gaseous component was introduced into the distillation column 604, and the low boiling point component was separated by distillation. A liquid phase component was supplied to the distillation column 609 from the line 68 provided at a portion of the distillation column 604 lower than the feed line and further subjected to distillative separation. The gaseous phase component was condensed in the condenser 610 via the line 69 and recovered in the storage tank 612 through the gas-liquid separator 611.

When the condensate was analyzed by $^1$H-NMR and gas chromatography, the condensate was found to contain about 99% by weight of hexamethylene diisocyanate.

Step (A-2): Reuse of N-Substituted Carbamic Acid-O-Aryl Ester not Undergoing Thermal Decomposition When the solution recovered in the storage tank 603 in step (F) above was analyzed by liquid chromatography, it was found to be a mixture containing N,N'-hexanediyl-di(carbamic acid (2-naphthyl)ester) and 2-naphthol.

The same method as step (A) above was carried out with the exception of using a mixture of about 5.9 kg of the mixture and 22.2 kg of 2-naphthol instead of 2-naphthol, 1.33 kg of hexamethylenediamine and 3.22 kg of urea. A reaction liquid was obtained that contained 7.2% by weight of 1,1'-(hexane-1,6-diyl)diurea and 6300 ppm of ammonia.

Example 84

Step (B-2): Reuse of N-Substituted Carbamic Acid-O-Aryl Ester not Undergoing Thermal Decomposition The same method as step (A) of Example 83 was carried out to obtain about 32.1 kg of a solution containing 7.2% by weight of 1,1'-(hexane-1,6-diyl)diurea.

6.0 kg of the mixture recovered in the storage tank 603 in step (F) above were added to this solution to obtain a mixture followed by carrying out the same method as step (B) above using this mixture. A reaction liquid was obtained that contained N,N'-hexanediyl-di(carbamic acid (2-naphthyl)ester), and the yield of N,N'-hexanediyl-di(carbamic acid (2-naphthyl)ester) based on hexamethylenediamine was about 97%.

Furthermore, yield referred to here indicates the yield of N,N'-hexanediyl-di(carbamic acid (2-naphthyl)ester) formed in the step (B). Namely, this refers to the value obtained by dividing the amount obtained by subtracting the amount of N,N'-hexanediyl-di(carbamic acid (2-naphthyl)ester) contained in the mixture recovered in the storage tank 603 used in this step from the amount of N,N'-hexanediyl-di(carbamic acid (2-napthyl)ester) contained in the reaction liquid by the amount of hexamethylenediamine used in step (A).

Example 85

Step (A): Production of Compound Having Ureido Groups

The same method as step (A) of Example 5 was carried out with the exception of using 11.7 kg of 1-hexanol instead of 1-octanol, using 1.64 kg of urea and 1.22 kg of 3-aminomethyl-3,5,5-trimethylcyclohexylamine, and heating the storage tank 103 to 120° C. As a result of analyzing the reaction liquid by liquid chromatography, the reaction liquid was found to contain about 7.8% by weight of 3-(ureidomethyl)-3,5,5-trimethylcyclohexylurea. In addition, the ammonia concentration in the solution was 7500 ppm. 12.2 kg of an aromatic hydroxy compound in the form of 4-phenyl phenol were added from the storage tank 101 to obtain a homogeneous solution. Line 13 was opened and the solution was transferred to the storage tank 104 via the line 13.

Steps (R) and (D): Production of N-Substituted Carbamic Acid-O-Alkyl Ester and Recovery of Urea The same method as steps (R) and (D) of Example 4 was carried out with the exception of heating the packed column 105 to 240° C., setting the pressure within the packed column 105 to about 10 kPa. When the reaction liquid recovered in the storage tank 110 was analyzed by liquid chromatography and $^1$H-NMR, the reaction liquid was found to contain 3-((1-hexyloxy)carbonylamidomethyl)-3,5,5-trimethylcyclohexyl carbamic acid (1-hexyl)ester, and the yield based on 3-aminomethyl-3,5,5-tricyclohexylamine was about 92%. The concentration of ammonia in the reaction liquid was about 10 ppm.

Step (P): Transesterification Reaction

The same method as step (P) of Example 4 was carried out with the exception of heating the packed column 502 to 250° C. and setting the internal pressure to 15 kPa. When the reaction liquid recovered in the storage tank 505 was analyzed by liquid chromatography and $^1$H-NMR, the reaction liquid was found to be a solution containing 3-((4-(phenylphenyloxy)carbonylamidomethyl)-3,5,5-trimethylcyclohexyl carbamic acid (4-phenylphenyl)ester, and the yield based on 3-aminomethyl-3,5,5-trimethylcyclohexylamine was 88%.

Step (F): Production of Isocyanate by Thermal Decomposition of N-Substituted Carbamic Acid-O-Aryl Ester The apparatus shown in FIG. 17 was used.

The thin film distillation apparatus 602 was heated to 230° C. and the pressure within the thin film distillation apparatus was set to about 1.0 kPa. The reaction liquid recovered in the storage tank 505 in step (P) above was placed in the storage tank 601 and supplied to the thin film distillation apparatus at the rate of about 1080 g/hr via the line 60. A liquid component was extracted from the line 62 provided in the bottom of thin film distillation apparatus 602 and recovered in the storage tank 603 (the liquid component recovered in the storage tank 603 was not supplied to the thin film distillation apparatus 602). A gaseous component containing isophorone diisocyanate and p-dodecyl phenol was extracted from the line 61 provided in the upper portion of the thin film distillation apparatus 602. The gaseous component was introduced into the distillation column 604, and the low boiling point component was separated by distillation. A liquid phase component was supplied to the distillation column 609 from the line 68 provided at a portion of the distillation column 604 lower than the feed line and further subjected to distillative separation. The gaseous phase component was condensed in the condenser 610 via the line 69 and recovered in the storage tank 612 through the gas-liquid separator 611.

When the condensate was analyzed by $^1$H-NMR and gas chromatography, the condensate was found to contain about 99% by weight of isophorone diisocyanate.

Step (R-2): Reuse of Mixture Containing Unreacted N-Substituted Carbamic Acid-O-Aryl Ester When the mixture recovered in the storage tank 603 in step (F) above was analyzed by liquid chromatography, the mixture was found to be a mixture containing 3-((4-phenylphenyloxy)carbonylamidomethyl)-3,5,5-trimethylcyclohexyl carbamic acid (4-phenylphenyl)ester and 4-phenyl phenol, and the content of 3-((4-phenylphenyloxy)carbonylamidomethyl)-3,5,5-trimethylcyclohexyl carbamic acid (4-phenylphenyl)ester was about 42% by weight.

The same method as steps (R) and (D) above was carried out with the exception of adding about 1.5 kg of the mixture recovered in the storage tank 603 to the reaction liquid obtained by carrying out the same method as step (A) above to obtain a mixture, and using that mixture. When the reaction liquid recovered in the storage tank 110 was analyzed by liquid chromatography and $^1$H-NMR, the reaction liquid was found to contain 3-((1-hexyloxy)carbonylamidomethyl)-3,5-5-trimethylcyclohexyl carbamic acid (1-hexyl)ester. The yield of the 3-((1-hexyloxy)carbonylamidomethyl)-3,5-5-trimethylcyclohexyl carbamic acid (1-hexyl)ester formed in this step (R-2) based on 3-aminomethyl-3,5,5-trimethylcyclohexylamine was about 92%. The ammonia concentration in the reaction liquid was about 10 ppm.

Example 86

Step (P-2): Reuse of Mixture Containing Unreacted N-Substituted Carbamic Acid-O-Aryl Ester The same method as steps (A) and (R) of Example 85 were carried out to obtain about 20.3 kg of a solution containing 3-((1-hexyloxy)carbonylamidomethyl)-3,5,5-trimethylcyclohexyl carbamic acid (1-hexyl)ester. About 2.5 kg of the mixture recovered in the storage tank 603 of step (F) above were mixed with this solution followed by carrying out the same method as step (P) above to obtain a solution containing 3-((4-phenylphenoxy)carbonylamidomethyl)-3,5,5-trimethylcyclohexyl carbamic acid (4-phenylphenyl)ester in the storage tank 505. The yield of the 3-((4-phenylphenyloxy)carbonylamidomethyl)-3,5,5-trimethylcyclohexyl carbamic acid (4-phenylphenyl)ester, excluding the 3-((4-phenylphenyloxy)carbonylamidomethyl)-3,5,5-trimethylcyclohexyl carbamic acid (4-phenylphenyl)ester produced in step (P-2) and contained in the mixture recovered in the storage tank 603 that was added as described above, based on 3-aminomethyl-3,5,5-trimethylcyclohexylamine was 88%.

Example 87

Step (A-2): Reuse of N-Substituted Carbamic Acid-O-Aryl Ester not Undergoing Thermal Decomposition The same method as steps (A) and (R) of Example 85 was carried out to obtain about 21.5 kg of a solution containing 3-((1-hexyloxy)carbonylamidomethyl)-3,5,5-trimethylcyclohexyl carbamic acid (1-hexyl)ester.

The same method as step (A) above was carried out with the exception of using a mixture of about 6.8 kg of this solution and 16.9 kg of 1-octanol instead of 1-octanol alone, and using 1.41 kg of hexamethylenediamine and 2.39 kg of urea. A reaction solution was obtained that contained 7.6% by weight of 1,1'-(hexane-1,6-diyl)diurea and 5300 ppm of ammonia.

Example 88

Step (A): Production of Compound Having Ureido Groups

The apparatus shown in FIG. 13 was used.

30.5 kg of p-heptyl phenol and 2.54 kg of urea were mixed in the storage tank 101 heated to 120° C. with the line 13 closed to obtain a mixture. The mixture was transferred to the stirring tank 103 (with baffles) heated to 120° C. The line 19 was connected to a vacuum pump and the pressure inside the stirring tank 103 was reduced to about 70 kPa. 1.23 kg of organic amine in the form of hexamethylenediamine were supplied at the rate of about 20 g/min (organic amine supply rate) from the storage tank 102 to the stirring tank 103 via the line 12 while stirring the stirring tank 103. Following completion of supplying hexamethylenediamine, stirring was continued for about 2 hours and the reaction liquid was sampled. As a result of analyzing the reaction liquid by liquid chromatography, 1,1'-(hexane-1,6-diyl)diurea was found to have been formed at a yield of about 97% based on hexamethylenediamine. In addition, the ammonia concentration in the solution was 1200 ppm. Unreacted amino group terminals were not detected.

Line 13 was then opened and the reaction liquid was transferred to the storage tank 104 via the line 13.

Steps (B) and (D): Production of N-Substituted Carbamic Acid-O-Aryl Ester and Recovery of Urea The apparatus shown in FIG. 13 was continued to be used.

A packed column 105 packed with a packing material (Helipack No. 3) was heated to 240° C. and the pressure inside the column was set to 26 kPa. The reaction liquid obtained in step (A) was fed from a line 14 provided in the packed column 105 at the rate of about 1.5 g/min. Since the reaction is initially in an unsteady state, the sample at that time was discarded. The amount of reaction liquid fed after the reaction had reached a steady state was about 35.1 kg. The reaction liquid was recovered in a storage tank 110 through a line 16 provided in the bottom of the packed column 105. A gaseous phase component was condensed from a line 15 provided in the top of the packed column 105 with a condenser 106 maintained at a temperature of about 85° C., and the resulting liquid phase component was recovered in a storage tank 109 via a gas-liquid separator 108. When reaction liquid recovered in the storage tank 109 was analyzed by $^1$H-NMR, the condensed component was found to contain urea and p-heptyl phenol. The amount of reaction liquid recovered in the storage tank 110 was 23.0 kg. When the reaction liquid was analyzed by liquid chromatography and $^1$H-NMR, the reaction liquid was found to contain N,N'-hexanediyl-di(carbamic acid(p-heptylphenyl)ester). The yield of N,N'-hexanediyl-di(carbamic acid(p-heptylphenyl)ester) based on the hexamethylene diamine was about 96%. Urea was not detected in the reaction liquid.

Step (F): Production of Isocyanate by Thermal Decomposition of N-Substituted Carbamic Acid-O-Aryl Ester The apparatus shown in FIG. 17 was used.

A thin film distillation apparatus 602 having a heat-conducting surface area of 0.2 m$^2$ was heated to 220° C. and the pressure within the thin film distillation apparatus was set to about 1.3 kPa. The reaction liquid recovered in the storage tank 110 in step (B) was placed in a storage tank 601 and supplied to the thin film distillation apparatus at the rate of about 1800 g/hr via a line 60. A liquid component was extracted from a line 62 provided in the bottom of thin film distillation apparatus 602 and recovered in a storage tank 603. The liquid component recovered in the storage tank 603 was again supplied to the thin film distillation apparatus 602 through a line 63. A gaseous component containing hexamethylene diisocyanate and p-heptyl phenol was extracted from a line 61 provided in the upper portion of the thin film distillation apparatus 602. The gaseous component was introduced into a distillation column 604, and the low boiling point component was separated by distillation. A liquid phase component was supplied to a distillation column 609 from a line 68 provided at a portion of the distillation column 604 lower than the feed line and further subjected to distillative separation. The gaseous phase component was condensed in a condenser 610 via a line 69 and recovered in a storage tank 612 through a gas-liquid separator 611.

When the condensate was analyzed by $^1$H-NMR and gas chromatography, the condensate was found to contain about 99% by weight of hexamethylene diisocyanate. The yield based on the organic amin (hexamethylene diamine) was about 92%.

Example 89

Step (A): Production of Compound Having Ureido Groups

The same method as step (A) of Example 88 was carried out with the exception of using 29.5 kg of p-heptyl phenol and 2.46 kg of urea, reducing the pressure in the stirring tank 103 to about 40 kPa, and using 1.19 kg of hexamethylenediamine. When the reaction liquid was analyzed, 1,1'-(hexane-1,6-diyl)diurea was found to have been formed at a yield of about 91% based on hexamethylenediamine. In addition, N,N'-hexanediyl-di(carbamic acid (p-heptylphenyl)ester) was found to have been formed at a yield of about 0.5% based on hexamethylenediamine. The ammonia concentration was 820 ppm. Unreacted amino group terminals were not detected.

Line 13 was then opened and the reaction liquid was transferred to the storage tank 104 via the line 13.

Steps (B) and (D): Production of N-Substituted Carbamic Acid-O-Aryl Ester and Recovery of Urea The same method as step (B) of Example 74 was carried out with the exception of using the reaction liquid of step (A) above. The reaction liquid recovered in the storage tank 110 was found to contain N,N'-hexanediyl-di(carbamic acid (p-heptylphenyl)ester), and the yield of N,N'-hexanediyl-di(carbamic acid (p-heptylphenyl)ester) based on hexamethylenediamine was about 91%. Urea was not detected in the reaction liquid.

Step (F): Production of Isocyanate by Thermal Decomposition of N-Substituted Carbamic Acid-O-Aryl Ester The same method as step (F) of Example 74 was carried out with the exception of using the reaction liquid of step (B) above. When the condensate recovered in the storage tank 612 was analyzed by $^1$H-NMR and gas chromatography, the condensate was found to contain about 99% by weight of hexamethylene diisocyanate. The yield based on hexamethylenediamine was about 86%.

Example 90

Step (A): Production of Compound Having Ureido Groups

The same method as step (A) of Example 88 was carried out with the exception of using 30.3 kg of p-heptyl phenol and 2.52 kg of urea, reducing the pressure in the stirring tank 103 to about 26 kPa, and using 1.22 kg of hexamethylenediamine. When the reaction liquid was analyzed, 1,1'-(hexane-1,6-diyl)diurea was found to have been formed at a yield of about 89% based on hexamethylenediamine. In addition, N,N'-hexanediyl-di(carbamic acid (p-heptylphenyl)ester) was found to have been formed at a yield of about 0.7% based on hexamethylenediamine. The ammonia concentration was 350 ppm. Unreacted amino group terminals were not detected.

Steps (B) and (D): Production of N-Substituted Carbamic Acid-O-Aryl Ester and Recovery of Urea The same method as step (B) of Example 74 was carried out with the exception of using the reaction liquid of step (A) above. The reaction liquid recovered in the storage tank 110 was found to contain N,N'-hexanediyl-di(carbamic acid (p-heptylphenyl)ester), and the yield of N,N'-hexanediyl-di(carbamic acid (p-heptylphenyl)ester) based on hexamethylenediamine was about 90%. Urea was not detected in the reaction liquid.

Step (F): Production of Isocyanate by Thermal Decomposition of N-Substituted Carbamic Acid-O-Aryl Ester The same method as step (F) of Example 74 was carried out with the exception of using the reaction liquid of step (B) above. When the condensate recovered in the storage tank 612 was analyzed by $^1$H-NMR and gas chromatography, the condensate was found to contain about 99% by weight of hexamethylene diisocyanate. The yield based on hexamethylenediamine was about 85%.

Example 91

Step (A): Production of Compound Having Ureido Groups

The same method as step (A) of Example 88 was carried out with the exception of using 31.8 kg of p-heptyl phenol and 2.64 kg of urea, reducing the pressure in the stirring tank 103 to about 20 kPa, and using 1.28 kg of hexamethylenediamine. When the reaction liquid was analyzed, 1,1'-(hexane-1,6-diyl)diurea was found to have been formed at a yield of about 82% based on hexamethylenediamine. In addition, N,N'-hexanediyl-di(carbamic acid (p-heptylphenyl)ester) was found to have been formed at a yield of about 5.2% based on hexamethylenediamine. The ammonia concentration was 280 ppm. Unreacted amino group terminals were not detected.

Steps (B) and (D): Production of N-Substituted Carbamic Acid-O-Aryl Ester and Recovery of Urea The same method as step (B) of Example 74 was carried out with the exception of using the reaction liquid of step (A) above. The reaction liquid recovered in the storage tank 110 was found to contain N,N'-hexanediyl-di(carbamic acid (p-heptylphenyl)ester), and the yield of N,N'-hexanediyl-di(carbamic acid (p-heptylphenyl)ester) based on hexamethylenediamine was about 85%. Urea was not detected in the reaction liquid.

Step (F): Production of Isocyanate by Thermal Decomposition of N-Substituted Carbamic Acid-O-Aryl Ester The same method as step (F) of Example 74 was carried out with the exception of using the reaction liquid of step (B) above. When the condensate recovered in the storage tank 612 was analyzed by $^1$H-NMR and gas chromatography, the condensate was found to contain about 99% by weight of hexamethylene diisocyanate. The yield based on hexamethylenediamine was about 82%.

Example 92

Step (A): Production of Compound Having Ureido Groups

The same method as step (A) of Example 88 was carried out with the exception of using 29.5 kg of p-heptyl phenol and 2.46 kg of urea, reducing the pressure in the stirring tank 103 to about 20 kPa, and using 1.19 kg of hexamethylenediamine. When the reaction liquid was analyzed, 1,1'-(hexane-1,6-diyl)diurea was found to have been formed at a yield of about 77% based on hexamethylenediamine. In addition, N,N'-hexanediyl-di(carbamic acid (p-heptylphenyl)ester) was found to have been formed at a yield of about 5.0% based on hexamethylenediamine. The ammonia concentration was 120 ppm. Unreacted amino group terminals were not detected.

Steps (B) and (D): Production of N-Substituted Carbamic Acid-O-Aryl Ester and Recovery of Urea The same method as step (B) of Example 74 was carried out with the exception of using the reaction liquid of step (A) above. The reaction liquid recovered in the storage tank 110 was found to contain N,N'-hexanediyl-di(carbamic acid (p-heptylphenyl)ester), and the yield of N,N'-hexanediyl-di(carbamic acid (p-heptylphenyl)ester) based on hexamethylenediamine was about 82%. Urea was not detected in the reaction liquid.

Step (F): Production of Isocyanate by Thermal Decomposition of N-Substituted Carbamic Acid-O-Aryl Ester The same method as step (F) of Example 74 was carried out with the exception of using the reaction liquid of step (B) above. When the condensate recovered in the storage tank 612 was analyzed by $^1$H-NMR and gas chromatography, the condensate was found to contain about 99% by weight of hexamethylene diisocyanate. The yield based on hexamethylenediamine was about 79%.

Example 93

Step (A): Production of Compound Having Ureido Groups

The same method as step (A) of Example 88 was carried out with the exception of using 32.5 kg of p-heptyl phenol and 2.71 kg of urea, reducing the pressure in the stirring tank 103 to about 20 kPa, and using 1.31 kg of hexamethylenediamine. When the reaction liquid was analyzed, 1,1'-(hexane-1,6-diyl)diurea was found to have been formed at a yield of about 68% based on hexamethylenediamine. In addition, N,N'-hexanediyl-di(carbamic acid (p-heptylphenyl)ester) was found to have been formed at a yield of about 9.1% based on hexamethylenediamine. The ammonia concentration was 90 ppm. Unreacted amino group terminals were not detected.

Steps (B) and (D): Production of N-Substituted Carbamic Acid-O-Aryl Ester and Recovery of Urea The same method as step (B) of Example 74 was carried out with the exception of using the reaction liquid of step (A) above. The reaction liquid recovered in the storage tank 110 was found to contain N,N'-hexanediyl-di(carbamic acid (p-heptylphenyl)ester), and the yield of N,N'-hexanediyl-di(carbamic acid (p-heptylphenyl)ester) based on hexamethylenediamine was about 76%. Urea was not detected in the reaction liquid.

Step (F): Production of Isocyanate by Thermal Decomposition of N-Substituted Carbamic Acid-O-Aryl Ester The same method as step (F) of Example 74 was carried out with the exception of using the reaction liquid of step (B) above. When the condensate recovered in the storage tank 612 was analyzed by $^1$H-NMR and gas chromatography, the condensate was found to contain about 99% by weight of hexamethylene diisocyanate. The yield based on hexamethylenediamine was about 71%.

Example 94

Step (A): Production of Compound Having Ureido Groups

The same method as step (A) of Example 88 was carried out with the exception of using 31.1 kg of p-heptyl phenol and 2.58 kg of urea, reducing the pressure in the stirring tank 103 to about 20 kPa, and using 1.25 kg of hexamethylenediamine. When the reaction liquid was analyzed, 1,1'-(hexane-1,6-diyl)diurea was found to have been formed at a yield of about 67% based on hexamethylenediamine. In addition, N,N'-hexanediyl-di(carbamic acid (p-heptylphenyl)ester) was found to have been formed at a yield of about 10.3% based on hexamethylenediamine. The ammonia concentration was 17 ppm. Unreacted amino group terminals were not detected.

Steps (B) and (D): Production of N-Substituted Carbamic Acid-O-Aryl Ester and Recovery of Urea The same method as step (B) of Example 74 was carried out with the exception of using the reaction liquid of step (A) above. The reaction liquid recovered in the storage tank 110 was found to contain N,N'-hexanediyl-di(carbamic acid (p-heptylphenyl)ester), and the yield of N,N'-hexanediyl-di(carbamic acid (p-heptylphenyl)ester) based on hexamethylenediamine was about 74%. Urea was not detected in the reaction liquid.

Step (F): Production of Isocyanate by Thermal Decomposition of N-Substituted Carbamic Acid-O-Aryl Ester The same method as step (F) of Example 74 was carried out with the exception of using the reaction liquid of step (B) above. When the condensate recovered in the storage tank 612 was analyzed by $^1$H-NMR and gas chromatography, the condensate was found to contain about 99% by weight of hexamethylene diisocyanate. The yield based on hexamethylenediamine was about 69%.

Example 95

Step (A): Production of Compound Having Ureido Groups

The same method as step (A) of Example 88 was carried out with the exception of using 31.8 kg of p-heptyl phenol and 2.65 kg of urea, reducing the pressure in the stirring tank 103 to about 20 kPa, and using 1.28 kg of hexamethylenediamine. When the reaction liquid was analyzed, 1,1'-(hexane-1,6-diyl)diurea was found to have been formed at a yield of about 52% based on hexamethylenediamine. In addition, N,N'-hexanediyl-di(carbamic acid (p-heptylphenyl)ester) was found to have been formed at a yield of about 16.1% based on hexamethylenediamine. The ammonia concentration was 8 ppm. Unreacted amino group terminals were not detected.

Steps (B) and (D): Production of N-Substituted Carbamic Acid-O-Aryl Ester and Recovery of Urea The same method as step (B) of Example 74 was carried out with the exception of using the reaction liquid of step (A) above. The reaction liquid recovered in the storage tank 110 was found to contain N,N'-hexanediyl-di(carbamic acid (p-heptylphenyl)ester), and the yield of N,N'-hexanediyl-di(carbamic acid (p-heptylphenyl)ester) based on hexamethylenediamine was about 65%. Urea was not detected in the reaction liquid.

Step (F): Production of Isocyanate by Thermal Decomposition of N-Substituted Carbamic Acid-O-Aryl Ester The same method as step (F) of Example 74 was carried out with the exception of using the reaction liquid of step (B) above. When the condensate recovered in the storage tank 612 was analyzed by $^1$H-NMR and gas chromatography, the condensate was found to contain about 99% by weight of hexamethylene diisocyanate. The yield based on hexamethylenediamine was about 61%.

Comparative Example 1

The apparatus shown in FIG. 13 was used.

1.21 kg of hexamethylenediamine, 2.51 kg of urea and 42.9 kg of 4-(1,1,3,3-tetramethylbutyl)phenol were mixed at 100° C. to obtain a raw material solution that was placed in the storage tank 104. The raw material solution was fed at the rate of about 3.0 g/min to the distillation column 105 heated to 240° C. and set to an internal pressure of 30 kPa and allowed to react. A gaseous phase component was introduced into the condenser 106 via the line 15 provided in the top of the distillation column 105 and the condensate was recovered in the storage tank 109. On the other hand, a reaction liquid was recovered from the line 16 provided in the bottom of the column and recovered in the storage tank 110. During the reaction, reaction liquid was sampled from a sampling line 18 provided between the line 14 and the bottom of the column, and the sampled liquid was analyzed by $^1$H-NMR and liquid chromatography. The sampled liquid was found to be a mixture containing 0.12% by weight of hexamethylenediamine, 0.42% by weight of 6-ureido-hexamethyleneamine, 1.26% by weight of 1,1'-(hexane-1,6-diyl)diurea, 3.49% by weight of N-(6-ureido-hexane-yl)-carbamic acid (4-(1,1,3,3-tetramethylbutyl)phenylester), and 1.30% by weight of N,N'-hexanediyl-di(carbamic acid (4-(1,1,3,3-tetramethylbutyl)phenylester). The amount of reaction liquid recovered in the storage tank 110 was 33.5 kg. When the reaction liquid was analyzed by $^1$H-NMR and liquid chromatography, it was found to be a reaction liquid that contained N,N'-hexanediyl-di(carbamic acid (4-(1,1,3,3-tetramethylbutyl)phenylester). The yield of N,N'-hexanediyl-di(carbamic acid (4-(1,1,3,3-tetramethylbutyl)phenylester) based on hexamethylenediamine was 53%. In addition, the reaction liquid contained about 13 mol % of N,N'-bis(6-(4-(1,1,3,3-tetramethylbutyl)phenoxycarbamino-hexyl)urea based on N,N'-hexanediyl-di (carbamic acid (4-(1,1,3,3-tetramethylbutyl)phenylester).

Comparative Example 2

Step (A): Production of Compound Having Ureido Groups

The apparatus used in FIG. 13 was used.

22.5 kg of 1-octanol and 2.27 kg of urea were mixed in the storage tank 101 heated to 120° C. with the line 13 closed, and the mixture was transferred to the stirring tank 103 heated to 120° C. 1.34 kg of organic amine in the form of 3-aminomethyl-3,5,5-trimethylcyclohexylamine were then supplied at the rate of about 10 g/min from the storage tank 102 to the stirring tank 103 via the line 12 while stirring the stirring tank 103. Following completion of supplying the 3-aminomethyl-3,5,5-trimethylcyclohexylamine, stirring was continued for about 2 hours and the reaction liquid was sampled. As a result of analyzing the reaction liquid by liquid chromatography, the reaction liquid was found to contain about 7.8% by weight of 3-(ureidomethyl)-3,5,5-trimethylcyclohexylurea. The concentration of ammonia in the reaction liquid was 6800 ppm. Line 13 was opened and the solution was transferred to the storage tank 104 via the line 13.

Steps (R) and (D): Production of N-Substituted Carbamic Acid-O-Alkyl Ester and Recovery of Urea The apparatus shown in FIG. 13 was continued to be used.

The packed column 105 packed with a packing material (Helipack No. 3) was heated to 190° C. The reaction liquid obtained in step (A) was fed from the line 14 provided in the packed column 105 at the rate of about 1.1 g/min. Since the reaction is initially in an unsteady state, the sample at that time was discarded. The amount of reaction liquid fed after the reaction had reached a steady state was about 23.4 kg. The reaction liquid was recovered in the storage tank 110 through the line 16 provided in the bottom of the packed column 105. A gaseous phase component was introduced into the condenser 106 from the line 15 provided in the top of the packed column 105, and the resulting liquid phase component was recovered in the storage tank 109 via the gas-liquid separator 108. When the condensed component recovered in the storage tank 109 was analyzed by $^1$H-NMR, the condensed component was found to contain 1-octanol and urea. The amount of the reaction liquid recovered in the storage tank 110 was 8.80 kg. When the reaction liquid was analyzed by liquid chromatography and $^1$H-NMR, the reaction liquid was found to contain 3-((1-octyloxy)carbonylamidomethyl)-3,5,5-trimethylcyclohexyl carbamic acid (1-octyl) ester, and the yield based on 3-aminomethyl-3,5,5-trimethylcyclohexylamine was about 90%.

Step (F): Production of Isocyanate by Thermal Decomposition of N-Substituted Carbamic Acid-O-Alkyl Ester The apparatus shown in FIG. 17 was used.

A thin film distillation apparatus 602 having a heat-conducting surface area of 0.2 m$^2$ was heated to 220° C. and the pressure within the thin film distillation apparatus was set to about 1.3 kPa. The reaction liquid recovered in the storage tank 110 in step (B) was placed in a storage tank 601 and supplied to the thin film distillation apparatus at the rate of about 1800 g/hr via a line 60. A liquid component was extracted from a line 62 provided in the bottom of thin film distillation apparatus 602 and recovered in a storage tank 603. The liquid component recovered in the storage tank 603 was again supplied to the thin film distillation apparatus 602 through a line 63. A gaseous component containing hexamethylene diisocyanate and p-heptyl phenol was extracted from a line 61 provided in the upper portion of the thin film distillation apparatus 602. The gaseous component was introduced into a distillation column 604, and the low boiling point component was separated by distillation. A liquid phase component was supplied to a distillation column 609 from a line 68 provided at a portion of the distillation column 604 lower than the feed line and further subjected to distillative separation. The gaseous component was condensed in the condenser 610 via a line 69 and recovered in a storage tank 612 through a gas-liquid separator 611.

When the condensate was analyzed by 1H-NMR and gas chromatography, the condensate was found to contain about 93% by weight of isophorone diisocyanate and about 4% by weight of 3-((1-octyloxy)carbonylamidomethyl)-3,5,5-trimethylcyclohexyl carbamic acid (1-octyl)ester. The yield based on organic amine (3-amino-methyl-3,5,5-trimethylcyclohexylamine) was about 53%.

Example 96

A composition containing 9% by weight of a compound having ureido groups in the form of 1,1'-(hexane-1,6-diyl) diurea, 89% by weight of an aromatic hydroxy composition in the form of 4-(2,4,4-trimethylpentan-2-yl)phenol, 0.01% by weight of ammonia and urea at a ratio of 0.1 (referring to the ratio of number of urea molecules to the number of ureido groups that compose (or are contained in) the compound having ureido groups, or in other words, 0.1 indicates 0.2 mole equivalents since the compound having ureido groups has two ureido groups in a molecule thereof) was placed in a 100 L SUS storage vessel to about ½ the volume thereof, followed by replacing the inside of the storage vessel with nitrogen, and storing for 1095 days in a storage environment found in the Kojima district of Kurashiki city in Okayama prefecture, Japan. The composition also contained other components for which the structure thereof was unclear (such as compounds containing ureylene groups and compounds containing terminal biuret bonds). During the storage period, the vessel was warmed with a circulating hot water jacket at 40° C. (controlled to roughly 30 to 50° C.). During the storage period, the temperature occasionally fell to about 0° C. or rose to about 50° C. due to the effects of water stoppages, power outages and factory utility maintenance. In addition, the temperature once rose to about 80° C. due to a malfunction. When the composition was analyzed after storage, the 1,1'-(hexane- 1,6-diyl)diurea was contained at about 92 mol % as compared with prior to storage. Following the storage period, the composition was heated to 180° C. and introduced through a preheater (device for preheating the composition to 230° C.) into the vicinity of the middle of a sieve tray distillation column having an inner diameter of 2.5 inches and 40 theoretical plates (operation of the distillation column was carried out while reducing the pressure from normal pressure to reduced pressure within a liquid phase temperature range in the lower portion of the distillation column of 150 to 300° C. and confirming operating conditions; the minimum pressure during operation was about 0.3 KPa). An N-substituted carbamic acid-O-aryl ester derived from the 1,1'-(hexane-1,6-diyl)diurea and aromatic hydroxy composition in the form of bis(4-(2,4,4-trimethylpentan-2-yl)phenyl)hexane-1,6-diyl carbamate was obtained from the lower portion of the distillation column. Ammonia formed as a by-product in the esterification reaction, a small amount of aromatic hydroxy composition, and a component having a lower boiling point than the aromatic hydroxy composition were extracted from the upper portion of the distillation column (and included a by-product in the form of a compound having a molecular weight of 178 or less and having a carbonyl group, although the structure thereof was unable to be identified). Although the yield changed from the start to completion of operation due to fluctuations in operating conditions, at the highest level of performance during the operating period, the yield of the bis-(4-(2,4,4-trimethylpentan-2-yl)phenyl)hexane-1,6-diyl) dicarbamate based on 1,1'-(hexane-1,6-diyl)diurea at the start of the storage period was 87 mol %. There was no clogging of lines during both storage and transfer, and formation of solid within the distillation column was not observed.

Examples 97 to 144 and Comparative Examples 3 to 6

Storage and esterification (reaction for obtaining N-substituted carbamic acid-O-aryl ester by reacting ureido groups with an aromatic hydroxy compound) were carried out using 1,1'-(hexane-1,6-diyl)diurea for the compound having ureido groups under the same conditions as Example 96 with the exception of the composite ratios of the compound having ureido groups, aromatic hydroxy composition, ammonia, carbonic acid derivative and the like, and the results of distillation are shown in Tables 37 to 44. Yields of N-substituted carbamic acid-O-aryl ester are indicated as values obtained by analyzing a liquid phase component from the lower portion of the sieve plate distillation column.

In the tables, ArOH represents an aromatic hydroxy compound that composes an aromatic hydroxy composition. The content of each component in the composition is represented as a weight percentage (wt %) obtained by rounding the contents of the compound having ureido groups, aromatic hydroxy composition, water and ammonia to the number of significant digits of the analysis apparatus or less, metal components are expressed in ppm, while other components (such as carbonic acid derivative) are indicated as the ratio of the number of molecules thereof to the number of ureido groups that compose (or are contained in) the compound having ureido groups. (Unless indicated otherwise, phenomena such as clogging or solid formation did not occur during storage or transfer.)

The $^1$H-NMR spectra of the compositions for transfer and storage of a compound having ureido groups of Examples 97, 106, 122 and 142 are shown in FIGS. 23, 24, 25 and 26, respectively.

TABLE 37

| | Content of compound having ureido groups in composition (wt %) | ArOH | Content of aromatic hydroxy compound in composition (wt %) | Content of ammonia in composition (wt %) | Other components and contents thereof in composition (%) | Ratio of compound having ureido groups after storage versus before storage (mol %) | Yield of N-substituted carbamic acid-O-aryl ester (mol %) (molar yield versus compound having ureido groups before storage) |
|---|---|---|---|---|---|---|---|
| Example 97 | 17.0 | phenol (C6H5-OH) | 81 | 0.0001 | Total ureylene group-containing compounds: 0.005, terminal biuret group-containing compounds: 0.005 | 95.0 | 92.0 |
| Example 98 | 9.7 | phenol (C6H5-OH) | 72 | 0.0001 | Total ureylene group-containing compounds: 0.005, terminal biuret group-containing compounds: 0.005, diphenylhexane-1,6-dilyl carbamate: 16.5 wt % | 85.0 | 82.0 |
| Example 99 | 1.0 | phenol (C6H5-OH) | 99 | 0.0001 | | 98.0 | 97.0 |
| Example 100 | 17.7 | phenol (C6H5-OH) | 51.5 | 0.05 | Fe ion: 20 ppm, Ni ion: 15 ppm | 98.3 | 93.7 |

TABLE 37-continued

| | Content of compound having ureido groups in composition (wt %) | ArOH | Content of aromatic hydroxy compound in composition (wt %) | Content of ammonia in composition (wt %) | Other components and contents thereof in composition (%) | Ratio of compound having ureido groups after storage versus before storage (mol %) | Yield of N-substituted carbamic acid-O-aryl ester (mol %) (molar yield versus compound having ureido groups before storage) |
|---|---|---|---|---|---|---|---|
| | | 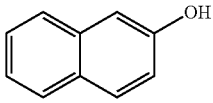 | 30 | | | | |
| Comparative Example 3 | 17.7 | | 0 | 0.0001 | 1-butanol: 79 wt %, urea: 0.01 | 3 | (solid formation, pump clogged) |
| Comparative Example 4 | 17.7 | | 0 | 0.001 | 1-butanol: 80 wt %, dibutyl tin dilaurate: 2010 ppm | 3 | (solid formation, pump clogged) |
| Comparative Example 5 | 96 | | 0 | 0.0001 | 1-butanol: 0.1 wt %, urea: 0.001, total ureylene group-containing compounds: 0.005, terminal biuret group-containing compounds: 0.005 | 98.0 | (sticking during heating, pump clogged) |

TABLE 38

| | Content of compound having ureido groups in composition (wt %) | ArOH | Content of aromatic hydroxy compound in composition (wt %) | Content of ammonia in composition (wt %) | Other components and contents thereof in composition (%) | Ratio of compound having ureido groups after storage versus before storage (mol %) | Yield of N-substituted carbamic acid-O-aryl ester (mol %) (molar yield versus compound having ureido groups before storage) |
|---|---|---|---|---|---|---|---|
| Example 101 | 97 | | 0 | 0.001 | 1-butanol: 0.1 wt %, urea: 0.001 | 98.0 | (although unable to be transferred after storage due to being a powder, able to be transferred when a separate stirring tank with stirrer was provided and a 17.7 wt % phenol solution was prepared at 120° C.; yield at that time: 70 mol %) |

TABLE 38-continued

| | Content of compound having ureido groups in composition (wt %) | ArOH | Content of aromatic hydroxy compound in composition (wt %) | Content of ammonia in composition (wt %) | Other components and contents thereof in composition (%) | Ratio of compound having ureido groups after storage versus before storage (mol %) | Yield of N-substituted carbamic acid-O-aryl ester (mol %) (molar yield versus compound having ureido groups before storage) |
|---|---|---|---|---|---|---|---|
| Comparative Example 6 | 98.5 | | 0 | 0.001 | 1-butanol: 0.1 wt %, urea: 0.001 | 97.5 | (unable to be transferred after storage due to being a powder, large amount of insoluble matter caused pump clogging even when a separate stirring tank with stirrer was provided and a 17.7 wt % 1-butanol solution was prepared at 110° C. |
| Example 102 | 17.7 | phenol; 2-naphthol | 51; 30 | 0.01 | Fe ion: 20 ppm, Ni ion: 15 ppm, dibutyl tin dilaurate: 2010 ppm | 18.1 | 17.3 |
| Example 103 | 15.8 | o-cresol; 4-(1,1,3,3-tetramethylbutyl)phenol | 10; 72 | 0.01 | Dibutyl tin dilaurate: 10 ppm, total carbonic acid ester: 0.001 | 99.4 | 97.6 |
| Example 104 | 15.8 | m-cresol; 4-(1,1,3,3-tetramethylbutyl)phenol | 10; 73.2 | 0.001 | Water: 90 ppm | 98.1 | 93.5 |

TABLE 38-continued

| | Content of compound having ureido groups in composition (wt %) | ArOH | Content of aromatic hydroxy compound in composition (wt %) | Content of ammonia in composition (wt %) | Other components and contents thereof in composition (%) | Ratio of compound having ureido groups after storage versus before storage (mol %) | Yield of N-substituted carbamic acid-O-aryl ester (mol %) (molar yield versus compound having ureido groups before storage) |
|---|---|---|---|---|---|---|---|
| Example 105 | 15.8 | 4-methylphenol | 10 | 0.01 | Fe ion: 20 ppm, Ni ion: 30 ppm dibutyl tin dilaurate: 300 ppm | 86.1 | 81.7 |
| | | 4-octylphenol | 73.2 | | | | |
| Example 106 | 14.2 | 2,4-dimethylphenol | 14 | 0.005 | Total biuret group-containing compounds: 0.005, Al ion: 40 ppm | 97.9 | 88.4 |
| | | 2-tert-butyl-4-tert-amylphenol | 70 | | | | |

TABLE 39

| | Content of compound having ureido groups in composition (wt %) | ArOH | Content of aromatic hydroxy compound in composition (wt %) | Content of ammonia in composition (wt %) | Other components and contents thereof in composition (%) | Ratio of compound having ureido groups after storage versus before storage (mol %) | Yield of N-substituted carbamic acid-O-aryl ester (mol %) (molar yield versus compound having ureido groups before storage) |
|---|---|---|---|---|---|---|---|
| Example 107 | 14.2 | 2,6-dimethylphenol | 20 | 0.01 | Urea: 1, Al ion: 40 ppm | 98.6 | 96.4 |
| | | 2-naphthol | 56 | | | | |

TABLE 39-continued

| | Content of compound having ureido groups in composition (wt %) | ArOH | Content of aromatic hydroxy compound in composition (wt %) | Content of ammonia in composition (wt %) | Other components and contents thereof in composition (%) | Ratio of compound having ureido groups after storage versus before storage (mol %) | Yield of N-substituted carbamic acid-O-aryl ester (mol %) (molar yield versus compound having ureido groups before storage) |
|---|---|---|---|---|---|---|---|
| Example 108 | 14.2 | (structure) | 14 70 | 0.04 | Urea: 0.005, dibutyl tin dilaurate: 590 ppm | 76.1 | 68.6 |
| Example 109 | 14.2 | (structure) | 45 39 | 0.1 | Total ureylene group-containing compounds: 0.005, dibutyl tin dilaurate: 290 ppm | 88.0 | 83.8 |
| Example 110 | 14.2 | (structure) | 45 39 | 0.5 | Total terminal biuret group-containing compounds: 0.005, dibutyl tin dilaurate: 60 ppm | 97.0 | 92.7 |
| Example 111 | 12.9 | (structure) | 25 60 | 0.01 | Total ureylene group-containing compounds: 0.005, dibutyl tin dilaurate: 30 ppm, water: 0.5 wt % | 97.0 | 88.9 |

TABLE 39-continued

| | Content of compound having ureido groups in composition (wt %) | ArOH | Content of aromatic hydroxy compound in composition (wt %) | Content of ammonia in composition (wt %) | Other components and contents thereof in composition (%) | Ratio of compound having ureido groups after storage versus before storage (mol %) | Yield of N-substituted carbamic acid-O-aryl ester (mol %) (molar yield versus compound having ureido groups before storage) |
|---|---|---|---|---|---|---|---|
| Example 112 | 12.9 | 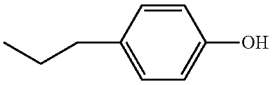 | 10 | 0.01 | Total ureylene group-containing compounds: 0.005, terminal biuret group-containing compounds: 0.005, dibutyl tin dilaurate: 60 ppm, water: 0.5 wt % | 97.0 | 92.7 |
| | | 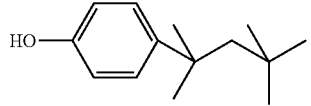 | 75 | | | | |
| Example 113 | 20.0 | 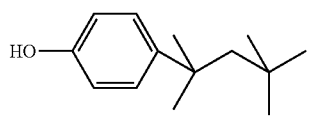 | 20 | 0.01 | Total ureylene group-containing compounds: 0.005 | 99.0 | 90.0 |
| | | 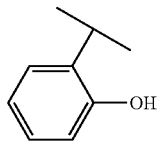 | 59 | | | | |

TABLE 40

| | Content of compound having ureido groups in composition (wt %) | ArOH | Content of aromatic hydroxy compound in composition (wt %) | Content of ammonia in composition (wt %) | Other components and contents thereof in compostion (%) | Ratio of compound having ureido groups after storage versus before storage (mol %) | Yield of N-substituted carbamic acid-O-aryl ester (mol %) (molar yield versus compound having ureido groups before storage) |
|---|---|---|---|---|---|---|---|
| Example 114 | 12.9 | 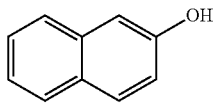 | 20 | 0.1 | Total ureylene group-containing compounds: 0.005 | 98.4 | 96.4 |
| | |  | 65 | | | | |

TABLE 40-continued

| | Content of compound having ureido groups in composition (wt %) | ArOH | Content of aromatic hydroxy compound in composition (wt %) | Content of ammonia in composition (wt %) | Other components and contents thereof in compostion (%) | Ratio of compound having ureido groups after storage versus before storage (mol %) | Yield of N-substituted carbamic acid-O-aryl ester (mol %) (molar yield versus compound having ureido groups before storage) |
|---|---|---|---|---|---|---|---|
| Example 115 | 12.9 | 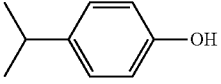 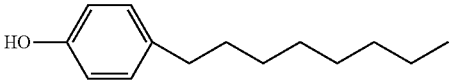 | 25<br>60 | 0.2 | Total ureylene group-containing compounds: 0.005, dibutyl tin dilaurate: 40 ppm, water: 0.5 wt % | 95.3 | 90.4 |
| Example 116 | 12.9 | 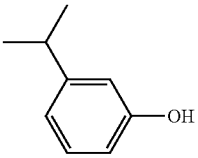 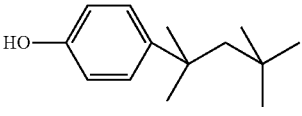 | 20<br>65 | 0.001 | Total ureylene group-containing compounds: 0.005, terminal biuret group-containing compounds: 0.005 | 98.4 | 93.5 |
| Example 117 | 11.9 | 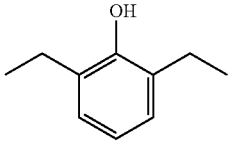 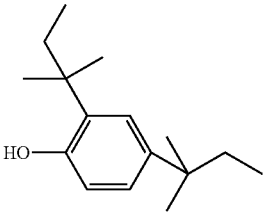 | 20<br>65 | 0.001 | Total ureylene group-containing compounds: 0.005, terminal biuret group-containing compounds: 0.005 | 98.3 | 88.6 |
| Example 118 | 11.9 | 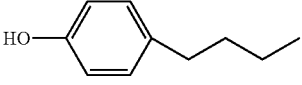 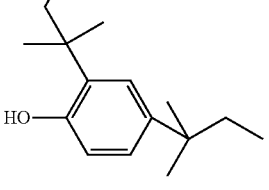 | 26<br>60 | 0.001 | Total ureylene group-containing compounds: 0.005, terminal biuret group-containing compounds: 0.005, dibutyl tin dilaurate: 60 ppm | 97.5 | 87.8 |

TABLE 40-continued

| | Content of compound having ureido groups in composition (wt %) | ArOH | Content of aromatic hydroxy compound in composition (wt %) | Content of ammonia in composition (wt %) | Other components and contents thereof in composition (%) | Ratio of compound having ureido groups after storage versus before storage (mol %) | Yield of N-substituted carbamic acid-O-aryl ester (mol %) (molar yield versus compound having ureido groups before storage) |
|---|---|---|---|---|---|---|---|
| Example 119 | 9.9 | 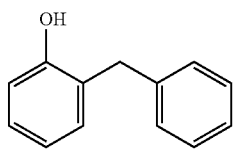 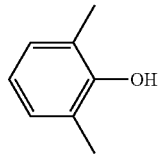 | 70<br><br>18 | 0.2 | Total ureylene group-containing compounds: 0.005, biuret group-containing compounds: 0.005 | 98.0 | 96.4 |
| Example 120 | 11.6 | 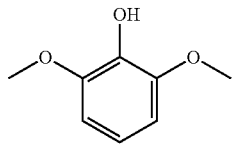 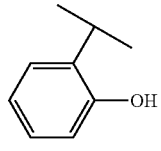 | 70<br><br>15 | 0.4 | Total ureylene group-containing compounds: 0.015, terminal biuret group-containing compounds: 0.015 | 97.4 | 87.9 |

TABLE 41

| | Content of compound having ureido groups in composition (wt %) | ArOH | Content of aromatic hydroxy compound in composition (wt %) | Content of ammonia in composition (wt %) | Other components and contents thereof in composition (%) | Ratio of compound having ureido groups after storage versus before storage (mol %) | Yield of N-substituted carbamic acid-O-aryl ester (mol %) (molar yield versus compound having ureido groups before storage) |
|---|---|---|---|---|---|---|---|
| Example 121 | 12.8 | 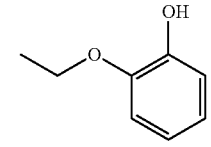 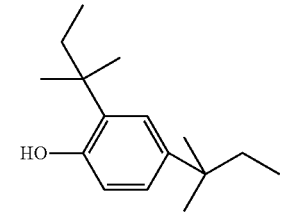 | 20<br><br>63 | 0.3 | Total ureylene group-containing compounds: 0.020, terminal biuret group-containing compounds: 0.015 | 97.7 | 87.9 |

TABLE 41-continued

| | Content of compound having ureido groups in composition (wt %) | ArOH | Content of aromatic hydroxy compound in composition (wt %) | Content of ammonia in composition (wt %) | Other components and contents thereof in composition (%) | Ratio of compound having ureido groups after storage versus before storage (mol %) | Yield of N-substituted carbamic acid-O-aryl ester (mol %) (molar yield versus compound having ureido groups before storage) |
|---|---|---|---|---|---|---|---|
| Example 122 | 9.5 | 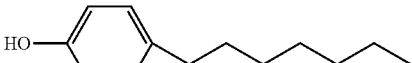 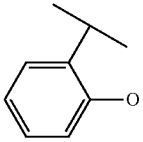 | 79.5<br><br>10 | 0.1 | Total ureylene group-containing compounds: 0.002, terminal biuret group-containing compounds: 0.005 | 95.8 | 94.1 |
| Example 123 | 8.9 | 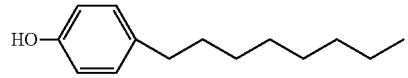 | 74 | 0.01 | Naphthalene: 15 wt % total ureylene group-containing compounds: 0.002, terminal biuret group-containing compounds: 0.005 | 96.6 | 91.2 |
| Example 124 | 10.8 | 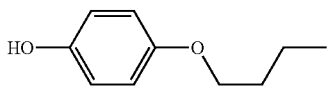 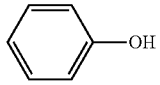 | 76<br><br>10 | 0.01 | Total ureylene group-containing compounds: 0.002, terminal biuret-group containing compounds: 0.005 | 96.3 | 91.2 |
| Example 125 | 12.3 | 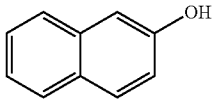 | 80 | 0.01 | Total ureylene group-containing compounds: 0.002, terminal biuret group-containing compounds: 0.005, butanol: 5 wt % | 95.9 | 94.1 |
| Example 126 | 12.3 | 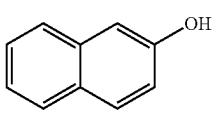 | 85 | 0.01 | Total ureylene group-containing compounds: 0.002, terminal biuret group-containing compounds: 0.005 | 98.4 | 96.4 |
| Example 127 | 12.3 | 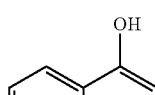 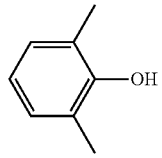 | 76<br><br>10 | 0.02 | Total ureylene group-containing compounds: 0.002, terminal biuret group-containing compounds: 0.005 | 98.4 | 88.6 |

TABLE 42

| | Content of compound having ureido groups in composition (wt %) | ArOH | Content of aromatic hydroxy compound in composition (wt %) | Content of ammonia in composition (wt %) | Other components and contents thereof in compostion (%) | Ratio of compound having ureido groups after storage versus before storage (mol %) | Yield of N-substituted carbamic acid-O-aryl ester (mol %) (molar yield versus compound having ureido groups before storage) |
|---|---|---|---|---|---|---|---|
| Example 128 | 5.2 | phenyl-O-C6H4-OH | 93.8 | 0.02 | Total ureylene group-containing compounds: 0.002, terminal biuret group-containing compounds: 0.005 | 99.0 | 98.0 |
| Example 129 | 14.5 | phenyl-O-C6H4-OH | 84 | 0.02 | Total ureylene group-containing compounds: 0.002, terminal biuret group-containing compounds: 0.005 | 98.0 | 95.0 |
| Example 130 | 21.4 | phenyl-O-C6H4-OH | 77 | 0.02 | Total ureylene group-containing compounds: 0.002, terminal biuret group-containing compounds: 0.005 | 95.8 | 60.0 |
| Example 131 | 13.6 | HO-C6H4-Cl / naphthalen-2-ol | 20 / 63 | 0.02 | Total ureylene group-containing compounds: 0.022, terminal biuret-group containing compounds: 0.015 | 83.8 | 42.0 |
| Example 132 | 12.8 | HO-C6H4-N(CH3)2 / 2,6-dimethylphenol | 72 / 10 | 0.05 | Total ureylene group-containing compounds: 0.022, terminal biuret group-containing compounds: 0.015 | 76.6 | 38.0 |
| Example 133 | 35.2 | phenyl-O-C6H4-OH | 62 | 0.001 | Total ureylene group-containing compounds: 0.002, terminal biuret group-containing compounds: 0.005 | 96.0 | 25.0 |
| Example 134 | 20.0 | phenyl-O-C6H4-OH | 78 | 0.001 | Total ureylene group-containing compounds: 0.002, terminal biuret group-containing compounds: 0.005 | 95.9 | 85.0 |

TABLE 43

| | Content of compound having ureido groups in composition (wt %) | ArOH | Content of aromatic hydroxy compound in composition (wt %) | Content of ammonia in composition (wt %) | Other components and contents thereof in composition (%) | Ratio of compound having ureido groups after storage versus before storage (mol %) | Yield of N-substituted carbamic acid-O-aryl ester (mol %) (molar yield versus compound having ureido groups before storage) |
|---|---|---|---|---|---|---|---|
| Example 135 | 17.5 | 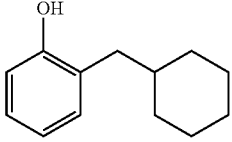<br>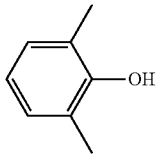 | 60<br><br>20 | 0.30 | Total ureylene group-containing compounds: 0.002, terminal biuret group-containing compounds: 0.005 | 98.3 | 88.2 |
| Example 136 | 20.0 | 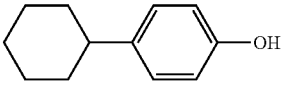<br>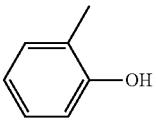 | 55<br><br>24 | 0.02 | Total ureylene group-containing compounds: 0.002, terminal biuret group-containing compounds: 0.005, ditolylcarbonate: 0.01 | 98.2 | 96.3 |
| Example 137 | 15.0 | 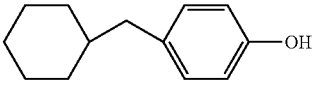<br>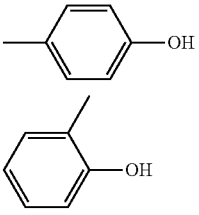 | 62<br><br>10<br><br>10 | 0.05 | Total ureylene group-containing compounds: 0002, terminal biuret group-containing compounds: 0.005, ditolylcarbonate: 0.01 | 97.3 | 95.3 |
| Example 138 | 9.2 | 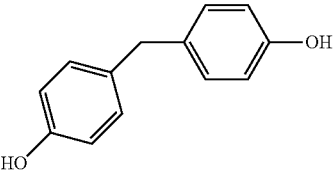<br>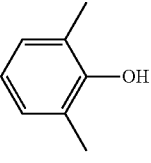 | 78<br><br>10 | 0.04 | Urea: 0.05, terminal biuret-group containing compounds: 0.05, dixylylcarbonate: 0.06, dibutyl tin dilaurate: 650 ppm | 73.9 | 66.6 |

TABLE 43-continued

| | Content of compound having ureido groups in composition (wt %) | ArOH | Content of aromatic hydroxy compound in composition (wt %) | Content of ammonia in composition (wt %) | Other components and contents thereof in compostion (%) | Ratio of compound having ureido groups after storage versus before storage (mol %) | Yield of N-substituted carbamic acid-O-aryl ester (mol %) (molar yield versus compound having ureido groups before storage) |
|---|---|---|---|---|---|---|---|
| Example 139 | 8.1 | 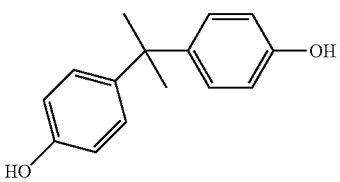 | 77 / 10 | 0.01 | Urea: 0.05, terminal biuret group-containing compounds: 0.05, dixylylcarbonate: 0.06 | 98.8 | 59.0 |
| Example 140 | 15.5 | 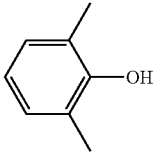 | 10 / 72 | 0.01 | Total ureylene group-containing compounds: 0.002, terminal biuret group-containing compounds: 0.005 | 98.7 | 73.0 |
| Example 141 | 9.9 | 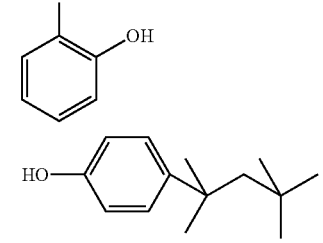 | 68 / 20 | 0.1 | Total ureylene group-containing compounds: 0.002, terminal biuret group-containing compounds: 0.005 | 98.0 | 96.4 |

TABLE 44

| | Content of compound having ureido groups in composition (wt %) | ArOH | Content of aromatic hydroxy compound in composition (wt %) | Content of ammonia in composition (wt %) | Other components and contents thereof in composition (%) | Ratio of compound having ureido groups after storage versus before storage (mol %) | Yield of N-substituted carbamic acid-O-aryl ester (mol %) (molar yield versus compound having ureido groups before storage) |
|---|---|---|---|---|---|---|---|
| Example 142 | 7.9 | (2,4-di-tert-pentylphenol structure) | 90 | 0.2 | Total ureylene group-containing compounds: 0.002, terminal biuret group-containing compounds: 0.005, urea: 0.001 | 73.0 | 51.2 |
| Example 143 | 8.0 | (4-(biphenyl-4-ylmethyl)phenol structure) | 90 | 0.3 | Total ureylene group-containing compounds: 0.002, terminal biuret group-containing compounds: 0.005, urea: 0.001 | 98.8 | 49.2 |
| Example 144 | 4.5 | (long alkyl chain phenol structure) | 90 | 0.5 | Total ureylene group-containing compounds: 0.02, terminal biuret group-containing compounds: 0.05, urea: 0.01 | 64.4 | 32.0 |

Example 145

A composition containing 21% by weight of a compound having ureido groups represented by the following formula (200), 77% by weight of an aromatic hydroxy composition in the form of phenol, 0.01% by weight of ammonia and urea at a ratio of 0.01 (referring to the ratio of number of urea molecules to the number of ureido groups that compose (or are contained in) the compound having ureido groups, or in other words, 0.01 indicates 0.02 mole equivalents since the compound having ureido groups has two ureido groups in a molecule thereof) was placed in a 100 L SUS storage vessel to about ½ the volume thereof, followed by replacing the inside of the storage vessel with nitrogen, and storing for 1095 days in a storage environment found in the Kojima district of Kurashiki city in Okayama prefecture, Japan. The composition also contained other components for which the structure thereof was unclear (such as compounds containing ureylene groups and compounds containing terminal biuret bonds). During the storage period, the vessel was warmed with a circulating hot water jacket at 40° C. (controlled to roughly 30 to 50° C.). During the storage period, the temperature occasionally fell to about 0° C. or rose to about 50° C. due to the effects of water stoppages, power outages and factory utility maintenance. In addition, the temperature once rose to about 80° C. due to a malfunction. When the composition was analyzed after storage, the compound having ureido groups was contained in the composition at about 93 mol % as compared with prior to storage. Following the storage period, the composition was heated to 180° C. and introduced through a preheater (device for preheating the composition to 230° C.) into the vicinity of the middle of a sieve tray distillation column having an inner diameter of 2.5 inches and 40 theoretical plates (operation of the distillation column was carried out while reducing the pressure from normal pressure to reduced pressure within a liquid phase temperature range in the lower portion of the distillation column of 150 to 300° C. and confirming operating conditions; the minimum pressure during operation was about 0.3 KPa). An N-substituted carbamic acid-O-aryl ester derived from the compound having ureido groups and aromatic hydroxy composition was obtained from the lower portion of the distillation column. Ammonia formed as a by-product in the esterification reaction, a small amount of aromatic hydroxy composition, and a component having a lower boiling point than the aromatic hydroxy composition were extracted from the upper portion of the distillation column (and included a by-product in the form of a compound having a molecular weight of 178 or less and having a carbonyl group, although the structure thereof was unable to be identified). Although the yield changed from the start to completion of operation due to fluctuations in operating conditions, at the highest level of performance during the operating period, the yield of the N-substituted carbamic acid-O-aryl ester based on the compound having ureido groups at the start of the storage period was 87 mol %. There was no clogging of lines during both storage and transfer, and formation of solid within the distillation column was not observed.

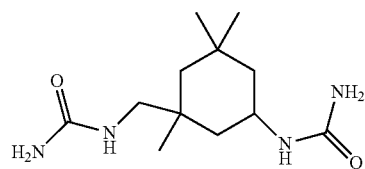

(200)

Examples 146 to 186 and Comparative Examples 7 to 10

Storage and esterification (reaction for obtaining N-substituted carbamic acid-O-aryl ester by reacting ureido groups with an aromatic hydroxy compound) were carried out using the compound having ureido groups represented by formula (200) in Example 145 under the same conditions as Example 145 with the exception of the composite ratios of the compound having ureido groups, aromatic hydroxy composition, ammonia, carbonic acid derivative and the like, and the results of distillation are shown in Tables 45 to 50. Yields of N-substituted carbamic acid-O-aryl ester are indicated as values obtained by analyzing a liquid phase component from the lower portion of the sieve plate distillation column.

In the tables, ArOH represents an aromatic hydroxy compound that composes an aromatic hydroxy composition. The content of each component in the composition is represented as a weight percentage (wt %) obtained by rounding the contents of the compound having ureido groups, aromatic hydroxy composition, water and ammonia to the number of significant digits of the analysis apparatus or less, metal components are expressed in ppm, while other components (such as carbonic acid derivative) are indicated as the ratio of the number of molecules thereof to the number of ureido groups that compose (or are contained in) the compound having ureido groups. (Unless indicated otherwise, phenomena such as clogging or solid formation did not occur during storage or transfer.)

TABLE 45

| | Content of compound having ureido groups in composition (wt %) | ArOH | Content of aromatic hydroxy compound in composition (wt %) | Content of ammonia in composition (wt %) | Other components and contents thereof in compostion (%) | Ratio of compound having ureido groups after storage versus before storage (mol %) | Yield of N-substituted carbamic acid-O-aryl ester (mol %) (molar yield versus compound having ureido groups before storage) |
|---|---|---|---|---|---|---|---|
| Example 146 | 12.0 | ⌬—OH | 68 | 0.0001 | Total ureylene group-containing compounds: 0.005, terminal biuret group-containing compounds: 0.005, diphenylhexane-1,6-diylcarbamate: 16.5 wt % | 95.0 | 92.0 |
| Example 147 | 1.0 | ⌬—OH | 99 | 0.0001 | | 98.0 | 91.0 |

TABLE 45-continued

| | Content of compound having ureido groups in composition (wt %) | ArOH | Content of aromatic hydroxy compound in composition (wt %) | Content of ammonia in composition (wt %) | Other components and contents thereof in compostion (%) | Ratio of compound having ureido groups after storage versus before storage (mol %) | Yield of N-substituted carbamic acid-O-aryl ester (mol %) (molar yield versus compound having ureido groups before storage) |
|---|---|---|---|---|---|---|---|
| Example 148 | 21.4 | phenol; 4,4'-(propan-2,2-diyl) substituted biphenol structure | 48; 30 | 0.05 | Fe ion: 20 ppm, Ni ion: 15 ppm | 98.6 | 93.7 |
| Comparative Example 7 | 20.0 | | 0 | 0.0001 | 1-butanol: 79 wt %, urea: 0.001 | 3 | (solid formation, pump clogged) |
| Comparative Example 8 | 20.0 | | 0 | 0.001 | 1-butanol: 79 wt %, dibutyl tin dilaurate: 2010 ppm | 4 | (solid formation, pump clogged) |
| Comparative Example 9 | 96 | | 0 | 0.01 | 1-butanol: 0.1 wt %, urea: 0.001, total ureylene group-containing compounds: 0.005, terminal biuret group-containing compounds: 0.005 | 99.0 | (sticking during heating, pump clogged) |
| Example 149 | 98 | | 0 | 0.0001 | 1-butanol: 0.1 wt %, urea: 0.001 | 99.0 | (although unable to be transferred after storage due to being a powder, able to be transferred when a separate stirring tank with stirrer was provided and a 17.7 wt % phenol solution was prepared at 120° C.; yield at that time: 70 mol %) |

TABLE 46

| | Content of compound having ureido groups in composition (wt %) | ArOH | Content of aromatic hydroxy compound in composition (wt %) | Content of ammonia in composition (wt %) | Other components and contents thereof in compostion (%) | Ratio of compound having ureido groups after storage versus before storage (mol %) | Yield of N-substituted carbamic acid-O-aryl ester (mol %) (molar yield versus compound having ureido groups before storage) |
|---|---|---|---|---|---|---|---|
| Comparative Example 10 | 98 | | 0 | 0.0001 | 1-butanol: 0.1 wt %, urea: 0.001 | 98.0 | (unable to be transferred after storage due to |

TABLE 46-continued

| | Content of compound having ureido groups in composition (wt %) | ArOH | Content of aromatic hydroxy compound in composition (wt %) | Content of ammonia in composition (wt %) | Other components and contents thereof in composition (%) | Ratio of compound having ureido groups after storage versus before storage (mol %) | Yield of N-substituted carbamic acid-O-aryl ester (mol %) (molar yield versus compound having ureido groups before storage) |
|---|---|---|---|---|---|---|---|
| | | | | | | | being a powder, large amount of insoluble matter caused pump clogging even when a separate stirring tank with stirrer was provided and a 17.7 wt % 1-butanol solution was prepared at 110° C. |
| Example 150 | 19.2 | (2-methylphenol) | 9 | 0.01 | Dibutyl tin dilaurate: 10 ppm, total carbonic acid ester: 0.001 | 89.0 | 85.0 |
| | | (4-hydroxyphenyl cumyl) | 70 | | | | |
| Example 151 | 19.2 | (3-methylphenol) | 9 | 0.001 | Water: 90 ppm | 98.4 | 98.4 |
| | | (4-phenoxyphenol) | 70 | | | | |
| Example 152 | 55.0 | (4-methylphenol) | 40 | 0.01 | Fe ion: 20 ppm, Ni ion: 30 ppm, dibutyl tin dilaurate: 300 ppm | 80.0 | 25.0 |
| | | (4-hydroxyphenyl cumyl) | 4.5 | | | | |
| Example 153 | 17.3 | (2,4-dimethylphenol) | 14 | 0.005 | Terminal biuret group-containing compounds 0.005, Al ion: 40 ppm | 98.3 | 88.4 |
| | | (2,4-dibenzylphenol) | 67 | | | | |

TABLE 46-continued

| | Content of compound having ureido groups in composition (wt %) | ArOH | Content of aromatic hydroxy compound in composition (wt %) | Content of ammonia in composition (wt %) | Other components and contents thereof in compostion (%) | Ratio of compound having ureido groups after storage versus before storage (mol %) | Yield of N-substituted carbamic acid-O-aryl ester (mol %) (molar yield versus compound having ureido groups before storage) |
|---|---|---|---|---|---|---|---|
| Example 154 | 17.3 | (2,5-dimethylphenol); (4-phenoxyphenol) | 20; 61 | 0.01 | Urea: 0.001, Al ion: 40 ppm | 98.8 | 96.4 |
| Example 155 | 17.3 | (2,5-dimethylphenol); (2-phenoxyphenol) | 14; 67 | 0.04 | Urea: 0.005, dibutyl tin dilaurate: 590 ppm | 76.3 | 68.6 |

TABLE 47

| | Content of compound having ureido groups in composition (wt %) | ArOH | Content of aromatic hydroxy compound in composition (wt %) | Content of ammonia in composition (wt %) | Other components and contents thereof in compostion (%) | Ratio of compound having ureido groups after storage versus before storage (mol %) | Yield of N-substituted carbamic acid-O-aryl ester (mol %) (molar yield versus compound having ureido groups before storage) |
|---|---|---|---|---|---|---|---|
| Example 156 | 17.3 | (3,4-dimethylphenol); (4-cumylphenol) | 21; 60 | 0.1 | Total ureylene group-containing compounds: 0.005, dibutyl tin dilaurate: 290 ppm | 88.4 | 83.8 |
| Example 157 | 45.0 | (3,5-dimethylphenol); (4-cumylphenol) | 44; 10 | 0.5 | Terminal biuret group-containing compounds: 0.005, dibutyl tin dilaurate: 60 ppm | 97.7 | 34.0 |

TABLE 47-continued

| | Content of compound having ureido groups in composition (wt %) | ArOH | Content of aromatic hydroxy compound in composition (wt %) | Content of ammonia in composition (wt %) | Other components and contents thereof in compostion (%) | Ratio of compound having ureido groups after storage versus before storage (mol %) | Yield of N-substituted carbamic acid-O-aryl ester (mol %) (molar yield versus compound having ureido groups before storage) |
|---|---|---|---|---|---|---|---|
| Example 158 | 15.8 | (2,4,6-trimethylphenol structure) / (dibenzyl phenol structure) | 22 / 60 | 0.01 | Total ureylene group-containing compounds: 0.005, dibutyl tin dilaurate: 30 ppm, water: 0.5 wt % | 99.4 | 88.9 |
| Example 159 | 15.8 | (4-propylphenol structure) / (bisphenol structure) | 23 / 60 | 0.01 | Total ureylene group-containing compounds: 0.005, terminal biuret group-containing compounds: 0.005, dibutyl tin dilaurate: 60 ppm, water: 0.5 wt % | 98.1 | 92.7 |
| Example 160 | 5.0 | (2-propylphenol structure) / (bisphenol structure) | 34 / 60 | 0.01 | Total ureylene group-containing compounds: 0.005 | 98.0 | 97.0 |
| Example 161 | 1.5 | (2-isopropylphenol structure) / (4-phenoxyphenol structure) | 38 / 60 | 0.1 | Total ureylene group-containing compounds: 0.005 | 98.0 | 96.4 |
| Example 162 | 15.8 | (4-isopropylphenol structure) / (bisphenol structure) | 22 / 60 | 0.2 | Total ureylene group-containing compounds: 0.005, dibutyl tin dilaurate: 40 ppm, water: 0.5 wt % | 95.6 | 90.4 |

TABLE 48

| | Content of compound having ureido groups in composition (wt %) | ArOH | Content of aromatic hydroxy compound in composition (wt %) | Content of ammonia in composition (wt %) | Other components and contents thereof in compostion (%) | Ratio of compound having ureido groups after storage versus before storage (mol %) | Yield of N-substituted carbamic acid-O-aryl ester (mol %) (molar yield versus compound having ureido groups before storage) |
|---|---|---|---|---|---|---|---|
| Example 163 | 15.8 | (isopropylphenol structure) / (diphenylpropane structure) | 23 / 60 | 0.001 | Total ureylene group-containing compounds: 0.005, terminal biuret group-containing compounds: 0.005 | 98.7 | 93.5 |
| Example 164 | 3.0 | (2,6-diethylphenol structure) / (4-phenoxyphenol structure) | 36 / 60 | 0.001 | Total ureylene group-containing compounds: 0.005, terminal biuret group-containing compounds: 0.005 | 97.9 | 88.6 |
| Example 165 | 14.6 | (4-butylphenol structure) / (dibenzylphenol structure) | 23 / 60 | 0.001 | Total ureylene group-containing compounds: 0.005, terminal biuret group-containing compounds: 0.005, dibutyl tin dilaurate: 60 ppm | 97.3 | 87.8 |
| Example 166 | 12.2 | (2-benzylphenol structure) / (2,6-dimethylphenol structure) | 60 / 16.5 | 0.2 | Total ureylene group-containing compounds: 0.005, terminal biuret group-containing compounds: 0.005 | 98.4 | 96.4 |
| Example 167 | 14.3 | (2,6-dimethoxyphenol structure) / (2-isopropylphenol structure) | 70 / 13.5 | 0.4 | Total ureylene group-containing compounds: 0.015, terminal biuret group-containing compounds: 0.015 | 97.2 | 87.9 |

TABLE 48-continued

| | Content of compound having ureido groups in composition (wt %) | ArOH | Content of aromatic hydroxy compound in composition (wt %) | Content of ammonia in composition (wt %) | Other components and contents thereof in compostion (%) | Ratio of compound having ureido groups after storage versus before storage (mol %) | Yield of N-substituted carbamic acid-O-aryl ester (mol %) (molar yield versus compound having ureido groups before storage) |
|---|---|---|---|---|---|---|---|
| Example 168 | 5.0 | 2-ethoxyphenol | 24.5 | 0.3 | Total ureylene group-containing compounds: 0.020, terminal biuret group-containing compounds: 0.015 | 97.5 | 87.9 |
| | | 4-phenoxyphenol | 70 | | | | |
| Example 169 | 11.8 | 4,4'-(propane-2,2-diyl)diphenol (mono-OH shown) | 70 | 0.1 | Total ureylene group-containing compounds: 0.002, terminal biuret group-containing compounds: 0.005 | 95.8 | 94.1 |
| Example 170 | 11.1 | 4,4'-(propane-2,2-diyl)diphenol (mono-OH shown) | 72 | 0.01 | Naphthalene: 15 wt %, total ureylene group-containing compounds: 0.002, terminal biuret group-containing compounds: 0.005 | 95.5 | 94.1 |

TABLE 49

| | Content of compound having ureido groups in composition (wt %) | ArOH | Content of aromatic hydroxy compound in composition (wt %) | Content of ammonia in composition (wt %) | Other components and contents thereof in compostion (%) | Ratio of compound having ureido groups after storage versus before storage (mol %) | Yield of N-substituted carbamic acid-O-aryl ester (mol %) (molar yield versus compound having ureido groups before storage) |
|---|---|---|---|---|---|---|---|
| Example 171 | 13.4 | 4-phenoxyphenol | 75 | 0.01 | Total ureylene group-containing compounds: 0.002, terminal biuret group-containing compounds: 0.005 | 93.3 | 91.7 |
| | | phenol | 10 | | | | |
| Example 172 | 15.1 | 4,4'-(propane-2,2-diyl)diphenol (mono-OH shown) | 78 | 0.01 | Total ureylene group-containing compounds: 0.002, terminal biuret group-containing compounds: 0.005, butanol: 5 wt % | 96.0 | 94.1 |

TABLE 49-continued

| | Content of compound having ureido groups in composition (wt %) | ArOH | Content of aromatic hydroxy compound in composition (wt %) | Content of ammonia in composition (wt %) | Other components and contents thereof in compostion (%) | Ratio of compound having ureido groups after storage versus before storage (mol %) | Yield of N-substituted carbamic acid-O-aryl ester (mol %) (molar yield versus compound having ureido groups before storage) |
|---|---|---|---|---|---|---|---|
| Example 173 | 15.1 | HO–C₆H₄–C(CH₃)₂–C₆H₅ | 83 | 0.01 | Total ureylene group-containing compounds: 0.002, terminal biuret group-containing compounds: 0.005 | 98.7 | 96.4 |
| Example 174 | 15.1 | HO–C₆H₄–O–C₆H₅ ; 2,6-dimethylphenol | 73.5 / 10 | 0.02 | Total ureylene group-containing compounds: 0.002, terminal biuret group-containing compounds: 0.005 | 99.3 | 97.2 |
| Example 175 | 6.4 | C₆H₅–O–C₆H₄–OH | 92 | 0.02 | Total ureylene group-containing compounds: 0.002, terminal biuret group-containing compounds: 0.005 | 96.9 | 94.1 |
| Example 176 | 18.0 | C₆H₅–O–C₆H₄–OH | 81 | 0.02 | Total ureylene group-containing compounds: 0.002, terminal biuret group-containing compounds: 0.005 | 95.9 | 94.1 |
| Example 177 | 25.6 | C₆H₅–O–C₆H₄–OH | 73 | 0.02 | Total ureylene group-containing compounds: 0.002, terminal biuret group-containing compounds: 0.005 | 96.1 | 38.0 |
| Example 178 | 40.8 | C₆H₅–O–C₆H₄–OH | 57 | 0.001 | Total ureylene group-containing compounds: 0.002, terminal biuret group-containing compounds: 0.005 | 95.8 | 25.0 |

TABLE 49-continued

| | Content of compound having ureido groups in composition (wt %) | ArOH | Content of aromatic hydroxy compound in composition (wt %) | Content of ammonia in composition (wt %) | Other components and contents thereof in composition (%) | Ratio of compound having ureido groups after storage versus before storage (mol %) | Yield of N-substituted carbamic acid-O-aryl ester (mol %) (molar yield versus compound having ureido groups before storage) |
|---|---|---|---|---|---|---|---|
| Example 179 | 25.0 | 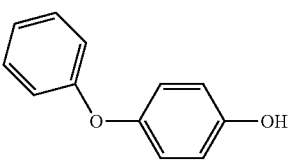 | 74 | 0.001 | Total ureylene group-containing compounds: 0.002, terminal biuret group-containing compounds: 0.005 | 95.9 | 85.0 |
| Example 180 | 18.3 | 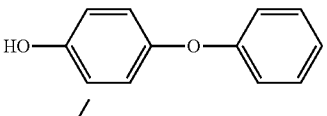<br>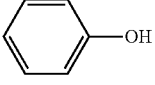 | 70<br><br>9 | 0.05 | Total ureylene group-containing compounds: 0.002, terminal biuret group-containing compounds: 0.005, ditolylcarbonate: 0.01 | 97.3 | 95.3 |

TABLE 50

| | Content of compound having ureido groups in composition (wt %) | ArOH | Content of aromatic hydroxy compound in composition (wt %) | Content of ammonia in composition (wt %) | Other components and contents thereof in composition (%) | Ratio of compound having ureido groups after storage versus before storage (mol %) | Yield of N-substituted carbamic acid-O-aryl ester (mol %) (molar yield versus compound having ureido groups before storage) |
|---|---|---|---|---|---|---|---|
| Example 181 | 11.3 | 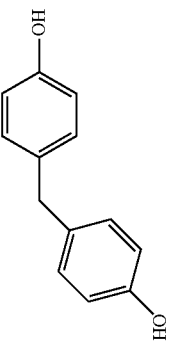 | 75 | 0.04 | Urea: 0.005, terminal biuret group-containing compounds: 0.05, dixylylcarbonate: 0.06, dibutyl tin dilaurate: 650 ppm | 74.3 | 66.6 |
| Example 182 | 10.1 | 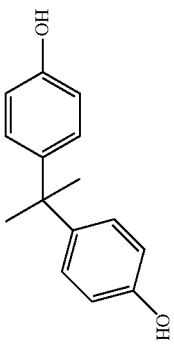 | 76 | 0.01 | Urea: 0.005, terminal biuret group-containing compounds: 0.05, dixylylcarbonate: 0.06 | 98.0 | 59.0 |

TABLE 50-continued

| | Content of compound having ureido groups in composition (wt %) | ArOH | Content of aromatic hydroxy compound in composition (wt %) | Content of ammonia in composition (wt %) | Other components and contents thereof in composition (%) | Ratio of compound having ureido groups after storage versus before storage (mol %) | Yield of N-substituted carbamic acid-O-aryl ester (mol %) (molar yield versus compound having ureido groups before storage) |
|---|---|---|---|---|---|---|---|
| Example 183 | 18.9 | catechol (1,2-dihydroxybenzene) | 10 | 0.01 | Total urelyene group-containing compounds: 0.002, terminal biuret group-containing compounds: 0.005 | 98.4 | 73.8 |
| | | 4-phenoxyphenol | 70 | | | | |
| Example 184 | 9.9 | 2,4-di-tert-pentylphenol | 89 | 0.2 | Total urelyene group-containing compounds: 0.002, terminal biuret group-containing compounds: 0.005, urea: 0.001 | 63.6 | 44.8 |
| Example 185 | 10.1 | 2,4-bis(α,α-dimethylbenzyl)phenol | 88 | 0.3 | Total urelyene group-containing compounds: 0.002, terminal biuret group-containing compounds: 0.005, urea: 0.001 | 98.0 | 39.4 |
| Example 186 | 5.6 | long-chain alkylphenol | 92 | 0.5 | Total urelyene group-containing compounds: 0.02, terminal biuret group-containing compounds: 0.05, urea: 0.01 | 64.3 | 32.0 |

Example 187

A composition containing 17.1% by weight of a compound having ureido groups represented by the following formula (201), 82% by weight of an aromatic hydroxy composition in the form of 4-(2-phenylpropane-2-yl)phenol, 0.01% by weight of ammonia and urea at a ratio of 0.001 (referring to the ratio of number of urea molecules to the number of ureido groups that compose (or are contained in) the compound having ureido groups, or in other words, 0.001 indicates 0.002 mole equivalents since the compound having ureido groups has two ureido groups in a molecule thereof) was placed in a 100 L SUS storage vessel to about ½ the volume thereof, followed by replacing the inside of the storage vessel with nitrogen, and storing for 1095 days in a storage environment found in the Kojima district of Kurashiki city in Okayama prefecture, Japan. The composition also contained other components for which the structure thereof was unclear (such as compounds containing ureylene groups and compounds containing terminal biuret bonds). During the storage period, the vessel was warmed with a circulating hot water jacket at 40° C. (controlled to roughly 30 to 50° C.). During the storage period, the temperature occasionally fell to about 0° C. or rose to about 50° C. due to the effects of water stoppages, power outages and factory utility maintenance. In addition, the temperature once rose to about 80° C. due to a malfunction. When the composition was analyzed after storage, the compound having ureido groups was contained in the composition at about 98 mol % as compared with prior to storage. Following the storage period, the composition was heated to 180° C. and introduced through a preheater (device for preheating the composition to 230° C.) into the vicinity of the middle of a sieve tray distillation column having an inner diameter of 2.5 inches and 40 theoretical plates (operation of the distillation column was carried out while reducing the pressure from normal pressure to reduced pressure within a liquid phase temperature range in the lower portion of the distillation column of 150 to 300° C. and confirming operating conditions; the minimum pressure during operation was about 0.3 KPa). An N-substituted carbamic acid-O-aryl ester derived from the compound having ureido groups and aromatic hydroxy composition was obtained from the lower portion of the distillation column. Ammonia formed as a by-product in the esterification reaction, a small amount of aromatic hydroxy composition, and a component having a lower boiling point than the aromatic hydroxy composition were extracted from the upper portion of the distillation column (and included a by-product in the form of a compound having a molecular weight of 178 or less and having a carbonyl group, although the structure thereof was unable to be identified). Although the yield changed from the start to completion of operation due to fluctuations in operating conditions, at the highest level of performance during the operating period, the yield of the N-substituted carbamic acid-O-aryl ester based on the compound having ureido groups at the start of the storage period was 96.4 mol %. There was no clogging of lines during both storage and transfer, and formation of solid within the distillation column was not observed.

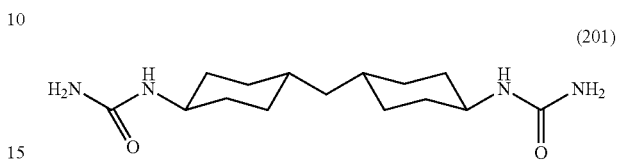

(201)

Examples 187-1 to 226 and Comparative Examples 11 to 14

Storage and esterification (reaction for obtaining N-substituted carbamic acid-O-aryl ester by reacting ureido groups with an aromatic hydroxy compound) were carried out using the compound having ureido groups represented by formula (201) in Example 187 under the same conditions as Example 187 with the exception of the composite ratios of the compound having ureido groups, aromatic hydroxy composition, ammonia, carbonic acid derivative and the like, and the results of distillation are shown in Tables 51 to 56. Yields of N-substituted carbamic acid-O-aryl ester are indicated as values obtained by analyzing a liquid phase component from the lower portion of the sieve plate distillation column.

In the tables, ArOH represents an aromatic hydroxy compound that composes an aromatic hydroxy composition. The content of each component in the composition is represented as a weight percentage (wt %) obtained by rounding the contents of the compound having ureido groups, aromatic hydroxy composition, water and ammonia to the number of significant digits of the analysis apparatus or less, metal components are expressed in ppm, while other components (such as carbonic acid derivative) are indicated as the ratio of the number of molecules thereof to the number of ureido groups that compose (or are contained in) the compound having ureido groups. (Unless indicated otherwise, phenomena such as clogging or solid formation did not occur during storage or transfer.)

TABLE 51

| | Content of compound having ureido groups in composition (wt %) | ArOH | Content of aromatic hydroxy compound in composition (wt %) | Content of ammonia in composition (wt %) | Other components and contents thereof in composition (%) | Content of compound having ureido groups in composition after storage (wt %) | Ratio of compound having ureido groups after storage versus before storage (mol %) | Yield of N-substituted carbamic acid-O-aryl ester (mol %) (molar yield versus compound having ureido groups before storage) |
|---|---|---|---|---|---|---|---|---|
| Example 187-1 | 24.0 | phenol (─OH) | 74 | 0.001 | Urea: 0.01 | 22.2 | 95.0 | 92.0 |

TABLE 51-continued

| | Content of compound having ureido groups in composition (wt %) | ArOH | Content of aromatic hydroxy compound in composition (wt %) | Content of ammonia in composition (wt %) | Other components and contents thereof in composition (%) | Content of compound having ureido groups in composition after storage (wt %) | Ratio of compound having ureido groups after storage versus before storage (mol %) | Yield of N-substituted carbamic acid-O-aryl ester (mol %) (molar yield versus compound having ureido groups before storage) |
|---|---|---|---|---|---|---|---|---|
| Example 188 | 13.0 | phenol (C₆H₅OH) | 85 | 0.001 | Total ureylene group-containing compounds: 0.005, terminal biuret group-containing compounds: 0.005, phenyl carbamate: 0.01 | 12.6 | 93.0 | 91.0 |
| Example 189 | 24.0 | phenol; 2-(4-hydroxyphenyl)-2-phenylpropane structure (bisphenol-type) | 25; 50 | 0.05 | Fe ion: 20 ppm Ni ion: 15 ppm | 23.6 | 98.3 | 93.7 |
| Comparative Example 11 | 29.6 | | 0 | 0.0001 | 1-butanol: 58 wt %, urea: 1 | 4.8 | 3 | (solid formation, pump clogged) |
| Comparative Example 12 | 20.0 | | 0 | 0.001 | 1-butanol: 79 wt %, dibutyl tin dilaurate: 2010 ppm | 0.9 | 4 | (solid formation, pump clogged) |
| Comparative Example 13 | 66 | | 0 | 0.0001 | 1-butanol: 0.1 wt %, urea: 0.5, total ureylene group-containing compounds: 0.005, terminal biuret group-containing compounds: 0.005 | 96.5 | 91.0 | (solid formation, pump clogged) |
| Example 190 | 67 | | 0 | 0.001 | 1-butanol: 0.1 wt %, urea: 1 | 97.5 | 95.0 | (although unable to be transferred after storage due to being a powder, able to be transferred when a separate stirring tank with stirrer was provided and a 17.7 wt % phenol solution was prepared at 120° C.; yield at that time: 89 mol %) |

TABLE 52

| | Content of compound having ureido groups in composition (wt %) | ArOH | Content of aromatic hydroxy compound in composition (wt %) | Content of ammonia in composition (wt %) | Other components and contents thereof in composition (%) | Content of compound having ureido groups in composition after storage (wt %) | Ratio of compound having ureido groups after storage versus before storage (mol %) | Yield of N-substituted carbamic acid-O-aryl ester (mol %) (molar yield versus compound having ureido groups before storage) |
|---|---|---|---|---|---|---|---|---|
| Comparative Example 14 | 67 | | 0 | 0.0001 | 1-butanol: 0.1 wt %, urea 1 | 96.5 | 95.0 | (unable to be transferred after storage due to being a powder, large amount of insoluble matter caused pump clogging even when a separate stirring tank with stirrer was provided and a 17.7 wt % 1-butanol solution was prepared at 110° C.) |
| Example 191 | 21.5 | 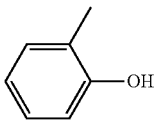 68 | 8 | 0.01 | Dibutyl tin dilaurate: 10 ppm, total carbonic acid ester: 0.001 | 21.4 | 99.5 | 97.6 |
| Example 192 | 21.5 | 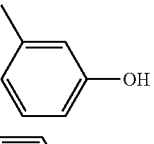 60 | 17 | 0.001 | Water: 90 ppm | 21.2 | 98.6 | 96.4 |
| Example 193 | 21.5 | 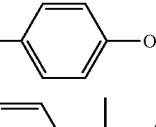 50 | 27 | 0.01 | Fe ion: 20 ppm, Ni ion: 30 ppm, dibutyl tin dilaurate: 300 ppm | 18.5 | 86.0 | 84.3 |

TABLE 52-continued

| | Content of compound having ureido groups in composition (wt %) | ArOH | Content of aromatic hydroxy compound in composition (wt %) | Content of ammonia in composition (wt %) | Other components and contents thereof in composition (%) | Content of compound having ureido groups in composition after storage (wt %) | Ratio of compound having ureido groups after storage versus before storage (mol %) | Yield of N-substituted carbamic acid-O-aryl ester (mol %) (molar yield versus compound having ureido groups before storage) |
|---|---|---|---|---|---|---|---|---|
| Example 194 | 19.5 | 2,4-dimethylphenol / dibenzyl-substituted phenol | 18 / 60 | 0.005 | Total biuret group-containing compounds: 0.005, Al ion: 40 ppm | 19.2 | 98.5 | 88.4 |
| Example 195 | 19.5 | 2,6-dimethylphenol / 4-phenoxyphenol | 29 / 50 | 0.01 | Urea: 0.001, Al ion: 40 ppm | 19.2 | 98.5 | 96.4 |
| Example 196 | 19.5 | 2,4-dimethylphenol / 2-phenoxyphenol (with OH) | 19 / 60 | 0.04 | Urea: 0.005, dibutyl tin dilaurate: 590 ppm | 14.9 | 76.4 | 68.6 |

TABLE 53

| | Content of compound having ureido groups in composition (wt %) | ArOH | Content of aromatic hydroxy compound in composition (wt %) | Content of ammonia in composition (wt %) | Other components and contents thereof in composition (%) | Content of compound having ureido groups in composition after storage (wt %) | Ratio of compound having ureido groups after storage versus before storage (mol %) | Yield of N-substituted carbamic acid-O-aryl ester (mol %) (molar yield versus compound having ureido groups before storage) |
|---|---|---|---|---|---|---|---|---|
| Example 197 | 19.5 | [structures: dimethylphenol-OH; HO-phenyl-C(CH₃)₂-phenyl] | 19 / 60 | 0.1 | Total ureylene group-containing compounds: 0.005, dibutyl tin dilaurate: 290 ppm | 17.2 | 88.2 | 83.8 |
| Example 198 | 19.5 | [structures: 3,5-dimethylphenol-OH; HO-phenyl-C(CH₃)₂-phenyl] | 19 / 60 | 0.5 | Total terminal biuret group-containing compounds: 0.005, dibutyl tin dilaurate: 60 ppm | 19.1 | 97.9 | 92.7 |
| Example 199 | 17.9 | [structures: trimethylphenol-OH; HO-phenyl with dibenzyl substituents] | 21 / 60 | 0.01 | Total ureylene group-containing compounds: 0.005, dibutyl tin dilaurate: 30 ppm, water: 0.5 wt % | 17.7 | 98.9 | 88.9 |
| Example 200 | 17.9 | [structures: propyl-phenol-OH; HO-phenyl-C(CH₃)₂-phenyl] | 20 / 60 | 0.01 | Total ureylene group-containing compounds: 0.005, terminal biuret group-containing compounds: 0.005, dibutyl tin dilaurate: 60 ppm, water: 0.5 wt % | 17.4 | 97.2 | 92.7 |

TABLE 53-continued

| | Content of compound having ureido groups in composition (wt %) | ArOH | Content of aromatic hydroxy compound in composition (wt %) | Content of ammonia in composition (wt %) | Other components and contents thereof in composition (%) | Content of compound having ureido groups in composition after storage (wt %) | Ratio of compound having ureido groups after storage versus before storage (mol %) | Yield of N-substituted carbamic acid-O-aryl ester (mol %) (molar yield versus compound having ureido groups before storage) |
|---|---|---|---|---|---|---|---|---|
| Example 201 | 17.9 | 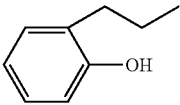 | 21 60 | 0.01 | Total ureylene group-containing compounds: 0.005 | 17.9 | 99.0 | 98.0 |
| Example 202 | 17.9 | 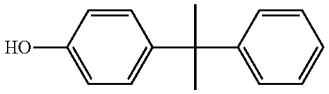 | 20 60 | 0.1 | Total ureylene group-containing compounds: 0.005 | 17.6 | 98.3 | 96.4 |
| Example 203 | 17.9 | 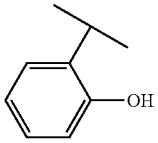 | 20 60 | 0.2 | Total ureylene group-containing compounds: 0.005, dibutyl tin dilaurate: 40 ppm, water: 0.5 wt % | 17.0 | 95.0 | 90.4 |

TABLE 54

| | Content of compound having ureido groups in composition (wt %) | ArOH | Content of aromatic hydroxy compound in composition (wt %) | Content of ammonia in composition (wt %) | Other components and contents thereof in composition (%) | Content of compound having ureido groups in composition after storage (wt %) | Ratio of compound having ureido groups after storage versus before storage (mol %) | Yield of N-substituted carbamic acid-O-aryl ester (mol %) (molar yield versus compound having ureido groups before storage) |
|---|---|---|---|---|---|---|---|---|
| Example 204 | 17.9 | (3-isopropylphenol); (4-cumylphenol / HO-C6H4-C(CH3)2-C6H5) | 20; 60 | 0.001 | Total ureylene group-containing compounds: 0.005, terminal biuret group-containing compounds: 0.005 | 17.6 | 98.3 | 93.5 |
| Example 205 | 16.5 | (2,6-diethylphenol); (4-phenoxyphenol) | 21; 60 | 0.001 | Total ureylene group-containing compounds: 0.005, terminal biuret group-containing compounds: 0.005 | 16.2 | 98.2 | 88.6 |
| Example 206 | 16.5 | (4-butylphenol); (2,4-dibenzylphenol) | 21; 60 | 0.001 | Total ureylene group-containing compounds: 0.005, terminal biuret group-containing compounds: 0.005, dibutyl tin dilaurate: 60 ppm | 16.1 | 97.6 | 87.8 |
| Example 207 | 13.9 | (2-benzylphenol); (2,6-dimethylphenol) | 68; 16 | 0.2 | Urea: 0.001 | 13.6 | 97.8 | 96.4 |

TABLE 54-continued

| | Content of compound having ureido groups in composition (wt %) | ArOH | Content of aromatic hydroxy compound in composition (wt %) | Content of ammonia in composition (wt %) | Other components and contents thereof in composition (%) | Content of compound having ureido groups in composition after storage (wt %) | Ratio of compound having ureido groups after storage versus before storage (mol %) | Yield of N-substituted carbamic acid-O-aryl ester (mol %) (molar yield versus compound having ureido groups before storage) |
|---|---|---|---|---|---|---|---|---|
| Example 208 | 16.1 | 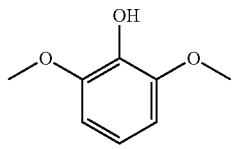 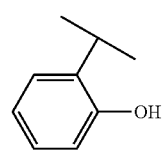 | 60 11 | 0.4 | Total ureylene group-containing compounds: 0.015, terminal biuret group-containing compounds: 0.015 | 15.7 | 97.5 | 90.0 |
| Example 209 | 17.7 | 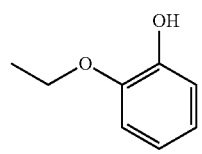 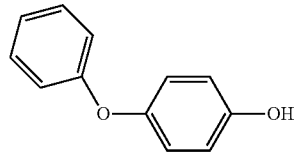 | 11.5 68 | 0.3 | Urea: 0.001 | 17.2 | 97.2 | 87.9 |
| Example 210 | 13.4 | 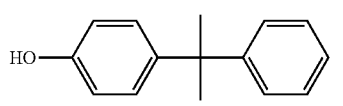 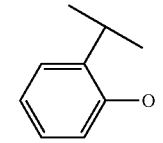 | 70 15.5 | 0.1 | Urea: 0.001 | 12.8 | 95.5 | 94.1 |

TABLE 55

| | Content of compound having ureido groups in composition (wt %) | ArOH | Content of aromatic hydroxy compound in composition (wt %) | Content of ammonia in composition (wt %) | Other components and contents thereof in composition (%) | Content of compound having ureido groups in composition after storage (wt %) | Ratio of compound having ureido groups after storage versus before storage (mol %) | Yield of N-substituted carbamic acid-O-aryl ester (mol %) (molar yield versus compound having ureido groups before storage) |
|---|---|---|---|---|---|---|---|---|
| Example 211 | 12.6 | HO–C₆H₄–C(CH₃)₂–C₆H₅ | 71 | 0.01 | Xyelene: 15 wt %, total ureylene group-containing compounds: 0.002, terminal biuret group-containing compounds: 0.005 | 12.1 | 96.0 | 94.1 |
| Example 212 | 15.1 | HO–C₆H₄–O–C₆H₅ <br> C₆H₅–OH | 73.5 <br><br> 10 | 0.01 | Urea: 0.01 | 14.2 | 94.0 | 91.7 |
| Example 213 | 17.1 | HO–C₆H₄–C(CH₃)₂–C₆H₅ | 76 | 0.01 | Total ureylene group-containing compounds: 0.002, terminal biuret group-containing compounds: 0.005, butanol: 5 wt % | 16.4 | 95.9 | 94.1 |
| Example 214 | 17.1 | HO–C₆H₄–O–C₆H₅ <br> 2,6-dimethylphenol | 71 <br><br> 10 | 0.02 | Total ureylene group-containing compounds: 0.002, terminal biuret group-containing compounds: 0.005 | 16.9 | 98.8 | 97.2 |
| Example 215 | 7.4 | C₆H₅–O–C₆H₄–OH | 91 | 0.02 | Urea: 0.001 | 7.1 | 99.0 | 98.0 |
| Example 216 | 27.0 | C₆H₅–O–C₆H₄–OH | 72 | 0.02 | Urea: 0.001 | 13.2 | 96.4 | 94.1 |

TABLE 55-continued

| | Content of compound having ureido groups in composition (wt %) | ArOH | Content of aromatic hydroxy compound in composition (wt %) | Content of ammonia in composition (wt %) | Other components and contents thereof in composition (%) | Content of compound having ureido groups in composition after storage (wt %) | Ratio of compound having ureido groups after storage versus before storage (mol %) | Yield of N-substituted carbamic acid-O-aryl ester (mol %) (molar yield versus compound having ureido groups before storage) |
|---|---|---|---|---|---|---|---|---|
| Example 217 | 28.5 | 4-phenoxyphenol | 70 | 0.02 | Urea: 0.001 | 27.3 | 95.8 | 75.0 |
| Example 218 | 44.3 | 4-phenoxyphenol | 54 | 0.001 | Urea: 0.001 | 42.5 | 95.9 | 25.0 |

TABLE 56

| | Content of compound having ureido groups in composition (wt %) | ArOH | Content of aromatic hydroxy compound in composition (wt %) | Content of ammonia in composition (wt %) | Other components and contents thereof in composition (%) | Content of compound having ureido groups in composition after storage (wt %) | Ratio of compound having ureido groups after storage versus before storage (mol %) | Yield of N-substituted carbamic acid-O-aryl ester (mol %) (molar yield versus compound having ureido groups before storage) |
|---|---|---|---|---|---|---|---|---|
| Example 219 | 34.7 | 4-phenoxyphenol | 64 | 0.001 | Urea: 0.001 | 33.3 | 96.0 | 38.0 |
| Example 220 | 20.6 | 4-phenoxyphenol; phenol | 66; 10 | 0.05 | Total ureylene group-containing compounds: 0.002, terminal biuret group-containing compounds: 0.005, ditolyl carbonate: 0.01 | 20.0 | 97.1 | 95.3 |
| Example 221 | 12.9 | 4-(4-hydroxybenzyl)phenol; 2,6-dimethylphenol | 73; 10 | 0.04 | Urea: 0.001, biuret group-containing compounds: 0.05, dixylyl carbonate: 0.06, dibutyl tin dilaurate: 650 ppm | 9.5 | 73.6 | 66.6 |

TABLE 56-continued

| | Content of compound having ureido groups in composition (wt %) | ArOH | Content of aromatic hydroxy compound in composition (wt %) | Content of ammonia in composition (wt %) | Other components and contents thereof in composition (%) | Content of compound having ureido groups in composition after storage (wt %) | Ratio of compound having ureido groups after storage versus before storage (mol %) | Yield of N-substituted carbamic acid-O-aryl ester (mol %) (molar yield versus compound having ureido groups before storage) |
|---|---|---|---|---|---|---|---|---|
| Example 222 | 11.5 | 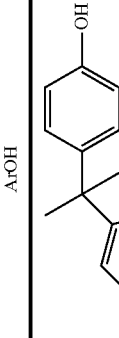 | 75 10 | 0.01 | Urea: 0.005, biuret group-containing compounds: 0.05, dixylyl carbonate: 0.06 | 11.3 | 98.3 | 59.0 |
| Example 223 | 21.2 | 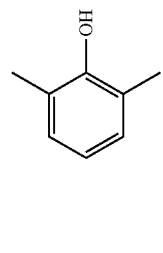 | 10 68 | 0.01 | Total ureylene group-containing compounds: 0.002, terminal biuret group-containing compounds: 0.005 | 20.9 | 98.6 | 73.8 |
| Example 224 | 11.2 | 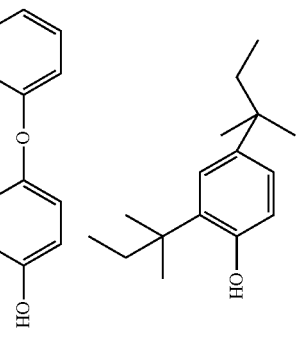 | 85 | 0.2 | Total ureylene group-containing compounds: 0.002, terminal biuret group-containing compounds: 0.005, urea: 0.1 | 7.2 | 64.3 | 44.8 |

TABLE 56-continued

| | Content of compound having ureido groups in composition (wt %) | ArOH | Content of aromatic hydroxy compound in composition (wt %) | Content of ammonia in composition (wt %) | Other components and contents thereof in composition (%) | Content of compound having ureido groups in composition after storage (wt %) | Ratio of compound having ureido groups after storage versus before storage (mol %) | Yield of N-substituted carbamic acid-O-aryl ester (mol %) (molar yield versus compound having ureido groups before storage) |
|---|---|---|---|---|---|---|---|---|
| Example 225 | 11.5 | (structure: 2,4-bis(α,α-dimethylbenzyl)phenol) | 86 | 0.3 | Total ureylene group-containing compounds: 0.002, terminal biuret group-containing compounds: 0.005, urea: 0.001 | 11.3 | 98.3 | 39.4 |
| Example 226 | 6.4 | (structure: long-chain alkyl-substituted phenol) | 92 | 0.5 | Total ureylene group-containing compounds: 0.02, terminal biuret group-containing compounds: 0.05, urea: 0.001 | 4.1 | 64.1 | 32.0 |

Example 227

A composition containing 12.6% by weight of a compound having ureido groups represented by the following formula (202), 86% by weight of an aromatic hydroxy composition in the form of 4-(2-phenylpropane-2-yl)phenol, 0.01% by weight of ammonia and urea at a ratio of 0.001 (referring to the ratio of number of urea molecules to the number of ureido groups that compose (or are contained in) the compound having ureido groups, or in other words, 0.001 indicates 0.002 mole equivalents since the compound having ureido groups has two ureido groups in a molecule thereof) was placed in a 100 L SUS storage vessel to about ½ the volume thereof, followed by replacing the inside of the storage vessel with nitrogen, and storing for 1095 days in a storage environment found in the Kojima district of Kurashiki city in Okayama prefecture, Japan. The composition also contained other components for which the structure thereof was unclear (such as compounds containing ureylene groups and compounds containing terminal biuret bonds). During the storage period, the vessel was warmed with a circulating hot water jacket at 40° C. (controlled to roughly 30 to 50° C.). During the storage period, the temperature occasionally fell to about 0° C. or rose to about 50° C. due to the effects of water stoppages, power outages and factory utility maintenance. In addition, the temperature once rose to about 80° C. due to a malfunction. When the composition was analyzed after storage, the compound having ureido groups was contained in the composition at 98.4 mol % as compared with prior to storage. Following the storage period, the composition was heated to 180° C. and introduced through a preheater (device for preheating the composition to 230° C.) into the vicinity of the middle of a sieve tray distillation column having an inner diameter of 2.5 inches and 40 theoretical plates (operation of the distillation column was carried out while reducing the pressure from normal pressure to reduced pressure within a liquid phase temperature range in the lower portion of the distillation column of 150 to 300° C. and confirming operating conditions; the minimum pressure during operation was about 0.3 KPa). An N-substituted carbamic acid-O-aryl ester derived from the compound having ureido groups and aromatic hydroxy composition was obtained from the lower portion of the distillation column. Ammonia formed as a by-product in the esterification reaction, a small amount of aromatic hydroxy composition, and a component having a lower boiling point than the aromatic hydroxy composition were extracted from the upper portion of the distillation column (and included a by-product in the form of a compound having a molecular weight of 178 or less and having a carbonyl group, although the structure thereof was unable to be identified). Although the yield changed from the start to completion of operation due to fluctuations in operating conditions, at the highest level of performance during the operating period, the yield of the N-substituted carbamic acid-O-aryl ester based on the compound having ureido groups at the start of the storage period was 96.4 mol %. There was no clogging of lines during both storage and transfer, and formation of solid within the distillation column was not observed.

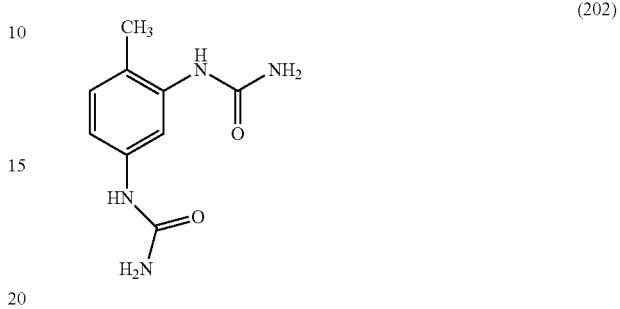

(202)

Examples 228 to 266 and Comparative Examples 15 to 17

Storage and esterification (reaction for obtaining N-substituted carbamic acid-O-aryl ester by reacting ureido groups with an aromatic hydroxy compound) were carried out using the compound having ureido groups represented by formula (202) in Example 227 under the same conditions as Example 227 with the exception of the composite ratios of the compound having ureido groups, aromatic hydroxy composition, ammonia, carbonic acid derivative and the like, and the results of distillation are shown in Tables 57 to 62. Yields of N-substituted carbamic acid-O-aryl ester are indicated as values obtained by analyzing a liquid phase component from the lower portion of the sieve plate distillation column.

In the tables, ArOH represents an aromatic hydroxy compound that composes an aromatic hydroxy composition. The content of each component in the composition is represented as a weight percentage (wt %) obtained by rounding the contents of the compound having ureido groups, aromatic hydroxy composition, water and ammonia to the number of significant digits of the analysis apparatus or less, metal components are expressed in ppm, while other components (such as carbonic acid derivative) are indicated as the ratio of the number of molecules thereof to the number of ureido groups that compose (or are contained in) the compound having ureido groups. (Unless indicated otherwise, phenomena such as clogging or solid formation did not occur during storage or transfer.)

TABLE 57

| | Content of compound having ureido groups in composition (wt %) | ArOH | Content of aromatic hydroxy compound in composition (wt %) | Content of ammonia in composition (wt %) | Other components and contents thereof in composition (%) | Ratio of compound having ureido groups after storage versus before storage (mol %) | Yield of N-substituted carbamic acid-O-aryl ester (mol %) (molar yield versus compound having ureido groups before storage) |
|---|---|---|---|---|---|---|---|
| Example 227 | 18.1 | 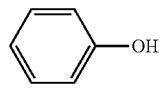 | 79 | 0.001 | Urea: 0.1 | 95.0 | 92.0 |

TABLE 57-continued

| | Content of compound having ureido groups in composition (wt %) | ArOH | Content of aromatic hydroxy compound in composition (wt %) | Content of ammonia in composition (wt %) | Other components and contents thereof in composition (%) | Ratio of compound having ureido groups after storage versus before storage (mol %) | Yield of N-substituted carbamic acid-O-aryl ester (mol %) (molar yield versus compound having ureido groups before storage) |
|---|---|---|---|---|---|---|---|
| Example 228 | 10.0 | phenol (C6H5OH) | 78 | 0.001 | Total ureylene group-containing compounds: 0.005, terminal biuret group-containing compounds: 0.005, diphenyl-4-methyl-1,3-phenylene dicarbamate: 10 wt % | 92.4 | 87.8 |
| Example 229 | 18.1 | phenol; 2,2-diphenylpropane-type bisphenol | 31; 50 | 0.05 | Fe ion: 20 ppm, Ni ion: 15 ppm | 98.6 | 93.7 |
| Comparative Example 15 | 20.0 | | 0 | 0.0001 | 1-butanol: 68 wt %, urea: 1 | 3 | (solid formation, pump clogged) |
| Comparative Example 16 | 32.0 | | 0 | 0.001 | 1-butanol: 67 wt %, dibutyl tin dilaurate: 2010 ppm | 4 | (solid formation, pump clogged) |
| Example 230 | 63 | | 0 | 0.0001 | 1-butanol: 0.1 wt %, urea: 1.0 | 93.0 | (although unable to be transferred after storage due to being a powder, able to be transferred when a separate stirring tank with stirrer was provided and a 17.7 wt % phenol solution was prepared at 120° C.; yield at that time: 93 mol %) |
| Comparative Example 17 | 63 | | 0 | 0.0001 | 1-butanol: 0.1 wt %, urea: 1.0 | 93.0 | (unable to be transferred after storage due to being a powder, large amount of insoluble matter caused pump clogging even when a separate stirring tank with stirrer was provided and a 17.7 wt % 1-butanol solution was prepared at 110° C. |

TABLE 58

| | Content of compound having ureido groups in composition (wt %) | ArOH | Content of aromatic hydroxy compound in composition (wt %) | Content of ammonia in composition (wt %) | Other components and contents thereof in composition (%) | Ratio of compound having ureido groups after storage versus before storage (mol %) | Yield of N-substituted carbamic acid-O-aryl ester (mol %) (molar yield versus compound having ureido groups before storage) |
|---|---|---|---|---|---|---|---|
| Example 231 | 16.1 | 2-methylphenol; 4-cumylphenol | 8 / 75 | 0.01 | Dibutyl tin dilaurate: 10 ppm, total carbamic acid ester: 0.001 | 99.6 | 97.6 |
| Example 232 | 16.1 | 3-methylphenol; 4-phenoxyphenol | 18 / 65 | 0.001 | Water: 90 ppm | 98.4 | 96.4 |
| Example 233 | 16.1 | 4-methylphenol; 4-cumylphenol | 28 / 55 | 0.01 | Fe ion: 20 ppm, Ni ion: 30 ppm, dibutyl tin dilaurate: 300 ppm | 86.0 | 84.3 |
| Example 234 | 14.6 | 2,4-dimethylphenol; 2,4-dibenzylphenol | 20 / 64 | 0.005 | Biuret group-containing compounds: 0.005, Al ion: 40 ppm | 98.2 | 88.4 |
| Example 235 | 14.6 | 2,6-dimethylphenol; 4-phenoxyphenol | 30 / 54 | 0.01 | Urea: 0.001, Al ion: 40 ppm | 98.4 | 96.4 |

TABLE 58-continued

| | Content of compound having ureido groups in composition (wt %) | ArOH | Content of aromatic hydroxy compound in composition (wt %) | Content of ammonia in composition (wt %) | Other components and contents thereof in composition (%) | Ratio of compound having ureido groups after storage versus before storage (mol %) | Yield of N-substituted carbamic acid-O-aryl ester (mol %) (molar yield versus compound having ureido groups before storage) |
|---|---|---|---|---|---|---|---|
| Example 236 | 14.6 | (structure: dimethylphenol with OH; and 2-phenoxyphenol) | 20 / 64 | 0.04 | Urea: 0.005, dibutyl tin dilaurate: 590 ppm | 76.2 | 68.6 |
| Example 237 | 14.6 | (structure: dimethylphenol with OH; and 4-(1-phenylethyl)phenol / bisphenol-type) | 20 / 63 | 0.1 | Total ureylene group-containing compounds: 0.005, dibutyl tin dilaurate: 290 ppm | 88.2 | 83.8 |

TABLE 59

| | Content of compound having ureido groups in composition (wt %) | ArOH | Content of aromatic hydroxy compound in composition (wt %) | Content of ammonia in composition (wt %) | Other components and contents thereof in composition (%) | Ratio of compound having ureido groups after storage versus before storage (mol %) | Yield of N-substituted carbamic acid-O-aryl ester (mol %) (molar yield versus compound having ureido groups before storage) |
|---|---|---|---|---|---|---|---|
| Example 238 | 1.0 | (structure: 3,5-dimethylphenol; and 4-(1-phenylethyl)phenol) | 20 / 79 | 0.5 | | 98.0 | 95.0 |

TABLE 59-continued

| | Content of compound having ureido groups in composition (wt %) | ArOH | Content of aromatic hydroxy compound in composition (wt %) | Content of ammonia in composition (wt %) | Other components and contents thereof in composition (%) | Ratio of compound having ureido groups after storage versus before storage (mol %) | Yield of N-substituted carbamic acid-O-aryl ester (mol %) (molar yield versus compound having ureido groups before storage) |
|---|---|---|---|---|---|---|---|
| Example 239 | 2.0 | (trimethylphenol structure with OH) | 20 | 0.01 | | 98.8 | 94.0 |
| | | (dibenzyl phenol structure) | 78 | | | | |
| Example 240 | 13.3 | (propyl phenol structure) | 21.5 | 0.01 | Total ureylene group-containing compounds: 0.005, terminal biuret group-containing compounds: 0.005, dibutyl tin dilaurate: 60 ppm, water: 0.5 wt % | 97.6 | 92.7 |
| | | (bisphenol structure) | 60 | | | | |
| Example 241 | 2.0 | (propyl phenol structure) | 20 | 0.01 | | 99.0 | 99.0 |
| | | (bisphenol structure) | 78 | | | | |
| Example 242 | 13.3 | (isopropyl phenol structure) | 21 | 0.1 | Total ureylene group-containing compounds: 0.005 | 98.4 | 96.4 |
| | | (diphenyl ether-phenol structure) | 64 | | | | |
| Example 243 | 13.3 | (isopropyl phenol structure) | 21 | 0.2 | Total ureylene group-containing compounds: 0.005, dibutyl tin dilaurate: 40 ppm, water: 0.5 wt % | 95.2 | 90.4 |
| | | (bisphenol structure) | 64 | | | | |

TABLE 59-continued

| | Content of compound having ureido groups in composition (wt %) | ArOH | Content of aromatic hydroxy compound in composition (wt %) | Content of ammonia in composition (wt %) | Other components and contents thereof in composition (%) | Ratio of compound having ureido groups after storage versus before storage (mol %) | Yield of N-substituted carbamic acid-O-aryl ester (mol %) (molar yield versus compound having ureido groups before storage) |
|---|---|---|---|---|---|---|---|
| Example 244 | 13.3 | 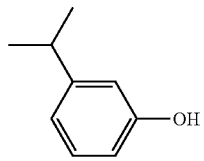 64 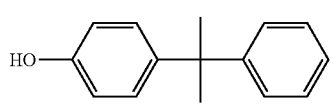 | 21 | 0.001 | Total ureylene group-containing compounds: 0.005, terminal biuret group-containing compounds: 0.005 | 98.4 | 93.5 |

TABLE 60

| | Content of compound having uriedo groups in composition (wt %) | ArOH | Content of aromatic hydroxy compound in composition (wt %) | Content of ammonia in composition (wt %) | Other components and contents thereof in composition (%) | Ratio of compound having ureido groups after storage versus before storage (mol %) | Yield of N-substituted carbamic acid-O-aryl ester (mol %) (molar yield versus compound having ureido groups before storage) |
|---|---|---|---|---|---|---|---|
| Example 245 | 1.0 | 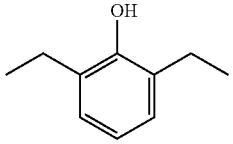 48.5 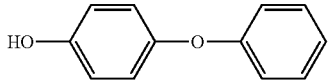 | 50 | 0.001 | Total ureylene group-containing compounds: 0.005, terminal biuret group-containing compounds: 0.005 | 98.4 | 97.0 |
| Example 246 | 12.2 | 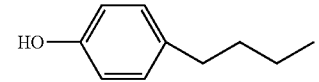 | 22 | 0.001 | Total ureylene group-containing compounds: 0.005, terminal biuret group-containing compounds: 0.005, dibutyl tin dilaurate: 60 ppm | 97.6 | 87.8 |

TABLE 60-continued

| | Content of compound having uriedo groups in composition (wt %) | ArOH | Content of aromatic hydroxy compound in composition (wt %) | Content of ammonia in composition (wt %) | Other components and contents thereof in composition (%) | Ratio of compound having ureido groups after storage versus before storage (mol %) | Yield of N-substituted carbamic acid-O-aryl ester (mol %) (molar yield versus compound having ureido groups before storage) |
|---|---|---|---|---|---|---|---|
| Example 247 | 10.2 | 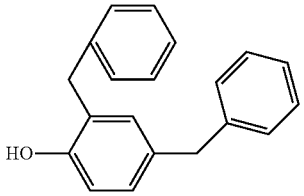 63<br><br>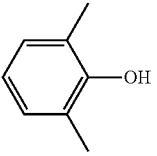 72<br><br>16 | | 0.2 | Urea: 0.01 | 98.4 | 96.4 |
| Example 248 | 11.9 | 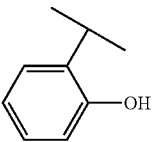 73<br><br>13 | | 0.4 | Total ureylene group-containing compounds: 0.015, terminal biuret group-containing compounds: 0.015 | 97.6 | 87.9 |
| Example 249 | 13.1 | 13<br><br>70 | | 0.3 | Urea: 0.01 | 97.6 | 93.0 |
| Example 250 | 9.8 | 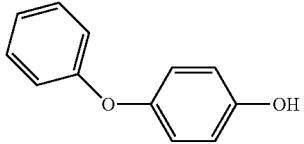 | 70 | 0.1 | Urea: 0.01 | 99.0 | 99.0 |

TABLE 60-continued

| | Content of compound having uriedo groups in composition (wt %) | ArOH | Content of aromatic hydroxy compound in composition (wt %) | Content of ammonia in composition (wt %) | Other components and contents thereof in composition (%) | Ratio of compound having uriedo groups after storage versus before storage (mol %) | Yield of N-substituted carbamic acid-O-aryl ester (mol %) (molar yield versus compound having uriedo groups before storage) |
|---|---|---|---|---|---|---|---|
| Example 251 | 9.2 | 2-isopropylphenol (17%); 4-hydroxyphenyl(phenyl)dimethylmethane | 74 | 0.01 | Xylene: 15 wt %, total ureylene group-containing compounds: 0.002, terminal biuret-group containing compounds: 0.005 | 96.0 | 94.1 |

TABLE 61

| | Content of compound having uriedo groups in composition (wt %) | ArOH | Content of aromatic hydroxy compound in composition (wt %) | Content of ammonia in composition (wt %) | Other components and contents thereof in composition (%) | Ratio of compound having uriedo groups after storage versus before storage (mol %) | Yield of N-substituted carbamic acid-O-aryl ester (mol %) (molar yield versus compound having uriedo groups before storage) |
|---|---|---|---|---|---|---|---|
| Example 252 | 11.1 | 4-hydroxyphenyl phenyl ether (15%); phenol | 72 | 0.01 | Urea: 0.01 | 93.6 | 91.7 |
| Example 253 | 12.6 | 4-hydroxyphenyl(phenyl)dimethylmethane | 81 | 0.01 | Total ureylene group-containing compounds: 0.002, terminal biuret group-containing compounds: 0.005, butanol 5 wt % | 96.0 | 94.1 |
| Example 254 | 12.6 | 4-hydroxyphenyl(phenyl)dimethylmethane | 86 | 0.01 | Urea: 0.001 | 98.4 | 96.4 |

TABLE 61-continued

| | Content of compound having uriedo groups in composition (wt %) | ArOH | Content of aromatic hydroxy compound in composition (wt %) | Content of ammonia in composition (wt %) | Other components and contents thereof in composition (%) | Ratio of compound having ureido groups after storage versus before storage (mol %) | Yield of N-substituted carbamic acid-O-aryl ester (mol %) (molar yield versus compound having ureido groups before storage) |
|---|---|---|---|---|---|---|---|
| Example 255 | 12.6 | HO—C6H4—O—C6H5 | 71.5 | 0.02 | Total ureylene group-containing compounds: 0.002, terminal biuret group-containing compounds: 0.005 | 99.2 | 97.2 |
| | | 2,6-dimethylphenol—OH | 14 | | | | |
| Example 256 | 5.3 | C6H5—O—C6H4—OH | 93 | 0.02 | Urea: 0.05 | 99.0 | 98.0 |
| Example 257 | 19.5 | C6H5—O—C6H4—OH | 80 | 0.02 | Urea: 0.05 | 96.0 | 94.1 |
| Example 258 | 21.8 | C6H5—O—C6H4—OH | 76 | 0.002 | Urea: 0.05 | 96.0 | 75.0 |
| Example 259 | 35.9 | C6H5—O—C6H4—OH | 62 | 0.001 | Urea: 0.05 | 96.0 | 25.0 |

TABLE 62

| | Content of compound having uriedo groups in composition (wt %) | ArOH | Content of aromatic hydroxy compound in composition (wt %) | Content of ammonia in composition (wt %) | Other components and contents thereof in composition (%) | Ratio of compound having ureido groups after storage versus before storage (mol %) | Yield of N-substituted carbamic acid-O-aryl ester (mol %) (molar yield versus compound having ureido groups before storage) |
|---|---|---|---|---|---|---|---|
| Example 260 | 27.2 | (phenyl-O-phenyl-OH) | 70 | 0.001 | Urea: 0.05 | 96.0 | 38.0 |
| Example 261 | 15.4 | (HO-phenyl-O-phenyl) | 68 | 0.05 | Total ureylene group-containing compounds: 0.002, terminal biuret group-containing compounds: 0.005, ditolyl carbonate: 0.01 | 97.2 | 95.3 |
| | | (o-cresol) | 13 | | | | |
| Example 262 | 9.4 | (bis(4-hydroxyphenyl)methane) | 76 | 0.04 | Urea: 0.05, terminal biuret group-containing compounds: 0.05, dixylyl carbonate: dibutyl tin dilaurate: 650 ppm | 74.0 | 66.6 |
| | | (2,6-dimethylphenol) | 10 | | | | |
| Example 263 | 8.4 | (bisphenol A) | 77 | 0.01 | Urea: 0.05, terminal biuret group-containing compounds: 0.05, dixylyl carbonate: 0.06 | 98.4 | 59.0 |

TABLE 62-continued

| | Content of compound having uriedo groups in composition (wt %) | ArOH | Content of aromatic hydroxy compound in composition (wt %) | Content of ammonia in composition (wt %) | Other components and contents thereof in composition (%) | Ratio of compound having ureido groups after storage versus before storage (mol %) | Yield of N-substituted carbamic acid-O-aryl ester (mol %) (molar yield versus compound having ureido groups before storage) |
|---|---|---|---|---|---|---|---|
| | | 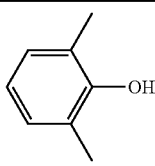 | 10 | | | | |
| Example 264 | 15.9 | 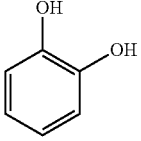 | 12 | 0.01 | Total ureylene group-containing compounds: 0.002, terminal biuret group-containing compounds: 0.005 | 98.4 | 73.8 |
| | | 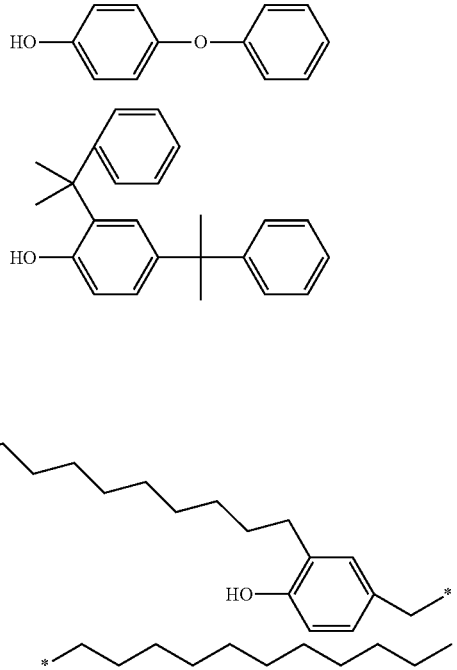 | 70 | | | | |
| Example 265 | 8.4 | | 90 | 0.3 | Total ureylene group-containing compounds: 0.002, terminal biuret group-containing compounds: 0.005, urea: 0.001 | 98.4 | 39.4 |
| Example 266 | 4.6 | | 93 | 0.5 | Total ureylene group-containing compounds: 0.02, terminal biuret group-containing compounds: 0.05, urea: 0.01 | 64.0 | 32.0 |

Example 267

A composition containing 16.5% by weight of a compound having ureido groups represented by the following formula (203), 81% by weight of an aromatic hydroxy composition in the form of 4-(2-phenylpropane-2-yl)phenol, 0.01% by weight of ammonia and urea at a ratio of 0.001 (referring to the ratio of number of urea molecules to the number of ureido groups that compose (or are contained in) the compound having ureido groups, or in other words, 0.001 indicates 0.002 mole equivalents since the compound having ureido groups has two ureido groups in a molecule thereof) was placed in a 100 L SUS storage vessel to about ½ the volume thereof, followed by replacing the inside of the storage vessel with nitrogen, and storing for 1095 days in a storage environment found in the Kojima district of Kurashiki city in Okayama prefecture, Japan. The composition also contained other components for which the structure thereof was unclear (such as compounds containing ureylene groups and compounds containing terminal biuret bonds). During the storage period, the vessel was warmed with a circulating hot water jacket at 40° C. (controlled to roughly 30 to 50° C.). During the storage period, the temperature occasionally fell to about 0° C. or rose to about 50° C. due to the effects of water stoppages, power outages and factory utility maintenance. In addition, the temperature once rose to about 80° C. due to a malfunction. When the composition was analyzed after storage, the compound having ureido groups was contained in the composition at 98.4 mol % as compared with prior to storage. Following the storage period, the composition was heated to 180° C. and introduced through a preheater (device for preheating the composition to 230° C.) into the vicinity of the middle of a sieve tray distillation column having an inner diameter of 2.5 inches and 40 theoretical plates (operation of the distillation column was carried out while reducing the pressure from normal pressure to reduced pressure within a liquid phase temperature range in the lower portion of the distillation column of 150 to 300° C. and confirming operating conditions; the minimum pressure during operation was about 0.3 KPa). An N-substituted carbamic acid-O-aryl ester derived from the compound having ureido groups and aromatic hydroxy composition was obtained from the lower portion of the distillation column. Ammonia formed as a by-product in the esterification reaction, a small amount of aromatic hydroxy composition, and a component having a lower boiling point than the aromatic hydroxy composition were extracted from the upper portion of the distillation column (and included a by-product in the form of a compound having a molecular weight of 178 or less and having a carbonyl group, although the structure thereof was unable to be identified). Although the yield changed from the start to completion of operation due to fluctuations in operating conditions, at the highest level of performance during the operating period, the yield of the N-substituted carbamic acid-O-aryl ester based on the compound having ureido groups at the start of the storage period was 96.4 mol %. There was no clogging of lines during both storage and transfer, and formation of solid within the distillation column was not observed.

(203)

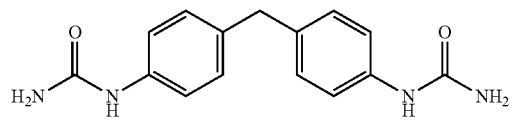

Examples 268 to 304 and Comparative Example 18

Storage and esterification (reaction for obtaining N-substituted carbamic acid-O-aryl ester by reacting ureido groups with an aromatic hydroxy compound) were carried out using the compound having ureido groups represented by formula (203) in Example 267 under the same conditions as Example 267 with the exception of the composite ratios of the compound having ureido groups, aromatic hydroxy composition, ammonia, carbonic acid derivative and the like, and the results of distillation are shown in Tables 63 to 67. Yields of N-substituted carbamic acid-O-aryl ester are indicated as values obtained by analyzing a liquid phase component from the lower portion of the sieve plate distillation column.

In the tables, ArOH represents an aromatic hydroxy compound that composes an aromatic hydroxy composition. The content of each component in the composition is represented as a weight percentage (wt %) obtained by rounding the contents of the compound having ureido groups, aromatic hydroxy composition, water and ammonia to the number of significant digits of the analysis apparatus or less, metal components are expressed in ppm, while other components (such as carbonic acid derivative) are indicated as the ratio of the number of molecules thereof to the number of ureido groups that compose (or are contained in) the compound having ureido groups. (Unless indicated otherwise, phenomena such as clogging or solid formation did not occur during storage or transfer.)

TABLE 63

| | Content of compound having uriedo groups in composition (wt %) | ArOH | Content of aromatic hydroxy compound in composition (wt %) | Content of ammonia in composition (wt %) | Other components and contents thereof in composition (%) | Ratio of compound having ureido groups after storage versus before storage (mol %) | Yield of N-substituted carbamic acid-O-aryl ester (mol %) (molar yield versus compound having ureido groups before storage) |
|---|---|---|---|---|---|---|---|
| Example 268 | 23.2 | ⌬—OH | 75 | 0.001 | Urea: 0.1 | 95.0 | 92.0 |
| Example 269 | 23.2 | ⌬—OH | 30 | 0.05 | Fe ion: 20 ppm, Ni ion: 15 ppm | 98.6 | 93.7 |

TABLE 63-continued

| | Content of compound having uriedo groups in composition (wt %) | ArOH | Content of aromatic hydroxy compound in composition (wt %) | Content of ammonia in composition (wt %) | Other components and contents thereof in composition (%) | Ratio of compound having ureido groups after storage versus before storage (mol %) | Yield of N-substituted carbamic acid-O-aryl ester (mol %) (molar yield versus compound having ureido groups before storage) |
|---|---|---|---|---|---|---|---|
| | | HO–C₆H₄–C(CH₃)(H)–C₆H₅ (4-cumylphenol-type structure) | 45 | | | | |
| Comparative Example 18 | 20.0 | | 0 | 0.0001 | 1-butanol: 79 wt % | 3 | (solid formation, pump clogged) |
| Example 270 | 98 | | 0 | 0.001 | 1-butanol: 0.1 wt % | 95.0 | (although unable to be transferred after storage due to being a powder, able to be transferred when a separate stirring tank with stirrer was provided and a 10 wt % phenol solution was prepared at 120° C.; yield at that time: 93 mol %) |
| Example 271 | 20.8 | 3-methylphenol (m-cresol) | 15 | 0.001 | Water: 90 ppm | 98.4 | 96.4 |
| | | HO–C₆H₄–O–C₆H₅ (4-phenoxyphenol) | 62 | | | | |
| Example 272 | 20.8 | 4-methylphenol (p-cresol) | 22 | 0.01 | Fe ion: 20 ppm, Ni ion: 30 ppm, dibutyl tin dilaurate: 300 ppm | 86.0 | 84.3 |
| | | HO–C₆H₄–C(CH₃)(H)–C₆H₅ | 55 | | | | |
| Example 273 | 18.9 | 2,4-dimethylphenol | 19 | 0.005 | Biuret group-containing compounds: 0.005, Al ion: 40 ppm | 98.2 | 88.4 |
| | | 2,4-dibenzylphenol | 60 | | | | |

TABLE 64

| | Content of compound having uriedo groups in composition (wt %) | ArOH | Content of aromatic hydroxy compound in composition (wt %) | Content of ammonia in composition (wt %) | Other components and contents thereof in composition (%) | Ratio of compound having ureido groups after storage versus before storage (mol %) | Yield of N-substituted carbamic acid-O-aryl ester (mol %) (molar yield versus compound having ureido groups before storage) |
|---|---|---|---|---|---|---|---|
| Example 274 | 18.9 | 2,6-dimethylphenol | 25 | 0.01 | Urea: 0.001, Al ion: 40 ppm | 98.4 | 96.4 |
| | | 4-phenoxyphenol | 54 | | | | |
| Example 275 | 18.9 | 3,5-dimethylphenol | 18 | 0.04 | Urea: 0.005, dibutyl tin dilaurate: 590 ppm | 76.2 | 68.6 |
| | | 2-phenoxyphenol | 60 | | | | |
| Example 276 | 18.9 | 3,4-dimethylphenol | 18 | 0.1 | Total ureylene group-containing compounds: 0.005, dibutyl tin dilaurate: 290 ppm | 88.2 | 83.8 |
| | | 4-(1-phenylethyl)phenol | 60 | | | | |
| Example 277 | 18.9 | 3,5-dimethylphenol | 18 | 0.5 | Terminal biuret group-containing compounds: 0.005, dibutyl tin dilaurate: 60 ppm | 97.6 | 92.7 |
| | | 4-(1-phenylethyl)phenol | 61 | | | | |
| Example 278 | 17.3 | 2,4,6-trimethylphenol | 20 | 0.01 | Total ureylene group-containing compounds: 0.005, dibutyl tin dilaurate: 30 ppm, water: 0.5 wt % | 98.8 | 88.9 |

TABLE 64-continued

| | Content of compound having uriedo groups in composition (wt %) | ArOH | Content of aromatic hydroxy compound in composition (wt %) | Content of ammonia in composition (wt %) | Other components and contents thereof in composition (%) | Ratio of compound having ureido groups after storage versus before storage (mol %) | Yield of N-substituted carbamic acid-O-aryl ester (mol %) (molar yield versus compound having ureido groups before storage) |
|---|---|---|---|---|---|---|---|
| Example 279 | 17.3 | 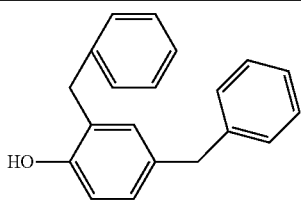 60 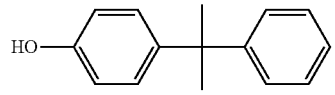 21 | | 0.01 | Total ureylene group-containing compounds: 0.005, terminal biuret group-containing compounds: 0.005, dibutyl tin dilaurate: 60 ppm, water: 0.5 wt % | 97.6 | 92.7 |
| Example 280 | 3.0 | 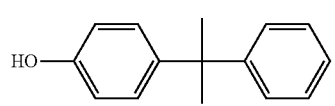 60 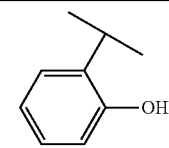 20 | | 0.01 | Total ureylene group-containing compounds: 0.005 | 99.0 | 98.0 |
| | | 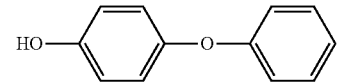 76.5 | | | | | |

TABLE 65

| | Content of compound having uriedo groups in composition (wt %) | ArOH | Content of aromatic hydroxy compound in composition (wt %) | Content of ammonia in composition (wt %) | Other components and contents thereof in composition (%) | Ratio of compound having ureido groups after storage versus before storage (mol %) | Yield of N-substituted carbamic acid-O-aryl ester (mol %) (molar yield versus compound having ureido groups before storage) |
|---|---|---|---|---|---|---|---|
| Example 281 | 5.0 | (structure) 30 (structure) 64.5 | | 0.1 | Total ureylene group-containing compounds: 0.005 | 99.0 | 99.0 |

TABLE 65-continued

| | Content of compound having uriedo groups in composition (wt %) | ArOH | Content of aromatic hydroxy compound in composition (wt %) | Content of ammonia in composition (wt %) | Other components and contents thereof in composition (%) | Ratio of compound having ureido groups after storage versus before storage (mol %) | Yield of N-substituted carbamic acid-O-aryl ester (mol %) (molar yield versus compound having ureido groups before storage) |
|---|---|---|---|---|---|---|---|
| Example 282 | 17.3 | 4-isopropylphenol / 4-(1-methyl-1-phenylethyl)phenol | 18 / 62 | 0.2 | Total ureylene group-containing compounds: 0.005, dibutyl tin dilaurate: 40 ppm, water: 0.5 wt % | 95.2 | 90.4 |
| Example 283 | 17.3 | 3-isopropylphenol / 4-(1-methyl-1-phenylethyl)phenol | 18 / 62 | 0.001 | Total ureylene group-containing compounds: 0.005, terminal biuret group-containing compounds: 0.005 | 98.4 | 93.5 |
| Example 284 | 15.9 | 2,6-diethylphenol / 4-phenoxyphenol | 20 / 61 | 0.001 | Total ureylene group-containing compounds: 0.005, terminal biuret group-containing compounds: 0.005 | 98.4 | 88.6 |
| Example 285 | 15.9 | 4-butylphenol | 18 | 0.001 | Total ureylene group-containing compounds: 0.005, terminal biuret group-containing compounds: 0.005, dibutyl tin dilaurate: 60 ppm | 97.6 | 87.8 |

TABLE 65-continued

| | Content of compound having uriedo groups in composition (wt %) | ArOH | Content of aromatic hydroxy compound in composition (wt %) | Content of ammonia in composition (wt %) | Other components and contents thereof in composition (%) | Ratio of compound having ureido groups after storage versus before storage (mol %) | Yield of N-substituted carbamic acid-O-aryl ester (mol %) (molar yield versus compound having ureido groups before storage) |
|---|---|---|---|---|---|---|---|
| | | 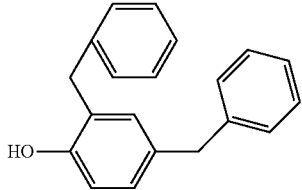 63 | | | | | |
| Example 286 | 13.4 | | 68 | 0.2 | Urea: 0.01 | 98.4 | 96.4 |
| | | 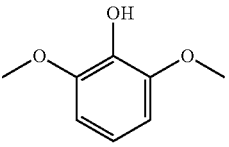 16 | | | | | |
| | | 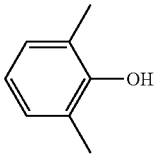 | | | | | |
| Example 287 | 15.6 | | 70 | 0.4 | Total ureylene group-containing compounds: 0.015, terminal biuret group-containing compounds: 0.015 | 97.6 | 87.9 |
| | | 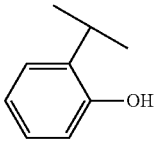 12 | | | | | |

TABLE 66

| | Content of compound having uriedo groups in composition (wt %) | ArOH | Content of aromatic hydroxy compound in composition (wt %) | Content of ammonia in composition (wt %) | Other components and contents thereof in composition (%) | Ratio of compound having ureido groups after storage versus before storage (mol %) | Yield of N-substituted carbamic acid-O-aryl ester (mol %) (molar yield versus compound having ureido groups before storage) |
|---|---|---|---|---|---|---|---|
| Example 288 | 17.1 | 2-ethoxyphenol; 4-phenoxyphenol | 10; 70 | 0.3 | Urea: 0.01 | 97.6 | 87.9 |
| Example 289 | 12.9 | 4-(1-phenylethyl)phenol; 2-isopropylphenol | 70; 15 | 0.1 | Urea: 0.01 | 96.0 | 94.1 |
| Example 290 | 12.1 | 4-(1-phenylethyl)phenol | 71 | 0.01 | Xylene: 15 wt %, total group-containing compounds: 0.002, terminal biuret group-containing compounds: 0.005 | 96.0 | 94.1 |
| Example 291 | 14.6 | 4-phenoxyphenol; phenol | 68; 15 | 0.01 | Urea: 0.01 | 93.6 | 91.7 |
| Example 292 | 16.5 | 4-(1-phenylethyl)phenol | 76 | 0.01 | Total ureylene group-containing compounds: 0.002, terminal biuret group-containing compounds: 0.005, butanol: 5 wt % | 96.0 | 94.1 |
| Example 293 | 16.5 | 4-phenoxyphenol | 68 | 0.02 | Total ureylene group-containing compounds: 0.002, terminal biuret group-containing compounds: 0.005 | 99.2 | 97.2 |

TABLE 66-continued

| | Content of compound having ureido groups in composition (wt %) | ArOH | Content of aromatic hydroxy compound in composition (wt %) | Content of ammonia in composition (wt %) | Other components and contents thereof in composition (%) | Ratio of compound having ureido groups after storage versus before storage (mol %) | Yield of N-substituted carbamic acid-O-aryl ester (mol %) (molar yield versus compound having ureido groups before storage) |
|---|---|---|---|---|---|---|---|
| | | 2,6-dimethylphenol | 12 | | | | |
| Example 294 | 7.1 | 4-phenoxyphenol | 90 | 0.02 | Urea: 0.05 | 99.0 | 98.0 |
| Example 295 | 25.0 | 4-phenoxyphenol | 73 | 0.02 | Urea: 0.05 | 96.0 | 94.1 |
| Example 296 | 27.6 | 4-phenoxyphenol | 70 | 0.02 | Urea: 0.05 | 96.0 | 75.0 |

TABLE 67

| | Content of compound having ureido groups in composition (wt %) | ArOH | Content of aromatic hydroxy compound in composition (wt %) | Content of ammonia in composition (wt %) | Other components and contents thereof in composition (%) | Ratio of compound having ureido groups after storage versus before storage (mol %) | Yield of N-substituted carbamic acid-O-aryl ester (mol %) (molar yield versus compound having ureido groups before storage) |
|---|---|---|---|---|---|---|---|
| Example 297 | 43.3 | 4-phenoxyphenol | 52 | 0.001 | Urea: 0.05 | 96.0 | 25.0 |

TABLE 67-continued

| | Content of compound having uriedo groups in composition (wt %) | ArOH | Content of aromatic hydroxy compound in composition (wt %) | Content of ammonia in composition (wt %) | Other components and contents thereof in composition (%) | Ratio of compound having ureido groups after storage versus before storage (mol %) | Yield of N-substituted carbamic acid-O-aryl ester (mol %) (molar yield versus compound having ureido groups before storage) |
|---|---|---|---|---|---|---|---|
| Example 298 | 33.7 | (4-phenoxyphenol) | 62 | 0.001 | Urea: 0.05 | 96.0 | 38.0 |
| Example 299 | 19.9 | (4-phenoxyphenol); (o-cresol) | 63; 11 | 0.05 | Total ureylene group-containing compounds: 0.002, terminal biuret group-containing compounds: 0.005, ditolyl carbonate: 0.01 | 97.2 | 95.3 |
| Example 300 | 12.4 | (bis(4-hydroxyphenyl)methane); (2,6-dimethylphenol) | 74; 10 | 0.04 | Urea: 0.05, terminal biuret group-containing compounds: 0.05, dixylyl carbonate: 0.06, dibutyl tin dilaurate: 650 ppm | 74.0 | 66.6 |

TABLE 67-continued

| Content of compound having uriedo groups in composition (wt %) | ArOH | Content of aromatic hydroxy compound in composition (wt %) | Content of ammonia in composition (wt %) | Other components and contents thereof in composition (%) | Ratio of compound having ureido groups after storage versus before storage (mol %) | Yield of N-substituted carbamic acid-O-aryl ester (mol %) (molar yield versus compound having ureido groups before storage) |
|---|---|---|---|---|---|---|
| Example 301 | 11.1 | ![bisphenol A structure] | 72 | 0.01 | Urea: 0.05, terminal biuret group-containing compounds: 0.05, dixylyl carbonate: 0.06 | 98.4 | 59.0 |
| | | ![2,6-dimethylphenol structure] | 10 | | | | |
| Example 302 | 20.5 | ![catechol structure] | 10 | 0.01 | Total ureylene group-containing compounds: 0.002, terminal biuret group-containing compounds: 0.005 | 98.4 | 73.8 |
| | | ![4-phenoxyphenol structure] | 65 | | | | |
| Example 303 | 11.1 | ![substituted phenol structure] | 85 | 0.3 | Total ureylene group-containing compounds: 0.002, terminal biuret group-containing compounds: 0.005, urea: 0.001 | 98.4 | 39.4 |

TABLE 67-continued

| Content of compound having uriedo groups in composition (wt %) | ArOH | Content of aromatic hydroxy compound in composition (wt %) | Content of ammonia in composition (wt %) | Other components and contents thereof in composition (%) | Ratio of compound having ureido groups after storage versus before storage (mol %) | Yield of N-substituted carbamic acid-O-aryl ester (mol %) (molar yield versus compound having ureido groups before storage) |
|---|---|---|---|---|---|---|
| Example 304 | 6.2 | [structure: 4-alkyl-substituted phenol with HO on benzene ring and long alkyl chain] | 88 | 0.5 | Total ureylene group-containing compounds: 0.02, terminal biuret group-containing compounds: 0.05, urea: 0.01 | 64.0 | 32.0 |

Example 305

A composition containing 16.5% by weight of a compound having ureido groups represented by the following formula (204) (having different methylene group crosslinking sites, and having an average structure in the form of a trimer structure as represented by the following formula), 81% by weight of an aromatic hydroxy composition in the form of 4-(2-phenylpropane-2-yl)phenol, 0.01% by weight of ammonia and urea at a ratio of 0.001 (referring to the ratio of number of urea molecules to the number of ureido groups that compose (or are contained in) the compound having ureido groups, or in other words, 0.001 indicates 0.003 mole equivalents since the compound having ureido groups has two ureido groups in a molecule thereof) was placed in a 100 L SUS storage vessel to about ½ the volume thereof, followed by replacing the inside of the storage vessel with nitrogen, and storing for 1095 days in a storage environment found in the Kojima district of Kurashiki city in Okayama prefecture, Japan. The composition also contained other components for which the structure thereof was unclear (such as compounds containing ureylene groups and compounds containing terminal biuret bonds). During the storage period, the vessel was warmed with a circulating hot water jacket at 40° C. (controlled to roughly 30 to 50° C.). During the storage period, the temperature occasionally fell to about 0° C. or rose to about 50° C. due to the effects of water stoppages, power outages and factory utility maintenance. In addition, the temperature once rose to about 80° C. due to a malfunction. When the composition was analyzed after storage, the compound having ureido groups was contained in the composition at 98.4 mol % as compared with prior to storage. Following the storage period, the composition was heated to 180° C. and introduced through a preheater (device for preheating the composition to 230° C.) into the vicinity of the middle of a sieve tray distillation column having an inner diameter of 2.5 inches and 40 theoretical plates (operation of the distillation column was carried out while reducing the pressure from normal pressure to reduced pressure within a liquid phase temperature range in the lower portion of the distillation column of 150 to 300° C. and confirming operating conditions; the minimum pressure during operation was about 0.3 KPa). An N-substituted carbamic acid-O-aryl ester derived from the compound having ureido groups and aromatic hydroxy composition was obtained from the lower portion of the distillation column. Ammonia formed as a by-product in the esterification reaction, a small amount of aromatic hydroxy composition, and a component having a lower boiling point than the aromatic hydroxy composition were extracted from the upper portion of the distillation column (and included a by-product in the form of a compound having a molecular weight of 178 or less and having a carbonyl group, although the structure thereof was unable to be identified). Although the yield changed from the start to completion of operation due to fluctuations in operating conditions, at the highest level of performance during the operating period, the yield of the N-substituted carbamic acid-O-aryl ester based on the compound having ureido groups at the start of the storage period was 96.4 mol %. There was no clogging of lines during both storage and transfer, and formation of solid within the distillation column was not observed.

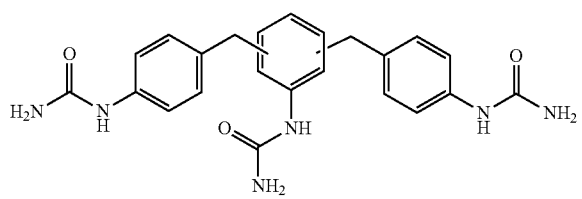

(204)

Example 306

A composition containing 12.5% by weight of a compound having ureido groups represented by the following formula (205) (having different methylene group crosslinking sites, and having an average structure in the form of a trimer structure as represented by the following formula), 85% by weight of an aromatic hydroxy composition in the form of cresol (isomer mixture), 0.01% by weight of ammonia and urea at a ratio of 0.001 (referring to the ratio of number of urea molecules to the number of ureido groups that compose (or are contained in) the compound having ureido groups, or in other words, 0.001 indicates 0.004 mole equivalents since the compound having ureido groups has two ureido groups in a molecule thereof) was placed in a 100 L SUS storage vessel to about ½ the volume thereof, followed by replacing the inside of the storage vessel with nitrogen, and storing for 1095 days in a storage environment found in the Kojima district of Kurashiki city in Okayama prefecture, Japan. The composition also contained other components for which the structure thereof was unclear (such as compounds containing ureylene groups and compounds containing terminal biuret bonds). During the storage period, the vessel was warmed with a circulating hot water jacket at 40° C. (controlled to roughly 30 to 50° C.). During the storage period, the temperature occasionally fell to about 0° C. or rose to about 50° C. due to the effects of water stoppages, power outages and factory utility maintenance. In addition, the temperature once rose to about 80° C. due to a malfunction. When the composition was analyzed after storage, the compound having ureido groups was contained in the composition at 97 mol % as compared with prior to storage. Following the storage period, the composition was heated to 180° C. and introduced through a preheater (device for preheating the composition to 230° C.) into the vicinity of the middle of a sieve tray distillation column having an inner diameter of 2.5 inches and 40 theoretical plates (operation of the distillation column was carried out while reducing the pressure from normal pressure to reduced pressure within a liquid phase temperature range in the lower portion of the distillation column of 150 to 300° C. and confirming operating conditions; the minimum pressure during operation was about 0.3 KPa). An N-substituted carbamic acid-O-aryl ester derived from the compound having ureido groups and aromatic hydroxy composition was obtained from the lower portion of the distillation column. Ammonia formed as a by-product in the esterification reaction, a small amount of aromatic hydroxy composition, and a component having a lower boiling point than the aromatic hydroxy composition were extracted from the upper portion of the distillation column (and included a by-product in the form of a compound having a molecular weight of 178 or less and having a carbonyl group, although the structure thereof was unable to be identified). Although the yield changed from the start to completion of operation due to fluctuations in operating conditions, at the highest level of performance during the operating period, the yield of the N-substituted carbamic acid-O-aryl ester based on the compound having ureido groups at the start of the storage period was 93 mol %. There was no clogging of lines during both storage and transfer, and formation of solid within the distillation column was not observed.

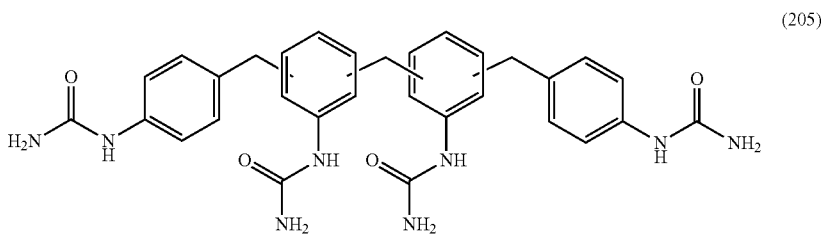

(205)

The present application is based on Japanese patent applications (Japanese Patent Application No. 2009-192250 and Japanese Patent Application No. 2009-192268) filed with the Japanese Patent Office on Aug. 21, 2009, the contents of which are incorporated herein by reference.

INDUSTRIAL APPLICABILITY

Since the N-substituted carbamic acid-O-aryl ester production method of the present embodiment inhibits side reactions and enables urea and the like used in excess in the reaction to be efficiently recovered and reused by producing an N-substituted carbamic acid-O-aryl ester from a compound having ureido groups and an aromatic hydroxy composition, N-substituted carbamic acid-O-aryl ester can be produced without impairing the amounts of urea and organic amine used. In addition, since various reaction by-products can be inhibited and can be dissolved by the aromatic hydroxy composition and removed outside the system, operating is possible over a long period of time. Moreover, a composition for transfer and storage of a compound having ureido groups can be preferably used as a production raw material of the N-substituted carbamic acid-O-aryl ester, and the N-substituted carbamic acid-O-aryl ester can be preferably used to produce isocyanate. Thus, the present invention is industrially extremely important.

DESCRIPTION OF REFERENCE NUMERICALS

FIG. 13
100, 101, 102, 104, 109, 110: storage tanks, 103: stirring tank, 106, 111: condensers: 107: reboiler, 108, 112: gas-liquid separator, 10, 11, 12, 13, 14, 15, 16, 17, 18, 19: lines

FIG. 14

200, 201, 202, 204, 208, 209, 213, 216: storage tanks, 203: stirring tank, 206, 211: condensers, 207, 212: gas-liquid separators, 214, 215: reboilers, 20, 21, 22, 23, 24, 25, 26, 27, 28, 29, 30, 31: lines

FIG. 15

110, 400, 401, 402, 404, 407: storage tanks, 408: stirring tank, 405: condenser, 406: gas-liquid separator, 40, 41, 42, 43, 44, 45, 46: lines

FIG. 16

501, 504, 505: storage tanks, 502: packed column, 503: condenser: 507: gas-liquid separator, 506: reboiler, 51, 52, 53, 54: lines

FIG. 17

601, 603, 608, 612, 614: storage tanks, 602: thin film distillation apparatus, 604, 609: packed columns, 605, 610: condensers, 606, 611: gas-liquid separators, 607, 613: reboilers, 60, 61, 62, 63, 64, 65, 66, 67, 68, 69, 70, 71: lines

FIG. 18

1001, 1003, 1008, 1013, 1019: storage tanks, 1002: thin film distillation apparatus, 1004, 1009: packed columns, 1005, 1010, 1015: condensers, 1007, 1012, 1017: reboilers, 1006, 1011, 1016: gas-liquid separators, A1, A2, A3, A4, A5, A6, A7, A8, A9, A10, A11, A12, A13, A14, A15: lines

FIG. 19

1100, 1101, 1102, 1105: storage tanks, 1103: stirring tank, 1104: pressurized filtration apparatus, B0, B1, B2, B3: lines

FIG. 20

1201, 1205, 1207: storage tanks, 1202: packed column, 1204: gas-liquid separator, 1206: reboiler, C1, C2, C3, C4: lines

FIG. 21

1300, 1301, 1305, 1307: storage tanks, 1302: packed column, 1303: condenser, 1304: gas-liquid separator, D1, D2, D3, D4, D5, D6: lines

FIG. 22

1401: urea synthesis tube, 1402: high-pressure separator, 1403: condenser, E1, E2, E3, E4, E5, E6, E7, E8: lines

We claim:

1. A method for producing at least one N-substituted carbamic acid-O-aryl ester wherein the N-substituted carbamic acid-O-aryl ester is an N-substituted carbamic acid ester in which oxygen atoms of the carbamic acid group (—NH-COO—) are bonded to an aromatic ring derived from an isolated compound having an ureido group of formula (1) and an aromatic hydroxy composition containing at least one type of aromatic hydroxy compound of formula (2), the method comprising the steps of obtaining the isolated compound having the ureido group of formula (1); and carrying out esterification with the compound of formula (2) or esterification with the compound of formula (4) and subsequent transesterification with the compound of formula (2) from the isolated compound having the ureido group of formula (1):

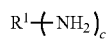  (3)

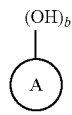  (2)

  (4)

wherein $R^1$ represents an organic group containing an integral number of carbon atoms within a range of from 1 to 85, that is substituted by a number a of ureido group(s), and the a represents an integer of from 1 to 10, ring A represents an organic group, which contains an aromatic group substituted by a number b of hydroxy group(s) at arbitrary location(s) that maintain aromatic properties, and wherein ring A contains an integral number of carbon atoms within a range of from 6 to 50, which may be a single or multiple heterocyclic ring, and which is substituted by at least one substituent selected from the groups of substituents indicated below (i)-(v), and the b represents an integer of from 1 to 6, and (i) a hydrogen atom;

(ii) a group composed of carbon atoms and hydrogen atoms (which may also form a ring structure by bonding with ring A);

(iii) a group composed of carbon atoms, hydrogen atoms and oxygen atoms (excluding groups containing a carbonyl group, an ester group, a terminal methine group and an alcoholic OH group, a carboxyl group, a $NH_2$ group, a NH group, a NOH a group, a SH group a $SO_3H$ group or a SOH group);

(iv) a halogen atom; and (v) a group composed of atoms selected from carbon atoms, hydrogen atoms, oxygen atoms, nitrogen atoms, sulfur atoms and halogen atoms (excluding groups containing a carbonyl group, an ester group, a terminal methine group and an alcoholic OH group, a carboxyl group a $NH_2$ group, a NH group, a NOH group, a SH group, a $SO_3H$ group or a SOH group), and $R^2$ represents an aliphatic group, or an aliphatic group in which an aromatic group is bonded, which contains an integral number of carbon atoms within a range of from 1 to 14, and the OH group of the alcohol of formula (4) is an OH group that is not bonded to an aromatic ring.

2. The production method according to claim 1, wherein the isolated compound having the ureido group of formula (1) is a compound having an ureido group obtained by step (A): reacting an organic primary amine of formula (3) and urea by ureidating the organic primary amine and the urea in a liquid phase and eliminating or extracting to a gaseous phase ammonia formed as a by-product in the ureidation reaction:

  (3)

wherein $R^1$ represents an organic group containing an integral number of carbon atoms within a range of from 1 to 85, that is substituted by number c of $NH_2$ group(s), and the c represents an integer of from 1 to 10.

3. The production method according to claim 2, wherein the organic primary amine is an organic primary monoamine or an organic primary diamine.

4. The production method according to claim 2, wherein step (A) is carried out in the presence of water and/or alcohol and/or an aromatic hydroxyl composition containing at least one type of aromatic hydroxyl compound.

5. The production method according to claim 2, wherein step (A) is carried out in the presence of an aromatic hydroxy composition containing at least one type of aromatic hydroxy compound of formula (2):

$$(OH)_b$$ 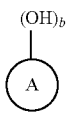 (2)

wherein
  ring A represents an organic group, which contains an aromatic group substituted by a number b of hydroxy group(s) at an arbitrary location(s) that maintain aromatic properties, wherein ring A contains an integral number of carbon atoms within a range of from 6 to 50, which may be a single or multiple heterocyclic ring, and which is substituted by at least one substituent selected from the groups of substituents indicated below (i)-(v), and the b represents an integer of from 1 to 6, and
  (i) a hydrogen atom;
  (ii) a group composed of carbon atoms and hydrogen atoms (which may also form a ring structure by bonding with ring A);
  (iii) a group composed of carbon atoms, hydrogen atoms and oxygen atoms (excluding groups containing a carbonyl group, an ester group, a terminal methine group and an alcoholic OH group, a carboxyl group, a $NH_2$ group, a NH group, a NOH group, a SH group, a $SO_3H$ group or a SOH group);
  (iv) a halogen atom; and
  (v) a group composed of atoms selected from carbon atoms, hydrogen atoms, oxygen atoms, nitrogen atoms, sulfur atoms and halogen atoms (excluding groups containing a carbonyl group, an ester group, a terminal methine group and an alcoholic OH group, a carboxyl group, a $NH_2$ group, a NH group, a NOH group, a SH group, a $SO_3H$ or a SOH group).

6. The production method according to claim 2, wherein step (A) is carried out in the presence of an alcohol of formula (4):

$$R^2OH \quad (4)$$

wherein
  $R^2$ represents an aliphatic group, or an aliphatic group in which an aromatic group is bonded, which contains an integral number of carbon atoms within a range of from 1 to 14, and the OH group of the alcohol of formula (4) is an OH group that is not bonded to an aromatic ring
wherein
  an esterification of the compound of formula (4) and the isolated compound having the ureido group of formula (1) is followed by a transesterification of the aromatic hydroxyl composition of formula (2) and the esterification product of formula (4) and formula (1) to produce the carbamic acid-O-aryl ester.

7. The production method according to claim 1, further comprising the following steps (A) and (B):
  step (A): a step of obtaining at least one type of the isolated compound having an ureido group of formula (1) derived from the reaction of an organic primary amine of formula (3) and urea by ureidating the organic primary amine and the urea in a liquid phase and eliminating or extracting to a gaseous phase ammonia formed as a by-product in the ureidation reaction, and step (B): a step of obtaining N-substituted carbamic acid-O-aryl ester by reacting the at least one type of the isolated compound having the ureido group of formula (1) and the aromatic hydroxy composition containing at least one type of aromatic hydroxy compound of formula (2) in a liquid phase, and extracting ammonia formed as a by-product to a gaseous phase:

 (3)

wherein
  $R^1$ represents an organic group containing an integral number of carbon atoms within a range of from 1 to 85, that is substituted by a number c of $NH_2$ group(s), and the c represents an integer of 1 to 10.

8. The production method according to claim 1, further comprising the following steps (A), (R) and (P):
  step (A): a step of obtaining at least one type of the isolated compound having an ureido group of formula (1) derived from the reaction of an organic primary amine of formula (3) and urea by ureidating the organic primary amine and the urea in a liquid phase and eliminating or extracting to a gaseous phase ammonia formed as a by-product in the ureidation reaction,
  step (R): a step of obtaining an N-substituted carbamic acid-O—$R^2$ ester by reacting the at least one type of the isolated compound having the ureido group of formula (1) and an alcohol of formula (4) in a liquid phase and extracting ammonia formed as a by-product to a gaseous phase wherein the N-substituted carbamic acid-O—$R^2$ ester represents an N-substituted carbamic acid ester in which oxygen atoms of the carbamic acid group (—NH-COO—) are bonded to an $R^2$ group derived from an alcohol, and
  step (P): a step of obtaining an N-substituted carbamic acid-O-aryl ester by reacting the N-substituted carbamic acid-O—$R^2$ ester and the aromatic hydroxy composition containing at least one type of aromatic hydroxy compound of formula (2) in a liquid phase and extracting alcohol formed as a by-product to a gaseous phase:

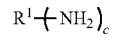 (3)

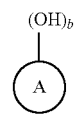 (2)

wherein
  $R^1$ represents an organic group containing an integral number of carbon atoms within a range of from 1 to 85, that is substituted by a number c of $NH_2$ group(s), and the c represents an integer of from 1 to 10, and
  ring A represents an organic group, which contains an aromatic group substituted by a number b of hydroxy group(s) at arbitrary location(s) that maintain aromatic properties, and wherein ring A contains an integral number of carbon atoms within a range of from 6 to 50, which may be a single or multiple heterocyclic ring, and which is substituted by at least one substituent selected from the groups of substituents indicated below (i)-(v), and the b represents an integer of from 1 to 6, and i) a hydrogen atom;
(ii) a group composed of carbon atoms and hydrogen atoms (which may also form a ring structure by bonding with ring A);
(iii) a group composed of carbon atoms, hydrogen atoms and oxygen atoms (excluding groups containing a carbonyl group, an ester group, a terminal methine group and an alcoholic OH group, a carboxyl group, a $NH_2$ group, a NH group, a NOH group, a SH group a $SO_3H$ group or a SOH group);
(iv) a halogen atom; and
(v) a group composed of atoms selected from carbon atoms, hydrogen atoms, oxygen atoms, nitrogen atoms, sulfur atoms and halogen atoms (excluding groups containing a carbonyl group, an ester group, a terminal methinerou and an alcoholic OH group, acarboxyl group, a $NH_2$ group, a NH group, a NOH group, a SH group, a $SO_3H$ group or a SOH group).

9. The production method according to claim 7 or 8, wherein the organic primary amine is an aromatic organic primary monoamine of formula (5), and the following step (C) is carried out after step (B), after step (R) or after step (P),
step (C): a step of obtaining N-substituted carbamic acid-O—($R^2$ or aryl) ester in which at least two molecules of the N-substituted carbamic acid-O—($R^2$ or aryl) ester are crosslinked with a methylene group (—$CH_2$—), by reacting the N-substituted carbamic acid-O—($R^2$ or aryl) ester obtained in step (B), step (R) or step (P) with formaldehyde or a methylenating crosslinking agent and crosslinking aromatic groups derived from the aromatic organic primary monoamine contained in the N-substituted carbamic acid—O—($R^2$ or aryl) ester with the methylene group (—$CH_2$—) wherein the N-substituted carbamic acid-O—($R^2$ or aryl) ester represents an N-substituted carbamic acid-O—$R^2$ ester or an N-substituted carbamic acid-O—aryl ester:

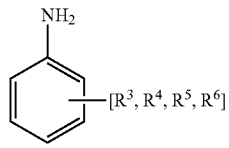

(5)

wherein
at least one location at the ortho position and/or para position of the $NH_2$ group of an aromatic organic primary monoamine of formula (5) is not substituted, groups $R^3$ to $R^6$ respectively represent a group substituted at an arbitrary location that maintains aromatic properties of the ring, groups $R^3$ to $R^6$ may respectively and independently substitute an aromatic ring or groups $R^3$ to $R^6$ may together bond to form a ring with an aromatic ring, groups $R^3$ to $R^6$ are hydrogen atoms or groups selected from the group consisting of groups in which a group selected from the group consisting of an alkyl group, an cycloalkyl group, an aryl group and an aryl group having a hydroxy group is bonded by saturated aliphatic bonds and/or ether bonds, the number of carbon atoms of groups $R^3$ to $R^6$ is an integral number within a range of 0 to 7, and a total number of carbon atoms that compose the aromatic organic primary monoamine of formula (5) is an integer of from 6 to 13.

10. The production method according to claim 7 or 8, comprising the step of recovering urea by carrying out the following step (D) before the step (B) or the step (P) and/or simultaneous to the step (B) or the step (P):
step (D): a step of removing urea by distillation or sublimation.

11. The production method according to claim 10, comprising the following step (E) of recycling the recovered urea to the step (A):
step (E): a step of recycling urea recovered in step (D) to step (A).

12. The production method according to claim 1, 7 or 8, comprising the step of obtaining an isocyanate of formula (6), which is derived from the N-substituted carbamic acid-O-aryl ester, and an aromatic hydroxy composition by carrying out thermal decomposition on the N-substituted carbamic acid-O-aryl ester in the following step (F):
step (F): a step of obtaining an isocyanate and an aromatic hydroxy composition from the N-substituted carbamic acid-O-aryl ester:

(6)

wherein
$R^1$ represents an organic group containing an integral number of carbon atoms within a range of from 1 to 85, that is substituted by number s of NCO group(s), and the s represents an integer of from 1 to 10.

13. The production method according to claim 12, comprising the step of separating the aromatic hydroxy composition obtained in the step (F) from the isocyanate, and recycling the aromatic hydroxy composition to the step (A) and/or the step (B), or to the step (A) and/or the step (R) and/or the step (P).

14. The production method according to any one of claim 1 or 7, wherein the aromatic hydroxy composition is at least one type of aromatic hydroxy compound of formula (7):

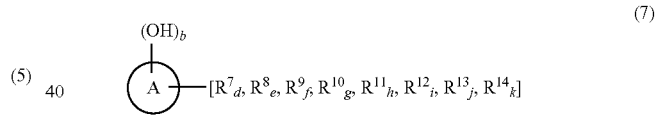

(7)

wherein
ring A represents an aromatic ring selected from a benzene ring, a naphthalene ring and an anthracene ring, the OH groups and groups $R^7$ to $R^{14}$ respectively represent groups substituted at arbitrary location(s) that maintain aromatic properties of ring A, groups $R^7$ to $R^{14}$ may respectively and independently substitute ring A, groups $R^7$ to $R^{14}$ may bond together to form a ring with an aromatic ring by bonding to ring A, groups $R^7$ to $R^{14}$ respectively and independently represent a hydrogen atom, a halogen atom or a group selected from the group consisting of an alkyl group, an cycloalkyl group, an aryl group, an aryl group having a hydroxy group, an aralkyl group and an ether group (substituted and/or unsubstituted alkyl ether and/or substituted and/or unsubstituted aryl ether and/or substituted and/or unsubstituted aralkyl ether group), and/or a group to which one or more types of groups selected from the group are bonded, and/or a group to which one or more types of groups selected from the group are bonded by saturated aliphatic bonds and/or ether bonds, and ring A and groups $R^7$ to $R^{14}$ are composed of an integral total number of carbon atoms within a range of from 6 to 50,
b represents an integer of from 1 to 6, d, e, f, g, h, i, j and k represent integers of from 0 to 5, the value of d+e+f+g+ h+i+j+k represents an integer equal to 6-b in the case ring A is the benzene ring, represents an integer equal to 8-b in the case ring A is the naphthalene ring, or represents an integer equal to 10-b in the case ring A is the anthracene ring, and a group selected from groups $R^7$ to $R^{14}$ as described above may be cyclically bonded to ring A by carbon-carbon bonds and/or ether bonds, and ring A is substituted by at least one substituent selected from the groups of substituents indicated below (i)-(v), and the b represents an integer of from 1 to 6, and (i) a hydrogen atom;
(ii) a group composed of carbon atoms and hydrogen atoms (which may also form a ring structure by bonding with ring A);
(iii) a group composed of carbon atoms, hydrogen atoms and oxygen atoms (excluding groups containing a carbonyl group, an ester group, a terminal methine group and an alcoholic OH group, a carboxyl group, a $NH_2$ group, a NH group, a NOH group, a SH group, a $SO_3H$ group or a SOH group);
(iv) a halogen atom; and
(v) a group composed of atoms selected from carbon atoms, hydrogen atoms, oxygen atoms, nitrogen atoms, sulfur atoms and halogen atoms (excluding groups containing a carbonyl group, an ester group, a terminal methine group and an alcoholic OH group, a carboxyl group, a $NH_2$ group, a NH group, a NOH group, a SH group, a $SO_3H$ group or a SOH group).

15. The production method according to any one of claim 2, 7 or 8, wherein the aromatic hydroxy compound that composes the aromatic hydroxy composition has a standard boiling point that differs by 10° C. or more from the standard boiling point of an isocyanate having a structure in which all amino groups of the organic primary amine (primary amino groups) are converted to isocyanate groups.

16. The production method according to any one of claim 1 or 7, wherein the aromatic hydroxy compound contained in the aromatic hydroxy composition is a monovalent and/or divalent aromatic hydroxy compound (b is 1 and/or 2).

17. The production method according to claim 12, comprising recycling unreacted N-substituted carbamic acid-O-aryl ester that has not been thermally decomposed in the step (F), to the step (A) and/or the step (B) and/or the step (R) and/or the step (P) and/or the step (F).

18. The production method according to claim 7 or 8, further comprising the following step (G) of recovering ammonia formed as a by-product in the step (A) and/or the step (B) and/or the step (R); regenerating urea by reacting the ammonia with carbon dioxide; and recycling the urea to the step (A):

step (G): a step of recovering ammonia formed as a by-product, regenerating urea by reacting the ammonia with carbon dioxide, and recycling the urea to step (A).

* * * * *